(12) United States Patent  
Fink et al.

(10) Patent No.: US 8,389,527 B2
(45) Date of Patent: Mar. 5, 2013

(54) SUBSTITUTED IMIDAZOPYRIDAZINES USEFUL AS KINASE INHIBITORS

(75) Inventors: Brian E. Fink, Yardley, PA (US); Soong-Hoon Kim, Titusville, NJ (US); Yufen Zhao, Pennington, NJ (US); Ping Chen, Franklin Park, NJ (US); Wayne Vaccaro, Yardley, PA (US); Litai Zhang, Lawrenceville, NJ (US); Ashvinikumar V Gavai, Princeton Junction, NJ (US); Dharmpal S Dodd, Princeton, NJ (US); Libing Chen, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 102 days.

(21) Appl. No.: 12/866,365

(22) PCT Filed: Feb. 6, 2009

(86) PCT No.: PCT/US2009/033455
§ 371 (c)(1),
(2), (4) Date: Aug. 5, 2010

(87) PCT Pub. No.: WO2009/100375
PCT Pub. Date: Aug. 13, 2009

(65) Prior Publication Data
US 2010/0323994 A1  Dec. 23, 2010

Related U.S. Application Data

(60) Provisional application No. 61/026,651, filed on Feb. 6, 2008.

(51) Int. Cl.
A01N 43/58 (2006.01)
A01N 43/60 (2006.01)
C61K 31/50 (2006.01)
C07D 487/00 (2006.01)

(52) U.S. Cl. ............................. 514/250; 544/236
(58) Field of Classification Search ................. 544/236; 514/250

See application file for complete search history.

(56) References Cited

U.S. PATENT DOCUMENTS

| 4,183,930 A | 1/1980 | Cohen |
| 4,464,372 A | 8/1984 | Bristol et al. |
| 4,716,169 A | 12/1987 | Heider et al. |
| 4,838,925 A | 6/1989 | Tseng |
| 2004/0048849 A1 | 3/2004 | Prevost et al. |
| 2004/0138245 A1 | 7/2004 | Prevost et al. |
| 2008/0045536 A1* | 2/2008 | Vaccaro et al. ............... 514/245 |
| 2010/0105676 A1 | 4/2010 | Liu et al. |
| 2010/0113458 A1 | 5/2010 | Fink et al. |

FOREIGN PATENT DOCUMENTS

| EP | 0 185 346 | 6/1986 |
| EP | 0 244 166 | 11/1987 |
| EP | 0 306 408 | 3/1989 |
| EP | 0 490 587 | 6/1992 |
| JP | 07 101958 | 4/1995 |
| JP | 07 133280 | 5/1995 |
| WO | WO 00/56734 | 9/2000 |
| WO | WO 01/83481 | 11/2001 |
| WO | WO 02/50079 | 6/2002 |
| WO | WO 02/066481 | 8/2002 |
| WO | WO 02/096348 | 12/2002 |
| WO | WO 03/076441 | 9/2003 |
| WO | WO 2004/017950 | 3/2004 |
| WO | WO 2004/076458 | 9/2004 |
| WO | WO 2004/092175 | 10/2004 |
| WO | WO 2005/000852 | 1/2005 |
| WO | WO 2005/026126 | 3/2005 |
| WO | WO 2005/097052 | 10/2005 |
| WO | WO 2006/015737 | 2/2006 |
| WO | WO 2006/016715 | 2/2006 |
| WO | WO 2006/070943 | 7/2006 |
| WO | WO 2006/098519 | 9/2006 |
| WO | WO 2006/099972 | 9/2006 |
| WO | WO 2006/102194 | 9/2006 |
| WO | WO 2006/107784 | 10/2006 |
| WO | WO 2007/013673 | 2/2007 |
| WO | WO 2007/038314 | * 4/2007 |
| WO | WO 2008/016192 | 2/2008 |
| WO | WO2010/011837 | 1/2010 |

OTHER PUBLICATIONS

Pinedo et al, "Translational Research . . . ", The Oncologist 2000; 5(suppl1); 1-2. [www.The Oncologist.com].*
McMahon, G., VEGF Receptor Signaling in Tumor Angiogenisis. The Oncologist 2000;5(suppl 1):3-10. [www.TheOncologist.com].*
Registry No. 910607-63-5, (2007).
Registry No. 910607-62-4, (2007).
Registry No. 910607-61-3, (2007).
Registry No. 785012-64-8, (2007).
Mass, R.D., "The HER receptor family: a rich target for therapeutic development," Int. Jo Radiation Oncology/Bio. Phys., vol. 58(3); pp. 932-940 (2004).
Fabbro et al., "Protein kinases as targets for anticancer agents: from inhibitors to useful drug," Pharmacology & Therapeutics, vol. 93, pp. 79-98 (2002).
Graninger et al., "One-year inhibition of tumor necrosis factor-alpha: a major success or a larger puzzle?" Curr. Opin. Rhematol. 13(3), pp. 209-13, (2001) (abstract only).
Duncan, J.S., et al., "Too much of a good thing: The role of protein kinase CK2 in tumorigenesis and prospects for therapeutic inhibition of CK2," Biochimica et Biophysica Acta 1784 (2008), pp. 33-47.
Nie, Z., et al., "Structure-based design, synthesis, and study of pyrazolo[1,5-a][1,3,5]triazine derivatives as potent inhibitors of protein kinase CK2," Bioorganic & Medicinal Chemistry Letters 17 (2007), pp. 4191-4195.
Nie, Z., et al., "Structure-based design and synthesis of novel macrocyclic pyrazolo[1,5-a][1,3,5]triazine compounds as potent inhibitors of protein kinase CK2 and their anticancer activities," Bioorganic & Medicinal Chemistry Letters (2008), pp. 1-5.

* cited by examiner

Primary Examiner — Paul V. Ward
(74) Attorney, Agent, or Firm — Hong Liu

(57) ABSTRACT

The invention provides compounds of formula I

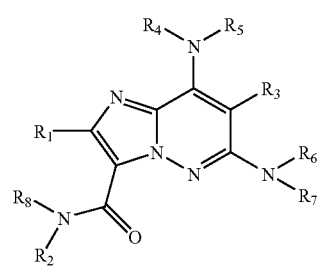

and pharmaceutically acceptable salts thereof. The formula I imidazopyridazines inhibit protein kinase activity thereby making them useful as anticancer agents.

12 Claims, No Drawings

SUBSTITUTED IMIDAZOPYRIDAZINES USEFUL AS KINASE INHIBITORS

This application claims the benefit of priority to U.S. Ser. No. 61/026,651, filed Feb. 6, 2008.

FIELD OF THE INVENTION

The invention relates to novel substituted imidazopyridazines that are useful as anti-cancer agents. This invention also relates to a method of using the compounds in the treatment of proliferative and other types of diseases and to pharmaceutical compositions containing the compounds.

BACKGROUND OF THE INVENTION

The invention relates to fused heterocyclic compounds which inhibit protein kinase enzymes, compositions which contain protein kinase inhibiting compounds and methods of using inhibitors of protein kinase enzymes to treat diseases which are characterized by an overexpression or upregulation of protein kinases. Protein kinases mediate intracellular signal transduction. They do this by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell. An extracellular stimulus may effect one or more cellular responses related to cell growth, migration, differentiation, secretion of hormones, activation of transcription factors, muscle contraction, glucose metabolism, control of protein synthesis and regulation of cell cycle.

Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

Serine/threonine kinases are a class of protein kinases that are among the most promising drug targets for future small molecule inhibitors. Inhibition of serine/threonine kinases is likely to have relevance to the treatment of cancer, diabetes and a variety of inflammatory disorders. The successful development of Gleevec as a Bcr/Abl protein kinase inhibitor has provided further evidence that protein kinases including protein kinase CK2 are valid drug targets for potential cancer therapies.

Protein kinase CK2 (formerly known as casein kinase II) is a highly conserved serine/threonine kinase. In mammals, the enzyme exists in two isozymic forms, CK2α (CK2A1) and CK2α' (CK2A2), due to variations in the catalytic subunits of the enzyme. Protein kinase CK2 is ubiquitously distributed and constitutively active in eukaryotes. It interacts with a variety of cellular proteins and has been implicated in cell replication such as cell proliferation and differentiation, cellular survival, and tumorigenesis. With respect to tumorigenesis, protein kinase CK2 has been implicated in kidney tumors (Stalter et al., "Asymmetric expression of protein kinase CK2 subunits in human kidney tumors", *Biochem. Biophys. Res. Commun.*, 202:141-147 (1994)), mammary gland tumors (Landesman-Bollag et al., "Protein kinase CK2 in mammary gland tumorigenesis", *Oncology*, 20:3247-3257 (2001)), lung carcinoma (Daya-Makin et al., "Activation of a tumor-associated protein kinase (p40TAK) and casein kinase II in human squamous cell carcinomas and adenocarcinomas of the lung", *Cancer Res.*, 54:2262-2268 (1994)), head and neck carcinoma (Faust et al., "Antisense oligonucleotides against protein kinase CK2-α inhibit growth of squamous cell carcinoma of the head and neck in vitro", *Head Neck*, 22:341-346 (2000)), and prostate cancer (Wang et al., "Role of protein kinase CK2 in the regulation of tumor necrosis factor-related apoptosis inducing ligand-induced apoptosis in prostate cancer cells", *Cancer Res.*, 66:2242-2249 (2006)).

Inhibitors of protein kinases are widely sought and several publications report effective classes of compounds. For example, pyrazolotriazines as CK2 kinase inhibitors were reported in Nie et al. (*Bioorganic & Medicinal Chemistry Letters*, 17 (2007)) and imidazopyridazines as IRAK kinase modulators were reported in WO 2008/030579. In addition, certain imidazopyridazine compounds were disclosed in WO 2007/038314, published Apr. 5, 2007, WO 2008/0045536, published Feb. 21, 2008, both assigned to the present assignee. The present invention relates to a new class of imidazopyridazineamides found to be effective inhibitors of protein kinases, particularly the CK2 kinase. These novel compounds are provided to be useful as pharmaceuticals with desirable stability, bioavailability, therapeutic index and toxicity values that are important to their drugability.

SUMMARY OF THE INVENTION

The invention is directed to fused heterocyclic compounds of Formulae (I)-(If) that inhibit protein kinase enzymes, especially protein kinase CK2 for the treatment of cancer, or stereoisomers, tautomers, pharmaceutically acceptable slats, solvates or prodrugs thereof.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibiting the activity of protein kinase CK2 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for inhibiting angiogenesis or treating cancers comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, in preparing a medicament for the treatment of cancer in a human patient, particularly a cancer receptive to treatment via inhibition of the CK2 enzyme.

These and other features of the invention will be set forth in the expanded form as the disclosure continues.

DETAILED DESCRIPTION OF THE INVENTION

The invention provides for novel imidazopyridazine compounds useful as anti-cancer agents, pharmaceutical compositions employing such novel compounds and for methods of using such compounds.

In accordance with the invention, there are disclosed compounds of formula I

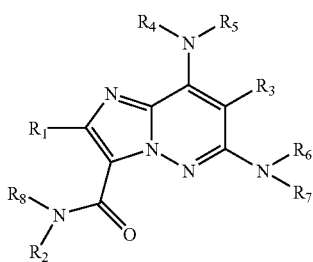

I or a pharmaceutically acceptable salt thereof, wherein $R_1$ and $R_3$ are each independently selected from hydrogen, halogen, cyano, and $C_{1-4}$alkyl;

$R_2$ is selected from cycloalkyl, substituted cycloalkyl, heterocyclo, substituted heterocyclo, aryl, substituted aryl, heteroaryl, and substituted heteroaryl;

$R_4$ is selected from hydrogen, alkyl, substituted alkyl, —C(=O)alkyl, —S(O)$_2$alkyl, cycloalkyl, substituted cycloalkyl, heterocyclo, substituted heterocyclo, aryl, substituted aryl, heteroaryl, and substituted heteroaryl;

$R_5$ is selected from hydrogen and $C_{1-4}$alkyl;

$R_6$ is selected from alkyl, substituted alkyl, cycloalkyl, substituted cycloalkyl, heterocyclo, substituted heterocyclo, aryl, substituted aryl, heteroaryl, and substituted heteroaryl; and $R_7$ is selected from hydrogen and $C_{1-4}$alkyl; or $R_6$ and $R_7$ together with the nitrogen atom to which they are attached form an optionally substituted 5-, 6- or 7-membered monocyclic heteroaryl or heterocyclo ring, or an optionally substituted 7- to 11-membered bicyclic heteroaryl or heterocyclo ring;

$R_8$ is selected from hydrogen and $C_{1-4}$alkyl; and
provided that if $R_2$ is

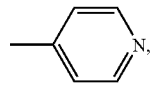

$R_4$ is

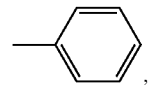

$R_6$ is

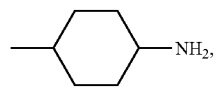

then $R_3$ is not hydrogen.

In one embodiment of the compounds of formula I, $R_2$ is selected from aryl, substituted aryl, $C_{3-7}$cycloalkyl, substituted $C_{3-7}$cycloalkyl, 5- or 6-membered heterocyclo and heteroaryl, and substituted 5- or 6-membered heterocyclo and heteroaryl.

In another embodiment of the compounds of formula I, $R_2$ is selected from phenyl, cyclohexyl, pyridyl, pyrimidinyl, pyrazinyl, benzothiazolyl, pyridazinyl pyrrolidinyl, pyrrolyl, pyrazolyl, imidazolyl, thiazolyl, thienyl, piperidinyl, piperazinyl, morpholinyl, thiamorpholinyl, triazinyl, and triazolyl, wherein each $R_2$ is optionally substituted with halogen, cyano, hydroxy, $C_{1-4}$alkyl, substituted $C_{1-4}$alkyl, alkenyl, substituted alkenyl, alkynyl, substituted alkynyl, $C_{1-4}$alkoxy, haloalkyl, $C_{3-7}$cycloalkyl, heterocyclo, heteroaryl, —NR$_{2a}$R$_{2b}$, —NR$_{2a}$C(O)R$_{2b}$, C(O)NR$_{2a}$R$_{2b}$—C(O)OR$_{2a}$, wherein R$_{2a}$ and R$_{2b}$ are each independently selected from hydrogen and $C_{1-4}$alkyl.

In another embodiment of the compounds of formula I, $R_4$ is selected from alkyl, aryl, cycloalkyl, heterocyclo, and heteroaryl, wherein each $R_4$ is optionally substituted by one to three groups, $T_1$, $T_2$, and/or $T_3$; $T_1$, $T_2$, and $T_3$ are each independently selected from halogen, alkyl, substituted alkyl, alkenyl, substituted alkenyl, alkynyl, substituted alkynyl, nitro, cyano, —(CHR)$_r$SO$_3$H, —(CHR)$_r$SR$_9$, —(CHR)$_r$S(O)$_p$R$_{11}$, —(CHR)$_r$S(O)$_p$NR$_9$R$_{10}$, —(CHR)$_r$NR$_9$S(O)$_p$R$_{11}$, —(CHR)$_r$OR$_9$, —(CHR)$_r$NR$_9$R$_{10}$, —(CHR)$_r$NR$_9$C(=O)R$_{10}$, —(CHR)$_r$NR$_9$C(=O)NR$_9$R$_{10}$, —(CHR)$_r$C(=O)OR$_9$, —(CHR)$_r$C(=O)R$_9$, —(CHR)$_r$C(=O)R$_9$, —(CHR)$_r$C(=O)NR$_9$R$_{10}$, —(CHR)$_r$-cycloalkyl, —(CHR)$_r$-heterocyclo, —(CHR)$_r$-aryl, and —(CHR)$_r$-heteroaryl, wherein said cycloalkyl, heterocyclo, aryl, or heteroaryl is optionally substituted as valence allows from one to three groups, R$_{12}$, R$_{13}$ and/or R$_{14}$; each p is independently 1 or 2; each r is independently zero, 1, 2, or 3; or $T_1$ and $T_2$, located on adjacent ring atoms are taken together with the ring atoms to which they are attached to form a fused cycloalkyl, aryl, heteroaryl, or heterocyclo, wherein said cycloalkyl, aryl, heteroaryl, or heterocyclo is optionally substituted as valence allows from one to three groups, R$_{12}$, R$_{13}$ and/or R$_{14}$;

each R is independently selected from alkyl, substituted alkyl, alkenyl, substituted alkenyl, alkynyl, substituted alkynyl, cycloalkyl, aryl, heteroaryl, and heterocyclo;

$R_9$ and $R_{10}$ are each independently selected from hydrogen, alkyl, substituted alkyl, alkenyl, substituted alkenyl, cycloalkyl, substituted cycloalkyl, aryl, substituted aryl, heteroaryl, substituted heteroaryl, heterocyclo, and substituted heterocyclo; or $R_9$ and $R_{10}$ together with the nitrogen atom to which they are attached form a heteroaryl or heterocyclo, wherein said heteroaryl or heterocyclo is optionally substituted as valence allows from one to three groups, R$_{12}$, R$_{13}$ and/or R$_{14}$; each R$_{11}$ is independently selected from alkyl, substituted alkyl, alkenyl, substituted alkenyl, alkynyl, substituted alkynyl, cycloalkyl, aryl, heteroaryl, and heterocyclo;

$R_{12}$, $R_{13}$, and $R_{14}$ are each independently selected from $C_{1-4}$alkyl, substituted $C_{1-4}$alkyl, $C_{2-4}$alkenyl, substituted $C_{2-4}$alkenyl, halogen, hydroxy, cyano, nitro, CF$_3$, —O(C$_{1-4}$ alkyl), —OCF$_3$, —C(=O)H, —C(=O)(C$_{1-4}$alkyl), —CO$_2$H, —CO$_2$(C$_{1-4}$alkyl), —NHCO$_2$(C$_{1-4}$alkyl), —S(C$_{1-4}$ alkyl), —NH$_2$, —NH(C$_{1-4}$alkyl), —N(C$_{1-4}$alkyl)$_2$, —N(C$_{1-4}$alkyl)$_3^+$, —SO$_2$(C$_{1-4}$alkyl), —C(=O)(C$_{1-4}$alkylene)NH$_2$, —C(=O)(C$_{1-4}$alkylene)NH(alkyl), —C(=O)(C$_{1-4}$alkylene)N(C$_{1-4}$alkyl)$_2$, and optionally substituted phenyl.

In yet another embodiment of the compounds of formula I, $R_4$ is selected from $C_{1-6}$alkyl, $C_{3-6}$cycloalkyl, phenyl, a 4-, 5-, or 6-membered monocyclic heteroaryl or heterocyclo, each group optionally substituted by one to three groups, $T_1$, $T_2$, and/or $T_3$; and $T_1$, $T_2$, and $T_3$ are each independently selected from F, Cl, Br, $C_{1-4}$alkyl, haloalkyl, $C_{1-4}$alkylthio, phenoxy, cyano, —$(CH_2)_rOR_9$, —$(CH_2)_rC(=O)R_9$, —$(CH_2)_rC(=O)OR_9$, —$(CH_2)_rC(=O)NR_9R_{10}$, —$(CH_2)_rNR_9R_{10}$, —$(CH_2)_rNR_9C(=O)R_{10}$, —$(CH_2)_rNR_9C(=O)NR_9R_{10}$, —$(CH_2)_rS(O)_2R_{11}$, —$(CH_2)_rS(O)_2NR_9R_{10}$, —$(CH_2)_rOH$, —$(CH_2)_rCN$, —$(CH_2)_r$cyclohexyl, —$(CH_2)_r$phenyl, —$(CH_2)_r$morpholinyl, —$(CH_2)_r$pyridyl, —$(CH_2)_r$pyrazolyl, —$(CH_2)_r$tetrazolyl, —$(CH_2)_r$cyclopropyl, —$(CH_2)_r$pyrrolidinyl, —$(CH_2)_r$piperidinyl, —$(CH_2)_r$furyl, —$(CH_2)_r$imidazolyl, —$(CH_2)_r$pyrimidinyl, —$(CH_2)_r$piperazinyl, and —$(CH_2)_r$pyradizinyl, —$(CH_2)_r$imidazolyl, —$(CH_2)_r$pyrazolyl, —$(CH_2)_r$triazolyl, —$(CH_2)_r$thiazolyl, each ring group optionally substituted as valence allows from one to three groups, $R_{12}$, $R_{13}$ and/or $R_{14}$; each r is independently zero, 1, or 2; $R_9$ and $R_{10}$ are each independently selected from hydrogen, $C_{1-4}$alkyl, halo$C_{1-4}$alkyl, —$(CH_2)_vOH$, —$(CH_2)_vN(alkyl)_2$, $C_{3-6}$cycloalkyl, phenyl, pyrrolidinyl, morpholinyl, and pyridyl, wherein said $C_{3-6}$cycloalkyl, pyrrolidinyl, morpholinyl, and pyridyl are optionally substituted with $NH_2$, hydroxy, $C_{1-4}$alkyl and aryl; each v is independently 1, 2, or 3; $R_{12}$, $R_{13}$, and $R_{14}$ are each independently selected from hydroxy, $C_{1-4}$alkyl and phenyl optionally substituted with hydroxy, nitro, and halogen.

In yet another embodiment of the compounds of formula I, $R_6$ is selected from $C_{1-4}$alkyl, aryl, $C_{3-7}$cycloalkyl, 5- or 6-membered monocyclic heterocyclo and heteroaryl ring, wherein $R_6$ is optionally substituted by one to three groups, $T_4$, $T_5$, and/or $T_6$; $T_4$, $T_5$ and $T_6$ are independently selected from halogen, alkyl, substituted alkyl, alkenyl, substituted alkenyl, alkynyl, substituted alkynyl, nitro, cyano, —$(CHR)_rSR_{15}$, —$(CHR)_rS(O)_qR_{17}$, —$(CHR)_rS(O)_qNR_{15}R_{16}$, —$(CHR)_rNR_{15}S(O)_qR_{17}$, —$(CHR)_rNR_{15}S(O)_qNR_{15}R_{16}$, —$(CHR)_rOR_{15}$, —$(CHR)_rNR_{15}R_{16}$, —$(CHR)_rNR_{15}C(=O)R_{16}$, —$(CHR)_rNR_{15}C(=O)OR_{16}$, —$(CHR)_rNR_{15}C(=O)NR_{15}R_{16}$, —$(CHR)_rC(=O)R_{15}$, —$(CHR)_rC(=O)OR_{15}$, —$(CHR)_rOC(=O)R_{15}$, —$(CHR)_rSO_3H$, —$(CHR)_rC(=O)NR_{15}R_{16}$, —$(CHR)_r$-cycloalkyl, —$(CHR)_r$-heterocyclo, —$(CHR)_r$-aryl, and —$(CHR)_r$-heteroaryl, wherein said cycloalkyl, heterocyclo, aryl, or heteroaryl is optionally substituted with OH and $NH_2$; each q is independently 1 or 2; each r is independently zero, 1, 2, or 3;

$R_{15}$ and $R_{16}$ are each independently selected from hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclo, and substituted heterocyclo; each $R_{17}$ is independently selected from alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclo, and substituted heterocyclo.

In yet another embodiment of the compounds of formula I, $R_6$ is selected from $C_{1-4}$alkyl, aryl, $C_{3-7}$cycloalkyl, 5- or 6-membered monocyclic heterocyclo and heteroaryl ring, wherein $R_6$ is optionally substituted by one to three groups, $T_4$, $T_5$, and/or $T_6$; $T_4$, $T_5$ and $T_6$ are independently selected from halogen, alkyl, substituted alkyl, alkenyl, substituted alkenyl, alkynyl, substituted alkynyl, nitro, cyano, —$(CHR)_rSR_{15}$, —$(CHR)_rS(O)_qR_{17}$, —$(CHR)_rS(O)_qNR_{15}R_{16}$, —$(CHR)_rNR_{15}S(O)_qR_{17}$, —$(CHR)_rNR_{15}S(O)_qNR_{15}R_{16}$, —$(CHR)_rOR_{15}$, —$(CHR)_rNR_{15}R_{16}$, —$(CHR)_rNR_{15}C(=O)R_{16}$, —$(CHR)_rNR_{15}C(=O)OR_{16}$, —$(CHR)_rNR_{15}C(=O)NR_{15}R_{16}$, —$(CHR)_rC(=O)R_{15}$, —$(CHR)_rC(=O)OR_{15}$, —$(CHR)_rOC(=O)R_{15}$, —$(CHR)_rSO_3H$, —$(CHR)_rC(=O)NR_{15}R_{16}$, —$(CHR)_r$-cycloalkyl, —$(CHR)_r$-heterocyclo, —$(CHR)_r$-aryl, and —$(CHR)_r$-heteroaryl, wherein said cycloalkyl, heterocyclo, aryl, or heteroaryl is optionally substituted with OH and $NH_2$; each q is independently 1 or 2; each r is independently zero, 1, 2, or 3;

$R_{15}$ and $R_{16}$ are each independently selected from hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclo, and substituted heterocyclo; each $R_{17}$ is independently selected from alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclo, and substituted heterocyclo.

In yet another embodiment of the compounds of formula I, $R_6$ is $C_{1-4}$ alkyl optionally substituted by one to three groups, $T_4$, $T_5$, and/or $T_6$; $T_4$, $T_5$ and $T_6$ are each independently selected from $OR_{15}$, $NR_{15}R_{16}$, $NR_{15}C(=O)R_{16}$, $NR_{15}C(=O)OR_{16}$, $NR_{15}C(=O)NR_{15}R_{16}$, —$C(=O)OR_{15}$, cycloalkyl, heterocyclo, aryl, and heteroaryl;

$R_{15}$ and $R_{16}$ are each independently selected from hydrogen, alkyl, cycloalkyl, substituted cycloalkyl, aryl, substituted aryl, heteroaryl, substituted heteroaryl, heterocyclo, and substituted heterocyclo; $R_7$ is selected from hydrogen and $C_{1-3}$alkyl; or $R_6$ and $R_7$ together with the nitrogen atom to which they are attached form an optionally substituted 5-, 6- or 7-membered monocyclic heteroaryl or heterocyclo ring, or an optionally substituted 7- to 11-membered bicyclic heteroaryl or heterocyclo ring.

Yet another embodiment of the invention relates to compounds having the formula I(a):

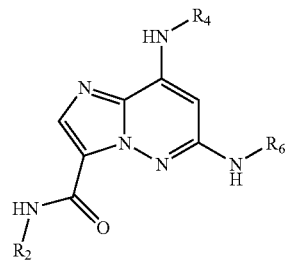

Ia wherein:

$R_2$ is selected from aryl, substituted aryl, $C_{3-7}$cycloalkyl, substituted $C_{3-7}$cycloalkyl, 5- or 6-membered heterocyclo and heteroaryl, and substituted 5- or 6-membered heterocyclo and heteroaryl optionally substituted with halogen, cyano, hydroxy, $C_{1-4}$alkyl, substituted $C_{1-4}$alkyl, alkenyl, substituted alkenyl, alkynyl, substituted alkynyl, $C_{1-4}$alkoxy, haloalkyl, $C_{3-7}$cycloalkyl, heterocyclo, heteroaryl, —$NR_{2a}R_{2b}$, —$NR_{2a}C(O)R_{2b}$, $C(O)NR_{2a}R_{2b}$—$C(O)OR_{2a}$, wherein $R_{2a}$ and $R_{2b}$ are each independently selected from hydrogen and $C_{1-4}$alkyl; $R_4$ is selected from hydrogen, $C_{1-4}$alkyl, aryl, $C_{3-7}$cycloalkyl, heterocyclo, and heteroaryl, each group optionally substituted by one to three groups, $T_1$, $T_2$, and/or $T_3$; $T_1$, $T_2$, and $T_3$ are each independently selected from halogen, alkyl, substituted alkyl, alkenyl, substituted alkenyl, alkynyl, substituted alkynyl, nitro, cyano, —$(CH_2)_rSO_3H$, —$(CH_2)_rSR_9$, —$(CH_2)_rS(O)_pR_{11}$, —$(CH_2)_rS(O)_pNR_9R_{10}$, —$(CH_2)_rNR_9S(O)_pR_{11}$, —$(CH_2)_rOR_9$, —$(CH_2)_rNR_9R_{10}$, —$(CH_2)_rNR_9C(=O)R_{10}$, —$(CH_2)_rNR_9C(=O)NR_9R_{10}$, —$(CH_2)_rC(=O)OR_9$, —$(CH_2)_rC(=O)R_9$, —$(CH_2)_rC(=O)R_9$, —$(CH_2)_rC(=O)NR_9R_{10}$, —$(CH_2)_r$-cycloalkyl, —$(CH_2)_r$-heterocyclo, —$(CH_2)_r$-aryl, and —$(CH_2)_r$-heteroaryl, wherein said cycloalkyl, heterocyclo, aryl, or heteroaryl is optionally substituted as valence allows from one to three groups, $R_{12}$, $R_{13}$ and/or $R_{14}$; or $T_1$ and $T_2$, located on adjacent ring atoms are taken together with the ring atoms to which they are attached to form a fused cycloalkyl, aryl, heteroaryl, or heterocyclo, wherein said cycloalkyl, aryl, heteroaryl, or heterocyclo is optionally substituted as valence allows from one to three groups, $R_{12}$, $R_{13}$ and/or $R_{14}$; each p is independently 1 or 2; each r is independently zero, 1, 2, or 3;

$R_9$ and $R_{10}$ are each independently selected from hydrogen, alkyl, substituted alkyl, alkenyl, substituted alkenyl, cycloalkyl, substituted cycloalkyl, aryl, substituted aryl, heteroaryl, substituted heteroaryl, heterocyclo, and substituted heterocyclo; or $R_9$ and $R_{10}$ together with the nitrogen atom to which they are attached form a heteroaryl or heterocyclo, wherein said heteroaryl or heterocyclo is optionally substituted as valence allows from one to three groups, $R_{12}$, $R_{13}$ and/or $R_{14}$; each $R_{11}$ is independently selected from alkyl, substituted alkyl, alkenyl, substituted alkenyl, alkynyl, substituted alkynyl, cycloalkyl, aryl, heteroaryl, and heterocyclo; $R_{12}$, $R_{13}$, and $R_{14}$ are each independently selected from $C_{1-4}$alkyl, substituted $C_{1-4}$alkyl, $C_{2-4}$alkenyl, substituted $C_{2-4}$alkenyl, halogen, hydroxy, cyano, nitro, $CF_3$, —O($C_{1-4}$alkyl), —OCF$_3$, —C(=O)H, —C(=O)($C_{1-4}$alkyl), —CO$_2$H, —CO$_2$($C_{1-4}$alkyl), —NHCO$_2$($C_{1-4}$alkyl), —S($C_{1-4}$alkyl), —NH$_2$, —NH($C_{1-4}$alkyl), —N($C_{1-4}$alkyl)$_2$, —N($C_{1-4}$alkyl)$_3^+$, —SO$_2$($C_{1-4}$alkyl), —C(=O)($C_{1-4}$alkylene)NH$_2$, —C(=O)($C_{1-4}$alkylene)NH(alkyl), —C(=O)($C_{1-4}$alkylene)N($C_{1-4}$alkyl)$_2$, and optionally substituted phenyl; $R_6$ is selected from $C_{1-4}$alkyl, aryl, $C_{3-7}$cycloalkyl, 5- or 6-membered monocyclic heterocyclo and heteroaryl, wherein $R_6$ is optionally substituted by one to three groups, $T_4$, $T_5$, and/or $T_6$; $T_4$, $T_5$ and $T_6$ are independently selected from halogen, alkyl, substituted alkyl, alkenyl, substituted alkenyl, alkynyl, substituted alkynyl, nitro, cyano, —(CH$_2$)$_r$SR$_{15}$, —(CH$_2$)$_r$S(O)$_q$R$_{17}$, —(CH$_2$)$_r$S(O)$_q$NR$_{15}$R$_{16}$, —(CH$_2$)$_r$NR$_{15}$S(O)$_q$R$_{17}$, —(CH$_2$)$_r$NR$_{15}$S(O)$_q$NR$_{15}$R$_{16}$, —(CH$_2$)$_r$OR$_{15}$, —(CH$_2$)$_r$NR$_{15}$R$_{16}$, —(CH$_2$)$_r$NR$_{15}$C(=O)R$_{16}$, —(CH$_2$)$_r$NR$_{15}$C(=O)OR$_{16}$, —(CH$_2$)$_r$NR$_{15}$C(=O)NR$_{15}$R$_{16}$, —(CH$_2$)$_r$C(=O)R$_{15}$, —(CH$_2$)$_r$C(=OC)OR$_{15}$, —(CH$_2$)$_r$OC(=O)R$_{15}$, —(CH$_2$)$_r$SO$_3$H, —(CH$_2$)$_r$C(=O)NR$_{15}$R$_{16}$, —(CH$_2$)$_r$-cycloalkyl, —(CH$_2$)$_r$-heterocyclo, —(CH$_2$)$_r$-aryl, and —(CH$_2$)$_r$-heteroaryl, wherein said cycloalkyl, heterocyclo, aryl, or heteroaryl is optionally substituted with OH or NH$_2$; each q is independently 1 or 2; each r is independently zero, 1, 2, or 3; $R_{15}$ and $R_{16}$ are each independently selected from hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclo, and substituted heterocyclo; each $R_{17}$ is independently selected from alkyl, substituted alkyl, alkenyl, substituted alkenyl, alkynyl, substituted alkynyl, cycloalkyl, aryl, heteroaryl, and heterocyclo.

In yet another embodiment of the compounds of formula I(a), $R_2$ is selected from phenyl, pyrazolyl, pyridyl, pyridazinyl, pyrimidinyl and benzothiazolyl, wherein each $R_2$ is optionally substituted with F, Cl, Br, cyano, $C_{1-4}$alkyl, $C_{1-4}$alkoxy, haloalkyl, $C_{3-7}$cycloalkyl, heterocyclo, heteroaryl, —OR$_{2a}$, —NR$_{2a}$R$_{2b}$, —NHC(O)R$_{2a}$—C(O)NR$_{2a}$R$_{2b}$ wherein $R_{2a}$ and $R_{2b}$ are each independently selected from hydrogen and $C_{1-4}$alkyl; $R_4$ is selected from $C_{1-4}$alkyl, phenyl, $C_{3-6}$cycloalkyl, and 4-, 5-, or 6-membered monocyclic heteroaryl or heterocyclo, each optionally substituted by one to two groups, $T_1$, and/or $T_2$; $T_1$ and $T_2$ are each independently selected from F, Cl, Br, $C_{1-4}$alkyl, haloalkyl, cyano, —(CH$_2$)$_r$OR$_9$, —(CH$_2$)$_r$C(=O)R$_9$, —(CH$_2$)$_r$C(=O)OR$_9$, —(CH$_2$)$_r$C(=O)NR$_9$R$_{10}$, —(CH$_2$)$_r$NR$_9$R$_{10}$, —(CH$_2$)$_r$NR$_9$C(=O)R$_{10}$, —(CH$_2$)$_r$NR$_9$C(=O)NR$_9$R$_{10}$, —(CH$_2$)$_r$S(O)$_2$R$_{11}$, —(CH$_2$)$_r$S(O)$_2$NR$_9$R$_{10}$, —(CH$_2$)$_r$CN, —(CH$_2$)$_r$cyclohexyl, —(CH$_2$)$_r$phenyl, —(CH$_2$)$_r$morpholinyl, —(CH$_2$)$_r$pyridyl, —(CH$_2$)$_r$pyrazolyl, —(CH$_2$)$_r$cyclopropyl, —(CH$_2$)$_r$pyrrolidinyl, —(CH$_2$)$_r$piperidinyl, —(CH$_2$)$_r$furyl, —(CH$_2$)$_r$imidazolyl, —(CH$_2$)$_r$pyrimidinyl, —(CH$_2$)$_r$piperazinyl, and —(CH$_2$)$_r$pyradizinyl, —(CH$_2$)$_r$imidazolyl, —(CH$_2$)$_r$pyrazolyl, —(CH$_2$)$_r$triazolyl, —(CH$_2$)$_r$tetrazolyl, —(CH$_2$)$_r$thiazolyl, each group optionally substituted as valence allows from one to three groups, $R_{12}$, $R_{13}$ and/or $R_{14}$; each r is independently zero, 1, 2, or 3;

$R_9$ and $R_{10}$ are each independently selected from hydrogen, $C_{1-4}$alkyl, halo$C_{1-4}$alkyl, —(CH$_2$)$_r$OH, —(CH$_2$)$_r$N(alkyl)$_2$, $C_{3-6}$cycloalkyl, phenyl, pyrrolidinyl, morpholinyl, and pyridyl, each ring optionally substituted with NH$_2$, $C_{1-4}$alkyl and aryl; each $R_{11}$ is selected from alkyl, substituted alkyl, alkenyl, substituted alkenyl, alkynyl, substituted alkynyl, cycloalkyl, aryl, heteroaryl, and heterocyclo; $R_{12}$, $R_{13}$, and $R_{14}$, are each independently selected from hydroxy, $C_{1-4}$alkyl optionally substituted with hydroxy and halogen and phenyl; $R_6$ is selected from $C_{1-4}$alkyl, $C_{3-7}$cycloalkyl, a 5- to 6-membered monocyclic heteroaryl or heterocyclo, each group optionally substituted by one to two groups, $T_4$ and $T_5$; $T_4$ and $T_5$ are each independently selected from —(CH$_2$)$_r$NR$_{15}$R$_{16}$, —(CH$_2$)$_r$NR$_{15}$S(O)$_q$R$_{17}$, —(CH$_2$)$_r$NR$_{15}$S(O)$_q$NR$_{15}$R$_{16}$, —(CH$_2$)$_r$OR$_{15}$, —(CH$_2$)$_r$NR$_{15}$C(=O)R$_{16}$, —(CH$_2$)$_r$NR$_{15}$C(=O)NR$_{15}$R$_{16}$, —(CH$_2$)$_r$NR$_{15}$C(=O)OR$_{16}$, —(CH$_2$)$_r$NR$_{15}$C(=O)NR$_{15}$R$_{16}$, —(CH$_2$)$_r$C(=O)OR$_{15}$, —(CH$_2$)$_r$-cycloalkyl, —(CH$_2$)$_r$-aryl, —(CH$_2$)$_r$-heteroaryl, and —(CH$_2$)$_r$-heterocyclo; each q is independently 1 or 2, each r is independently zero, 1, or 2; $R_{15}$ and $R_{16}$ are each independently selected from hydrogen, cyano, —(CR$_{20}$R$_{21}$)$_w$R$_{22}$, —(CR$_{20}$R$_{21}$)$_w$NR$_{18}$R$_{19}$, —(CR$_{20}$R$_{21}$)$_w$NR$_{18}$C(O)R$_{19}$, —(CR$_{20}$R$_{21}$)$_w$C(=O)R$_{18}$, —(CR$_{20}$R$_{21}$)$_w$C(=O)NR$_{18}$R$_{19}$, —(CR$_{20}$R$_{21}$)$_w$C(=O)OR$_{18}$, —(CR$_{20}$R$_{21}$)$_w$OR$_{18}$, —(CR$_{20}$R$_{21}$)$_w$S(O)$_2$R$_{22}$, alkenyl, substituted alkenyl, alkynyl, substituted alkynyl, cycloalkyl, substituted cycloalkyl, aryl, substituted aryl, heteroaryl, substituted heteroaryl, heterocyclo, substituted heterocyclo, wherein the substituent is selected from $C_{1-4}$alkyl, F, Cl, Br, NH$_2$, NO$_2$, CN, and OH; or $R_{15}$ and $R_{16}$ together with the nitrogen atom to which they are attached form a 5-, 6- or 7-membered monocyclic heterocyclo or heteroaryl optionally substituted with OH, $C_{1-4}$alkyl unsubstituted and substituted with —O($C_{1-4}$alkyl); each w is independently 1, 2, or 3; $R_{17}$ is independently selected from cyano, —(CR$_{20}$R$_{21}$)$_w$R$_{22}$, —(CR$_{20}$R$_{21}$)$_w$NR$_{18}$R$_{19}$, —(CR$_{20}$R$_{21}$)$_w$NR$_{18}$C(O)R$_{19}$, —(CR$_{20}$R$_{21}$)$_w$C(=O)R$_{18}$R$_{19}$, —(CR$_{20}$R$_{21}$)$_w$C(=O)OR$_{18}$, —(CR$_{20}$R$_{21}$)$_w$OR$_{18}$; each w is independently 1, 2, or 3; alkenyl, substituted alkenyl, alkynyl, substituted alkynyl, cycloalkyl, substituted cycloalkyl, aryl, substituted aryl, heteroaryl, substituted heteroaryl, heterocyclo, substituted heterocyclo, wherein the substituent is selected from $C_{1-4}$alkyl, F, Cl, Br, NH$_2$, NO$_2$, CN, and OH; $R_{18}$ and $R_{19}$ are each independently selected from hydrogen, $C_{1-4}$alkyl, $C_{2-4}$alkenyl, and $C_{2-4}$alkynyl, each optionally substituted with $C_{1-6}$ alkyl —(CH$_2$)$_r$—$C_{3-6}$cycloalkyl, F, Cl, Br, CN, NO$_2$, NH$_2$, CO$_2$H, —OC(CH$_3$)$_3$, —(CH$_2$)$_r$OC$_{1-5}$ alkyl, OH, SH; or $R_{18}$ and $R_{19}$ together with the nitrogen atom to which they are attached form an optionally substituted 5-, 6- or 7-membered monocyclic heterocyclo or heteroaryl; $R_{20}$ and $R_{21}$ are each independently selected from hydrogen, F, Cl, Br, CN, NO$_2$, NH$_2$, CO$_2$H, —OC(CH$_3$)$_3$, —(CH$_2$)$_r$OC$_{1-5}$ alkyl, OH, SH, $C_{1-4}$alkyl, $C_{2-4}$alkenyl, and $C_{2-4}$alkynyl, $C_{3-6}$cycloalkyl, aryl, heterocyclo, and heteroaryl; $R_{22}$ is selected from hydrogen, $C_{1-4}$alkyl, $C_{2-4}$alkenyl, $C_{2-4}$alkynyl, halogen, hydroxy, cyano, nitro, CF$_3$, —O($C_{1-4}$alkyl), —NHCO$_2$($C_{1-4}$alkyl), —S($C_{1-4}$alkyl), —SO$_2$($C_{1-4}$alkyl), —C(=O)($C_{1-4}$alkylene)NH$_2$, —C(=O)($C_{1-4}$alkylene)NH (alkyl), NHC(=NH)NH$_2$, —C(=O)(C$_{1-4}$alkylene)N(C$_{1-4}$alkyl)$_2$, heterocyclo, heteroaryl, and phenyl, wherein said heterocyclo, heteroaryl, and phenyl are optionally substituted with C$_{1-4}$alkyl, halogen, and =O.

Further embodiments of the invention relate to compounds of formula I(b), I(c), I(d), I(e), and I(f), below, wherein the variables R$_2$, R$_4$, R$_6$, T$_4$, where they appear, can be selected from any of the embodiments as set forth above for compounds of formula I(a) and/or I(b) (including as recited in any of the further or preferred embodiments); and wherein X$_1$ can be hydrogen, halogen, cyano, hydroxy, C$_{1-4}$alkyl, C$_{1-4}$alkoxy, haloalkyl, C$_{3-7}$cycloalkyl, heterocyclo, heteroaryl, —NR$_{2a}$R$_{2b}$, —C(O)NR$_{2a}$R$_{2b}$ wherein R$_{2a}$ and R$_{2b}$ are each independently selected from hydrogen and C$_{1-4}$alkyl:

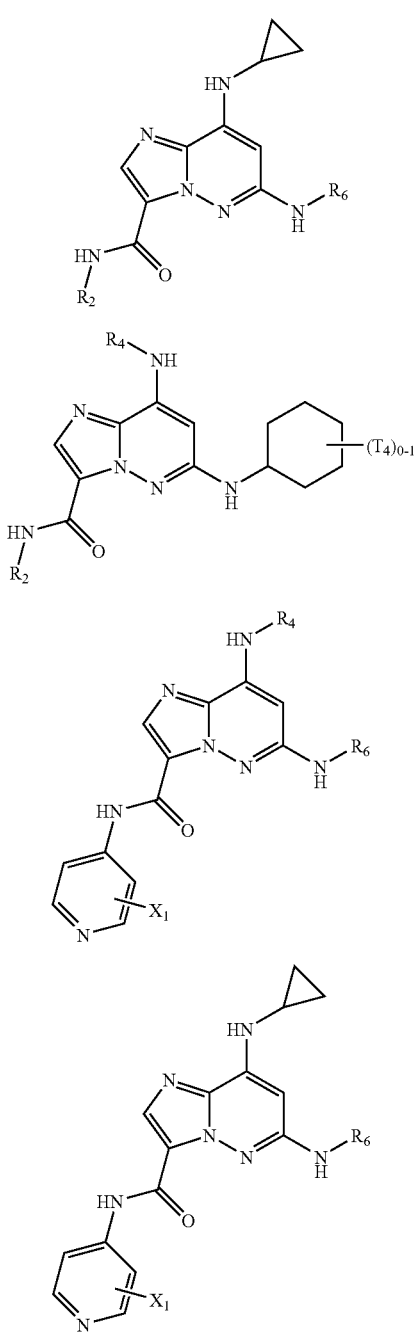

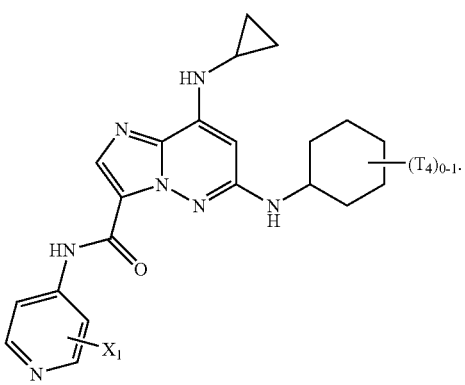

Compounds of the invention include, without limitation, the following:

6-((trans-4-aminocyclohexyl)amino)-8-((4-(cyclopropylcarbamoyl)phenyl)amino)-N-4-pyridinylimidazo[1,2-b]pyridazine-3-carboxamide, 6-((trans-4-aminocyclohexyl)amino)-8-(3-azetidinylamino)-N-4-pyridinylimidazo[1,2-b]pyridazine-3-carboxamide, 6-((trans-4-aminocyclohexyl)amino)-8-(cyclobutylamino)-N-4-pyridinylimidazo[1,2-b]pyridazine-3-carboxamide, 6-((trans-4-aminocyclohexyl)amino)-8-(ethylamino)-N-(3-fluoro-4-pyridinyl)imidazo[1,2-b]pyridazine-3-carboxamide, 6-((trans-4-((dimethylcarbamoyl)amino)cyclohexyl)amino)-N-(3-fluoro-4-pyridinyl)-8-(2-pyridinylamino)imidazo[1,2-b]pyridazine-3-carboxamide, 6-((trans-4-(D-alanylamino)cyclohexyl)amino)-N-(3-fluoro-4-pyridinyl)-8-(2-pyridinylamino)imidazo[1,2-b]pyridazine-3-carboxamide, methyl trans-4-((8-(cyclopropylamino)-3-((3-fluoro-4-pyridinyl)carbamoyl)imidazo[1,2-b]pyridazin-6-yl)amino)cyclohexanecarboxylate, methyl (trans-4-((8-(cyclopropylamino)-3-((3-fluoro-4-pyridinyl)carbamoyl)imidazo[1,2-b]pyridazin-6-yl)amino)cyclohexyl)carbamate, 8-(cyclopropylamino)-N-(3-fluoro-4-pyridinyl)-6-((trans-4-((isopropylcarbamoyl)amino)cyclohexyl)amino)imidazo[1,2-b]pyridazine-3-carboxamide, 6-((trans-4-(L-alanylamino)cyclohexyl)amino)-8-(cyclopropylamino)-N-(3-fluoro-4-pyridinyl)imidazo[1,2-b]pyridazine-3-carboxamide, 8-(cyclopropylamino)-6-((trans-4-((dimethylsulfamoyl)amino)cyclohexyl)amino)-N-(3-fluoro-4-pyridinyl)imidazo[1,2-b]pyridazine-3-carboxamide, methyl N-(trans-4-((8-(cyclopropylamino)-3-((2-fluoro-4-pyridinyl)carbamoyl)imidazo[1,2-b]pyridazin-6-yl)amino)cyclohexyl)glycinate, 8-(cyclopropylamino)-N-(2-fluoro-4-pyridinyl)-6-((trans-4-hydroxycyclohexyl)amino)imidazo[1,2-b]pyridazine-3-carboxamide, 8-(cyclopropylamino)-6-((trans)-4-(3-pyridin-3-ylureido)cyclohexylamino)-N-(pyrimidin-4-yl)imidazo[1,2-b]pyridazine-3-carboxamide, 6-((trans-4-(D-alanylamino)cyclohexyl)amino)-8-(cyclopropylamino)-N-(6-oxo-1,6-dihydro-4-pyrimidinyl)imidazo[1,2-b]pyridazine-3-carboxamide, 6-((trans-4-aminocyclohexyl)amino)-N-(3-fluoro-4-pyridinyl)-8-((5-fluoro-2-pyridinyl)amino)imidazo[1,2-b]pyridazine-3-carboxamide, 6-((trans-4-aminocyclohexyl)amino)-N-(3-fluoro-4-pyridinyl)-8-((1-methyl-1H-pyrazol-3-yl)amino)imidazo[1,2-b]pyridazine-3-carboxamide, 8-acetamido-6-((trans-4-aminocyclohexyl)amino)-N-(3-fluoro-4-pyridinyl)imidazo[1,2-b]pyridazine-3-carboxamide, 6-((trans-4-aminocyclohexyl)amino)-N-(3-fluoro-4-pyridinyl)-8-((6-(4-methyl-1-piperazinyl)-2-pyridinyl)amino)imidazo[1,2-b]pyridazine-3-carboxamide, and 6-((trans-4-aminocyclohexyl)amino)-N-(3-fluoro-4-pyridinyl)-8-((methylsulfonyl)amino)imidazo[1,2-b]pyridazine-3-carboxamide.

Yet another embodiment is directed to use of a compound according to formula I, and/or use of a compound of formula I(a), in preparing a medicament for the treatment of cancer in a human patient, particularly a cancer receptive to treatment via inhibition of the CK2 enzyme.

The following are definitions of terms that may be used in the specification. The initial definition provided for a group or term herein applies to that group or term throughout the specification individually or as part of another group, unless otherwise indicated.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. SO$_2$NH$_2$, substituted sulfonamido, nitro, cyano, carboxy, carbamyl, e.g. CONH$_2$, substituted carbamyl e.g. CONHalkyl, CONHaryl, CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. Where noted above where the substituent is further substituted it will be with alkyl, alkoxy, aryl or arylalkyl.

The term "halogen" or "halo" refers to fluorine (fluoro), chlorine (chloro), bromine (bromo) and iodine (iodo).

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively.

The term "arylsulfonylaminocarbonyl" refers to an arylsulfonyl bonded to an aminocarbonyl.

The terms "aryloxyalkyl", "aryloxycarbonyl" or "aryloxyaryl" refer to an aryloxy bonded to an alkyl or substituted alkyl; a carbonyl; or an aryl or substituted aryl, respectively.

The term "arylalkyl" refers to an alkyl or substituted alkyl in which at least one of the hydrogen atoms bonded to at least one of the carbon atoms is replaced with an aryl or substituted aryl. Typical arylalkyls include, but are not limited to, for example, benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethan-1-yl.

The term "arylalkyloxy" refers to an arylalkyl bonded through an oxygen linkage (—O-arylalkyl).

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or arylalkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole, thiophene, indole, pyrimidine.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g. imidazolyl, furyl, thienyl, thiazolyl, pyrrolidyl, pyridyl, pyrimidyl and the like.

The terms "heterocycle", "heterocyclic", "heterocyclo", and "heterocyclyl" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, homopiperazinyl, 2-oxohomopiperazinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include indolyl, 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzopyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, pyrrolotriazinyl, quinazolinyl, tetrahydroquinolinyl, thienofuryl, thienopyridyl, thienothienyl, and the like.

Exemplary substituents include one or more alkyl or arylalkyl groups as described above or one or more groups described above as alkyl substituents.

Also included are smaller heterocyclyls, such as, epoxides and aziridines.

The term "carbocyclic ring" or "carbocyclyl" refers to stable, saturated, partially saturated or unsaturated, mono or bicyclic hydrocarbon rings that contain 3-12 atoms. Particularly, this includes a monocyclic ring containing 5 or 6 atoms or a bicyclic ring containing 9 or 10 atoms. Suitable values include cyclopropyl, cyclobutyl, cyclopentyl, cyclohexyl, cycloheptyl, dihydroindenyl and tetrahydronaphthyl. The term "optionally substituted" as it refers to "carbocyclic ring" or "carbocyclyl" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The term "alkylsulfone" refers to $-R^kS(=O)_2R^k$, wherein $R^k$ is an alkyl or substituted alkyl.

The term "oxo" refers to the divalent radical =O.

The term "carbamate" refers to the group $-OC(=O)NH_2$.

The term "amide" refers to the group $-C(=O)NH_2$.

The term "sulfonamide" refers to the group $-SO_2NH_2$.

The terms "substituted amide", "substituted sulfonamide", or "substituted carbamate" refer to an amide, sulfonamide, or carbamate, respectively, having at least one hydrogen replaced with a group chosen from alkyl, substituted alkyl, alkenyl, substituted alkenyl, cycloalkyl, and substituted cycloalkyl.

A substituted amide, for example, refers to the group $-C(=O)NR'''R''$ wherein $R'''$ and $R''$ are independently selected from H, alkyl, substituted alkyl, alkenyl, substituted alkenyl, cycloalkyl, and substituted cycloalkyl, provided at least one of $R'''$ or $R''$ is a substituted moiety.

A substituted sulfonamide, for example, refers to the group $-SO_2NR^oR^p$ wherein $R^o$ and $R^p$ are independently selected from alkyl, substituted alkyl, alkenyl, substituted alkenyl, cycloalkyl, and substituted cycloalkyl, provided at least one of $R^o$ or $R^p$ is a substituted moiety.

A substituted carbamate, for example, refers to the group $-OC(=O)NR^qR^r$ wherein $R^q$ and $R^r$ are independently selected from alkyl, substituted alkyl, alkenyl, substituted alkenyl, cycloalkyl, and substituted cycloalkyl, provided at least one of $R^q$ or $R^r$ is a substituted moiety.

The term "ureido" refers to the group $-NHC(=O)NH_2$.

The term "cyano" refers to the group $-CN$.

The terms "cycloalkylalkyl" or "cycloalkylalkoxy" refer to a cycloalkyl or substituted cycloalkyl bonded to an alkyl or substituted alkyl; or an alkoxy, respectively.

The term "nitro" refers to the group $-N(O)_2$.

The term "thio" refers to the group $-SH$.

The term "alkylthio" refers to the group $-SR^s$ where $R^s$ is an alkyl, substituted alkyl, cycloalkyl, or substituted cycloalkyl.

The term "thioalkyl" refers to the group $-R^tS$ where $R^t$ is an alkyl, substituted alkyl, cycloalkyl, or substituted cycloalkyl.

The term "alkylsulfonyl" refers to the group $-S(=O)_2R^u$ where $R^u$ is an alkyl, substituted alkyl, cycloalkyl, or substituted cycloalkyl.

The term "alkylsulfinyl" refers to the group $-S(=O)R^v$ where $R^v$ is an alkyl, substituted alkyl, cycloalkyl, or substituted cycloalkyl.

The term "carboxy" refers to the group $-C(=O)OH$.

The terms "carboxyalkoxy" or "alkoxycarbonylalkoxy" refer to a carboxy, or an alkoxycarbonyl, respectively, bonded to an alkoxy.

The term "alkoxycarbonyl" refers to the group $-C(=O)OR^w$ where $R^w$ is an alkyl, substituted alkyl, cycloalkyl or substituted cycloalkyl.

The term "arylalkoxycarbonyl" refers to an aryl or substituted aryl bonded to an alkoxycarbonyl.

The terms "alkylcarbonyloxy" or "arylcarbonyloxy" refer to the group $-OC(=O)R^x$, where $R^x$ is an alkyl or substituted alkyl, or an aryl or substituted aryl, respectively.

The term "carbamoyl" refers to the groups $-OC(=O)NH_2$, $-OC(=O)NHR^x$, and/or $-OC(=O)NR^yR^z$, wherein $R^y$ and $R^z$ are independently selected from alkyl and substituted alkyl.

The term "carbonyl" refers to a $C(=O)$.

The terms "alkylcarbonyl", "aminocarbonyl", "alkylaminocarbonyl" "aminoalkylcarbonyl", or "arylaminocarbonyl" refer to an alkyl or substituted alkyl; an amino; an alkylamino or substituted alkylamino; an aminoalkyl or substituted aminoalkyl; or an arylamino, respectively, bonded to a carbonyl.

The terms "aminocarbonylaryl" or "aminocarbonylalkyl" refer to an aminocarbonyl bonded to an aryl or substituted aryl; or an alkyl or substituted alkyl, respectively.

The term "sulfonyl" refers to the group $S(=O)_2$.

The term "sulfinyl" refers to an $S(=O)$.

The term "carboxyalkyl" refers to an alkyl or substituted alkyl bonded to a carboxy.

The term "hydroxy" herein alone or as part of another group refers to —OH.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxy, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, pp. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, 8:1-38 (1992).

UTILITY

The compounds of the invention modulate kinase activity. Types of kinase activity may be modulated by the compounds of the invention including, but not limited to, AAK1, ABL, ACK, ACTR2, ACTR2B, ADCK3, ADCK4, AKT1, AKT2, AKT3, ALK, ALK1, ALK2, ALK4, AMPKA1, AMPKA2, ARG, AURA, AURB, AURC, AXL, BCR-ABL, BIKE, BLK, BMPR1A, BMX, BRAF, BRSK2, BRK, BTK, CAMK1A, CAMK2A, CAMK2B, CAMK1D, CAMK2D, CAMK1G, CAMK2G, CAMKK1, CAMKK2, CDK1, CDK2, CDK5, CHK2, CK1A2, CK1D, CK1E, CK1G1, CK1G2, CK2A1, CK2A2, CLK1, CLK2, CLK3, CLK4, CSK, DAPK2, DAPK3, DCAMKL3, DDR2, DMPK1, DRAK1, DRAK2, DYRK1, DYRK2, EGFR, EPHA1, EPHA2, EPHA3, EPHA4, EPHA5, EPHA6, EPHA7, EPHA8, EPHB1, EPHB2, EPHB3, EPHB4, ERK1, ERK2, FAK, FER, FES, FGFR1, FGFR2, FGFR3, FGFR4, FGR, FLT1, FLT3, FLT4, FMS, FRK, FYN, FUSED, GAK, GCN2, GPRK4, GPRK5, GPRK6, GSK3A, GSK3B, HCK, HPK1, HER2/ERBB2, HER4/ERBB4, HH498, IGF1R, IKKα, IKKβ, INSR, IRR, IRAK4, ITK, JAK1, JAK2, JAK3, JNK1, JNK2, JNK3, KDR, KHS1, KHS2, KIT, LCK, LIMK1, LIMK2, LKB1, LOK, LTK, LYN, MAP3K4, MAP3K5, MAPK1, MAPKAP-K2, MARK1, MARK2, MARK4, MEK1, MER, MET, MKK4, MKK6, MLK3, MNK2, MPSK1, MRCKA, MSK1, MSK2, MST1, MST2, MST3, MST4, MUSK, MYT1, NDR2, NEK2, NEK6, NEK7, NEK9, NLK, P38A, P38B, P38G, PAK1, PAK2, PAK3, PAK4, PAK5, PAK6, PCTAIRE1, PDGFRA, PDGFRB, PDK1, PHKG1, PHKG2, PIM1, PIM2, PKA, PKACA, PKACB, PKCA, PKCD, PKCH, PKCI, PKCT, PKCZ, PKD2, PKG1, PKG2, PKN2, PLK1, PLK3, PLK4, PRKX, PYK2, QIK, RAF1, RET, RIPK2, ROCK-I, ROCK-II, RON, ROS, RSK1, RSK2, RSK4, SAPK2a, SAPK2b, SAPK3, SAPK4, SGK, SIK, SLK, SKMLCK, SRC, SRPK1, STK33, SYK, TESK1, TGFBR1, TIE2, TLK1, TLK2, TNK1, TRKA, TRKB, TRKC, TTK, TXK, TYK2, TYRO3, ULK3, WNK3, YANK2, YANK3, YES, YSK1, ZAP70, ZC1/HGK, ZC2/TNIK, and mutants thereof.

Applicants have discovered that compounds of Formula (I), (Ia), (Ib), (Ic), (Id), (Ie), or (If) have particular utility in treating proliferative conditions associated with the modulation of kinase activity, and particularly the inhibition of tyrosine and serine/threonine kinase activities. The compounds of the present invention can be used to treat proliferative disorders associated with abnormal kinase activity. As used herein, the terms "treating" and "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

Accordingly, one aspect of the invention is the use of a compound of the Formula (I), (Ia), (Ib), (Ic), (Id), (Ie), (If), or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of Formula (I), (Ia), (Ib), (Ic), (Id), (Ie), or (If) or a pharmaceutically acceptable salt thereof as defined herein before.

It should further be understood that solvates (e.g., hydrates) of the compounds of formula I are also within the scope of the invention. Methods of solvation are generally known in the art.

According to a further aspect of the invention, there is provided the use of a compound of the formula I, or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of formula I or a pharmaceutically acceptable salt thereof as defined herein before.

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, Zoladex; matrix metalloproteinase inhibitors; VEGF inhibitors, such as anti-VEGF antibodies (AVASTIN®) and small molecules such as ZD6474 and SU6668; Vatalanib, BAY-43-9006, SU11248, CP-547632, and CEP-7055; HER 1 and HER 2 inhibitors including anti-HER2 antibodies (Herceptin); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, e.g. GLEEVEC® and dasatinib; CASODEX® (bicalutamide, Astra Zeneca), Tamoxifen; MEK-1 kinase inhibitors, MAPK kinase inhibitors, PI3 kinase inhibitors; PDGF inhibitors, such as imatinib; anti-angiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (ixabepilone), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof; CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g. 6-thioguanine and 6-mercaptopurine; glutamine antagonists, e.g. DON (AT-125; d-oxo-norleucine); ribonucleotide reductase inhibitors; mTOR inhibitors; and haematopoietic growth factors.

Additional cytotoxic agents include, cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein before may be surgery, radiotherapy or chemotherapy. Such chemotherapy may cover three main categories of therapeutic agent:

(i) antiangiogenic agents that work by different mechanisms from those defined herein before (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestens, antiandrogens (for example, flutamide, nilutamide, bicalutamide, cyproterone acetate), LHRH agonists and antagonists (for example, goserelin acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as AVASTIN® (bevacizumab) and ERBITUX® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); intercalating antitumour antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide nitrosoureas, thiotepa; antimitotic agents (for example, vinca alkaloids like vincristine, vinorelbine, vinblastine and vinflunine) and taxoids such as TAXOL® (paclitaxel), TAXOTERE® (docetaxel) and newer microbtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as VELCADE® (bortezomib).

As stated above, the formula I compounds of the invention are of interest for their antiproliferative effects. Such compounds of the invention are expected to be useful in a wide range of disease states including cancer, psoriasis, and rheumatoid arthritis.

More specifically, the compounds of formula I are useful in the treatment of a variety of cancers, including (but not limited to) the following:

carcinoma, including that of the prostate, pancreatic ductal adreno-carcinoma, breast, colon, lung, ovary, pancreas, and thyroid;

tumors of the central and peripheral nervous system, including neuroblastoma, glioblastoma, and medulloblastoma; and other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease.

The compounds of formula I are especially useful in treatment of tumors having a high incidence of protein kinase activity, such as prostate, colon, brain, thyroid and pancreatic tumors. Additionally, the compounds of the invention may be useful in treatment of sarcomas and pediatric sarcomas. By the administration of a composition (or a combination) of the compounds of this invention, development of tumors in a mammalian host is reduced.

The pharmaceutical compositions of the invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ Model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

If formulated as a fixed dose, a combination product can, for example, utilize a dosage of the compound of formula I within the dosage range described above and the dosage of another anti-cancer agent/treatment within the approved dosage range for such known anti-cancer agent/treatment. If a combination product is inappropriate, the compound of formula I and the other anti-cancer agent/treatment can, for example, be administered simultaneously or sequentially. If administered sequentially, the present invention is not limited to any particular sequence of administration. For example, compounds of formula I can be administered either prior to, or after, administration of the known anti-cancer agent or treatment.

The compounds may be administered in a dosage range of about 0.05 to 200 mg/kg/day, preferably less than 100 mg/kg/day, in a single dose or in 2 to 4 divided doses.

Biological Assays

A. CK2 Kinase Assay

The effectiveness of compounds of the present invention as inhibitors of protein kinases can be readily tested by assays known to those skilled in the art. For example, in vitro protein kinase assays may be conducted with a relevant purified protein kinase and an appropriate synthetic substrate to determine the inhibitory activities of the compounds. Assays for inhibition of CK2 by the instant compounds were performed in 384-well plates with reaction mixtures containing 10 μM of peptide substrate (RRRADDSDDDDD-NH2), [$\gamma$-$^{33}$P]ATP (10 μCi) at 25 μM (CK2A1) or 5 μM (CK2A2), 20 mM Hepes (pH 7.4), 100 mM NaCl, 10 mM $MgCl_2$, 0.25 mM dithiothreitol, Brij-35 at 0.015%, and recombinant CK2A1 (10 nM, Invitrogen) or CK2A2 (5 nM, Upstate Biotechnology). Reaction mixtures were incubated at 30° C. for 1 h, and reaction products were captured by binding to phosphocellulose (P81) filter plates. Incorporation of radioactive phosphate into the peptide substrate was determined by liquid scintillation counting. The potency of compounds in inhibiting CK2 is expressed as $IC_{50}$, defined as the concentrations of compounds required to inhibit the enzymatic activity by 50%.

B. Cell Proliferation Inhibition Assay

Compounds were evaluated for their ability to inhibit cell proliferation, using an assay that measures mitochondrial metabolic activity, that is directly correlated with cell numbers. Cells were plated at 2000 cells/well in 96-well plates and were cultured for 24 h in RPMI-1640 supplemented with 2% fetal bovine serum, before test compounds were added. Compounds were diluted in culture medium such that the final concentration of dimethyl sulfoxide never exceeded 1%. Following the addition of compounds, the cells were cultured for an additional 72 h before cell viability was determined by measuring the conversion of 3-(4,5-dimethylthiazol-2-yl)-2, 5-diphenyltetrazolium bromide (MTT) dye using the CellTiter96 kit (Promega).

The following compounds were found to have the $IC_{50}$ described in Table 1 when measured in the assays described above.

TABLE 1

| Example | CK2A1 $IC_{50}$ (µM) | CK2A2 $IC_{50}$ (µM) | HCT116 $IC_{50}$ (µM) |
| --- | --- | --- | --- |
| 3 | 0.035 | 0.015 | 0.08 |
| 6 | 0.011 | 0.003 | 0.09 |
| 13 | 0.042 | 0.017 | 0.17 |
| 25C | 0.086 | 0.011 | 0.17 |
| 27 | 0.247 | 0.072 | 0.43 |
| 34 | 0.0115 | 0.0008 | 0.17 |
| 39 | 0.102 | 0.043 | 9.95 |
| 45 | 0.034 | 0.008 | 0.14 |
| 83 | 12.270 | 4.388 | >1.00 |
| 104 | 0.038 | 0.010 | 0.20 |
| 124 | 0.031 | 0.008 | 0.30 |
| 134 | 0.055 | 0.013 | 0.17 |
| 138 | 0.021 | 0.009 | 0.61 |
| 143 | 0.199 | 0.070 | 0.34 |
| 144 | 0.183 | 0.070 | >2.50 |

TABLE 1-continued

| Example | CK2A1 $IC_{50}$ (µM) | CK2A2 $IC_{50}$ (µM) | HCT116 $IC_{50}$ (µM) |
| --- | --- | --- | --- |
| 146 | 0.0259 | 0.0015 | 0.59 |
| 154 | 0.0385 | 0.0002 | 0.21 |
| 159 | 0.0341 | 0.0021 | 0.28 |
| 163 | 0.0296 | 0.0004 | 0.56 |
| 164 | 0.0228 | 0.0021 | >2.50 |
| 167 | 0.0265 | 0.0004 | >2.50 |
| 172 | 0.0373 | 0.0009 | 0.36 |
| 179 | 0.0138 | 0.0007 | 0.92 |
| 195 | 0.0174 | 0.0017 | 0.22 |
| 197 | 0.0135 | 0.0008 | 0.23 |
| 198 | 0.0036 | 0.0015 | 0.09 |
| 202 | 0.0095 | 0.0017 | 0.43 |
| 272 | 0.0019 | 0.0008 | 0.40 |
| 276 | 0.0155 | 0.0011 | 0.16 |
| 278 | 0.0626 | 0.0015 | 0.50 |
| 333 | 0.026 | 0.005 | 0.22 |
| 378 | 0.205 | 0.290 | >1.00 |
| 390 | 0.015 | 0.006 | 0.30 |
| 414 | 0.115 | 0.047 | 0.54 |
| 468 | 0.007 | 0.003 | 0.09 |
| 469 | 0.019 | 0.005 | 0.05 |
| 476 | 0.043 | 0.046 | 2.31 |
| 481 | 0.121 | 0.034 | >2.50 |
| 501 | 0.234 | 0.087 | 0.45 |
| 518 | 0.058 | 0.042 | 0.17 |
| 523 | 0.057 | 0.0.036 | 0.388 |
| 524 | 0.021 | 0.004 | 1.152 |
| 526 | 0.153 | 0.061 | >2.5 |
| 531 | 0.028 | 0.003 | 0.26 |
| 534 | 0.559 | 0.145 | 1.61 |
| 538 | 0.331 | 0.042 | 0.34 |
| 542 | 0.071 | 0.018 | 0.29 |
| 549 | 0.0263 | 0.00003 | 0.02 |
| 553 | 0.0196 | 0.0021 | 0.04 |
| 559 | 0.0055 | 0.0010 | 0.08 |
| 560 | 0.0125 | 0.0008 | 0.87 |
| 562 | 0.0097 | 0.0012 | 0.06 |
| 571 | 0.428 | 0.097 | 0.89 |
| 572 | 0.306 | 0.073 | 0.80 |

Compounds of the present invention exhibit enhanced CK2 inhibitory activity. Compared to certain examples in US 2007/038314 (data shown in Table 2), the compounds of the invention herein, e.g., compounds of Formula (I) (including Formulae (Ia), (Ib), (Ic), (Id), (Ie), and (If) are surprisingly advantageous for their CK2 enzyme inhibition activity and/or other drugability properties, e.g., having desirable stability, bioavailability, therapeutic index and/or toxicity values that are important to their use as pharmaceutical agents.

TABLE 2

| Example No. in U.S. 2007/038314 | Structure | CK2A1 $IC_{50}$ (µM) | CK2A2 $IC_{50}$ (µM) |
| --- | --- | --- | --- |
| I(1) Page 55 | [structure shown] | >50 | 10.35 |

TABLE 2-continued

| Example No. in U.S. 2007/038314 | Structure | CK2A1 IC$_{50}$ (µM) | CK2A2 IC$_{50}$ (µM) |
|---|---|---|---|
| I(7) Page 58 | 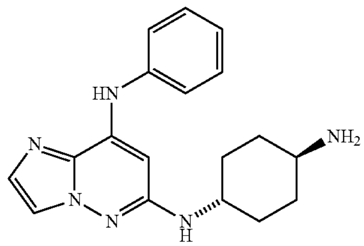 | >50 | >50 |
| II(16) Page 72 | 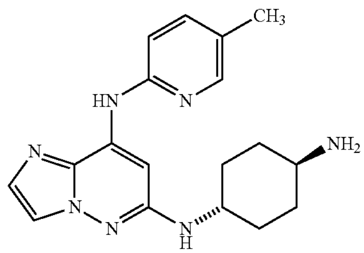 | >50 | 31.77 |

Methods of Preparation

The compounds of the present invention may be prepared by methods such as those illustrated in the following schemes. Solvents, temperatures, pressures, and other reaction conditions may readily be selected by one of ordinary skill in the art. Starting materials are commercially available or readily prepared by one of ordinary skill in the art. These schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). All documents cited herein are incorporated herein by reference in their entirety.

In general, the time taken to complete a reaction procedure will be judged by the person performing the procedure, preferably with the aid of information obtained by monitoring the reaction by methods such as HPLC or TLC. A reaction does not have to go to completion to be useful to this invention. The methods for the preparation of various heterocycles used to this invention can be found in standard organic reference books, for example, *Comprehensive Heterocyclic Chemistry, The Structure, Reactions, Synthesis and Uses, of Heterocyclic Compounds*, Katritzky, A. R., Rees, C. W., eds. Pergamon Press New York, First edition (1984), and *Comprehensive Heterocyclic Chemistry II, A Review of the Literature 1982-1995: The Structure, Reactions, Synthesis and Uses, of Heterocyclic Compounds*, Katritzky, A. R., Rees, C. W. and Scriven, E. F., eds., Pergamon Press New York (1996).

Unless otherwise specified, the various substituents of the compounds are defined in the same manner as the formula I compound of the invention.

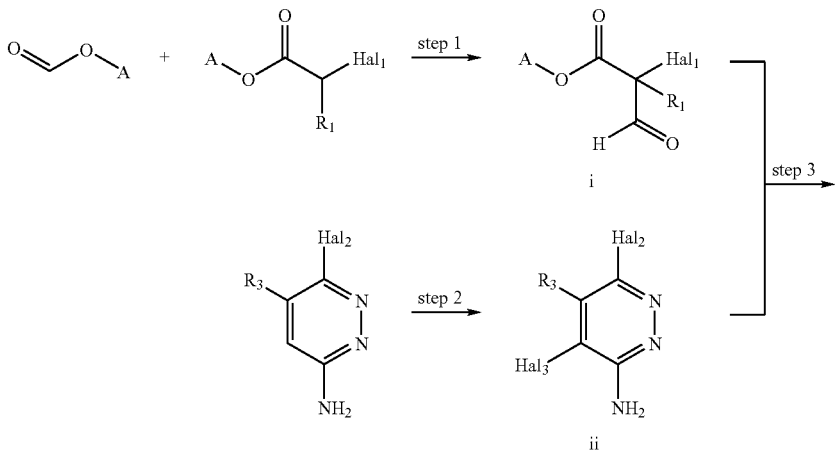

Scheme 1

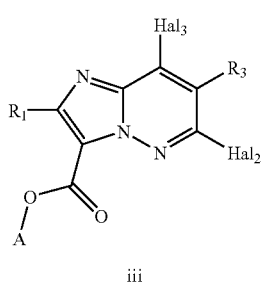
iii
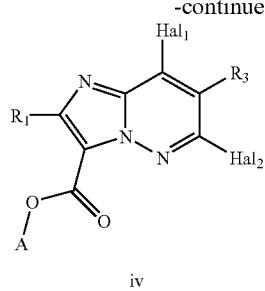
iv
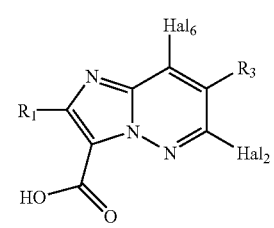
iv
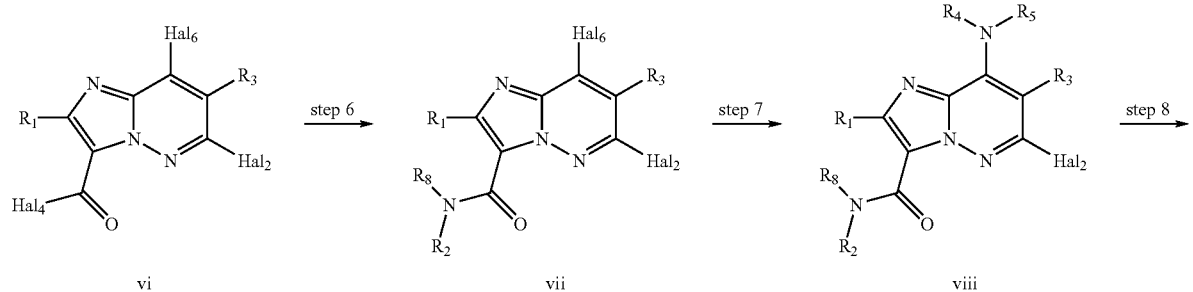
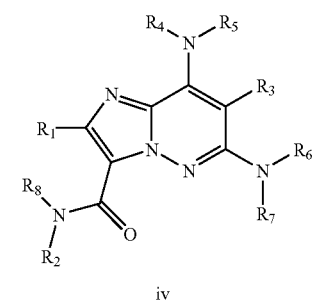
iv

Step 1

The first step in Scheme 1 is accomplished by treating an appropriately substituted α-haloester (A=$C_{1-4}$ lower alkyl, $Hal_1$-$Hal_4$=Cl, Br, I, F) with a formate ester such as ethyl formate in the presence of a base such as sodium ethoxide in a suitable solvent such as ethanol to afford a compound of formula i.

Step 2

Halogenation of a suitably substituted pyridazine-3-amine such as 6-chloropyridazine-3-amine using a reagent such as bromine in an appropriate solvent such as ethanol provides compounds of formula ii.

Step 3

The reaction of compounds i and ii at elevated temperature results in formation of a mixture of esters iii and iv ($Hal_6$=$Hal_1$ or $Hal_3$) that may be used in subsequent steps without separation.

Step 4

The acid catalyzed hydrolysis of iii/iv using, for example, aqueous HCl in a solvent such as methanol at elevated temperature affords compounds of formula v.

Step 5

Activation of the carboxylic acid of compound v through, for example, formation of the acid chloride with thionyl chloride in a suitable solvent such as dichloromethane affords compounds of formula vi.

Step 6

Reaction of vi with an amine in a solvent such as dichloromethane or dimethylformamide in the presence of a tertiary amine base such as triethyl amine affords amides of formula vii. Alternatively, steps 5-6 may be accomplished in a single step through use of a coupling reagent such as BOP or DCC.

Step 7

Treatment of compound vii with an amine such as cyclopropylamine or 2-aminopyridine in the presence of a base such as diisopropylethylamine or sodium tert-butoxide in an aprotic solvent such as THF affords compounds of formula viii.

Step 8

Compound viii may be treated with a suitable amine either neat or in an appropriate solvent such as dimethylformamide or N-methylpyrrolidine at elevated temperature or in a microwave to afford compounds of formula ix.

Scheme 2

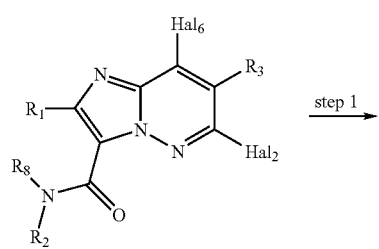

vi step 1 →

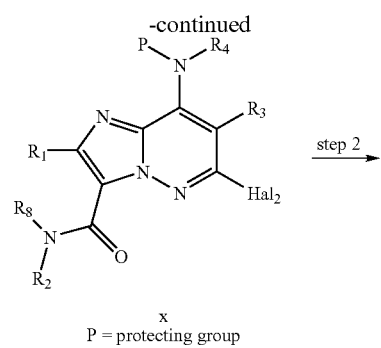

x
P = protecting group step 2 →

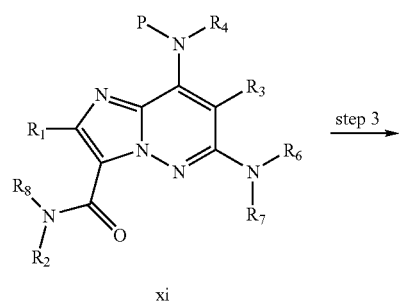

xi step 3 →

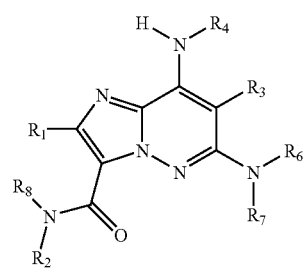

xii

Step 1

Alternatively, compounds of formula vi may be treated with an amine containing a suitable N-protecting group (P=protecting group) such as p-methoxybenzyl in the presence of a base such as diisopropylethylamine or potassium tert-butoxide to afford compounds of formula x.

Step 2

Treatment of compound x with a suitable amine either neat or in an appropriate solvent such as dimethylformamide or N-methylpyrrolidine at elevated temperature or in a microwave to afford compounds of formula xi.

Step 3

Removal of the protecting group can be effected through known methods, for example, in the case where P=p-methoxybenzyl, treatment with trifluoroacetic acid either neat or in an appropriate solvent such as dichlormethane to afford compounds of formula xii.

Compounds of general formula xiii containing an additional amino group may be further elaborated as described in Schemes 3 to 4.

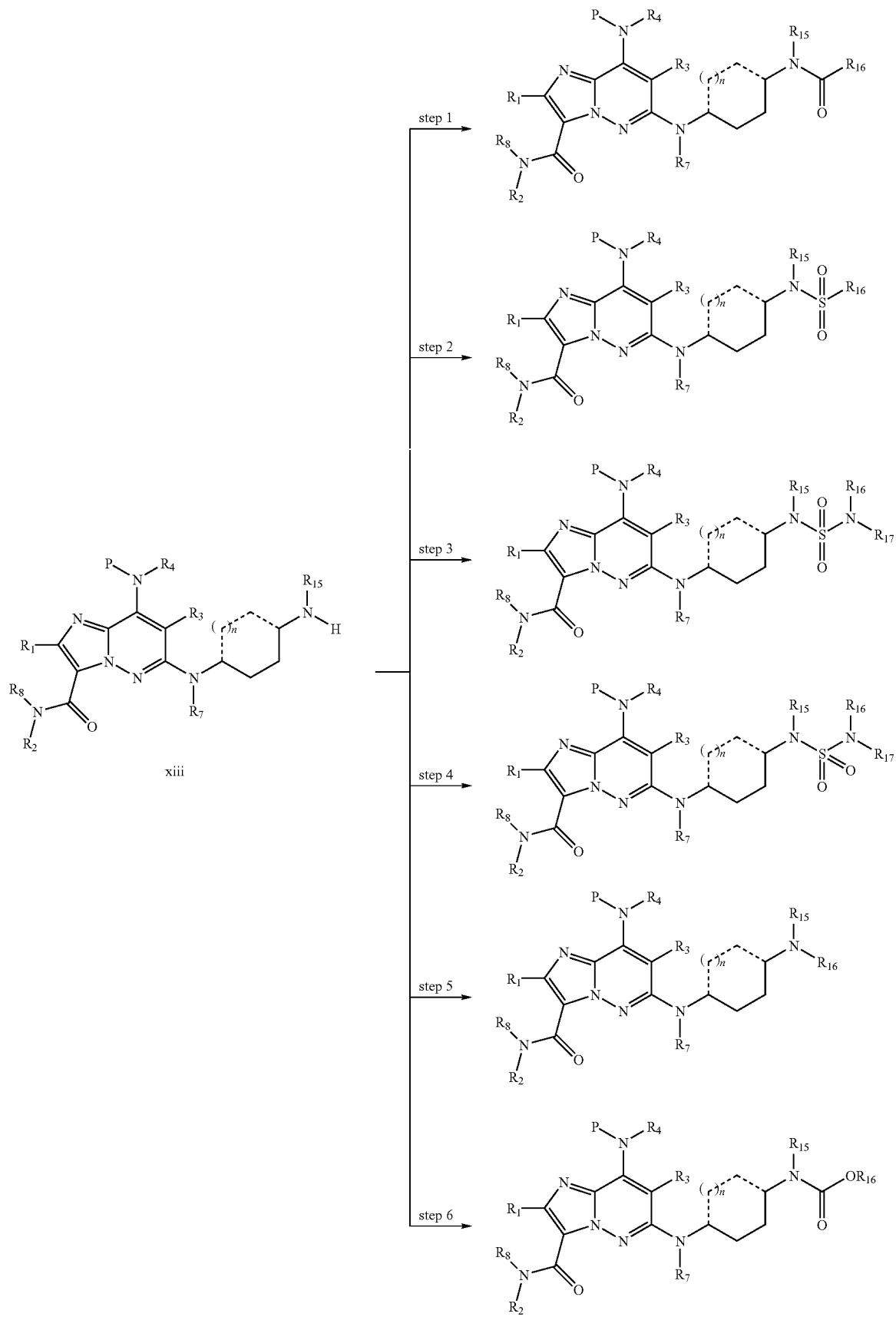

Step 1
Treatment of xiii with a carboxylic acid in the presence of a coupling reagent such as BOP reagent or DCC in an appropriate solvent such as dichloromethane or dimethylformamide affords compounds of general formula xiv. Alternatively, acylation may be effected by treatment with a reagent such as an acid chloride in a solvent such as dichloromethane in the presence of a base such as triethylamine.

Step 2
Sulfonamides may be prepared by treatment of xiii with a sulfonylchloride in an appropriate solvent such as dichloromethane or THF in the presence of a base such as triethylamine or diisopropylamine to afford compounds of general formula xv.

Step 3
Ureas may be prepared by treatment of xiii with an appropriately substituted isocyanate in a solvent such as dimethylformamide or THF to afford compounds of general formula xvi.

Step 4
Treatment of compounds of general formula xiii with a sulfamoyl chloride in the presence of a base such as diisopropylethylamine in a suitable solvent such as dichloromethane affords sulfonyl ureas of general formula xvii.

Step 5
Treatment of xiii with an appropriate alkyl bromide such as methyl 2-bromoacetate in the presence of a base such as diisopropylethyl amine in an aprotic solvent such as dichloromethane or THF affords alkyl substituted amines of formula xviii.

Step 6
Additionally, treatment of xiii with a chlorocarbonate in the presence of a base such as diisopropylethylamine in an appropriate solvent such as dichloromethane affords carbamates of general formula xix.

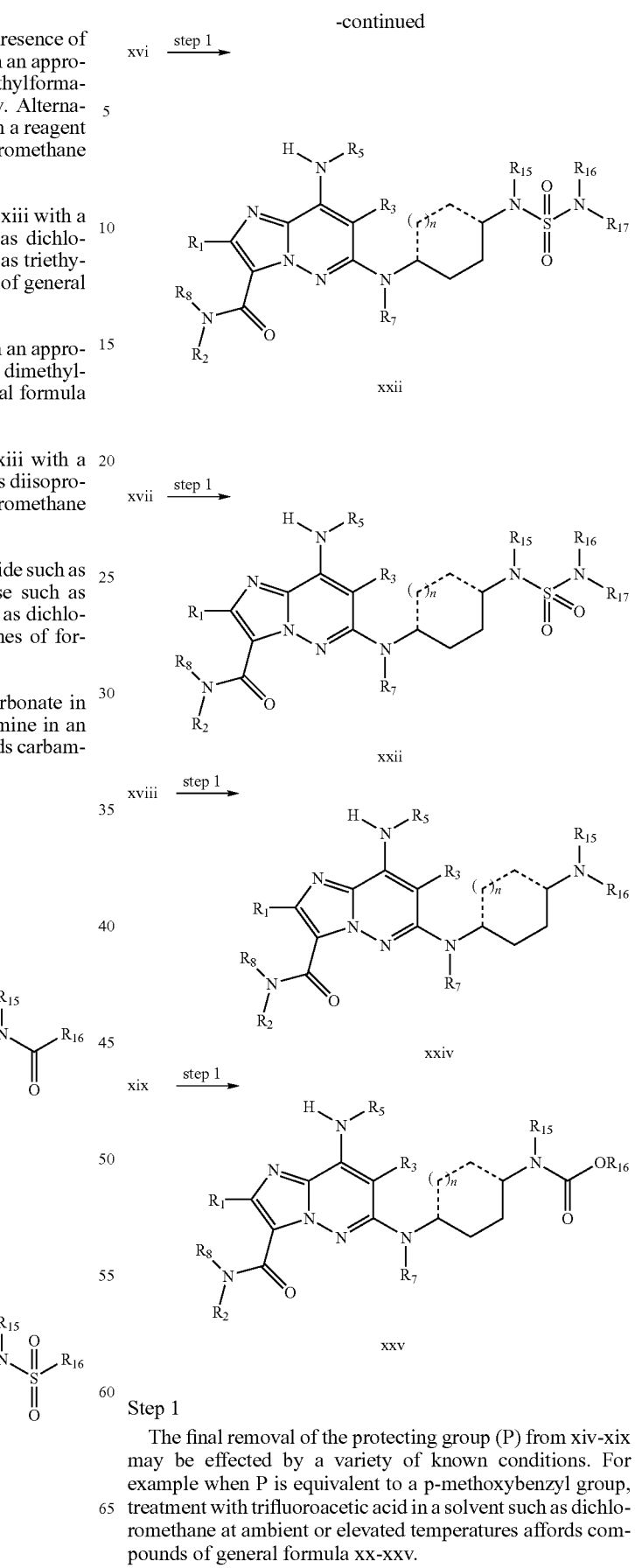

Step 1
The final removal of the protecting group (P) from xiv-xix may be effected by a variety of known conditions. For example when P is equivalent to a p-methoxybenzyl group, treatment with trifluoroacetic acid in a solvent such as dichloromethane at ambient or elevated temperatures affords compounds of general formula xx-xxv.

Scheme 4

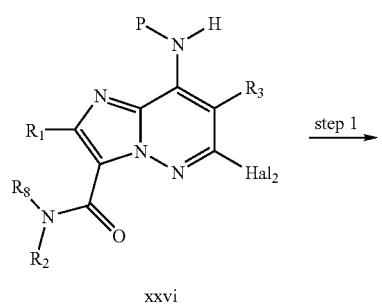

xxvi

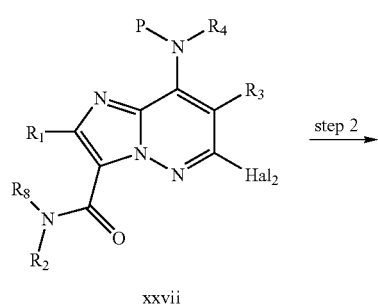

xxvii

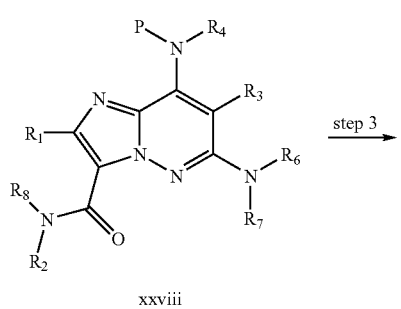

xxviii

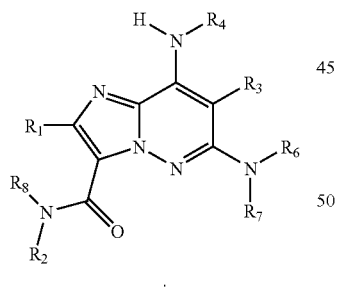

xxix

Scheme 5

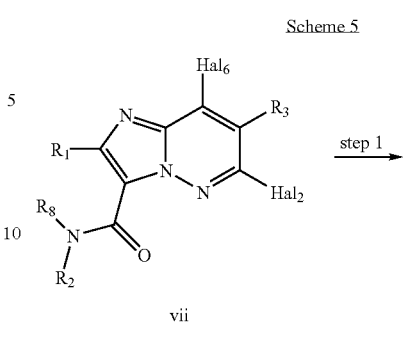

vii

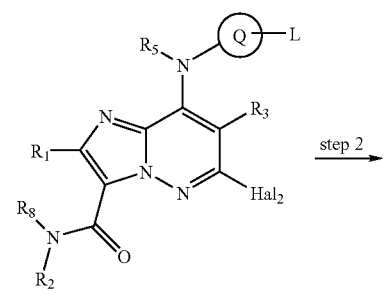

xxx

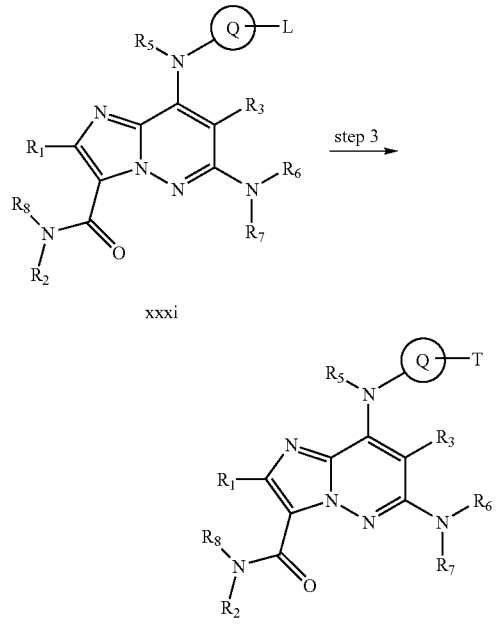

xxxi xxxii

Alternatively, compounds of formula xxvi (where $R_4$ is equal to hydrogen) may be reacted with an acylating reagent such as an acid chloride or sulfonyl chloride in the presence of a base such as sodium hydride in a solvent such as dimethylformamide to afford compounds of general formula xxvii (Step 1). Displacement of the halogen in xxvii with an amine, either neat or in a solvent such as N-methylpyrrolidinone at elevated temperatures affords compounds of formula xxviii (Step 2). Final removal of the protecting group, for example, P=p-methoxybenzyl with trifluoroacetic acid in a solvent such as dichloromethane affords compounds of formula xxix (Step 3).

Treatment of compounds of formula vii with an aryl or heteroaryl amine (Q=aryl, heteroaryl or heterocyclic) containing an appropriate functional group (L=functional group such as a bromine or triflate) in the presence of a base such as sodium tert-butoxide or sodium hydride in an appropriate solvent such as dimethylformamide or N-methylpyrrolidinone affords compounds of formula xxx (Step 1). Displacement of the halogen in xxx with an amine, either neat or in a solvent such as N-methylpyrrolidinone at elevated temperatures affords compounds of formula xxxi (Step 2). Compounds of formula xxxi may be converted to compounds of formula xxxii with an appropriate nucleophile, such as an amine or through coupling reactions, such as standard palladium catalyzed reactions.

EXAMPLES

Example 1

6-((trans-4-aminocyclohexyl)amino)-8-((4-(cyclopropylcarbamoyl)phenyl)amino)-N-4-pyridinylimidazo[1,2-b]pyridazine-3-carboxamide

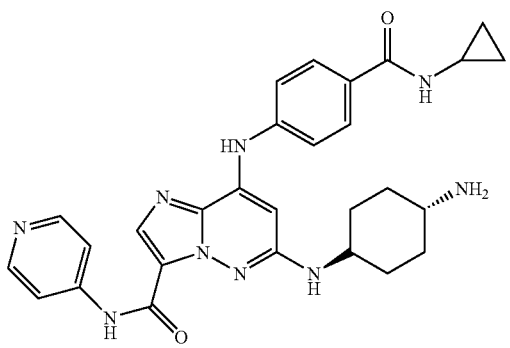

1A. Preparation of 4-bromo-6-chloropyridazin-3-amine

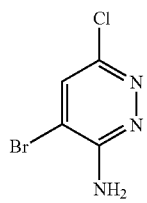

To a 250 mL round-bottomed flask was added 6-chloropyridazin-3-amine (3.92 g, 30.3 mmol), sodium bicarbonate (5.08 g, 60.5 mmol) and ethanol (20 mL). To the resulting solution, bromine (1.559 mL, 30.3 mmol) was added dropwise. The resulting mixture was stirred at room temperature for 16 hours. The solution was filtered and then concentrated in vacuo. The residue was dissolved in water and the product extracted with ethyl acetate (3×). The organic layers were combined, dried over anhydrous sodium sulfate and concentrated in vacuo to give 4-bromo-6-chloropyridazin-3-amine (4.5 g, 21.59 mmol, 71.3% yield). LC/MS, m/z 207.88 (M+1). HPLC Rt, 1.25 min. Waters Sunfire C18 column (4.6×50 mm) 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 4 min, hold at 100% B 1 min, flow rate 4 mL/min.

1B. Preparation of ethyl 2-chloro-3-oxopropanoate

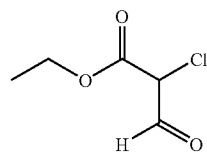

To a flask was added sodium (4.45 g, 194 mmol) and ethanol (56.5 mL, 968 mmol) and the mixture was stirred at room temperature for 4 hours until all of the metal had dissolved. Diethyl ether (100 mL) was added, followed by the slow addition of a solution of ethyl formate (17.20 mL, 213 mmol) and ethyl chloroacetate (22.79 mL, 213 mmol) in diethyl ether (100 mL). The reaction solution was stirred at room temperature for 16 hours. The resulting precipitate that formed was filtered and washed with ether, and dissolved in water. The aqueous layer was acidified with HCl (1N) to pH 4 and the product was extracted with diethyl ether (3×). The organic layers were combined, dried over anhydrous sodium sulfate and concentrated to give ethyl 2-chloro-3-oxopropanoate (4.5 g, 29.9 mmol, 15.44% yield).

1C. Preparation of ethyl 8-bromo-6-chloroimidazo[1,2-b]pyridazine-3-carboxylate and ethyl 6,8-dichloroimidazo[1,2-b]pyridazine-3-carboxylate

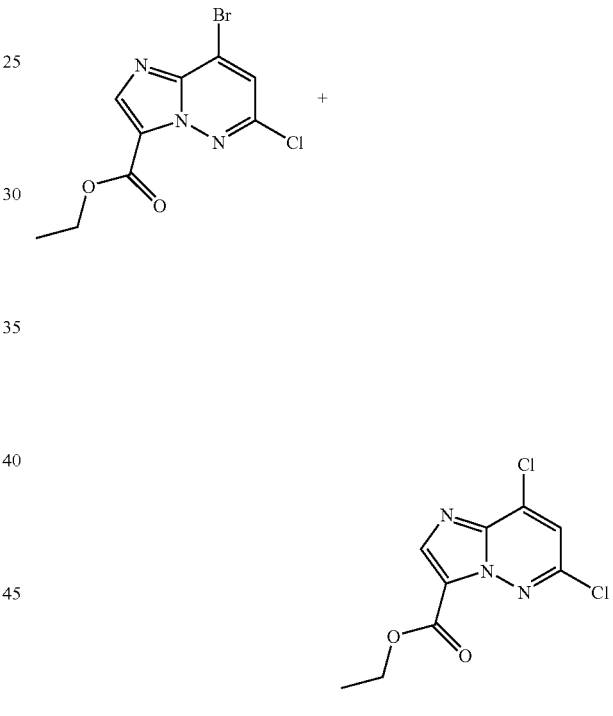

To a 250 mL round-bottomed flask was added ethyl 2-chloro-3-oxopropanoate (4.33 g, 28.8 mmol) and 4-bromo-6-chloropyridazin-3-amine (5 g, 23.99 mmol). The solution was heated to 90° C. for 16 hours. The solution was quenched with ethyl acetate and washed with water. The organic layer was dried over anhydrous sodium sulfate and concentrated in vacuo. The crude material was purified by ISCO (10% ethyl acetate/dichloromethane; 80 g column) to give a mixture of ethyl 8-bromo-6-chloroimidazo[1,2-b]pyridazine-3-carboxylate and ethyl 6,8-dichloroimidazo[1,2-b]pyridazine-3-carboxylate (2.1 g, 29% yield). LC/MS, m/z 256.96 (M+1). HPLC Rt, 2.54 min. LC/MS, m/z 303.92 (M+1). HPLC Rt, 2.63 min. Waters Sunfire C18 column (4.6×50 mm) 0%-100% B. Solvent B: (90% MeOH, 10% H$_2$O, 0.1% TFA).

Solvent A: (10% MeOH, 90% H$_2$O, 0.1% TFA). Gradient, start % B=0, final % B=100, gradient time 4 min, hold at 100% B 1 min, flow rate 4 mL/min.

1D. Preparation of 8-bromo-6-chloroimidazo[1,2-b]pyridazine-3-carboxylic acid and 6,8-dichloroimidazo[1,2-b]pyridazine-3-carboxylic acid

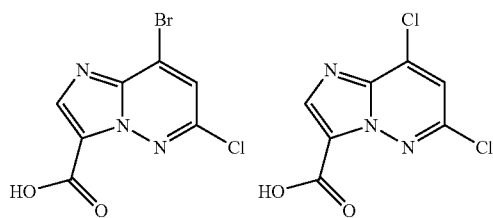 [SMILES: O=C(O)c1cnc2c(Br)cc(Cl)nn12 ; O=C(O)c1cnc2c(Cl)cc(Cl)nn12]

To a vial was added the mixture of ethyl 8-bromo-6-chloroimidazo[1,2-b]pyridazine-3-carboxylate and ethyl 6,8-dichloroimidazo[1,2-b]pyridazine-3-carboxylate (300 mg, 0.985 mmol) in methanol (10 mL). To this mixture was added 6 N HCl (1.642 mL, 9.85 mmol). The solution was heated at 90° C. for 16 hours. The solution was quenched with ethyl acetate and the product extracted with saturated sodium bicarbonate solution. The aqueous layer was acidified with HCl (1N) to pH 4 and then extracted with ethyl acetate (3×). The ethyl acetate extracts were combined, dried over anhydrous sodium sulfate, and concentrated in vacuo to give a mixture of 8-bromo-6-chloroimidazo[1,2-b]pyridazine-3-carboxylic acid and 6,8-dichloroimidazo[1,2-b]pyridazine-3-carboxylic acid (150 mg, 0.543 mmol, 55%). LC/MS, m/z 231.87 (M+1). HPLC Rt, 1.67 min. LC/MS, m/z 275.79 (M+1). HPLC Rt, 1.81 min. Waters Sunfire C18 column (4.6×50 mm) 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 4 min, hold at 100% B 1 min, flow rate 4 mL/min.

1E. Preparation of 6,8-dichloro-N-(pyridin-4-yl)imidazo[1,2-b]pyridazine-3-carboxamide and 8-bromo-6-chloro-N-(pyridin-4-yl)imidazo[1,2-b]pyridazine-3-carboxamide

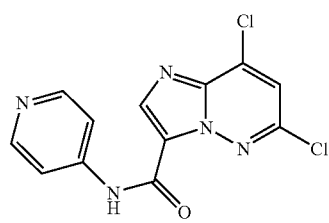

To a 2 dram vial was added a mixture of 8-bromo-6-chloroimidazo[1,2-b]pyridazine-3-carboxylic acid and 6,8-dichloroimidazo[1,2-b]pyridazine-3-carboxylic acid (250 mg, 1.077 mmol), and oxalyl chloride (1.077 mL, 2.155 mmol) in dichloromethane (2 mL). The solution was stirred at 25° C. for 1 hour. The solvent and excess oxalyl chloride were removed in vacuo. The residue was dissolved in dichloromethane (2 mL), and triethylamine (0.451 mL, 3.23 mmol), pyridin-4-amine (152 mg, 1.616 mmol), and 2 crystals of DMAP were added. The reaction solution was stirred at 25° C. for 6 hours. The solution was quenched with dichloromethane, washed 2× with water, dried over anhydrous sodium sulfate, and concentrated in vacuo to give a mixture of 6,8-dichloro-N-(pyridin-4-yl)imidazo[1,2-b]pyridazine-3-carboxamide and 8-bromo-6-chloro-N-(pyridin-4-yl)imidazo[1,2-b]pyridazine-3-carboxamide (202 mg, 0.656 mmol, 60.8% yield). LC/MS, m/z 307.93 (M+1). HPLC Rt, 1.49 min. Waters Sunfire C18 column (4.6×50 mm) 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 4 min, hold at 100% B 1 min, flow rate 4 mL/min.

1F. Preparation of tert-butyl 4-(cyclopropylcarbamoyl)phenylcarbamate

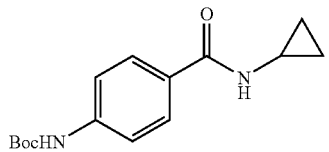 [SMILES: CC(C)(C)OC(=O)Nc1ccc(C(=O)NC2CC2)cc1]

To a flask was added 4-(tert-butoxycarbonylamino)benzoic acid (1 g, 4.21 mmol) and oxalyl chloride (0.443 mL, 5.06 mmol) in dichloromethane (20 mL). The reaction solution was stirred at room temperature for 30 minutes, and then concentrated in vacuo. The resulting acid chloride was dissolved in dichloromethane (20 mL) before the addition of cyclopropylamine (0.35 mL, 5.06 mL). The reaction solution was stirred at room temperature for 2 hours. The solution was concentrated in vacuo to give a residue that was purified via ISCO (5% ethyl acetate/dichloromethane; 40 g column) giving the product tert-butyl 4-(cyclopropylcarbamoyl)phenylcarbamate (0.326 g, 1.180 mmol, 28.0% yield). LC/MS, m/z 277.05 (M+1). HPLC Rt, 2.83 min. Waters Sunfire C18 column (4.6×50 mm) 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 4 min, hold at 100% B 1 min, flow rate 4 mL/min.

1G. Preparation of 4-amino-N-cyclopropylbenzamide

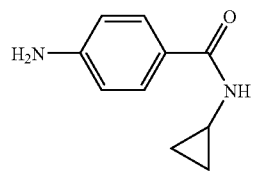 [SMILES: Nc1ccc(C(=O)NC2CC2)cc1]

To a vial was added tert-butyl 4-(cyclopropylcarbamoyl)phenylcarbamate (326 mg, 1.18 mmol) and TFA (2 mL). The solution was stirred at 25° C. for 1 hour. The solution was concentrated in vacuo to give the crude product mixture which was purified by passing through a SCX column (2 g), eluting with the 2N ammonia in methanol to yield the pure product 4-amino-N-cyclopropylbenzamide (210 mg, 100%). LC/MS, m/z 177.05 (M+1). HPLC Rt, 0.63 min. Waters Sunfire C18 column (4.6×50 mm) 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 4 min, hold at 100% B 1 min, flow rate 4 mL/min.

1H. Preparation of 6-chloro-8-(4-(cyclopropylcarbamoyl)phenylamino)-N-(pyridin-4-yl)imidazo[1,2-b]pyridazine-3-carboxamide

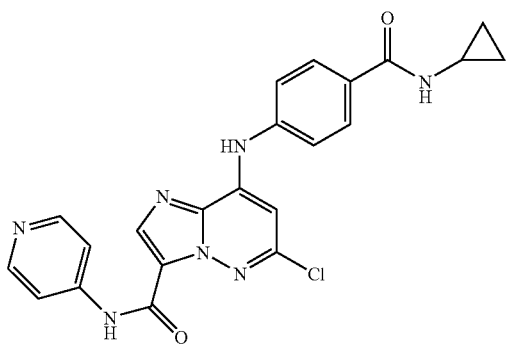 [SMILES: O=C(NC1CC1)c1ccc(Nc2cc(Cl)nn3c(C(=O)Nc4ccncc4)cnc23)cc1]

To a vial was added 1E (50 mg, 0.162 mmol) and 4-amino-N-cyclopropylbenzamide (28.6 mg, 0.162 mmol) in THF (2 mL) under nitrogen. To the reaction solution was added potassium tert-butoxide (0.487 mL, 0.487 mmol) and the reaction solution was stirred at room temperature for 1 hour. The reaction was quenched with ethyl acetate, washed with sodium bicarbonate solution, water, dried over anhydrous sodium sulfate and concentrated to give 6-chloro-8-(4-(cyclopropylcarbamoyl)phenylamino)-N-(pyridin-4-yl)imidazo[1,2-b]pyridazine-3-carboxamide (39 mg, 0.087 mmol, 53.7% yield). LC/MS, m/z 448.05 (M+1). HPLC Rt, 2.33 min. Waters Sunfire C18 column (4.6×50 mm) 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 4 min, hold at 100% B 1 min, flow rate 4 mL/min.

1I. Preparation of 6-((trans-4-aminocyclohexyl)amino)-8-((4-(cyclopropylcarbamoyl)phenyl)amino)-N-4-pyridinylimidazo[1,2-b]pyridazine-3-carboxamide

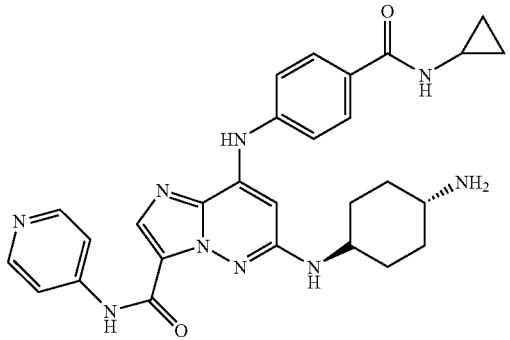

To a 1 dram vial was added 6-chloro-8-(4-(cyclopropylcarbamoyl)phenylamino)-N-(pyridin-4-yl)imidazo[1,2-b]pyridazine-3-carboxamide (39 mg, 0.087 mmol) and (trans)-cyclohexane-1,4-diamine (99 mg, 0.871 mmol). The reaction solution was heated neat at 160° C. for 1 hour. The solution was cooled and purified by preparative HPLC to yield 6-((trans-4-aminocyclohexyl)amino)-8-((4-(cyclopropylcarbamoyl)phenyl)amino)-N-4-pyridinylimidazo[1,2-b]pyridazine-3-carboxamide (11.90 mg, 0.023 mmol, 26.0% yield) as a TFA salt. $^1$H NMR (500 MHz, CD$_3$OD) δ ppm 8.73-8.76 (2H, m), 8.28-8.32 (2H, m), 8.19 (1H, s), 7.86-7.90 (2H, m), 7.41-7.45 (2H, m), 6.48-6.50 (1H, m), 3.78-3.85 (1H, m), 3.14-3.21 (1H, m), 2.83-2.88 (1H, m), 2.32-2.38 (2H, m), 2.12-2.18 (3H, m), 1.55-1.64 (3H, m), 1.42-1.51 (3H, m), 0.78-0.84 (2H, m), 0.62-0.69 (2H, m) LC/MS, m/z 526.17 (M+1). HPLC Rt, 2.21 min. Waters Sunfire C18 column (4.6×50 mm) 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 4 min, hold at 100% B 1 min, flow rate 4 mL/min.

Example 2

6-((trans-4-aminocyclohexyl)amino)-8-(3-azetidinylamino)-N-4-pyridinylimidazo[1,2-b]pyridazine-3-carboxamide

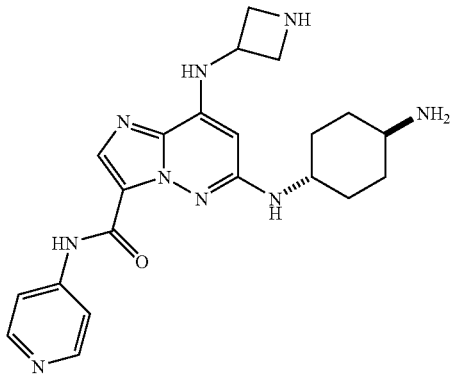

2A. Preparation of tert-butyl 3-(6-((trans)-4-aminocyclohexylamino)-3-(pyridin-4-ylcarbamoyl)imidazo[1,2-b]pyridazin-8-ylamino)azetidine-1-carboxylate

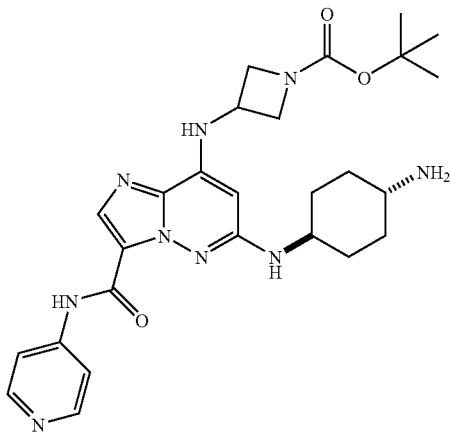

A suspension of 1E (25 mg, 0.08 mmol) in THF (1 mL) was treated with tert-butyl 3-aminoazetidine-1-carboxylate (15 mg, 0.09 mmol) and heated to 80° C. for 18 hours. The resulting mixture was concentrated under reduced pressure and then treated with trans-cyclohexane-1,4-diamine (400 mg) and heated to 160° C. for four hours. After cooling to room temperature, the crude product was purified by reversed-phase preparative HPLC (YMC ODS-A 5 um 20×100 mm, 10% to 90% MeOH/H$_2$O) containing 0.1% TFA, 30 minute gradient, 20 mL/min) to afford the title compound (6.0 mg, 15%). LC/MS, m/z 522.3 (M+1). HPLC Rt=2.90 min. YMC S5 ODS-A column (4.6×50 mm) 0%-100% B. Solvent B: (90% MeOH, 10% H$_2$O, 0.2% H$_3$PO$_4$). Solvent A: (10% MeOH, 90% H$_2$O, 0.2% H$_3$PO$_4$). Gradient, start % B=0, final % B=100, gradient time 4 min, hold at 100% 1 min, flow rate 4 mL/min.

2B. Preparation of 6-((trans-4-aminocyclohexyl)amino)-8-(3-azetidinylamino)-N-4-pyridinylimidazo[1,2-b]pyridazine-3-carboxamide

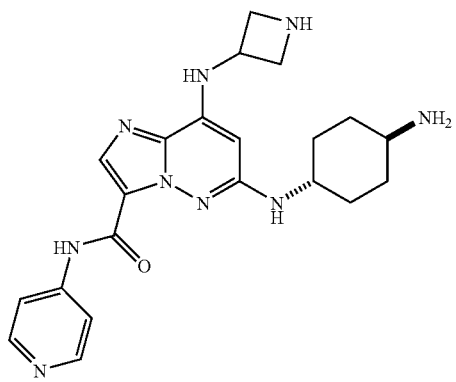

A solution of 2A (4.0 mg, 0.008 mmol) in CH$_2$Cl$_2$ (1 mL) was treated with TFA (0.1 mL) and stirred at room temperature for five hours. The resulting solution was concentrated and the crude product was purified by reversed-phase preparative HPLC ((YMC ODS-A 5 um 20×100 mm, 10% to 90% MeOH/H2) containing 0.1% TFA, 30 minute gradient, 20 mL/min) to afford the title compound (2.0 mg, 61%). LC/MS, m/z 422.27 (M+1). HPLC Rt=1.405 min. YMC S5 ODS-A column (4.6×50 mm) 0%-100% B. Solvent B: (90% MeOH, 10% H$_2$O, 0.2% H$_3$PO$_4$). Solvent A: (10% MeOH, 90% H$_2$O, 0.2% H$_3$PO$_4$). Gradient, start % B=0, final % B=100, gradient time 4 min, hold at 100% 1 min, flow rate 4 mL/min.

Example 3
6-((trans-4-aminocyclohexyl)amino)-8-(cyclobutylamino)-N-4-pyridinylimidazo[1,2-b]pyridazine-3-carboxamide

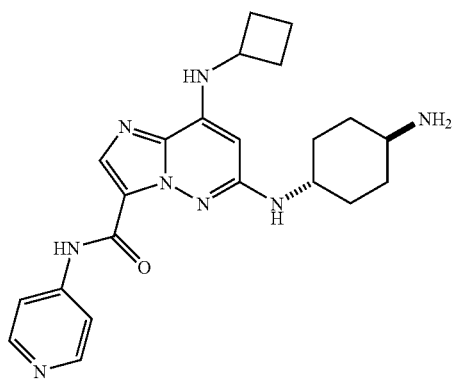

A solution of 1E (25 mg, 0.08 mmol) in THF (1 mL) was treated with cyclobutylamine (7 mg, 0.09 mmol) and heated to 80° C. for three hours. The resulting mixture was concentrated under reduced pressure and then treated with trans-cyclohexane-1,4-diamine (400 mg) and heated to 160° C. for four hours. After cooling to room temperature, the crude product was purified by reversed-phase preparative HPLC (YMC ODS-A 5 um 20×100 mm, 10% to 90% MeOH/H$_2$O) containing 0.1% TFA, 30 minute gradient, 20 mL/min)) to afford the title compound (10 mg, 30%). LC/MS, m/z 421.3 (M+1). HPLC Rt=2.563 min. YMC S5 ODS-A column (4.6×50 mm) 0%-100% B. Solvent B: (90% MeOH, 10% H$_2$O, 0.2% H$_3$PO$_4$). Solvent A: (10% MeOH, 90% H$_2$O, 0.2% H$_3$PO$_4$). Gradient, start % B=0, final % B=100, gradient time 4 min, hold at 100% 1 min, flow rate 4 mL/min Example 4
6-((trans-4-aminocyclohexyl)amino)-8-(ethylamino)-N-(3-fluoro-4-pyridinyl)imidazo[1,2-b]pyridazine-3-carboxamide

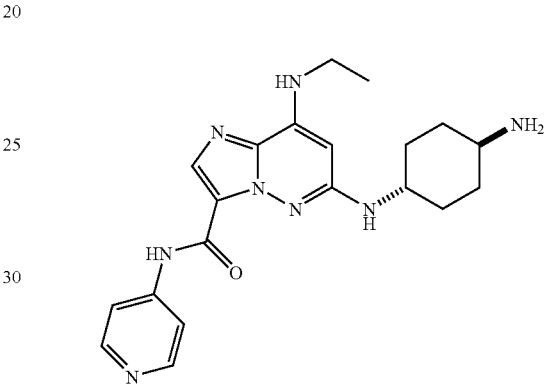

A solution of 1E (50 mg, 0.08 mmol) in THF (1 mL) was treated with ethylamine (0.12 mL, 0.23 mmol) and heated to 80° C. for five hours. The resulting mixture was concentrated under reduced pressure and then treated with trans-cyclohexane-1,4-diamine (400 mg) and heated to 160° C. for four hours. After cooling to room temperature, the crude product was purified by reversed-phase preparative HPLC (YMC ODS-A 5 um 20×100 mm, 10% to 90% MeOH/H$_2$O) containing 0.1% TFA, 30 minute gradient, 20 mL/min) to afford the title compound (7 mg, 12%). LC/MS, m/z 396.3 (M+1). HPLC Rt=2.964 min. YMC S5 ODS-A column (4.6×50 mm) 0%-100% B. Solvent B: (90% MeOH, 10% H$_2$O, 0.2% H$_3$PO$_4$). Solvent A: (10% MeOH, 90% H$_2$O, 0.2% H$_3$PO$_4$). Gradient, start % B=0, final % B=100, gradient time 4 min, hold at 100% 1 min, flow rate 4 mL/min.

Example 5
6-((trans-4-((dimethylcarbamoyl)amino)cyclohexyl)amino)-N-(3-fluoro-4-pyridinyl)-8-(2-pyridinylamino)imidazo[1,2-b]pyridazine-3-carboxamide

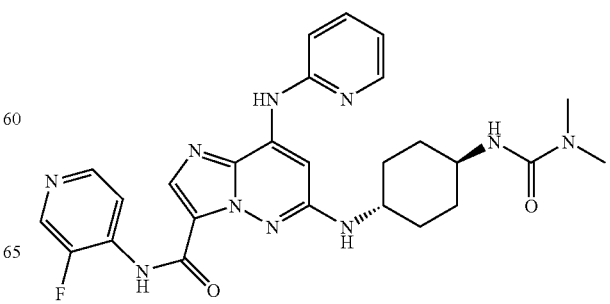

5A. Preparation of 6,8-dichloro-N-(3-fluoropyridin-4-yl)imidazo[1,2-b]pyridazine-3-carboxamide and 8-bromo-6-chloro-N-(3-fluoropyridin-4-yl)imidazo[1,2-b]pyridazine-3-carboxamide

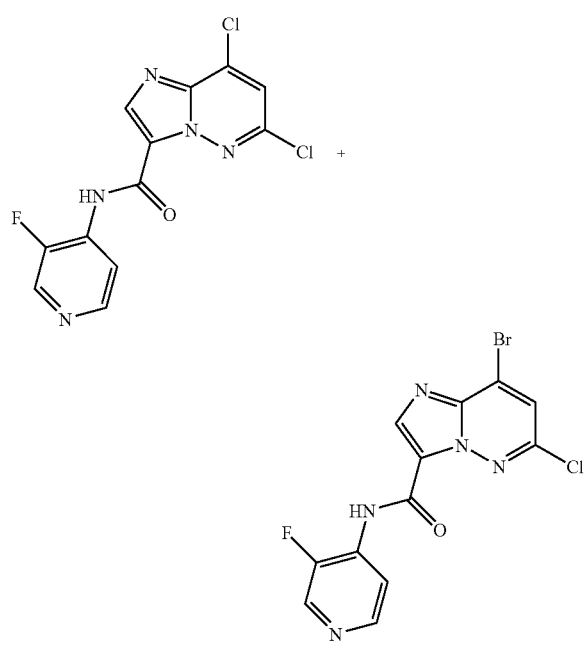

A 250 mL round bottomed flask was charged with a mixture of 6,8-dichloroimidazo[1,2-b]pyridazine-3-carboxylic acid and 8-bromo-6-chloroimidazo[1,2-b]pyridazine-3-carboxylic acid (1.0 g, 4.31 mmol) 1D, 1,2-dichloroethane (33.2 mL), and DMF (0.267 mL, 3.45 mmol). To the resulting white suspension under nitrogen at room temperature was added oxalyl chloride (6.46 mL, 12.93 mmol) solution slowly via syringe, carefully monitoring gas evolution. Following cessation of bubbling, the reaction mixture was fitted with a reflux condenser and heated to 65° C. for 1 h, whereupon it slowly became a light yellow, homogeneous solution. The mixture was cooled to room temperature, toluene was added, and the solution was concentrated in vacuo. (This process was repeated two more times to remove excess oxalyl chloride.) The resulting solid was dried in vacuo. The light yellow solid was then suspended in 1,2-dichloroethane (33.2 mL) and charged with 3-fluoropyridin-4-amine (1.160 g, 10.34 mmol) and DIEA (4.52 mL, 25.9 mmol). The resulting light tan suspension stirred overnight at room temperature. The light brown suspension was filtered and washed with copious amounts of dichloromethane, which furnished a mixture of 6,8-dichloro-N-(3-fluoropyridin-4-yl)imidazo[1,2-b]pyridazine-3-carboxamide and 8-bromo-6-chloro-N-(3-fluoropyridin-4-yl)imidazo[1,2-b]pyridazine-3-carboxamide (1.240 g, 84% yield) as a tan solid. LC/MS, m/z 325.0 (M+1). HPLC Rt=2.823 min. LC/MS, m/z 369.8 (M+1). HPLC Rt=2.946 min. YMC S5 ODS-A column (4.6×50 mm) 0%-100% B. Solvent B: (90% MeOH, 10% H$_2$O, 0.2% H$_3$PO$_4$). Solvent A: (10% MeOH, 90% H$_2$O, 0.2% H$_3$PO$_4$). Gradient, start % B=0, final % B=100, gradient time 4 min, hold at 100% 1 min, flow rate 4 mL/min.

5B. Preparation of 6-chloro-N-(3-fluoropyridin-4-yl)-8-((4-methoxybenzyl)(pyridin-2-yl)amino)imidazo[1,2-b]pyridazine-3-carboxamide

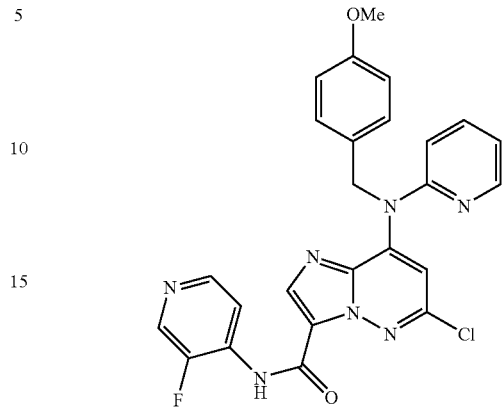

To a suspension containing a mixture of 6,8-dichloro-N-(3-fluoropyridin-4-yl)imidazo[1,2-b]pyridazine-3-carboxamide and 8-bromo-6-chloro-N-(3-fluoropyridin-4-yl)imidazo[1,2-b]pyridazine-3-carboxamide 5A (1.2 g, 3.68 mmol) was added N-(4-methoxybenzyl)pyridin-2-amine (1.183 g, 5.52 mmol) in THF (36.8 mL) at 0° C. This mixture was charged with a 1M solution of potassium tert-butoxide (7.36 mL, 7.36 mmol), slowly via syringe. The dark suspension was stirred for 20 min at room temperature. Volatiles were removed in vacuo and the resulting residue was triturated with MeOH and cooled to 0° C. Filtration, with cold MeOH washes afforded a tan solid which was dissolved in THF and azeotroped with PhMe to remove residual MeOH, then dried in vacuo overnight, which afforded 6-chloro-N-(3-fluoropyridin-4-yl)-8-((4-methoxybenzyl)(pyridin-2-yl)amino)imidazo[1,2-b]pyridazine-3-carboxamide (1.31 g, 68.5% yield) as a tan solid. LC/MS, m/z 504.0 (M+1). HPLC Rt=4.265 min. YMC S5 ODS-A column (4.6×50 mm) 0%-100% B. Solvent B: (90% MeOH, 10% H$_2$O, 0.2% H$_3$PO$_4$). Solvent A: (10% MeOH, 90% H$_2$O, 0.2% H$_3$PO$_4$). Gradient, start % B=0, final % B=100, gradient time 4 min, hold at 100% 1 min, flow rate 4 mL/min. $^1$H NMR (400 MHz, DMSO-d$_6$) δ ppm 11.02 (1H, d, J=2.27 Hz), 8.62 (1H, d, J=2.27 Hz), 8.35-8.48 (4H, m), 8.23 (1H, s), 7.67-7.83 (1H, m), 7.32 (2H, dd, J=8.56, 2.27 Hz), 7.24 (1H, dd, J=7.05, 5.29 Hz), 7.00 (1H, s), 6.79-6.89 (2H, m), 5.60 (2H, s), 3.62-3.72 (3H, s).

5C. Preparation of 6-((trans)-4-aminocyclohexylamino)-N-(3-fluoropyridin-4-yl)-8-((4-methoxybenzyl)(pyridin-2-yl)amino)imidazo[1,2-b]pyridazine-3-carboxamide

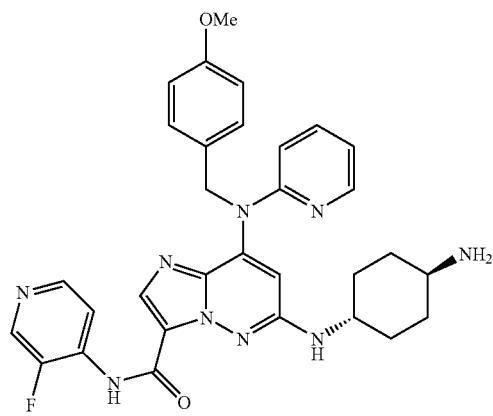 [SMILES: COc1ccc(CN(c2ccccn2)c2cc(N[C@H]3CC[C@H](N)CC3)nn3c(C(=O)Nc4ccncc4F)cnc23)cc1]

A suspension of 6-chloro-N-(3-fluoropyridin-4-yl)-8-((4-methoxybenzyl)(pyridin-2-yl)amino)imidazo[1,2-b]pyridazine-3-carboxamide 5B (0.500 g, 0.992 mmol) and (trans)-cyclohexane-1,4-diamine (1.360 g, 11.91 mmol) in NMP (2.5 mL) was subjected to 110° C. in a 300 W CEM Discover microwave for 20 min. The mixture was diluted with MeOH and purified via preparatory HPLC using a YMC ODS C-18 column (30×250 mm) 0%-100% B. Solvent B: (90% MeOH, 10% H$_2$O, 0.1% TFA). Solvent A: (10% MeOH, 90% H$_2$O, 0.1% TFA). Gradient, start %B=0, final % B=100, gradient time 60 min, flow rate 25 mL/min. Rt=42 min. 6-((trans)-4-aminocyclohexylamino)-N-(3-fluoropyridin-4-yl)-8-((4-methoxybenzyl)(pyridin-2-yl)amino)imidazo[1,2-b]pyridazine-3-carboxamide (0.500 g, 54.6% yield) was obtained as a light yellow solid. LC/MS, m/z 582.1 (M+1). HPLC Rt=3.211 min. YMC S5 ODS-A column (4.6× 50 mm) 0%-100% B. Solvent B: (90% MeOH, 10% H$_2$O, 0.2% H$_3$PO$_4$). Solvent A: (10% MeOH, 90% H$_2$O, 0.2% H$_3$PO$_4$). Gradient, start %B=0, final %B=100, gradient time 4 min, hold at 100% 1 min, flow rate 4 mL/min. $^1$H NMR (400 MHz, DMSO-d$_6$) δ ppm 11.20 (1H, d, J=1.76 Hz), 8.69 (1H, d, J=2.77 Hz), 8.46-8.53 (1H, m), 8.41-8.47 (1H, m), 8.28 (1H, dd, J=4.78, 1.26 Hz), 8.01 (1H, s), 7.89 (2H, d, J=4.28 Hz), 7.57-7.72 (1H, m), 7.26 (2H, d, J=8.81 Hz), 7.18 (1H, d, J=7.81 Hz), 7.11 (1H, d, J=8.31 Hz), 7.03 (1H, dd, J=6.55, 5.04 Hz), 6.83 (2H, d, J=8.81 Hz), 6.52 (1H, s), 5.43 (2H, s), 3.72-3.84 (1H, m), 3.64-3.72 (3H, s), 3.06 (1H, d, J=4.78 Hz), 2.03-2.15 (2H, m), 1.95 (2H, d, J=10.07 Hz), 1.34-1.49 (2H, m), 1.26 (2H, d, J=12.34 Hz).

5D. Preparation of 6-((trans-4-((dimethylcarbamoyl)amino)cyclohexyl)amino)-N-(3-fluoro-4-pyridinyl)-8-(2-pyridinylamino)imidazo[1,2-b]pyridazine-3-carboxamide

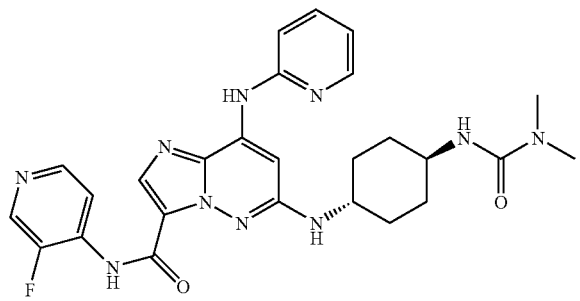 [SMILES: CN(C)C(=O)N[C@H]1CC[C@H](Nc2cc(Nc3ccccn3)c3ncc(C(=O)Nc4ccncc4F)n3n2)CC1]

To a solution of 6-((trans)-4-aminocyclohexylamino)-N-(3-fluoropyridin-4-yl)-8-((4-methoxybenzyl)(pyridin-2-yl)amino)imidazo[1,2-b]pyridazine-3-carboxamide 5C (41.5 mg, 0.051 mmol) and DIEA (0.045 mL, 0.256 mmol) in CH$_2$Cl$_2$ (1 mL) at room temperature was added dimethylcarbamic chloride (4.94 μL, 0.054 mmol), slowly, via syringe. The reaction was stirred overnight at room temperature. Volatiles were removed via a stream of nitrogen and TFA (0.5 mL) was added. The mixture was then heated at 60° C. in an oil bath for 4 h. The reaction was then cooled to room temperature and the TFA was removed under reduced pressure. The resulting crude material was diluted with 1 mL of THF and purified via preparatory HPLC using a YMC ODS C-18 column (30×250 mm) 0%-100% B. Solvent B: (90% MeOH, 10% H$_2$O, 0.1% TFA). Solvent A: (10% MeOH, 90% H$_2$O, 0.1% TFA). Gradient, start %B=0, final %B=100, gradient time 60 min, flow rate 25 mL/min. Rt=56.165 min. 6-((trans-4-((dimethylcarbamoyl)amino)cyclohexyl)amino)-N-(3-fluoro-4-pyridinyl)-8-(2-pyridinylamino)imidazo[1,2-b]pyridazine-3-carboxamide, 2TFA (18 mg, 45.2% yield) was obtained as a white foam. LC/MS, m/z 533.1 (M+1). HPLC Rt=4.200 min. YMC S5 ODS-A column (4.6×50 mm) 0%-100% B. Solvent B: (90% MeOH, 10% H$_2$O, 0.2% H$_3$PO$_4$). Solvent A: (10% MeOH, 90% H$_2$O, 0.2% H$_3$PO$_4$). Gradient, start % B=0, final % B=100, gradient time 4 min, hold at 100% 1 min, flow rate 4 mL/min. $^1$H NMR (500 MHz, DMSO-d$_6$) δ ppm 11.31 (1H, s), 9.82 (1 H, s), 8.73 (1H, d, J=2.47 Hz), 8.51 (1H, t, J=6.05 Hz), 8.44 (1H, d, J=5.22 Hz), 8.34 (1H, d, J=3.85 Hz), 8.12 (1H, s), 7.97 (1H, s), 7.68-7.80 (1H, m), 7.50 (1H, d, J=8.52 Hz), 7.17-7.26 (1H, m), 7.02 (1H, dd, J=6.74, 5.36 Hz), 5.84-5.93 (1H, m), 3.77-3.87 (1H, m), 3.40 (1H, d, J=6.05 Hz), 2.78 (6H, s), 2.06 (2H, s), 1.80 (2H, s), 1.34 (4H, d, J=12.10 Hz).

Example 6

6-((trans-4-(D-alanylamino)cyclohexyl)amino)-N-(3-fluoro-4-pyridinyl)-8-(2-pyridinylamino)imidazo[1,2-b]pyridazine-3-carboxamide

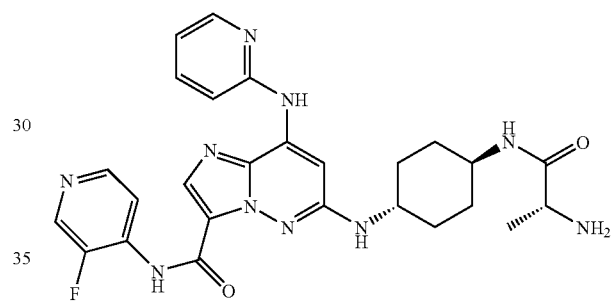

6A. Preparation of 6-((trans)-4-aminocyclohexylamino)-N-(3-fluoropyridin-4-yl)-8-(pyridin-2-ylamino)imidazo[1,2-b]pyridazine-3-carboxamide

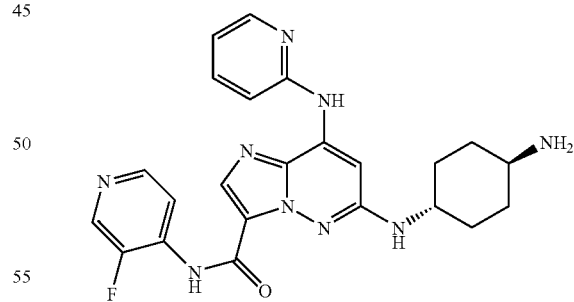

A suspension of 6,8-dichloro-N-(3-fluoropyridin-4-yl)imidazo[1,2-b]pyridazine-3-carboxamide (100 mg, 0.307 mmol) in THF (1 mL) was treated with pyridin-2-amine (57.7 mg, 0.613 mmol). A solution of potassium tert-butoxide (0.613 mL, 0.613 mmol) in THF was added and the reaction was stirred at room temperature. The solvent was removed under a stream of nitrogen and the residue was taken up in MeOH and filtered. The solid material was dried under vacuum. The material was taken up in NMP (2 mL) and transferred to a microwave vial. (trans)-Cyclohexane-1,4-diamine (0.350 g, 3.07 mmol) was added and the reaction was irradiated at 300 W power, 110° C. for 40 minutes. After cooling, the crude material was diluted with 2 mL of MeOH and purified via preparative HPLC using a YMC ODS C-18 30×250 mm column with 10-100% B (Solvent A: 10% aq MeOH with 0.1% TFA; Solvent B: 90% aq. MeOH with 0.1% TFA) and a linear gradient over 60 min at 25 mL/min, monitoring at 220 nm, and a total run time of 70 min. (RT of desired=45.100 min). The appropriate fractions were concentrated under reduced pressure and lyophilized overnight, furnishing 6-((trans)-4-aminocyclohexylamino)-N-(3-fluoropyridin-4-yl)-8-(pyridin-2-ylamino)imidazo[1,2-b]pyridazine-3-carboxamide (0.057 g, 0.083 mmol) as a white, fluffy solid. LC/MS, m/z 462.3 (M+1). HPLC Rt=3.345 min. YMC S5 ODS-A column (4.6×50 mm) 0%-100% B. Solvent B: (90% MeOH, 10% $H_2O$, 0.2% $H_3PO_4$). Solvent A: (10% MeOH, 90% $H_2O$, 0.2% $H_3PO_4$). Gradient, start % B=0, final % B=100, gradient time 4 min, hold at 100% 1 min, flow rate 4 mL/min.

6B. Preparation of 6-((trans-4-(D-alanylamino)cyclohexyl)amino)-N-(3-fluoro-4-pyridinyl)-8-(2-pyridinylamino)imidazo[1,2-b]pyridazine-3-carboxamide

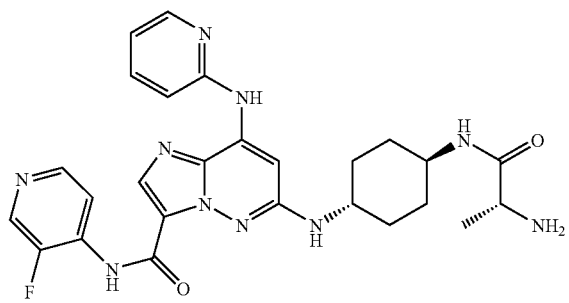 [SMILES: C[C@@H](N)C(=O)N[C@H]1CC[C@H](Nc2cc(Nc3ccccn3)c3ncc(C(=O)Nc4ccncc4F)n3n2)CC1]

To a solution of 6-((trans)-4-aminocyclohexylamino)-N-(3-fluoropyridin-4-yl)-8-(pyridin-2-ylamino)imidazo[1,2-b]pyridazine-3-carboxamide (0.020 g, 0.043 mmol) in DMF (1 mL) at room temperature was added DIEA (0.038 mL, 0.217 mmol), (R)-2-(tert-butoxycarbonylamino)propanoic acid (0.016 g, 0.087 mmol), and BOP (0.058 g, 0.130 mmol). The resulting clear, colorless solution was stirred at room temperature for 30 minutes. Volatiles were removed in vacuo and the crude material was suspended in dichloromethane (0.5 mL) and TFA (0.5 mL). The resulting suspension was stirred vigorously at room temperature for 1.5 h. Volatiles were removed via a stream of nitrogen, and the crude material was diluted with 1 mL MeOH and purified via preparatory HPLC using a YMC ODS C-18 column (30×250 mm) 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 60 min, flow rate 25 mL/min. Rt=49.547 min. 6-((trans-4-(D-alanylamino)cyclohexyl)amino)-N-(3-fluoro-4-pyridinyl)-8-(2-pyridinylamino)imidazo[1,2-b]pyridazine-3-carboxamide (0.006 g, 18.20% yield) was obtained as a white solid. LC/MS, m/z 533.2 (M+1). HPLC Rt=3.616 min. YMC S5 ODS-A column (4.6× 50 mm) 0%-100% B. Solvent B: (90% MeOH, 10% $H_2O$, 0.2% $H_3PO_4$). Solvent A: (10% MeOH, 90% $H_2O$, 0.2% $H_3PO_4$). Gradient, start % B=0, final % B=100, gradient time 4 min, hold at 100% 1 min, flow rate 4 mL/min. $^1$H NMR (400 MHz, DMSO-$d_6$) δ ppm 11.27 (1H, d, J=1.76 Hz), 9.85 (1H, s), 8.67 (1H, d, J=2.77 Hz), 8.48-8.55 (1H, m), 8.44 (1H, d, J=5.54 Hz), 8.34 (1H, dd, J=4.91, 1.38 Hz), 8.28 (1H, d, J=7.55 Hz), 8.13 (1H, s), 8.04 (2H, d, J=4.53 Hz), 7.98 (1H, s), 7.71-7.78 (1H, m), 7.51 (1H, d, J=8.31 Hz), 7.28 (1H, d, J=8.31 Hz), 7.02 (1H, dd, J=7.05, 5.79 Hz), 3.87 (1H, s), 3.73-3.81 (1H, m), 3.58 (1H, s), 2.07 (2H, d, J=3.78 Hz), 1.86 (2H, s), 1.34 (3H, d, J=6.80 Hz), 1.28-1.44 (4H, m).

Example 7

Methyl trans-4-((8-(cyclopropylamino)-3-((3-fluoro-4-pyridinyl)carbamoyl)imidazo[1,2-b]pyridazin-6-yl)amino)cyclohexanecarboxylate

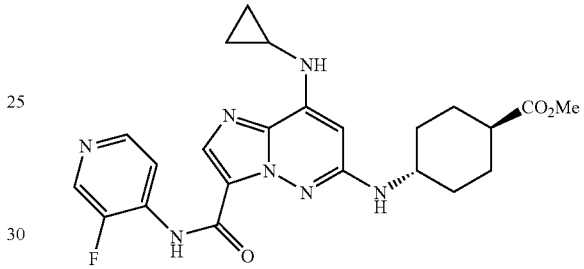

7A. Preparation of 6-chloro-8-(cyclopropylamino)-N-(3-fluoropyridin-4-yl)imidazo[1,2-b]pyridazine-3-carboxamide

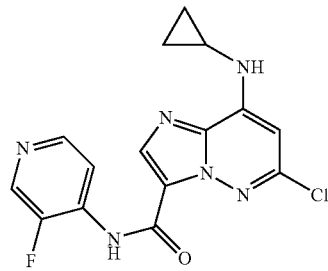 [SMILES: O=C(Nc1ccncc1F)c1cnc2c(NC3CC3)cc(Cl)nn12]

To a yellow suspension containing a mixture of 6,8-dichloro-N-(3-fluoropyridin-4-yl)imidazo[1,2-b]pyridazine-3-carboxamide and 8-bromo-6-chloro-N-(3-fluoropyridin-4-yl)imidazo[1,2-b]pyridazine-3-carboxamide 5A (1.97 g, 6.04 mmol) and DIEA (1.583 mL, 9.06 mmol) in THF (60.4 mL) at 22° C. in a sealed tube apparatus was added cyclopropanamine (0.628 mL, 9.06 mmol). The suspension was heated to 80° C. for 8 hours, then cooled to room temperature and concentrated to dryness. The crude material was triturated with 30 mL MeOH and stirred for 1 h at room temperature. The resulting solid was collected by filtration and dried to affored 6-chloro-8-(cyclopropylamino)-N-(3-fluoropyri din-4-yl)imidazo[1,2-b]pyridazine-3-carboxamide (1.6 g, 4.61 mmol, 76% yield) as a light tan solid. MS (m+1)=347.2. HPLC Peak R$_f$=3.976 minutes is product.

7B. Preparation of methyl trans-4-((8-(cyclopropylamino)-3-((3-fluoro-4-pyridinyl)carbamoyl)imidazo[1,2-b]pyridazin-6-yl)amino)cyclohexanecarboxylate

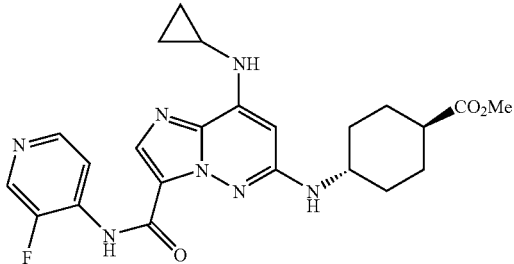 [SMILES: COC(=O)[C@H]1CC[C@H](Nc2cc(NC3CC3)c3ncc(C(=O)Nc4ccncc4F)n3n2)CC1]

To a suspension of 6-chloro-8-(cyclopropylamino)-N-(3-fluoropyridin-4-yl)imidazo[1,2-b]pyridazine-3-carboxamide (0.030 g, 0.087 mmol) and DIEA (0.227 mL, 1.298 mmol) in NMP (1 mL) was added trans-methyl 4-aminocyclohexanecarboxylate, HCl (0.201 g, 1.038 mmol). The resulting suspension was heated to 120° C. in a 300 W CEM Discover microwave for 60 min. The crude material was diluted with 1 mL MeOH and purified via preparatory HPLC using a YMC ODS C-18 column (30×250 mm) 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 240 min, hold at 100% B 40 min, flow rate 25 mL/min. Material was redissolved in DMSO/THF and purified via preparatory HPLC using a YMC ODS C-18 column (30×250 mm) 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 60 min, flow rate 25 mL/min, to afford methyl trans-4-((8-(cyclopropylamino)-3-((3-fluoro-4-pyridinyl)carbamoyl)imidazo[1,2-b]pyridazin-6-yl)amino)cyclohexanecarboxylate, 2TFA (0.006 g, 9.97% yield) obtained as a white foam. LC/MS, m/z 468.0 (M+1). HPLC Rt=4.120 min. YMC S5 ODS-A column (4.6×50 mm) 0%-100% B. Solvent B: (90% MeOH, 10% H$_2$O, 0.2% H$_3$PO$_4$). Solvent A: (10% MeOH, 90% H$_2$O, 0.2% H$_3$PO$_4$). Gradient, start % B=0, final % B=100, gradient time 4 min, hold at 100% 1 min, flow rate 4 mL/min. $^1$H NMR (500 MHz, DMSO-d$_6$) δ ppm 11.46 (1H, s), 8.67 (1H, d, J=2.75 Hz), 8.55 (1H, t, J=5.91 Hz), 8.41 (1H, d, J=5.77 Hz), 8.00 (1H, s), 7.57 (1H, s), 7.00 (1H, s), 6.07 (1H, s), 2.06 (3H, s), 1.91 (4H, s), 1.58 (1H, d), 1.30 (4H, d, J=10.45 Hz), 1.05 (2H, d, J=11.27 Hz), 0.76 (2H, d, J=4.95 Hz), 0.57-0.67 (2H, m).

Example 8

Methyl (trans-4-((8-(cyclopropylamino)-3-((3-fluoro-4-pyridinyl)carbamoyl)imidazo[1,2-b]pyridazin-6-yl)amino)cyclohexyl)carbamate

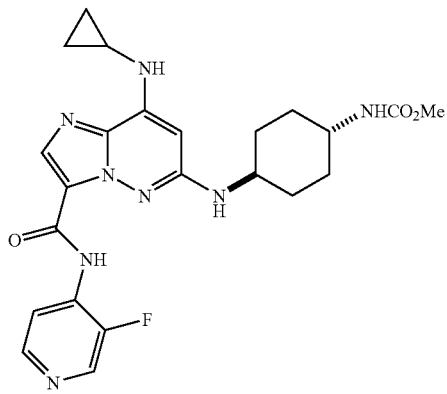

8A. Preparation of 6,8-dichloro-N-(3-fluoropyridin-4-yl)imidazo[1,2-b]pyridazine-3-carboxamide and 8-bromo-6-chloro-N-(3-fluoropyridin-4-yl)imidazo[1,2-b]pyridazine-3-carboxamide

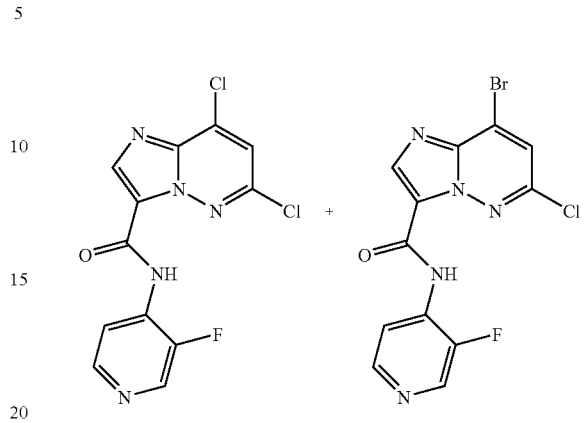

A ~1:1 mixture 6,8-dichloroimidazo[1,2-b]pyridazine-3-carboxylic acid and 8-bromo-6-chloroimidazo[1,2-b]pyridazine-3-carboxylic acid 1D (4.7 g, 18.6 mmol) was suspended in DCE (140 mL), and treated with neat oxalyl chloride (2.65 mL 30.4 mmol) followed by N,N-dimethylformamide (0.08 mL, 1.034 mmol). The reaction mixture was heated at 65° C. for 5 hours, concentrated and dried under high vacuum for 1 hr and taken into the next step without further purification. The crude mixture of acid chloride was suspended in DCE (100 mL) and treated with 3-fluoropyridin-4-amine (2.73 g, 24.31 mmol) and N,N-diisopropylethylamine (5.31 mL, 30.4 mmol) and stirred at room temperature for 2 hours. The reaction mixture was filtered through Buchner funnel, washed with DCE (2×25 mL) to isolate a 1:1 mixture of 6,8-dichloro-N-(3-fluoropyridin-4-yl)imidazo[1,2-b]pyridazine-3-carboxamide and 8-bromo-6-chloro-N-(3-fluoropyridin-4-yl)imidazo[1,2-b]pyridazine-3-carboxamide (5.2 g, 15.0 mmol, 80% yield) as light brown solid. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA) Rt=1.1 (M+H=326.07 and M+H=372.01).

8B. Preparation of 6-((trans)-4-aminocyclohexylamino)-8-(cyclopropyl(4-methoxybenzyl)amino)-N-(3-fluoropyridin-4-yl)imidazo[1,2-b]pyridazine-3-carboxamide

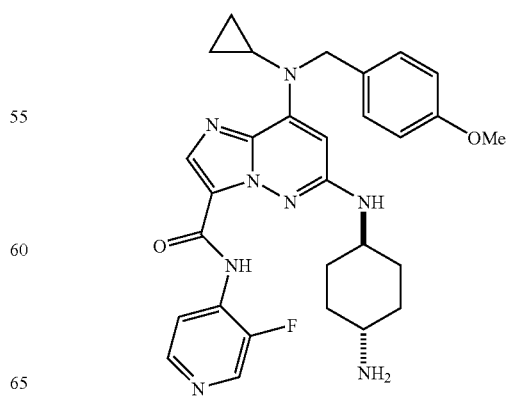

A ~1:1 mixture of 6,8-dichloro-N-(3-fluoropyridin-4-yl) imidazo[1,2-b]pyridazine-3-carboxamide and 8-bromo-6-chloro-N-(3-fluoropyridin-4-yl)imidazo[1,2-b]pyridazine-3-carboxamide 8A (3 g, 8.6 mmol), N-(4-methoxybenzyl)cyclopropanamine (1.79 g, 10.12 mmol) and N,N-diisopropylethylamine (2.41 mL, 13.80 mmol) were suspended in DMF (30 mL) and heated at 80° C. for 1 hr. The reaction mixture was concentrated, dried under reduced pressure for 16 hrs, suspended in methanol (20 mL) and an off-white solid collected via Buchner filtration (2×10 mL methanol rinse) and taken to the next step without further purification. The reaction mixture was combined with trans-1,4-diaminocyclohexane (16.28 g, 143 mmol) and heated at 160° C. for 2.5 hours. The reaction was cooled to room temperature, and water (40 mL) was added, and the solid collected via Buchner filtration. The crude product was purified with silica gel chromatography using a stepwise gradient of 10% methanol/chloroform to 25% methanol/chloroform/1% triethylamine to isolated a foamy solid. The solid was suspended in water (50 mL) and collected with Buchner filtration (2×25 mL water wash) and dried for 16 hrs under reduced pressure to isolate 6-((trans)-4-aminocyclohexylamino)-8-(cyclopropyl(4-methoxybenzyl)amino)-N-(3-fluoropyridin-4-yl)imidazo[1,2-b]pyridazine-3-carboxamide (3.2 g, 5.58 mmol, 63% yield) as a off white solid. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA) Rt=1.68 (M+H=545.22).

8C. Preparation of methyl (trans-4-((8-(cyclopropylamino)-3-((3-fluoro-4-pyridinyl)carbamoyl)imidazo[1,2-b]pyridazin-6-yl)amino)cyclohexyl)carbamate

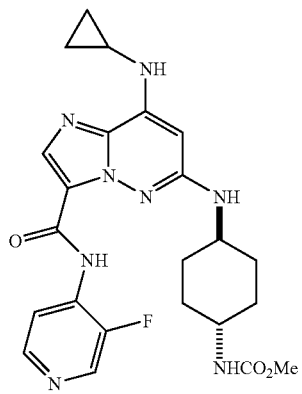

Methyl carbonochloridate (7.81 mg, 0.083 mmol) was added to a solution of 6-((trans)-4-aminocyclohexylamino)-8-(cyclopropyl(4-methoxybenzyl)amino)-N-(3-fluoropyridin-4-yl)imidazo[1,2-b]pyridazine-3-carboxamide (30 mg, 0.055 mmol) and DIEA (0.00617 mL, 0.035 mmol) in $CH_2Cl_2$ (1 mL). The reaction mixture was stirred at room temperature for 2 hrs, concentrated and treated with TFA (0.127 mL, 1.653 mmol) at 65° C. for 1 h. The reaction mixture was concentrated and purified by preparative HPLC (Phenomenex Axia Luna 5 micron 30×100 mm) 20% B (Solvent B=90% MeOH-10% $H_2O$-0.1% TFA) to 100% B in A (Solvent A=10% MeOH-90% $H_2O$-0.1% TFA)). The title compound, methyl (trans-4-((8-(cyclopropylamino)-3-((3-fluoro-4-pyridinyl)carbamoyl)imidazo[1,2-b]pyridazin-6-yl)amino)cyclohexyl)carbamate, was isolated as a white solid (15 mg, 56.4%). LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA) Rt=1.63 (M+H=483.24). $^1$H NMR (400 MHz, DMSO-$d_6$) δ ppm 11.42 (1H, s), 8.74 (1H, d, J=2.27 Hz), 8.51 (1H, t, J=6.17 Hz), 8.44 (1H, d, J=5.54 Hz), 8.01 (1H, s), 7.61 (1H, s), 7.18 (1H, d, J=8.06 Hz), 6.94 (1H, d, J=8.31 Hz), 5.98 (1H, s), 3.79 (1H, br. s.), 3.42-3.64 (4H, m), 3.30 (1H, br. s.), 2.02 (2H, d, J=9.57 Hz), 1.79 (2H, br. s.), 1.17-1.45 (4H, m), 0.70-0.82 (2H, m), 0.54-0.68 (2H, m).

Example 9

8-(cyclopropylamino)-N-(3-fluoro-4-pyridinyl)-6-((trans-4-((isopropylcarbamoyl)amino)cyclohexyl)amino)imidazo[1,2-b]pyridazine-3-carboxamide

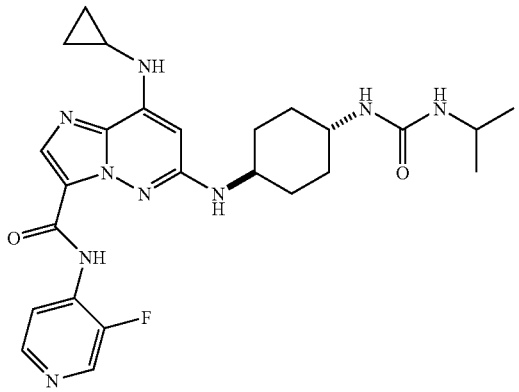

To a solution of 6-((trans)-4-aminocyclohexylamino)-8-(cyclopropyl(4-methoxybenzyl)amino)-N-(3-fluoropyridin-4-yl)imidazo[1,2-b]pyridazine-3-carboxamide 8B (40.0 mg, 0.073 mmol) in $CH_2Cl_2$ (1 mL) was added 2-isocyanatopropane (0.0072 mL, 0.073 mmol). The reaction solution was stirred at room temperature for 30 min. The reaction mixture was concentrated and treated with TFA (1.132 mL, 14.69 mmol) at 70° C. for 1 hr. The reaction mixture was purified by preparative HPLC (Phenomenex Axia Luna 5 micron 30×100 mm) 20% B (Solvent B=90% MeOH-10% $H_2O$-0.1% TFA) to 100% B in A (Solvent A=10% MeOH-90% $H_2O$-0.1% TFA)) to obtain the title compound, 8-(cyclopropylamino)-N-(3-fluoro-4-pyridinyl)-6-((trans-4-((isopropylcarbamoyl)amino)cyclohexyl)amino)imidazo[1,2-b]pyridazine-3-carboxamide, as a white solid (16.9 mg, 45.2%). LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA) Rt=1.73 (M+H=510.32). $^1$H NMR (500 MHz, DMSO-$d_6$) δ ppm 11.38 (1H, s), 8.68 (1H, d, J=2.75 Hz), 8.51 (1H, t, J=6.05 Hz), 8.44 (1H, d, J=5.50 Hz), 8.01 (1H, s), 7.59 (1H, s), 6.92 (1H, br. s.), 5.99 (1H, s), 5.61 (2H, br. s.), 3.79 (2H, br. s.), 3.52-3.74 (2H, m), 2.00 (2H, d, J=9.90 Hz), 1.83 (2H, d, J=10.45 Hz), 1.12-1.41 (4H, m), 1.02 (6H, d, J=6.60 Hz), 0.71-0.83 (2H, m), 0.54-0.69 (2H, m).

Example 10

6-((trans-4-(L-alanylamino)cyclohexyl)amino)-8-(cyclopropylamino)-N-(3-fluoro-4-pyridinyl)imidazo[1,2-b]pyridazine-3-carboxamide

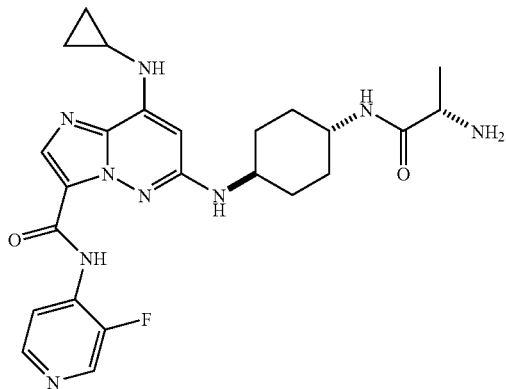

BOP (62.5 mg, 0.141 mmol) was added to a solution of 6-((trans)-4-aminocyclohexylamino)-8-(cyclopropyl(4-methoxybenzyl)amino)-N-(3-fluoropyridin-4-yl)imidazo[1,2-b]pyridazine-3-carboxamide 8B (20 mg, 0.047 mmol), DIEA (0.0062 mL, 0.035 mmol) and (S)-2-(tert-butoxycarbonylamino)propanoic acid (17.83 mg, 0.094 mmol) in DMF (1 mL). The clear reaction mixture was stirred at room temperature for 30 min. The reaction mixture was concentrated down, dissolved in $CH_2Cl_2$ (0.50 mL) and TFA (0.545 mL, 7.07 mmol) and stirred at rt for 30 min. The reaction mixture was concentrated and purified with HPLC (Phenomenex Axia Luna 5 micron 30×100 mm) 20% B (Solvent B=90% MeOH-10% $H_2O$-0.1% TFA) to 100% B in A (Solvent A=10% MeOH-90% $H_2O$-0.1% TFA) to isolate the title compound, 6-((trans-4-(L-alanylamino)cyclohexyl)amino)-8-(cyclopropylamino)-N-(3-fluoro-4-pyridinyl)imidazo[1,2-b]pyridazine-3-carboxamide (10 mg, 42.8%), as a white solid. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). Rt=1.41 (M+H=496.3). $^1$H NMR (400 MHz, MeOD) δ ppm 8.85 (1H, t, J=6.55 Hz), 8.69 (1H, d, J=3.53 Hz), 8.48 (1H, d, J=6.04 Hz), 8.13 (1H, s), 6.11 (1H, s), 3.97 (1H, d, J=4.28 Hz), 3.87 (1H, q, J=7.13 Hz), 3.72 (1H, br. s.), 2.59 (1H, td, J=6.80, 3.53 Hz), 2.21 (2H, br. s.), 1.99 (2H, br. s.), 1.32-1.62 (7H, m), 0.78-0.96 (2H, m), 0.55-0.76 (2H, m).

Example 11

8-(cyclopropylamino)-6-((trans-4-((dimethylsulfamoyl)amino)cyclohexyl)amino)-N-(3-fluoro-4-pyridinyl)imidazo[1,2-b]pyridazine-3-carboxamide

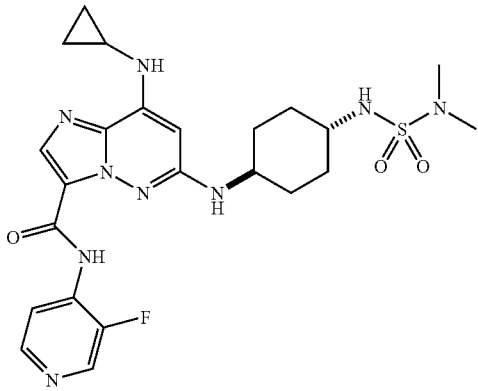

To a solution of 6-((trans)-4-aminocyclohexylamino)-8-(cyclopropyl(4-methoxybenzyl)amino)-N-(3-fluoropyridin-4-yl)imidazo[1,2-b]pyridazine-3-carboxamide 8B (30 mg, 0.055 mmol) in $CH_2Cl_2$ (1 mL) was added DIEA (0.0062 mL, 0.035 mmol) and dimethylsulfamoyl chloride (1.5 mg, 10.45 μmol). The reaction mixture was stirred at room temperature for 2 hrs, concentrated, re-dissolved in TFA (0.849 mL, 11.02 mmol) and heated at 70° C. for 1 hr. The reaction mixture was concentrated and purified by HPLC (Phenomenex Axia Luna 5 micron 30×100 mm) 30% B (Solvent B=90% MeOH-10% $H_2O$-0.1% TFA) to 100% B in A (Solvent A=10% MeOH-90% $H_2O$-0.1% TFA)) to isolate the title compound, 8-(cyclopropylamino)-6-((trans-4-((dimethylsulfamoyl)amino)cyclohexyl)amino)-N-(3-fluoro-4-pyridinyl)imidazo[1,2-b]pyridazine-3-carboxamide, as a white solid (13.0 mg, 44.4%). LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). Rt=1.61 (M+H=532.26). $^1$H NMR (400 MHz, DMSO-$d_6$) δ ppm 11.39 (1H, s), 8.71 (1H, d, J=2.52 Hz), 8.49 (1H, t, J=6.17 Hz), 8.43 (1H, d, J=5.29 Hz), 8.00 (1H, s), 7.61 (1H, s), 7.28 (1H, d, J=8.06 Hz), 6.92 (1H, d, J=8.31 Hz), 5.98 (1H, s), 3.78 (1H, br. s.), 3.00 (2H, br. s.), 2.58-2.73 (6H, m), 2.01 (2H, br. s.), 1.90 (2H, br. s.), 1.26 (4H, d, J=13.09 Hz), 0.68-0.85 (2H, m), 0.51-0.69 (2H, m).

Example 12

Methyl N-(trans-4-((8-(cyclopropylamino)-3-((2-fluoro-4-pyridinyl)carbamoyl)imidazo[1,2-b]pyridazin-6-yl)amino)cyclohexyl)glycinate

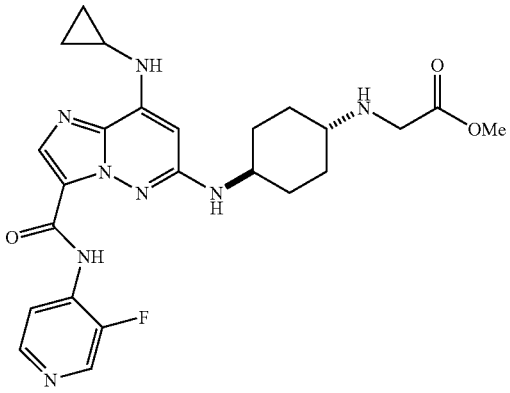

To a solution of 6-((trans)-4-aminocyclohexylamino)-8-(cyclopropyl(4-methoxybenzyl)amino)-N-(3-fluoropyridin-4-yl)imidazo[1,2-b]pyridazine-3-carboxamide 8B (50.0 mg, 0.092 mmol) and DIEA (0.064 mL, 0.367 mmol) in $CH_2Cl_2$ (1 mL) was added methyl 2-bromoacetate (21.07 mg, 0.138 mmol), and the reaction mixture was heated 45° C. in a seal-tube apparatus for 14 hrs. The reaction mixture was concentrated, treated with TFA (0.424 mL, 5.51 mmol) and heated at 65° C. for 1 hr. The reaction mixture was concentrated and diluted with methanol and purified using preparative HPLC (Phenomenex Axia Luna 5 micron 30×100 mm) 30% B (Solvent B=90% MeOH-10% $H_2O$-0.1% TFA) to 100% B in A (Solvent A=10% MeOH-90% $H_2O$-0.1% TFA)) to isolate the title compound, methyl N-(trans-4-((8-(cyclopropylamino)-3-((2-fluoro-4-pyridinyl)carbamoyl)imidazo[1,2-b]pyridazin-6-yl)amino)cyclohexyl)glycinate, as an off-white solid ((23 mg, 0.046 mmol, 50.5% yield). LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). Rt=1.32 (M+H=497.3).

Example 13

8-(cyclopropylamino)-N-(2-fluoro-4-pyridinyl)-6-((trans-4-hydroxycyclohexyl)amino)imidazo[1,2-b]pyridazine-3-carboxamide

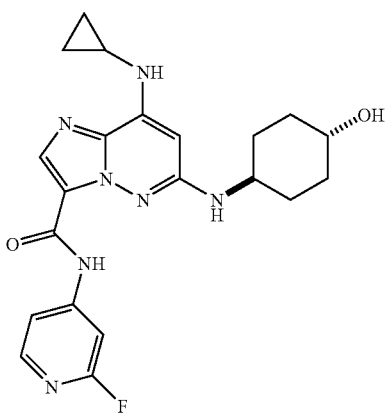

13A. Preparation of 6,8-dichloro-N-(2-fluoropyridin-4-yl)imidazo[1,2-b]pyridazine-3-carboxamide and 8-bromo-6-chloro-N-(2-fluoropyridin-4-yl)imidazo[1,2-b]pyridazine-3-carboxamide

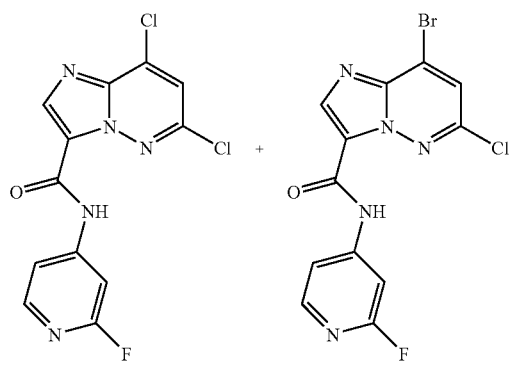 [SMILES: O=C(Nc1ccnc(F)c1)c1cnc2c(Cl)cc(Cl)nn12 ; O=C(Nc1ccnc(F)c1)c1cnc2c(Br)cc(Cl)nn12]

A ~1:1 mixture of 6,8-dichloroimidazo[1,2-b]pyridazine-3-carboxylic acid and 8-bromo-6-chloroimidazo[1,2-b]pyridazine-3-carboxylic acid 1D (2.0 g, 8.62 mmol) was suspended in DCE (20 mL), and treated with neat oxalyl dichloride (4.37 g, 34.5 mmol) followed by N,N-Dimethylformamide (0.534 mL, 6.90 mmol). The reaction mixture was heated at 70° C. for 6 hours, concentrated and dried under high vacuum for 1 hr and taken to the next step without further purification. The crude mixture of acid chloride was suspended in DCM (10 mL) and treated with 2-fluoropyridin-4-amine (1.0 g, 8.92 mmol) and triethylamine (3.75 mL, 26.8 mmol) and stirred at room temperature for 14 hours. The reaction mixture was filtered through a Buchner funnel, and washed with water (2×25 mL) to isolate 1:1 mixture of 6,8-dichloro-N-(2-fluoropyridin-4-yl)imidazo[1,2-b]pyridazine-3-carboxamide and 8-bromo-6-chloro-N-(2-fluoropyridin-4-yl)imidazo[1,2-b]pyridazine-3-carboxamide (1.18 g, 8.92 mmol, 40.5% yield) as yellow solid. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA) Rt=1.47 (M+H=326.1 and M+H=372.04).

13B. Preparation of 8-(cyclopropylamino)-N-(2-fluoro-4-pyridinyl)-6-((trans-4-hydroxycyclohexyl)amino)imidazo[1,2-b]pyridazine-3-carboxamide

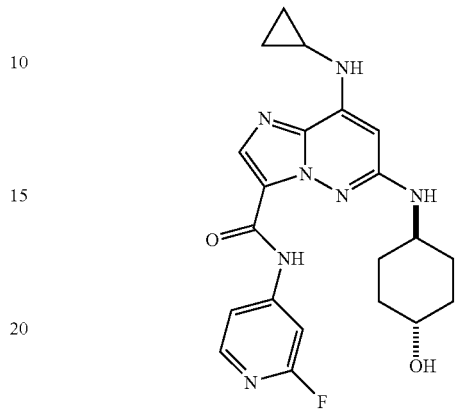

To a ~1:1 mixture of 6,8-dichloro-N-(2-fluoropyridin-4-yl)imidazo[1,2-b]pyridazine-3-carboxamide and 8-bromo-6-chloro-N-(2-fluoropyridin-4-yl)imidazo[1,2-b]pyridazine-3-carboxamide (600 mg, 1.84 mmol) and DIEA (0.482 mL, 2.76 mmol) in THF (10.00 mL) was added cyclopropanamine (158 mg, 2.76 mmol), and the reaction was heated at 80° C. in a sealed tube apparatus for 2 hrs. The reaction mixture was concentrated, dissolved in NMP (5 mL), and trans-4-aminocyclohexanol (4238 mg, 36.8 mmol) was added. The reaction mixture was heated at 100° C. for 24 hrs, and purified using preparative HPLC (Phenomenex Axia Luna 5 micron 30×100 mm) with 40% to 100% MeOH (0.1% TFA) in water (0.1% TFA)) to isolate the title compound, 8-(cyclopropylamino)-N-(2-fluoro-4-pyridinyl)-6-((trans-4-hydroxycyclohexyl)amino)imidazo[1,2-b]pyridazine-3-carboxamide (179 mg, 0.421 mmol, 22.87% yield), as a white solid. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA) Rt=1.722 (M+H=426.15). $^1$H NMR (400 MHz, DMSO-$d_6$) δ ppm 11.51 (1H, s), 8.19 (1H, d, J=5.52 Hz), 7.96 (1H, s), 7.60 (1H, s), 7.41-7.57 (2H, m), 6.94 (1H, d, J=7.28 Hz), 5.99 (1H, s), 4.60 (1H, d, J=4.02 Hz), 3.67 (1H, br. s.), 3.47 (1H, br. s.), 2.08 (2H, br. s.), 1.88 (2H, d, J=2.76 Hz), 1.15-1.45 (4H, m), 0.70-0.89 (2H, m), 0.52-0.71 (2H, m).

Example 14

8-(cyclopropylamino)-6-((trans)-4-(3-pyridin-3-ylureido)cyclohexylamino)-N-(pyrimidin-4-yl)imidazo[1,2-b]pyridazine-3-carboxamide

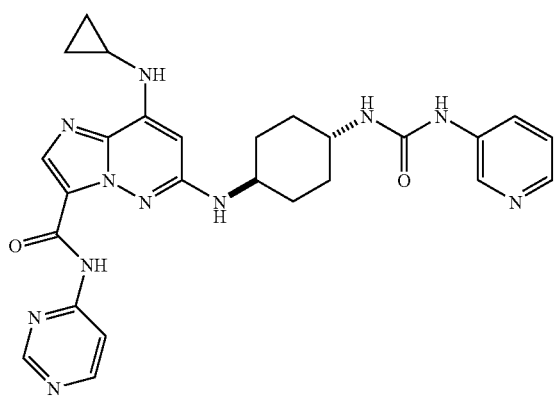

14A. Preparation of 6,8-dichloroimidazo[1,2-b]pyridazine-3-carbonyl chloride and 8-bromo-6-chloroimidazo[1,2-b]pyridazine-3-carbonyl chloride

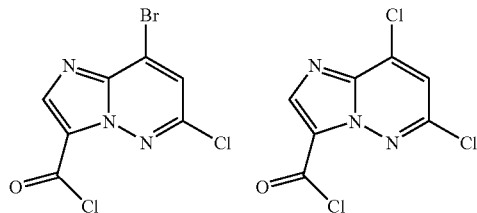 [SMILES: O=C(Cl)c1cnc2c(Br)cc(Cl)nn12 ; O=C(Cl)c1cnc2c(Cl)cc(Cl)nn12]

A mixture 6,8-dichloroimidazo[1,2-b]pyridazine-3-carboxylic acid and 8-bromo-6-chloroimidazo[1,2-b]pyridazine-3-carboxylic acid (2.0 g, 8.62 mmol, 1D.) was suspended in DCE (20 mL), and treated with neat oxalyl chloride (4.37 g, 34.5 mmol) followed by N,N-dimethylformamide (0.534 mL, 6.90 mmol). The reaction mixture was heated at 70° C. for 6 hours, and then concentrated and dried under high vacuum for 1 hr and then taken into the next step without further purification.

14B. Preparation of 6-chloro-8-(cyclopropyl(4-methoxybenzyl)amino)-N-(pyrimidin-4-yl)imidazo[1,2-b]pyridazine-3-carboxamide

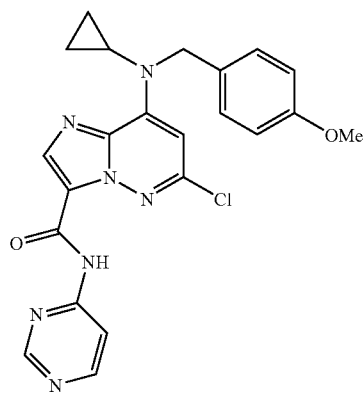 [SMILES: COc1ccc(CN(c2cc(Cl)nn3c(C(=O)Nc4ccncn4)cnc23)C2CC2)cc1]

Pyrimidin-4-amine (251 mg, 2.64 mmol) was added to a ~1:1 mixture of 6,8-dichloroimidazo[1,2-b]pyridazine-3-carbonyl chloride and 8-bromo-6-chloroimidazo[1,2-b]pyridazine-3-carbonyl chloride 14A (600 mg, 2.396 mmol) and TEA (0.334 mL, 2.396 mmol) in DCM (6 mL), and the reaction mixture was stirred at room temperature for 14 hrs. The reaction mixture was filtered via Buchner funnel The solid was washed with water, and dried under high vacuum to isolate 6,8-dichloro-N-(pyrimidin-4-yl)imidazo[1,2-b]pyridazine-3-carboxamide and 8-bromo-6-chloro-N-(pyrimidin-4-yl)imidazo[1,2-b]pyridazine-3-carboxamide as a brown yellow solid (726 mg, 98%), which was taken to next step without further purification. N-(4-methoxybenzyl)cyclopropanamine (381 mg, 2.148 mmol) was added to ~1:1 mixture of 6,8-dichloro-N-(pyrimidin-4-yl)imidazo[1,2-b]pyridazine-3-carboxamide and 8-bromo-6-chloro-N-(pyrimidin-4-yl)imidazo[1,2-b]pyridazine-3-carboxamide (467 mg, 1.432 mmol) and DIEA (0.500 mL, 2.86 mmol) in DMF (10 mL). The reaction mixture was heated at 80° C. for 1.5 hrs. Water (20 mL) was added to the reaction mixture, and the solid was collected via Buchner filtration (with methanol wash) to isolate the title compound 6-chloro-8-(cyclopropyl(4-methoxybenzyl)amino)-N-(2-fluoropyridin-4-yl)imidazo[1,2-b]pyridazine-3-carboxamide 14A (519 mg, 78%) as a light yellow powder. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA) Rt=2.107 (M+H=450.22).

14B. Preparation of 8-(cyclopropylamino)-6-((trans)-4-(3-pyridin-3-ylureido)cyclohexylamino)-N-(pyrimidin-4-yl)imidazo[1,2-b]pyridazine-3-carboxamide

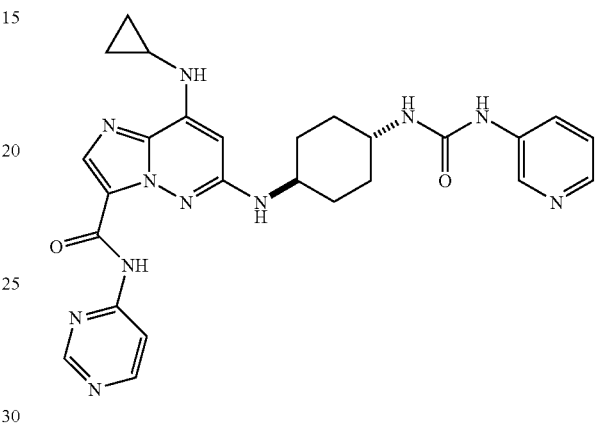

6-Chloro-8-(cyclopropyl(4-methoxybenzyl)amino)-N-(pyrimidin-4-yl)imidazo[1,2-b]pyridazine-3-carboxamide (70 mg, 0.156 mmol) and trans-1,4-diaminocyclohexane (533 mg, 4.67 mmol) were heated together at 160° C. for 1.5 hrs. The reaction mixture was suspended in water, filtered through a Buchner funnel, dried under high vacuum and taken to the next step without further purification. The crude product from the above reaction (40.0 mg, 0.076 mmol) was dissolved in DCM (1 mL) and treated with 3-isocyanatopyridine (9.11 mg, 0.076 mmol). The reaction mixture was stirred at room temperature for 30 minutes, concentrated, and treated with TFA (1.168 mL, 15.16 mmol). The reaction mixture was heated at 70° C. for 1 hr, concentrated and purified by preparative HPLC (Phenomenex Axia Luna 5 micron 30×100 mm) 30% B (Solvent B=90% MeOH-10% $H_2O$-0.1% TFA) to 100% B in A (Solvent A=10% MeOH-90% $H_2O$-0.1% TFA)) to isolate the title compound, 8-(cyclopropylamino)-6-((trans)-4-(3-pyridin-3-ylureido)cyclohexylamino)-N-(pyrimidin-4-yl)imidazo[1,2-b]pyridazine-3-carboxamide (18.4 mg, 46%), as a white solid. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). Rt=1.59 (M+H=528.28). $^1$H NMR (400 MHz, MeOD) δ ppm 9.27 (1H, d, J=2.27 Hz), 9.03 (1H, s), 8.71 (1H, d, J=6.04 Hz), 8.36-8.49 (2H, m), 8.32 (1H, ddd, J=8.69, 2.52, 1.13 Hz), 8.12 (1H, s), 7.95 (1H, dd, J=8.81, 5.54 Hz), 6.11 (1H, s), 3.98 (1H, s), 3.66 (1H, s), 2.60 (1H, ddd, J=6.86, 3.34, 3.15 Hz), 2.22-2.38 (2H, m), 2.08 (2H, d, J=10.58 Hz), 1.73 (2H, dd, J=12.46, 2.64 Hz), 1.31-1.57 (2H, m), 0.80-0.99 (2H, m), 0.55-0.78 (2H, m).

Example 15

6-((trans-4-(D-alanylamino)cyclohexyl)amino)-8-(cyclopropylamino)-N-(6-oxo-1,6-dihydro-4-pyrimidinyl)imidazo[1,2-b]pyridazine-3-carboxamide

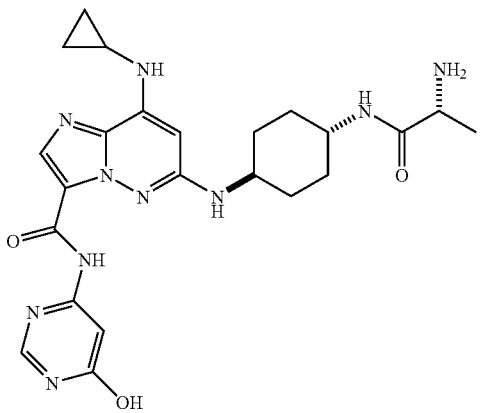

15A. Preparation of 6-(benzyloxy)pyrimidin-4-amine

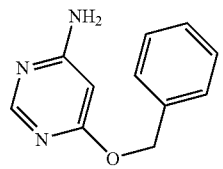 [SMILES: Nc1cc(OCc2ccccc2)ncn1]

6-Chloropyrimidin-4-amine (500 mg, 3.86 mmol) and sodium phenylmethanolate (1 M solution in benzyl alcohol, 4.67 mL, 4.67 mmol) were heated at 120° C. for 16 hrs. 6-(Benzyloxy)pyrimidin-4-amine (210 mg, 27% yield) was isolated as clear oil following HPLC purification (Phenomenex Axia Luna 5 micron 30×100 mm) 30% B (Solvent B=90% MeOH-10% H₂O-0.1% TFA) to 100% B in A (Solvent A=10% MeOH-90% H₂O-0.1% TFA). The purified material (a TFA salt) was converted to its free base by dissolving in ethyl acetate (20 mL) and washing with saturated NaHCO₃ (20 mL) for use in the next step. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). Rt=0.96 (M+H=202.24).

15B. Preparation of N-(6-(benzyloxy)pyrimidin-4-yl)-6,8-dichloroimidazo[1,2-b]pyridazine-3-carboxamide and N-(6-(benzyloxy)pyrimidin-4-yl)-8-bromo-6-chloroimidazo[1,2-b]pyridazine-3-carboxamide

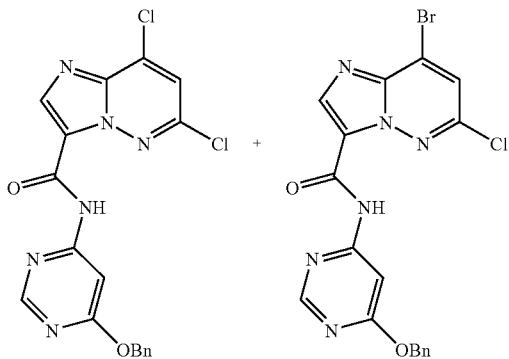 [SMILES: O=C(Nc1cc(OCc2ccccc2)ncn1)c1cnc2c(Cl)cc(Cl)nn12 ; O=C(Nc1cc(OCc2ccccc2)ncn1)c1cnc2c(Br)cc(Cl)nn12]

6-(Benzyloxy)pyrimidin-4-amine (56.2 mg, 0.279 mmol) was added to a ~1:1 mixture of 6,8-dichloroimidazo[1,2-b]pyridazine-3-carbonyl chloride and 8-bromo-6-chloroimidazo[1,2-b]pyridazine-3-carbonyl chloride (prepared as shown in Example 1, 70 mg, 0.28 mmol) and TEA (0.33 mL, 2.4 mmol) in DCM (3 mL) and heated at 40° C. for 3 hrs. The reaction mixture was purified with ISCO chromatography (stepwise gradient 0 to 5% methanol in DCM) to isolate a ~1:1 mixture of N-(6-(benzyloxy)pyrimidin-4-yl)-6,8-dichloroimidazo[1,2-b]pyridazine-3-carboxamide and N-(6-(benzyloxy)pyrimidin-4-yl)-8-bromo-6-chloroimidazo[1,2-b]pyridazine-3-carboxamide (51 mg, 43.9%) as a light yellow solid. LC/MS (Phenomenex Luna 5 micron C18 4.6× 30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). Rt=1.96 (M+H=415.12).

15C. Preparation of N-(6-(benzyloxy)pyrimidin-4-yl)-6-chloro-8-(cyclopropylamino)imidazo[1,2-b]pyridazine-3-carboxamide

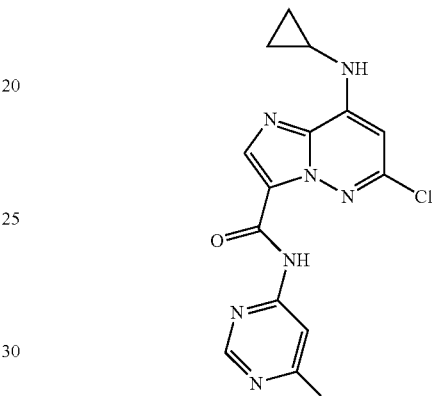

A ~1:1 mixture of N-(6-(benzyloxy)pyrimidin-4-yl)-6,8-dichloroimidazo[1,2-b]pyridazine-3-carboxamide and N-(6-(benzyloxy)pyrimidin-4-yl)-8-bromo-6-chloroimidazo[1,2-b]pyridazine-3-carboxamide (279 mg, 0.672 mmol), cyclopropanamine (57.5 mg, 1.008 mmol) and DIEA (0.319 mL, 1.826 mmol) in THF (5 mL) were heated in sealed tube apparatus at 80° C. for 2 hrs. The reaction mixture was concentrated, triturated with ether, and N-(6-(benzyloxy)pyrimidin-4-yl)-6-chloro-8-(cyclopropylamino)imidazo[1,2-b]pyridazine-3-carboxamide (217 mg, 0.498 mmol, 74.1% yield) was isolated as a white solid following a Buchner filtration. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/ 0.1% TFA; Solvent B: 10% water/90% methanol/0.1% TFA) Rt=2.217 (M+H=436.12).

15D. Preparation of 6-((trans)-4-aminocyclohexylamino)-N-(6-(benzyloxy)pyrimidin-4-yl)-8-(cyclopropylamino)imidazo[1,2-b]pyridazine-3-carboxamide

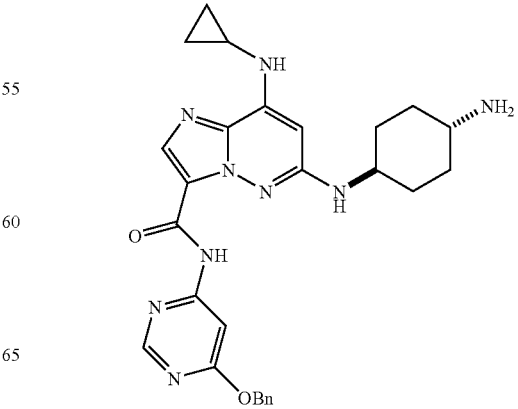

N-(6-(benzyloxy)pyrimidin-4-yl)-6-chloro-8-(cyclopropylamino)imidazo[1,2-b]pyridazine-3-carboxamide (70 mg, 0.161 mmol) and trans-1,4-diaminocyclohexane (367 mg, 3.21 mmol) were heated at 160° C. for 2 hrs. The reaction mixture was diluted with methanol and purified by preparative HPLC (Phenomenex Axia Luna 5 micron 30×100 mm) 10% B (Solvent B=90% MeOH-10% H$_2$O-0.1% TFA) to 100% B in A (Solvent A=10% MeOH-90% H$_2$O-0.1% TFA)) to isolate 6-((trans)-4-aminocyclohexylamino)-N-(6-(benzyloxy)pyrimidin-4-yl)-8-(cyclopropylamino)imidazo[1,2-b]pyridazine-3-carboxamide (37 mg, 0.072 mmol, 44.9% yield) as light yellow solid. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA) Rt=1.818 (M+H=514.25).

15E. Preparation of 6-((trans-4-(D-alanylamino)cyclohexyl)amino)-8-(cyclopropylamino)-N-(6-oxo-1,6-dihydro-4-pyrimidinyl)imidazo[1,2-b]pyridazine-3-carboxamide

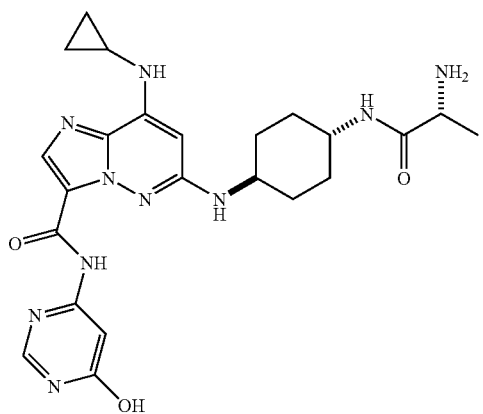

BOP (129 mg, 0.292 mmol) was added to a solution of 6-((trans)-4-aminocyclohexylamino)-N-(6-(benzyloxy)pyrimidin-4-yl)-8-(cyclopropylamino)imidazo[1,2-b]pyridazine-3-carboxamide (50.0 mg, 0.097 mmol), DIEA (0.068 mL, 0.39 mmol) and (R)-2-(tert-butoxycarbonylamino)propanoic acid (36.8 mg, 0.195 mmol) in DCM (1 mL). The clear reaction mixture was stirred at room temperature for 30 min and concentrated. TFA (0.450 mL, 5.84 mmol) was added, and the reaction mixture was heated at 70° C. for 1 hr. The reaction mixture was diluted in methanol and purified with HPLC (Phenomenex Axia Luna 5 micron 30×100 mm) 10% B (Solvent B=90% MeOH-10% H$_2$O-0.1% TFA) to 100% B in A (Solvent A=10% MeOH-90% H$_2$O-0.1% TFA)) to isolate the title compound, 6-((trans-4-(D-alanylamino)cyclohexyl)amino)-8-(cyclopropylamino)-N-(6-oxo-1,6-dihydro-4-pyrimidinyl)imidazo[1,2-b]pyridazine-3-carboxamide, as a white solid (26 mg, 0.053 mmol, 54.0% yield). LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA) Rt=1.393 (M+H=495.16).). $^1$H NMR (400 MHz, DMSO-d$_6$) δ ppm 12.56 (1H, br. s.), 11.73 (1H, s), 8.29 (1H, d, J=7.78 Hz), 8.18 (1H, s), 8.06 (3H, d, J=4.27 Hz), 7.90-8.00 (1H, m), 7.61 (1H, s), 7.05 (1H, s), 7.00 (1H, d, J=7.78 Hz), 5.96 (1H, s), 3.68-3.92 (2H, m), 3.46-3.69 (1H, m), 2.10 (2H, d, J=10.54 Hz), 1.82 (2H, d, J=2.51 Hz), 1.43-1.69 (2H, m), 1.16-1.43 (5H, m), 0.69-0.86 (2H, m), 0.51-0.70 (2H, m).

Example 16

6-((trans-4-aminocyclohexyl)amino)-N-(3-fluoro-4-pyridinyl)-8-((5-fluoro-2-pyridinyl)amino)imidazo[1,2-b]pyridazine-3-carboxamide

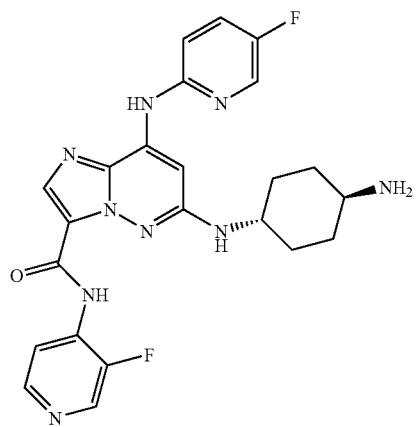 [SMILES: N[C@H]1CC[C@H](Nc2cc(Nc3ccc(F)cn3)c3ncc(C(=O)Nc4ccncc4F)n3n2)CC1]

16A. Preparation of 6-chloro-8-(5-fluoropyridin-2-ylamino)-N-(3-fluoropyridin-4-yl)imidazo[1,2-b]pyridazine-3-carboxamide

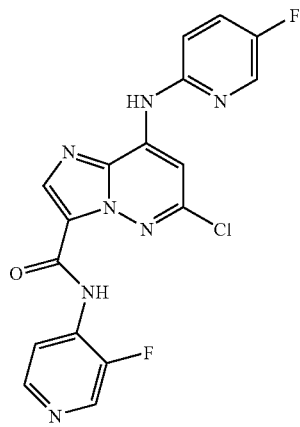 [SMILES: O=C(Nc1ccncc1F)c1cnc2c(Nc3ccc(F)cn3)cc(Cl)nn12]

To a solution of 5-fluoropyridin-2-amine (20.63 mg, 0.184 mmol) in DMF (1 mL) was added 60% NaH (7.36 mg, 0.184 mmol). The mixture was stirred for 10 min until cessation of H$_2$ evolution. 8A (24 mg, 0.074 mmol) was added. The mixture was stirred at room temperature overnight. Water was added, and the yellow solid was collected by filtration and dried to give 16A (25.2 mg, 57%). [M+H]=4 01. HPLC Peak Rt=3.345 minutes (Chromolith column 4.6×50 mm eluting 16B. Preparation of 6-((trans-4-aminocyclohexyl)amino)-N-(3-fluoro-4-pyridinyl)-8-((5-fluoro-2-pyridinyl)amino)imidazo[1,2-b]pyridazine-3-carboxamide

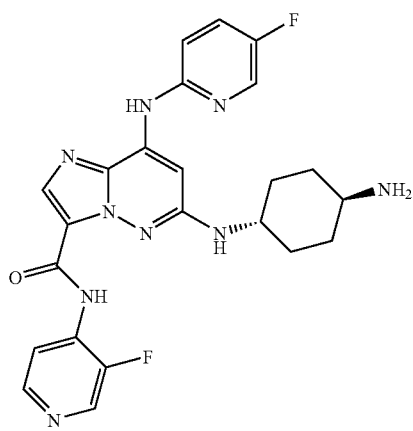 [SMILES: N[C@H]1CC[C@H](Nc2cc(Nc3ccc(F)cn3)c3ncc(C(=O)Nc4ccncc4F)n3n2)CC1]

A mixture of 16A (25 mg, 0.042 mmol) and trans-cyclohexane-1,4-diamine (47.6 mg, 0.417 mmol) in NMP (0.7 mL) was heated at 110° C. overnight. The reaction mixture was cooled to room temperature, diluted with MeOH and purified by preparative HPLC. The desired fraction was concentrated to give the TFA salt of 16B as light a brown solid (23.6 mg, 68%). [M+H]=480. HPLC Peak Rt=2.673 minutes. (Chromolith column 4.6×50 mm eluting with 10-90% aqueous methanol over 4 minutes containing 0.1% TFA, 4 mL/min, monitoring at 220 nm.)

Example 17

6-((trans-4-aminocyclohexyl)amino)-N-(3-fluoro-4-pyridinyl)-8-(6-(4-methyl-1-piperazinyl)-2-pyridinyl)amino)imidazo[1,2-b]pyridazine-3-carboxamide

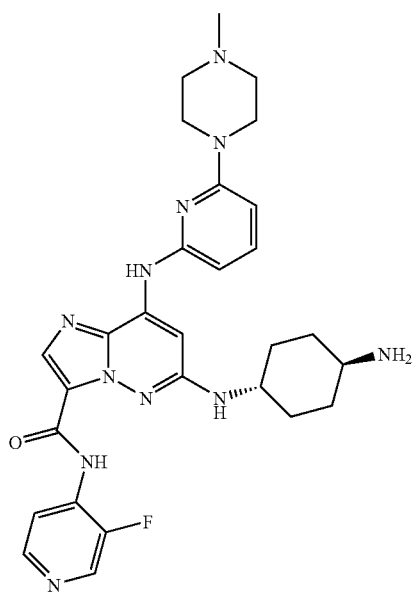 [SMILES: CN1CCN(c2cccc(Nc3cc(N[C@H]4CC[C@H](N)CC4)nn4c(C(=O)Nc5ccncc5F)cnc34)n2)CC1]

17A. Preparation of 8-(6-bromopyridin-2-ylamino)-6-chloro-N-(3-fluoropyridin-4-yl)imidazo[1,2-b]pyridazine-3-carboxamide To a solution of 6-bromopyridin-2-amine (1.24 g, 7.17 mmol) in THF (10.00 mL) was added 60% NaH (294 mg, 7.35 mmol). The mixture was stirred for 30 min until cessation $H_2$ evolution. The resulting dark green solution was added by syringe to a suspension of 8A (800 mg, 2.453 mmol) in DMF (10 mL). The reaction mixture was stirred at room temperature overnight, and then added to ice water. The brown solid was collected by filtration and dried under vacuum to give 17A (1.125 g, 89%) MS (m+1)=462. HPLC Peak Rt=3.696 minutes (Chromolith column 4.6×50 mm eluting with 10-90% aqueous methanol over 4 minutes containing 0.1% TFA, 4 mL/min, monitoring at 220 nm).

17B. Preparation 6-(trans-4-aminocyclohexylamino)-8-(6-bromopyridin-2-ylamino)-N-(3-fluoropyridin-4-yl)imidazo[1,2-b]pyridazine-3-carboxamide

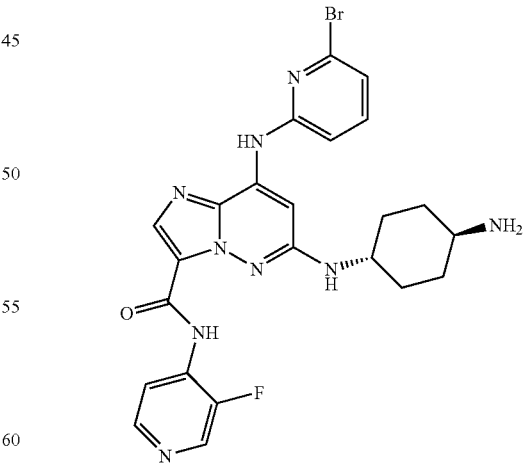

A mixture of 8-(6-bromopyridin-2-ylamino)-6-chloro-N-(3-fluoropyridin-4-yl)imidazo[1,2-b]pyridazine-3-carboxamide 17A (550 mg, 1.189 mmol) and trans-cyclohexane-1,4-diamine (1.086 g, 9.51 mmol) in NMP (4 mL) was heated at 100° C. overnight. The reaction mixture was cooled to room temperature, and then added to ice water. The yellow solid was collected by filtration, and rinsed with water. The still wet solid pad was azeotroped with DCM/MeOH three times. The resulting solid residue was treated with a small amount of MeOH, filtered and dried to give 17B (456 mg, 71%) as a yellow solid. MS (m+1)=540. HPLC Peak Rt=2.870 minutes. (Chromolith column 4.6×50 mm eluting with 10-90% aqueous methanol over 4 minutes containing 0.1% TFA, 4 mL/min, monitoring at 220 nm).

17C. Preparation of 6-((trans-4-aminocyclohexyl)amino)-N-(3-fluoro-4-pyridinyl)-8-((6-(4-methyl-1-piperazinyl)-2-pyridinyl)amino)imidazo[1,2-b]pyridazine-3-carboxamide

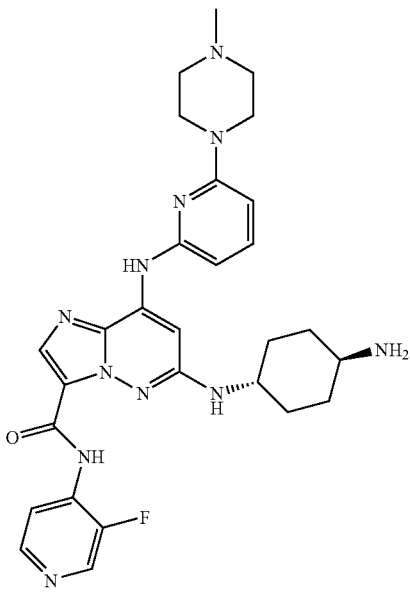 [SMILES: CN1CCN(c2cccc(Nc3cc(N[C@H]4CC[C@H](N)CC4)nn4c(C(=O)Nc5ccncc5F)cnc34)n2)CC1]

A mixture of 6-((trans-4-aminocyclohexylamino)-8-(6-bromopyridin-2-ylamino)-N-(3-fluoropyridin-4-yl)imidazo[1,2-b]pyridazine-3-carboxamide 17B (35.0 mg, 0.065 mmol) and 1-methylpiperazine (32.4 mg, 0.324 mmol) in NMP (0.4 mL) was heated to 120° C. overnight. The reaction mixture was cooled to room temperature and purified by preparative HPLC. The desired fraction was concentrated and lyophilized to give 17C (23.9 mg, 40%) as light yellow solid. [M+H]=560. HPLC Peak Rt=2.313 minutes. (Chromolith column 4.6×50 mm eluting with 10-90% aqueous methanol over 4 minutes containing 0.1% TFA, 4 mL/min, monitoring at 220 nm.)

Example 18

6-((trans-4-aminocyclohexyl)amino)-N-(3-fluoro-4-pyridinyl)-8-((1-methyl-1H-pyrazol-3-yl)amino)imidazo[1,2-b]pyridazine-3-carboxamide

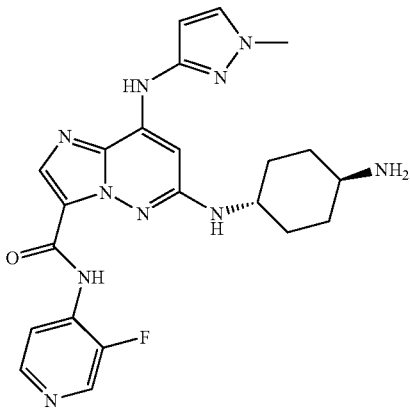 [SMILES: Cn1ccc(Nc2cc(N[C@H]3CC[C@H](N)CC3)nn3c(C(=O)Nc4ccncc4F)cnc23)n1]

18A. Preparation of 6-chloro-N-(3-fluoropyridin-4-yl)-8-(1-methyl-1H-pyrazol-3-ylamino)imidazo[1,2-b]pyridazine-3-carboxamide

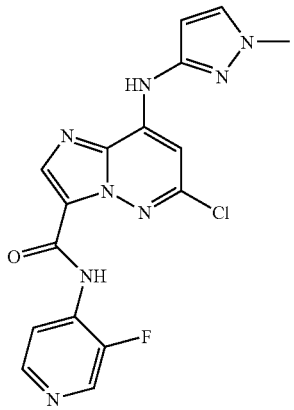 [SMILES: Cn1ccc(Nc2cc(Cl)nn3c(C(=O)Nc4ccncc4F)cnc23)n1]

To a solution of 1-methyl-1H-pyrazol-3-amine (37.2 mg, 0.383 mmol) in DMF (0.8 mL) was added 60% NaH (14.10 mg, 0.353 mmol). The mixture was stirred for 10 min. Solid 8A (50 mg, 0.153 mmol) was added in one portion. The reaction mixture was stirred at room temperature for 3 h. Methanol (5 mL) was added and a solid precipitated that was collected by filtration and dried to give 18A (26 mg, 37%) as an off white solid. [M+H]=387. HPLC Peak Rt=2.753 minutes. (Chromolith column 4.6×50 mm eluting with 10-90% aqueous methanol over 4 minutes containing 0.1% TFA, 4 mL/min, monitoring at 254 nm.)

18B. Preparation of 6-((trans-4-aminocyclohexyl)amino)-N-(3-fluoro-4-pyridinyl)-8-((1-methyl-1H-pyrazol-3-yl)amino)imidazo[1,2-b]pyridazine-3-carboxamide

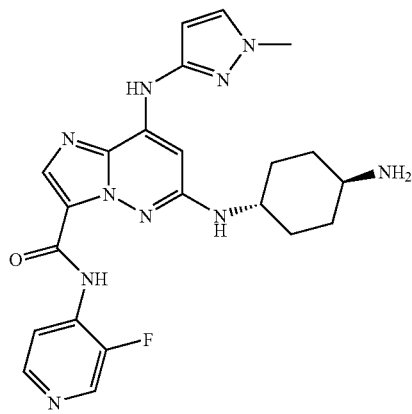 [SMILES: Cn1ccc(Nc2cc(N[C@H]3CC[C@H](N)CC3)nn3c(C(=O)Nc4ccncc4F)cnc23)n1]

A mixture of 6-chloro-N-(3-fluoropyridin-4-yl)-8-(1-methyl-1H-pyrazol-3-ylamino)imidazo[1,2-b]pyridazine-3-carboxamide 18A (19.9 mg, 0.044 mmol) and trans-cyclohexane-1,4-diamine (47.6 mg, 0.417 mmol) in NMP (0.7 mL) was heated at 110° C. overnight. The reaction mixture was cooled to room temperature and purified by preparative HPLC. The desired fraction was concentrated and lyophilized to give 18B (14.9 mg, 40%) as a brown solid. [M+H]=465. HPLC Peak Rt=2.263 minutes. (Chromolith column 4.6×50 mm eluting with 10-90% aqueous methanol over 4 minutes containing 0.1% TFA, 4 mL/min, monitoring at 220 nm.)

Example 19

8-acetamido-6-((trans-4-aminocyclohexyl)amino)-N-(3-fluoro-4-pyridinyl)imidazo[1,2-b]pyridazine-3-carboxamide

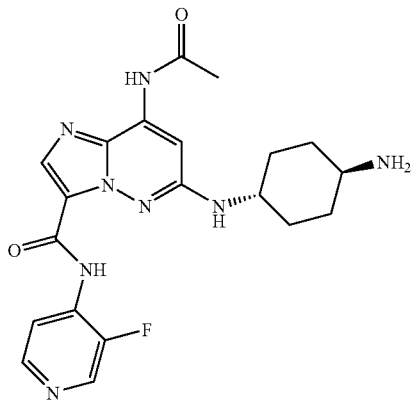 [SMILES: CC(=O)Nc1cc(N[C@H]2CC[C@H](N)CC2)nn2c(C(=O)Nc3ccncc3F)cnc12]

19A. Preparation of 6-chloro-N-(3-fluoropyridin-4-yl)-8-(4-methoxybenzylamino)imidazo[1,2-b]pyridazine-3-carboxamide

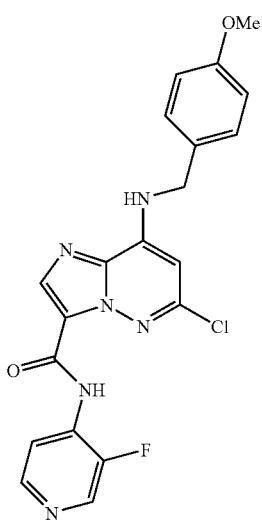 [SMILES: COc1ccc(CNc2cc(Cl)nn3c(C(=O)Nc4ccncc4F)cnc23)cc1]

To a suspension of 8A (300 mg, 0.920 mmol) in NMP (2 mL) was added (4-methoxyphenyl)methanamine (0.120 mL, 0.920 mmol) and DIEA (0.161 mL, 0.920 mmol). The reaction mixture was stirred at 80° C. for 1 h, and then cooled to room temperature. Water was added. The light yellow solid was collected by filtration, rinsed with water and dried under vacuum to give 19A (348 mg, 89%). [M+H]=426. HPLC Peak Rt=3.000 minutes. (Chromolith column 4.6×50 mm eluting with 10-90% aqueous methanol over 4 minutes containing 0.1% TFA, 4 mL/min, monitoring at 254 nm.)

19B. Preparation of 6-chloro-N-(3-fluoropyridin-4-yl)-8-(N-(4-methoxybenzyl)acetamido)imidazo[1,2-b]pyridazine-3-carboxamide

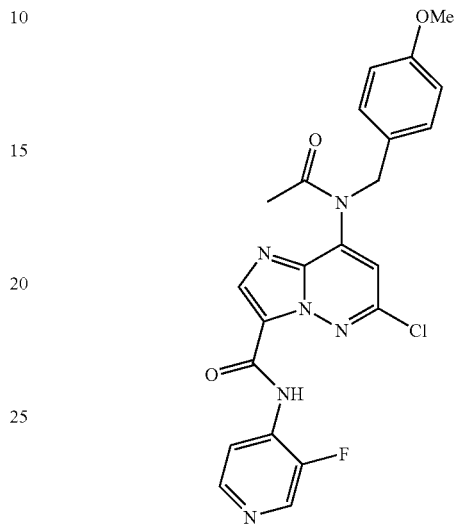

To a solution of 6-chloro-N-(3-fluoropyridin-4-yl)-8-(4-methoxybenzylamino)imidazo[1,2-b]pyridazine-3-carboxamide 19A (80 mg, 0.187 mmol) in DMF (2 mL) was added 60% NaH (18.74 mg, 0.469 mmol). The mixture was stirred for 20 minutes and then a solution of acetyl chloride (0.038 mL, 0.540 mmol) in DMF (0.4 mL) was added, and the mixture was stirred for 30 min. The reaction mixture was quenched with sat. NH$_4$Cl. The light brown solid was collected by filtration, washed with water and dried under vacuum to give 19B (78 mg, 89%). {M+H]=469. HPLC Peak Rt=2.303 minutes (Chromolith column 4.6×50 mm eluting with 10-90% aqueous methanol over 4 minutes containing 0.1% TFA, 4 mL/min, monitoring at 220 nm.)

19C. Preparation of 8-acetamido-6-((trans-4-aminocyclohexyl)amino)-N-(3-fluoro-4-pyridinyl)imidazo[1,2-b]pyridazine-3-carboxamide

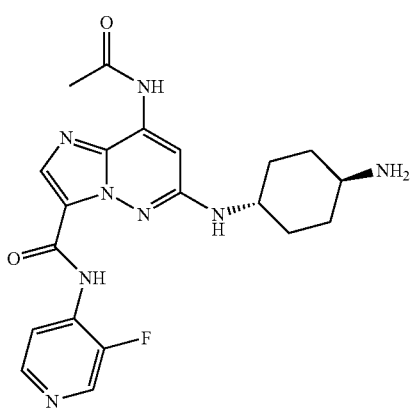 [SMILES: CC(=O)Nc1cc(N[C@H]2CC[C@H](N)CC2)nn2c(C(=O)Nc3ccncc3F)cnc12]

A solution of 6-chloro-N-(3-fluoropyridin-4-yl)-8-(N-(4-methoxybenzyl)acetamido)imidazo[1,2-b]pyridazine-3-carboxamide 19B (30 mg, 0.064 mmol) and trans-cyclohexane-1,4-diamine (14.61 mg, 0.128 mmol) in NMP (0.5 mL) was heated at 70° C. for 2.5 h, and then cooled to room temperature. Water was added. The mixture was extracted with EtOAc for three times, the combined extracts were washed with H$_2$O and brine, and then concentrated. The resulting residue was treated with MeOH. The solid was filtered off, and the filtrate was purified by preparative HPLC. The desired fraction was concentrated to dryness and then dissolved in TFA (1 mL). The solution was stirred at 70° C. for 6 h and then concentrated. The residue was treated with MeOH/DCM, and concentrated again to give a solid, which was triturated with ether. The solid was collected by filtration, rinsed with ether, and dried under vacuum to give 19C (7.3 mg, 21%) as an off white solid. [M+H]=427. HPLC Peak Rt=2.018 minutes. (Chromolith column 4.6×50 mm eluting with 10-90% aqueous methanol over 4 minutes containing 0.1% TFA, 4 mL/min, monitoring at 220 nm.)

Example 20

6-((trans-4-aminocyclohexyl)amino)-N-(3-fluoro-4-pyridinyl)-8-((methylsulfonyl)amino)imidazo[1,2-b]pyridazine-3-carboxamide

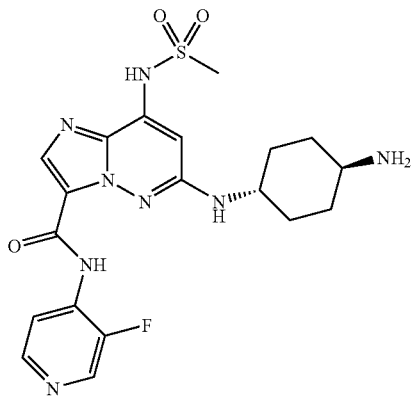 [SMILES: CS(=O)(=O)Nc1cc(N[C@H]2CC[C@H](N)CC2)nn2c(C(=O)Nc3ccncc3F)cnc12]

20A. Preparation of 6-(trans-4-aminocyclohexylamino)-N-(3-fluoropyridin-4-yl)-8-(N-(4-methoxybenzyl)methylsulfonamido)imidazo[1,2-b]pyridazine-3-carboxamide

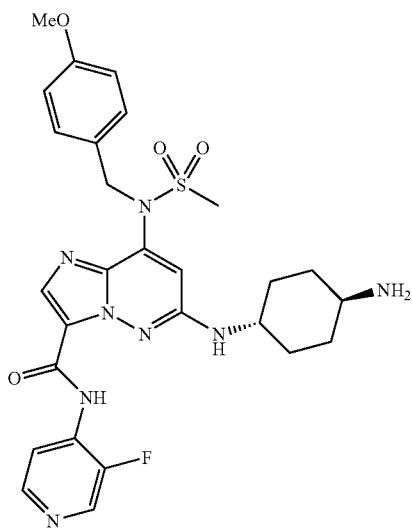 [SMILES: COc1ccc(CN(c2cc(N[C@H]3CC[C@H](N)CC3)nn3c(C(=O)Nc4ccncc4F)cnc23)S(C)(=O)=O)cc1]

To a solution of 6-chloro-N-(3-fluoropyridin-4-yl)-8-(4-methoxybenzylamino)imidazo[1,2-b]pyridazine-3-carboxamide 19A (50 mg, 0.117 mmol) in DMF (1.3 mL) was added 60% NaH (9.37 mg, 0.234 mmol). The mixture was stirred for 15 min. A solution of methanesulfonyl chloride (10.88 μL, 0.141 mmol) in DMF (0.2 mL) was added dropwise. The resulting mixture was stirred at room temperature for 20 minutes and then quenched with saturated aqueous NH$_4$Cl, and extracted with EtOAc. The combined extracts were washed with water and brine, dried over MgSO$_4$, concentrated, and purified by ISCO (12 g, 2% MeOH/DCM) to give 35 mg of a white solid. A mixture of the solid and trans-cyclohexane-1,4-diamine (39.6 mg, 0.347 mmol) in NMP (0.4 mL) was heated at 70° C. for 30 minutes and then cooled to room temperature and purified by preparative HPLC. The desired fraction was concentrated to dryness, and dried in vacuum over night to give 20A (30 mg, 31%). [M+H]=583. HPLC Peak Rt=2.368 minutes. (Chromolith column 4.6×50 mm eluting with 10-90% aqueous methanol over 4 minutes containing 0.1% TFA, 4 mL/min, monitoring at 220 nm.)

20B. Preparation of 6-((trans-4-aminocyclohexyl)amino)-N-(3-fluoro-4-pyridinyl)-8-((methylsulfonyl)amino)imidazo[1,2-b]pyridazine-3-carboxamide

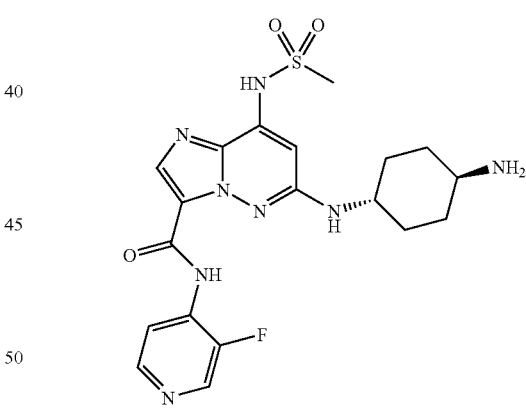

A mixture of 6-(trans-4-aminocyclohexylamino)-N-(3-fluoropyridin-4-yl)-8-(N-(4-methoxybenzyl)methylsulfonamido)imidazo[1,2-b]pyridazine-3-carboxamide (30 mg, 0.037 mmol) in TFA (1 mL) was heated to 80° C. for 1.5 h. The reaction mixture was concentrated and evaporated from DCM/MeOH to give 20B (26 mg, 102%) as a white solid. [M+H]=463. HPLC Peak Rt=1.758 minutes. (Chromolith column 4.6×50 mm eluting with 10-90% aqueous methanol over 4 minutes containing 0.1% TFA, 4 mL/min, monitoring at 220 nm.)

A 1-dram vial equipped with a stir bar and septum cap was charged with dioxane (0.767 mL) and the solvent was degassed by bubbling argon through it with vigorous stirring for 10 min. 5A (0.050 g, 0.153 mmol), 6-aminonicotinonitrile (0.022 g, 0.184 mmol), cesium carbonate (0.100 g, 0.307 mmol), Xantphos (4.44 mg, 7.67 μmol), and Pd$_2$(dba)$_3$ (7.02 mg, 7.67 μmol) were added to the degassed solvent in one portion, and the resulting dark brown suspension was pump/purged with argon three times. The mixture was then heated to 100° C. for 24 h. The suspension was cooled to room temperature and then triturated with water. The resulting olive green suspension, was carefully filtered through a medium-porosity frit. The solid was collected, suspended in THF, and azeotroped with PhMe to remove residual water and MeOH. The crude solid was suspended in NMP (0.767 mL) and (trans)-cyclohexane-1,4-diamine (0.210 g, 1.840 mmol) was added. The resulting brown suspension was irradiated in a CEM Discover 300 W microwave at 110° C. for 20 min. Upon cooling, the mixture was diluted with DMF and purified via preparatory HPLC using a YMC ODS C-18 column (30×250 mm) 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 60 min, flow rate 25 mL/min. Rt=48.454 min. The appropriate fractions were concentrated and lyophilized overnight, and 6-((trans)-4-aminocyclohexylamino)-8-(5-cyanopyridin-2-ylamino)-N-(3-fluoropyridin-4-yl)imidazo[1,2-b]pyridazine-3-carboxamide (0.006 g, 6.11 μmol, 3.99% yield) was obtained as a light tan lyophile. HPLC: Rt=3.445 min. YMC S5 ODS-A column (4.6×50 mm) 0%-100% B. Solvent B: (90% MeOH, 10% H$_2$O, 0.2% H$_3$PO$_4$). Solvent A: (10% MeOH, 90% H$_2$O, 0.2% H$_3$PO$_4$). Gradient, start % B=0, final % B=100, gradient time 4 min, hold at 100% 1 min, flow rate 4 mL/min. MS: [M+H]=487.1. $^1$H NMR (400 MHz, DMSO-D6) δ ppm 11.16 (1H, s), 10.48 (1H, s), 8.75 (1H, d, J=2.01 Hz), 8.65 (1H, d, J=2.52 Hz), 8.44-8.50 (1H, m), 8.40-8.44 (1H, m), 8.17 (1H, d, J=2.27 Hz), 8.13-8.16 (1H, m), 7.97 (1H, s), 7.81 (2H, s), 7.65 (1H, d, J=8.81 Hz), 7.45 (1H, s), 3.83 (1H, s), 3.07 (1H, s), 2.12 (2H, s), 1.95 (2H, d, J=1.01 Hz), 1.26-1.47 (4H, m).

Example 22

6-(6-((trans)-4-aminocyclohexylamino)-3-(3-fluoro-pyridin-4-ylcarbamoyl)imidazo[1,2-b]pyridazin-8-ylamino)nicotinic acid

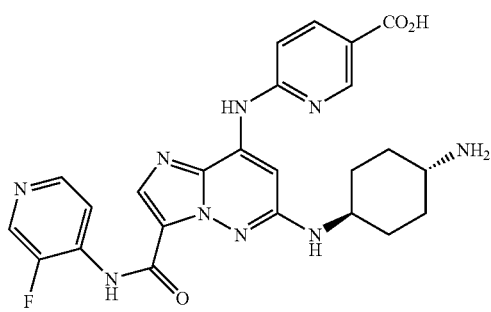 [SMILES: N[C@H]1CC[C@H](Nc2cc(Nc3ccc(C(=O)O)cn3)c3ncc(C(=O)Nc4ccncc4F)n3n2)CC1]

To a suspension of 5A (0.050 g, 0.153 mmol) and methyl 6-aminonicotinate (0.028 g, 0.184 mmol) in THF (0.767 mL) at room temperature was added potassium tert-butoxide (0.337 mL, 0.337 mmol). The resulting suspension was stirred 2 h at room temperature. The solvent was then removed via a stream of nitrogen. The solid was taken up in NMP (0.767 mL), (trans)-cyclohexane-1,4-diamine (0.210 g, 1.840 mmol) was added, and the mixture was heated to 110° C. in a CEM Discover 300 W microwave for 20 min. Analysis of the mixture by HPLC and LC/MS indicates a mixture of free acid and hydroxylation at C8. The mixture was diluted with DMF and purified via preparatory HPLC using a YMC ODS C-18 column (30×250 mm), 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 60 min, flow rate 25 mL/min. Rt=48.545 min. The appropriate fractions were concentrated and lyophilized overnight, and 6-(6-((trans)-4-aminocyclohexylamino)-3-(3-fluoropyridin-4-ylcarbamoyl)imidazo[1,2-b]pyridazin-8-ylamino)nicotinic acid, 3 TFA (7.4 mg, 8.29 μmol, 5.41% yield) was obtained as a white lyophile. HPLC: Rt=3.466 min. YMC S5 ODS-A column (4.6×50 mm) 0%-100% B. Solvent B: (90% MeOH, 10% H$_2$O, 0.2% H$_3$PO$_4$). Solvent A: (10% MeOH, 90% H$_2$O, 0.2% H$_3$PO$_4$). Gradient, start % B=0, final % B=100, gradient time 4 min, hold at 100% 1 min, flow rate 4 mL/min. MS: [M+H]=506.1. $^1$H NMR (400 MHz, DMSO-D6) δ ppm 11.20 (1H, s), 10.31 (1H, s), 8.85 (1H, d, J=2.27 Hz), 8.70 (1H, d, J=1.26 Hz), 8.45-8.51 (1H, m), 8.43 (1H, s), 8.12-8.19 (1H, m), 8.07 (1H, s), 7.93 (2H, s), 7.58 (1H, d, J=8.56 Hz), 7.24 (1H, s), 7.11 (1H, s), 6.99 (1H, s), 3.79-3.93 (1H, m), 3.00-3.13 (1H, m), 2.05-2.18 (2H, m), 1.97 (2H, s), 1.47 (2H, s), 1.33 (2H, s).

Example 23

6-((trans)-4-aminocyclohexylamino)-N-(2-chloropyridin-4-yl)-8-(cyclopropylamino)imidazo[1,2-b]pyridazine-3-carboxamide

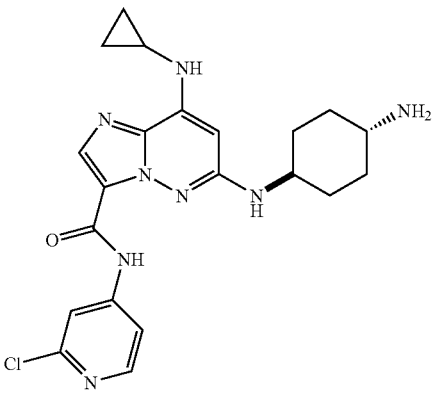 [SMILES: N[C@H]1CC[C@H](Nc2cc(NC3CC3)c3ncc(C(=O)Nc4ccnc(Cl)c4)n3n2)CC1]

23A. Preparation of 6,8-dichloro-N-(2-chloropyridin-4-yl)imidazo[1,2-b]pyridazine-3-carboxamide and 8-bromo-6-chloro-N-(2-chloropyridin-4-yl)imidazo[1,2-b]pyridazine-3-carboxamide

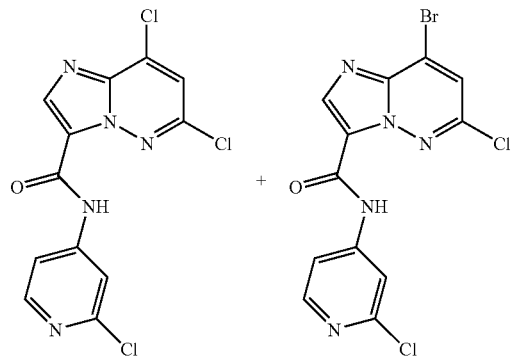 [SMILES: O=C(Nc1ccnc(Cl)c1)c1cnc2c(Cl)cc(Cl)nn12 ; O=C(Nc1ccnc(Cl)c1)c1cnc2c(Br)cc(Cl)nn12]

A ~1:1 mixture 6,8-dichloroimidazo[1,2-b]pyridazine-3-carboxylic acid and 8-bromo-6-chloroimidazo[1,2-b]pyridazine-3-carboxylic acid (6.57 g, 28.3) was suspended in DCE (140 mL), and treated with neat oxalyl chloride (5.52 g, 42.5 mmol) followed by N,N-dimethylformamide (0.207 g, 2.83 mmol). The reaction mixture was heated at 65° C. for 5 hours, concentrated and dried under high vacuum for 1 hr and taken into the next step without further purification. The crude mixture of acid chloride was suspended in DCE (100 mL) and treated with 2-chloropyridin-4-amine (4.37 g, 34.0 mmol) and N,N-diisopropylethylamine (5.49 g, 42.5 mmol) and stirred at room temperature for 2 hours. The reaction mixture was filtered through a Buchner funnel, and washed with DCE (2×25 mL) to isolate a 1:1 mixture of 6,8-dichloro-N-(2-chloropyridin-4-yl)imidazo[1,2-b]pyridazine-3-carboxamide and 8-bromo-6-chloro-N-(2-chloropyridin-4-yl)imidazo[1,2-b]pyridazine-3-carboxamide (7.7 g, 22.5 mmol, 79% yield) as a light brown solid. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA) Rt=1.51 minutes. [M+H[=343.84, and [M+H[=387.8.

23B. Preparation of 6-chloro-N-(2-chloropyridin-4-yl)-8-(cyclopropyl(4-methoxybenzyl)amino)imidazo[1,2-b]pyridazine-3-carboxamide

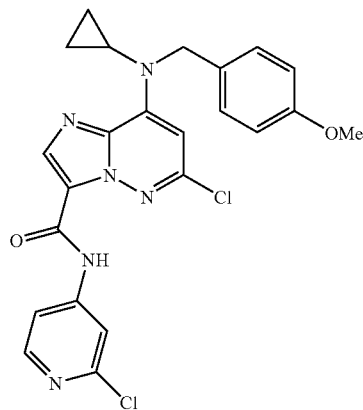 [SMILES: COc1ccc(CN(c2cc(Cl)nn3c(C(=O)Nc4ccnc(Cl)c4)cnc23)C2CC2)cc1]

A ~1:1 mixture 6,8-dichloro-N-(2-chloropyridin-4-yl)imidazo[1,2-b]pyridazine-3-carboxamide and 8-bromo-6-chloro-N-(2-chloropyridin-4-yl)imidazo[1,2-b]pyridazine-3-carboxamide (3 g, 8.6 mmol), N-(4-methoxybenzyl)cyclopropanamine (8.16 g, 23.82 mmol) and N,N-diisopropylethylamine (3.08 g, 23.82 mmol) was suspended in DMF (100 mL) and heated at 80° C. for 1.5 hrs. The reaction mixture was concentrated and dried under reduced pressure for 16 hrs. The residue was suspended in methanol (75 mL) and an off-white solid was collected via Buchner filtration (2×25 mL methanol rinse) to isolate 6-chloro-N-(2-chloropyridin-4-yl)-8-(cyclopropyl(4-methoxybenzyl)amino)imidazo[1,2-b]pyridazine-3-carboxamide (10.2 g, 21.1 mmol, 89%) as a tan solid. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA) Rt=2.21 minutes. [M+H]=483.06.

23C. Preparation of 6-((trans)-4-aminocyclohexylamino)-N-(2-chloropyridin-4-yl)-8-(cyclopropyl(4-methoxybenzyl)amino)imidazo[1,2-b]pyridazine-3-carboxamide

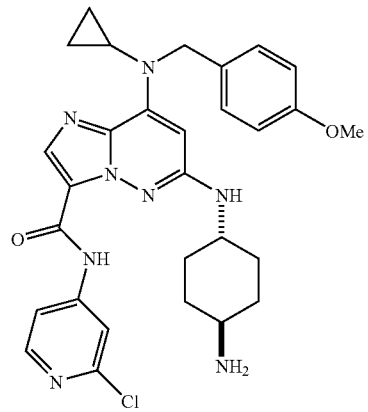

6-chloro-N-(2-chloropyridin-4-yl)-8-(cyclopropyl(4-methoxybenzyl)amino)imidazo[1,2-b]pyridazine-3-carboxamide (9 g, 18.6 mmol) was combined with trans-1,4-diaminocyclohexane (31.9 g, 279 mmol) in N-methyl-2-pyrrolidinone (50 mL) and heated at 80° C. for 16 hours and at 120° C. for 6 hrs. The reaction was cooled to room temperature, and water (200 mL) was added, and the solid collected via Buchner filtration. The crude product was purified with silica gel chromatography using a stepwise gradient of 10% methanol/chloroform to 25% methanol/chloroform/1% triethylamine to isolated foamy solid. The solid was suspended in water (400 mL) and collected with Buchner filtration (2×50 mL water wash) and dried for 16 hrs under reduced pressure to afford 6-((trans)-4-aminocyclohexylamino)-N-(2-chloropyridin-4-yl)-8-(cyclopropyl(4-methoxybenzyl)amino)imidazo[1,2-b]pyridazine-3-carboxamide (10.2 g, 18.18 mmol, 98% yield) as a off white solid. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA) Rt=1.77 minutes. [M+H]=561.16.

23D. Preparation of 6-((trans)-4-aminocyclohexylamino)-N-(2-chloropyridin-4-yl)-8-(cyclopropylamino)imidazo[1,2-b]pyridazine-3-carboxamide

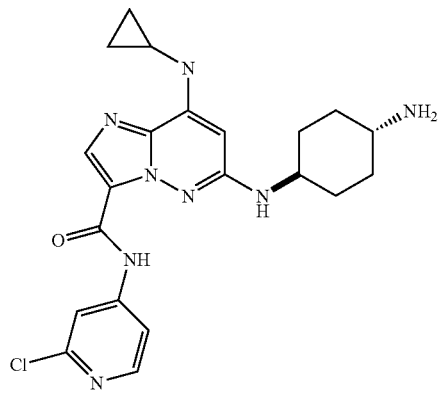

To 23C (0.464 mmol, 260 mg) in NMP (2 mL) was added TFA (0.2 mL). The resulting reaction mixture was heated at 100° C. for 24 hrs. The reaction mixture was diluted with MeOH and purified by HPLC Phenomenex Axia Luna 5 micron 30×100 mm) with 20% to 100% MeOH (0.1% TFA) in water (0.1% TFA) to isolate 6-((trans)-4-aminocyclohexylamino)-N-(2-chloropyridin-4-yl)-8-(cyclopropylamino) imidazo[1,2-b]pyridazine-3-carboxamide (107 mg, 0.243 mmol, 52.3% yield) as white solid. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). Rt=1.500 minutes. [M+H]=441.12. $^1$H NMR (400 MHz, MeOD) δ ppm 8.21-8.35 (1H, m), 8.01 (1H, s), 7.96 (1H, d, J=1.76 Hz), 7.33-7.51 (1H, m), 6.07 (1H, s), 3.60-3.85 (1H, m), 3.08-3.27 (1H, m), 2.49-2.66 (1H, m), 2.25-2.45 (2H, m), 2.06-2.28 (2H, m), 1.35-1.69 (4H, m), 0.77-0.97 (2H, m), 0.50-0.73 (2H, m).

Example 24

6-((trans-4-aminocyclohexyl)amino)-8-((5-methyl-2-pyridinyl)amino)-N-4-pyridinylimidazo[1,2-b]pyridazine-3-carboxamide

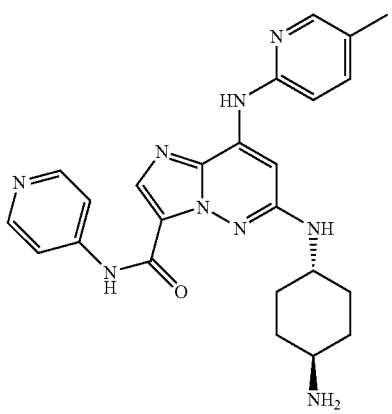 [SMILES: Cc1ccc(Nc2cc(N[C@H]3CC[C@H](N)CC3)nn3c(C(=O)Nc4ccncc4)cnc23)nc1]

24A. Preparation of 6-chloro-N-(4-methoxybenzyl)-N-(5-methylpyridin-2-yl)imidazo[1,2-b]pyridazin-8-amine

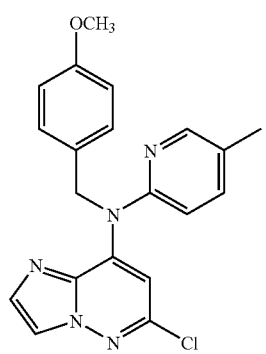 [SMILES: COc1ccc(CN(c2ccc(C)cn2)c2cc(Cl)nn3ccnc23)cc1]

To a flask was added N-(4-methoxybenzyl)-5-methylpyridin-2-amine (147 g, 645 mmol) in THF (5 mL) at 25° C. The solution was stirred at 25° C. and potassium t-butoxide (1936 mL, 1936 mmol) was added. The reaction solution was stirred at 25° C. for 30 minutes. Next, 8-bromo-6-chloroimidazo[1,2-b]pyridazine (150 g, 645 mmol, Example 1 from WO 2007/038314) was added and the reaction solution was stirred at room temperature for 1 hour. The reaction was quenched with ethyl acetate and the solvent was removed in vacuo. The residue was redissolved in ethyl acetate, washed with sat NaHCO$_3$, and sat. NaCl and dried (Na$_2$SO$_4$), filt and concentrated in vacuo to give the crude product. The residue was purified via ISCO (5% EtOAC/DCM; 12 g column) to give pure product 6-chloro-N-(4-methoxybenzyl)-N-(5-methylpyridin-2-yl)imidazo[1,2-b]pyridazin-8-amine (0.1367 g, 0.360 mmol, 0.056% yield).

24B. Preparation of 6-chloro-8-((4-methoxybenzyl) (5-methylpyridin-2-yl)amino)imidazo[1,2-b]pyridazine-3-carboxylic acid

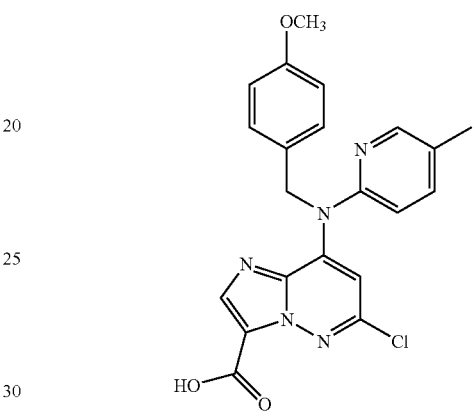

To a flask was added 6-chloro-N-(4-methoxybenzyl)-N-(5-methylpyridin-2-yl)imidazo[1,2-b]pyridazin-8-amine (0.13 g, 0.342 mmol), and nBuLi (0.205 mL, 0.411 mmol) in THF at −78° C. The solution was stirred at −78° C. for 30 minutes. The anion was quenched with carbon dioxide gas for 5 minutes and the reaction was allowed to warmed up to room temperature. The solution was quenched with water/ethyl acetate, washed with sat NaHCO$_3$ and sat. NaCl. The organic layer was dried Na$_2$SO$_4$, filtered and concentrated in vacuo to give the crude product mixture. The aqueous layer was back-extracted with DCM (3×5 mL). Combined the organic layers and wash with water (1×5 mL). The organic was dried Na$_2$SO$_4$, filtered and concentrated in vacuo to give the pure product 6-chloro-8-((4-methoxybenzyl)(5-methylpyridin-2-yl)amino)imidazo[1,2-b]pyridazine-3-carboxylic acid (70 mg, 0.165 mmol, 48.3% yield): [M+H]=424.

24C. Preparation of 6-chloro-8-((4-methoxybenzyl) (5-methylpyridin-2-yl)amino)-N-(pyridin-4-yl)imidazo[1,2-b]pyridazine-3-carboxamide

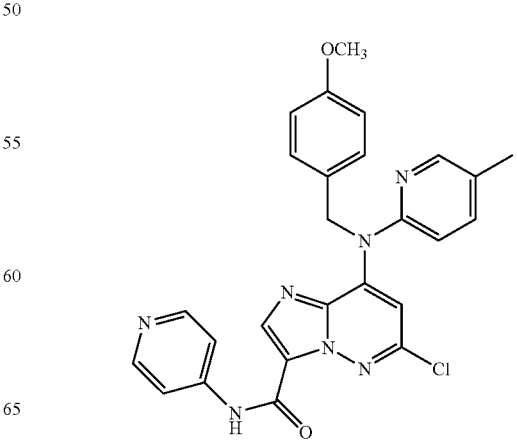

A solution of 6-chloro-8-((4-methoxybenzyl)(5-methylpyridin-2-yl)amino)imidazo[1,2-b]pyridazine-3-carboxylic acid (0.07 g, 0.165 mmol), 1-(3-(dimethylamino)propyl)-3-ethylcarbodiimide hydrochloride (0.047 g, 0.248 mmol), 1-hydroxybenzotriazole (0.033 g, 0.248 mmol), TEA (0.069 mL, 0.495 mmol) and pyridin-4-amine (0.023 g, 0.248 mmol) in acetonitrile (2 mL) was heated to 80° C. for 16 hours. The solution was quenched with EA/water. The organic layer was washed with sat NaHCO₃ and sat NaCl. The organic layer was dried with Na₂SO₄, filtered and concentrated in vacuo to give the crude product mixture. The crude product was purified by ISCO (5% EtOAC/DCM; 12 g column), followed by ISCO (5% MeOH/DCM; 12 g column) to afford the title compound (32 mg). [M+H]=500.

24D. Preparation of 6-((trans-4-aminocyclohexyl)amino)-8-((5-methyl-2-pyridinyl)amino)-N-4-pyridinylimidazo[1,2-b]pyridazine-3-carboxamide

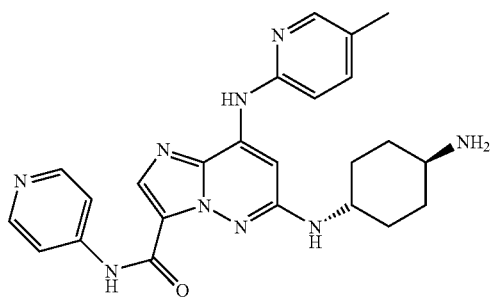

To a 2 dram vial was added 6-chloro-8-((4-methoxybenzyl)(5-methylpyridin-2-yl)amino)-N-(pyridin-4-yl)imidazo[1,2-b]pyridazine-3-carboxamide (32 mg, 0.064 mmol) and (trans)-cyclohexane-1,4-diamine (146 mg, 1.280 mmol). The reaction mixture was heated neat at 160° C. for 1 hour. The solution was diluted with DCM and washed with water. The organic layer was concentrated to dryness and then dissolved in neat TFA and heated to 80° C. for 2 hours. The solution was concentrated in vacuo and the residue was purified via preparative HPLC to give 6-((trans-4-aminocyclohexyl)amino)-8-((5-methyl-2-pyridinyl)amino)-N-4-pyridinylimidazo[1,2-b]pyridazine-3-carboxamide (14.2 mg, 0.031 mmol, 48.5% yield). HPLC Rt=2.19 minutes (Waters Sunfire C18 column 4.6×50 mm):0%-100% B. Solvent B: 90% MeOH, 10% H₂O, 0.1% TFA). Solvent A: 10% MeOH, 90% H₂O, 0.1% TFA). Gradient, start % B=0, final % B=100, gradient time 4 min, hold at 100% B 1 min, flow rate 4 mL/min) [M+H]=458.

Example 25
8-(cyclopropylamino)-N-(2-fluoropyridin-4-yl)-6-((trans)-4-(phenylsulfonamido)cyclohexylamino)imidazo[1,2-b]pyridazine-3-carboxamide

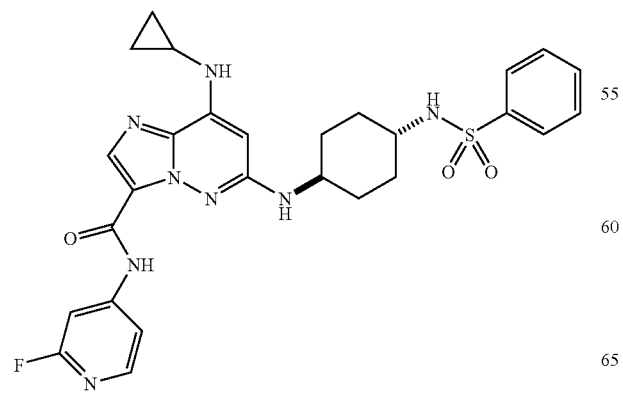

25A. Preparation of 6-chloro-8-(cyclopropyl(4-methoxybenzyl)amino)-N-(2-fluoropyridin-4-yl)imidazo[1,2-b]pyridazine-3-carboxamide

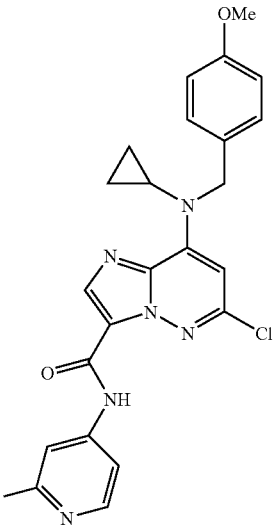

N-(4-methoxybenzyl)cyclopropanamine (381 mg, 2.148 mmol) was added to ~1:1 mixture of 6,8-dichloro-N-(2-fluoropyridin-4-yl)imidazo[1,2-b]pyridazine-3-carboxamide and 8-bromo-6-chloro-N-(2-fluoropyridin-4-yl)imidazo[1,2-b]pyridazine-3-carboxamide 8-bromo-6-chloro-N-(2-fluoropyridin-4-yl)imidazo[1,2-b]pyridazine-3-carboxamide (467 mg, 1.432 mmol, example 13A) and DIEA (0.500 mL, 2.86 mmol) in DMF (10 mL). The reaction mixture was heated at 80° C. for 1.5 hrs. Water (20 mL) was added, and the solid was collected via Buchner filtration and dried under reduced pressure overnight to afford 6-Chloro-8-(cyclopropyl(4-methoxybenzyl)amino)-N-(2-fluoropyridin-4-yl)imidazo[1,2-b]pyridazine-3-carboxamide as a yellow solid (519 mg, 78%). The crude material was taken into the next step without further purification. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). Rt=2.22 minutes. [M+H]= 467.21.

25B. Preparation of 6-((trans)-4-aminocyclohexylamino)-8-(cyclopropyl(4-methoxybenzyl)amino)-N-(2-fluoropyridin-4-yl)imidazo[1,2-b]pyridazine-3-carboxamide

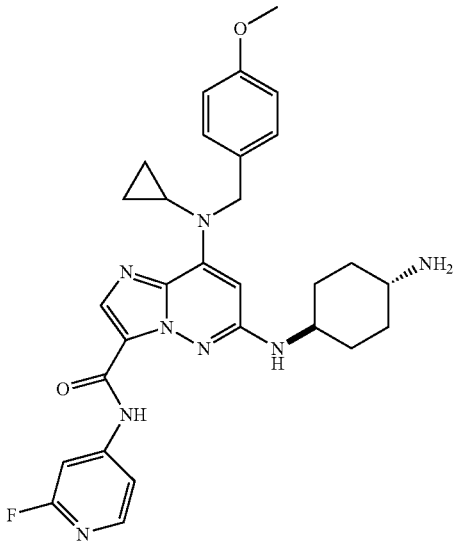

A solution of 6-chloro-8-(cyclopropyl(4-methoxybenzyl) amino)-N-(2-fluoropyridin-4-yl)imidazo[1,2-b]pyridazine-3-carboxamide (60 mg, 0.129 mmol) and (trans)-cyclohexane-1,4-diamine (147 mg, 1.285 mmol) in NMP (2 mL) was heated in a microwave reactor at 90° C. for 40 min. The reaction mixture was diluted with methanol and purified by HPLC (Phenomenex Axia Luna 5 micron 30×100 mm) 20% B (Solvent B=90% MeOH-10% H$_2$O-0.1% TFA) to 100% B in A (Solvent A=10% MeOH-90% H$_2$O-0.1% TFA)] to afford 6-((trans)-4-aminocyclohexylamino)-8-(cyclopropyl(4-methoxybenzyl)amino)-N-(2-fluoropyridin-4-yl)imidazo[1,2-b]pyridazine-3-carboxamide.

25C. Preparation of 6-((trans)-4-aminocyclohexylamino)-8-(cyclopropylamino)-N-(2-fluoropyridin-4-yl)imidazo[1,2-b]pyridazine-3-carboxamide

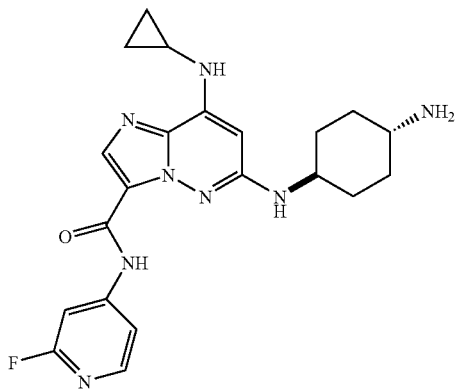

6-((trans)-4-aminocyclohexylamino)-8-(cyclopropyl(4-methoxybenzyl)amino)-N-(2-fluoropyridin-4-yl)imidazo[1,2-b]pyridazine-3-carboxamide (25B) was dissolved in TFA (2 mL) and heated at 70° C. for 2 hrs. The reaction mixture was concentrated and purified by HPLC (Phenomenex Axia Luna 5 micron 30×100 mm) 20% B (Solvent B=90% MeOH-10% H$_2$O-0.1% TFA) to 100% B in A (Solvent A=10% MeOH-90% H$_2$O-0.1% TFA) to afford 6-((trans)-4-aminocyclohexylamino)-8-(cyclopropylamino)-N-(2-fluoropyridin-4-yl)imidazo[1,2-b]pyridazine-3-carboxamide (23 mg, 43.2% yield) as a white solid. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). Rt=1.448 minutes. [M+H]=425.29. $^1$H NMR (400 MHz, MeOD) δ ppm 8.08-8.26 (1H, m), 8.04 (1H, s), 7.60-7.74 (1H, m), 7.29-7.45 (1H, m), 5.99-6.16 (1H, m), 3.61-3.92 (1H, m), 3.08-3.28 (1H, m), 2.48-2.69 (1H, m), 2.26-2.48 (2H, m), 2.07-2.28 (2H, m), 1.37-1.69 (4H, m), 0.79-1.00 (2H, m), 0.53-0.76 (2H, m).

25D. Preparation of 8-(cyclopropylamino)-N-(2-fluoropyridin-4-yl)-6-((trans)-4-(phenylsulfonamido)cyclohexylamino)imidazo[1,2-b]pyridazine-3-carboxamide

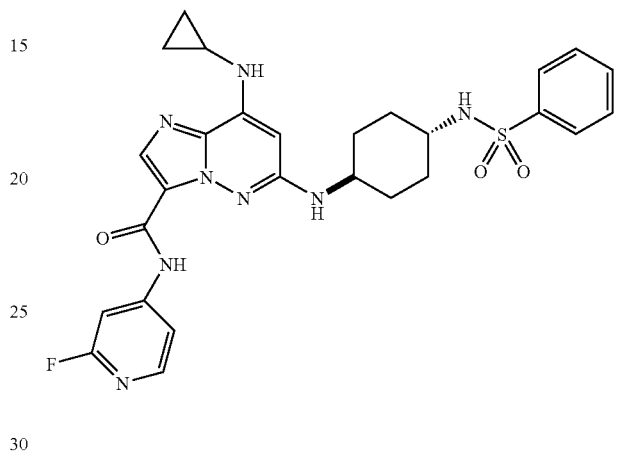

To a solution of 6-((trans)-4-aminocyclohexylamino)-8-(cyclopropyl(4-methoxybenzyl)amino)-N-(2-fluoropyridin-4-yl)imidazo[1,2-b]pyridazine-3-carboxamide (20.00 mg, 0.037 mmol) in CH$_2$Cl$_2$ (1 mL) was added DIEA (0.00617 mL, 0.035 mmol) and benzenesulfonyl chloride (1.5 mg, 8.49 μmol). The reaction solution was stirred at room temperature for 30 min, concentrated and then treated with TFA (1.132 mL, 14.69 mmol) at 70° C. for 1 hr. The reaction mixture was concentrated and purified by HPLC (Phenomenex Axia Luna 5 micron 30×100 mm) 30% B (Solvent B=90% MeOH-10% H$_2$O-0.1% TFA) to 100% B in A (Solvent A=10% MeOH-90% H$_2$O-0.1% TFA)) to isolate the title compound, 8-(cyclopropylamino)-N-(2-fluoropyridin-4-yl)-6-((trans)-4-(phenylsulfonamido)cyclohexylamino)imidazo[1,2-b]pyridazine-3-carboxamide (2.6 mg, 12.54% yield) as a white solid (13.0 mg, 44.4%). LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). Rt=1.910 minutes. [M+H]=565.25. $^1$H NMR (400 MHz, DMSO-d$_6$) δ ppm 11.36-11.55 (1H, m), 8.13-8.33 (1H, m), 7.89-8.01 (1H, m), 7.76-7.91 (3H, m), 7.47-7.70 (5H, m), 7.20-7.38 (1H, m), 6.78-6.96 (1H, m), 5.83-6.02 (1H, m), 3.48-3.72 (1H, m), 2.92-3.13 (1H, m), 1.83-2.12 (2H, m), 1.53-1.80 (2H, m), 0.99-1.41 (5H, m), 0.66-0.85 (2 H, m), 0.41-0.67 (2H, m), 1.80-2.05 (2H, m), 1.39-1.70 (2H, m), 1.14-1.41 (2H, m), 0.77 (2H, d, J=4.77 Hz), 0.63 (2H, d, J=3.01 Hz).

m), 2.21 (2H, d, J=10.79 Hz), 2.10 (2H, d, J=11.54 Hz), 1.61 (2H, br. s.), 1.24 (2H, d, J=12.30 Hz), 0.76 (2H, d, J=5.02 Hz), 0.62 (2H, d, J=2.51 Hz).

Example 26

Methyl 2-((trans)-4-(8-(cyclopropylamino)-3-(6-hydroxypyrimidin-4-ylcarbamoyl)imidazo[1,2-b]pyridazin-6-ylamino)cyclohexylamino)acetate

Example 27

8-(cyclopropylamino)-N-(2-fluoropyridin-4-yl)-6-((trans)-4-morpholinocyclohexylamino)imidazo[1,2-b]pyridazine-3-carboxamide

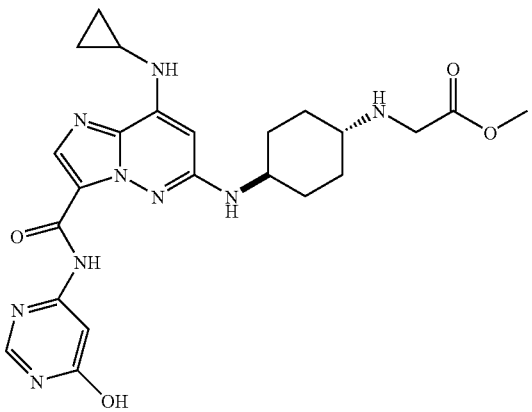

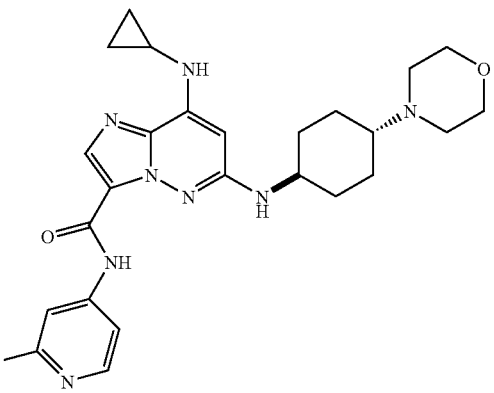

To a solution of 6-((trans)-4-aminocyclohexylamino)-N-(6-(benzyloxy)pyrimidin-4-yl)-8-(cyclopropylamino)imidazo[1,2-b]pyridazine-3-carboxamide (30.0 mg, 0.058 mmol) in DCM (2 mL) was added DIEA (0.041 mL, 0.234 mmol) and methyl 2-bromoacetate (13.40 mg, 0.088 mmol). The reaction solution was stirred at 45° C. for 14 hrs. The reaction mixture was concentrated and treated with TFA (0.270 mL, 3.50 mmol) at 65° C. for 1 hr. The reaction mixture was concentrated and diluted with MeOH, and purified by HPLC (Phenomenex Axia Luna 5 micron 30×100 mm) 30% B (Solvent B=90% MeOH-10% $H_2O$-0.1% TFA) to 100% B in A (Solvent A=10% MeOH-90% $H_2O$-0.1% TFA) to obtain methyl 2-((trans)-4-(8-(cyclopropylamino)-3-(6-hydroxypyrimidin-4-ylcarbamoyl)imidazo[1,2-b]pyridazin-6-ylamino)cyclohexylamino)acetate (11 mg, 0.022 mmol, 38.0% yield). LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). Rt=1.295 minutes. [M+H]=496.19. $^1$H NMR (400 MHz, DMSO-$d_6$) δ ppm 12.43-12.79 (1H, m), 11.67 (1H, s), 9.11 (2H, d, J=4.77 Hz), 8.31 (1H, s), 7.96 (1H, s), 7.63 (1H, s), 6.90-7.18 (2H, m), 5.95 (1H, s), 4.14 (2H, t, J=5.65 Hz), 3.80 (3H, s), 3.53-3.79 (1H, m), 2.91-3.21 (1H, To a solution of 6-((trans)-4-aminocyclohexylamino)-8-(cyclopropyl(4-methoxybenzyl)amino)-N-(2-fluoropyridin-4-yl)imidazo[1,2-b]pyridazine-3-carboxamide (100 mg, 0.184 mmol) in 1,2-dichloroethane (2 mL) was added DIEA (0.128 mL, 0.734 mmol) and 1-bromo-2-(2-bromoethoxy)ethane (42.6 mg, 0.184 mmol), and the reaction solution was stirred at 60° C. for 9 hrs. The reaction mixture was treated with TFA (0.849 mL, 11.02 mmol) at 65° C. for 1 hr, concentrated, diluted with methanol, and purified by HPLC (Phenomenex Axia Luna 5 micron 30×100 mm) 30% B (Solvent B=90% MeOH-10% $H_2O$-0.1% TFA) to 100% B in A (Solvent A=10% MeOH-90% $H_2O$-0.1% TFA) to obtain 8-(cyclopropylamino)-N-(2-fluoropyridin-4-yl)-6-((trans)-4-morpholinocyclohexylamino)imidazo[1,2-b]pyridazine-3-carboxamide (36.3 mg, 0.073 mmol, 40.0% yield). LC/MS (BEH C18 2.1×50 mm 1.7u, Phenomenex Luna 5 micron C18 4.6×30 mm, 0 to 100 B in 2.2 min with 1 min hold time, Flow rate=2 mL/min, detection at 254 nm, Solvent A: 100% water/0.05% TFA; Solvent B: 100% ACN/0.05% TFA). Rt=0.67 minutes. [M+H]=495.3. $^1$H NMR (400 MHz, DMSO-$d_6$) δ ppm 11.40 (1H, s), 9.57-9.89 (1H, m), 8.26 (1H, d, J=5.77 Hz), 7.99 (1H, d, J=1.76 Hz), 7.67 (1H, s), 7.60 (1H, s), 7.44 (1H, d, J=4.77 Hz), 6.88-7.14 (1H, m), 5.98 (1H, s), 4.04 (2H, d, J=11.80 Hz), 3.58-3.83 (3H, m), 3.40 (2H, d, J=12.05 Hz), 2.98-3.23 (2H, m), 2.28 (2H, d, J=11.80 Hz), 2.17 (2H, d, J=11.29 Hz), 1.55 (2H, br. s.), 1.35 (2H, br. s.), 0.78 (2H, d, J=6.53 Hz), 0.63 (2H, br. s.)

Example 28

8-(cyclopropylamino)-N-(2-fluoropyridin-4-yl)-6-((trans)-4-(2-hydroxyethylamino)cyclohexylamino)imidazo[1,2-b]pyridazine-3-carboxamide and 6-((trans)-4-(bis(2-hydroxyethyl)amino)cyclohexylamino)-8-(cyclopropylamino)-N-(2-fluoropyridin-4-yl)imidazo[1,2-b]pyridazine-3-carboxamide

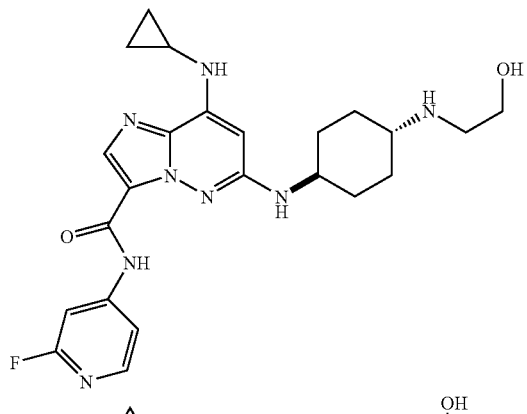

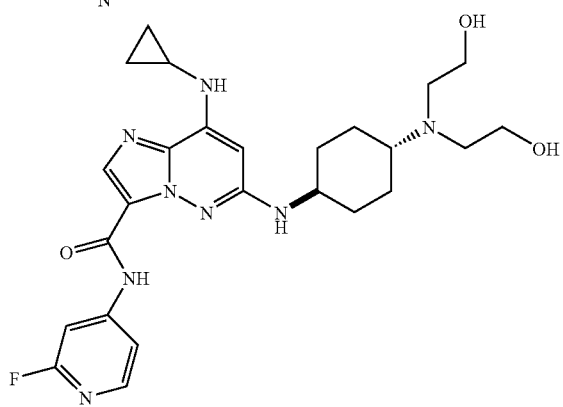

To a solution of 6-((trans)-4-aminocyclohexylamino)-8-(cyclopropyl(4-methoxybenzyl)amino)-N-(2-fluoropyridin-4-yl)imidazo[1,2-b]pyridazine-3-carboxamide (80 mg, 0.147 mmol) in MeCN (3 mL) was added DIEA (0.038 mL, 0.220 mmol) and 2-bromoethanol (36.7 mg, 0.294 mmol) and the reaction solution was stirred at 60° C. for 8 hrs. The reaction mixture was concentrated and treated with TFA (0.679 mL, 8.81 mmol) at 65° C. for 1 hr. The reaction mixture was diluted with MeOH and purified by HPLC (Phenomenex Axia Luna 5 micron 30×100 mm) 30% B (Solvent B=90% MeOH-10% H$_2$O-0.1% TFA) to 100% B in A (Solvent A=10% MeOH-90% H$_2$O-0.1% TFA) to isolate 8-(cyclopropylamino)-N-(2-fluoropyridin-4-yl)-6-((trans)-4-(2-hydroxyethylamino)cyclohexylamino)imidazo[1,2-b]pyridazine-3-carboxamide (19.9 mg, 0.042 mmol, 28.9% yield). LC/MS (BEH C18 2.1×50 mm 1.7u, Phenomenex Luna 5 micron C18 4.6×30 mm, 0 to 100 B in 2.2 min with 1 min hold time, Flow rate=2 mL/min, detection at 254 nm, Solvent A: 100% water/0.05% TFA; Solvent B: 100% ACN/0.05% TFA). Rt=0.65 (M+H=496.2). $^1$H NMR (400 MHz, MeOD) δ ppm 8.11-8.22 (1H, m), 8.04 (1H, s), 7.56-7.70 (1H, m), 7.21-7.40 (1H, m), 6.08 (1H, s), 3.66-3.89 (3H, m), 3.07-3.28 (3H, m), 2.50-2.69 (1H, m), 2.34-2.50 (2H, m), 2.20-2.35 (2H, m), 1.37-1.72 (4H, m), 0.78-0.99 (2H, m), 0.56-0.75 (2H, m) and 6-((trans)-4-(bis(2-hydroxyethyl)amino)cyclohexylamino)-8-(cyclopropylamino)-N-(2-fluoropyridin-4-yl)imidazo[1,2-b]pyridazine-3-carboxamide (18.7 mg, 0.036 mmol, 24.84% yield). LC/MS (BEH C18 2.1×50 mm 1.7u, Phenomenex Luna 5 micron C18 4.6×30 mm, 0 to 100 B in 2.2 min with 1 min hold time, Flow rate=2 mL/min, detection at 254 nm, Solvent A: 100% water/0.05% TFA; Solvent B: 100% ACN/0.05% TFA). Rt=0.65 (M+H=513.3). $^1$H NMR (500 MHz, DMSO-d$_6$) δ ppm 11.38 (1H, s), 8.65-8.90 (1H, m), 8.22 (1H, d, J=5.50 Hz), 7.99 (1H, s), 7.60-7.71 (1H, m), 7.56 (2H, s), 6.82-7.14 (1H, m), 5.98 (1H, s), 3.78 (5H, t, J=5.50 Hz), 3.42-3.59 (1H, m), 3.14-3.36 (4H, m), 2.17-2.32 (2H, m), 1.98-2.17 (2H, m), 1.46-1.77 (2H, m), 1.18-1.44 (2H, m), 0.78 (2H, d, J=4.95 Hz), 0.63 (2H, d, J=2.75 Hz).

Example 29

8-(cyclopropylamino)-6-((trans)-4-(ethylamino)cyclohexylamino)-N-(2-fluoropyridin-4-yl)imidazo[1,2-b]pyridazine-3-carboxamide and 8-(cyclopropylamino)-6-((trans)-4-(diethylamino)cyclohexylamino)-N-(2-fluoropyridin-4-yl)imidazo[1,2-b]pyridazine-3-carboxamide

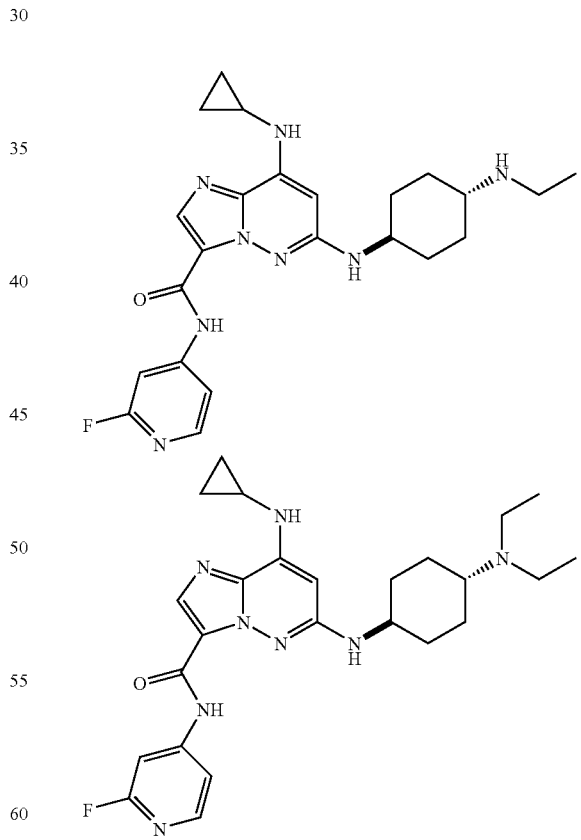

To a solution of 6-((trans)-4-aminocyclohexylamino)-8-(cyclopropyl(4-methoxybenzyl)amino)-N-(2-fluoropyridin-4-yl)imidazo[1,2-b]pyridazine-3-carboxamide (60.0 mg, 0.110 mmol), acetaldehyde (14.56 mg, 0.331 mmol) and acetic acid (13.23 mg, 0.220 mmol) in DCM (2 mL) was stirred at room temperature for 5 minutes, then sodium triacetoxyborohydride (46.7 mg, 0.220 mmol) was added and the reaction was stirred at 25° C. for 2 hrs. The reaction mixture was concentrated down and treated with TFA (0.509 mL, 6.61 mmol) at 65° C. for 1 hr, concentrated, diluted in methanol and purified by preparative HPLC (Phenomenex Axia Luna 5 micron 30×100 mm) 30% B (Solvent B=90% MeOH-10% $H_2O$-0.1% TFA) to 100% B in A (Solvent A=10% MeOH-90% $H_2O$-0.1% TFA) to isolate 8-(cyclopropylamino)-6-((trans)-4-(ethylamino)cyclohexylamino)-N-(2-fluoropyridin-4-yl)imidazo[1,2-b]pyridazine-3-carboxamide (19.3 mg, 0.043 mmol, 38.7% yield). LC/MS (BEH C18 2.1×50 mm 1.7u, Phenomenex Luna 5 micron C18 4.6×30 mm, 0 to 100 B in 2.2 min with 1 min hold time, Flow rate=2 mL/min, detection at 254 nm, Solvent A: 100% water/0.05% TFA; Solvent B: 100% ACN/0.05% TFA). Rt=0.67 minutes [M+H]= 453.2. $^1$H NMR (400 MHz, DMSO-$d_6$) δ ppm 11.52 (1H, s), 8.21 (1H, d, J=5.52 Hz), 7.96 (1H, s), 7.60 (1H, d, J=1.51 Hz), 7.51 (2H, s), 6.86-7.03 (1H, m), 5.98 (1H, s), 3.57-3.76 (1H, m), 2.56 (2H, d, J=7.03 Hz), 2.33-2.47 (1H, m), 2.02-2.20 (2H, m), 1.80-2.02 (2H, m), 1.18-1.37 (2H, m), 1.04-1.18 (2H, m), 1.01 (3H, t, J=7.03 Hz), 0.69-0.85 (2H, m), 0.53-0.71 (2H, m) and 8-(cyclopropylamino)-6-((trans)-4-(diethylamino)cyclohexylamino)-N-(2-fluoropyridin-4-yl)imidazo[1,2-b]pyridazine-3-carboxamide (25.6 mg, 0.053 mmol, 48.4% yield).). LC/MS (BEH C18 2.1×50 mm 1.7u, Phenomenex Luna 5 micron C18 4.6×30 mm, 0 to 100 B in 2.2 min with 1 min hold time, Flow rate=2 mL/min, detection at 254 nm, Solvent A: 100% water/0.05% TFA; Solvent B: 100% ACN/0.05% TFA). Rt=0.69 minutes [M+H]=481.3. $^1$H NMR (400 MHz, DMSO-$d_6$) δ ppm 11.33-11.48 (1H, m), 8.29-8.48 (1H, m), 8.21 (1H, d, J=5.52 Hz), 7.98 (1H, s), 7.64 (1H, d, J=1.25 Hz), 7.53-7.63 (1H, m), 7.51 (1H, s), 6.97-7.11 (1H, m), 6.00 (1H, s), 3.62-3.81 (1H, m), 2.97-3.14 (1H, m), 2.92 (4H, q, J=7.28 Hz), 2.15-2.32 (2H, m), 1.95-2.09 (2H, m), 1.49-1.67 (2H, m), 1.27-1.46 (2H, m), 1.02-1.30 (6H, m), 0.71-0.85 (2H, m), 0.56-0.72 (2H, m)

Example 30

N-(2-chloropyridin-4-yl)-8-(cyclopropylamino)-6-((trans)-4-(2-hydroxy-2-methylpropylamino)cyclohexylamino)imidazo[1,2-b]pyridazine-3-carboxamide

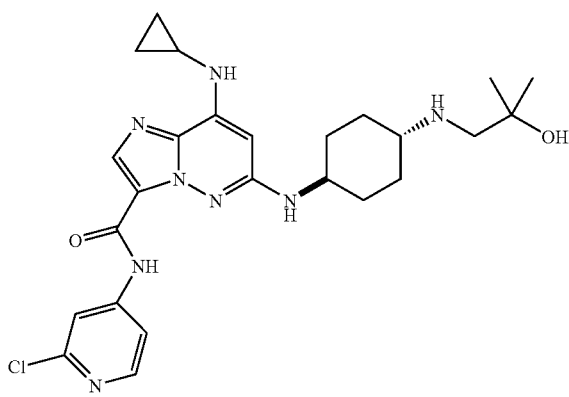

A solution of 6-((trans)-4-aminocyclohexylamino)-N-(2-chloropyridin-4-yl)-8-(cyclopropyl(4-methoxybenzyl) amino)imidazo[1,2-b]pyridazine-3-carboxamide (100 mg, 0.178 mmol), lithium bromide (0.774 mg, 8.91 μmol) and 2,2-dimethyloxirane (12.85 mg, 0.178 mmol) in MeOH (5 mL) was stirred at 50° C. for 7 hrs. The reaction mixture was concentrated down, diluted in methanol (1 mL) and treated with TFA (0.824 mL, 10.69 mmol). After 10 minutes, the reaction mixture was concentrated, diluted with methanol and purified by preparative HPLC (Phenomenex Axia Luna 5 micron 30×100 mm) 30% B (Solvent B=90% MeOH-10% $H_2O$-0.1% TFA) to 100% B in A (Solvent A=10% MeOH-90% $H_2O$-0.1% TFA) to isolate N-(2-chloropyridin-4-yl)-8-(cyclopropylamino)-6-((trans)-4-(2-hydroxy-2-methylpropylamino)cyclohexylamino)imidazo[1,2-b]pyridazine-3-carboxamide (41.9 mg, 0.082 mmol, 45.8% yield) as a white solid. LC/MS (BEH C18 2.1×50 mm 1.7u, Phenomenex Luna 5 micron C18 4.6×30 mm, 0 to 100 B in 2.2 min with 1 min hold time, Flow rate=2 mL/min, detection at 254 nm, Solvent A: 100% water/0.05% TFA; Solvent B: 100% ACN/0.05% TFA). Rt=0.71 minutes. [M+H]=513.3. $^1$H NMR (400 MHz, MeOD) δ ppm 8.47 (2H, s), 7.96-8.08 (1H, m), 7.52-7.70 (1H, m), 6.44 (1H, s), 3.69-3.92 (1H, m), 3.15-3.30 (1H, m), 3.05 (2H, s), 2.60-2.77 (1H, m), 2.36-2.48 (2H, m), 2.17-2.37 (2H, m), 1.60-1.80 (2H, m), 1.41-1.62 (2H, m), 1.35 (6H, s), 0.87-1.05 (2H, m), 0.63-0.78 (2H, m)

Example 31

6-((trans)-4-aminocyclohexylamino)-8-(cyclopropylamino)-N-(6-hydroxypyrimidin-4-yl)imidazo[1,2-b] pyridazine-3-carboxamide

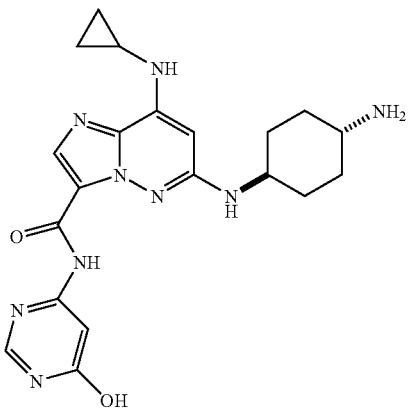

A mixture of N-(6-(benzyloxy)pyrimidin-4-yl)-6-chloro-8-(cyclopropylamino)imidazo[1,2-b]pyridazine-3-carboxamide (70 mg, 0.161 mmol, 15C) and (trans)-cyclohexane-1,4-diamine (367 mg, 3.21 mmol) was heated at 160° C. for 2 hrs. The reaction mixture was diluted with methanol and purified by preparative HPLC (Phenomenex Axia Luna 5 micron 30×100 mm) 10% B (Solvent B=90% MeOH-10% $H_2O$-0.1% TFA) to 100% B in A (Solvent A=10% MeOH-90% $H_2O$-0.1% TFA)) to isolate 6-((trans)-4-aminocyclohexylamino)-8-(cyclopropylamino)-N-(6-hydroxypyrimidin-4-yl)imidazo[1,2-b]pyridazine-3-carboxamide (13 mg, 19.12% yield) as a white solid. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA) Rt=1.280 minutes. [M+H]= 424.15. $^1$H NMR (400 MHz, DMSO-$d_6$) δ ppm 12.35-12.78 (1H, m), 11.67 (1H, s), 8.29 (1H, s), 7.96 (1H, s), 7.69-7.94

(2H, m), 7.63 (1H, d, J=1.76 Hz), 7.05 (2H, s), 5.96 (1H, s), 3.62-3.85 (1H, m), 2.93-3.17 (1H, m), 2.05-2.24 (2H,

Example 32

Preparation of 8-(cyclopropylamino)-N-(3-fluoropyridin-4-yl)-6-((trans)-4-(piperazine-1-carboxamido)cyclohexylamino)imidazo[1,2-b]pyridazine-3-carboxamide

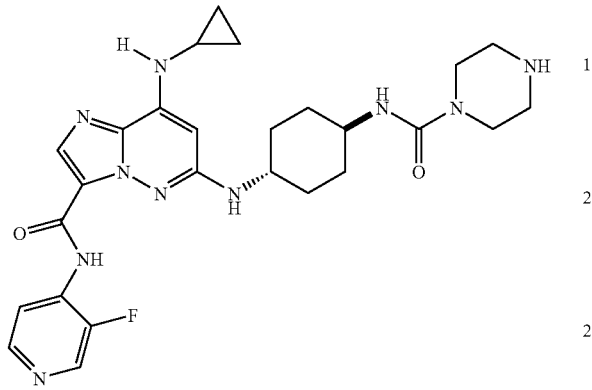

To di-tert-butyl dicarbonate (10.66 µL, 0.046 mmol) in dichloromethane (1 mL) was added DMAP (2.80 mg, 0.023 mmol) followed by 6-((trans)-4-aminocyclohexylamino)-8-(cyclopropyl(4-methoxybenzyl)amino)-N-(3-fluoropyridin-4-yl)imidazo[1,2-b]pyridazine-3-carboxamide (25 mg, 0.046 mmol, 83A). The clear yellow solution was stirred at room temperature for 10 minutes then tert-butyl piperazine-1-carboxylate (8.55 mg, 0.046 mmol) was added, and stirred at room temperature for 1 hr. TFA (0.5 mL) was added, and after 10 minutes, the reaction mixture was concentrated to dryness, taken up in DMSO and methanol and purified using reverse phase HPLC to isolate 8-(cyclopropylamino)-N-(3-fluoropyridin-4-yl)-6-((trans)-4-(piperazine-1-carboxamido)cyclohexylamino)imidazo[1,2-b]pyridazine-3-carboxamide (22 mg, 0.027 mmol, 59.5% yield) as a white solid. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA) Rt=1.39 minutes [M+H]=537.37. $^1$H NMR (500 MHz, METHANOL-$d_3$) δ ppm 8.90 (1H, t, J=6.64 Hz), 8.76 (1H, d, J=3.67 Hz), 8.50 (1H, d, J=5.96 Hz), 8.05-8.22 (1H, m), 6.11 (1H, s), 3.84-4.03 (1H, m), 3.61-3.72 (4H, m), 3.58 (1H, t, J=10.77 Hz), 3.14-3.27 (4H, m), 2.51-2.62 (1H, m, J=6.76, 6.76, 3.67, 3.44 Hz), 2.19 (2H, d, J=12.37 Hz), 1.98 (2H, d, J=13.29 Hz), 1.21-1.69 (4H, m), 0.84-1.05 (2H, m), 0.51-0.71 (2H, m)

Example 33

Preparation of 2-(dimethylamino)ethyl (trans)-4-(8-(cyclopropylamino)-3-(3-fluoropyridin-4-ylcarbamoyl)imidazo[1,2-b]pyridazin-6-ylamino)cyclohexylcarbamate

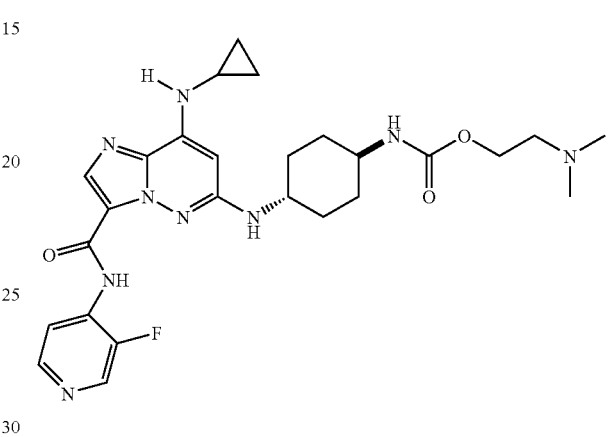

To di-tert-butyl dicarbonate (10.66 µL, 0.046 mmol) in dichloromethane (1 mL) was added DMAP (2.80 mg, 0.023 mmol), followed by 6-((trans)-4-aminocyclohexylamino)-8-(cyclopropyl(4-methoxybenzyl)amino)-N-(3-fluoropyridin-4-yl)imidazo[1,2-b]pyridazine-3-carboxamide (25 mg, 0.046 mmol, 83A). The clear yellow solution was stirred at room temperature for 10 minutes, and then 2-(dimethylamino)ethanol (5.11 mg, 0.057 mmol) was added, and stirred at room temperature for 1 hr. TFA (0.5 mL) was added, and after 10 minutes, the reaction mixture was concentrated to dryness, taken up in DMSO and methanol and purified using reverse phase HPLC to isolate 2-(dimethylamino)ethyl (trans)-4-(8-(cyclopropylamino)-3-(3-fluoropyridin-4-ylcarbamoyl)imidazo[1,2-b]pyridazin-6-ylamino)cyclohexylcarbamate. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA) Rt=1.41 minutes. [M+H]=540.37. $^1$H NMR (500 MHz, METHANOL-$d_3$) δ ppm 8.84 (2H, br. s.), 8.38-8.59 (1H, m), 8.10 (1H, s), 6.09 (1H, s), 4.29-4.51 (2H, m), 3.82-4.08 (1H, m), 3.37-3.58 (4H, m), 2.97 (6 H, s), 2.50-2.68 (1H, m), 2.17

(2H, br. s.), 1.99 (2H, d, J=3.30 Hz), 1.29-1.63 (4H, m), 0.80-1.00 (2H, m), 0.56-0.72 (2H, m).

Example 34

N-(2-chloropyridin-4-yl)-6-((trans)-4-(2-cyanoacetamido)cyclohexylamino)-8-(cyclopropylamino)imidazo[1,2-b]pyridazine-3-carboxamide

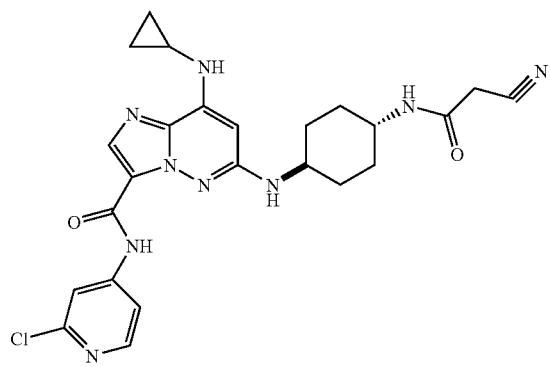

BOP (60.2 mg, 0.136 mmol) was added to a solution of 6-((trans)-4-aminocyclohexylamino)-N-(2-chloropyridin-4-yl)-8-(cyclopropylamino)imidazo[1,2-b]pyridazine-3-carboxamide (20.00 mg, 0.045 mmol), DIEA (0.032 mL, 0.181 mmol) and 2-cyanoacetic acid (7.72 mg, 0.091 mmol) in DCM (1 mL). The clear reaction mixture was stirred at room temperature for 30 min, concentrated and diluted with MeOH and purified by HPLC (Phenomenex Axia Luna 5 micron 30×100 mm) 20% B (Solvent B=90% MeOH-10% $H_2O$-0.1% TFA) to 100% B in A (Solvent A=10% MeOH-90% $H_2O$-0.1% TFA) to isolate N-(2-chloropyridin-4-yl)-6-((trans)-4-(2-cyanoacetamido)cyclohexylamino)-8-(cyclopropylamino)imidazo[1,2-b]pyridazine-3-carboxamide (11 mg, 0.022 mmol, 47.7% yield) as white solid. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). Rt=1.772 minutes. [M+H]=508.11. $^1$H NMR (400 MHz, MeOD) δ ppm 8.24-8.39 (1H, m), 7.95-8.03 (1H, m), 7.87-7.97 (1H, m), 7.51-7.67 (1H, m), 5.98-6.11 (1H, m), 3.60-3.83 (2H, m), 2.47-2.66 (1H, m), 2.19-2.37 (2H, m), 1.96-2.19 (2H, m), 1.28-1.55 (4H, m), 0.77-0.96 (2H, m), 0.52-0.75 (2H, m).

Example 35

6-((trans)-4-aminocyclohexylamino)-7-methyl-8-(5-methylpyridin-2-ylamino)-N-(pyridin-4-yl)imidazo[1,2-b]pyridazine-3-carboxamide

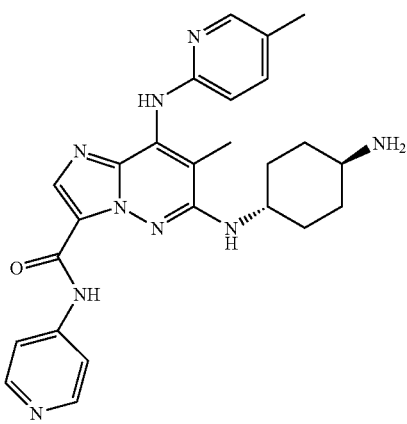 [SMILES: Cc1ccc(Nc2c(C)c(N[C@H]3CC[C@H](N)CC3)nn3c(C(=O)Nc4ccncc4)cnc23)nc1]

35A. Preparation of 6-chloro-5-methylpyridazin-3-amine and 6-chloro-4-methylpyridazin-3-amine

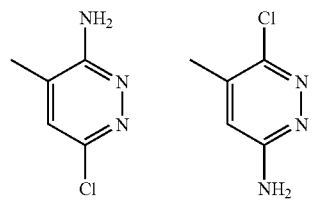

A 20 mL microwave vial was charged with, a stir bar, 3,6-dichloro-4-methylpyridazine (4.0 g, 24.54 mmol) and 14 mL of a new, freshly opened bottle of ammonium hydroxide. The vial was quickly sealed. The solution was heated in a microwave (Personal Chemistry, Emrys Optimizer) to 100° C. for 3 h. The vial was cooled, opened, and a stream of nitrogen was used to remove excess ammonium hydroxide. Water was added, the solid was collected by filtration, washed with water and dried to provide a mixture of 6-chloro-5- methylpyridazin-3-amine and 6-chloro-4-methylpyridazin-3-amine (3 g, 20.90 mmol, 85% yield). The mixture was used without further purification.

35B. Preparation of 4-bromo-6-chloro-5-methylpyridazin-3-amine

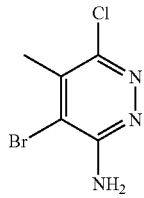

Bromine (1.074 mL, 20.90 mmol) was drop wise added to a 0° C. suspension of 35A (3.0 g, 20.90 mmol) and sodium bicarbonate (3.51 g, 41.8 mmol) in methanol (20 mL) in a round bottom flask equipped with a stir bar. The mixture was allowed to warm to room temperature overnight. The mixture was filtered and the precipitate was washed with ethyl acetate. The filtrate was concentrated in vacuo. The resulting residue was dissolved in water and extracted with ethyl acetate (3×). The extracts were combined washed with brine, dried over sodium sulfate, and concentrated in vacuo to provide 4-bromo-6-chloro-5-methylpyridazin-3-amine (2.1 g, 9.44 mmol, 45.2% yield) as a yellow brown solid which was used without further purification

35C. Preparation of ethyl 8-bromo-6-chloro-7-methylimidazo[1,2-b]pyridazine-3-carboxylate and ethyl 6,8-dichloro-7-methylimidazo[1,2-b]pyridazine-3-carboxylate

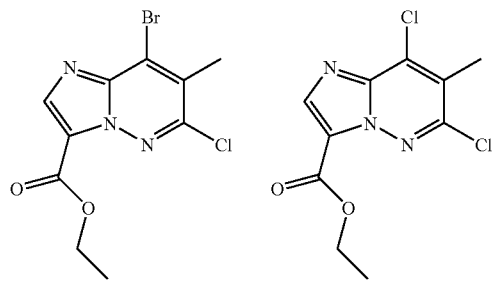 [SMILES: CCOC(=O)c1cnc2c(Br)c(C)c(Cl)nn12 ; CCOC(=O)c1cnc2c(Cl)c(C)c(Cl)nn12]

To a 250 mL round-bottom pressure flask equipped with a teflon screw cap was added 4-bromo-6-chloro-5-methylpyridazin-3-amine (35B) (2.1 g, 9.44 mmol), ethyl 2-chloro-3-oxopropanoate (2.3 g, 15.28 mmol) and ethanol (50 mL). The flask was purged with nitrogen, sealed and heated to 90° C. The reaction was cooled to room temperature. The mixture was concentrated in vacuo to remove the ethanol. The mixture was adjusted to pH 7 with 1N NaOH, transferred to a separatory funnel, extracted with ethyl acetate (3×), washed with brine (3×), dried over anhydrous sodium sulfate and concentrated in vacuo to give ~4 g of a very dark semi-solid. The solid was purified on an ISCO 16× chromatography system (120 g silica cartridge, 0-100% Ethyl Acetate/Dichloromethane gradient, 70 mL/min). to provide 2.92 g of a mixture of ~60% ethyl 8-bromo-6-chloro-7-methylimidazo[1,2-b]pyridazine-3-carboxylate and 40% ethyl 6,8-dichloro-7-methylimidazo[1,2-b]pyridazine-3-carboxylate. Ethyl 6-chloro-7-methylimidazo[1,2-b]pyridazine-3-carboxylate (0.28 g, 1.168 mmol, 12.38% yield) was also isolated.

35D. Preparation of 8-bromo-6-chloro-7-methylimidazo[1,2-b]pyridazine-3-carboxylic acid and 6,8-dichloro-7-methylimidazo[1,2-b]pyridazine-3-carboxylic acid

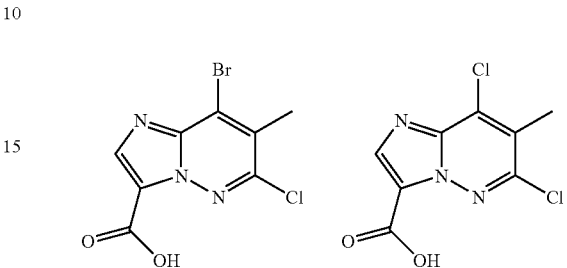

A mixture of ethyl 8-bromo-6-chloro-7-methylimidazo[1,2-b]pyridazine-3-carboxylate and ethyl 6,8-dichloro-7-methylimidazo[1,2-b]pyridazine-3-carboxylate (1.0 g, 3.65 mmol) 35C was dissolved in 6N HCl (20 mL), and transferred to a vial (40 mL, 28 mm OD×95 mm height, screw cap). A magnetic stir bar was added, and the vial was sealed with a teflon lined cap (24-400 screw cap, open top, PTFE faced silicone septa). The clear orange solution was warmed to 85° C. overnight. The reaction was continued for a second day. The mixture was cooled to room temperature. The precipitate was collected by filtration and the resulting solid was washed with water, and dried in vacuo to provide 0.256 g as a 2:1 mixture of 8-bromo-6-chloro-7-methylimidazo[1,2-b]pyridazine-3-carboxylic acid and 6,8-dichloro-7-methylimidazo[1,2-b]pyridazine-3-carboxylic acid which were used without further purification.

35E. Preparation of 8-bromo-6-chloro-7-methyl-N-(pyridin-4-yl)imidazo[1,2-b]pyridazine-3-carboxamide and 6,8-dichloro-7-methyl-N-(pyridin-4-yl)imidazo[1,2-b]pyridazine-3-carboxamide

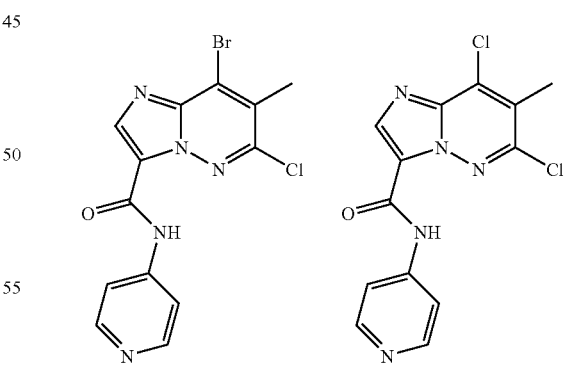

Oxalyl dichloride (4 mL, 8 mmol, 2M in dichloromethane) was added to a 100 mL round bottom flask charged with a mixture of 8-bromo-6-chloro-7-methylimidazo[1,2-b]pyridazine-3-carboxylic acid and 6,8-dichloro-7-methylimidazo[1,2-b]pyridazine-3-carboxylic acid 35D (0.256 g, 0.881 mmol), a stir bar and a septum which was wired on. Catalytic DMF was added and the suspension was stirred overnight at room temperature. The mixture was concentrated in vacuo.

The resulting residue was purged with nitrogen, and suspended in dichloromethane (6 mL). Triethylamine (0.368 mL, 2.64 mmol), catalytic DMAP, and pyridin-4-amine (0.124 g, 1.322 mmol) were added. The mixture was allowed to stir overnight. The mixture was quenched with water, transferred to a separatory funnel, and extracted with dichloromethane (3×). The extracts were combined, washed with water, dried over sodium sulfate and concentrated in vacuo to provide 0.27 g of a mixture of 8-bromo-6-chloro-7-methyl-N-(pyridin-4-yl)imidazo[1,2-b]pyridazine-3-carboxamide and 6,8-dichloro-7-methyl-N-(pyridin-4-yl)imidazo[1,2-b]pyridazine-3-carboxamide which was used without further purification.

35F. Preparation of 6-((trans)-4-aminocyclohexylamino)-7-methyl-8-(5-methylpyridin-2-ylamino)-N-(pyridin-4-yl)imidazo[1,2-b]pyridazine-3-carboxamide

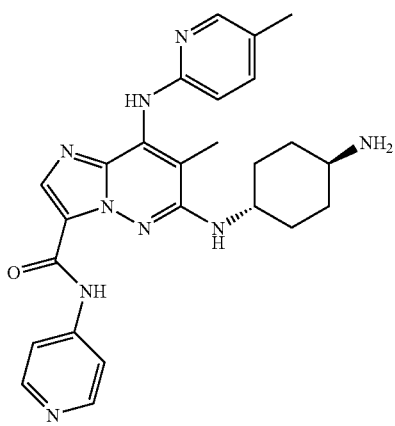 [SMILES: Cc1ccc(Nc2c(C)c(N[C@H]3CC[C@H](N)CC3)nn3c(C(=O)Nc4ccncc4)cnc23)nc1]

A vial charged with a mixture of 8-bromo-6-chloro-7-methyl-N-(pyridin-4-yl)imidazo[1,2-b]pyridazine-3-carboxamide and 6,8-dichloro-7-methyl-N-(pyridin-4-yl)imidazo[1,2-b]pyridazine-3-carboxamide 35E (0.108 g, 0.295 mmol) and 5-methylpyridin-2-amine (0.032 g, 0.295 mmol) was purged with nitrogen. THF (1 mL) and lithium bis(trimethylsilyl)amide) (0.88 mL, 0.88 mmol, 1M in THF) were added and the mixture was stirred at room temperature and monitored by LC/MS. After 5 h the mixture was concentrated to dryness under a stream of N₂. Trans-cyclohexyldiamine (0.168 g, 1.47 mmol) was added to the resulting residue and the mixture was heated at 160° C. After 30 min, 1.5 mL water and 1.5 mL dichloromethane are added to the vial and the vial was shaken until all solids dissolve. The dichloromethane layer was drawn off with a pipette and concentrated to dryness. The resulting residue was dissolved in 2 mL methanol and 2 mL Solvent B (90% MeOH, 10% water, 0.1% TFA). 1 drop of TFA was added to the solution, the sample was split into 3 equal volumes and purified by reverse phase preparative HPLC on a Phenx Luna Axia Column 5u (21.2×100 mm) Solvent A (10% MeOH, 90% water, 0.1% TFA), Solvent B (90% MeOH, 10% water, 0.1% TFA) 10-60% solvent B gradient, 20 mL/min, 220 nM UV detection to provide 6-((trans)-4-aminocyclohexylamino)-7-methyl-8-(5-methylpyridin-2-ylamino)-N-(pyridin-4-yl)imidazo[1,2-b]pyridazine-3-carboxamide (0.0063 g, 6.83 μmol, 2.320% yield). ¹H NMR (500 MHz, MeOH-D4) δ ppm 8.65 (2H, d, J=7.15 Hz), 8.21 (2H, d, J=7.15 Hz), 8.08 (1H, s), 7.89-7.91 (1H, m), 7.72 (1H, s), 7.13 (1H, d, J=8.80 Hz), 3.95-4.01 (1H, m), 3.08 (1H, m), 2.27 (2H, m), 2.22 (3H, s), 2.19 (3H, s), 2.69 (2H, m), 1.47-1.54 (4H, m). LC/MS: HPLC Retention time: 1.17 min, MS: 472 (M+1) (Shimidazu LC, Waters Sunfire C-18 column (4.65×50 mm, 5 um, 0-100% Solvent B, 4 min gradient, 4 mL/min, 220 UV detection. Solvent A: 10% MeOH/90% Water/0.1% TFA, Solvent B 90% MeOH/10% Water/0.1% TFA.)

Example 36

6-((trans-4-aminocyclohexyl)amino)-8-anilino-7-methyl-N-4-pyridinylimidazo[1,2-b]pyridazine-3-carboxamide

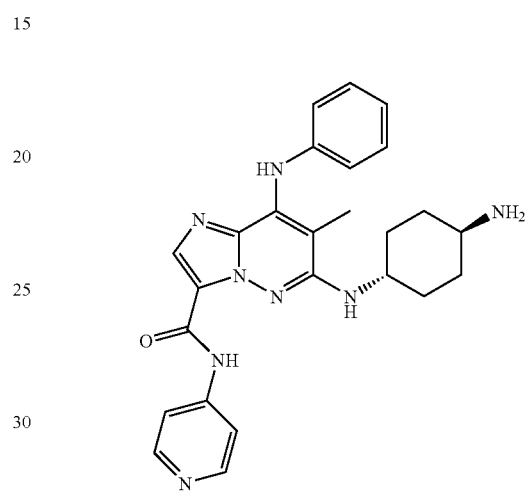

Example 36 may be prepared in a similar manner to that described for Example 35. HPLC Rt=2.04 min., Waters Sunfire C-18 column 4 65×50 mm, 5 um: 0-100% Solvent B, 4 min gradient, 4 mL/min, 220 UV detection. Solvent A: 10% MeOH/90% Water/0.1% TFA, Solvent B 90% MeOH/10% Water/0.1% TFA. [M+H]=457.

Example 37

(S)-6-(1-benzylpiperidin-3-ylamino)-8-(pyridin-2-ylamino)-N-(pyridin-4-yl)imidazo[1,2-b]pyridazine-3-carboxamide

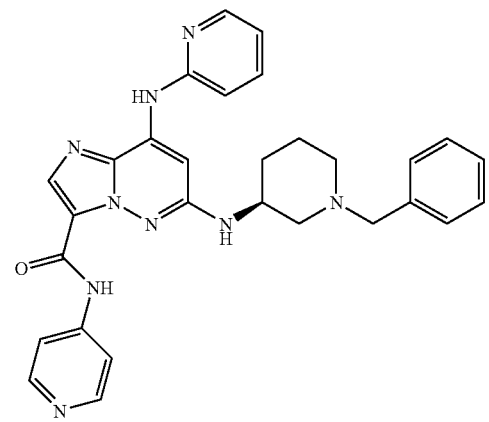 [SMILES: O=C(Nc1ccncc1)c1cnc2c(Nc3ccccn3)cc(N[C@H]3CCCN(Cc4ccccc4)C3)nn12]

37A. Preparation of 6-chloro-8-(pyridin-2-ylamino)-N-(pyridin-4-yl)imidazo[1,2-b]pyridazine-3-carboxamide

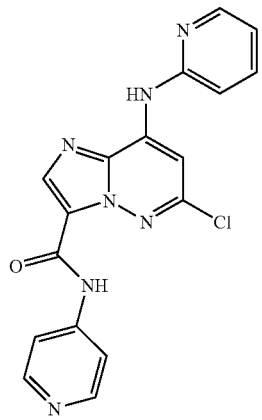 [SMILES: O=C(Nc1ccncc1)c1cnc2c(Nc3ccccn3)cc(Cl)nn12]

To a vial was added a mixture of 8-bromo-6-chloro-N-(pyridin-4-yl)imidazo[1,2-b]pyridazine-3-carboxamide and 6,8-dichloro-N-(pyridin-4-yl)imidazo[1,2-b]pyridazine-3-carboxamide 1E (0.316 g, 0.896 mmol) and pyridin-2-amine (0.084 g, 0.896 mmol). The vial was purged with nitrogen, and THF (1 mL) was added. Potassium tert-butoxide (2.69 mL, 2.69 mmol, 1M in THF) was added and the mixture was stirred at room temperature. After 1 h, the reaction was quenched with a few drops of TFA and methanol. The precipitate was filtered and the powder was washed with methanol to provide 6-chloro-8-(pyridin-2-ylamino)-N-(pyridin-4-yl)imidazo[1,2-b]pyridazine-3-carboxamide (0.2952 g, 0.497 mmol, 55.5% yield) as a pink solid.

37B. Preparation of (S)-6-(1-benzylpiperidin-3-ylamino)-8-(pyridin-2-ylamino)-N-(pyridin-4-yl)imidazo[1,2-b]pyridazine-3-carboxamide

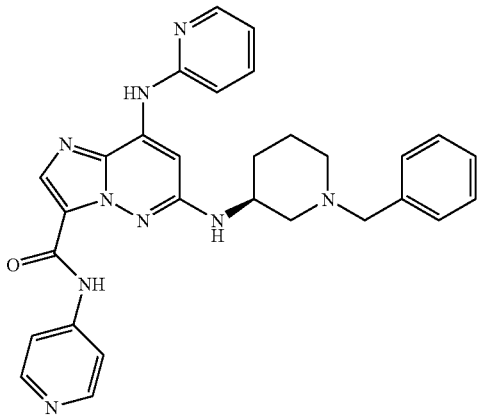 [SMILES: O=C(Nc1ccncc1)c1cnc2c(Nc3ccccn3)cc(N[C@H]3CCCN(Cc4ccccc4)C3)nn12]

A vial containing a mixture of (S)-1-benzylpiperidin-3-amine (0.385 g, 2.021 mmol) and 6-chloro-8-(pyridin-2-ylamino)-N-(pyridin-4-yl)imidazo[1,2-b]pyridazine-3-carboxamide 37A (0.08 g, 0.135 mmol) was heated to 170° C. overnight. The mixture was dissolved in 3 mL methanol and 3 mL Solvent B (90% MeOH, 10% water, 0.1% TFA). One drop of TFA was added to the solution, the sample was split into 4 equal volumes and purified by reverse phase preparative HPLC on a Phenx Luna Axia Column 5u (21.2×100 mm) Solvent A (10% MeOH, 90% water, 0.1% TFA), Solvent B (90% MeOH, 10% water, 0.1% TFA) 20-100% solvent B gradient, 20 mL/min, 220 nM UV detection to provide (S)-6-(1-benzylpiperidin-3-ylamino)-8-(pyridin-2-ylamino)-N-(pyridin-4-yl)imidazo[1,2-b]pyridazine-3-carboxamide (0.0082 g, 9.52 μmol, 7.06% yield). $^1$H NMR (500 MHz, CD3OD) δ ppm 8.42 (2H, m), 8.02-7.68 (5H, m), 7.49 (1H, m), 7.29-6.76 (9H, m), 4.2-3.95 (2H, m), 3.73-3.58 (1H, m), 3.37 (1H, m), 3.06-2.64 (2H, m), 2.32-1.78 (3H, m). LC/MS: HPLC Retention time: 2.15 min, MS: 520 (M+1) (Shimidazu LC, Waters Sunfire C-18 column (4.65×50 mm, 5 um, 0-100% Solvent B, 4 min gradient, 4 mL/min, 220 UV detection. Solvent A: 10% MeOH/90% Water/0.1% TFA, Solvent B 90% MeOH/10% Water/0.1% TFA.)

Example 38

(S)-6-(piperidin-3-ylamino)-8-(pyridin-2-ylamino)-N-(pyridin-4-yl)imidazo[1,2-b]pyridazine-3-carboxamide

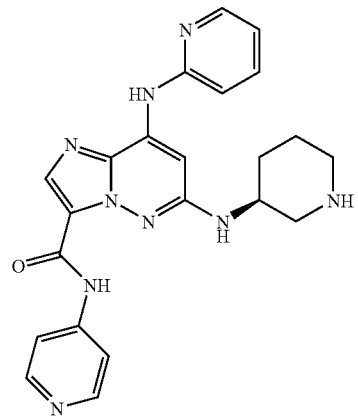 [SMILES: O=C(Nc1ccncc1)c1cnc2c(Nc3ccccn3)cc(N[C@H]3CCCNC3)nn12]

A Parr bottle was charged with (S)-6-(1-benzylpiperidin-3-ylamino)-8-(pyridin-2-ylamino)-N-(pyridin-4-yl)imidazo[1,2-b]pyridazine-3-carboxamide 37B (0.055 g, 0.106 mmol), and dissolved in 30 mL of methanol with heating. The solution was purged with nitrogen and 200 mgs of 10% Pd/C was added. The resulting mixture was hydrogenated overnight on a Parr apparatus at 50 psi hydrogen. The mixture was filtered through celite and concentrated in vacuo. The resulting residue was dissolved in 2 mL methanol and 2 mL Solvent B (90% MeOH, 10% water, 0.1% TFA). One drop of TFA was added to the solution and the sample was split into 3 equal volumes and purified by reverse phase preparative HPLC on a Phenx Luna Axia Column 5u (21.2×100 mm) Solvent A (10% MeOH, 90% water, 0.1% TFA), Solvent B (90% MeOH, 10% water, 0.1% TFA) 20-100% solvent B gradient, 20 mL/min, 220 nM UV detection to provide (S)-6-(piperidin-3-ylamino)-8-(pyridin-2-ylamino)-N-(pyridin-4-yl)imidazo[1,2-b]pyridazine-3-carboxamide (0.0169 g, 0.022 mmol, 20.69% yield). $^1$H NMR (500 MHz, CD3OD) δ ppm 8.58 (2 H, m), 8.26 (1H, m), 8.19 (2H, m), 8.13 (1H, s), 8.02 (1H, s), 7.66 (1H, m), 7.08 (1H, m), 6.93 (1H, m), 4.18 (1H, m), 3.433 (1H, m), 3.27 (1H, m), 3.06 (2H, m), 2.14 (1H, m), 2.04 (1H, m), 1.86 (2H, m). LC/MS: HPLC Retention time: 2.15 min, MS: 430 (M+1) (Shimidazu LC, Waters Sunfire C-18 column (4.65×50 mm, 5 um, 0-100% Solvent B, 4 min

Example 39

(S)-6-(piperidin-3-ylamino)-8-(pyridin-2-ylamino)-N-(pyridin-4-yl)imidazo[1,2-b]pyridazine-3-carboxamide

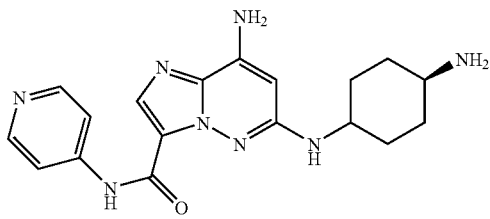

39A. Preparation of 6-((trans)-4-aminocyclohexylamino)-8-(4-methoxybenzylamino)-N-(pyridin-4-yl)imidazo[1,2-b]pyridazine-3-carboxamide

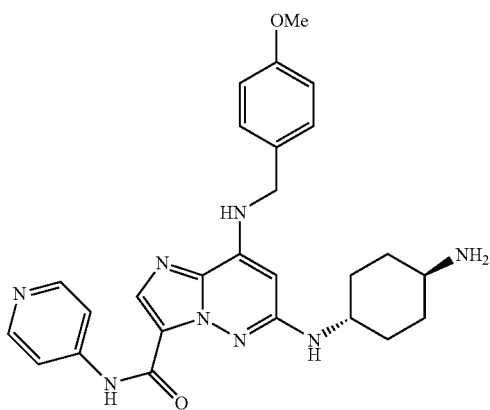 [SMILES: COc1ccc(CNc2cc(N[C@H]3CC[C@H](N)CC3)nn3c(C(=O)Nc4ccncc4)cnc23)cc1]

(4-methoxyphenyl)methanamine (0.050 mL, 0.383 mmol) was added to a suspension of a mixture of 8-bromo-6-chloro-N-(pyridin-4-yl)imidazo[1,2-b]pyridazine-3-carboxamide and a 6,8-dichloro-N-(pyridin-4-yl)imidazo[1,2-b]pyridazine-3-carboxamide 1E (0.118 g, 0.383 mmol) in tetrahydrofuran (1.0 mL) in a 2 dram screw vial equipped with a stir bar and a teflon coated screw cap. The mixture was heated at 80° C. overnight. The reaction was cooled to room temperature. The reaction was concentrated to dryness under a stream of nitrogen. (trans)-Cyclohexane-1,4-diamine (0.437 g, 3.83 mmol) was added and the mixture was heated to 160° C. After 2 h, the reaction was partitioned between dichloromethane (1.5 mL) and water (1.5 mL). The dichloromethane was removed and concentrated under a stream of nitrogen to provide 6-((trans)-4-aminocyclohexylamino)-8-(4-methoxybenzylamino)-N-(pyridin-4-yl)imidazo[1,2-b]pyridazine-3-carboxamide (0.103 g).

39B. Preparation of 8-amino-6-(4-aminocyclohexylamino)-N-(pyridin-4-yl)imidazo[1,2-b]pyridazine-3-carboxamide

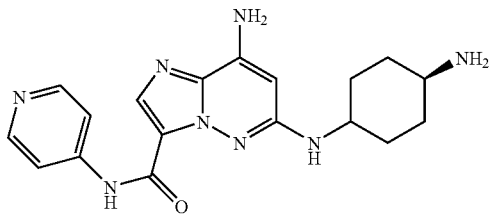

TFA (1 mL) was added to a 2 dram vial containing 6-((trans)-4-aminocyclohexylamino)-8-(4-methoxybenzylamino)-N-(pyridin-4-yl)imidazo[1,2-b]pyridazine-3-carboxamide 39A and the mixture was heated at 40° C. After 40 min, the mixture was concentrated to dryness under a stream of nitrogen. The residue was dissolved in 3 mL of methanol and 3 mL of Solvent B (90% MeOH, 10% water, 0.1% TFA). One drop of TFA was added to the solution, the sample was split into 3 equal volumes and purified by reverse phase preparative HPLC on a Phenx Luna Axia Column 5u (21.2× 100 mm) Solvent A (10% MeOH, 90% water, 0.1% TFA), Solvent B (90% MeOH, 10% water, 0.1% TFA) 10-80% solvent B gradient, 20 mL/min, 220 nM UV detection to provide 8-amino-6-(4-aminocyclohexylamino)-N-(pyridin-4-yl)imidazo[1,2-b]pyridazine-3-carboxamide (0.0419 g, 0.059 mmol, 15.44% yield). $^1$H NMR (500 MHz, CD3OD) δ ppm 8.65 (3H, d, J=7.15 Hz), 8.26 (3H, d, J=7.15 Hz), 8.08 (1H, s), 5.87 (1H, s), 3.66 (1H, m), 3.10 (1H, m), 2.22-2.27 (2H, m), 2.08 (2H, m), 1.53 (2H, m), 1.36-1.44 (2H, m). LC/MS: HPLC Retention time: 1.38 min, MS: 367 (M+1) (Shimidazu LC, Waters Sunfire C-18 column (4.65×50 mm, 5 um, 0-100% Solvent B, 4 min gradient, 4 mL/min, 220 UV detection. Solvent A: 10% MeOH/90% Water/0.1% TFA, Solvent B 90% MeOH/10% Water/0.1% TFA.)

Example 40

8-((6-amino-4-chloro-2-pyridinyl)amino)-6-((trans-4-aminocyclohexyl)amino)-N-(3-fluoro-4-pyridinyl)imidazo[1,2-b]pyridazine-3-carboxamide

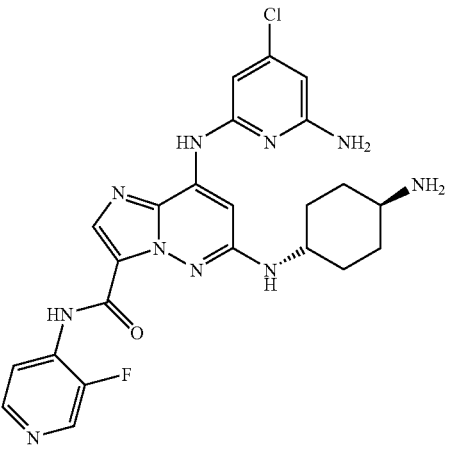

40A. Preparation of 8-(6-amino-4-chloropyridin-2-ylamino)-6-chloro-N-(3-fluoropyridin-4-yl)imidazo[1,2-b]pyridazine-3-carboxamide

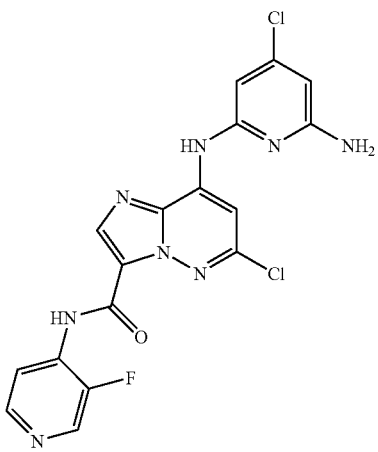 [SMILES: Nc1cc(Cl)cc(Nc2cc(Cl)nn3c(C(=O)Nc4ccncc4F)cnc23)n1]

To a solution of 4-chloropyridine-2,6-diamine (35.2 mg, 0.245 mmol) in THF (0.5 mL) was added 60% NaH (12.26 mg, 0.307 mmol). The mixture was stirred for 10 min. 5A (40 mg, 0.123 mmol) was added, followed by DMF (0.5 mL). The mixture was stirred at room temperature for 1 h. Water was added and the precipitated solid was collected by filtration, and dried to give crude 40A (42 mg, 59%). HPLC $R_t$=3.131 min (Chromolith SpeedROD 4.6×50 mm, 10-90% aqueous methanol containing 0.1% TFA, 4 min gradient, monitored at 220 nm), [M+H]=433.

40B. Preparation of 8-((6-amino-4-chloro-2-pyridinyl)amino)-6-((trans-4-aminocyclohexyl)amino)-N-(3-fluoro-4-pyridinyl)imidazo[1,2-b]pyridazine-3-carboxamide

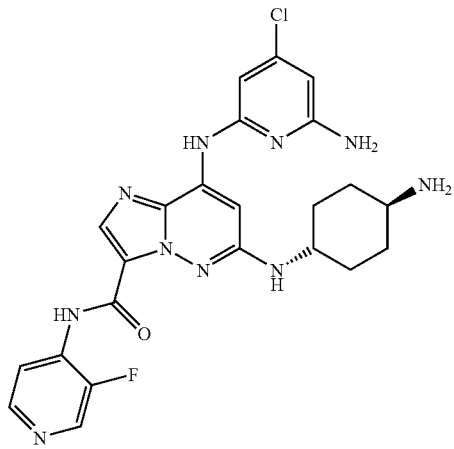

A mixture of 8-(6-amino-4-chloropyridin-2-ylamino)-6-chloro-N-(3-fluoropyridin-4-yl)imidazo[1,2-b]pyridazine-3-carboxamide (42 mg, 0.073 mmol) and trans-cyclohexane-1,4-diamine (74.2 mg, 0.650 mmol) in NMP (0.4 mL) was heated at 110° C. overnight. The reaction mixture was then cooled to room temperature and purified by reversed-phase HPLC. The fractions containing the title compounds were lyophilized to dryness to afford 8-((6-amino-4-chloro-2-pyridinyl)amino)-6-((trans-4-aminocyclohexyl)amino)-N-(3-fluoro-4-pyridinyl)imidazo[1,2-b]pyridazine-3-carboxamide (16.5 mg, 25%). HPLC $R_t$=2.813 minutes (Chromolith SpeedROD 4.6×50 mm, 10-90% aqueous methanol containing 0.1% TFA, 4 min gradient, monitored at 220 nm), [M+H]=511.

Example 41
8-((6-acetamido-4-chloro-2-pyridinyl)amino)-6-((trans-4-aminocyclohexyl)amino)-N-(3-fluoro-4-pyridinyl)imidazo[1,2-b]pyridazine-3-carboxamide

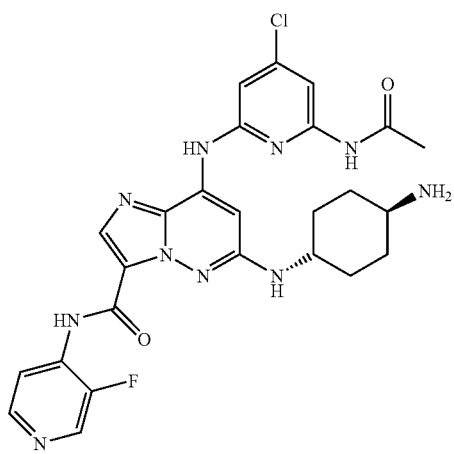

41A. 8-(6-acetamido-4-chloropyridin-2-ylamino)-6-chloro-N-(3-fluoropyridin-4-yl)imidazo[1,2-b]pyridazine-3-carboxamide

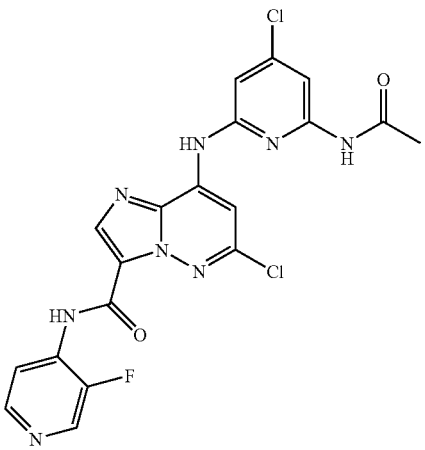 [SMILES: CC(=O)Nc1cc(Cl)cc(Nc2cc(Cl)nn3c(C(=O)Nc4ccncc4F)cnc23)n1]

To a solution of 4-chloropyridine-2,6-diamine (35.2 mg, 0.245 mmol) in THF (0.5 mL) was added 60% NaH (12.26 mg, 0.307 mmol). The mixture was stirred for 10 min. 5A (40 mg, 0.123 mmol) was added, followed by DMF (0.5 mL). The mixture was stirred at room temperature overnight. To the reaction mixture was added acetyl chloride (0.052 mL, 0.736 mmol) and a few drops of DIEA. The mixture was stirred at 65° C. for 20 min and then cooled to room temperature. Saturated NH$_4$Cl was added and the resulting precipitate was collected by filtration, washed with water, and dried in vacuum to give crude 41A as a yellow solid (40 mg, 49%). HPLC $R_t$=3.283 min. (Chromolith SpeedROD 4.6×50 mm, 10-90% aqueous methanol containing 0.1% TFA, 4 min gradient, monitored at 220 nm), [M+H]=475.

41B. 8-((6-acetamido-4-chloro-2-pyridinyl)amino)-6-((trans-4-aminocyclohexyl)amino)-N-(3-fluoro-4-pyridinyl)imidazo[1,2-b]pyridazine-3-carboxamide

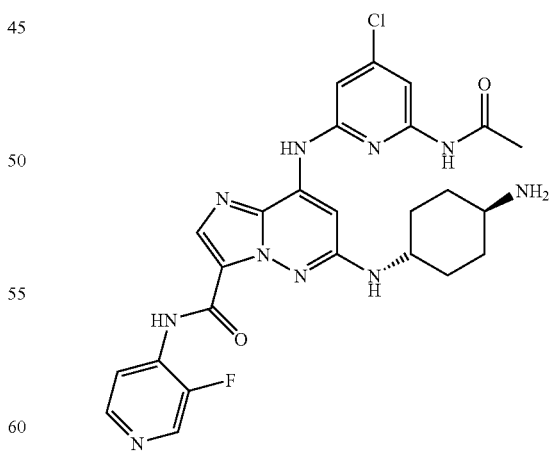

The title compound was prepared with trans-cyclohexane-1,4-diamine using the procedures detailed in Example 40. HPLC $R_t$=3.128 min (Chromolith SpeedROD 4.6×50 mm, 10-90% aqueous methanol containing 0.1% TFA, 4 min gradient, monitored at 220 nm), [M+H]=553.

Example 42

6-((trans-4-aminocyclohexyl)amino)-N-(3-fluoro-4-pyridinyl)-8-(4-pyrimidinylamino)imidazo[1,2-b]pyridazine-3-carboxamide

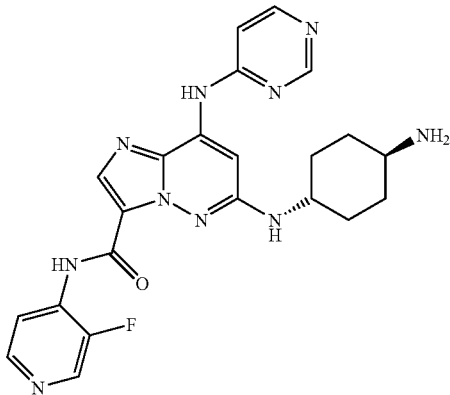

The title compound was prepared in a similar way as Example 40. HPLC $R_t$=1.887 min (Chromolith SpeedROD 4.6×50 mm, 10-90% aqueous methanol containing 0.1% TFA, 4 min gradient, monitored at 220 nm), [M+H]=463.

Example 43

6-((trans-4-aminocyclohexyl)amino)-N-(3-fluoro-4-pyridinyl)-8-(3-isoxazolylamino)imidazo[1,2-b]pyridazine-3-carboxamide

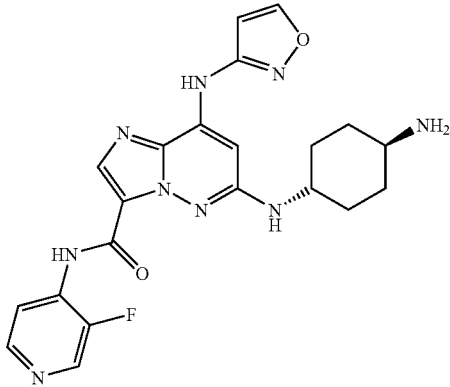

43A. Preparation of 6-chloro-N-(3-fluoropyridin-4-yl)-8-(isoxazol-3-ylamino)imidazo[1,2-b]pyridazine-3-carboxamide

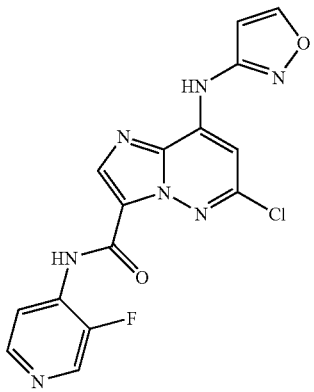 [SMILES: O=C(Nc1ccncc1F)c1cnc2c(Nc3ccon3)cc(Cl)nn12]

To a solution of isoxazol-3-amine (25.8 mg, 0.307 mmol) in THF (0.5 mL) was added 60% NaH (12.26 mg, 0.307 mmol). The mixture was stirred for 10 min and 5A (40 mg, 0.123 mmol) was added followed by DMF (0.5 mL). The mixture was stirred overnight. The solvent was removed under a stream of nitrogen and water was added. The resulting solid was collected by filtration, rinsed with water, and dried on vacuum to give the title compound as a yellow solid.

43B. Preparation of 6-((trans-4-aminocyclohexyl)amino)-N-(3-fluoro-4-pyridinyl)-8-(3-isoxazolylamino)imidazo[1,2-b]pyridazine-3-carboxamide

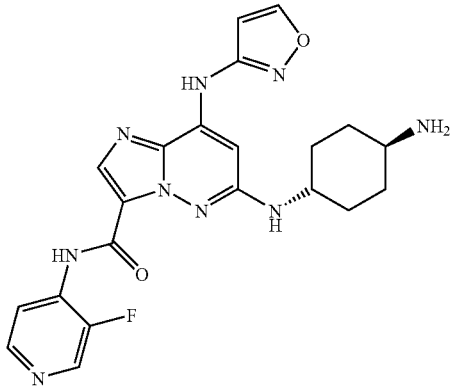

A mixture of 6-chloro-N-(3-fluoropyridin-4-yl)-8-(isoxazol-3-ylamino)imidazo[1,2-b]pyridazine-3-carboxamide (20 mg, 0.054 mmol) and trans-cyclohexane-1,4-diamine (61.1 mg, 0.535 mmol) in NMP (0.4 mL) was heated at 110° C. overnight, then cooled to room temperature. The resulting mixture was purified by reversed-phase preparative HPLC. The desired fractions were concentrated and dried to give 18.7 mg of 6-((trans-4-aminocyclohexyl)amino)-N-(3-fluoro-4-pyridinyl)-8-(3-isoxazolylamino)imidazo[1,2-b]pyridazine-3-carboxamide as a beige solid. HPLC $R_t$=2.292 min (Chromolith SpeedROD 4.6×50 mm, 10-90% aqueous methanol containing 0.1% TFA, 4 min gradient, monitored at 220 nm), [M+1]=452.

Example 44

N-(3-fluoro-4-pyridinyl)-6-((trans-4-hydroxycyclohexyl)amino)-8-(3-isoxazolylamino)imidazo[1,2-b]pyridazine-3-carboxamide

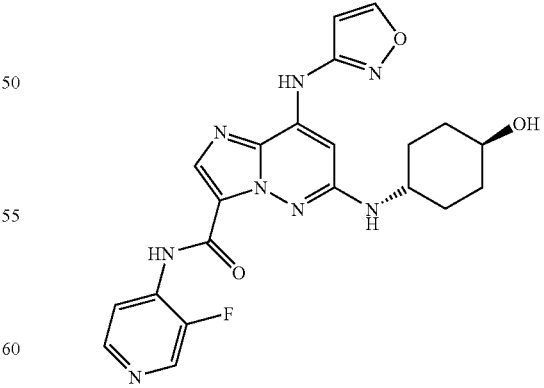

A mixture of 6-chloro-N-(3-fluoropyridin-4-yl)-8-(isoxazol-3-ylamino)imidazo[1,2-b]pyridazine-3-carboxamide (20 mg, 0.054 mmol) and (trans)-4-aminocyclohexanol (61.6 mg, 0.535 mmol) in NMP (0.4 mL) was heated at 110° C. overnight. The reaction mixture was cooled to room temperature, and purified by reversed-phase preparative HPLC. The desired fractions were concentrated and dried to give 15 mg the title compound as a beige solid. HPLC $R_f$=2.615 min (Chromolith SpeedROD 4.6×50 mm, 10-90% aqueous methanol containing 0.1% TFA, 4 min gradient, monitored at 220 nm), [M+1]=453.

Example 45

N-(3-fluoro-4-pyridinyl)-6-((trans-4-hydroxycyclohexyl)amino)-8-((6-((trans-4-hydroxycyclohexyl)amino)-2-pyridinyl)amino)imidazo[1,2-b]pyridazine-3-carboxamide

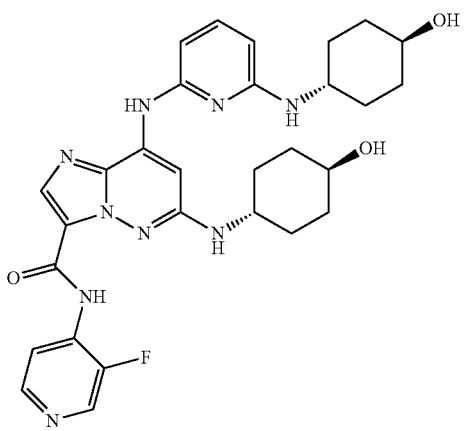

45A. 8-(6-bromopyridin-2-ylamino)-6-chloro-N-(3-fluoropyridin-4-yl)imidazo[1,2-b]pyridazine-3-carboxamide

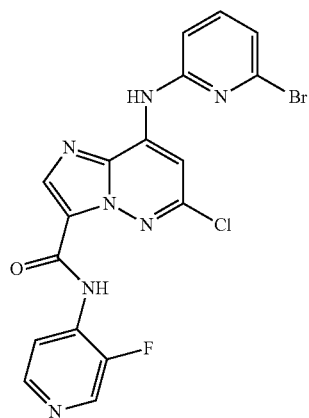 [SMILES: O=C(Nc1ccncc1F)c1cnc2c(Nc3cccc(Br)n3)cc(Cl)nn12]

Compound 45A was prepared from 6-bromopyridin-2-amine in a similar way as Example 40A. HPLC $R_f$=3.696 min (Chromolith SpeedROD 4.6×50 mm, 10-90% aqueous methanol containing 0.1% TFA, 4 min gradient, monitored at 220 nm), [M+1]=463.

45B. Preparation of N-(3-fluoropyridin-4-yl)-6-((trans)-4-hydroxycyclohexylamino)-8-(6-((trans)-4-hydroxycyclohexylamino)pyridin-2-ylamino)imidazo[1,2-b]pyridazine-3-carboxamide

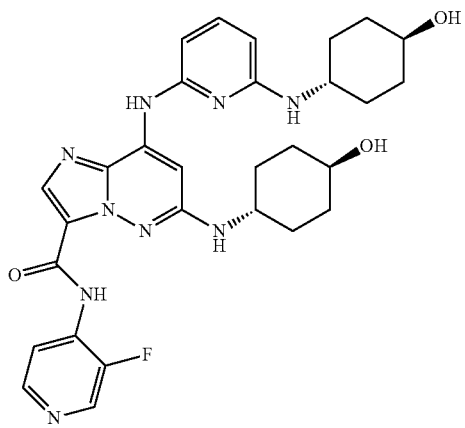 [SMILES: O=C(Nc1ccncc1F)c1cnc2c(Nc3cccc(N[C@H]4CC[C@H](O)CC4)n3)cc(N[C@H]3CC[C@H](O)CC3)nn12]

A mixture of 8-(6-bromopyridin-2-ylamino)-6-chloro-N-(3-fluoropyridin-4-yl)imidazo[1,2-b]pyridazine-3-carboxamide (40 mg, 0.086 mmol) and (trans)-4-aminocyclohexanol (100 mg, 0.868 mmol) in NMP (0.5 mL) was heated at 160° C. in a microwave for 1.5 h (300 W power). The reaction mixture was cooled to room temperature and purified by preparative reversed-phase HPLC to give 45B (39.7 mg, 62%) as yellow solid. HPLC $R_f$=2.780 min (Chromolith SpeedROD 4.6×50 mm, 10-90% aqueous methanol containing 0.1% TFA, 4 min gradient, monitored at 220 nm), [M+H]= 576.

Example 46

6-((trans-4-aminocyclohexyl)amino)-N-(3-fluoro-4-pyridinyl)-8-((6-((trans-4-hydroxycyclohexyl)amino)-2-pyridinyl)amino)imidazo[1,2-b]pyridazine-3-carboxamide

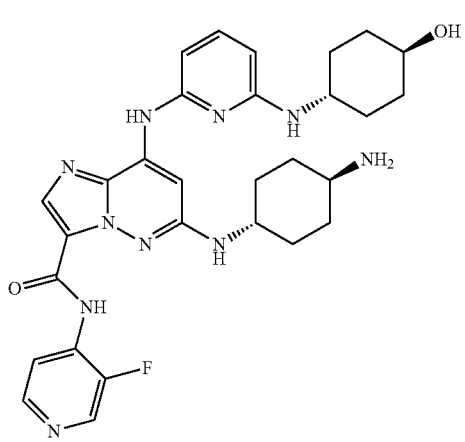

46A. 6-((trans)-4-aminocyclohexylamino)-8-(6-bromopyridin-2-ylamino)-N-(3-fluoropyridin-4-yl)imidazo[1,2-b]pyridazine-3-carboxamide

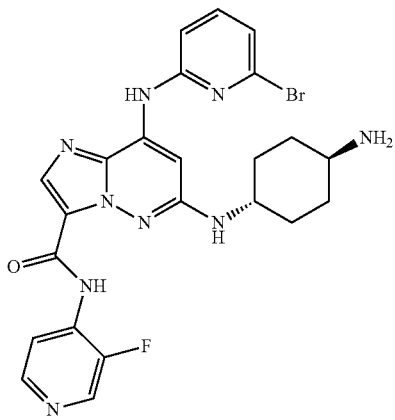 [SMILES: N[C@H]1CC[C@H](Nc2cc(Nc3cccc(Br)n3)c3ncc(C(=O)Nc4ccncc4F)n3n2)CC1]

A mixture of 8-(6-bromopyridin-2-ylamino)-6-chloro-N-(3-fluoropyridin-4-yl)imidazo[1,2-b]pyridazine-3-carboxamide (550 mg, 1.189 mmol) and (trans)-cyclohexane-1,4-diamine (1086 mg, 9.51 mmol) in NMP (4 mL) was heated at 100° C. overnight. The reaction mixture was cooled to room temperature and poured onto ice. The resulting yellow solid was collected by filtration and rinsed with water. The still wet solid pad was concentrated from DCM/MeOH 3 times until dryness. The solid residue was treated with a small amount of MeOH, and the yellow solid was collected by filtration and dried under vacuum to give the title compound (456 mg, 71%). HPLC $R_t$=2.870 min (Chromolith SpeedROD 4.6×50 mm, 10-90% aqueous methanol containing 0.1% TFA, 4 min gradient, monitored at 220 nm), [M+H]=542.

46B. 6-((trans-4-aminocyclohexyl)amino)-N-(3-fluoro-4-pyridinyl)-8-((6-((trans-4-hydroxycyclohexyl)amino)-2-pyridinyl)amino)imidazo[1,2-b]pyridazine-3-carboxamide

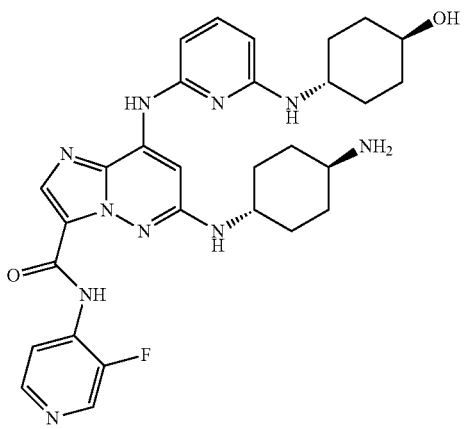

A mixture of 46A (25 mg, 0.046 mmol) and (trans)-4-aminocyclohexanol (100 mg, 0.868 mmol) in NMP (0.4 mL) was heated at 160° C. in a microwave for 1.5 h (300 W), and then cooled to room temperature. The mixture was diluted by MeOH, and purified by preparative reversed-phase HPLC to give 6-((trans-4-aminocyclohexyl)amino)-N-(3-fluoro-4-pyridinyl)-8-((6-((trans-4-hydroxycyclohexyl)amino)-2-pyridinyl)amino)imidazo[1,2-b]pyridazine-3-carboxamide (12 mg, 28%) as a yellow solid. HPLC $R_t$=2.517 min (Chromolith SpeedROD 4.6×50 mm, 10-90% aqueous methanol containing 0.1% TFA, 4 min gradient, monitored at 220 nm), [M+H]= 575.

Example 47

6-((trans-4-aminocyclohexyl)amino)-N-(3-fluoro-4-pyridinyl)-8-((6-((2-hydroxyethyl)amino)-2-pyridinyl)amino)imidazo[1,2-b]pyridazine-3-carboxamide

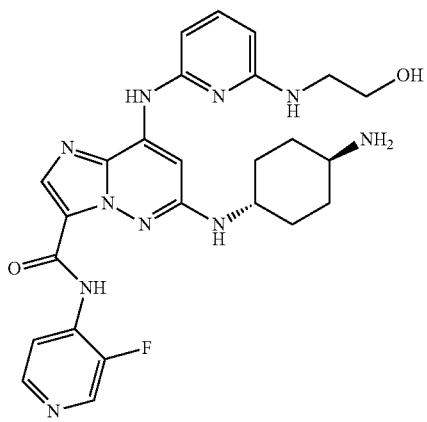 [SMILES: N[C@H]1CC[C@H](Nc2cc(Nc3cccc(NCCO)n3)c3ncc(C(=O)Nc4ccncc4F)n3n2)CC1]

The title compound was prepared from 46A and 2-aminoethanol in a similar way as 46B. HPLC $R_t$=2.373 min (Chromolith SpeedROD 4.6×50 mm, 10-90% aqueous methanol containing 0.1% TFA, 4 min gradient, monitored at 220 nm), [M+H]=521.

Example 48

6-((trans-4-aminocyclohexyl)amino)-N-(3-fluoro-4-pyridinyl)-8-((1-isopropyl-1H-pyrazol-3-yl)amino)imidazo[1,2-b]pyridazine-3-carboxamide

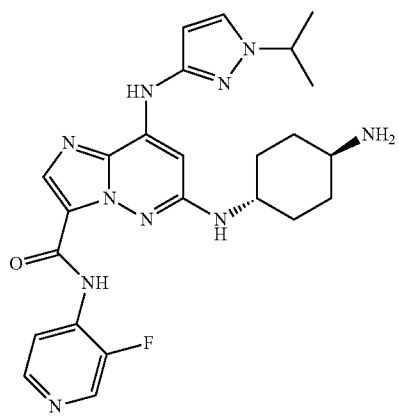 [SMILES: CC(C)n1ccc(Nc2cc(N[C@H]3CC[C@H](N)CC3)nn3c(C(=O)Nc4ccncc4F)cnc23)n1]

48A. 6-chloro-N-(3-fluoropyridin-4-yl)-8-(1-isopropyl-1H-pyrazol-3-ylamino)imidazo[1,2-b]pyridazine-3-carboxamide

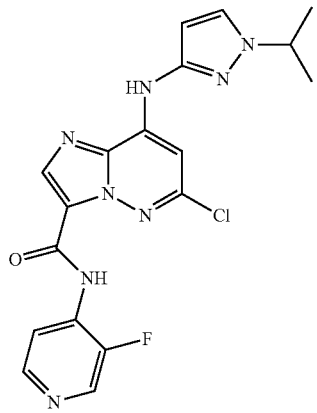 [SMILES: CC(C)n1ccc(Nc2cc(Cl)nn3c(C(=O)Nc4ccncc4F)cnc23)n1]

A mixture of 5A (80 mg, 0.245 mmol), 1-isopropyl-1H-pyrazol-3-amine (36.8 mg, 0.294 mmol), Pd$_2$(dba)$_3$ (11.23 mg, 0.012 mmol), 9,9-Dimethyl-4,5-bis(diphenylphosphino)xanthene (7.10 mg, 0.012 mmol) and Cs$_2$CO$_3$ (160 mg, 0.491 mmol) in dioxane (2.0 mL) was degassed with argon. The mixture was heated at 110° C. under a nitrogen atmosphere overnight. After cooling to room temperature, the mixture was concentrated to remove dioxane and then water was added. The resulting precipitate was collected by filtration, rinsed with water and dried to give crude 48A (94 mg, 92%) as a dark brown solid. HPLC R$_t$=3.416 min (Chromolith SpeedROD 4.6×50 mm, 10-90% aqueous methanol containing 0.1% TFA, 4 min gradient, monitored at 220 nm), [M+H]=415.

48B. 6-((trans-4-aminocyclohexyl)amino)-N-(3-fluoro-4-pyridinyl)-8-((1-isopropyl-1H-pyrazol-3-yl)amino)imidazo[1,2-b]pyridazine-3-carboxamide

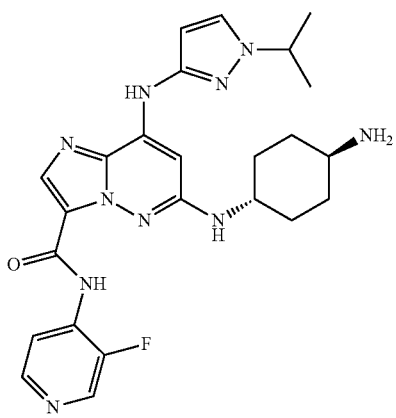 [SMILES: CC(C)n1ccc(Nc2cc(N[C@H]3CC[C@H](N)CC3)nn3c(C(=O)Nc4ccncc4F)cnc23)n1]

The title compound was prepared with trans-cyclohexane-1,4-diamine in a similar way as Example 40B. HPLC R$_t$=2.523 min (Chromolith SpeedROD 4.6×50 mm, 10-90% aqueous methanol containing 0.1% TFA, 4 min gradient, monitored at 220 nm), [M+H]=493.

Example 49

N-(3-fluoro-4-pyridinyl)-6-((trans-4-hydroxycyclohexyl)amino)-8-((1-isopropyl-1H-pyrazol-3-yl)amino)imidazo[1,2-b]pyridazine-3-carboxamide

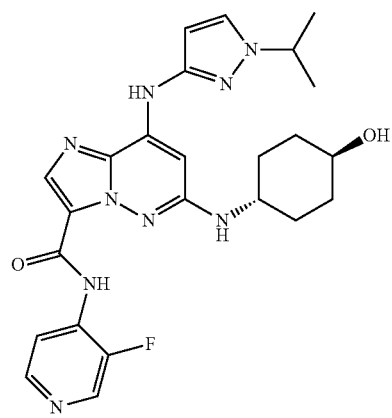 [SMILES: CC(C)n1ccc(Nc2cc(N[C@H]3CC[C@H](O)CC3)nn3c(C(=O)Nc4ccncc4F)cnc23)n1]

The title compound was prepared from 48A and (trans)-4-aminocyclohexanol in a similar way as Example 44. HPLC R$_t$=2.850 min (Chromolith SpeedROD 4.6×50 mm, 10-90% aqueous methanol containing 0.1% TFA, 4 min gradient, monitored at 220 nm), [M+1]=494.

Example 50

6-((trans-4-aminocyclohexyl)amino)-N-(3-fluoro-4-pyridinyl)-8-((1-(2-hydroxyethyl)-1H-pyrazol-3-yl)amino)imidazo[1,2-b]pyridazine-3-carboxamide

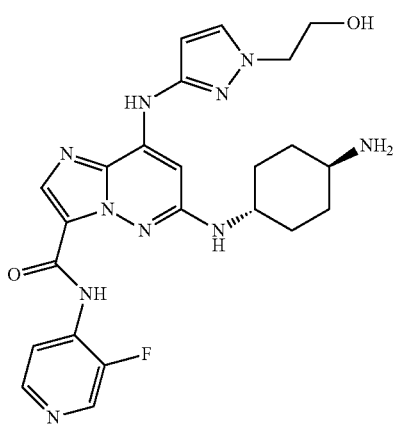 [SMILES: N[C@H]1CC[C@H](Nc2cc(Nc3ccn(CCO)n3)c3ncc(C(=O)Nc4ccncc4F)n3n2)CC1]

50A. 8-(1-(2-(tert-butyldimethylsilyloxy)ethyl)-1H-pyrazol-3-ylamino)-6-chloro-N-(3-fluoropyridin-4-yl)imidazo[1,2-b]pyridazine-3-carboxamide

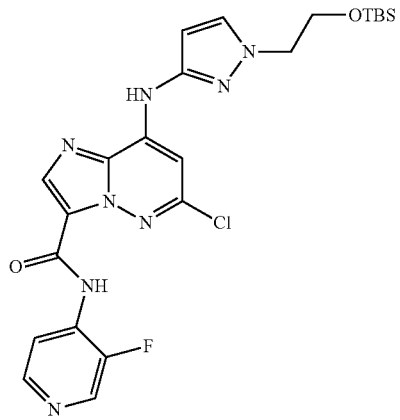 [SMILES: CC(C)(C)[Si](C)(C)OCCn1ccc(Nc2cc(Cl)nn3c(C(=O)Nc4ccncc4F)cnc23)n1]

Compound 50A was prepared from 6,8-dichloro-N-(3-fluoropyridin-4-yl)imidazo[1,2-b]pyridazine-3-carboxamide and 1-(2-(tert-butyldimethylsilyloxy)ethyl)-1H-pyrazol-3-amine in a similar way as 48A. HPLC $R_t$=3.891 min (Chromolith SpeedROD 4.6×50 mm, 10-90% aqueous methanol containing 0.1% TFA, 4 min gradient, monitored at 220 nm), [M+H]=531.

50B. 6-((trans-4-aminocyclohexyl)amino)-N-(3-fluoro-4-pyridinyl)-8-((1-(2-hydroxyethyl)-1H-pyrazol-3-yl)amino)imidazo[1,2-b]pyridazine-3-carboxamide

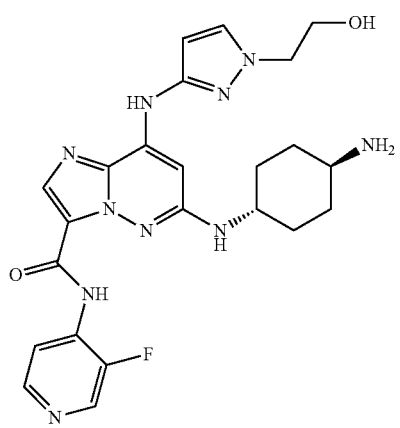 [SMILES: N[C@H]1CC[C@H](Nc2cc(Nc3ccn(CCO)n3)c3ncc(C(=O)Nc4ccncc4F)n3n2)CC1]

A mixture of 50A (40 mg, 0.075 mmol) and trans-cyclohexane-1,4-diamine (86 mg, 0.753 mmol) in NMP (0.5 mL) was heated at 110° C. overnight. The reaction mixture was cooled to room temperature and purified by reversed-phase preparative HPLC. The desired fractions were concentrated and dried to give 50B (19.3 mg, 51%) as a beige solid. HPLC $R_t$=2.037 min (Chromolith SpeedROD 4.6×50 mm, 10-90% aqueous methanol containing 0.1% TFA, 4 min gradient, monitored at 220 nm), [M+H]=495.

Example 51

6-((trans-4-aminocyclohexyl)amino)-N-(3-fluoro-4-pyridinyl)-8-((5-methyl-3-isoxazolyl)amino)imidazo[1,2-b]pyridazine-3-carboxamide

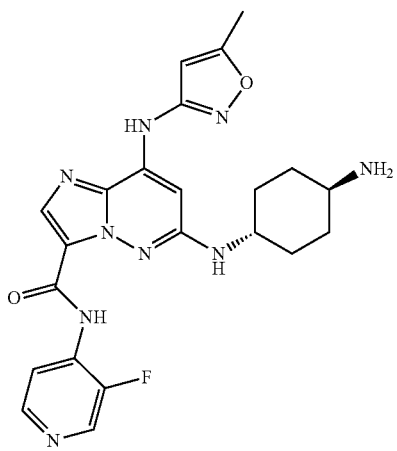 [SMILES: Cc1cc(Nc2cc(N[C@H]3CC[C@H](N)CC3)nn3c(C(=O)Nc4ccncc4F)cnc23)no1]

51A. 6-chloro-N-(3-fluoropyridin-4-yl)-8-(5-methyl-isoxazol-3-ylamino)imidazo[1,2-b]pyridazine-3-carboxamide

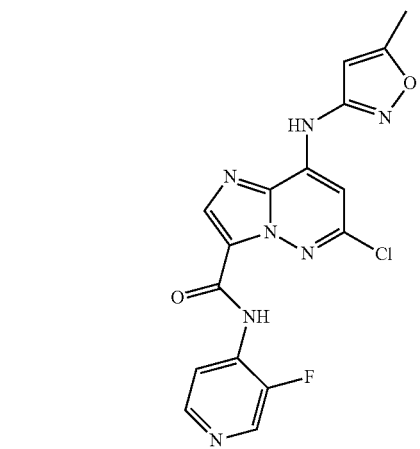 [SMILES: Cc1cc(Nc2cc(Cl)nn3c(C(=O)Nc4ccncc4F)cnc23)no1]

A mixture of 5A (40 mg, 0.123 mmol), 5-methylisoxazol-3-amine (30.1 mg, 0.307 mmol) and sodium t-butoxide (29.5 mg, 0.307 mmol) in THF (1.5 mL) was heated at 70° C. for 2 h, the cooled to room temperature. The solvent was removed and the residue was purified by ISCO column chromatography (4 g column, MeOH/DCM=0-10%) to give 51A (23 mg, 48%). HPLC $R_t$=3.043 min (Chromolith SpeedROD 4.6×50 mm, 10-90% aqueous methanol containing 0.1% TFA, 4 min gradient, monitored at 220 nm), [M+H]=388.

51B. 6-((trans-4-aminocyclohexyl)amino)-N-(3-fluoro-4-pyridinyl)-8-((5-methyl-3-isoxazolyl)amino)imidazo[1,2-b]pyridazine-3-carboxamide

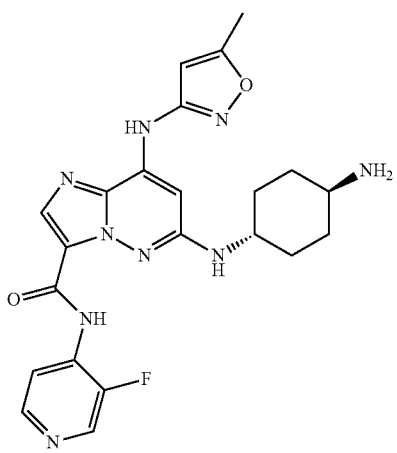 [SMILES: Cc1cc(Nc2cc(N[C@H]3CC[C@H](N)CC3)nn3c(C(=O)Nc4ccncc4F)cnc23)no1]

The title compound was prepared from 51A and (trans)-4-aminocyclohexanol in a similar way as Example 40B. HPLC $R_t$=2.468 min (Chromolith SpeedROD 4.6×50 mm, 10-90% aqueous methanol containing 0.1% TFA, 4 min gradient, monitored at 220 nm), [M+H]=466.

Example 52

6-((trans-4-((cyanoacetyl)amino)cyclohexyl)amino)-N-(3-fluoro-4-pyridinyl)-8-((1-isopropyl-1H-pyrazol-3-yl)amino)imidazo[1,2-b]pyridazine-3-carboxamide

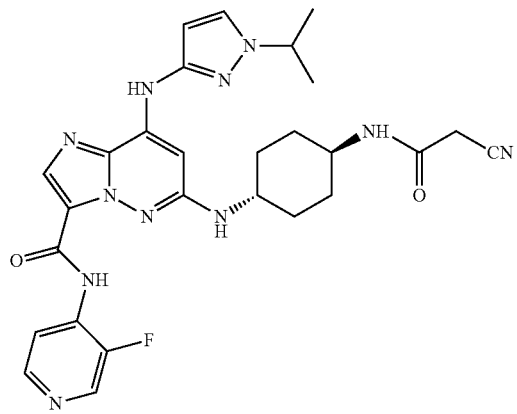 [SMILES: CC(C)n1ccc(Nc2cc(N[C@H]3CC[C@H](NC(=O)CC#N)CC3)nn3c(C(=O)Nc4ccncc4F)cnc23)n1]

To a suspension of Example 48 and 2-cyanoacetic acid (4.01 mg, 0.047 mmol) in DCM (1 mL) was added DIEA (0.035 mL, 0.200 mmol) and BOP (20.87 mg, 0.047 mmol). The mixture was stirred at room temperature for 30 minutes and then concentrated. The crude reaction mixture was purified by reversed-phase preparative HPLC to give the title compound (8.1 mg, 61%) as white solid. HPLC $R_t$=2.981 min (Chromolith SpeedROD 4.6×50 mm, 10-90% aqueous methanol containing 0.1% TFA, 4 min gradient, monitored at 220 nm), [M+H]=560.

Example 53

6-((trans)-4-aminocyclohexylamino)-8-(5-cyanopyridin-2-ylamino)-N-(3-fluoropyridin-4-yl)imidazo[1,2-b]pyridazine-3-carboxamide

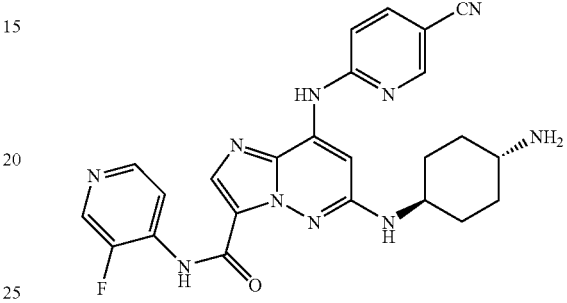

A 1-dram vial equipped with a stir bar and septum cap was charged with dioxane (0.767 mL) and the solvent was degassed by bubbling argon through it with vigorous stirring for 10 min. 5A (0.050 g, 0.153 mmol), 6-aminonicotinonitrile (0.022 g, 0.184 mmol), cesium carbonate (0.100 g, 0.307 mmol), Xantphos (4.44 mg, 7.67 µmol), and Pd$_2$(dba)$_3$ (7.02 mg, 7.67 µmol) were added to the degassed solvent in one portion, and the resulting dark brown suspension was pump/purged with argon three times. The mixture was then heated to 100° C. 24 h. The suspension was cooled to room temperature and then triturated with water resulting in an olive green suspension, which was carefully filtered through a medium-porosity frit. The solid contains impure desired product, while the filtrate appears to contain only SM. The solid was collected, suspended in THF, and azeotroped with PhMe to remove residual water and MeOH. The crude solid was suspended in NMP (0.767 mL) and (trans)-cyclohexane-1,4-diamine (0.210 g, 1.840 mmol) was added. The resulting brown suspension was irradiated in a CEM Discover 300 W microwave at 110° C. for 20 min. Upon cooling, the mixture was diluted with DMF and purified via preparatory HPLC using a YMC ODS C-18 column (30×250 mm) 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 60 min, flow rate 25 mL/min. Rt=48.454 min. The appropriate fractions were concentrated and lyophilized overnight, and 6-((trans)-4-aminocyclohexylamino)-8-(5-cyanopyridin-2-ylamino)-N-(3-fluoropyridin-4-yl)imidazo[1,2-b]pyridazine-3-carboxamide (0.006 g, 6.11 µmol, 3.99% yield) was obtained as a light tan lyophile. HPLC: Rt=3.445 min. YMC S5 ODS-A column (4.6×50 mm) 0%-100% B. Solvent B: (90% MeOH, 10% H$_2$O, 0.2% H$_3$PO$_4$). Solvent A: (10% MeOH, 90% H$_2$O, 0.2% H$_3$PO$_4$). Gradient, start % B=0, final % B=100, gradient time 4 min, hold at 100% 1 min, flow rate 4 mL/min. MS: [M+H]=487.1. $^1$H NMR (400 MHz, DMSO-D6) δ ppm 11.16 (1H, s), 10.48 (1H, s), 8.75 (1H, d, J=2.01 Hz), 8.65 (1H, d, J=2.52 Hz), 8.44-8.50 (1H, m), 8.40-8.44 (1H, m), 8.17 (1H, d, J=2.27 Hz), 8.13-8.16 (1H, m), 7.97 (1H, s), 7.81 (2H, s), 7.65 (1H, d, J=8.81 Hz), 7.45 (1H, s), 3.83 (1H, s), 3.07 (1H, s), 2.12 (2H, s), 1.95 (2H, d, J=1.01 Hz), 1.26-1.47 (4H, m).

Example 54

6-(6-((trans)-4-aminocyclohexylamino)-3-(3-fluoro-pyridin-4-ylcarbamoyl)imidazo[1,2-b]pyridazin-8-ylamino)nicotinic acid

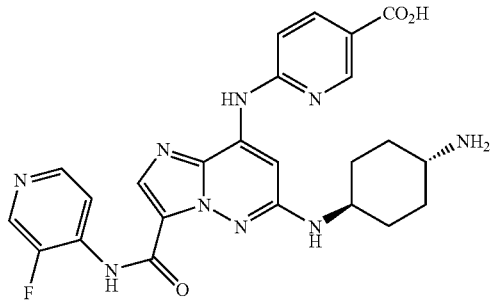

To a suspension of 5A (0.050 g, 0.153 mmol) and methyl 6-aminonicotinate (0.028 g, 0.184 mmol) in THF (0.767 mL) at room temperature was added potassium tert-butoxide (0.337 mL, 0.337 mmol). The resulting suspension was stirred 2 h at room temperature. The solvent was then removed via a stream of nitrogen. The solid was taken up in NMP (0.767 mL), (trans)-cyclohexane-1,4-diamine (0.210 g, 1.840 mmol) was added, and the mixture was heated to 110° C. in a CEM Discover 300 W microwave for 20 min. The mixture was diluted with DMF and purified via preparatory HPLC using a YMC ODS C-18 column (30×250 mm), 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 60 min, flow rate 25 mL/min. Rt=48.545 min. The appropriate fractions were concentrated and lyophilized overnight, and 6-(6-((trans)-4-aminocyclohexylamino)-3-(3-fluoropyridin-4-ylcarbamoyl) imidazo[1,2-b]pyridazin-8-ylamino)nicotinic acid (7.4 mg, 8.29 μmol, 5.41% yield) was obtained as a white lyophile. HPLC: Rt=3.466 min. YMC S5 ODS-A column (4.6×50 mm) 0%-100% B. Solvent B: (90% MeOH, 10% $H_2O$, 0.2% $H_3PO_4$). Solvent A: (10% MeOH, 90% $H_2O$, 0.2% $H_3PO_4$). Gradient, start % B=0, final % B=100, gradient time 4 min, hold at 100% 1 min, flow rate 4 mL/min. MS: [M+H]=506.1. $^1$H NMR (400 MHz, DMSO-D6) δ ppm 11.20 (1H, s), 10.31 (1H, s), 8.85 (1H, d, J=2.27 Hz), 8.70 (1H, d, J=1.26 Hz), 8.45-8.51 (1H, m), 8.43 (1H, s), 8.12-8.19 (1H, m), 8.07 (1H, s), 7.93 (2H, s), 7.58 (1H, d, J=8.56 Hz), 7.24 (1H, s), 7.11 (1H, s), 6.99 (1H, s), 3.79-3.93 (1H, m), 3.00-3.13 (1H, m), 2.05-2.18 (2H, m), 1.97 (2H, s), 1.47 (2H, s), 1.33 (2H, s).

Example 55

6-((trans)-4-aminocyclohexylamino)-N-(4-fluorophenyl)-8-(phenylamino)imidazo[1,2-b]pyridazine-3-carboxamide

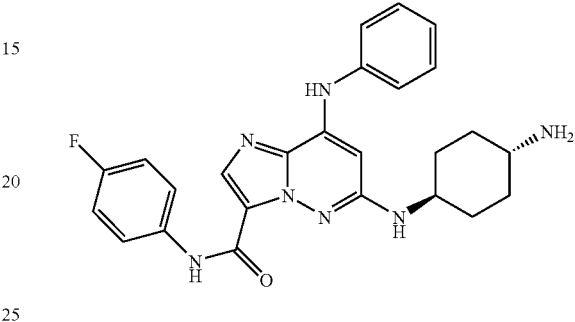

In a 2 dram reaction vial containing acetonitrile (1 mL) at ambient temperature was added 6-chloro-8-((4-methoxybenzyl)(phenyl)amino)imidazo[1,2-b]pyridazine-3-carboxylic acid (0.025 g, 0.06 mmol), 4-fluoroaniline (0.010 g, 0.09 mmol), EDCI (0.018 g, 0.09 mmol), HOBt (0.012 g, 0.09 mmol), and triethylamine (0.025 mL, 0.18 mmol). The suspension was stirred overnight at room temperature. The reaction mixture was then concentrated in vacuo and the residue mixed with trans-1,4-diaminocyclohexane (0.5 g, 4.39 mmol) and heated to 160° C. for 5 h. After cooling to room temperature, the reaction mixture was diluted with DCM/water and the layers were separated. The organic phase was dried over anhydrous sodium sulfate, filtered, and concentrated under reduced pressure. The residue was dissolved in DCM (1 mL) at room temperature and charged with TFA (1 mL). The mixture was stirred 3 h, whereupon the volatiles were removed via a stream of nitrogen and the crude mixture was purified via preparative HPLC (Waters Sunfire column 5u, 100 A°, 19×100 mm, 20-100% Solvent B, (Solvent A (90% water, 10% methanol, 0.1% TFA), Solvent B (10% water, 90% methanol, 0.1% TFA), 10 min gradient, 10 minute run, 25 mL/min)), affording the title compound, 6-((trans)-4-aminocyclohexylamino)-N-(4-fluorophenyl)-8-(phenylamino)imidazo[1,2-b]pyridazine-3-carboxamide (0.009 g, 22%). HPLC: Rt=3.04 min. (Waters sunfire 4.6×50 mm C18.5 um 4 min/1 min hold time 0-100% (A-B) A=10%

MeOH-90% water-0.1% TFA, B=90% MeOH-10% water-0.1% TFA). MS: [M+H]=460.0.

Example 56

6-((trans)-2-aminocyclohexylamino)-N-(2-fluorophenyl)-8-(phenylamino)imidazo[1,2-b]pyridazine-3-carboxamide

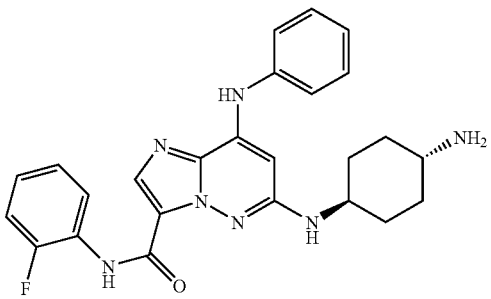

In a 2 dram reaction vial containing acetonitrile (1 mL) at room temperature was added 6-chloro-8-((4-methoxybenzyl)(phenyl)amino)imidazo[1,2-b]pyridazine-3-carboxylic acid (0.025 g, 0.06 mmol), 2-fluoroaniline (0.010 g, 0.09 mmol), EDCI (0.018 g, 0.09 mmol), HOBt (0.012 g, 0.09 mmol), and triethylamine (0.025 mL, 0.18 mmol). The suspension was stirred overnight at room temperature. The reaction mixture was then concentrated in vacuo and the residue mixed with trans-1,4-diaminocyclohexane (0.5 g, 4.39 mmol) and heated to 160° C. for 5 h. After cooling to room temperature, the reaction mixture was diluted with DCM/water and the layers were separated. The organic phase was dried over anhydrous sodium sulfate, filtered, and concentrated under reduced pressure. The residue was dissolved in DCM (1 mL) at room temperature and charged with TFA (1 mL). The mixture was stirred 3 h, whereupon the volatiles were removed via a stream of nitrogen and the crude mixture was purified via preparative HPLC (Waters Sunfire column 5u, 100 A°, 19×100 mm, 20-100% Solvent B, (Solvent A (90% water, 10% methanol, 0.1% TFA), Solvent B (10% water, 90% methanol, 0.1% TFA), 10 min gradient, 10 minute run, 25 mL/min)), affording the title compound, 6-((trans)-4-aminocyclohexylamino)-N-(2-fluorophenyl)-8-(phenylamino)imidazo[1,2-b]pyridazine-3-carboxamide (0.009 g, 22%). HPLC: Rt=3.12 min. (Waters sunfire 4.6×50 mm C18.5 um 4 min/1 min hold time 0-100% (A-B) A=10% MeOH-90% water-0.1% TFA, B=90% MeOH-10% water-0.1% TFA). MS: [M+H]=460.0.

Example 57

6-((trans)-4-aminocyclohexylamino)-8-(phenylamino)-N-(pyridin-3-yl)imidazo[1,2-b]pyridazine-3-carboxamide

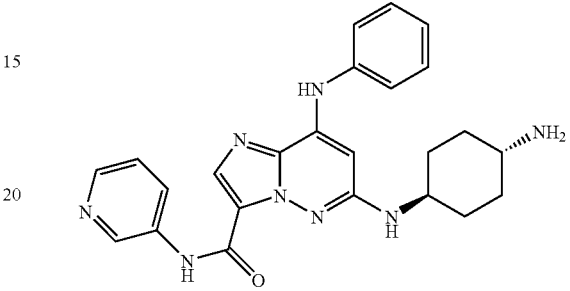

In a 2 dram reaction vial containing acetonitrile (1 mL) at room temperature was added 6-chloro-8-((4-methoxybenzyl)(phenyl)amino)imidazo[1,2-b]pyridazine-3-carboxylic acid (0.025 g, 0.06 mmol), 3-aminopyridine (0.009 g, 0.09 mmol), EDCI (0.018 g, 0.09 mmol), HOBt (0.012 g, 0.09 mmol), and triethylamine (0.025 mL, 0.18 mmol). The suspension was stirred overnight at room temperature. The reaction mixture was then concentrated in vacuo and the residue mixed with trans-1,4-diaminocyclohexane (0.5 g, 4.39 mmol) and heated to 160° C. for 5 h. After cooling to room temperature, the reaction mixture was diluted with DCM/water and the layers separated. The organic phase was dried over anhydrous sodium sulfate, filtered, and concentrated under reduced pressure. The residue was dissolved in DCM (1 mL) at room temperature and charged with TFA (1 mL). The mixture was stirred 3 h, whereupon the volatiles were removed via a stream of nitrogen and the crude mixture was purified via preparative HPLC (Waters Sunfire column 5u, 100 A°, 19×100 mm, 20-100% Solvent B, (Solvent A (90% water, 10% methanol, 0.1% TFA), Solvent B (10% water, 90% methanol, 0.1% TFA), 10 min gradient, 10 minute run, 25 mL/min)), affording the title compound, 6-((trans)-4-aminocyclohexylamino)-8-(phenylamino)-N-(pyridin-3-yl)imidazo[1,2-b]pyridazine-3-carboxamide. HPLC: Rt=2.48 min. (Waters sunfire 4.6×50 mm C18.5 um 4 min/1 min hold time 0-100% (A-B) A=10% MeOH-90% water-0.1% TFA, B=90% MeOH-10% water-0.1% TFA). MS: [M+H]=443.0.

Example 58

6-((trans)-4-aminocyclohexylamino)-N-phenyl-8-(phenylamino)imidazo[1,2-b]pyridazine-3-carboxamide

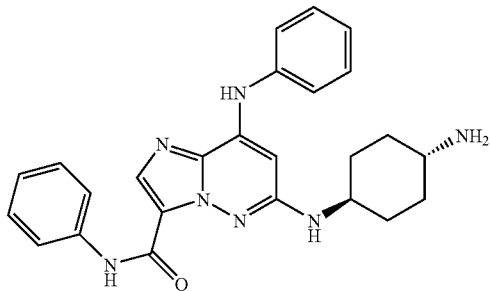 [SMILES: N[C@H]1CC[C@H](Nc2cc(Nc3ccccc3)c3ncc(C(=O)Nc4ccccc4)n3n2)CC1]

In a 2 dram reaction vial containing acetonitrile (1 mL) at ambient temperature was added 6-chloro-8-((4-methoxybenzyl)(phenyl)amino)imidazo[1,2-b]pyridazine-3-carboxylic acid (0.025 g, 0.06 mmol), aniline (0.008 g, 0.09 mmol), EDCI (0.018 g, 0.09 mmol), HOBt (0.012 g, 0.09 mmol), and triethylamine (0.025 mL, 0.18 mmol). The suspension was stirred overnight at room temperature. The reaction mixture was then concentrated in vacuo and the residue mixed with trans-1,4-diaminocyclohexane (0.5 g, 4.39 mmol) and heated to 160° C. for 5 h. After cooling to room temperature, the reaction mixture was diluted with DCM/water and the layers separated. The organic phase was dried over anhydrous sodium sulfate, filtered, and concentrated under reduced pressure. The residue was dissolved in DCM (1 mL) at room temperature and charged with TFA (1 mL). The mixture stirred 3 h, whereupon the volatiles were removed via a stream of nitrogen and the crude mixture was purified via preparative HPLC (Waters Sunfire column 5u, 100 A, 19×100 mm, 20-100% Solvent B, (Solvent A (90% water, 10% methanol, 0.1% TFA), Solvent B (10% water, 90% methanol, 0.1% TFA), 10 min gradient, 10 minute run, 25 mL/min), affording the title compound, 6-((trans)-4-aminocyclohexylamino)-N-phenyl-8-(phenylamino)imidazo[1,2-b]pyridazine-3-carboxamide. HPLC: Rt=3.02 min. (Waters sunfire 4.6×50 mm C18.5 um 4 min/1 min hold time 0-100% (A-B) A=10% MeOH-90% water-0.1% TFA, B=90% MeOH-10% water-0.1% TFA). MS: [M+H]=442.

Example 59

6-((trans-4-acetamidocyclohexyl)amino)-8-(cyclobutylamino)-N-4-pyridinylimidazo[1,2-b]pyridazine-3-carboxamide

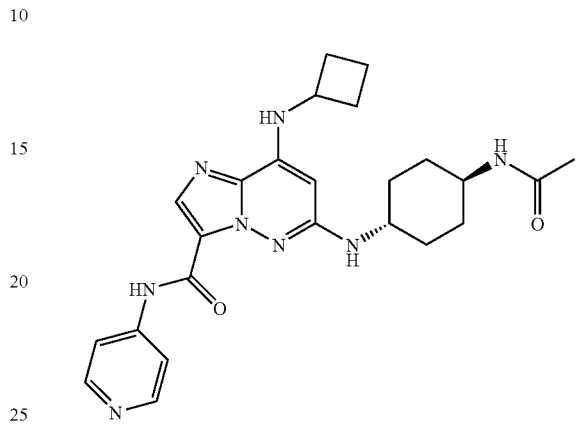

A solution of 3 (3.5 mg, 0.008 mmol) in THF (1 mL) was treated with acetic anhydride (0.001 mL, 0.01 mmol) and stirred at room temperature overnight. The resulting solution was concentrated under a stream of nitrogen and purified by reversed-phase preparative HPLC (YMC ODS-A 5 um 30×250 mm, 10-90% aqueous methanol containing 0.1% TFA, 25 mL/min, 40 min gradient, monitored at 254 nm) to afford the title compound (2.2 mg. 50%). HPLC Rt=3.306 min. (YMC S5 ODS 4.6×50 mm, 10-90% aqueous methanol containing 0.2% $H_3PO_4$, 4 min gradient, monitored at 220 nm). [M+H+]=463.33.

Example 60

8-(cyclobutylamino)-N-(3-fluoro-4-pyridinyl)-6-((trans-4-hydroxycyclohexyl)amino)imidazo[1,2-b]pyridazine-3-carboxamide

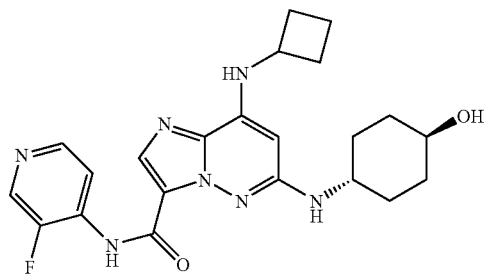 [SMILES: O=C(Nc1ccncc1F)c1cnc2c(NC3CCC3)cc(N[C@H]3CC[C@H](O)CC3)nn12]

A 1 dram vial was charged with 8A (25 mg, 0.077 mmol) and THF (1 mL). Cyclobutylamine (8.54 µL, 0.100 mmol) was added and the reaction was heated to 80° C. After 4 hours at 80° C., the reaction was cooled to room temperature and the solvent was removed under a stream of nitrogen. Trans-4-aminocyclohexanol (400 mg, 3.47 mmol) was added and the mixture was heated to 130° C. and then cooled to room temperature after 4 hours. The crude reaction product was dissolved in a small amount of MeOH and purified by reversed phase HPLC (YMC ODS-A 5 um 30×250 mm, 10-90% aqueous methanol containing 0.1% TFA, 25 mL/min, 40 min gradient, monitored at 220 nm). The product (retention time=39.317 minutes) was isolated and lyophilized to dryness to afford 8-(cyclobutylamino)-N-(3-fluoropyridin-4-yl)-6-((trans)-4-hydroxycyclohexylamino)imidazo[1,2-b]pyridazine-3-carboxamide (5 mg, 11.78%). HPLC Rt=3.971 min. (YMC S5 ODS 4.6×50 mm, 10-90% aqueous methanol containing 0.2% $H_3PO_4$, 4 min gradient, monitored at 220 nm). [M+H+]=440.28.

Example 61

8-(cyclobutylamino)-6-(cyclohexylamino)-N-(3-fluoro-4-pyridinyl)imidazo[1,2-b]pyridazine-3-carboxamide

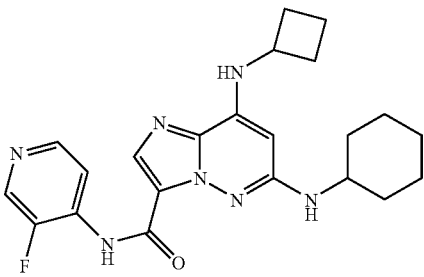 [SMILES: O=C(Nc1ccncc1F)c1cnc2c(NC3CCC3)cc(NC3CCCCC3)nn12]

A 1 dram vial was charged with 8A (25 mg, 0.077 mmol) and THF (1 mL). Cyclobutylamine (8.54 μL, 0.100 mmol) was added and the reaction was heated to 80° C. After 4 hours at 80° C., the reaction was cooled to room temperature and the solvent was removed under a stream of nitrogen. Cyclohexylamine (500 μL, 4.37 mmol) was added and the reaction was heated to 140° C. for 12 hours. The crude reaction product was dissolved in a small amount of MeOH and purified by reversed phase HPLC (YMC ODS-A 5 um 30×250 mm, 10-90% aqueous methanol containing 0.1% TFA, 25 mL/min, 50 min gradient, monitored at 220 nm). The product (retention time=35.6 minutes) was isolated and lyophilized to dryness to afford 8-(cyclobutylamino)-6-(cyclohexylamino)-N-(3-fluoropyridin-4-yl)imidazo[1,2-b]pyridazine-3-carboxamide (6 mg, 14.56%). $^1$H NMR (400 MHz, DMSO-D6) δ ppm 11.33-11.47 (1H, m), 8.71-8.82 (1H, m), 8.51-8.62 (1H, m), 8.41-8.51 (1H, m), 8.01-8.09 (1H, m), 7.42-7.56 (1H, m), 6.69-6.86 (1H, m), 5.65-5.74 (1H, m), 3.89-4.02 (1H, m), 3.78-3.89 (1H, m), 2.28-2.42 (2H, m), 2.05-2.21 (2H, m), 1.87-2.01 (2H, m), 1.64-1.85 (4H, m), 1.53-1.64 (1H, m), 1.13-1.46 (5H, m). HPLC $t_R$=4.775 min (YMC S5 ODS 4.6×50 mm, 10-90% aqueous methanol containing 0.2% $H_3PO_4$, 4 min gradient, monitored at 220 nm). [M+H+]= 424.32.

Example 62

6-((trans-4-aminocyclohexyl)amino)-N-(2-fluoro-4-pyridinyl)-8-(2-pyridinylamino)imidazo[1,2-b]pyridazine-3-carboxamide

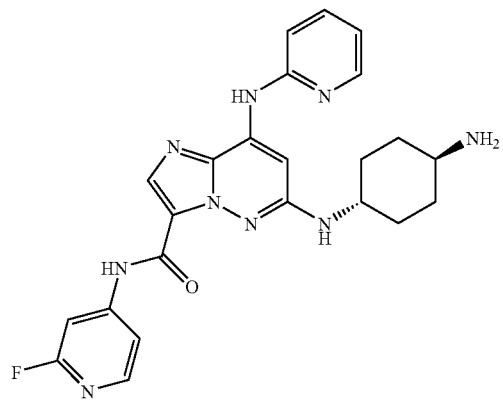 [SMILES: N[C@H]1CC[C@H](Nc2cc(Nc3ccccn3)c3ncc(C(=O)Nc4ccnc(F)c4)n3n2)CC1]

62A. Preparation of 6-chloro-N-(2-fluoropyridin-4-yl)-8-((4-methoxybenzyl)(pyridin-2-yl)amino)imidazo[1,2-b]pyridazine-3-carboxamide

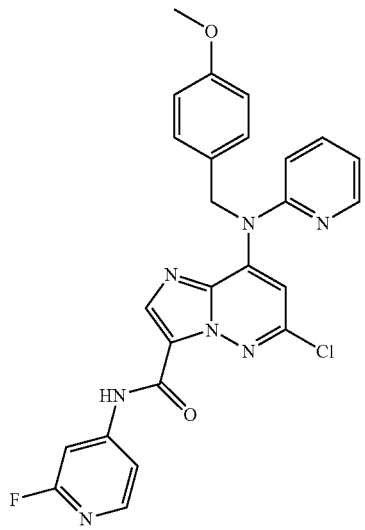 [SMILES: COc1ccc(CN(c2ccccn2)c2cc(Cl)nn3c(C(=O)Nc4ccnc(F)c4)cnc23)cc1]

A solution of N-(4-methoxybenzyl)pyridin-2-amine (591 mg, 2.76 mmol) in THF was stirred at room temperature and potassium tert-butoxide (5.52 mL, 5.52 mmol) (1 M solution in THF) was added. The reaction solution was stirred at room temperature for 30 min before 13A (600 mg, 1.840 mmol) was added at 0° C. and the resulting solution was warmed to room temperature over 30 min. The reaction was quenched with water and extracted with EtOAc. The organic layers were washed with water, brine and dried over $Na_2SO_4$. The organics were concentrated and purified by ISCO chromatography (10% to 70% EtOAc in Hexane) to obtain 6-chloro-N-(2-fluoropyridin-4-yl)-8-((4-methoxybenzyl)(pyridin-2-yl)amino)imidazo[1,2-b]pyridazine-3-carboxamide (569 mg, 1.129 mmol, 61.4% yield) as a yellow solid which was carry to next step without further purification.

62B. Preparation of 6-((trans)-4-aminocyclohexylamino)-N-(2-fluoropyridin-4-yl)-8-((4-methoxybenzyl)(pyridin-2-yl)amino)imidazo[1,2-b]pyridazine-3-carboxamide

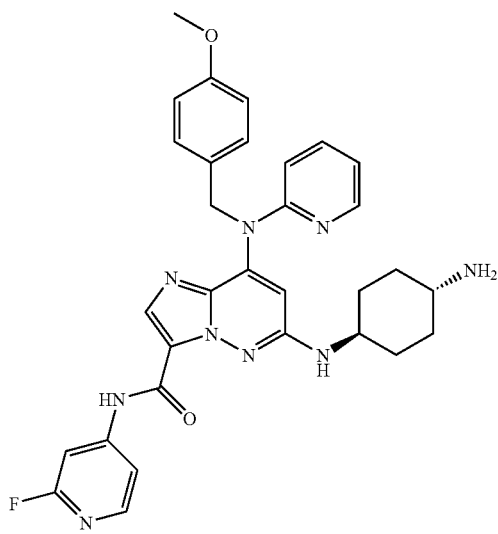 [SMILES: COc1ccc(CN(c2ccccn2)c2cc(N[C@H]3CC[C@H](N)CC3)nn3c(C(=O)Nc4ccnc(F)c4)cnc23)cc1]

A solution of 6-chloro-N-(2-fluoropyridin-4-yl)-8-((4-methoxybenzyl)(pyridin-2-yl)amino)imidazo[1,2-b]pyridazine-3-carboxamide (60 mg, 0.119 mmol) and (trans)-cyclohexane-1,4-diamine (136 mg, 1.191 mmol) in NMP (1 mL) was heated at 90° C. for 8 h and then cooled to room temperature. The crude reaction mixture was purified by preparative HPLC (Phenomenex Axia Luna 5 micron 30×100 mm) to obtain the pure product as a white solid, which was used without further purification.

62C. Preparation of 6-((trans-4-aminocyclohexyl)amino)-N-(2-fluoro-4-pyridinyl)-8-(2-pyridinylamino)imidazo[1,2-b]pyridazine-3-carboxamide

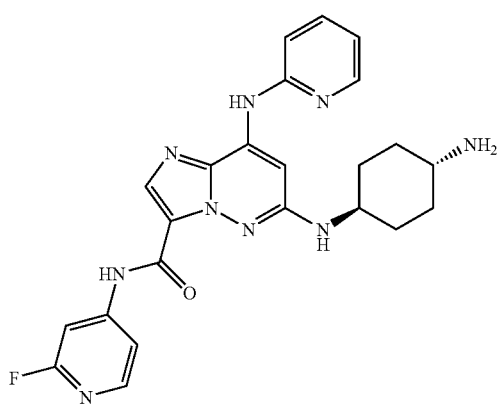 [SMILES: N[C@H]1CC[C@H](Nc2cc(Nc3ccccn3)c3ncc(C(=O)Nc4ccnc(F)c4)n3n2)CC1]

The solid from 62B was dissolved in TFA and heated to 70° C. for 1 h and then cooled to room temperature and purified by preparative HPLC (Phenomenex Axia Luna 5 micron 30×100 mm) to obtain the pure product 6-((trans-4-aminocyclohexyl)amino)-N-(2-fluoro-4-pyridinyl)-8-(2-pyridinylamino)imidazo[1,2-b]pyridazine-3-carboxamide (23 mg, 0.050 mmol, 41.9% yield) HPLC Rt=1.542 minutes (Phenomenex Luna 5 micron C18 4.6×30 mm: 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). [M+H]=462.17.

Example 63

6-((trans-4-(L-alanylamino)cyclohexyl)amino)-N-(2-fluoro-4-pyridinyl)-8-(2-pyridinylamino)imidazo[1,2-b]pyridazine-3-carboxamide

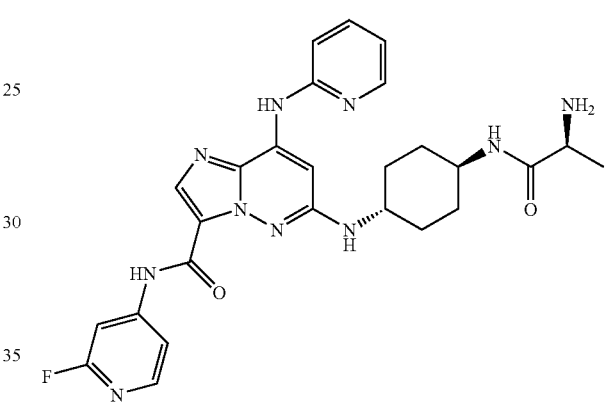

BOP (68.4 mg, 0.155 mmol) was added to a solution of 62B (30.0 mg, 0.052 mmol), DIEA (0.036 mL, 0.206 mmol) and (S)-2-(tert-butoxycarbonylamino)propanoic acid (19.52 mg, 0.103 mmol) in DCM (1 mL). The clear reaction mixture was stirred at room temperature for 30 min, and then concentrated to dryness. TFA (0.238 mL, 3.09 mmol) was added and the reaction solution was stirred at 70° C. for 1 h. The resulting mixture was concentrated and then diluted with MeOH and purified by preparative HPLC (Phenomenex Axia Luna 5 micron 30×100 mm) 10% B (Solvent B=90% MeOH-10% H₂O-0.1% TFA) to 90% B in A (Solvent A=10% MeOH-90% H₂O-0.1% TFA) to afford 6-((trans-4-(L-alanylamino)cyclohexyl)amino)-N-(2-fluoro-4-pyridinyl)-8-(2-pyridinylamino)imidazo[1,2-b]pyridazine-3-carboxamide (13.7 mg, 0.026 mmol, 49.9% yield) as white solid. HPLC Rt=1.618 minutes (Phenomenex Luna 5 micron C18 4.6×30 mm: 0 to 100 B in 2 min with 1 min hold time, Flow rate=5 mL/min, detection at 254 nm, Solvent A: 10% methanol/90% water/ 0.1% TFA; Solvent B: 10% water/90% methanol/0.1% TFA). [M+H]=533.17.

Example 64

6-((trans-4-(D-alanylamino)cyclohexyl)amino)-N-(2-fluoro-4-pyridinyl)-8-(2-pyridinylamino)imidazo[1,2-b]pyridazine-3-carboxamide

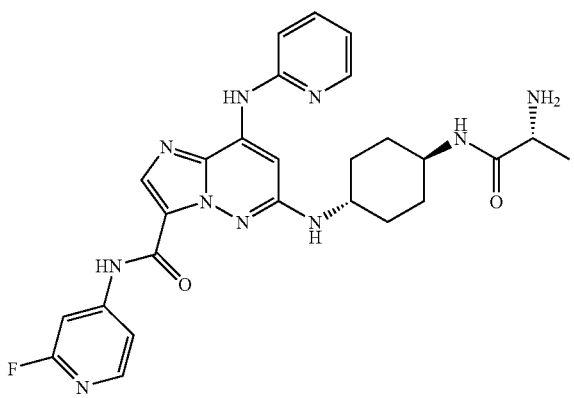 [SMILES: C[C@@H](N)C(=O)N[C@H]1CC[C@H](Nc2cc(Nc3ccccn3)c3ncc(C(=O)Nc4ccnc(F)c4)n3n2)CC1]

BOP (68.4 mg, 0.155 mmol) was added to a solution of 62B (30.0 mg, 0.052 mmol), DIEA (0.036 mL, 0.206 mmol) and (R)-2-(tert-butoxycarbonylamino)propanoic acid (19.52 mg, 0.103 mmol) in DCM (1 mL). The clear reaction mixture was stirred at room temperature for 30 minutes and then concentrated to dryness. TFA (0.238 mL, 3.09 mmol) was added and the reaction solution was stirred at 70° C. for 1 h. The reaction mixture was then concentrated and diluted with MeOH. The crude product was purified by HPLC (Phenomenex Axia Luna 5 micron 30×100 mm) 10% B (Solvent B=90% MeOH-10% $H_2O$-0.1% TFA) to 90% B in A (Solvent A=10% MeOH-90% $H_2O$-0.1% TFA) to afford 6-((trans-4-(D-alanylamino) cyclohexyl)amino)-N-(2-fluoro-4-pyridinyl)-8-(2-pyridinylamino)imidazo[1,2-b]pyridazine-3-carboxamide (11.5 mg, 0.022 mmol, 41.9% yield) as a white solid. HPLC Rt=1.613 (Phenomenex Luna 5 micron C18 4.6×30 mm: 0 to 100 B in 2 min with 1 min hold time, Flow rate=5 mL/min, detection at 254 nm, Solvent A: 10% methanol/90% water/ 0.1% TFA; Solvent B: 10% water/90% methanol/0.1% TFA). [M+H]=533.17.

Example 65

6-((trans-4-aminocyclohexyl)amino)-N-(3-fluoro-4-pyridinyl)-8-(2-pyridinylamino)imidazo[1,2-b]pyridazine-3-carboxamide

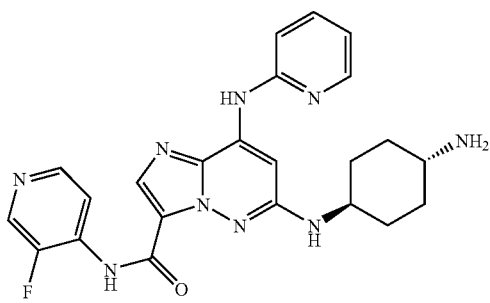

A suspension of 5A (20 mg, 0.061 mmol) in THF (1 mL) was treated with pyridin-2-amine (11.54 mg, 0.123 mmol). A solution of potassium t-butoxide (0.123 mL, 0.123 mmol) in THF was added and the reaction was stirred at room temperature. After two hours the solvent was removed under a stream of nitrogen. (trans)-cyclohexane-1,4-diamine (200 mg, 1.751 mmol) was added and the reaction mixture was heated to 160° C. for 3 hours. The solution was cooled to room temperature and diluted with MeOH. The solid residue was filtered and dried. The crude reaction product was dissolved in a small amount of MeOH and purified by reversed phase HPLC (YMC ODS-A 5 um 30×250 mm, 10-90% aqueous methanol containing 0.1% TFA, 25 mL/min, 30 min gradient, monitored at 220 nm). The product (retention time=28.731 minutes) was isolated and lyophilized to dryness to afford 6-((trans-4-aminocyclohexyl)amino)-N-(3-fluoro-4-pyridinyl)-8-(2-pyridinylamino)imidazo[1,2-b]pyridazine-3-carboxamide (1.5 mg, 4.25%). HPLC Rt=3.343 min (YMC S5 ODS 4.6×50 mm, 10-90% aqueous methanol containing 0.2% $H_3PO_4$, 4 min gradient, monitored at 220 nm). [M+H+]= 462.1.

Example 66

N-(3-fluoro-4-pyridinyl)-6-((trans-4-(glycylamino) cyclohexyl)amino)-8-(2-pyridinylamino)imidazo[1,2-b]pyridazine-3-carboxamide

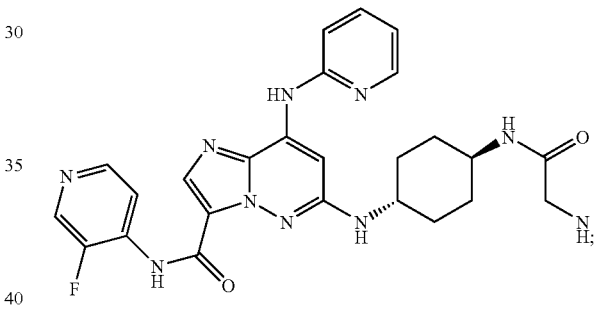

To a solution of 65 (0.020 g, 0.043 mmol) in DMF (1 mL), DIEA (0.038 mL, 0.217 mmol), and 2-(tert-butoxycarbonylamino)acetic acid (0.015 g, 0.087 mmol) was added BOP (0.058 g, 0.130 mmol). The resulting clear, colorless solution was stirred at room temperature for 30 min. The reaction was diluted with THF and water and the biphasic mixture was washed with brine, and the layers were separated. The organics were dried (MgSO$_4$), filtered, and concentrated to a viscous yellow oil which was transferred to a vial with dichloromethane and blown down under a stream of nitrogen overnight. The resulting residue was suspended in dichloromethane (0.5 mL) and TFA (0.5 mL) was added. The resulting suspension was stirred vigorously at room temperature for 20 minutes and the solvent was removed under a stream of nitrogen. The crude material was diluted with 1 mL of MeOH and purified via preparatory HPLC using a YMC ODS C-18 30×250 mm column with 10-100% B (Solvent A: 10% aq MeOH with 0.1% TFA; Solvent B: 90% aq. MeOH with 0.1% TFA) and a linear gradient over 60 min at 25 mL/min, monitoring at 220 nm, and a total run time of 70 min. (Rt of desired=48.392 min) to afford N-(3-fluoro-4-pyridinyl)-6-((trans-4-(glycylamino)cyclohexyl)amino)-8-(2-pyridinylamino)imidazo[1,2-b]pyridazine-3-carboxamide (0.012 g, 0.016 mmol, 37.1% yield). HPLC Rt=3.521 minutes (Phenomenex Luna 5 micron C18 4.6×30 mm: 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). [M+H]=519.2.

Example 67

Methyl N-(trans-4-((3-((3-fluoro-4-pyridinyl)carbamoyl)-8-(2-pyridinylamino)imidazo[1,2-b]pyridazin-6-yl)amino)cyclohexyl)glycinate

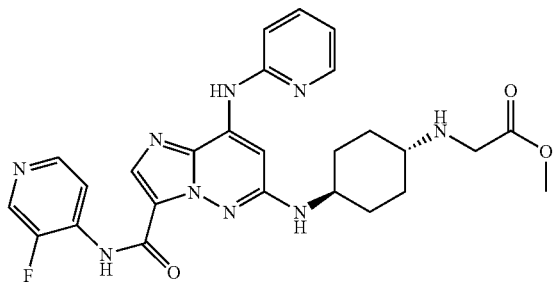 [SMILES: COC(=O)CN[C@H]1CC[C@H](Nc2cc(Nc3ccccn3)c3ncc(C(=O)Nc4ccncc4F)n3n2)CC1]

To a solution of 5C (40 mg, 0.057 mmol) in CH$_2$Cl$_2$ (1 mL) was added DIEA (0.043 mL, 0.248 mmol) and methyl 2-bromoacetate (9.68 mg, 0.063 mmol). The solution was heated to 50° C. overnight. The volatiles were removed via a stream of nitrogen. The resulting dark brown oil was taken up in TFA (0.75 mL) and heated to 65° C. for 2 h, and then cooled to room temperature. The volatiles were removed under a stream of nitrogen and the crude material was diluted with 1 mL of THF and purified via preparatory HPLC using a YMC ODS C-18 30×250 mm column with 10-100% B (Solvent A: 10% aq MeOH with 0.1% TFA; Solvent B: 90% aq. MeOH with 0.1% TFA) and a linear gradient over 60 min at 25 mL/min, monitoring at 220 nm, and a total run time of 70 min. (Rt of desired=46.365 min) Appropriate fractions were concentrated and lyophilized overnight to afford methyl N-(trans-4-((3-((3-fluoro-4-pyridinyl)carbamoyl)-8-(2-pyridinylamino)imidazo[1,2-b]pyridazin-6-yl)amino)cyclohexyl)glycinate (23 mg, 0.030 mmol, 52.5% yield). HPLC Rt=3.335 minutes. (Phenomenex Luna 5 micron C18 4.6×30 mm: 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA. [M+H]=534.1.

Example 68

N-(2-chloro-4-pyridinyl)-8-(cyclopropylamino)-6-((trans-4-hydroxycyclohexyl)amino)imidazo[1,2-b]pyridazine-3-carboxamide

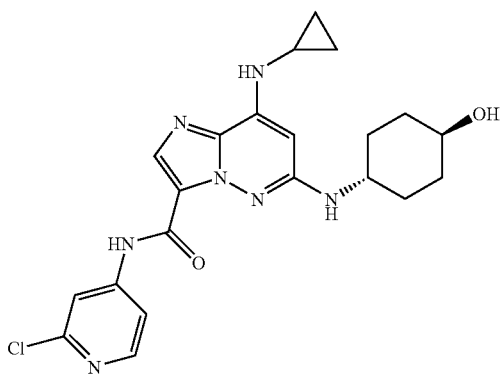 [SMILES: O=C(Nc1ccnc(Cl)c1)c1cnc2c(NC3CC3)cc(N[C@H]3CC[C@H](O)CC3)nn12]

To a yellow suspension of 23A (156 mg, 0.455 mmol) and DIEA (0.119 mL, 0.683 mmol) in THF (2 mL) at room temperature in a sealed tube apparatus was added cyclopropanamine (39.0 mg, 0.683 mmol). The suspension was heated to 80° C. for 2 h. The THF was removed via a stream of nitrogen. To the crude product in NMP (2 mL) was added trans-4-aminocyclohexanol (1049 mg, 9.11 mmol) and the resulting solution was heated at 100° C. for 24 h. After cooling to room temperature, the mixture was diluted with MeOH and purified by preparative HPLC (Phenomenex Axia Luna 5 micron 30×100 mm) with 20% to 100% MeOH (0.1% TFA) in water (0.1% TFA) to obtain N-(2-chloro-4-pyridinyl)-8-(cyclopropylamino)-6-((trans-4-hydroxycyclohexyl)amino)imidazo[1,2-b]pyridazine-3-carboxamide (79 mg, 0.179 mmol, 39.3% yield). HPLC Rt=1.80 minutes (Phenomenex Luna 5 micron C18 4.6×30 mm: 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). [M+H]=442.16.

Example 69

Methyl N-(trans-4-((3-((2-fluoro-4-pyridinyl)carbamoyl)-8-(2-pyridinylamino)imidazo[1,2-b]pyridazin-6-yl)amino)cyclohexyl

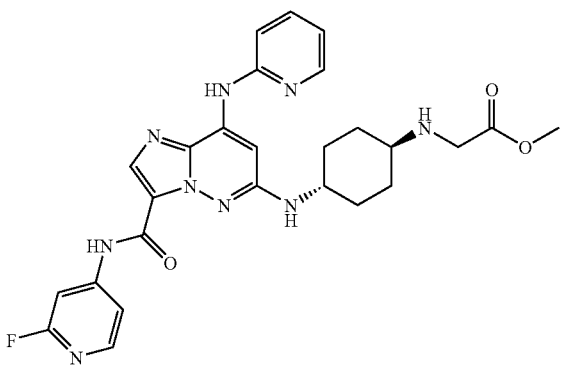 [SMILES: COC(=O)CN[C@H]1CC[C@H](Nc2cc(Nc3ccccn3)c3ncc(C(=O)Nc4ccnc(F)c4)n3n2)CC1]

To a solution of 62B (30.0 mg, 0.052 mmol) in DCM (2 mL) was added DIEA (0.036 mL, 0.206 mmol) and methyl 2-bromoacetate (11.84 mg, 0.077 mmol) and the reaction solution was stirred at 45° C. for 14 h. The solvent was removed under reduced pressure and the residue was treated with TFA (0.238 mL, 3.09 mmol). The reaction mixture was stirred at 65° C. for 1 h, and then concentrated, diluted with MeOH and purified by preparative HPLC (Phenomenex Axia Luna 5 micron 30×100 mm) 30% B (Solvent B=90% MeOH-10% H$_2$O-0.1% TFA) to 100% B in A (Solvent A=10% MeOH-90% H$_2$O-0.1% TFA) to obtain methyl N-(trans-4-((3-((2-fluoro-4-pyridinyl)carbamoyl)-8-(2-pyridinylamino)imidazo[1,2-b]pyridazin-6-yl)amino)cyclohexyl)glycinate (9.6 mg, 0.018 mmol, 34.9% yield).). HPLC Rt=1.528 minutes (Phenomenex Luna 5 micron C18 4.6×30 mm: 0 to 100 B in 2 min with 1 min hold time, Flow rate=5 mL/min, detection at 254 nm, Solvent A: 10% methanol/90% water/ 0.1% TFA; Solvent B: 10% water/90% methanol/0.1% TFA). [M+H]=534.18.

Example 70

2-methoxyethyl(trans-4-((8-(cyclopropylamino)-3-((6-oxo-1,6-dihydro-4-pyrimidinyl)carbamoyl)imidazo[1,2-b]pyridazin-6-yl)amino)cyclohexyl)carbamate

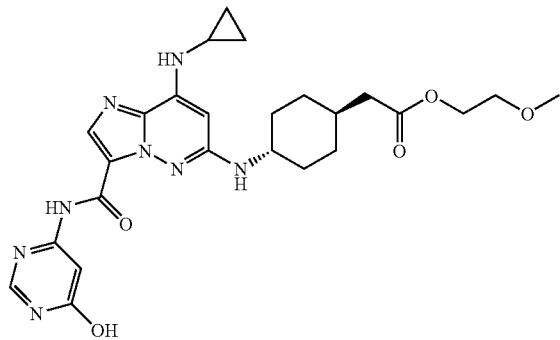 [SMILES: COCCOC(=O)C[C@H]1CC[C@H](Nc2cc(NC3CC3)c3ncc(C(=O)Nc4cc(O)ncn4)n3n2)CC1]

To a solution of di-tert-butyl dicarbonate (0.014 mL, 0.058 mmol) in DCM (1 mL) was added 15D (30.0 mg, 0.058 mmol) and DMAP (3.57 mg, 0.029 mmol). The reaction mixture was stirred at room temperature for 10 minutes and then 2-methoxyethanol (5.56 mg, 0.073 mmol) was added. After 2 h the solvent was removed under reduced pressure and to the residue was added TFA (0.270 mL, 3.50 mmol). The reaction mixture was stirred at 65° C. for 1 h, and then concentrated and diluted with MeOH. The crude product was purified by preparative HPLC (Phenomenex Axia Luna 5 micron 30×100 mm) 30% B (Solvent B=90% MeOH-10% H$_2$O-0.1% TFA) to 100% B in A (Solvent A=10% MeOH-90% H$_2$O-0.1% TFA) to obtain the pure product 2-methoxyethyl(trans)-4-(8-(cyclopropylamino)-3-(6-hydroxypyrimidin-4-ylcarbamoyl)imidazo[1,2-b]pyridazin-6-ylamino) cyclohexylcarbamate (7.7 mg, 0.015 mmol, 25.08% yield). HPLC Rt=1.657 minutes (Phenomenex Luna 5 micron C18 4.6×30 mm: 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). [M+H]=526.23.

Example 71

6-((trans-4-aminocyclohexyl)amino)-N-(2-chloro-4-pyridinyl)-8-(2-pyridinylamino)imidazo[1,2-b]pyridazine-3-carboxamide

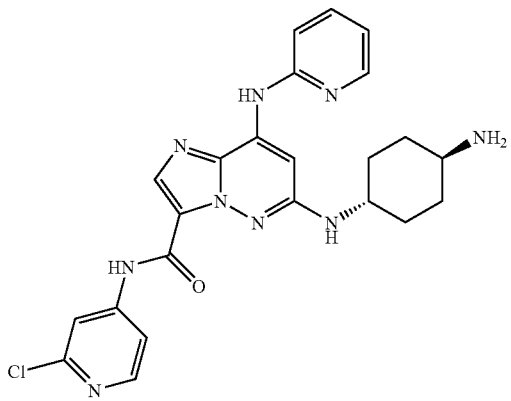 [SMILES: N[C@H]1CC[C@H](Nc2cc(Nc3ccccn3)c3ncc(C(=O)Nc4ccnc(Cl)c4)n3n2)CC1]

A suspension of 23A (60.0 mg, 0.175 mmol) in THF (2 mL) was treated with pyridin-2-amine (33.0 mg, 0.350 mmol). A solution of potassium tert-butoxide (0.350 mL, 0.350 mmol) in THF was added and the reaction was stirred at room temperature. After 2 hours, the solvent was removed under a stream of nitrogen. The residue was taken up in MeOH and filtered. The solid material was dried under vacuum. The solid material was taken up in NMP (2 mL) and (trans)-cyclohexane-1,4-diamine (200 mg, 1.751 mmol) was added and the reaction was heated at 90° C. for 24 h, and then cooled to room temperature. The crude mixture was diluted with MeOH and purified by preparative HPLC (Phenomenex Axia Luna 5 micron 30×100 mm) 30% B (Solvent B=90% MeOH-10% H$_2$O-0.1% TFA) to 100% B in A (Solvent A=10% MeOH-90% H$_2$O-0.1% TFA) to afford 6-((trans-4-aminocyclohexyl)amino)-N-(2-chloro-4-pyridinyl)-8-(2-pyridinylamino)imidazo[1,2-b]pyridazine-3-carboxamide (31 mg, 0.065 mmol, 37.0% yield). HPLC Rt=1.890 minutes (Phenomenex Luna 5 micron C18 4.6×30 mm: 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). [M+H]=478.1.

Example 72

N-(2-chloro-4-pyridinyl)-6-((trans-4-hydroxycyclohexyl)amino)-8-(2-pyridinylamino)imidazo[1,2-b]pyridazine-3-carboxamide

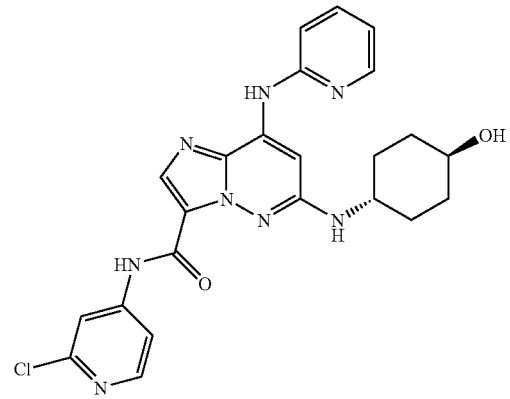 [SMILES: O=C(Nc1ccnc(Cl)c1)c1cnc2c(Nc3ccccn3)cc(N[C@H]3CC[C@H](O)CC3)nn12]

A suspension of 23A (50.0 mg, 0.146 mmol) in THF (2 mL) was treated with pyridin-2-amine (27.5 mg, 0.292 mmol). A solution of potassium tert-butoxide (0.292 mL, 0.292 mmol) in THF was added and the reaction was stirred at room temperature. The reaction was complete after two hours. The solvent was removed under a stream of nitrogen. The residue was taken up in MeOH and filtered. The solid material was dried under vacuum. The solid was taken up in NMP (2 mL) and (trans)-4-aminocyclohexanol (168 mg, 1.460 mmol) was added and the reaction was heated at 90° C. for 24 h, and then cooled to room temperature. The crude mixture was diluted with MeOH and purified by preparative HPLC (Phenomenex Axia Luna 5 micron 30×100 mm) 30% B (Solvent B=90% MeOH-10% H$_2$O-0.1% TFA) to 100% B in A (Solvent A=10% MeOH-90% H$_2$O-0.1% TFA) to obtain N-(2-chloro-4-pyridinyl)-6-((trans-4-hydroxycyclohexyl)amino)-8-(2-pyridinylamino)imidazo[1,2-b]pyridazine-3-carboxamide (13.7 mg, 0.029 mmol, 19.60% yield). HPLC Rt=2.19 minutes (Phenomenex Luna 5 micron C18 4.6×30 mm: 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). [M+H]=479.1.

Example 73

N-(2-fluoro-4-pyridinyl)-6-((trans-4-hydroxycyclohexyl)amino)-8-(2-pyridinylamino)imidazo[1,2-b]pyridazine-3-carboxamide

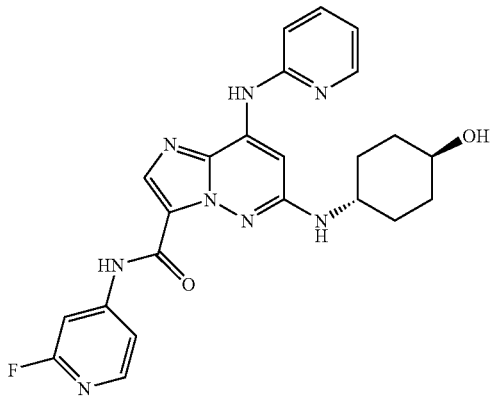 [SMILES: O=C(Nc1ccnc(F)c1)c1cnc2c(Nc3ccccn3)cc(N[C@H]3CC[C@H](O)CC3)nn12]

A suspension of 13A (40.0 mg, 0.123 mmol) in THF (2 mL) was treated with pyridin-2-amine (23.09 mg, 0.245 mmol). A solution of potassium tert-butoxide (0.245 mL, 0.245 mmol) in THF was added and the reaction was stirred at room temperature. The reaction was complete after two hours. The solvent was removed under a stream of nitrogen. The residue was taken up in MeOH and filtered. The solid material was dried under vacuum. The solid was taken up in NMP (2 mL) and (trans)-4-aminocyclohexanol (141 mg, 1.227 mmol) was added and the reaction was heated at 90° C. for 24 h, and then cooled to room temperature. The crude mixture was diluted with MeOH and purified by preparative HPLC (Phenomenex Axia Luna 5 micron 30×100 mm) 30% B (Solvent B=90% MeOH-10% $H_2O$-0.1% TFA) to 100% B in A (Solvent A=10% MeOH-90% $H_2O$-0.1% TFA) to afford N-(2-fluoro-4-pyridinyl)-6-((trans-4-hydroxycyclohexyl)amino)-8-(2-pyridinylamino)imidazo[1,2-b]pyridazine-3-carboxamide (6.6 mg, 0.014 mmol, 11.63% yield) HPLC Rt=1.828 minutes (Phenomenex Luna 5 micron C18 4.6×30 mm: 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). [M+H]=463.13.

Example 74

N-(2-fluoro-4-pyridinyl)-6-((trans-4-hydroxycyclohexyl)amino)-8-((5-methyl-2-pyridinyl)amino)imidazo[1,2-b]pyridazine-3-carboxamide

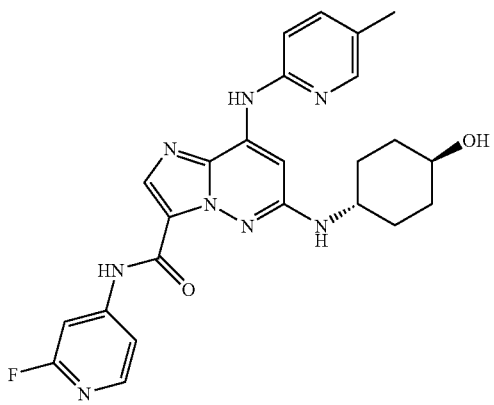 [SMILES: Cc1ccc(Nc2cc(N[C@H]3CC[C@H](O)CC3)nn3c(C(=O)Nc4ccnc(F)c4)cnc23)nc1]

A suspension of 13A (20.00 mg, 0.061 mmol) in THF (2 mL) was treated with 5-methylpyridin-2-amine (13.26 mg, 0.123 mmol). A solution of potassium tert-butoxide (0.123 mL, 0.123 mmol) in THF was added and the reaction was stirred at room temperature. The reaction was complete after two hours. The solvent was removed under a stream of nitrogen. The residue was taken up in MeOH and filtered. The solid material was dried under vacuum. The solid was taken up in NMP (2 mL) and (trans)-4-aminocyclohexanol (70.6 mg, 0.613 mmol) was added and the reaction was heated at 100° C. for 24 h, and then cooled to room temperature. The crude mixture was diluted with MeOH and purified by preparative HPLC (Phenomenex Axia Luna 5 micron 30×100 mm) 30% B (Solvent B=90% MeOH-10% $H_2O$-0.1% TFA) to 100% B in A (Solvent A=10% MeOH-90% $H_2O$-0.1% TFA) to afford N-(2-fluoro-4-pyridinyl)-6-((trans-4-hydroxycyclohexyl)amino)-8-((5-methyl-2-pyridinyl)amino)imidazo[1,2-b]pyridazine-3-carboxamide (5.6 mg, 0.012 mmol, 19.16% yield). HPLC Rt=2.170 minutes (Phenomenex Luna 5 micron C18 4.6×30 mm: 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). [M+H]=477.2.

Example 75

N-(2-chloro-4-pyridinyl)-6-((trans-4-hydroxycyclohexyl)amino)-8-((5-methyl-2-pyridinyl)amino)imidazo[1,2-b]pyridazine-3-carboxamide

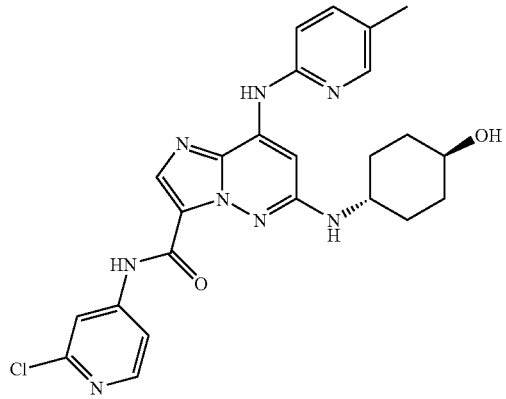 [SMILES: Cc1ccc(Nc2cc(N[C@H]3CC[C@H](O)CC3)nn3c(C(=O)Nc4ccnc(Cl)c4)cnc23)nc1]

A suspension of 23A (50.0 mg, 0.146 mmol) in THF (2 mL) was treated with 5-methylpyridin-2-amine (31.6 mg, 0.292 mmol). A solution of potassium tert-butoxide (0.292 mL, 0.292 mmol) in THF was added and the reaction was stirred at room temperature. The reaction was complete after two hours. The solvent was removed under a stream of nitrogen. The residue was taken up in MeOH and filtered. The solid material was dried under vacuum. The solid was taken up in NMP (2 mL) and (trans)-4-aminocyclohexanol (168 mg, 1.460 mmol) was added and the reaction was heated at 100° C. for 24 h, and then cooled to room temperature. The crude reaction mixture was diluted with MeOH and purified by preparative HPLC (Phenomenex Axia Luna 5 micron 30×100 mm) 30% B (Solvent B=90% MeOH-10% $H_2O$-0.1% TFA) to 100% B in A (Solvent A=10% MeOH-90% $H_2O$-0.1% TFA) to afford N-(2-chloro-4-pyridinyl)-6-((trans-4-hydroxycyclohexyl)amino)-8-((5-methyl-2-pyridinyl)amino)imidazo[1,2-b]pyridazine-3-carboxamide (17.7 mg, 0.036 mmol, 24.60% yield). HPLC Rt=0.870 minutes (Phenomenex Luna 5 micron C18 4.6×30 mm: 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). [M+H]=493.2.

Example 76

6-((trans-4-aminocyclohexyl)amino)-N-(2-chloro-4-pyridinyl)-8-((5-methyl-2-pyridinyl)amino)imidazo[1,2-b]pyridazine-3-carboxamide

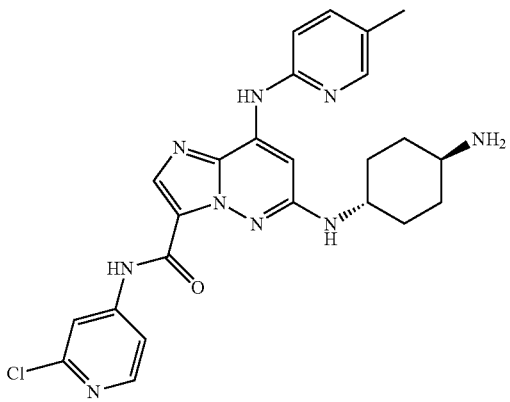 [SMILES: Cc1ccc(Nc2cc(N[C@H]3CC[C@H](N)CC3)nn3c(C(=O)Nc4ccnc(Cl)c4)cnc23)nc1]

A suspension of 23A (50.0 mg, 0.146 mmol) in THF (2 mL) was treated with 5-methylpyridin-2-amine (31.6 mg, 0.292 mmol). A solution of potassium tert-butoxide (0.292 mL, 0.292 mmol) in THF was added and the reaction was stirred at room temperature. The reaction was complete after two hours. The solvent was removed under a stream of nitrogen. The residue was taken up in MeOH and filtered. The solid material was dried under vacuum. The solid was taken up in NMP (2 mL) and (trans)-cyclohexane-1,4-diamine (167 mg, 1.460 mmol) was added and the reaction was heated at 90° C. for 24 h, and then cooled to room temperature. The crude material was diluted with MeOH and purified by preparative HPLC (Phenomenex Axia Luna 5 micron 30×100 mm) 30% B (Solvent B=90% MeOH-10% $H_2O$-0.1% TFA) to 100% B in A (Solvent A=10% MeOH-90% $H_2O$-0.1% TFA) to afford 6-((trans-4-aminocyclohexyl)amino)-N-(2-chloro-4-pyridinyl)-8-((5-methyl-2-pyridinyl)amino)imidazo[1,2-b]pyridazine-3-carboxamide (18.2 mg, 0.037 mmol, 25.3% yield). HPLC Rt=0.720 minutes (Phenomenex Luna 5 micron C18 4.6×30 mm: 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). [M+H]=492.2.

Example 77

6-((trans-4-aminocyclohexyl)amino)-N-(2-fluoro-4-pyridinyl)-8-((5-methyl-2-pyridinyl)amino)imidazo[1,2-b]pyridazine-3-carboxamide

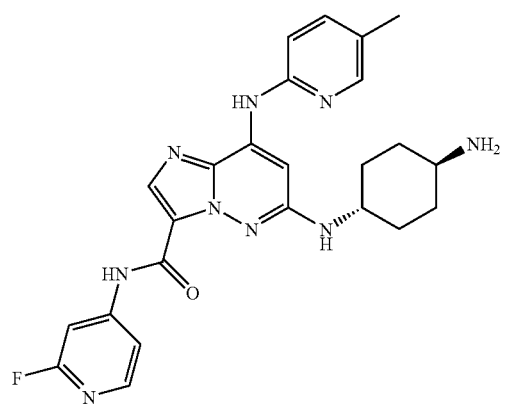 [SMILES: Cc1ccc(Nc2cc(N[C@H]3CC[C@H](N)CC3)nn3c(C(=O)Nc4ccnc(F)c4)cnc23)nc1]

A suspension of 13A (30.0 mg, 0.092 mmol) in THF (2 mL) was treated with 5-methylpyridin-2-amine (19.90 mg, 0.184 mmol). A solution of potassium tert-butoxide (0.184 mL, 0.184 mmol) in THF was added and the reaction was stirred at room temperature. The reaction was complete after two hours. The solvent was removed under a stream of nitrogen. The residue was taken up in MeOH and filtered. The solid material was dried under vacuum. The solid was taken up in NMP (2 mL) and (trans)-cyclohexane-1,4-diamine (105 mg, 0.920 mmol) was added and the reaction was heated at 90° C. for 24 h, and then cooled to room temperature. The crude material was diluted with MeOH and purified by preparative HPLC (Phenomenex Axia Luna 5 micron 30×100 mm) 30% B (Solvent B=90% MeOH-10% $H_2O$-0.1% TFA) to 100% B in A (Solvent A=10% MeOH-90% $H_2O$-0.1% TFA) to afford 6-((trans-4-aminocyclohexyl)amino)-N-(2-fluoro-4-pyridinyl)-8-((5-methyl-2-pyridinyl)amino)imidazo[1,2-b]pyridazine-3-carboxamide (10.2 mg, 0.021 mmol, 23.32% yield). HPLC Rt=0.690 minutes (Phenomenex Luna 5 micron C18 4.6×30 mm: 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). [M+H]=476.3.

Example 78

6-((trans-4-aminocyclohexyl)amino)-N-(2-cyano-4-pyridinyl)-8-(cyclopropylamino)imidazo[1,2-b]pyridazine-3-carboxamide

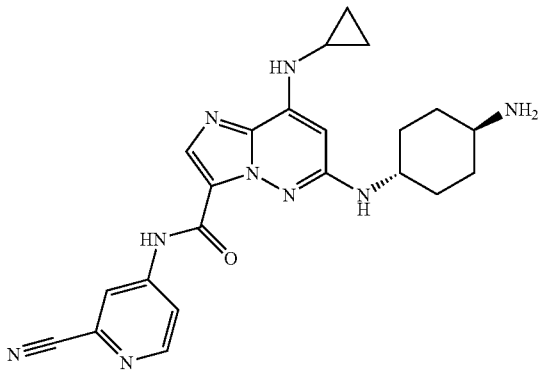 [SMILES: N#Cc1cc(NC(=O)c2cnc3c(NC4CC4)cc(N[C@H]4CC[C@H](N)CC4)nn23)ccn1]

Compound 25B (200 mg, 0.367 mmol) and sodium cyanide (54.0 mg, 1.102 mmol) were added to DMSO (1 mL) and heated to 100° C. for 15 min in a microwave reactor. The mixture was cooled to room temperature and then diluted with water, filtered and washed with additional water. The resulting material was dried under high vacuum.

The crude material was dissolved in TFA (0.849 mL, 11.02 mmol) and treated with triethylsilane (0.352 mL, 2.203 mmol). The mixture was stirred at room temperature for 1 h. The TFA and $Et_3SiH$ were removed via a stream of nitrogen and the crude material was purified by preparative HPLC (Phenomenex Axia Luna 5 micron 30×100 mm) 20% B (Solvent B=90% MeOH-10% $H_2O$-0.1% TFA) to 100% B in A (Solvent A=10% MeOH-90% $H_2O$-0.1% TFA) 40 min run to afford 6-((trans-4-aminocyclohexyl)amino)-N-(2-cyano-4-pyridinyl)-8-(cyclopropylamino)imidazo[1,2-b]pyridazine-3-carboxamide (13.7 mg, 0.032 mmol, 8.65% yield). HPLC Rt=1.373 minutes (Phenomenex Luna 5 micron C18 4.6×30 mm: 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). [M+H]=432.21.

Example 79

6-((trans-4-acetamidocyclohexyl)amino)-8-(cyclopropylamino)-N-4-pyridinylimidazo[1,2-b]pyridazine-3-carboxamide

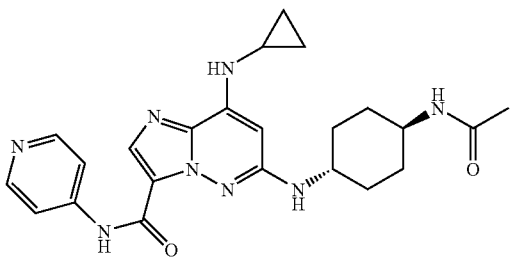 [SMILES: CC(=O)N[C@H]1CC[C@H](Nc2cc(NC3CC3)c3ncc(C(=O)Nc4ccncc4)n3n2)CC1]

6-((trans-4-acetamidocyclohexyl)amino)-8-(cyclopropylamino)-N-4-pyridinylimidazo[1,2-b]pyridazine-3-carboxamide was prepared according to the procedures detailed for Example 59, starting from 1E and cyclopropyl amine HPLC Rt=2.320 (Chromolith SpeedROD 4.6×50 mm, 10-90% aqueous methanol containing 0.1% TFA, 4 min gradient, monitored at 220 nm). [M+H]=449.

Example 80

6-((4-acetamidocyclohexyl)amino)-8-((6-methyl-2-pyridinyl)amino)-N-4-pyridinylimidazo[1,2-b]pyridazine-3-carboxamide

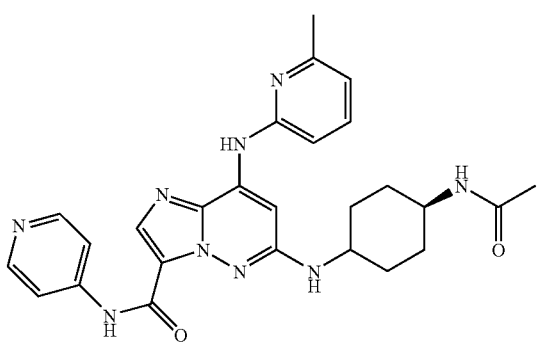

6-((4-acetamidocyclohexyl)amino)-8-((6-methyl-2-pyridinyl)amino)-N-4-pyridinylimidazo[1,2-b]pyridazine-3-carboxamide was prepared from Example 377 according to the procedures described in Example 59. HPLC Rt=2.567 minutes (Chromolith SpeedROD 4.6×50 mm, 10-90% aqueous methanol containing 0.1% TFA, 4 min gradient, monitored at 220 nm). [M+H]=500.0.

Example 81

6-((trans-4-acetamidocyclohexyl)amino)-8-((4-methyl-2-pyridinyl)amino)-N-4-pyridinylimidazo[1,2-b]pyridazine-3-carboxamide

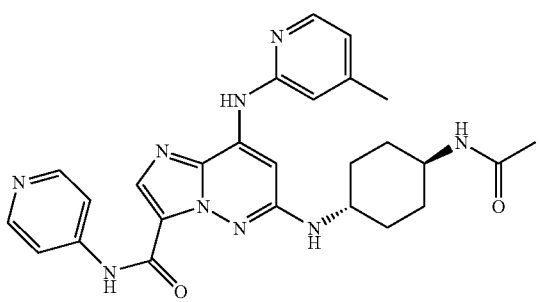 [SMILES: CC(=O)N[C@H]1CC[C@H](Nc2cc(Nc3cc(C)ccn3)c3ncc(C(=O)Nc4ccncc4)n3n2)CC1]

6-((trans-4-acetamidocyclohexyl)amino)-8-((4-methyl-2-pyridinyl)amino)-N-4-pyridinylimidazo[1,2-b]pyridazine-3-carboxamide was prepared from Example 24 according to the procedures described in Example 59. HPLC Rt=2.545 minutes (Chromolith SpeedROD 4.6×50 mm, 10-90% aqueous methanol containing 0.1% TFA, 4 min gradient, monitored at 220 nm). [M+H]=500.0.

Example 82

8-(ethylamino)-6-((trans-4-(((4-fluorophenyl)carbamoyl)amino)cyclohexyl)amino)-N-(3-fluoro-4-pyridinyl)imidazo[1,2-b]pyridazine-3-carboxamide

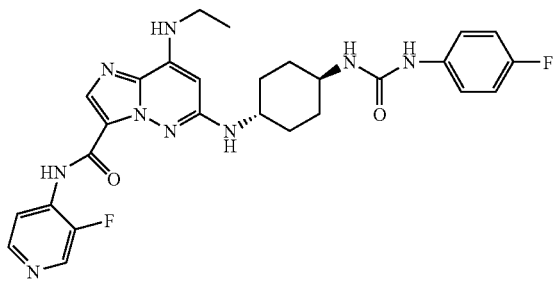 [SMILES: CCNc1cc(N[C@H]2CC[C@H](NC(=O)Nc3ccc(F)cc3)CC2)nn2c(C(=O)Nc3ccncc3F)cnc12]

82A. Preparation of 6-chloro-8-(ethylamino)-N-(3-fluoropyridin-4-yl)imidazo[1,2-b]pyridazine-3-carboxamide

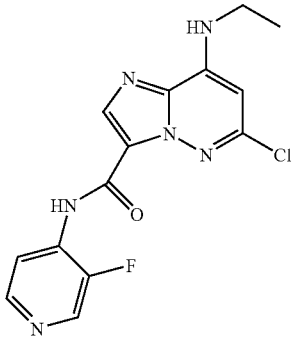 [SMILES: CCNc1cc(Cl)nn2c(C(=O)Nc3ccncc3F)cnc12]

A suspension of 5A (80 mg, 0.245 mmol), ethanamine (0.6 mL, 1.200 mmol, 2 M/THF) and DIEA (0.086 mL, 0.491 mmol) in NMP (0.7 mL) was heated at 80° C. for 5 h. The reaction mixture was cooled to room temperature and the solid was collected by filtration and washed with a small amount of DCM to give 6-chloro-8-(ethylamino)-N-(3-fluoropyridin-4-yl)imidazo[1,2-b]pyridazine-3-carboxamide as a yellow solid 62.8 mg. HPLC $R_f$=2.517 minutes (Chromolith SpeedROD 4.6×50 mm, 10-90% aqueous methanol containing 0.1% TFA, 4 min gradient, monitored at 220 nm). [M+H]= 335.

82B. Preparation 6-((trans)-4-aminocyclohexylamino)-8-(ethylamino)-N-(3-fluoropyridin-4-yl)imidazo[1,2-b]pyridazine-3-carboxamide

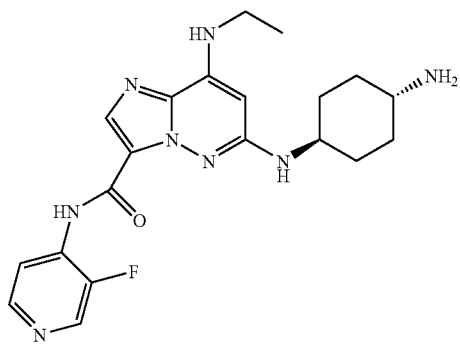 [SMILES: CCNc1cc(N[C@H]2CC[C@H](N)CC2)nn2c(C(=O)Nc3ccncc3F)cnc12]

A mixture of 82A (62.7 mg, 0.187 mmol), trans-cyclohexane-1,4-diamine (214 mg, 1.873 mmol) and DIEA (0.033 mL, 0.187 mmol) in NMP (1 mL) was heated in a microwave reactor at 120° C. for 50 minutes. The resulting mixture was diluted with water and made basic with saturated aqueous NaHCO₃. The resulting solid was collected by filtration and dried under vacuum to give 6-((trans)-4-aminocyclohexylamino)-8-(ethylamino)-N-(3-fluoropyridin-4-yl)imidazo[1,2-b]pyridazine-3-carboxamide as an off white solid (66.1 mg). HPLC $R_t$=2.122 minutes (Chromolith SpeedROD 4.6×50 mm, 10-90% aqueous methanol containing 0.1% TFA, 4 min gradient, monitored at 220 nm). [M+H]=413.

82C. Preparation of 8-(ethylamino)-6-((trans-4-(((4-fluorophenyl)carbamoyl)amino)cyclohexyl)amino)-N-(3-fluoro-4-pyridinyl)imidazo[1,2-b]pyridazine-3-carboxamide

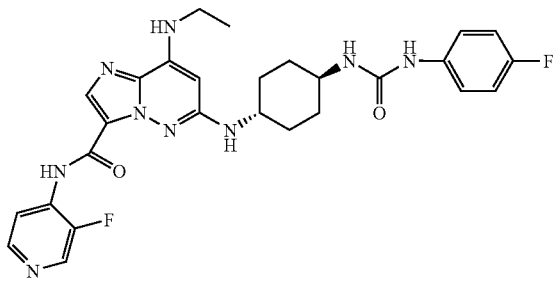 [SMILES: CCNc1cc(N[C@H]2CC[C@H](NC(=O)Nc3ccc(F)cc3)CC2)nn2c(C(=O)Nc3ccncc3F)cnc12]

To suspension of 82B (20 mg, 0.048 mmol) in THF was added 4-fluorophenylisocyanate (6.54 μL, 0.058 mmol). The mixture was stirred at room temperature overnight. The solvent was removed under reduced and MeOH (1 mL) was added. The mixture was sonicated and the solid was collected by filtration, rinsed with a small amount of MeOH and dried under vacuum to give 8-(ethylamino)-6-((trans-4-(((4-fluorophenyl)carbamoyl)amino)cyclohexyl)amino)-N-(3-fluoro-4-pyridinyl)imidazo[1,2-b]pyridazine-3-carboxamide (20.8 mg) as an off white solid. HPLC $R_t$=3.176 minutes (Chromolith SpeedROD 4.6×50 mm, 10-90% aqueous methanol containing 0.1% TFA, 4 min gradient, monitored at 220 nm). [M+H]=550.

Example 83

N-(3-acetamidophenyl)-6-((trans)-4-aminocyclohexylamino)-8-(cyclopropylamino)imidazo[1,2-b]pyridazine-3-carboxamide

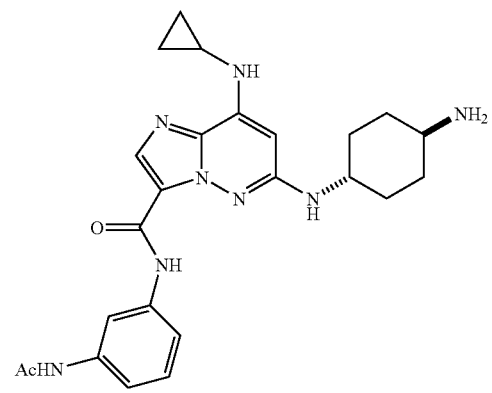 [SMILES: CC(=O)Nc1cccc(NC(=O)c2cnc3c(NC4CC4)cc(N[C@H]4CC[C@H](N)CC4)nn23)c1]

83A. Preparation of 6-((trans)-4-aminocyclohexylamino)-8-(cyclopropyl(4-methoxybenzyl)amino)-N-(3-fluoropyridin-4-yl)imidazo[1,2-b]pyridazine-3-carboxamide

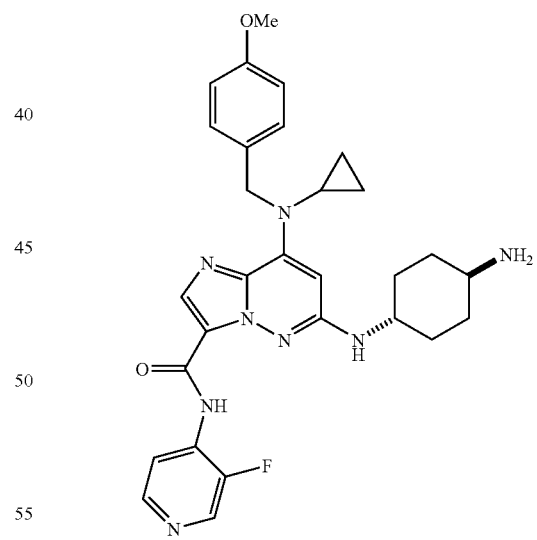

A ~1:1 mixture of 6,8-dichloro-N-(3-fluoropyridin-4-yl)imidazo[1,2-b]pyridazine-3-carboxamide) and 8-bromo-6-chloro-N-(3-fluoropyridin-4-yl)imidazo[1,2-b]pyridazine-3-carboxamide (850 mg, 2.61 mmol, 5A), N-(4-methoxybenzyl)cyclopropanamine (508 mg, 2.87 mmol) and N,N-diisopropylethylamine (0.683 mL, 3.91 mmol) were heated in DMF (10 mL) at 80° C. After 1 hr, the reaction mixture was concentrated to dryness under reduced pressure, suspended in methanol (20 mL), and the solid was isolated via Buchner filtration. The solid was combined with 4.8 g of trans-cyclohexane)-1,4-diamine and heated at 160° C. After 2.5 hrs, the reaction was cooled to room temperature, suspended in water (20 mL), and the isolated solid was purified with silica gel chromatography (10% methanol to 20% methanol/chloroform). The desired fractions were concentrated, and the solid suspended in water (25 mL), and filtered to isolate 6-((trans)-4-aminocyclohexylamino)-8-(cyclopropyl(4-methoxybenzyl)amino)-N-(3-fluoropyridin-4-yl)imidazo[1,2-b]pyridazine-3-carboxamide (834 mg, 1.531 mmol, 58.8% yield) as an off-white solid. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA) Rt=1.69 minutes. [M+H]=545.35.

83B. Preparation of tert-butyl (trans)-4-(8-(cyclopropyl(4-methoxybenzyl)amino)-3-(3-fluoropyridin-4-ylcarbamoyl)imidazo[1,2-b]pyridazin-6-ylamino)cyclohexylcarbamate

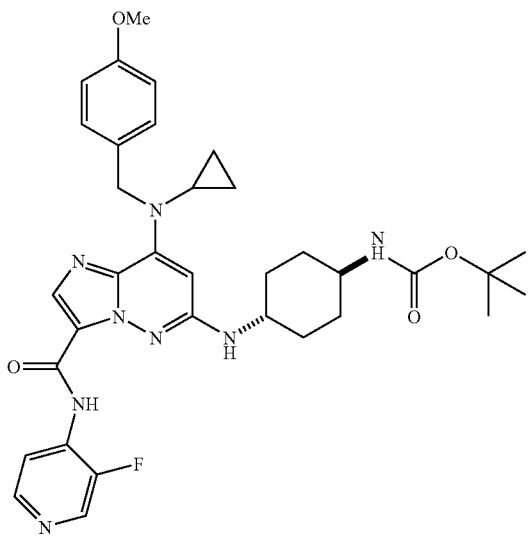 [SMILES: COc1ccc(CN(c2cc(N[C@H]3CC[C@H](NC(=O)OC(C)(C)C)CC3)nn3c(C(=O)Nc4ccncc4F)cnc23)C2CC2)cc1]

83A (31 mg, 0.057 mmol), di-tert-butyl dicarbonate (12.42 mg, 0.057 mmol), and triethylamine (7.93 µL, 0.057 mmol) in methanol (1 mL) were combined at room temperature. After 10 minutes, the reaction mixture was concentrated, and purified using silica gel chromatography (50% ethyl acetate/hexanes to ethyl acetate) to isolate tert-butyl (trans)-4-(8-(cyclopropyl(4-methoxybenzyl)amino)-3-(3-fluoropyridin-4-ylcarbamoyl)imidazo[1,2-b]pyridazin-6-ylamino)cyclohexylcarbamate (34 mg, 0.053 mmol, 93% yield) as a glassy white solid. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA) Rt=2.1 minutes. [M+H]=645.42.

83C. Preparation 6-((trans)-4-(tert-butoxycarbonylamino)cyclohexylamino)-8-(cyclopropyl(4-methoxybenzyl)amino)imidazo[1,2-b]pyridazine-3-carboxylic acid

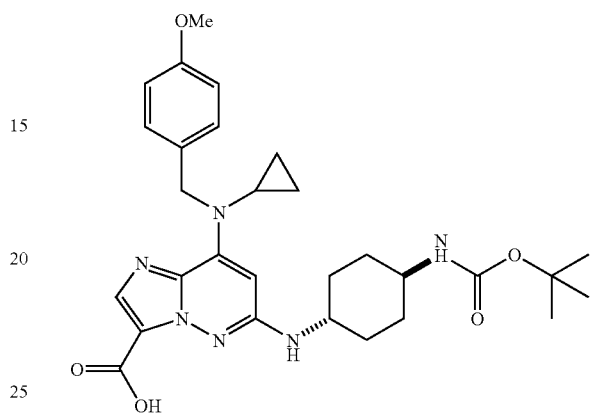

83B (19 mg, 0.029 mmol) was dissolved in MeOH (1 mL). 0.5 mL of 1N NaOH was added, and the cloudy reaction mixture was stirred at 65° C. After 2 hrs, the reaction mixture was cooled to room temperature, the pH adjusted to pH 7 with 1N HCl, and the solid was collected via Buchner filtration to afford 6-((trans)-4-(tert-butoxycarbonylamino)cyclohexylamino)-8-(cyclopropyl(4-methoxybenzyl)amino)imidazo[1,2-b]pyridazine-3-carboxylic acid as a white solid (10.6 mg, 0.019 mmol, 65.3% yield). LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA) Rt=2.1 minutes. [M+H]=551.36.

83D. Preparation of N-(3-acetamidophenyl)-6-((trans)-4-aminocyclohexylamino)-8-(cyclopropylamino)imidazo[1,2-b]pyridazine-3-carboxamide

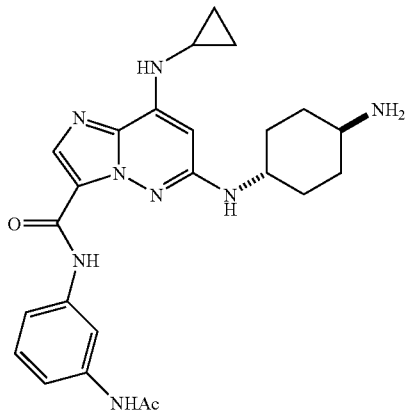 [SMILES: CC(=O)Nc1cccc(NC(=O)c2cnc3c(NC4CC4)cc(N[C@H]4CC[C@H](N)CC4)nn23)c1]

To N-(3-aminophenyl)acetamide (4.09 mg, 0.027 mmol), 83C (10 mg, 0.018 mmol) and DIEA in DMF (0.5 mL) was added benzotriazol-1-yloxytris(dimethylamino)phosphonium hexafluorophosphate (16.06 mg, 0.036 mmol) and the reaction was stirred at room temperature overnight. One mL of TFA was added to the reaction mixture and heated at 60° C. After 1 hr, the reaction mixture was concentrated under reduced pressure and purified using preparative HPLC containing TFA to isolate N-(3-acetamidophenyl)-6-((trans)-4-aminocyclohexylamino)-8-(cyclopropylamino)imidazo[1,2-b]pyridazine-3-carboxamide (4 mg, 5.02 μmol, 27.6% yield) as a white solid. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA) Rt=1.3 minutes. [M+H]=463.23. $^1$H NMR (500 MHz, METHANOL-$d_3$) δ ppm 10.99 (1H, s), 7.92 (1H, d, J=1.83 Hz), 7.62 (1H, d, J=8.25 Hz), 7.37 (2H, t, J=8.25 Hz), 7.16 (1H, d, J=8.25 Hz), 6.08 (1H, s), 3.80 (1H, t, J=4.35 Hz), 3.09-3.26 (1H, m), 2.51-2.72 (1H, m, J=6.76, 6.76, 3.67, 3.44 Hz), 2.35 (2H, d, J=10.08 Hz), 2.11-2.24 (3H, m), 1.98-2.14 (2H, m), 1.67-1.89 (2H, m, J=12.72, 12.43, 12.43, 3.21 Hz), 1.37-1.53 (2H, m), 1.20-1.38 (1H, m), 0.82-1.00 (2H, m), 0.58-0.76 (2H, m).

Example 84

6-((trans)-4-(2-aminoacetamido)cyclohexylamino)-8-(ethylamino)-N-(3-fluoropyridin-4-yl)imidazo[1,2-b]pyridazine-3-carboxamide

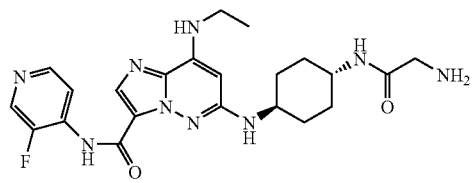 [SMILES: CCNc1cc(N[C@H]2CC[C@H](NC(=O)CN)CC2)nn2c(C(=O)Nc3ccncc3F)cnc12]

To a suspension containing 6-((trans)-4-aminocyclohexylamino)-8-(ethylamino)-N-(3-fluoropyridin-4-yl)imidazo[1,2-b]pyridazine-3-carboxamide (0.025 g, 0.061 mmol), diisopropylethylamine (0.053 mL, 0.303 mmol), and BOP (0.080 g, 0.182 mmol) in DMF at room temperature was added BOC-glycine (0.021 g, 0.121 mmol). The resulting suspension was stirred 30 min at ambient temperature. The dark brown solution was diluted with ethyl acetate and water. The layers were separated and the aqueous phase extracted three times with 5 mL ethyl acetate. The organic extracts were combined, washed with water and 10% aq. lithium chloride five times before drying over anhydrous sodium sulfate. Filtration and concentration under reduced pressure revealed a white solid which was suspended in $CH_2Cl_2$ (0.5 mL) at room temperature. TFA (0.5 mL) was added, resulting in a homogeneous solution. After 30 min at room temperature, the crude material was diluted with 1 mL of THF and purified via preparative HPLC using a YMC ODS C-18 30×250 mm column with 10-100% B (Solvent A: 10% aq MeOH with 0.1% TFA; Solvent B: 90% aq. MeOH with 0.1% TFA) and a linear gradient over 30 min at 25 mL/min, monitoring at 220 nm (Rt=27.545 min) The appropriate fractions were concentrated and lyophilized overnight, furnishing 6-((trans)-4-(2-aminoacetamido)cyclohexylamino)-8-(ethylamino)-N-(3-fluoropyridin-4-yl)imidazo[1,2-b]pyridazine-3-carboxamide (19 mg, 0.027 mmol, 44.9% yield) as a white foam. MS: [M+H]=470.0. HPLC: Rt=3.121 min. (Waters sunfire 4.6×50 mm C18.5 um 4 min/1 min hold time 0-100% (A-B) A=10% MeOH-90% water-0.1% TFA, B=90% MeOH-10% water-0.1% TFA).

Example 85

6-((trans-4-aminocyclohexyl)amino)-8-anilino-N-(2-methyl-4-pyridinyl)imidazo[1,2-b]pyridazine-3-carboxamide

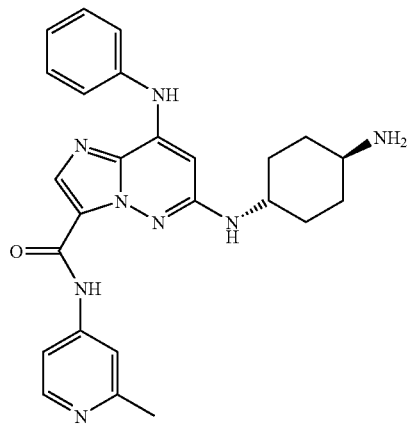

85A. Preparation of 6-chloro-N-(4-methoxybenzyl)-N-phenylimidazo[1,2-b]pyridazin-8-amine

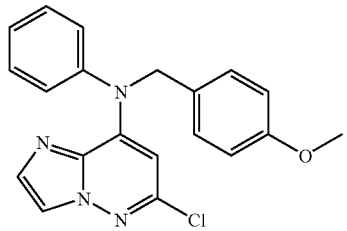 [SMILES: COc1ccc(CN(c2ccccc2)c2cc(Cl)nn3ccnc23)cc1]

A solution of N-(4-methoxybenzyl)aniline (6.42 g, 30.10 mmol) in THF (10 mL) was stirred at 25° C., and potassium tert-butoxide (1M in THF, 90.30 mL, 90.30 mmol) was added. After 30 minutes, 8-bromo-6-chloroimidazo[1,2-b]pyridazine (7.00 g, 30.10 mmol, Example 1 from WO 2007/038314) was added, and the reaction solution stirred at room temperature for 2 hours. The reaction was quenched with water (50 mL) and extracted with ethyl acetate (2×200 mL). The organic layer was washed with saturated aqueous $NaHCO_3$ (100 mL) and saturated aqueous at NaCl (100 mL). The organic phase was dried $Na_2SO_4$, filtered and concentrated in vacuo. The residue was purified via ISCO (5% EtOAC/DCM; 120 g column) to give 6-chloro-N-(4-methoxybenzyl)-N-phenylimidazo[1,2-b]pyridazin-8-amine (9.09 g, 83% yield) as a tan solid. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). Rt=3.918 minutes [M+H]= 365.07.

85B. Preparation of 6-chloro-8-((4-methoxybenzyl)(phenyl)amino)imidazo[1,2-b]pyridazine-3-carboxylic acid

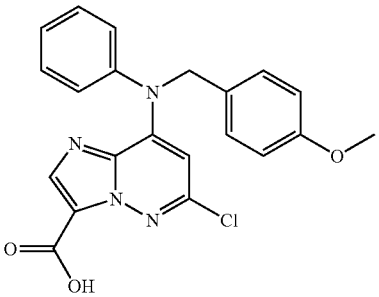 [SMILES: COc1ccc(CN(c2ccccc2)c2cc(Cl)nn3c(C(=O)O)cnc23)cc1]

To 6-chloro-N-(4-methoxybenzyl)-N-phenylimidazo[1,2-b]pyridazin-8-amine (1.00 g, 2.754 mmol) in THF (20 mL) at −78° C. was added n-BuLi (1.32 mL, 3.305 mmol, 2.5 M in hexanes). After 30 minutes, a stream of $CO_2$ gas was introduced into the reaction mixture for 20 minutes at −78° C. and at room temperature for additional 20 minutes. The reaction mixture was quenched with $H_2O$ (25 mL) and extracted with DCM (3×100 mL). The combined organic layer was washed with saturated $NaHCO_3$ (100 mL) and water (100 mL), dried $Na_2SO_4$, filtered and concentrated in vacuo to give 6-chloro-8-((4-methoxybenzyl)(phenyl)amino)imidazo[1,2-b]pyridazine-3-carboxylic acid (0.629 g, 56% yield)) as a yellow solid. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). Rt=3.736 minutes. [M+H]=409.02.

85C. Preparation of 6-chloro-8-((4-methoxybenzyl)(phenyl)amino)-N-(2-methylpyridin-4-yl)imidazo[1,2-b]pyridazine-3-carboxamide

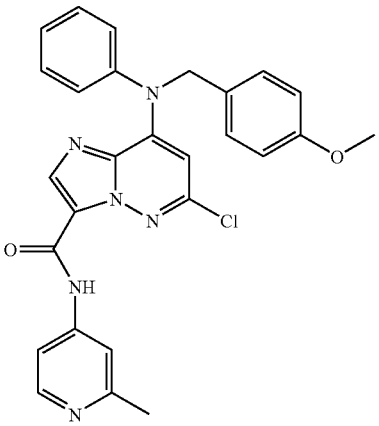 [SMILES: COc1ccc(CN(c2ccccc2)c2cc(Cl)nn3c(C(=O)Nc4ccnc(C)c4)cnc23)cc1]

6-Chloro-8-((4-methoxybenzyl)(phenyl)amino)imidazo[1,2-b]pyridazine-3-carboxylic acid (150 mg, 0.37 mmol) in $SOCl_2$ (2 mL) was heated at 60° C. for 1 hour. The reaction mixture was concentrated, dried under reduced pressure and dissolved in DCM (3 mL). 2-Methylpyridin-4-amine (45 mg, 0.41 mmol), and TEA (0.16 mL, 1.11 mmol) were added and the reaction mixture was stirred at room temperature for 12 hours, concentrated and then purified by silica gel chromatography (5% MeOH in DCM) to obtain 6-chloro-8-((4-methoxybenzyl)(phenyl)amino)-N-(2-methylpyridin-4-yl)imidazo[1,2-b]pyridazine-3-carboxamide (102 mg, 55% yield) as a yellow solid. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). Rt=3.263 minutes. [M+H]=499.06.

85D. Preparation of 6-((trans-4-aminocyclohexyl)amino)-8-anilino-N-(2-methyl-4-pyridinyl)imidazo[1,2-b]pyridazine-3-carboxamide

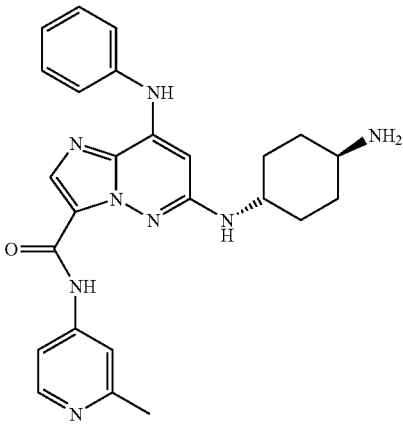

6-Chloro-8-((4-methoxybenzyl)(phenyl)amino)-N-(2-methylpyridin-4-yl)imidazo[1,2-b]pyridazine-3-carboxamide (100 mg, 0.201 mmol) and (trans)-cyclohexane-1,4-diamine (9459 mg, 4.016 mmol) were heated at 160° C. for 1 hour. The reaction mixture was dissolved in TFA (5 mL) and heated at 70° C. for 2 hours. The reaction mixture was concentrated, dissolved in methanol and purified by preparative HPLC (Phenomenex Axia Luna 5 micron 30×100 mm) 30% B (Solvent B=90% MeOH-10% $H_2O$-0.1% TFA) to 100% B in A (Solvent A=10% MeOH-90% $H_2O$-0.1% TFA) to afford 6-((trans-4-aminocyclohexyl)amino)-8-anilino-N-(2-methyl-4-pyridinyl)imidazo[1,2-b]pyridazine-3-carboxamide (39 mg, 48.5% yield) as a white solid. LC/MS (Phenomenex Luna 5 micron C18 4.6×30 mm, 0 to 100 B in 2 min with 1 min hold time, Flow rate=5 mL/min, detection at 254 nm, Solvent A: 10% methanol/90% water/0.1% TFA; Solvent B: 10% water/90% methanol/0.1% TFA). Rt=1.320 minutes, [M+H]=457.28. $^1$H NMR (400 MHz, DMSO-$d_6$) δ ppm 11.35-11.58 (1H, m), 9.33 (1H, s), 8.48-8.74 (1H, m), 8.14 (1H, s), 7.93-8.04 (1H, m), 7.87 (3H, d, J=4.28 Hz), 7.59-7.81 (1H, m), 7.31-7.52 (3H, m), 7.07-7.26 (1H, m), 6.87-7.06 (1H, m), 6.29 (1H, s), 3.53-3.77 (1H, m), 2.93-3.22 (1H, m), 2.65 (3H, s), 2.05-2.25 (2H, m), 1.87-2.09 (2H, m), 1.09-1.52 (4H, m).

Example 86
6-((trans-4-aminocyclohexyl)amino)-8-((1,5-dimethyl-1H-pyrazol-3-yl)amino)-N-(3-fluoro-4-pyridinyl)imidazo[1,2-b]pyridazine-3-carboxamide

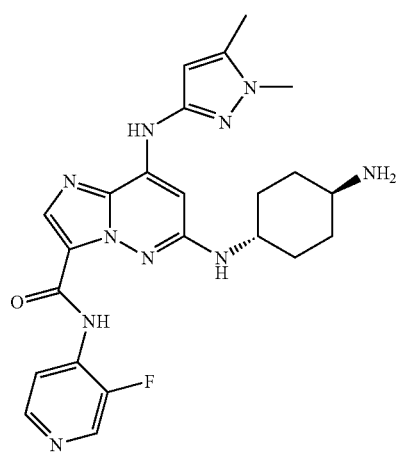 [SMILES: Cc1cc(Nc2cc(N[C@H]3CC[C@H](N)CC3)nn3c(C(=O)Nc4ccncc4F)cnc23)nn1C]

86A. Preparation of 6-chloro-8-(1,5-dimethyl-1H-pyrazol-3-ylamino)-N-(3-fluoropyridin-4-yl)imidazo[1,2-b]pyridazine-3-carboxamide

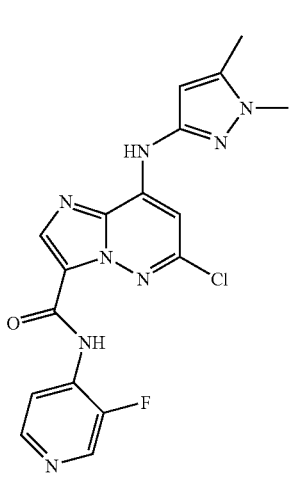 [SMILES: Cc1cc(Nc2cc(Cl)nn3c(C(=O)Nc4ccncc4F)cnc23)nn1C]

Example 86A was prepared in the same manner as detailed in Example 48A using the appropriate starting materials.

86B. Preparation of 6-((trans-4-aminocyclohexyl)amino)-8-((1,5-dimethyl-1H-pyrazol-3-yl)amino)-N-(3-fluoro-4-pyridinyl)imidazo[1,2-b]pyridazine-3-carboxamide

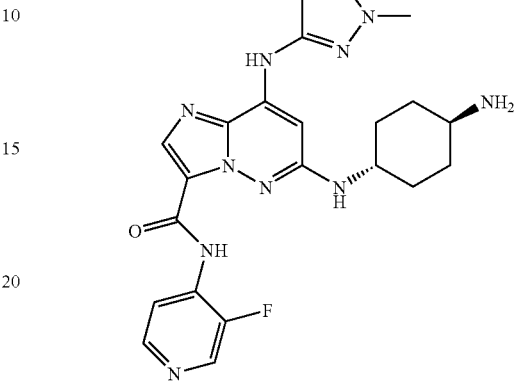

Example 86B was prepared from 86A using the procedures described in Example 40. HPLC Rt=2.413 minutes (Chromolith SpeedROD 4.6×50 mm, 10-90% aqueous methanol containing 0.1% TFA, 4 min gradient, monitored at 220 nm). [M+H]=479.0

The following Examples in Table 1 may be prepared from 8B in a manner analogous the procedures described in Example 34.

TABLE 1

| Example | Structure | Name | [M + H] | HPLC Ret Time (min) |
|---|---|---|---|---|
| 87 | (structure) | N~1~-(trans-4-((8-(cyclopropylamino)-3-((3-fluoro-4-pyridinyl)carbamoyl)imidazo[1,2-b]pyridazin-6-yl)amino)cyclohexyl)-L-aspartamide | 539.34 | 1.75[a] |

TABLE 1-continued

| Example | Structure | Name | [M + H] | HPLC Ret Time (min) |
|---|---|---|---|---|
| 88 | 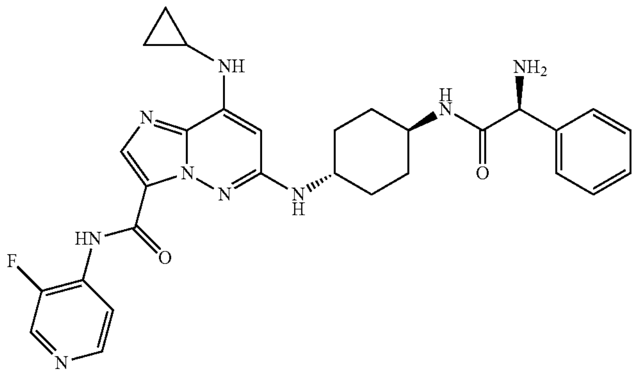 [SMILES: N[C@H](C(=O)N[C@H]1CC[C@H](Nc2cc(NC3CC3)c3ncc(C(=O)Nc4ccncc4F)n3n2)CC1)c1ccccc1] | 6-((trans-4-(((2S)-2-amino-2-phenylacetyl)amino)cyclohexyl)amino)-8-(cyclopropylamino)-N-(3-fluoro-4-pyridinyl)imidazo[1,2-b]pyridazine-3-carboxamide | 558.35 | 2.24[a] |
| 89 | 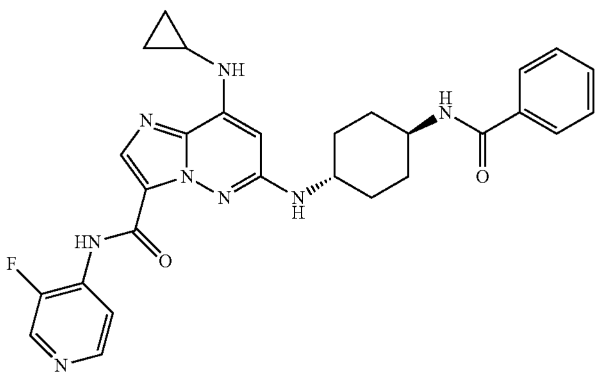 [SMILES: O=C(N[C@H]1CC[C@H](Nc2cc(NC3CC3)c3ncc(C(=O)Nc4ccncc4F)n3n2)CC1)c1ccccc1] | 6-((trans-4-(benzoylamino)cyclohexyl)amino)-8-(cyclopropylamino)-N-(3-fluoro-4-pyridinyl)imidazo[1,2-b]pyridazine-3-carboxamide | 529.35 | 2.64[a] |
| 90 | 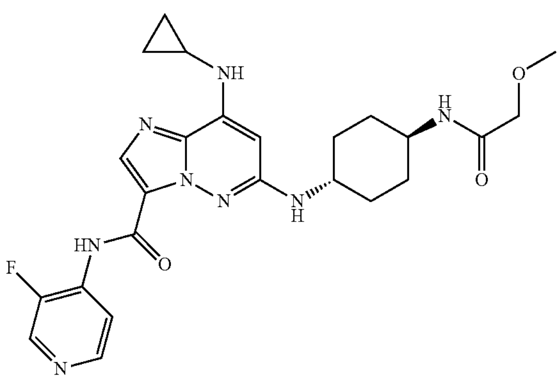 [SMILES: COCC(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-((methoxyacetyl)amino)cyclohexyl)amino)imidazo[1,2-b]pyridazine-3-carboxamide | 497.32 | 2.22[a] |
| 91 | 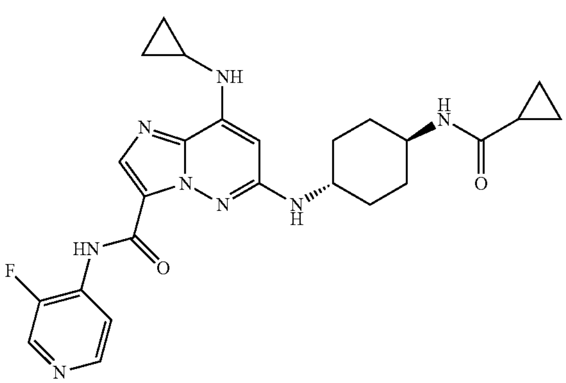 [SMILES: O=C(Nc1ccncc1F)c1cnc2c(NC3CC3)cc(N[C@H]3CC[C@H](NC(=O)C4CC4)CC3)nn12] | 8-(cyclopropylamino)-6-((trans-4-((cyclopropylcarbonyl)amino)cyclohexyl)amino)-N-(3-fluoro-4-pyridinyl)imidazo[1,2-b]pyridazine-3-carboxamide | 493.06 | 1.9[a] |

TABLE 1-continued

| Example | Name | [M + H] | HPLC Ret Time (min) |
|---|---|---|---|
| 92 | 6-((trans-4-((cyanoacetyl)amino) cyclohexyl)amino)-8-(cyclopropyl- amino)-N-(3-fluoro-4-pyridinyl) imidazo[1,2-b]pyridazine-3- carboxamide | 492.05 | 1.83[a] |
| 93 | 8-(cyclopropylamino)-N-(3-fluoro- 4-pyridinyl)-6-((trans-4-((2- pyrazinylcarbonyl)amino) cyclohexyl)amino) imidazo[1,2-b]pyridazine-3- carboxamide | 531.04 | 1.91[a] |
| 94 | 8-(cyclopropylamino)-N-(3-fluoro- 4-pyridinyl)-6-((trans-4-((2- pyridinylcarbonyl)amino) cyclohexyl)amino)imidazo [1,2-b]pyridazine-3- carboxamide | 530.36 | 2.1[a] |
| 95 | 8-(cyclopropylamino)-N-(3-fluoro-4- pyridinyl)-6-((trans-4-((3-pyridinyl- carbonyl)amino)cyclohexyl)amino) imidazo[1,2-b]pyridazine-3- carboxamide | 530.36 | 1.81[a] |

TABLE 1-continued

| Example | Structure | Name | [M + H] | HPLC Ret Time (min) |
|---|---|---|---|---|
| 96 | 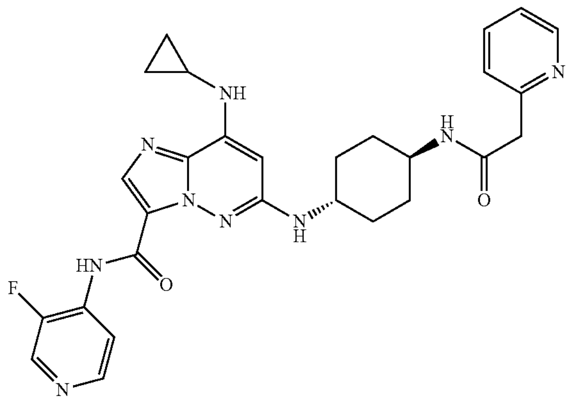 [SMILES: O=C(Cc1ccccn1)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-((2-pyridinyl-acetyl)amino)cyclohexyl)amino)imidazo[1,2-b]pyridazine-3-carboxamide | 544.05 | 1.81[a] |
| 97 | 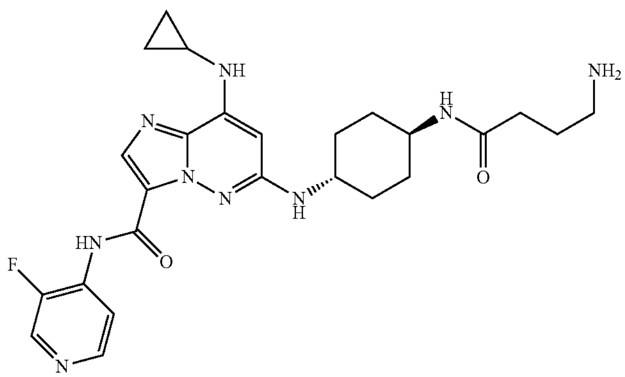 [SMILES: NCCCC(=O)N[C@H]1CC[C@H](Nc2cc(NC3CC3)c3ncc(C(=O)Nc4ccncc4F)n3n2)CC1] | 6-((trans-4-((4-aminobutanoyl)amino)cyclohexyl)amino-8-(cyclopropylamino)-N-(3-fluoro-4-pyridinyl)imidazo[1,2-b]pyridazine-3-carboxamide | 510.07 | 1.47[a] |
| 98 | 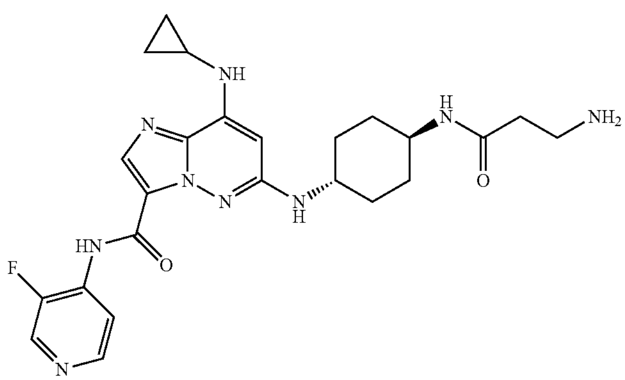 [SMILES: NCCC(=O)N[C@H]1CC[C@H](Nc2cc(NC3CC3)c3ncc(C(=O)Nc4ccncc4F)n3n2)CC1] | 6-((trans-4-(beta-alanylamino)cyclohexyl)amino)-8-(cyclopropylamino)-N-(3-fluoro-4-pyridinyl)imidazo[1,2-b]pyridazine-3-carboxamide | 496.05 | 1.46[a] |
| 99 | 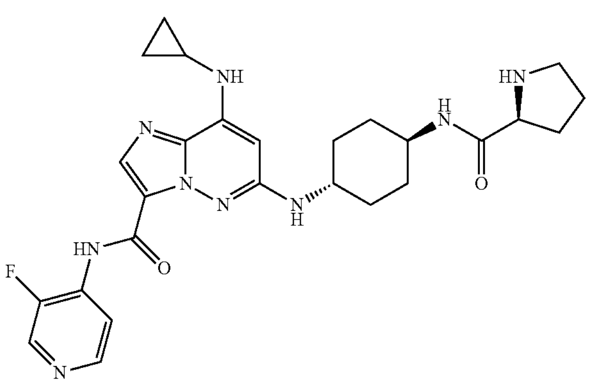 [SMILES: O=C(Nc1ccncc1F)c1cnc2c(NC3CC3)cc(N[C@H]3CC[C@H](NC(=O)[C@@H]4CCCN4)CC3)nn12] | 8-(cyclopropylamino)-N-(3-fluoro-4-pyridinyl)-6-((trans-4-(L-prolylamino)cyclohexyl)amino)imidazo[1,2-b]pyridazine-3-carboxamide | 522.09 | 1.55[a] |

TABLE 1-continued

| Example | Structure | Name | [M + H] | HPLC Ret Time (min) |
|---|---|---|---|---|
| 100 | 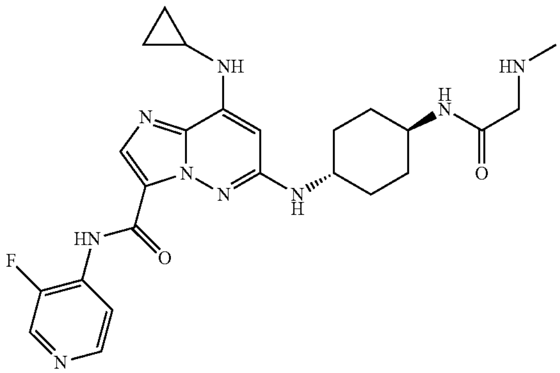 [SMILES: CNCC(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-((N-methyl-glycyl)amino)cyclohexyl)amino)imidazo[1,2-b]pyridazine-3-carboxamide | 496.06 | 1.48[a] |
| 101 | 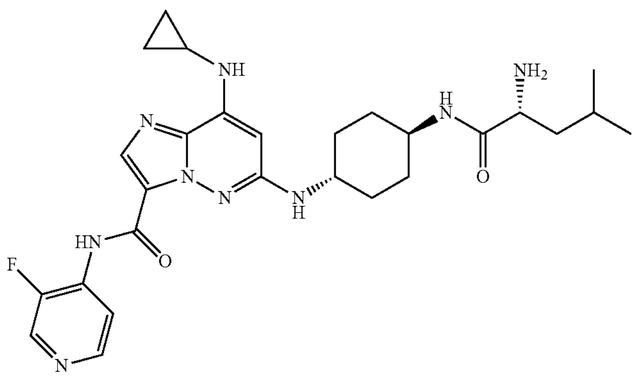 [SMILES: CC(C)C[C@@H](N)C(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-(D-leucylamino)cyclohexyl)amino)imidazo[1,2-b]pyridazine-3-carboxamide | 538.10 | 1.79[a] |
| 102 | 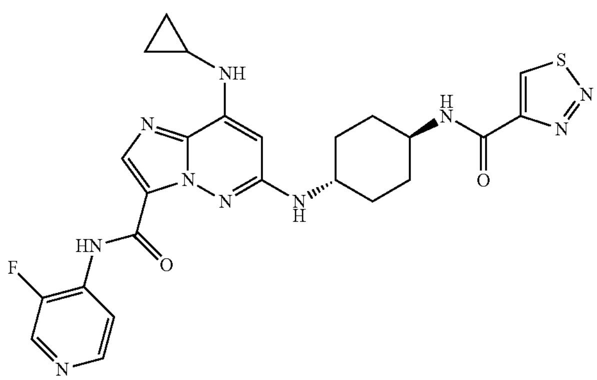 [SMILES: O=C(N[C@H]1CC[C@H](Nc2cc(NC3CC3)c3ncc(C(=O)Nc4ccncc4F)n3n2)CC1)c1csnn1] | 8-(cyclopropylamino)-N-(3-fluoro-4-pyridinyl)-6-((trans-4-((1,2,3-thiadiazol-4-ylcarbonyl)amino)cyclohexyl)amino)imidazo[1,2-b]pyridazine-3-carboxamide | 536.99 | 2.01[a] |
| 103 | 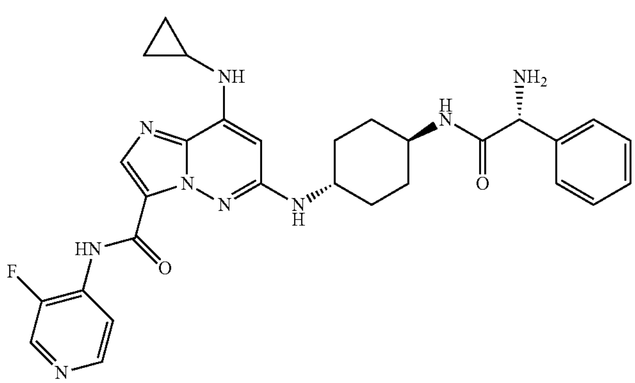 [SMILES: N[C@@H](C(=O)N[C@H]1CC[C@H](Nc2cc(NC3CC3)c3ncc(C(=O)Nc4ccncc4F)n3n2)CC1)c1ccccc1] | 6-((trans-4-(((2R)-2-amino-2-phenylacetyl)amino)cyclohexyl)amino)-8-(cyclopropylamino)-N-(3-fluoro-4-pyridinyl)imidazo[1,2-b]pyridazine-3-carboxamide | 558.06 | 1.83[a] |

TABLE 1-continued

| Example | Name | [M + H] | HPLC Ret Time (min) |
|---|---|---|---|
| 104 | 8-(cyclopropylamino)-N-(3-fluoro-4-pyridinyl)-6-((trans-4-(D-prolylamino)cyclohexyl)amino)imidazo[1,2-b]pyridazine-3-carboxamide | 522.08 | 1.53[a] |
| 105 | N~1~-(trans-4-((8-(cyclopropylamino)-3-((3-fluoro-4-pyridinyl)carbamoyl)imidazo[1,2-b]pyridazin-6-yl)amino)cyclohexyl)-D-aspartamide | 539.05 | 1.43[a] |
| 106 | 8-(cyclopropylamino)-N-(3-fluoro-4-pyridinyl)-6-((trans-4-(L-leucylamino)cyclohexyl)amino)imidazo[1,2-b]pyridazine-3-carboxamide | 538.10 | 1.77[a] |
| 107 | 8-(cyclopropylamino)-N-(3-fluoro-4-pyridinyl)-6-((trans-4-((3-(3-pyridinyl)-D-alanyl)amino)cyclohexyl)amino)imidazo[1,2-b]pyridazine-3-carboxamide | 573.07 | 1.59[a] |

| Example | Structure | Name | [M + H] | HPLC Ret Time (min) |
|---|---|---|---|---|
| 108 | 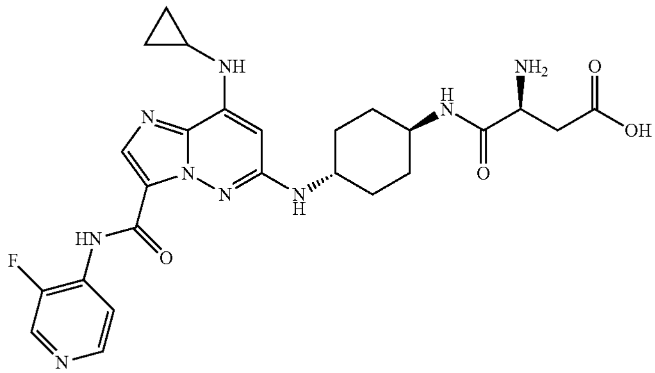 [SMILES: N[C@@H](CC(=O)O)C(=O)N[C@H]1CC[C@H](Nc2cc(NC3CC3)c3ncc(C(=O)Nc4ccncc4F)n3n2)CC1] | N-(trans-4-((8-(cyclopropyl-amino)-3-((3-fluoro-4-pyridinyl)carbamoyl)imidazo[1,2-b]pyridazin-6-yl)amino)cyclohexyl)-L-alpha-asparagine | 540.03 | 1.34[a] |
| 109 | 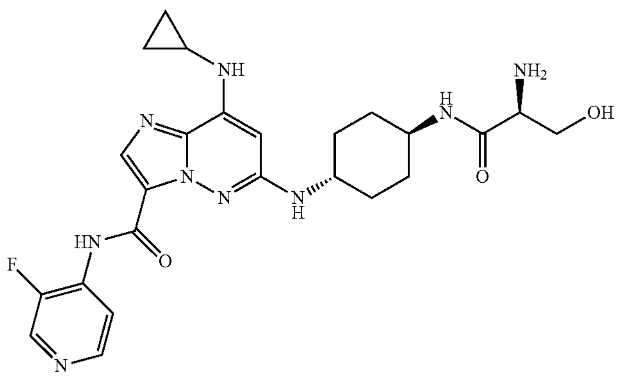 [SMILES: N[C@@H](CO)C(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-(L-serylamino)cyclohexyl)amino)imidazo[1,2-b]pyridazine-3-carboxamide | 512.05 | 1.43[a] |
| 110 | 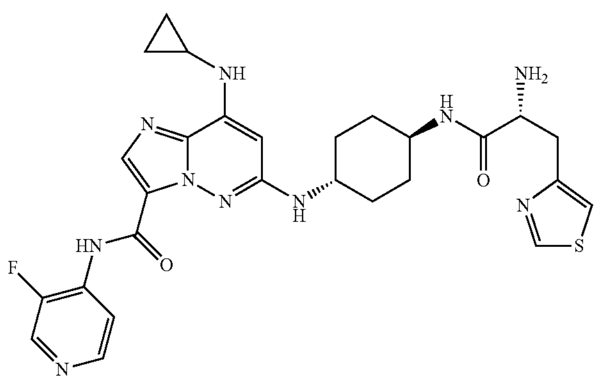 [SMILES: N[C@H](Cc1cscn1)C(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-((3-(1,3-thiazol-4-yl)-D-alanyl)amino)cyclohexyl)amino)imidazo[1,2-b]pyridazine-3-carboxamide | 579.06 | 1.63[a] |
| 111 | 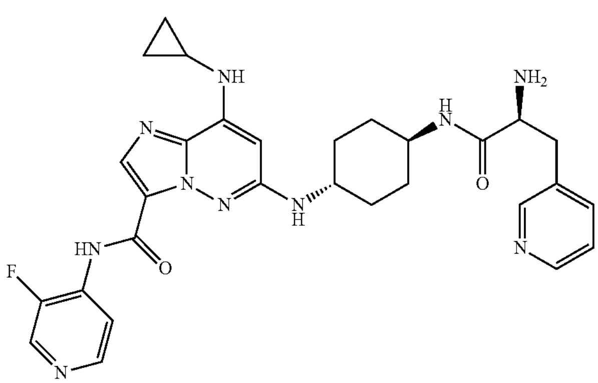 [SMILES: N[C@@H](Cc1cccnc1)C(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-((3-(3-pyridinyl)-L-alanyl)amino)cyclohexyl)amino)imidazo[1,2-b]pyridazine-3-carboxamide | 573.06 | 1.57[a] |

TABLE 1-continued

| Example | Structure | Name | [M + H] | HPLC Ret Time (min) |
|---|---|---|---|---|
| 112 | 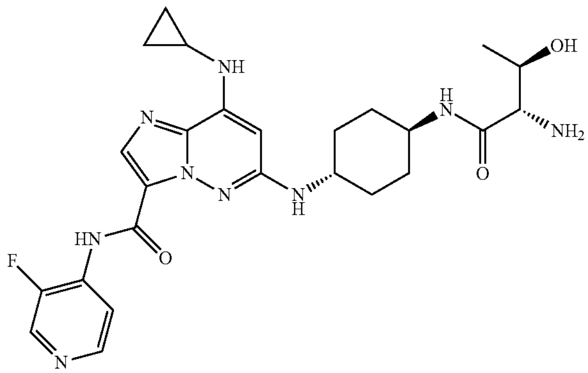 [SMILES: C[C@@H](O)[C@H](N)C(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-(L-threonylamino)cyclohexyl)amino)imidazo[1,2-b]pyridazine-3-carboxamide | 526.06 | 1.48[a] |
| 113 | 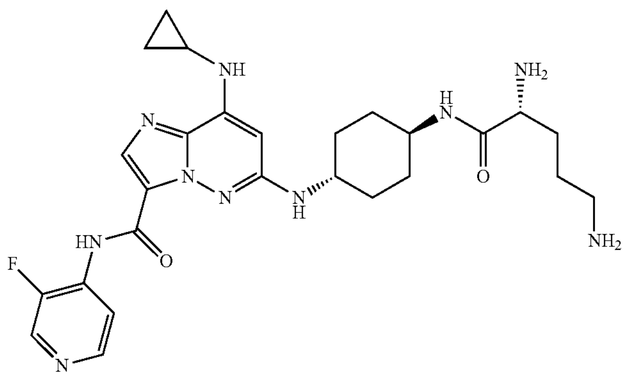 [SMILES: NCCC[C@@H](N)C(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-(D-ornithylamino)cyclohexyl)amino)imidazo[1,2-b]pyridazine-3-carboxamide | 539.10 | 1.33[a] |
| 114 | 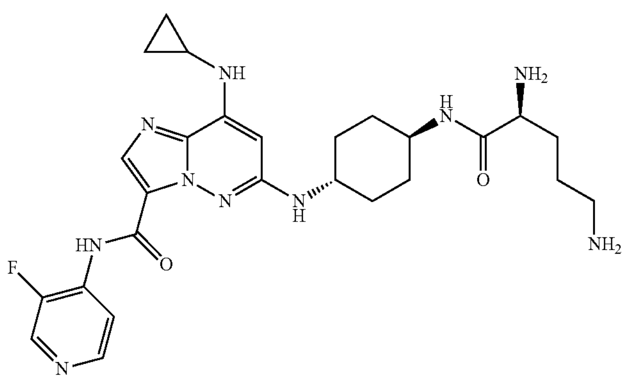 [SMILES: NCCC[C@H](N)C(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-(L-ornithylamino)cyclohexyl)amino)imidazo[1,2-b]pyridazine-3-carboxamide | 539.08 | 1.38[a] |
| 115 | 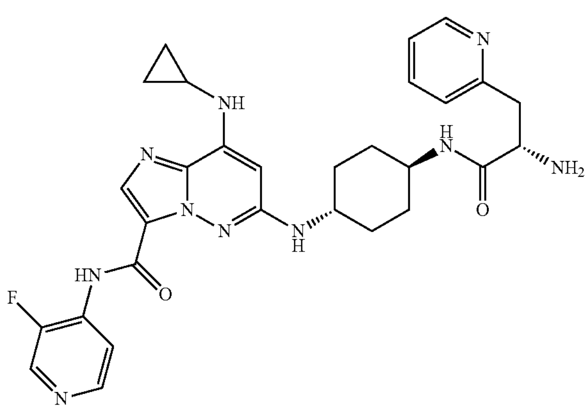 [SMILES: N[C@@H](Cc1ccccn1)C(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-((3-(2-pyridinyl)-L-alanyl)amino)cyclohexyl)amino)imidazo[1,2-b]pyridazine-3-carboxamide | 573.05 | 1.64[a] |

| Example | Structure | Name | [M + H] | HPLC Ret Time (min) |
|---|---|---|---|---|
| 116 | 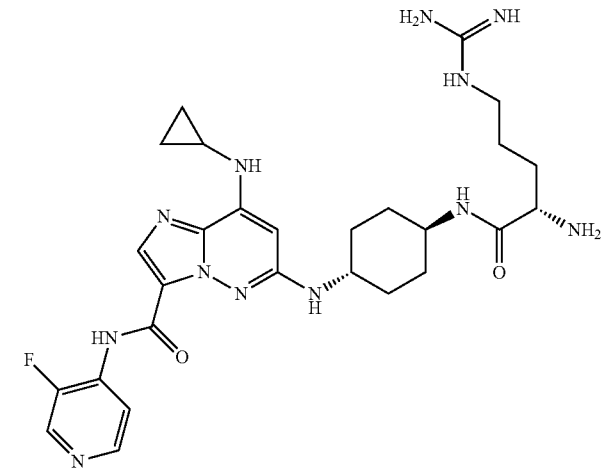 [SMILES: N=C(N)NCCC[C@H](N)C(=O)N[C@H]1CC[C@H](Nc2cc(NC3CC3)c3ncc(C(=O)Nc4ccncc4F)n3n2)CC1] | 6-((trans-4-(L-arginylamino)cyclohexyl)amino)-8-(cyclopropylamino)-N-(3-fluoro-4-pyridinyl)imidazo[1,2-b]pyridazine-3-carboxamide | 581.29 | 2.24[a] |
| 117 | 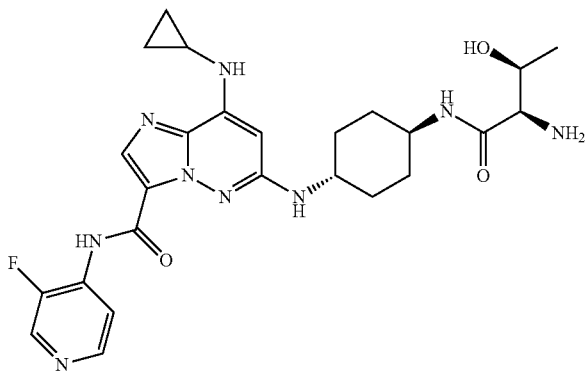 [SMILES: C[C@H](O)[C@@H](N)C(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-(D-threonylamino)cyclohexyl)amino)imidazo[1,2-b]pyridazine-3-carboxamide | 526.06 | 1.49[a] |
| 118 | 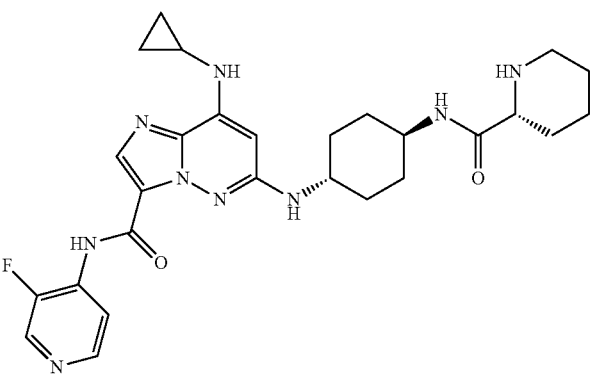 [SMILES: O=C(Nc1ccncc1F)c1cnc2c(NC3CC3)cc(N[C@H]3CC[C@H](NC(=O)[C@H]4CCCCN4)CC3)nn12] | 8-(cyclopropylamino)-N-(3-fluoro-4-pyridinyl)-6-((trans-4-(((2R)-2-piperidinyl-carbonyl)amino)cyclohexyl)amino)imidazo[1,2-b]pyridazine-3-carboxamide | 536.06 | 1.57[a] |

TABLE 1-continued

| Example | Structure | Name | [M + H] | HPLC Ret Time (min) |
|---|---|---|---|---|
| 119 | 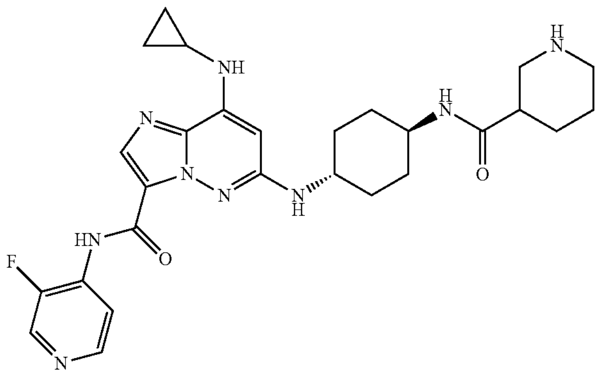 [SMILES: O=C(Nc1ccncc1F)c1cnc2c(NC3CC3)cc(N[C@H]3CC[C@H](NC(=O)C4CCCNC4)CC3)nn12] | 8-(cyclopropylamino)-N-(3-fluoro-4-pyridinyl)-6-((trans-4-((3-piperidinylcarbonyl)amino)cyclohexyl)amino)imidazo[1,2-b]pyridazine-3-carboxamide | 536.07 | 1.54[a] |
| 120 | 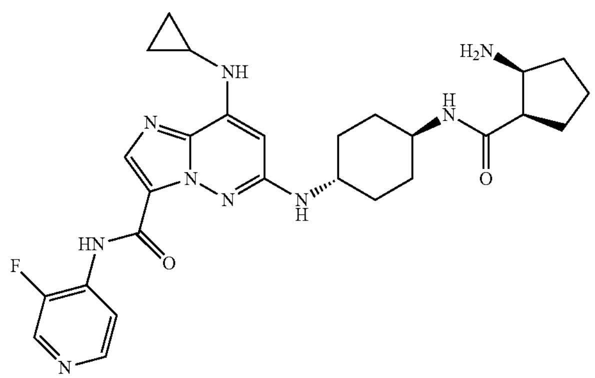 [SMILES: N[C@H]1CCC[C@H]1C(=O)N[C@H]1CC[C@H](Nc2cc(NC3CC3)c3ncc(C(=O)Nc4ccncc4F)n3n2)CC1] | 6-((trans-4-((((1R,2S)-2-amino-cyclopentyl)carbonyl)amino)cyclohexyl)amino)-8-(cyclopropylamino)-N-(3-fluoro-4-pyridinyl)imidazo[1,2-b]pyridazine-3-carboxamide | 536.08 | 1.56[a] |
| 121 | 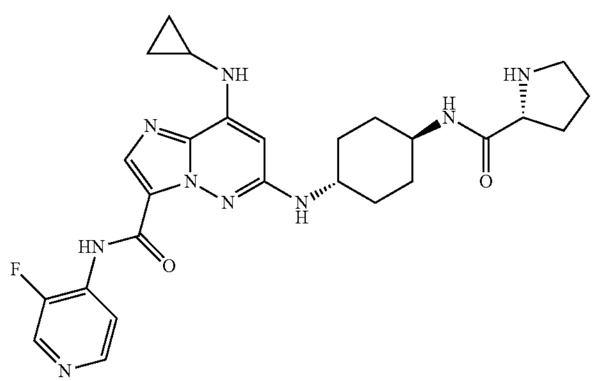 [SMILES: O=C(Nc1ccncc1F)c1cnc2c(NC3CC3)cc(N[C@H]3CC[C@H](NC(=O)[C@H]4CCCN4)CC3)nn12] | 8-(cyclopropylamino)-N-(3-fluoro-4-pyridinyl)-6-((trans-4-(D-prolylamino)cyclohexyl)amino)imidazo[1,2-b]pyridazine-3-carboxamide | 522.23 | 1.4[b] |
| 122 | 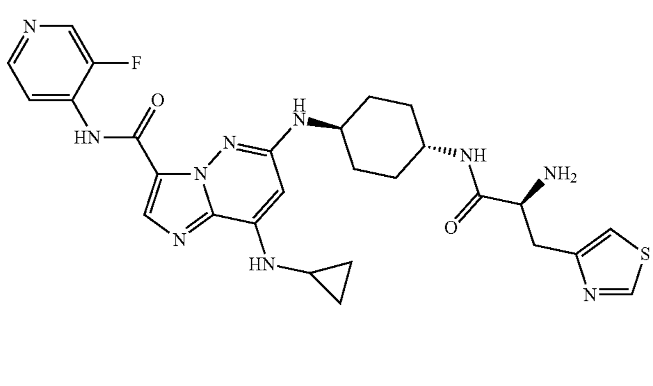 [SMILES: N[C@@H](Cc1cscn1)C(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-((3-(1,3-thiazol-4-yl)-L-alanyl)amino)cyclohexyl)amino)imidazo[1,2-b]pyridazine-3-carboxamide | 580.14 | 1.48[b] |

TABLE 1-continued

| Example | Structure | Name | [M + H] | HPLC Ret Time (min) |
|---|---|---|---|---|
| 123 | 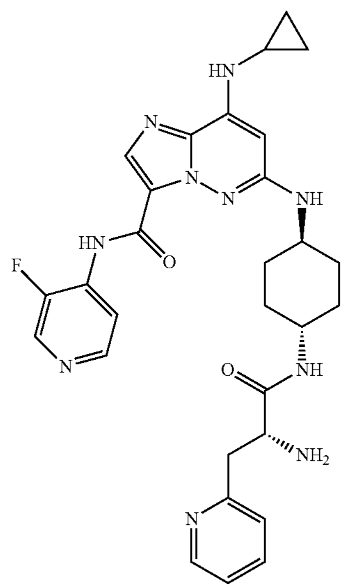 [SMILES: N[C@H](Cc1ccccn1)C(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-((3-(2-pyridinyl)-D-alanyl)amino)cyclohexyl)amino)imidazo[1,2-b]pyridazine-3-carboxamide | 573.22 | 1.44[b] |
| 124 | 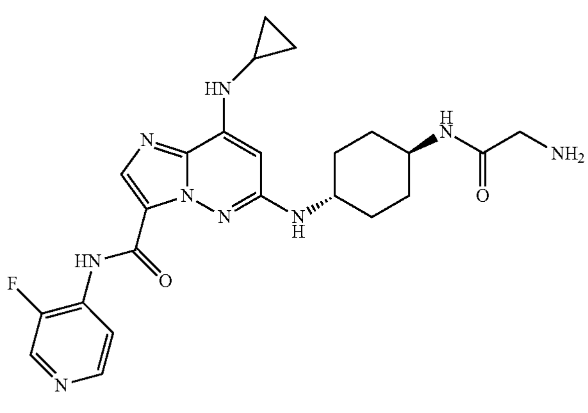 [SMILES: NCC(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-(glycylamino)cyclohexyl)amino)imidazo[1,2-b]pyridazine-3-carboxamide | 482.28 | 1.378[c] |
| 125 | 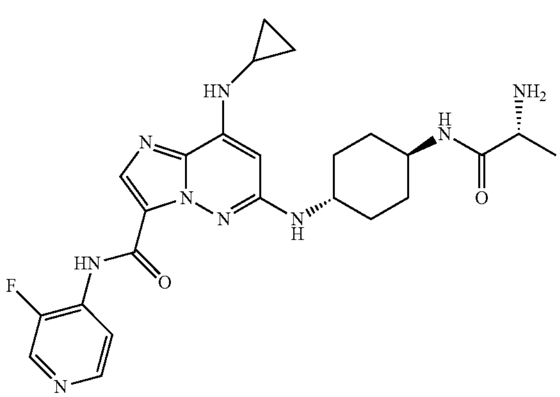 [SMILES: C[C@@H](N)C(=O)N[C@H]1CC[C@H](Nc2cc(NC3CC3)c3ncc(C(=O)Nc4ccncc4F)n3n2)CC1] | 6-((trans-4-(D-alanylamino)cyclohexyl)amino)-8-(cyclopropylamino)-N-(3-fluoro-4-pyridinyl)imidazo[1,2-b]pyridazine-3-carboxamide | 496.30 | 1.415[c] |

TABLE 1-continued

| Example | Structure | Name | [M + H] | HPLC Ret Time (min) |
|---|---|---|---|---|
| 126 | 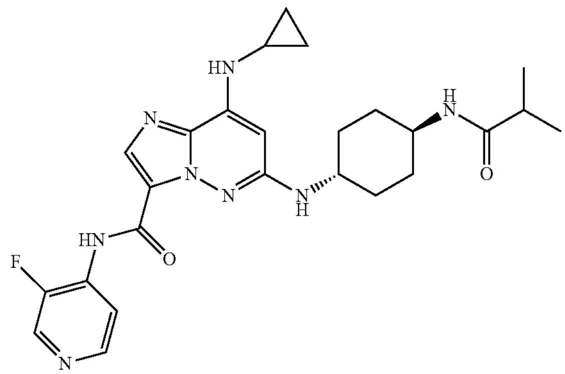 [SMILES: CC(C)C(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-(isobutyrylamino)cyclohexyl)amino)imidazo[1,2-b]pyridazine-3-carboxamide | 495.33 | 1.687[c] |
| 127 | 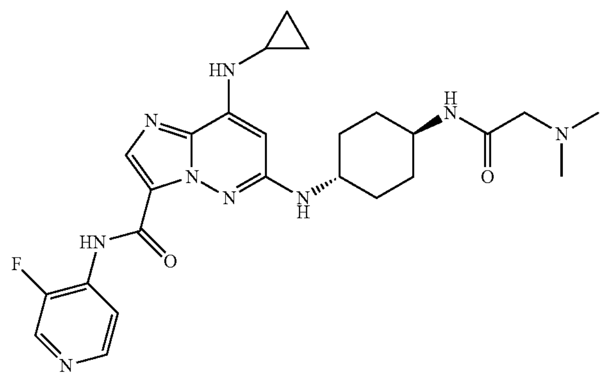 [SMILES: CN(C)CC(=O)N[C@H]1CC[C@H](Nc2cc(NC3CC3)c3ncc(C(=O)Nc4ccncc4F)n3n2)CC1] | 8-(cyclopropylamino)-6-((trans-4-((N,N-dimethylglycyl)amino)cyclohexyl)amino)-N-(3-fluoro-4-pyridinyl)imidazo[1,2-b]pyridazine-3-carboxamide | 510.32 | 1.390[b] |
| 128 | 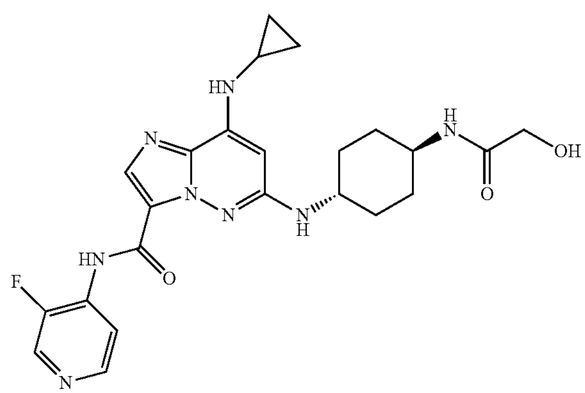 [SMILES: O=C(CO)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-(glycoloylamino)cyclohexyl)amino)imidazo[1,2-b]pyridazine-3-carboxamide | 483.24 | 1.470[c] |
| 129 | 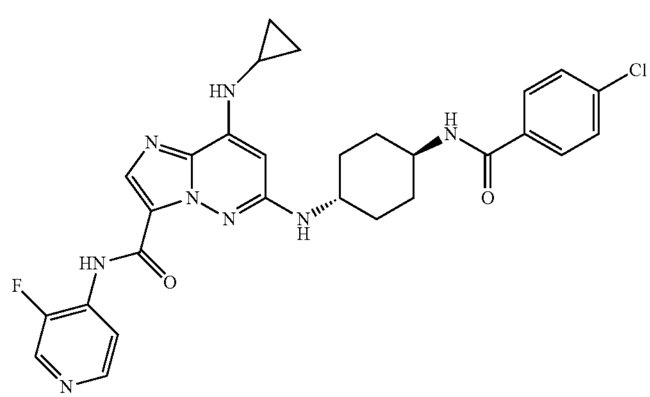 [SMILES: O=C(N[C@H]1CC[C@H](Nc2cc(NC3CC3)c3ncc(C(=O)Nc4ccncc4F)n3n2)CC1)c1ccc(Cl)cc1] | 6-((trans-4-((4-chlorobenzoyl)amino)cyclohexyl)amino)-8-(cyclopropylamino)-N-(3-fluoro-4-pyridinyl)imidazo[1,2-b]pyridazine-3-carboxamide | 563.12 | 1.917[c] |

TABLE 1-continued

| Example | Structure | Name | [M + H] | HPLC Ret Time (min) |
|---|---|---|---|---|
| 130 | 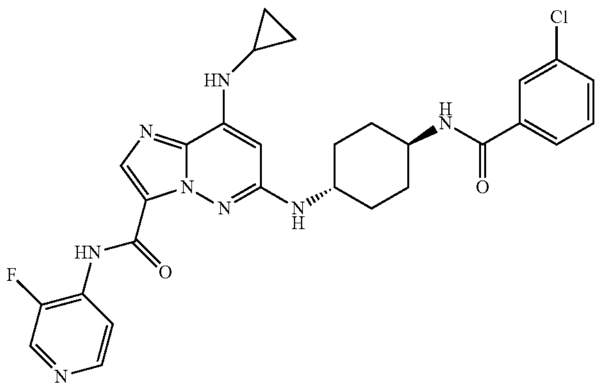 [SMILES: O=C(N[C@H]1CC[C@H](Nc2cc(NC3CC3)c3ncc(C(=O)Nc4ccncc4F)n3n2)CC1)c1cccc(Cl)c1] | 6-((trans-4-((3-chlorobenzoyl)amino)cyclohexyl)amino)-8-(cyclopropylamino)-N-(3-fluoro-4-pyridinyl)imidazo[1,2-b]pyridazine-3-carboxamide | 563.14 | 1.930[c] |
| 131 | 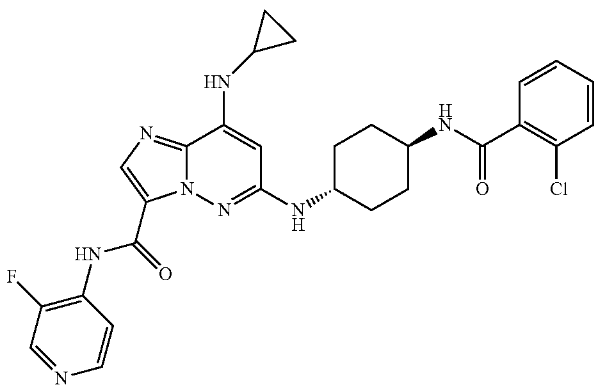 [SMILES: O=C(N[C@H]1CC[C@H](Nc2cc(NC3CC3)c3ncc(C(=O)Nc4ccncc4F)n3n2)CC1)c1ccccc1Cl] | 6-((trans-4-((2-chlorobenzoyl)amino)cyclohexyl)amino)-8-(cyclopropylamino)-N-(3-fluoro-4-pyridinyl)imidazo[1,2-b]pyridazine-3-carboxamide | 563.13 | 1.807[c] |

HPLC Conditions:
[a]Waters XBridge 4.6 × 50 mm 5 um C18 Column: 0%-100% solvent B. Solvent B: 95% CH$_3$CN, 5% H$_2$O, Modifier = 10 mM NH$_4$OAc).
Solvent A: 5% CH$_3$CN, 95% H$_2$O, Modifier = 10 mM NH$_4$OAc). 4 min gradient, monitored at 220 nm.
[b]Phenomenex Luna 5 micron C18 4.6 × 30 mm. 0 to 100 B in 2 min with 1 min hold time, Flow rate = 5 mL/min, detection at 254 nm, Solvent A: 10% methanol/90% water/0.1% TFA; Solvent B: 10% water/90% methanol/0.1 % TFA
[c]Phenomenex Luna 5 micron C18 4.6 × 30 mm. 0 to 100 B in 2 min with 1 min hold time, Flow rate = 5 mL/min, detection at 254 nm, Solvent A: 10% methanol/90%water/0.1% TFA; Solvent B: 10% water/90% methanol/0.1% TFA The following Examples in Table 2 may be prepared from 25B in a manner analogous the procedures described in Example 34.

TABLE 2

| Example | Structure | Name | [M + H] | HPLC Ret Time (min) |
|---|---|---|---|---|
| 132 | 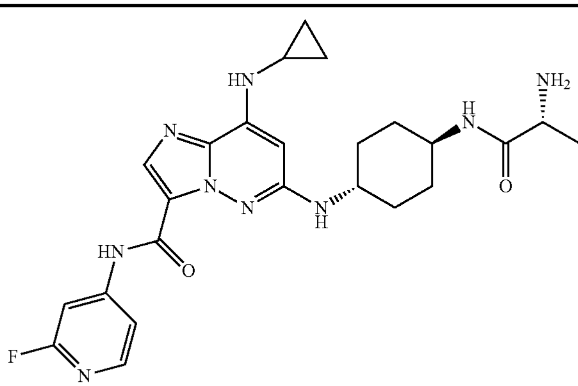 | 6-((trans-4-(D-alanylamino)cyclohexyl)amino)-8-(cyclopropylamino)-N-(2-fluoro-4-pyridinyl)imidazo[1,2-b]pyridazine-3-carboxamide | 496.18 | 1.535[a] |

TABLE 2-continued

| Example | Structure | Name | [M + H] | HPLC Ret Time (min) |
|---|---|---|---|---|
| 133 | 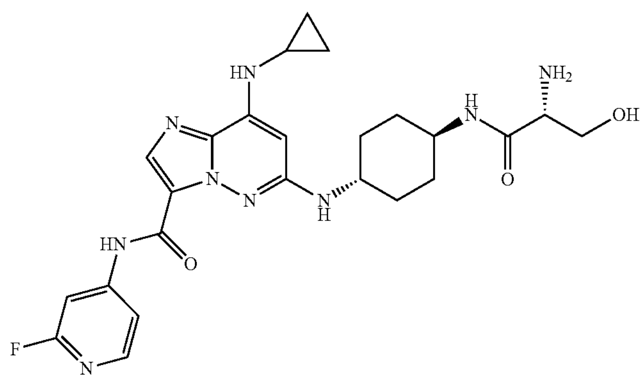 [SMILES: N[C@H](CO)C(=O)N[C@H]1CC[C@H](Nc2cc(NC3CC3)c3ncc(C(=O)Nc4ccnc(F)c4)n3n2)CC1] | 8-(cyclopropylamino)-N-(2-fluoro-4-pyridinyl)-6-((trans-4-(D-serylamino)cyclohexyl)amino)imidazo[1,2-b]pyridazine-3-carboxamide | 512.18 | 1.503[a] |
| 134 | 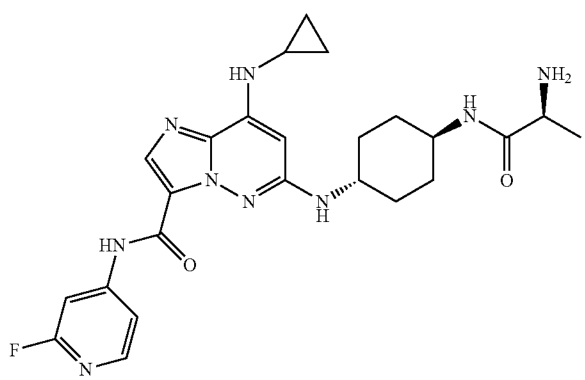 [SMILES: C[C@H](N)C(=O)N[C@H]1CC[C@H](Nc2cc(NC3CC3)c3ncc(C(=O)Nc4ccnc(F)c4)n3n2)CC1] | 6-((trans-4-(L-alanylamino)cyclohexyl)amino)-8-(cyclopropylamino)-N-(2-fluoro-4-pyridinyl)imidazo[1,2-b]pyridazine-3-carboxamide | 496.19 | 1.538[a] |
| 135 | 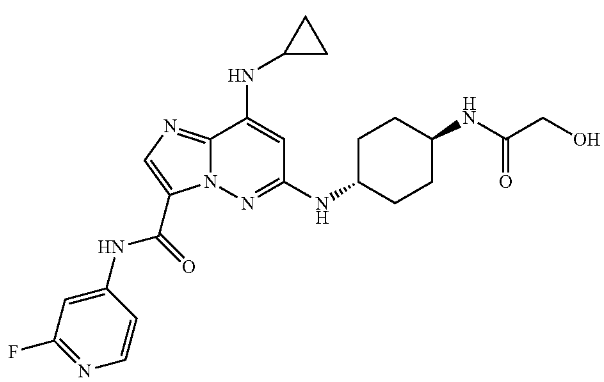 [SMILES: O=C(CO)N[C@H]1CC[C@H](Nc2cc(NC3CC3)c3ncc(C(=O)Nc4ccnc(F)c4)n3n2)CC1] | 8-(cyclopropylamino)-N-(2-fluoro-4-pyridinyl)-6-((trans-4-(glycoloylamino)cyclohexyl)amino)imidazo[1,2-b]pyridazine-3-carboxamide | 483.23 | 1.682[a] |
| 136 | 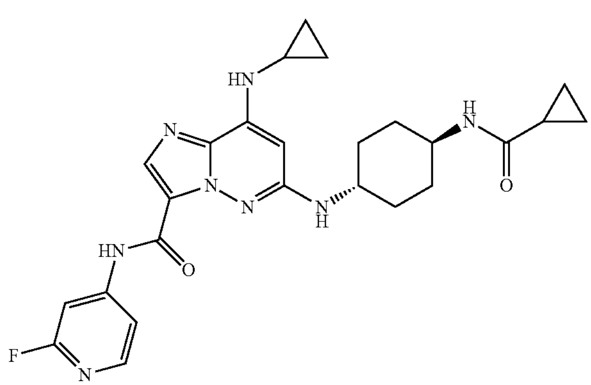 [SMILES: O=C(Nc1ccnc(F)c1)c1cnc2c(NC3CC3)cc(N[C@H]3CC[C@H](NC(=O)C4CC4)CC3)nn12] | 8-(cyclopropylamino)-6-((trans-4-((cyclopropylcarbonyl)amino)cyclohexyl)amino)-N-(2-fluoro-4-pyridinyl)imidazo[1,2-b]pyridazine-3-carboxamide | 496.23 | 1.847[a] |

TABLE 2-continued

| Example | Structure | Name | [M + H] | HPLC Ret Time (min) |
|---|---|---|---|---|
| 137 | 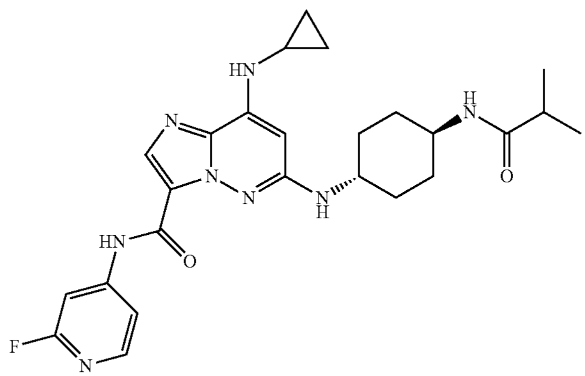 [SMILES: CC(C)C(=O)N[C@H]1CC[C@H](Nc2cc(NC3CC3)c3ncc(C(=O)Nc4ccnc(F)c4)n3n2)CC1] | 8-(cyclopropylamino)-N-(2-fluoro-4-pyridinyl)-6-((trans-4-(isobutyrylamino)cyclohexyl)amino)imidazo[1,2-b]pyridazine-3-carboxamide | 495.18 | 1.880[a] |
| 138 | 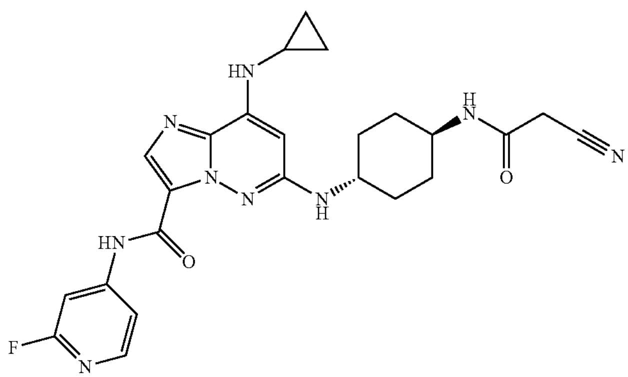 [SMILES: N#CCC(=O)N[C@H]1CC[C@H](Nc2cc(NC3CC3)c3ncc(C(=O)Nc4ccnc(F)c4)n3n2)CC1] | 6-((trans-4-((cyanoacetyl)amino)cyclohexyl)amino)-8-(cyclopropylamino)-N-(2-fluoro-4-pyridinyl)imidazo[1,2-b]pyridazine-3-carboxamide | 492.14 | 1.727[a] |
| 139 | 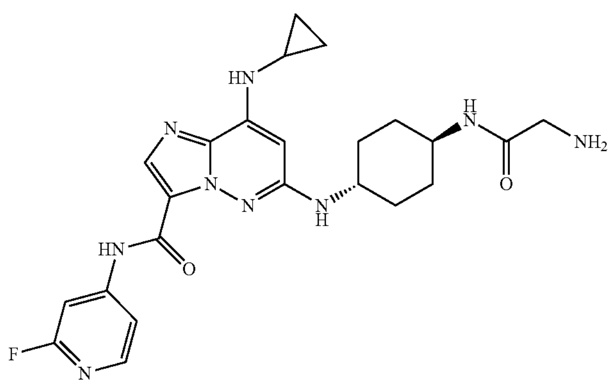 [SMILES: NCC(=O)N[C@H]1CC[C@H](Nc2cc(NC3CC3)c3ncc(C(=O)Nc4ccnc(F)c4)n3n2)CC1] | 8-(cyclopropylamino)-N-(2-fluoro-4-pyridinyl)-6-((trans-4-(glycylamino)cyclohexyl)amino)imidazo[1,2-b]pyridazine-3-carboxamide | 482.29 | 1.525 |
| 140 | 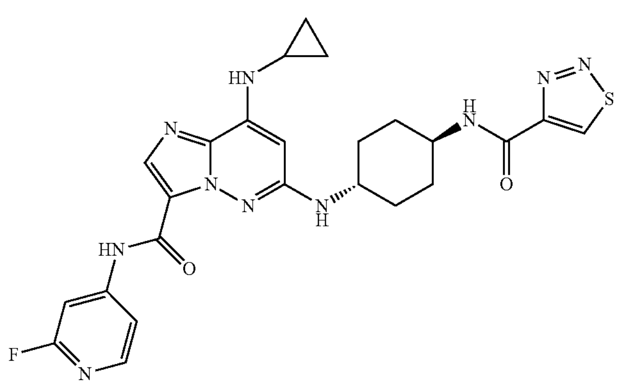 [SMILES: O=C(N[C@H]1CC[C@H](Nc2cc(NC3CC3)c3ncc(C(=O)Nc4ccnc(F)c4)n3n2)CC1)c1csnn1] | 8-(cyclopropylamino)-N-(2-fluoro-4-pyridinyl)-6-((trans-4-((1,2,3-thiadiazol-4-ylcarbonyl)amino)cyclohexyl)amino)imidazo[1,2-b]pyridazine-3-carboxamide | 537.1 | 1.880 |

TABLE 2-continued

| Example | Structure | Name | [M + H] | HPLC Ret Time (min) |
|---|---|---|---|---|
| 141 | 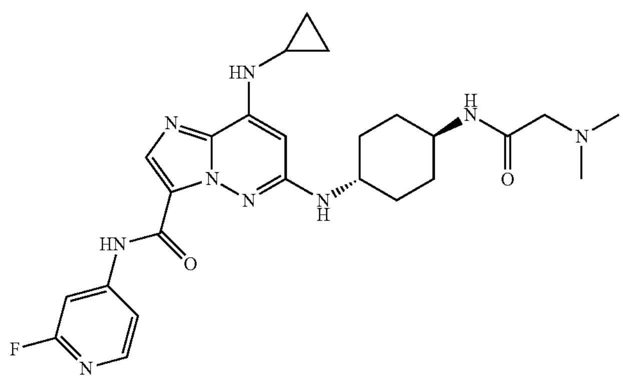 [SMILES: CN(C)CC(=O)N[C@H]1CC[C@H](Nc2cc(NC3CC3)c3ncc(C(=O)Nc4ccnc(F)c4)n3n2)CC1] | 8-(cyclopropylamino)-6-((trans-4-((N,N-dimethylglycyl)amino)cyclohexyl)amino)-N-(2-fluoro-4-pyridinyl)imidazo[1,2-b]pyridazine-3-carboxamide | 510.2 | 0.680 |
| 142 | 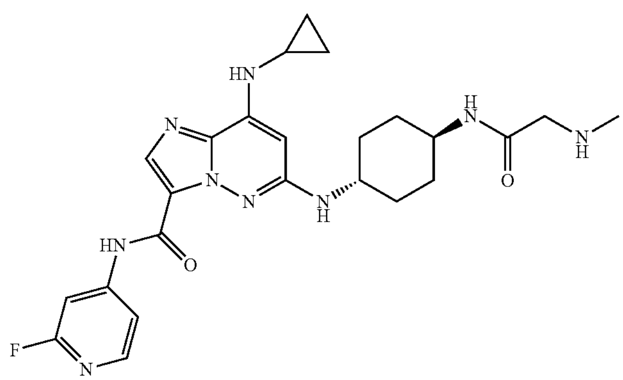 [SMILES: CNCC(=O)N[C@H]1CC[C@H](Nc2cc(NC3CC3)c3ncc(C(=O)Nc4ccnc(F)c4)n3n2)CC1] | 8-(cyclopropylamino)-N-(2-fluoro-4-pyridinyl)-6-((trans-4-((N-methylglycyl)amino)cyclohexyl)amino)imidazo[1,2-b]pyridazine-3-carboxamide | 496.2 | 0.682 |
| 143 | 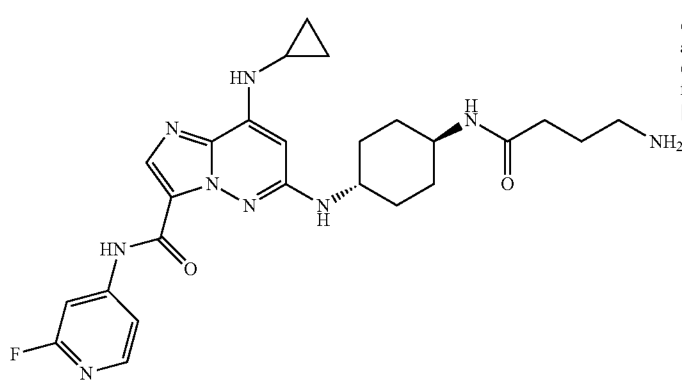 [SMILES: NCCCC(=O)N[C@H]1CC[C@H](Nc2cc(NC3CC3)c3ncc(C(=O)Nc4ccnc(F)c4)n3n2)CC1] | 6-((trans-4-((4-aminobutanoyl)amino)cyclohexyl)amino)-8-(cyclopropylamino)-N-(2-fluoro-4-pyridinyl)imidazo[1,2-b]pyridazine-3-carboxamide | 510.2 | 1.488 |
| 144 | 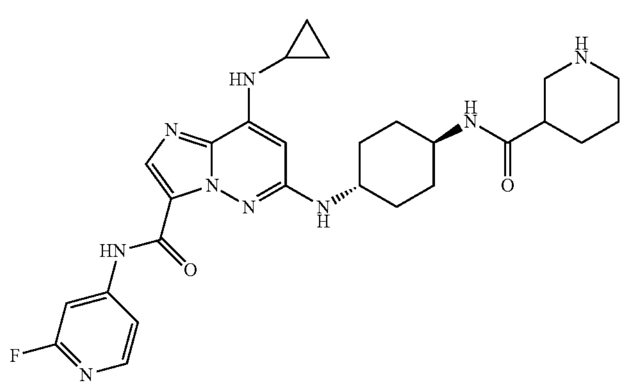 [SMILES: O=C(Nc1ccnc(F)c1)c1cnc2c(NC3CC3)cc(N[C@H]3CC[C@H](NC(=O)C4CCCNC4)CC3)nn12] | 8-(cyclopropylamino)-N-(2-fluoro-4-pyridinyl)-6-((trans-4-((3-piperidinylcarbonyl)amino)cyclohexyl)amino)imidazo[1,2-b]pyridazine-3-carboxamide | 536.2 | 1.532 |

TABLE 2-continued

| Example | Structure | Name | [M + H] | HPLC Ret Time (min) |
|---|---|---|---|---|
| 145 | 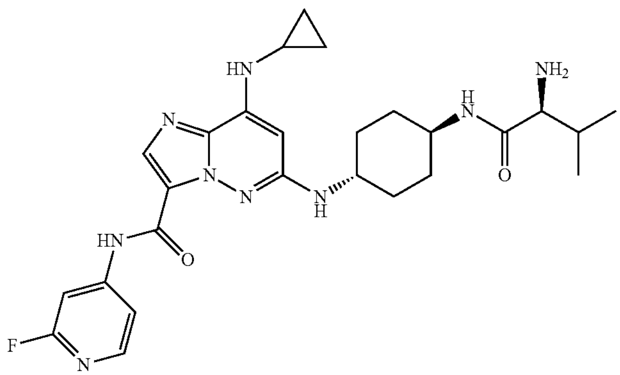 [SMILES: CC(C)[C@H](N)C(=O)N[C@H]1CC[C@H](Nc2cc(NC3CC3)c3ncc(C(=O)Nc4ccnc(F)c4)n3n2)CC1] | 8-(cyclopropylamino)-N-(2-fluoro-4-pyridinyl)-6-((trans-4-(L-valylamino)cyclohexyl)amino)imidazo[1,2-b]pyridazine-3-carboxamide | 524.2 | 1.648 |

HPLC Conditions:
Phenomenex Luna 5 micron C18 4.6 × 30 mm: 0 to 100 B in 2 min with 1 min hold time, Flow rate = 5 mL/min, detection at 254 nm, Solvent A: 10% methanol/90% water/0.1% TFA; Solvent B: 10% water/90% methanol/0.1% TFA.

The following Examples in Table 3 may be prepared from 23C in a manner analogous the procedures described in Example 34.

TABLE 3

| Example | Structure | Name | [M + H] | HPLC Ret Time (min) |
|---|---|---|---|---|
| 146 | 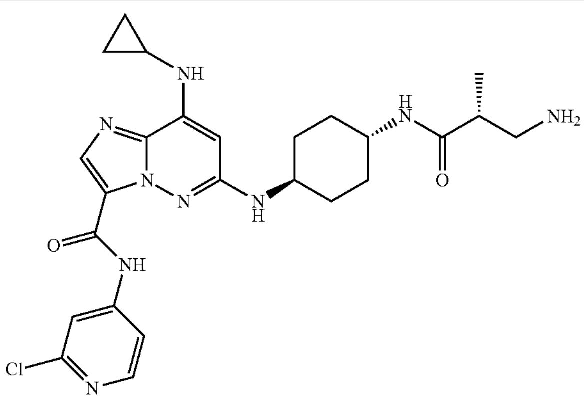 [SMILES: C[C@H](CN)C(=O)N[C@H]1CC[C@H](Nc2cc(NC3CC3)c3ncc(C(=O)Nc4ccnc(Cl)c4)n3n2)CC1] | 6-((trans-4-(((2R)-3-amino-2-methylpropanoyl)amino)cyclohexyl)amino)-N-(2-chloro-4-pyridinyl)-8-(cyclopropylamino)imidazo[1,2-b]pyridazine-3-carboxamide | 525.93 | 2.22 |
| 147 | 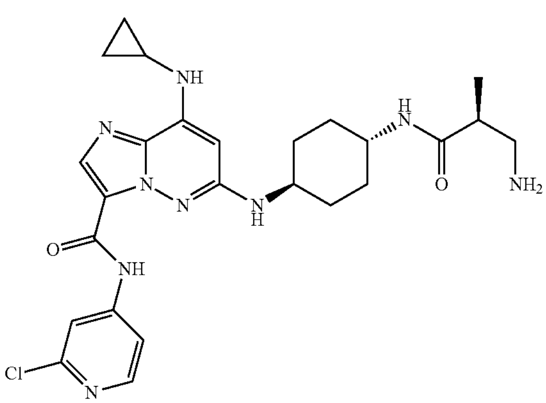 [SMILES: C[C@@H](CN)C(=O)N[C@H]1CC[C@H](Nc2cc(NC3CC3)c3ncc(C(=O)Nc4ccnc(Cl)c4)n3n2)CC1] | 6-((trans-4-(((2S)-3-amino-2-methylpropanoyl)amino)cyclohexyl)amino)-N-(2-chloro-4-pyridinyl)-8-(cyclopropylamino)imidazo[1,2-b]pyridazine-3-carboxamide | 525.93 | 2.17 |

TABLE 3-continued

| Example | Structure | Name | [M + H] | HPLC Ret Time (min) |
|---|---|---|---|---|
| 148 | 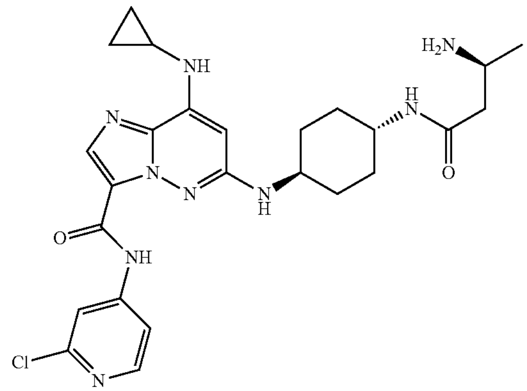 [SMILES: C[C@H](N)CC(=O)N[C@H]1CC[C@H](Nc2cc(NC3CC3)c3ncc(C(=O)Nc4ccnc(Cl)c4)n3n2)CC1] | 6-((trans-4-(((3S)-3-aminobutanoyl)amino)cyclohexyl)amino)-N-(2-chloro-4-pyridinyl)-8-(cyclopropylamino)imidazo[1,2-b]pyridazine-3-carboxamide | 525.94 | 2.11 |
| 149 | 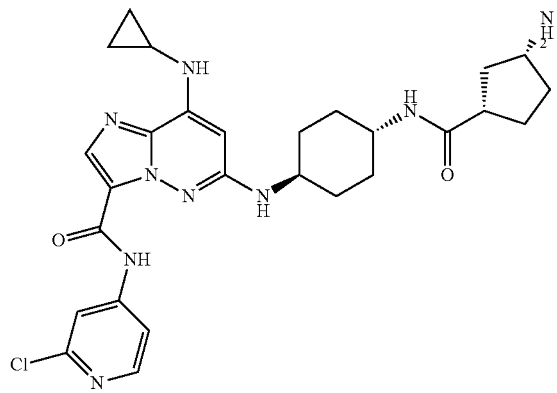 [SMILES: N[C@@H]1CC[C@H](C(=O)N[C@H]2CC[C@H](Nc3cc(NC4CC4)c4ncc(C(=O)Nc5ccnc(Cl)c5)n4n3)CC2)C1] | 6-((trans-4-((((1S,3R)-3-aminocyclopentyl)carbonyl)amino)cyclohexyl)amino)-N-(2-chloro-4-pyridinyl)-8-(cyclopropylamino)imidazo[1,2-b]pyridazine-3-carboxamide | 551.98 | 2.15 |
| 150 | 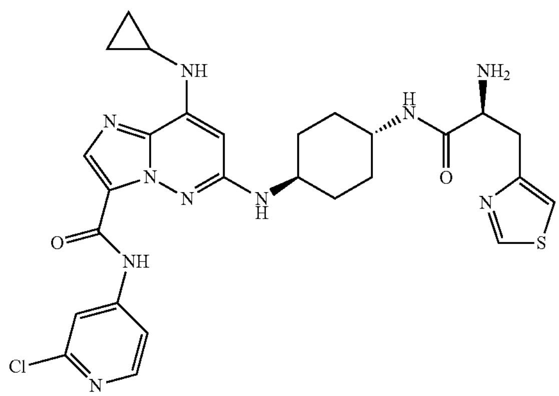 [SMILES: N[C@@H](Cc1cscn1)C(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-((3-(1,3-thiazol-4-yl)-L-alanyl)amino)cyclohexyl)amino)imidazo[1,2-b]pyridazine-3-carboxamide | 594.94 | 2.18 |
| 151 | 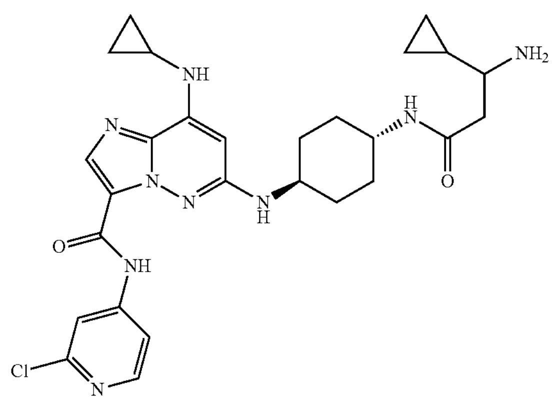 [SMILES: NC(CC(=O)N[C@H]1CC[C@H](Nc2cc(NC3CC3)c3ncc(C(=O)Nc4ccnc(Cl)c4)n3n2)CC1)C1CC1] | 6-((trans-4-((3-amino-3-cyclopropylpropanoyl)amino)cyclohexyl)amino)-N-(2-chloro-4-pyridinyl)-8-(cyclopropylamino)imidazo[1,2-b]pyridazine-3-carboxamide | 551.94 | 2.11 |

TABLE 3-continued

| Example | Name | [M + H] | HPLC Ret Time (min) |
|---|---|---|---|
| 152 | N-(2-chloro-4-pyridinyl)-8-(cyclopropylamino)-6-((trans-4-(((3R)-3-pyrrolidinylacetyl)amino)cyclohexyl)amino)imidazo[1,2-b]pyridazine-3-carboxamide | 551.95 | 2.02 |
| 153 | N-(2-chloro-4-pyridinyl)-8-(cyclopropylamino)-6-((trans-4-((N-methyl-beta-alanyl)amino)cyclohexyl)amino)imidazo[1,2-b]pyridazine-3-carboxamide | 525.94 | 2.02 |
| 154 | N-(2-chloro-4-pyridinyl)-8-(cyclopropylamino)-6-((trans-4-((N-methyl-D-alanyl)amino)cyclohexyl)amino)imidazo[1,2-b]pyridazine-3-carboxamide | 525.94 | 2.04 |
| 155 | 6-((trans-4-(((2S)-2-amino-4-(methylsulfonyl)butanoyl)amino)cyclohexyl)amino)-N-(2-chloro-4-pyridinyl)-8-(cyclopropylamino)imidazo[1,2-b]pyridazine-3-carboxamide | 603.93 | 2.02 |

TABLE 3-continued

| Example | Structure | Name | [M + H] | HPLC Ret Time (min) |
|---|---|---|---|---|
| 156 | 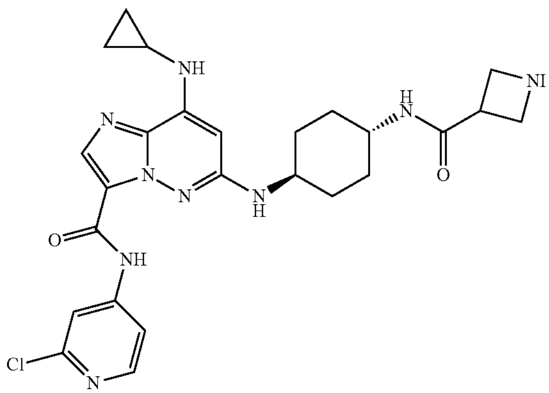 | 6-((trans-4-((3-azetidinylcarbonyl)amino)cyclohexyl)amino)-N-(2-chloro-4-pyridinyl)-8-(cyclopropylamino)imidazo[1,2-b]pyridazine-3-carboxamide | 523.94 | 1.98 |
| 157 | 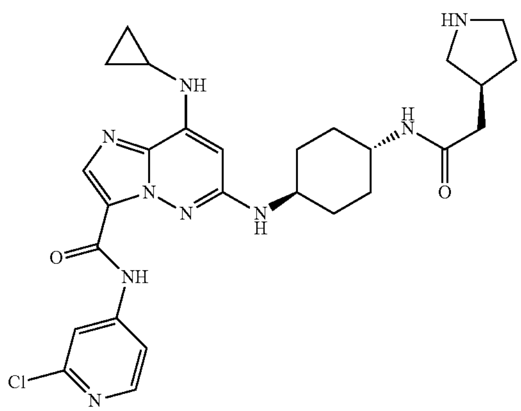 [SMILES: O=C(C[C@@H]1CCNC1)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-(((3S)-3-pyrrolidinylacetyl)amino)cyclohexyl)amino)imidazo[1,2-b]pyridazine-3-carboxamide | 551.94 | 1.96 |
| 158 | 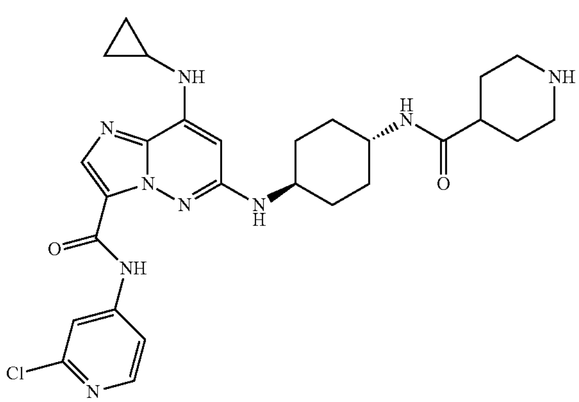 [SMILES: O=C(Nc1ccnc(Cl)c1)c1cnc2c(NC3CC3)cc(N[C@H]3CC[C@H](NC(=O)C4CCNCC4)CC3)nn12] | N-(2-chloro-4-pyridinyl)-8-(cyclopropylamino)-6-((trans-4-((4-piperidinylcarbonyl)amino)cyclohexyl)amino)imidazo[1,2-b]pyridazine-3-carboxamide | 551.94 | 1.97 |

TABLE 3-continued

| Example | Structure | Name | [M + H] | HPLC Ret Time (min) |
|---|---|---|---|---|
| 159 | 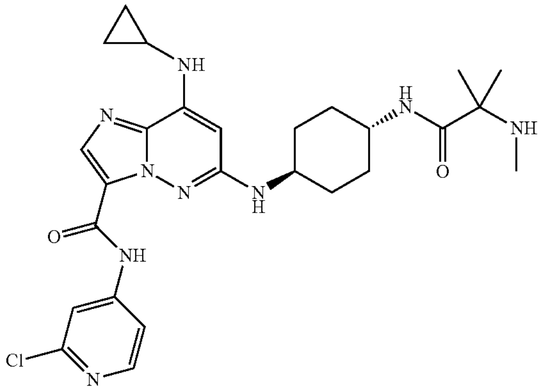 [SMILES: CNC(C)(C)C(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-((N,2-dimethylalanyl)amino)cyclohexyl)amino)imidazo[1,2-b]pyridazine-3-carboxamide | 539.95 | 2.02 |
| 160 | 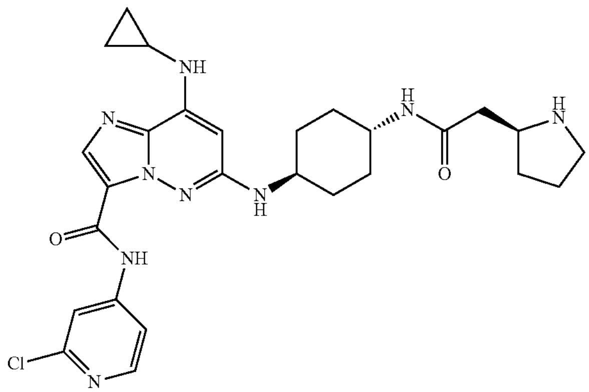 [SMILES: O=C(C[C@@H]1CCCN1)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-(((2S)-2-pyrrolidinylacetyl)amino)cyclohexyl)amino)imidazo[1,2-b]pyridazine-3-carboxamide | 551.94 | 1.99 |
| 161 | 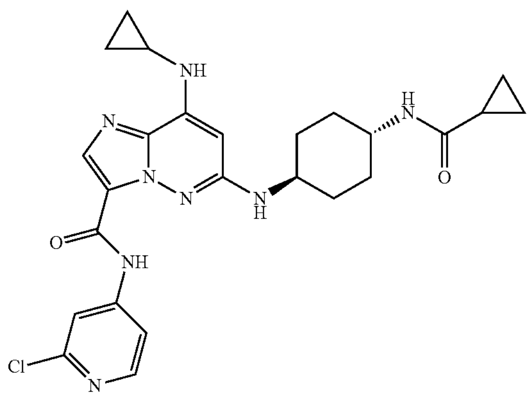 [SMILES: O=C(Nc1ccnc(Cl)c1)c1cnc2c(NC3CC3)cc(N[C@H]3CC[C@H](NC(=O)C4CC4)CC3)nn12] | N-(2-chloro-4-pyridinyl)-8-(cyclopropylamino)-6-((trans-4-((cyclopropylcarbonyl)amino)cyclohexyl)amino)imidazo[1,2-b]pyridazine-3-carboxamide | 508.90 | 2.33 |
| 162 | 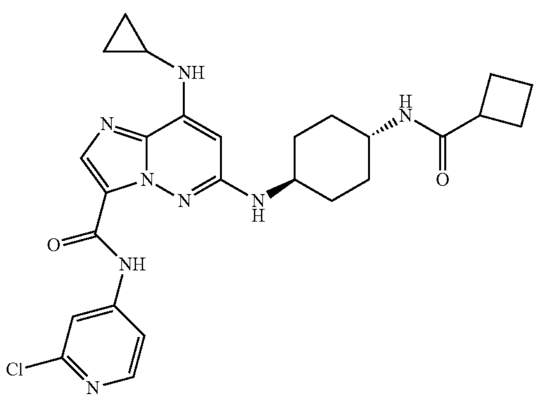 [SMILES: O=C(Nc1ccnc(Cl)c1)c1cnc2c(NC3CC3)cc(N[C@H]3CC[C@H](NC(=O)C4CCC4)CC3)nn12] | N-(2-chloro-4-pyridinyl)-6-((trans-4-((cyclobutylcarbonyl)amino)cyclohexyl)amino)-8-(cyclopropylamino)imidazo[1,2-b]pyridazine-3-carboxamide | 522.91 | 2.42 |

TABLE 3-continued

| Example | Name | [M + H] | HPLC Ret Time (min) |
|---|---|---|---|
| 163 | N-(2-chloro-4-pyridinyl)-8-(cyclopropylamino)-6-((trans-4-(glycylamino)cyclohexyl)amino)imidazo[1,2-b]pyridazine-3-carboxamide | 497.90 | 1.94 |
| 164 | N-(2-chloro-4-pyridinyl)-8-(cyclopropylamino)-6-((trans-4-((3-methylbutanoyl)amino)cyclohexyl)amino)imidazo[1,2-b]pyridazine-3-carboxamide | 524.94 | 2.46 |
| 165 | N-(2-chloro-4-pyridinyl)-8-(cyclopropylamino)-6-((trans-4-(propionylamino)cyclohexyl)amino)imidazo[1,2-b]pyridazine-3-carboxamide | 496.91 | 2.24 |
| 166 | N-(2-chloro-4-pyridinyl)-8-(cyclopropylamino)-6-((trans-4-((N,N-dimethylglycyl)amino)cyclohexyl)amino)imidazo[1,2-b]pyridazine-3-carboxamide | 525.92 | 2.14 |

TABLE 3-continued

| Example | Structure | Name | [M + H] | HPLC Ret Time (min) |
|---|---|---|---|---|
| 167 | 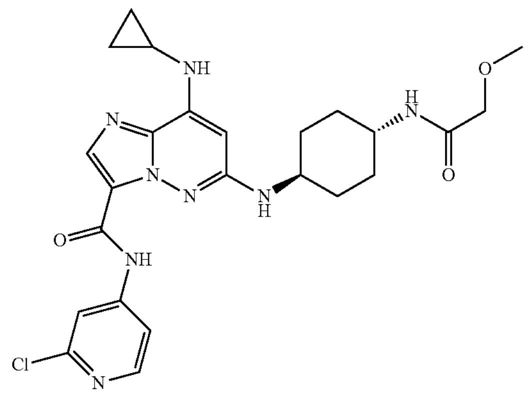 [SMILES: COCC(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-((methoxyacetyl)amino)cyclohexyl)amino)imidazo[1,2-b]pyridazine-3-carboxamide | 512.88 | 2.22 |
| 168 | 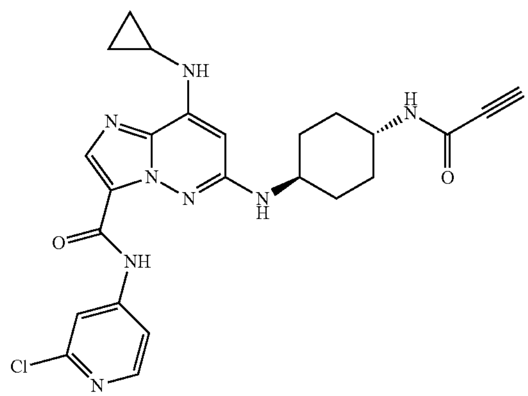 [SMILES: C#CC(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-(propioloylamino)cyclohexyl)amino)imidazo[1,2-b]pyridazine-3-carboxamide | 492.87 | 2.27 |
| 169 | 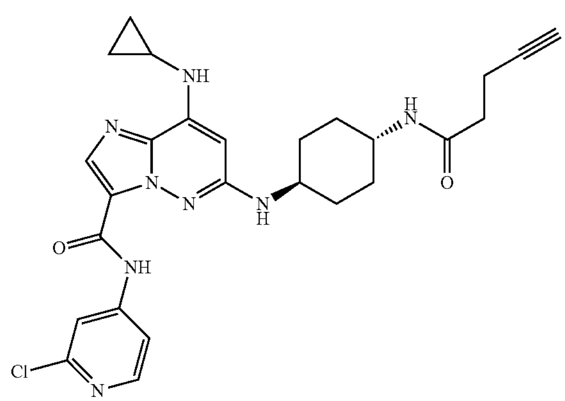 [SMILES: C#CCCC(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-(4-pentynoylamino)cyclohexyl)amino)imidazo[1,2-b]pyridazine-3-carboxamide | 520.89 | 2.33 |
| 170 | 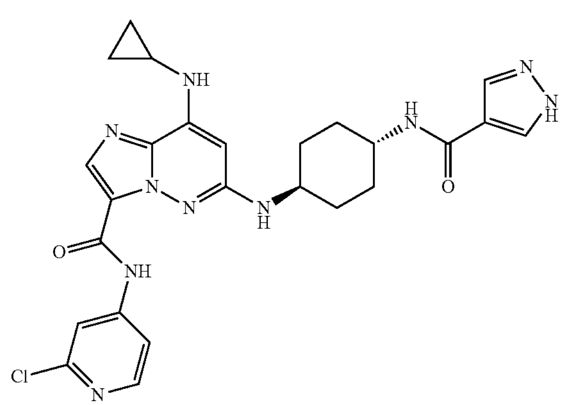 [SMILES: O=C(N[C@H]1CC[C@H](Nc2cc(NC3CC3)c3ncc(C(=O)Nc4ccnc(Cl)c4)n3n2)CC1)c1cn[nH]c1] | N-(2-chloro-4-pyridinyl)-8-(cyclopropylamino)-6-((trans-4-((1H-pyrazol-4-ylcarbonyl)amino)cyclohexyl)amino)imidazo[1,2-b]pyridazine-3-carboxamide | 534.88 | 2.07 |

TABLE 3-continued

| Example | Structure | Name | [M + H] | HPLC Ret Time (min) |
|---|---|---|---|---|
| 171 | 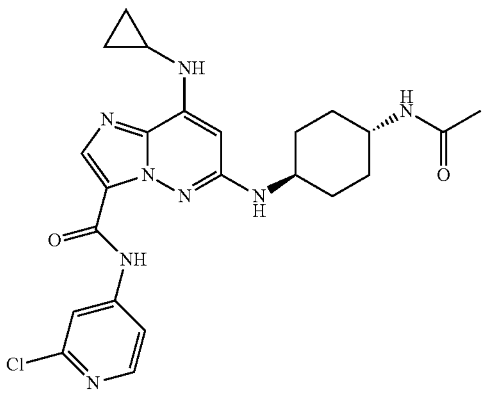 [SMILES: CC(=O)N[C@H]1CC[C@H](Nc2cc(NC3CC3)c3ncc(C(=O)Nc4ccnc(Cl)c4)n3n2)CC1] | 6-((trans-4-acetamidocyclohexyl)amino)-N-(2-chloro-4-pyridinyl)-8-(cyclopropylamino)imidazo[1,2-b]pyridazine-3-carboxamide | 482.92 | 2.12 |
| 172 | 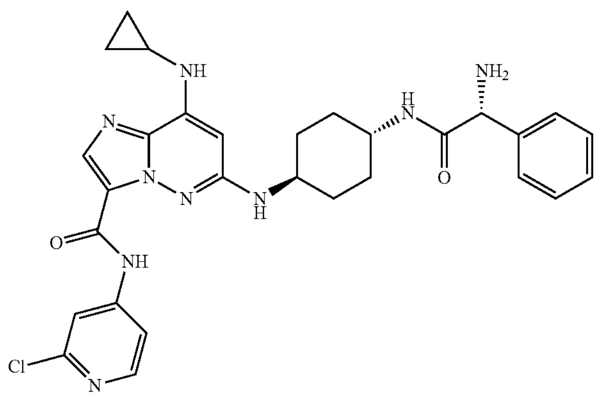 [SMILES: N[C@@H](C(=O)N[C@H]1CC[C@H](Nc2cc(NC3CC3)c3ncc(C(=O)Nc4ccnc(Cl)c4)n3n2)CC1)c1ccccc1] | 6-((trans-4-(((2R)-2-amino-2-phenylacetyl)amino)cyclohexyl)amino)-N-(2-chloro-4-pyridinyl)-8-(cyclopropylamino)imidazo[1,2-b]pyridazine-3-carboxamide | 573.91 | 2.25 |
| 173 | 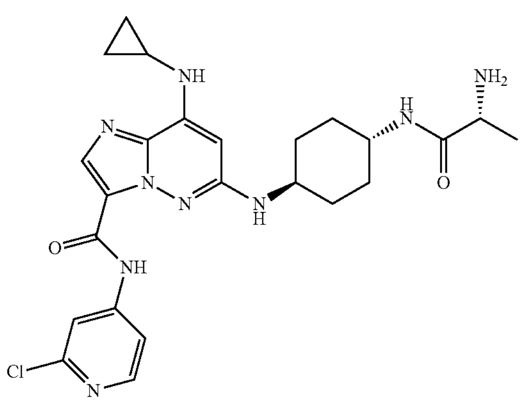 [SMILES: C[C@@H](N)C(=O)N[C@H]1CC[C@H](Nc2cc(NC3CC3)c3ncc(C(=O)Nc4ccnc(Cl)c4)n3n2)CC1] | 6-((trans-4-(D-alanylamino)cyclohexyl)amino)-N-(2-chloro-4-pyridinyl)-8-(cyclopropylamino)imidazo[1,2-b]pyridazine-3-carboxamide | 511.92 | 1.96 |
| 174 | 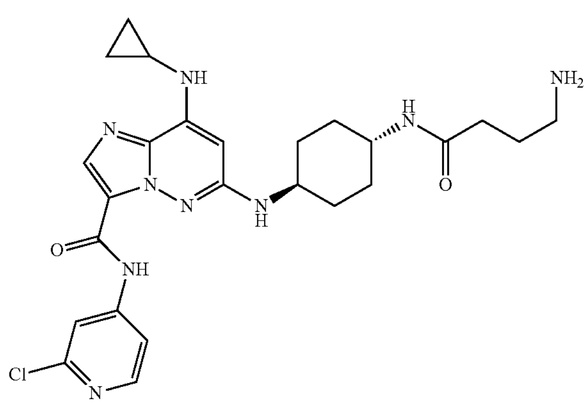 [SMILES: NCCCC(=O)N[C@H]1CC[C@H](Nc2cc(NC3CC3)c3ncc(C(=O)Nc4ccnc(Cl)c4)n3n2)CC1] | 6-((trans-4-((4-aminobutanoyl)amino)cyclohexyl)amino)-N-(2-chloro-4-pyridinyl)-8-(cyclopropylamino)imidazo[1,2-b]pyridazine-3-carboxamide | 525.93 | 1.91 |

TABLE 3-continued

| Example | Name | [M + H] | HPLC Ret Time (min) |
|---|---|---|---|
| 175 | N-(2-chloro-4-pyridinyl)-8-(cyclopropylamino)-6-((trans-4-(L-prolylamino)cyclohexyl)amino)imidazo[1,2-b]pyridazine-3-carboxamide | 537.91 | 2.02 |
| 176 | N-(2-chloro-4-pyridinyl)-8-(cyclopropylamino)-6-((trans-4-(D-prolylamino)cyclohexyl)amino)imidazo[1,2-b]pyridazine-3-carboxamide | 537.90 | 1.99 |
| 177 | N~1~-(trans-4-((3-((2-chloro-4-pyridinyl)carbamoyl)-8-(cyclopropylamino)imidazo[1,2-b]pyridazin-6-yl)amino)cyclohexyl)-D-aspartamide | 554.91 | 1.89 |
| 178 | N~1~-(trans-4-((3-((2-chloro-4-pyridinyl)carbamoyl)-8-(cyclopropylamino)imidazo[1,2-b]pyridazin-6-yl)amino)cyclohexyl)-L-aspartamide | 554.90 | 1.90 |

TABLE 3-continued

| Example | Structure | Name | [M + H] | HPLC Ret Time (min) |
|---|---|---|---|---|
| 179 | 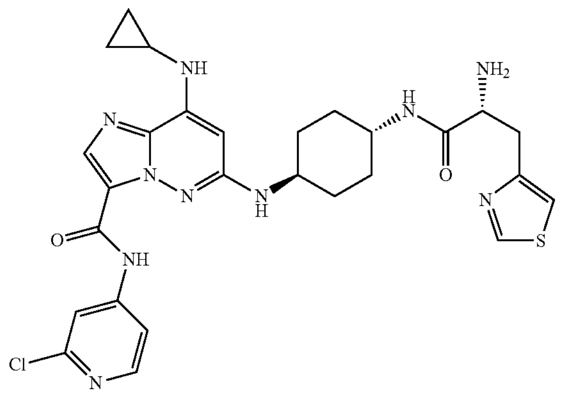 [SMILES: N[C@H](Cc1cscn1)C(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-((3-(1,3-thiazol-4-yl)-D-alanyl)amino)cyclohexyl)amino)imidazo[1,2-b]pyridazine-3-carboxamide | 594.88 | 2.07 |
| 180 | 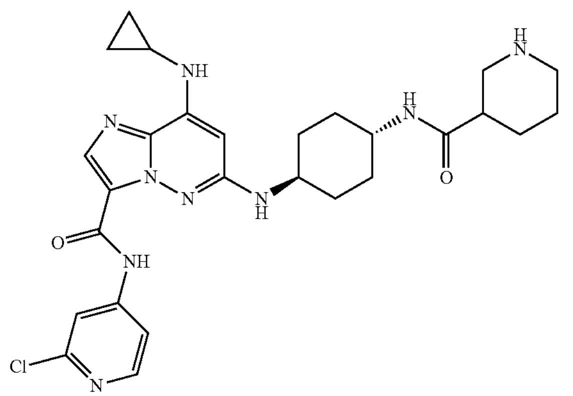 [SMILES: O=C(Nc1ccnc(Cl)c1)c1cnc2c(NC3CC3)cc(N[C@H]3CC[C@H](NC(=O)C4CCCNC4)CC3)nn12] | N-(2-chloro-4-pyridinyl)-8-(cyclopropylamino)-6-((trans-4-((3-piperidinylcarbonyl)amino)cyclohexyl)amino)imidazo[1,2-b]pyridazine-3-carboxamide | 551.94 | 1.95 |
| 181 | 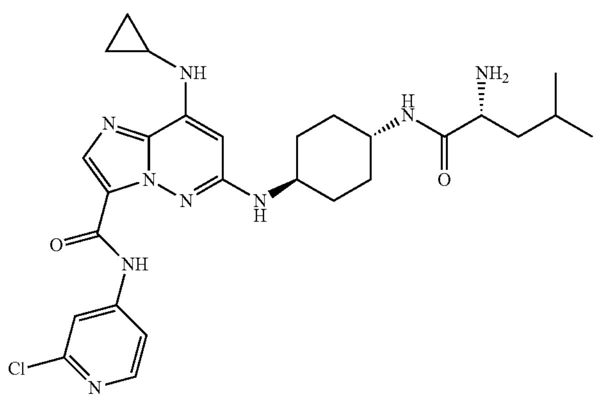 [SMILES: CC(C)C[C@@H](N)C(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-(D-leucylamino)cyclohexyl)amino)imidazo[1,2-b]pyridazine-3-carboxamide | 553.96 | 2.18 |
| 182 | 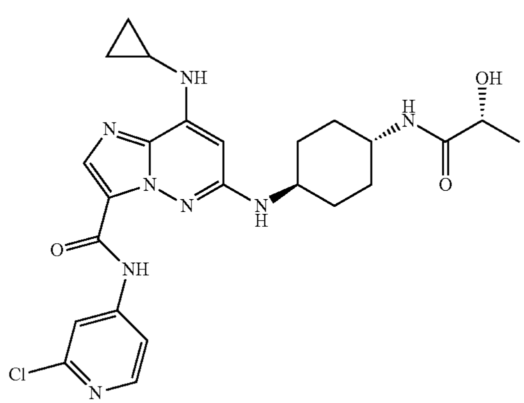 [SMILES: C[C@@H](O)C(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-(((2R)-2-hydroxypropanoyl)amino)cyclohexyl)amino)imidazo[1,2-b]pyridazine-3-carboxamide | 512.88 | 2.15 |

TABLE 3-continued

| Example | Name | [M + H] | HPLC Ret Time (min) |
|---|---|---|---|
| 183 | N-(2-chloro-4-pyridinyl)-8-(cyclopropylamino)-6-((trans-4-(L-threonylamino)cyclohexyl)amino)imidazo[1,2-b]pyridazine-3-carboxamide | 541.87 | 2.17 |
| 184 | N-(2-chloro-4-pyridinyl)-8-(cyclopropylamino)-6-((trans-4-((N-methyl-L-seryl)amino)cyclohexyl)amino)imidazo[1,2-b]pyridazine-3-carboxamide | 541.90 | 2.19 |
| 185 | N-(2-chloro-4-pyridinyl)-8-(cyclopropylamino)-6-((trans-4-(((4R)-4-hydroxy-L-prolyl)amino)cyclohexyl)amino)imidazo[1,2-b]pyridazine-3-carboxamide | 553.87 | 2.18 |
| 186 | N-(2-chloro-4-pyridinyl)-8-(cyclopropylamino)-6-((trans-4-((N-methyl-L-alanyl)amino)cyclohexyl)amino)imidazo[1,2-b]pyridazine-3-carboxamide | 525.90 | 2.04 |

TABLE 3-continued

| Example | Structure | Name | [M + H] | HPLC Ret Time (min) |
|---|---|---|---|---|
| 187 | 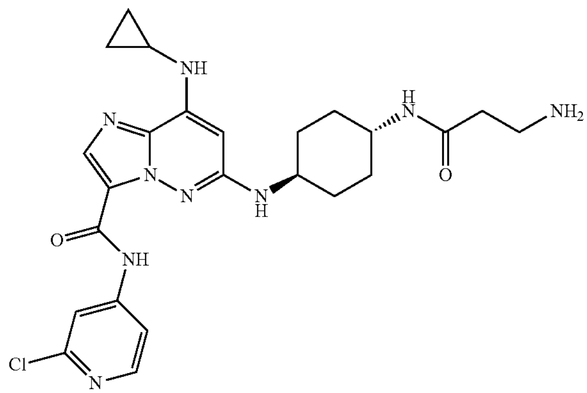 [SMILES: NCCC(=O)N[C@H]1CC[C@H](Nc2cc(NC3CC3)c3ncc(C(=O)Nc4ccnc(Cl)c4)n3n2)CC1] | 6-((trans-4-(beta-alanylamino)cyclohexyl)amino)-N-(2-chloro-4-pyridinyl)-8-(cyclopropylamino)imidazo[1,2-b]pyridazine-3-carboxamide | 511.90 | 2.03 |
| 188 | 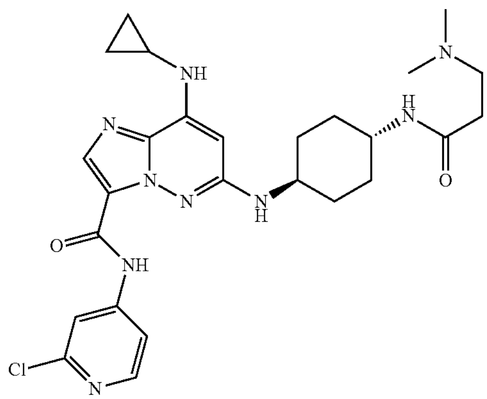 [SMILES: CN(C)CCC(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-((N,N-dimethyl-beta-alanyl)amino)cyclohexyl)amino)imidazo[1,2-b]pyridazine-3-carboxamide | 539.93 | 2.09 |
| 189 | 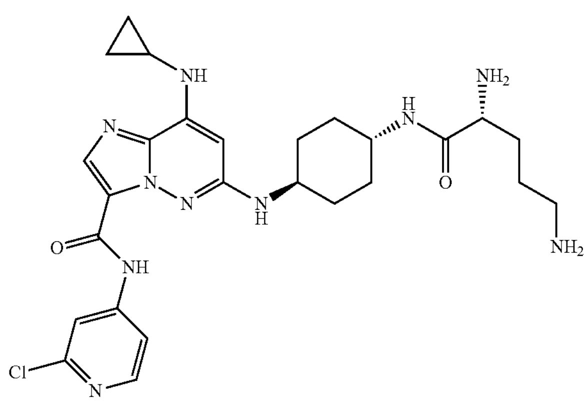 [SMILES: NCCC[C@@H](N)C(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-(D-ornithylamino)cyclohexyl)amino)imidazo[1,2-b]pyridazine-3-carboxamide | 555.13 | 2.46 |
| 190 | 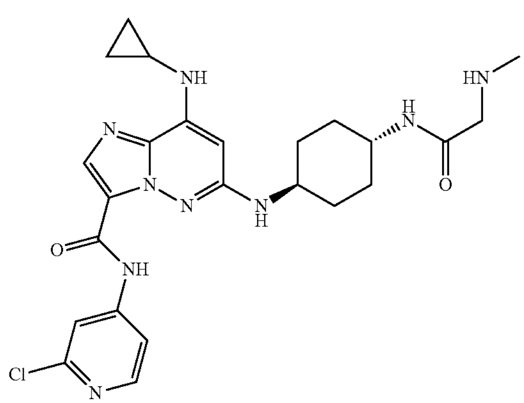 [SMILES: CNCC(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-((N-methylglycyl)amino)cyclohexyl)amino)imidazo[1,2-b]pyridazine-3-carboxamide | 511.87 | 2.06 |

TABLE 3-continued

| Example | Structure | Name | [M + H] | HPLC Ret Time (min) |
|---|---|---|---|---|
| 191 | 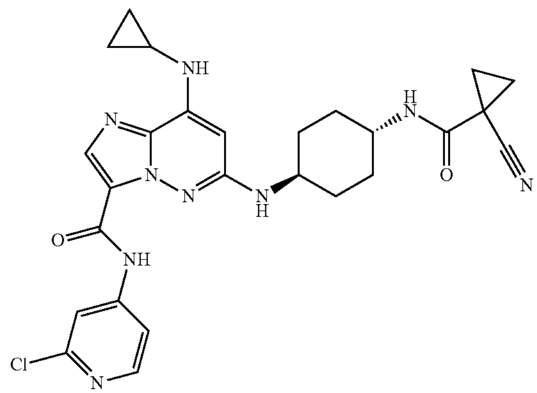 [SMILES: N#CC1(C(=O)N[C@H]2CC[C@H](Nc3cc(NC4CC4)c4ncc(C(=O)Nc5ccnc(Cl)c5)n4n3)CC2)CC1] | N-(2-chloro-4-pyridinyl)-6-((trans-4-(((1-cyanocyclopropyl)carbonyl)amino)cyclohexyl)amino)-8-(cyclopropylamino)imidazo[1,2-b]pyridazine-3-carboxamide | 533.87 | 2.51 |
| 192 | 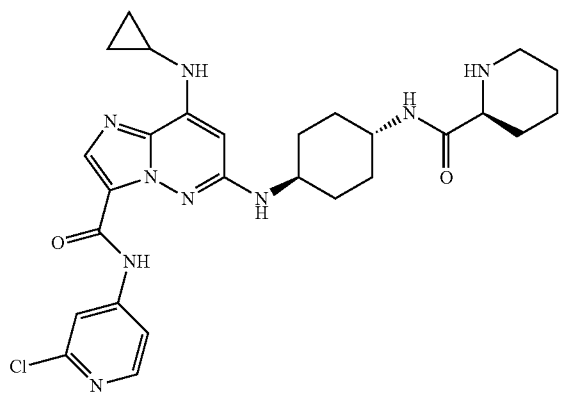 [SMILES: O=C(Nc1ccnc(Cl)c1)c1cnc2c(NC3CC3)cc(N[C@H]3CC[C@H](NC(=O)[C@@H]4CCCCN4)CC3)nn12] | N-(2-chloro-4-pyridinyl)-8-(cyclopropylamino)-6-((trans-4-(((2S)-2-piperidinylcarbonyl)amino)cyclohexyl)amino)imidazo[1,2-b]pyridazine-3-carboxamide | 551.92 | 2.11 |
| 193 | 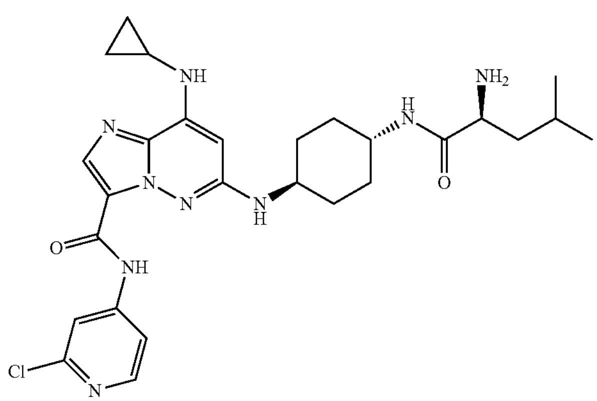 [SMILES: CC(C)C[C@H](N)C(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-(L-leucylamino)cyclohexyl)amino)imidazo[1,2-b]pyridazine-3-carboxamide | 553.91 | 2.27 |
| 194 | 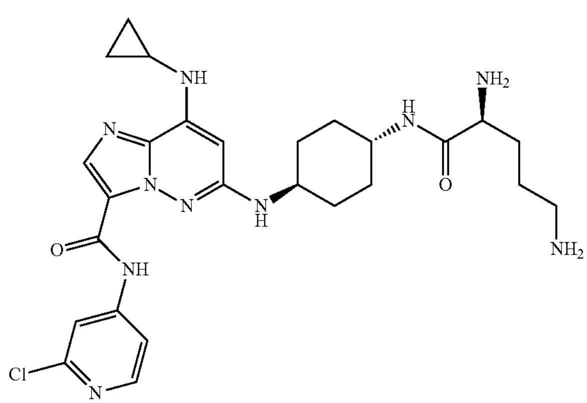 [SMILES: NCCC[C@H](N)C(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-(L-ornithylamino)cyclohexyl)amino)imidazo[1,2-b]pyridazine-3-carboxamide | 555.14 | 2.46 |

TABLE 3-continued

| Example | Structure | Name | [M + H] | HPLC Ret Time (min) |
|---|---|---|---|---|
| 195 | 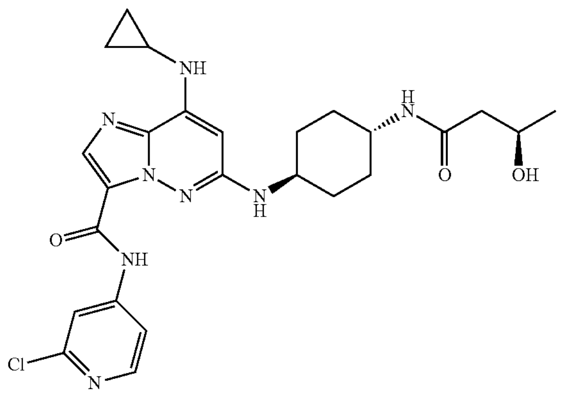 [SMILES: C[C@@H](O)CC(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-(((3R)-3-hydroxybutanoyl)amino)cyclohexyl)amino)imidazo[1,2-b]pyridazine-3-carboxamide | 526.93 | 2.25 |
| 196 | 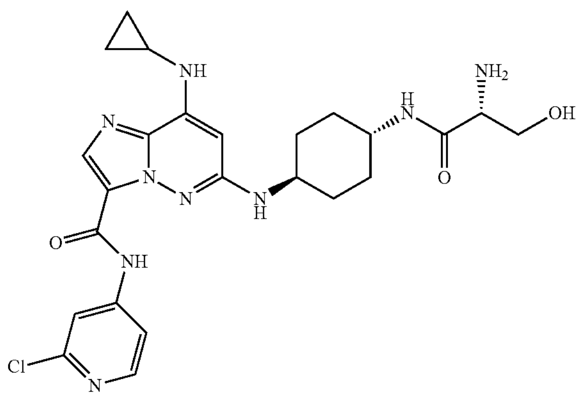 [SMILES: N[C@H](CO)C(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-(D-serylamino)cyclohexyl)amino)imidazo[1,2-b]pyridazine-3-carboxamide | 527.93 | 2.12 |
| 197 | 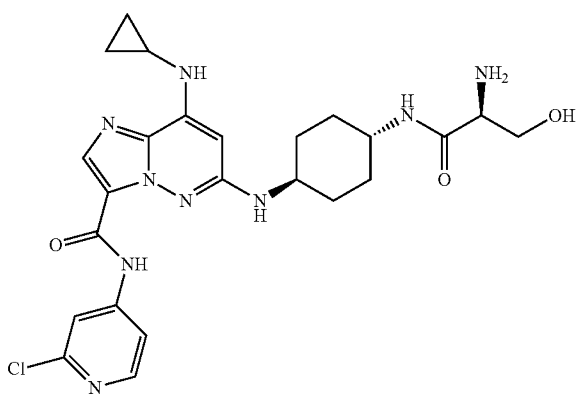 [SMILES: N[C@@H](CO)C(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-(L-serylamino)cyclohexyl)amino)imidazo[1,2-b]pyridazine-3-carboxamide | 527.91 | 2.08 |
| 198 | 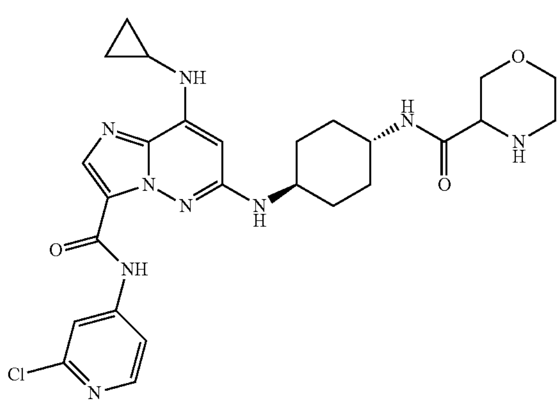 [SMILES: O=C(Nc1ccnc(Cl)c1)c1cnc2c(NC3CC3)cc(N[C@H]3CC[C@H](NC(=O)C4COCCN4)CC3)nn12] | N-(2-chloro-4-pyridinyl)-8-(cyclopropylamino)-6-((trans-4-((3-morpholinylcarbonyl)amino)cyclohexyl)amino)imidazo[1,2-b]pyridazine-3-carboxamide | 554.15 | 2.28 |

TABLE 3-continued

| Example | Structure | Name | [M + H] | HPLC Ret Time (min) |
|---|---|---|---|---|
| 199 | 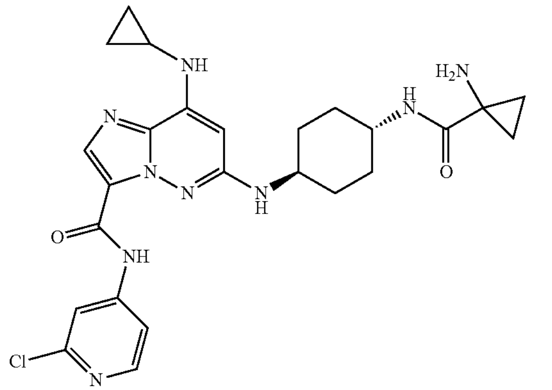 [SMILES: NC1(C(=O)N[C@H]2CC[C@H](Nc3cc(NC4CC4)c4ncc(C(=O)Nc5ccnc(Cl)c5)n4n3)CC2)CC1] | 6-((trans-4-(((1-aminocyclopropyl)carbonyl)amino)cyclohexyl)amino)-N-(2-chloro-4-pyridinyl)-8-(cyclopropylamino)imidazo[1,2-b]pyridazine-3-carboxamide | 524.14 | 2.36 |
| 200 | 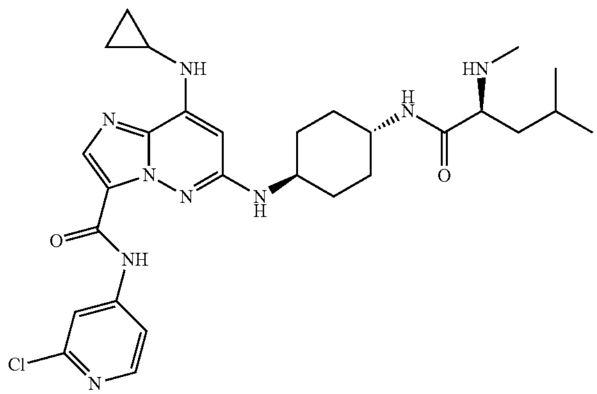 [SMILES: CN[C@@H](CC(C)C)C(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-((N-methyl-L-leucyl)amino)cyclohexyl)amino)imidazo[1,2-b]pyridazine-3-carboxamide | 568.21 | 2.42 |
| 201 | 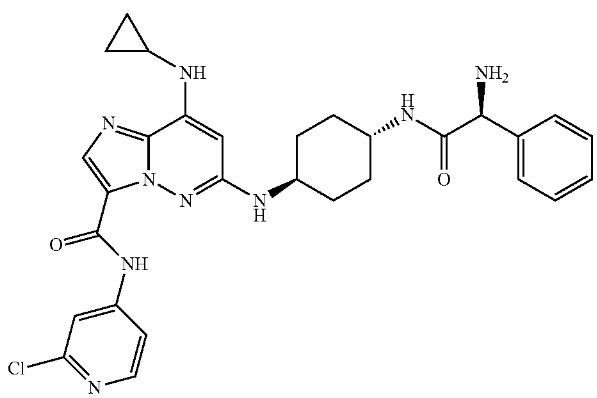 [SMILES: N[C@H](C(=O)N[C@H]1CC[C@H](Nc2cc(NC3CC3)c3ncc(C(=O)Nc4ccnc(Cl)c4)n3n2)CC1)c1ccccc1] | 6-((trans-4-(((2S)-2-amino-2-phenylacetyl)amino)cyclohexyl)amino)-N-(2-chloro-4-pyridinyl)-8-(cyclopropylamino)imidazo[1,2-b]pyridazine-3-carboxamide | 574.18 | 2.41 |
| 202 | 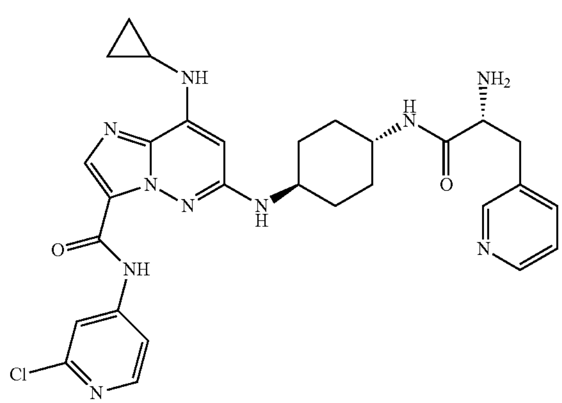 [SMILES: N[C@H](Cc1cccnc1)C(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-((3-(3-pyridinyl)-D-alanyl)amino)cyclohexyl)amino)imidazo[1,2-b]pyridazine-3-carboxamide | 589.17 | 2.19 |

TABLE 3-continued

| Example | Structure | Name | [M + H] | HPLC Ret Time (min) |
|---|---|---|---|---|
| 203 | 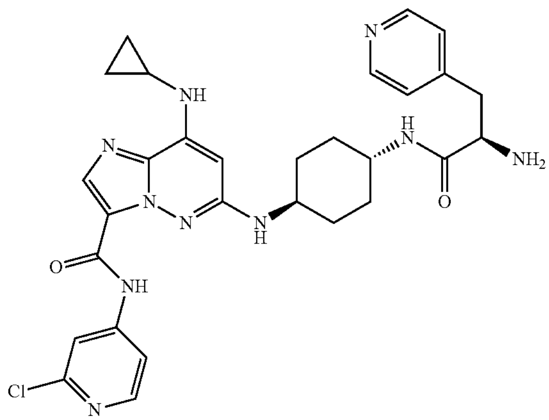 [SMILES: N[C@H](Cc1ccncc1)C(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-((3-(4-pyridinyl)-D-alanyl)amino)cyclohexyl)amino)imidazo[1,2-b]pyridazine-3-carboxamide | 589.19 | 1.8 |
| 204 | 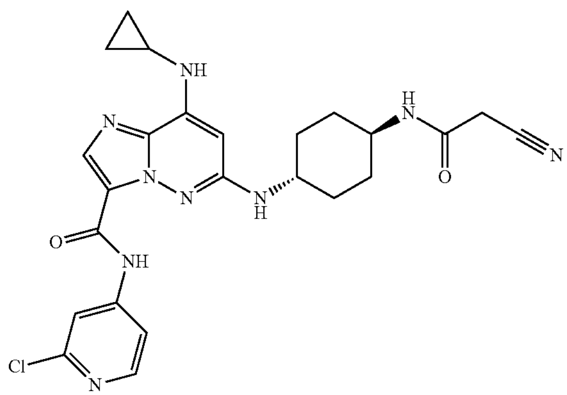 [SMILES: N#CCC(=O)N[C@H]1CC[C@H](Nc2cc(NC3CC3)c3ncc(C(=O)Nc4ccnc(Cl)c4)n3n2)CC1] | N-(2-chloro-4-pyridinyl)-6-((trans-4-((cyanoacetyl)amino)cyclohexyl)amino)-8-(cyclopropylamino)imidazo[1,2-b]pyridazine-3-carboxamide | 1.7720 | 508.1100 |

HPLC Conditions:
Waters XBridge 4.6 × 50 mm 5-um C18; A = 5:95 Acetonitrile:Water; B = 95:5 Acetonitrile:Water; Modifier = 10 mM NH$_4$OAc; 0 to 100% in 4 min; flow 4 mL/min.

The following Examples in Table 4 may be prepared from 8B in a manner analogous the procedures described in Example 32.

TABLE 4

| Example | Structure | Name | [M + H] | HPLC Ret Time (min) |
|---|---|---|---|---|
| 205 | 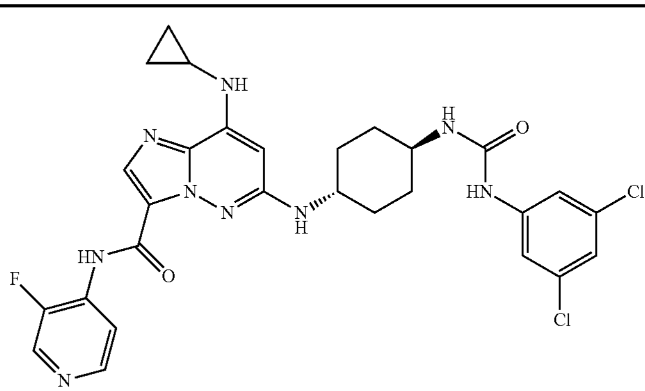 | 8-(cyclopropylamino)-6-((trans-4-(((3,5-dichlorophenyl)carbamoyl)amino)cyclohexyl)amino)-N-(3-fluoro-4-pyridinyl)imidazo[1,2-b]pyridazine-3-carboxamide | 612.26 | 2.98[a] |

TABLE 4-continued

| Example | Structure | Name | [M + H] | HPLC Ret Time (min) |
|---|---|---|---|---|
| 206 | 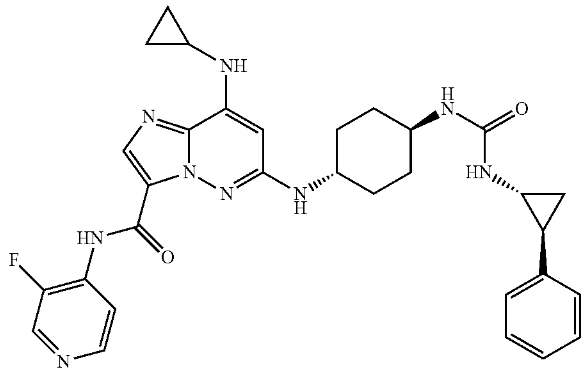 [SMILES: O=C(N[C@@H]1C[C@H]1c1ccccc1)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-(((((1R,2S)-2-phenyl-cyclopropyl)carbamoyl)amino)cyclohexyl)amino)imidazo[1,2-b]pyridazine-3-carboxamide | 584.32 | 2.43[a] |
| 207 | 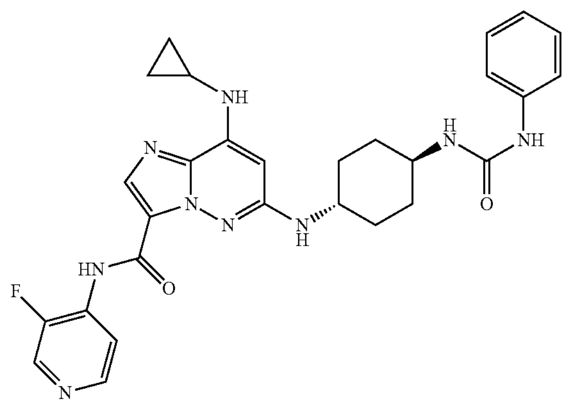 [SMILES: O=C(Nc1ccccc1)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-((phenylcarbamoyl)amino)cyclohexyl)amino)imidazo[1,2-b]pyridazine-3-carboxamide | 544.29 | 2.43[a] |
| 208 | 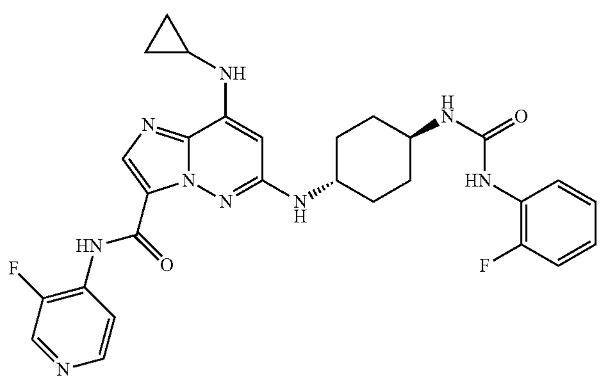 [SMILES: O=C(Nc1ccccc1F)N[C@H]1CC[C@H](Nc2cc(NC3CC3)c3ncc(C(=O)Nc4ccncc4F)n3n2)CC1] | 8-(cyclopropylamino)-6-((trans-4-(((2-fluorophenyl)carbamoyl)amino)cyclohexyl)amino)-N-(3-fluoro-4-pyridinyl)imidazo[1,2-b]pyridazine-3-carboxamide | 562.30 | 2.5[a] |
| 209 | 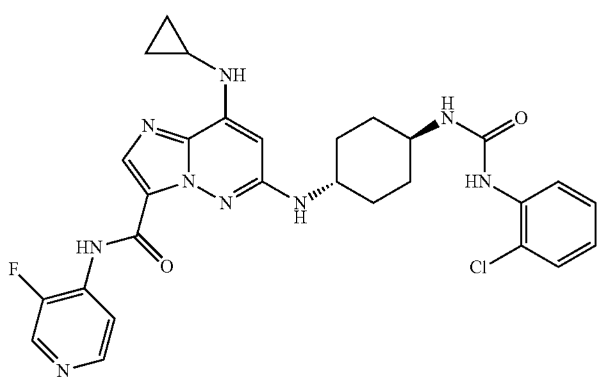 [SMILES: O=C(Nc1ccccc1Cl)N[C@H]1CC[C@H](Nc2cc(NC3CC3)c3ncc(C(=O)Nc4ccncc4F)n3n2)CC1] | 6-((trans-4-(((2-chlorophenyl)carbamoyl)amino)cyclohexyl)amino)-8-(cyclopropylamino)-N-(3-fluoro-4-pyridinyl)imidazo[1,2-b]pyridazine-3-carboxamide | 578.25 | 2.61[a] |

TABLE 4-continued

| Example | Structure | Name | [M + H] | HPLC Ret Time (min) |
|---|---|---|---|---|
| 210 | 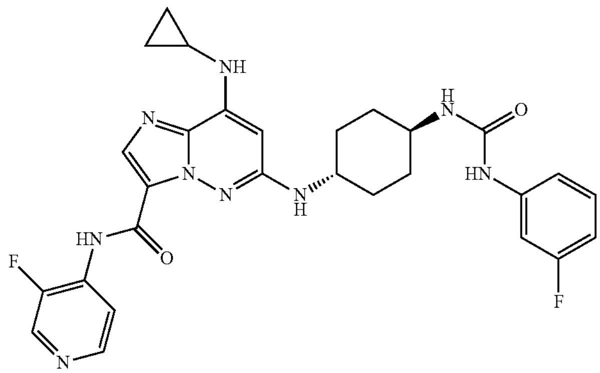 [SMILES: O=C(Nc1cccc(F)c1)N[C@H]1CC[C@H](Nc2cc(NC3CC3)c3ncc(C(=O)Nc4ccncc4F)n3n2)CC1] | 8-(cyclopropylamino)-6-((trans-4-(((3-fluorophenyl)carbamoyl)amino)cyclohexyl)amino)-N-(3-fluoro-4-pyridinyl)imidazo[1,2-b]pyridazine-3-carboxamide | 562.31 | 2.55[a] |
| 211 | 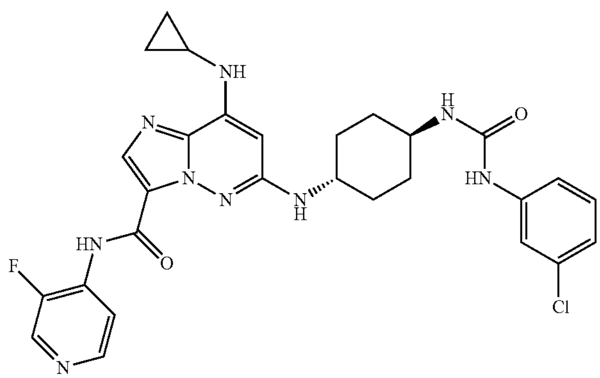 [SMILES: O=C(Nc1cccc(Cl)c1)N[C@H]1CC[C@H](Nc2cc(NC3CC3)c3ncc(C(=O)Nc4ccncc4F)n3n2)CC1] | 6-((trans-4-(((3-chlorophenyl)carbamoyl)amino)cyclohexyl)amino)-8-(cyclopropylamino)-N-(3-fluoro-4-pyridinyl)imidazo[1,2-b]pyridazine-3-carboxamide | 578.26 | 2.64[a] |
| 212 | 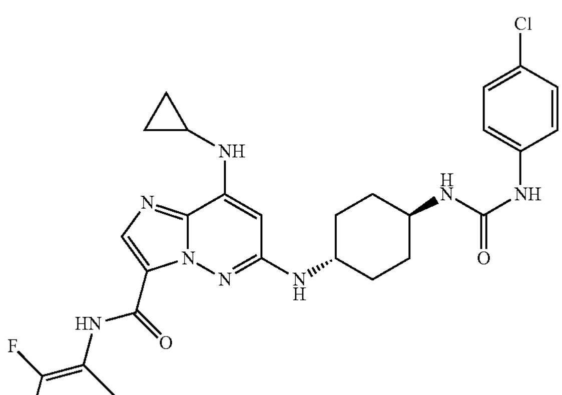 | 6-((trans-4-(((4-chlorophenyl)carbamoyl)amino)cyclohexyl)amino)-8-(cyclopropylamino)-N-(3-fluoro-4-pyridinyl)imidazo[1,2-b]pyridazine-3-carboxamide | 578.26 | 2.61[a] |

TABLE 4-continued

| Example | Structure | Name | [M + H] | HPLC Ret Time (min) |
|---|---|---|---|---|
| 213 | 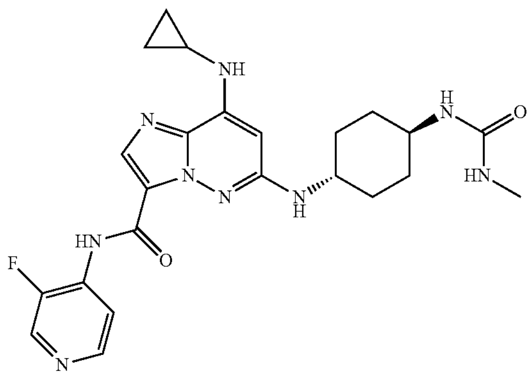 [SMILES: CNC(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-((methylcarbamoyl)amino)cyclohexyl)amino)imidazo[1,2-b]pyridazine-3-carboxamide | 482.29 | 1.87[a] |
| 214 | 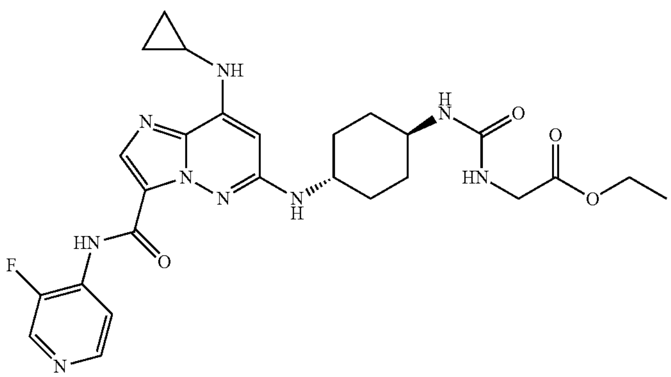 [SMILES: CCOC(=O)CNC(=O)N[C@H]1CC[C@H](Nc2cc(NC3CC3)c3ncc(C(=O)Nc4ccncc4F)n3n2)CC1] | ethyl N-((trans-4-((8-(cyclopropylamino)-3-((3-fluoro-4-pyridinyl)carbamoyl)imidazo[1,2-b]pyridazin-6-yl)amino)cyclohexyl)carbamoylglycinate | 554.29 | 2.05[a] |
| 215 | 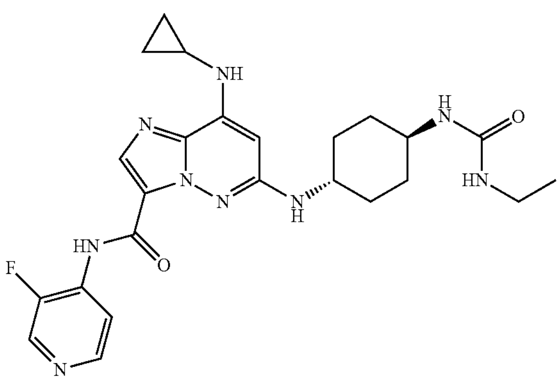 [SMILES: CCNC(=O)N[C@H]1CC[C@H](Nc2cc(NC3CC3)c3ncc(C(=O)Nc4ccncc4F)n3n2)CC1] | 8-(cyclopropylamino)-6-((trans-4-((ethylcarbamoyl)amino)cyclohexyl)amino)-N-(3-fluoro-4-pyridinyl)imidazo[1,2-b]pyridazine-3-carboxamide | 496.31 | 1.95[a] |
| 216 | 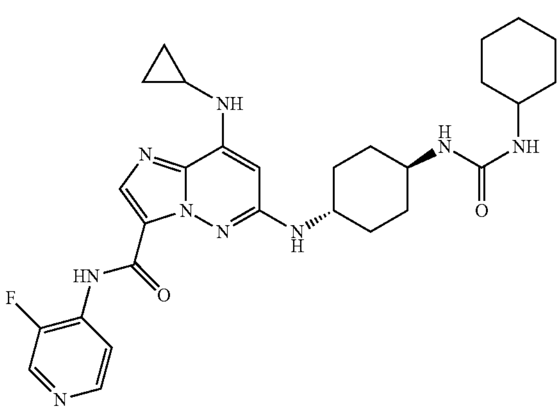 [SMILES: O=C(NC1CCCCC1)N[C@H]1CC[C@H](Nc2cc(NC3CC3)c3ncc(C(=O)Nc4ccncc4F)n3n2)CC1] | 6-((trans-4-((cyclohexylcarbamoyl)amino)cyclohexyl)amino)-8-(cyclopropylamino)-N-(3-fluoro-4-pyridinyl)imidazo[1,2-b]pyridazine-3-carboxamide | 550.35 | 2.37[a] |

TABLE 4-continued

| Example | Structure | Name | [M + H] | HPLC Ret Time (min) |
|---|---|---|---|---|
| 217 | 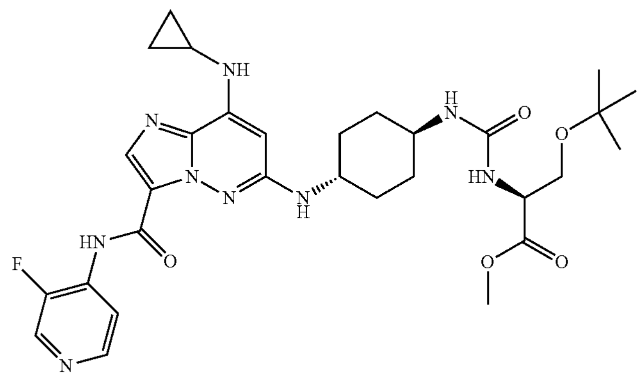 [SMILES: COC(=O)[C@H](COC(C)(C)C)NC(=O)N[C@H]1CC[C@H](Nc2cc(NC3CC3)c3ncc(C(=O)Nc4ccncc4F)n3n2)CC1] | methyl O-tert-butyl-N-((trans-4-((8-(cyclopropylamino)-3-((3-fluoro-4-pyridinyl)carbamoyl)imidazo[1,2-b]pyridazin-6-yl)amino)cyclohexyl)carbamoyl)-L-serinate | 626.38 | 2.45[a] |
| 218 | 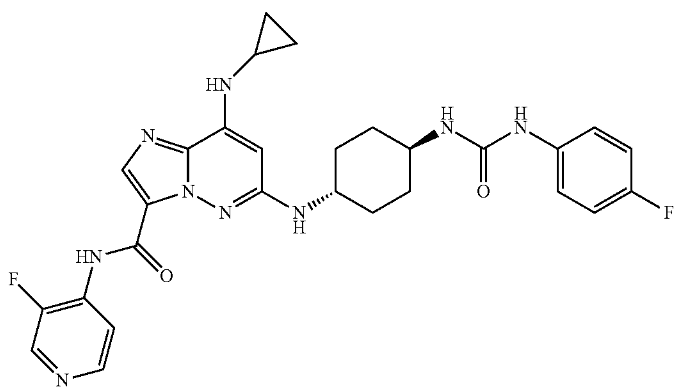 [SMILES: O=C(Nc1ccc(F)cc1)N[C@H]1CC[C@H](Nc2cc(NC3CC3)c3ncc(C(=O)Nc4ccncc4F)n3n2)CC1] | 8-(cyclopropylamino)-6-((trans-4-(((4-fluorophenyl)carbamoyl)amino)cyclohexyl)amino)-N-(3-fluoro-4-pyridinyl)imidazo[1,2-b]pyridazine-3-carboxamide | 561.97 | 2.51[a] |
| 219 | 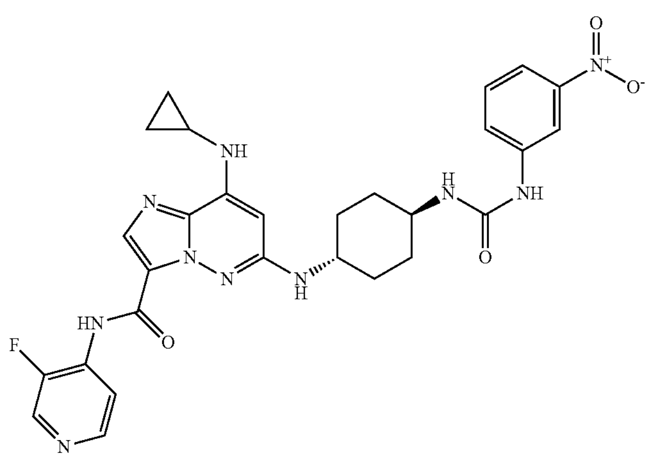 [SMILES: O=C(Nc1cccc([N+](=O)[O-])c1)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-(((3-nitrophenyl)carbamoyl)amino)cyclohexyl)amino)imidazo[1,2-b]pyridazine-3-carboxamide | 588.94 | 2.61[a] |
| 220 | 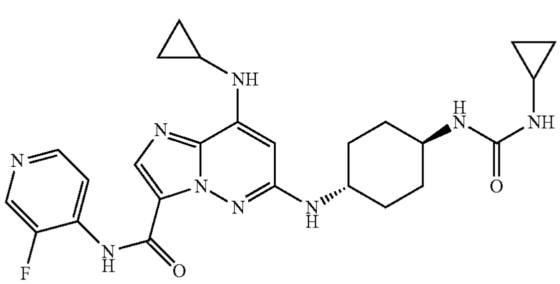 [SMILES: O=C(NC1CC1)N[C@H]1CC[C@H](Nc2cc(NC3CC3)c3ncc(C(=O)Nc4ccncc4F)n3n2)CC1] | 8-(cyclopropylamino)-6-((trans-4-((cyclopropylcarbamoyl)amino)cyclohexyl)amino)-N-(3-fluoro-4-pyridinyl)imidazo[1,2-b]pyridazine-3-carboxamide | 508.05 | 2.38[a] |

TABLE 4-continued

| Example | Structure | Name | [M + H] | HPLC Ret Time (min) |
|---|---|---|---|---|
| 221 | 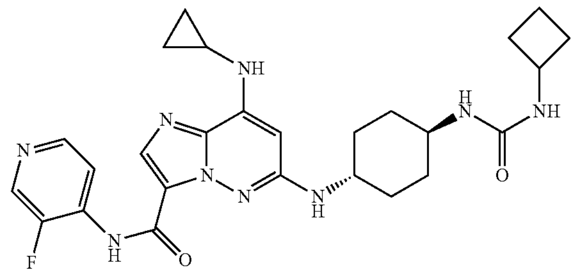 [SMILES: O=C(NC1CCC1)N[C@H]1CC[C@H](Nc2cc(NC3CC3)c3ncc(C(=O)Nc4ccncc4F)n3n2)CC1] | 6-((trans-4-((cyclobutylcarbamoyl)amino)cyclohexyl)amino)-8-(cyclopropylamino)-N-(3-fluoro-4-pyridinyl)imidazo[1,2-b]pyridazine-3-carboxamide | 522.06 | 2.47[a] |
| 222 | 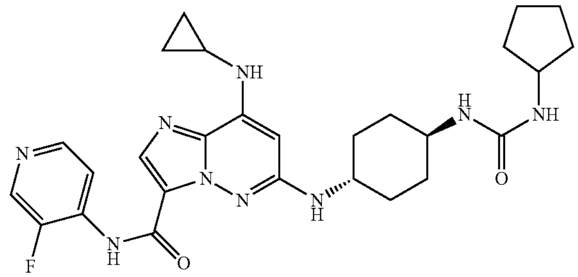 [SMILES: O=C(NC1CCCC1)N[C@H]1CC[C@H](Nc2cc(NC3CC3)c3ncc(C(=O)Nc4ccncc4F)n3n2)CC1] | 6-((trans-4-((cyclopentylcarbamoyl)amino)cyclohexyl)amino)-8-(cyclopropylamino)-N-(3-fluoro-4-pyridinyl)imidazo[1,2-b]pyridazine-3-carboxamide | 536.06 | 2.5[a] |
| 223 | 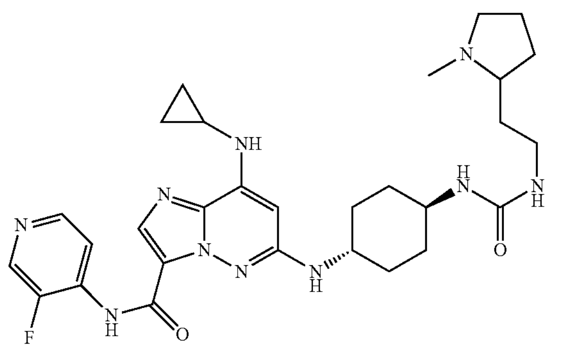 [SMILES: CN1CCCC1CCNC(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-(((2-(1-methyl-4-pyrrolidinyl)ethyl)carbamoyl)amino)cyclohexyl)amino)imidazo[1,2-b]pyridazine-3-carboxamide | 579.10 | 2.19[a] |
| 224 | 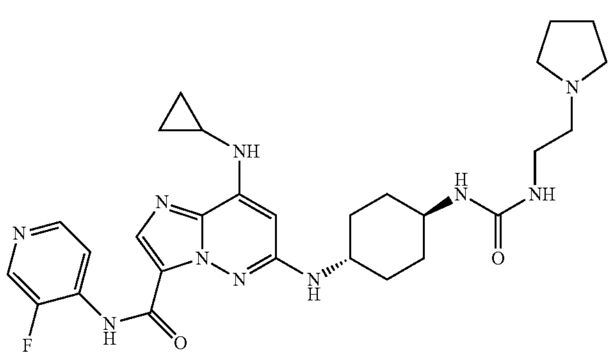 [SMILES: O=C(NCCN1CCCC1)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-(((2-(1-pyrrolidinyl)ethyl)carbamoyl)amino)cyclohexyl)amino)imidazo[1,2-b]pyridazine-3-carboxamide | 565.06 | 2.21[a] |

TABLE 4-continued

| Example | Structure | Name | [M + H] | HPLC Ret Time (min) |
|---|---|---|---|---|
| 225 | 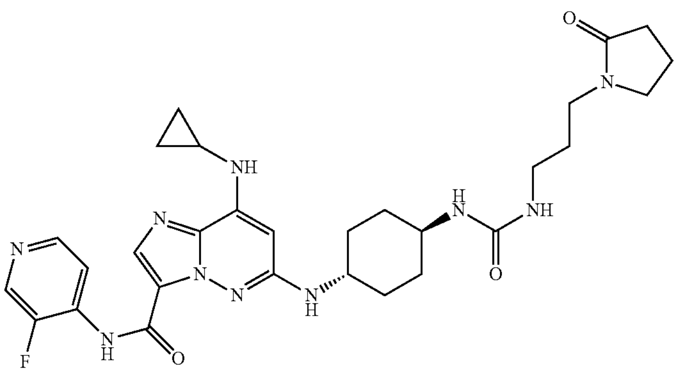 [SMILES: O=C(NCCCN1CCCC1=O)N[C@H]1CC[C@H](Nc2cc(NC3CC3)c3ncc(C(=O)Nc4ccncc4F)n3n2)CC1] | 8-(cyclopropylamino)-N-(3-fluoro4-pyridinyl)-6-((trans-4-(((3-(2-oxo-1-pyrrolidinyl)propyl)carbamoyl)amino)cyclohexyl)amino)imidazo[1,2-b]pyridazine-3-carboxamide | 593.07 | 2.26[a] |
| 226 | 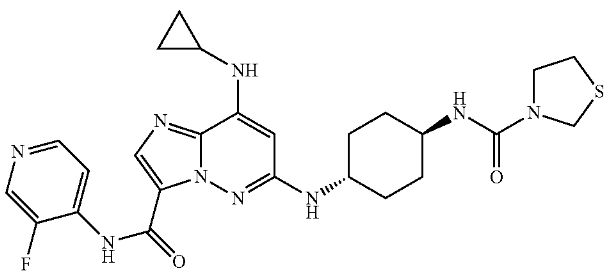 [SMILES: O=C(Nc1ccncc1F)c1cnc2c(NC3CC3)cc(N[C@H]3CC[C@H](NC(=O)N4CCSC4)CC3)nn12] | 8-(cyclopropylamino)-N-(3-fluoro-4-pyridinyl)-6-((trans-4-((1,3-thiazolidin-3-ylcarbonyl)amino)cyclohexyl)amino)imidazo[1,2-b]pyridazine-3-carboxamide | 540.00 | 2.46[a] |
| 227 | 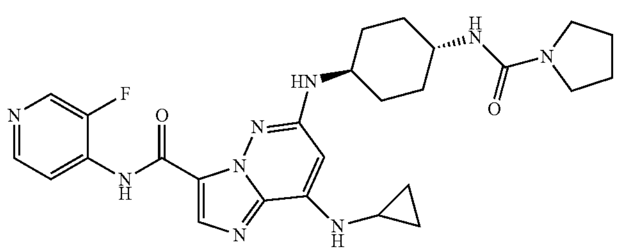 [SMILES: O=C(Nc1ccncc1F)c1cnc2c(NC3CC3)cc(N[C@H]3CC[C@H](NC(=O)N4CCCC4)CC3)nn12] | 8-(cyclopropylamino)-N-(3-fluoro-4-pyridinyl)-6-((trans-4-((1-pyrrolidinylcarbonyl)amino)cyclohexyl)amino)imidazo[1,2-b]pyridazine-3-carboxamide | 522.05 | 2.37[a] |
| 228 | 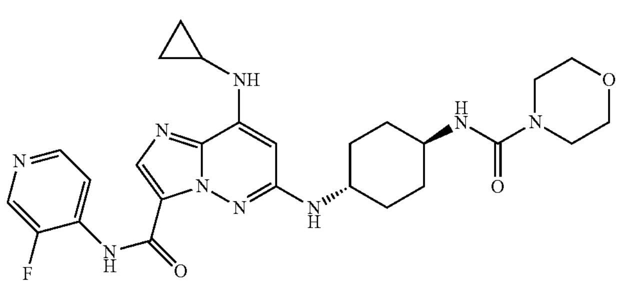 [SMILES: O=C(Nc1ccncc1F)c1cnc2c(NC3CC3)cc(N[C@H]3CC[C@H](NC(=O)N4CCOCC4)CC3)nn12] | 8-(cyclopropylamino)-N-(3-fluoro-4-pyridinyl)-6-((trans-4-((4-morpholinylcarbonyl)amino)cyclohexyl)amino)imidazo[1,2-b]pyridazine-3-carboxamide | 538.06 | 2.35[a] |
| 229 | 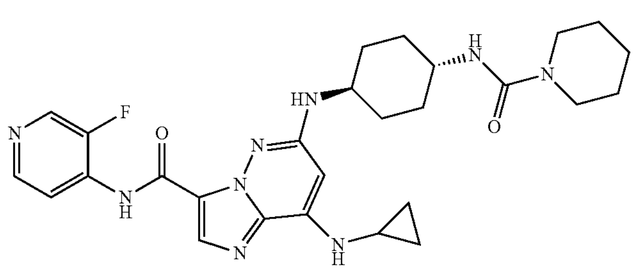 [SMILES: O=C(Nc1ccncc1F)c1cnc2c(NC3CC3)cc(N[C@H]3CC[C@H](NC(=O)N4CCCCC4)CC3)nn12] | 8-(cyclopropylamino)-N-(3-fluoro-4-pyridinyl)-6-((trans-4-((1-piperidinylcarbonyl)amino)cyclohexyl)amino)imidazo[1,2-b]pyridazine-3-carboxamide | 536.06 | 2.5[a] |

TABLE 4-continued

| Example | Structure | Name | [M + H] | HPLC Ret Time (min) |
|---|---|---|---|---|
| 230 | 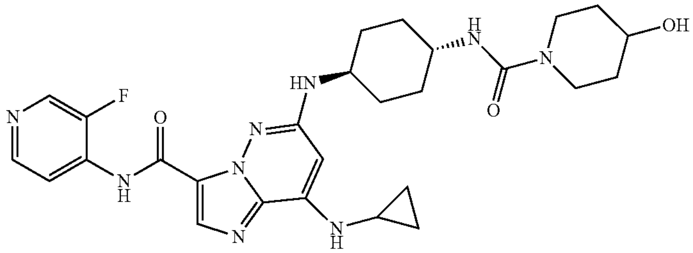 [SMILES: O=C(Nc1ccncc1F)c1cnc2c(NC3CC3)cc(N[C@H]3CC[C@H](NC(=O)N4CCC(O)CC4)CC3)nn12] | 8-(cyclopropylamino)-N-(3-fluoro-4-pyridinyl)-6-((trans-4-(((4-hydroxy-1-piperidinyl)carbonyl)amino)cyclohexyl)amino)imidazo[1,2-b]pyridazine-3-carboxamide | 552.06 | 2.23[a] |
| 231 | 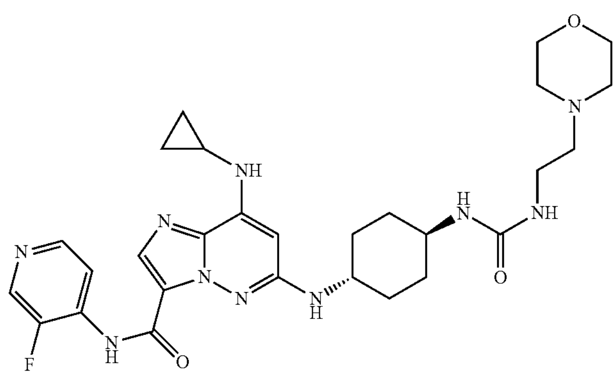 [SMILES: O=C(NCCN1CCOCC1)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-(((2-(4-morpholinyl)ethyl)carbamoyl)amino)cyclohexyl)amino)imidazo[1,2-b]pyridazine-3-carboxamide | 581.05 | 2.26[a] |
| 232 | 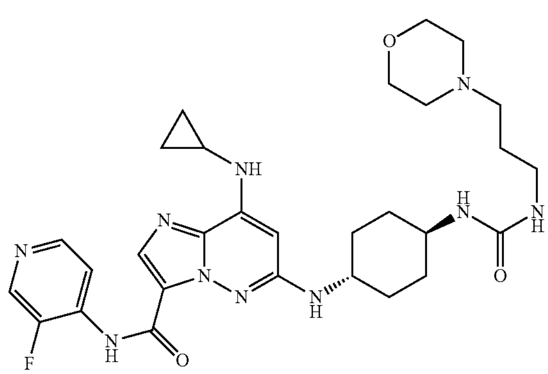 [SMILES: O=C(NCCCN1CCOCC1)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-(((3-(4-morpholinyl)propyl)carbamoyl)amino)cyclohexyl)amino)imidazo[1,2-b]pyridazine-3-carboxamide | 595.07 | 2.23[a] |
| 233 | 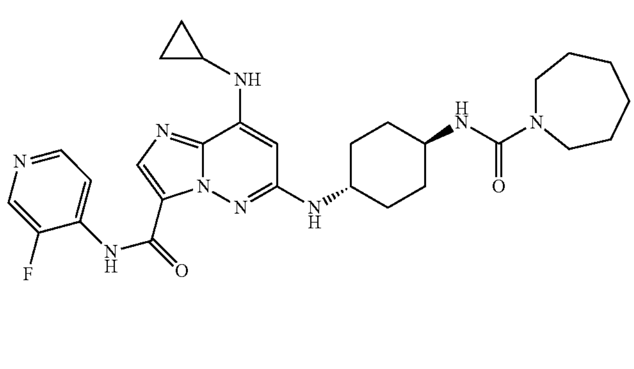 [SMILES: O=C(Nc1ccncc1F)c1cnc2c(NC3CC3)cc(N[C@H]3CC[C@H](NC(=O)N4CCCCCC4)CC3)nn12] | 6-((trans-4-((1-azepanylcarbonyl)amino)cyclohexyl)amino)-8-(cyclopropylamino)-N-(3-fluoro-4-pyridinyl)imidazo[1,2-b]pyridazine-3-carboxamide | 550.06 | 2.58[a] |

TABLE 4-continued

| Example | Structure | Name | [M + H] | HPLC Ret Time (min) |
|---|---|---|---|---|
| 234 | 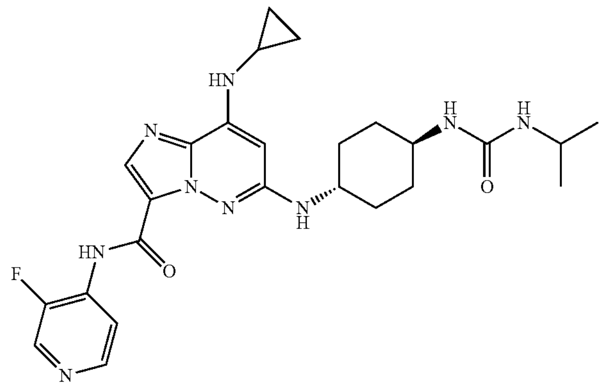 [SMILES: CC(C)NC(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-((isopropylcarbamoyl)amino)cyclohexyl)amino)imidazo[1,2-b]pyridazine-3-carboxamide | 510.07 | 2.43[a] |
| 235 | 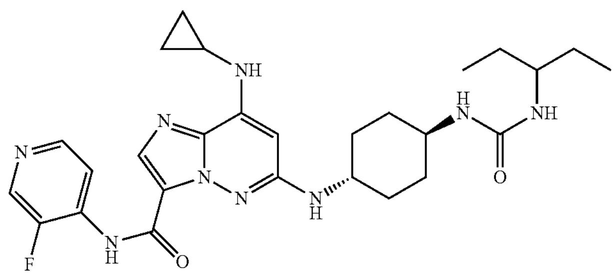 [SMILES: CCC(CC)NC(=O)N[C@H]1CC[C@H](Nc2cc(NC3CC3)c3ncc(C(=O)Nc4ccncc4F)n3n2)CC1] | 8-(cyclopropylamino)-6-((trans-4-(((1-ethylpropyl)carbamoyl)amino)cyclohexyl)amino)-N-(3-fluro-4-pyridinyl)imidazo[1,2-b]pyridazine-3-carboxamide | 538.08 | 2.59[a] |
| 236 | 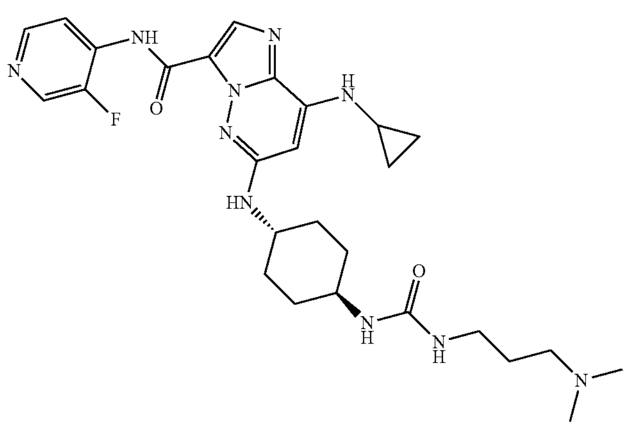 [SMILES: CN(C)CCCNC(=O)N[C@H]1CC[C@H](Nc2cc(NC3CC3)c3ncc(C(=O)Nc4ccncc4F)n3n2)CC1] | 8-(cyclopropylamino)-6-((trans-4-(((3-(dimethylamino)propyl)carbamoyl)amino)cyclohexyl)amino)-N-(3-fluoro-4-pyridinyl)imidazo[1,2-b]pyridazine-3-carboxamide | 553.06 | 2.33[a] |
| 237 | 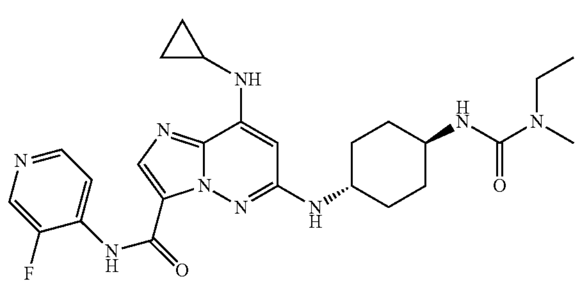 [SMILES: CCN(C)C(=O)N[C@H]1CC[C@H](Nc2cc(NC3CC3)c3ncc(C(=O)Nc4ccncc4F)n3n2)CC1] | 8-(cyclopropylamino)-6-((trans-4-((ethyl(methyl)carbamoyl)amino)cyclohexyl)amino)-N-(3-fluoro-4-pyridinyl)imidazo[1,2-b]pyridazine-3-carboxamide | 510.05 | 2.44[a] |

TABLE 4-continued

| Example | Structure | Name | [M + H] | HPLC Ret Time (min) |
|---|---|---|---|---|
| 238 | 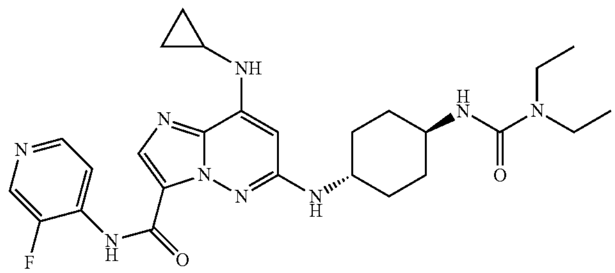 [SMILES: CCN(CC)C(=O)N[C@H]1CC[C@H](Nc2cc(NC3CC3)c3ncc(C(=O)Nc4ccncc4F)n3n2)CC1] | 8-(cyclopropylamino)-6-((trans-4-((diethylcarbamoyl)amino)cyclohexyl)amino)-N-(3-fluoro-4-pyridinyl)imidazo[1,2-b]pyridazine-3-carboxamide | 524.06 | 2.52[a] |
| 239 | 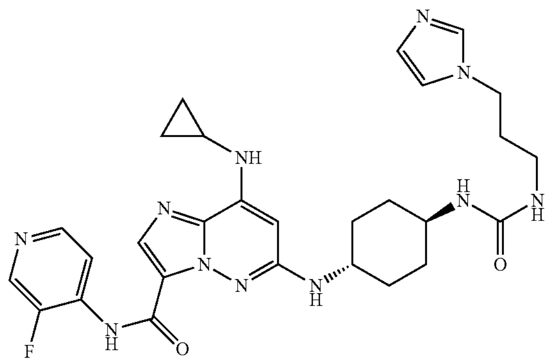 [SMILES: O=C(NCCCn1ccnc1)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-(((3-(1H-imidazol-1-yl)propyl)carbamoyl)amino)cyclohexyl)amino)imidazo[1,2-b]pyridazine-3-carboxamide | 576.06 | 2.3[a] |
| 240 | 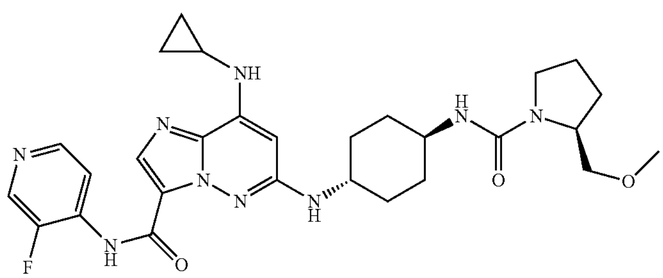 [SMILES: COC[C@@H]1CCCN1C(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-((((2S)-2-(methoxymethyl)-1-pyrrolidinyl)carbonyl)amino)cyclohexyl)amino)imidazo[1,2-b]pyridazine-3-carboxamide | 566.01 | 2.55[a] |
| 241 | 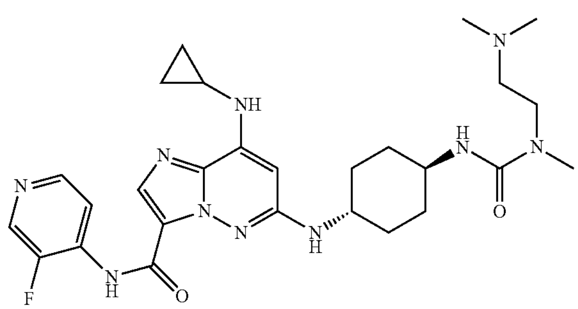 [SMILES: CN(C)CCN(C)C(=O)N[C@H]1CC[C@H](Nc2cc(NC3CC3)c3ncc(C(=O)Nc4ccncc4F)n3n2)CC1] | 8-(cyclopropylamino)-6-((trans-4-((((2-(dimethylamino)ethyl)(methyl)carbamoyl)amino)cyclohexyl)amino)-N-(3-fluoro-4-pyridinyl)imidazo[1,2-b]pyridazine-3-carboxamide | 553.05 | 2.29[a] |
| 242 | 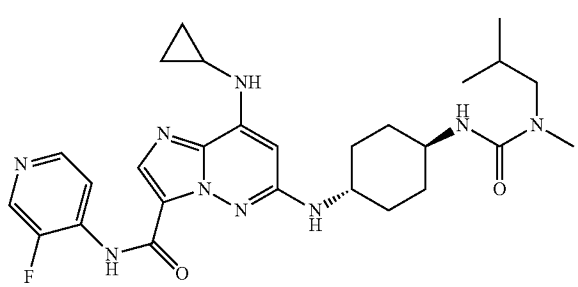 [SMILES: CC(C)CN(C)C(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-((isobutyl)(methyl)carbamoyl)amino)cyclohexyl)amino)imidazo[1,2-b]pyridazine-3-carboxamide | 538.03 | 2.65[a] |

TABLE 4-continued

| Example | Structure | Name | [M + H] | HPLC Ret Time (min) |
|---|---|---|---|---|
| 243 | 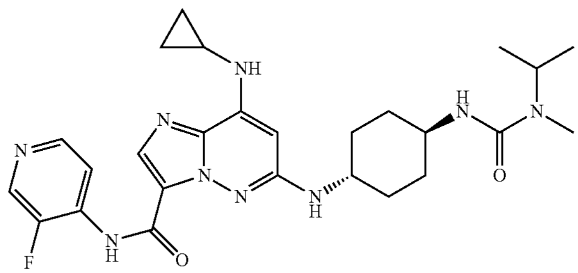 [SMILES: CC(C)N(C)C(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-((isopropyl(methyl)carbamoyl)amino)cyclohexyl)amino)imidazo[1,2-b]pyridazine-3-carboxamide | 524.01 | 2.55[a] |
| 244 | 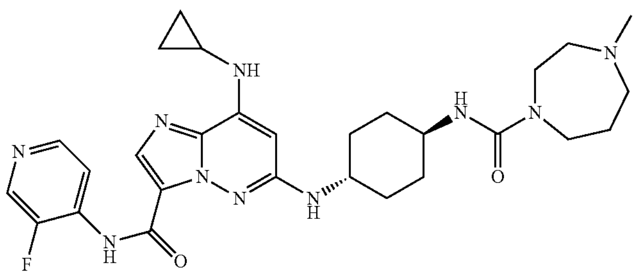 [SMILES: CN1CCCN(C(=O)N[C@H]2CC[C@H](Nc3cc(NC4CC4)c4ncc(C(=O)Nc5ccncc5F)n4n3)CC2)CC1] | 8-(cyclopropylamino)-N-(3-fluoro-4-pyridinyl)-6-((trans-4-(((4-methyl-1,4-diazepan-1-yl)carbonyl)amino)cyclohexyl)amino)imidazo[1,2-b]pyridazine-3-carboxamide | 565.03 | 2.27[a] |
| 245 | 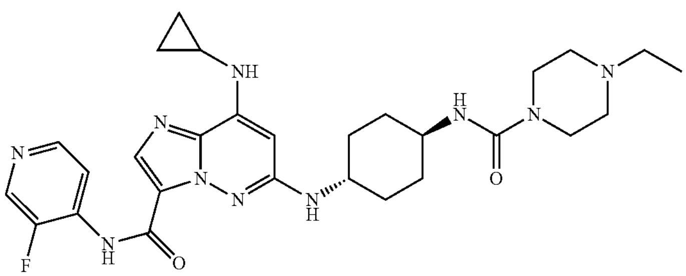 [SMILES: CCN1CCN(C(=O)N[C@H]2CC[C@H](Nc3cc(NC4CC4)c4ncc(C(=O)Nc5ccncc5F)n4n3)CC2)CC1] | 8-(cyclopropylamino)-6-((trans-4-(((4-ethyl-1-piperazinyl)carbonyl)amino)cyclohexyl)amino)-N-(3-fluoro-4-pyridinyl)imidazo[1,2-b]pyridazine-3-carboxamide | 565.01 | 2.32[a] |
| 246 | 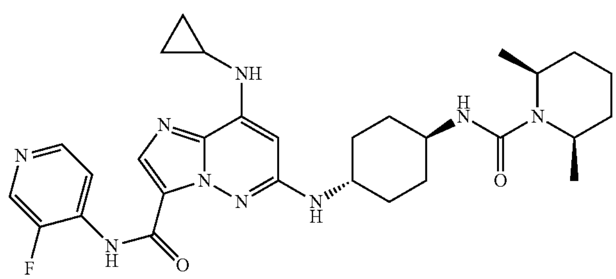 [SMILES: C[C@@H]1CCC[C@H](C)N1C(=O)N[C@H]1CC[C@H](Nc2cc(NC3CC3)c3ncc(C(=O)Nc4ccncc4F)n3n2)CC1] | 8-(cyclopropylamino)-6-((trans-4-(((((2R,6S)-2,6-dimethyl-1-piperidinyl)carbonyl)amino)cyclohexyl)amino)-N-(3-fluoro-4-pyridinyl)imidazo[1,2-b]pyridazine-3-carboxamide | 564.03 | 2.75[a] |
| 247 | 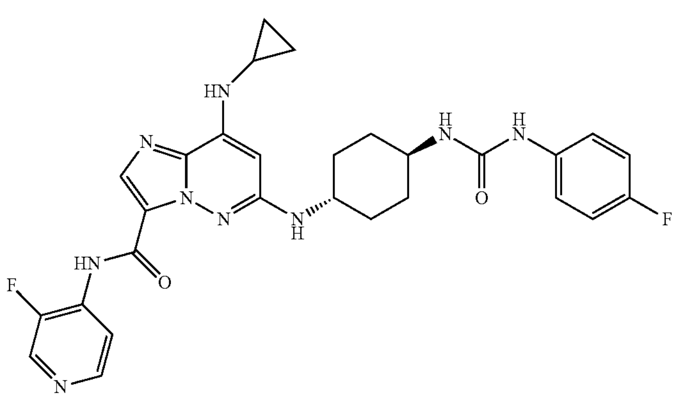 [SMILES: O=C(Nc1ccc(F)cc1)N[C@H]1CC[C@H](Nc2cc(NC3CC3)c3ncc(C(=O)Nc4ccncc4F)n3n2)CC1] | 8-(cyclopropylamino)-6-((trans-4-(((4-fluorophenyl)carbamoyl)amino)cyclohexyl)amino)-N-(3-fluoro-4-pyridinyl)imidazo[1,2-b]pyridazine-3-carboxamide | 562.0 | 2.513[a] |

TABLE 4-continued

| Example | Structure | Name | [M + H] | HPLC Ret Time (min) |
| --- | --- | --- | --- | --- |
| 248 | 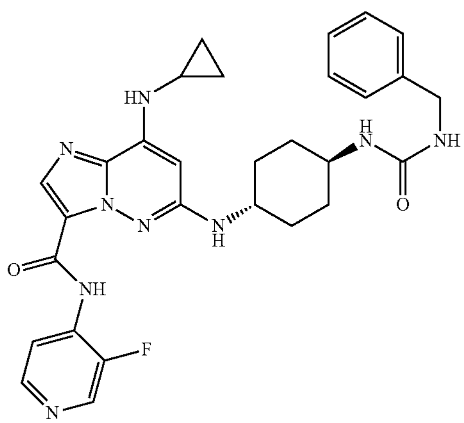 [SMILES: O=C(NCc1ccccc1)N[C@H]1CC[C@H](Nc2cc(NC3CC3)c3ncc(C(=O)Nc4ccncc4F)n3n2)CC1] | 6-((trans-4-((benzylcarbamoyl)amino)cyclohexyl)amino)-8-(cyclopropylamino)-N-(3-fluoro-4-pyridinyl)imidazo[1,2-b]pyridazine-3-carboxamide | 558.0 | 2.520[a] |
| 249 | 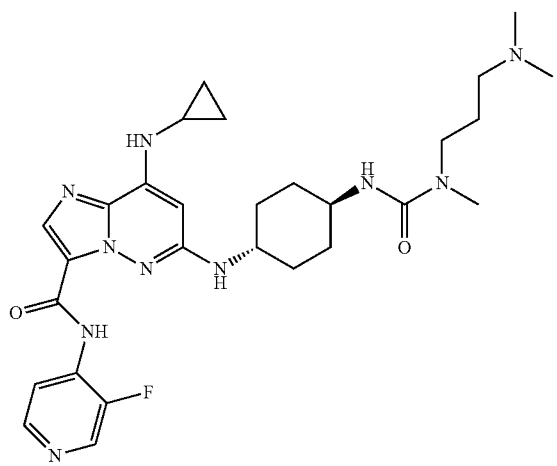 [SMILES: CN(C)CCCN(C)C(=O)N[C@H]1CC[C@H](Nc2cc(NC3CC3)c3ncc(C(=O)Nc4ccncc4F)n3n2)CC1] | 8-(cyclopropylamino)-6-((trans-4-(((3-(dimethylamino)propyl)(methyl)carbamoyl)amino)cyclohexyl)amino)-N-(3-fluoro-4-pyridinyl)imidazo[1,2-b]pyridazine-3-carboxamide | 567.4 | 1.870[a] |
| 250 | 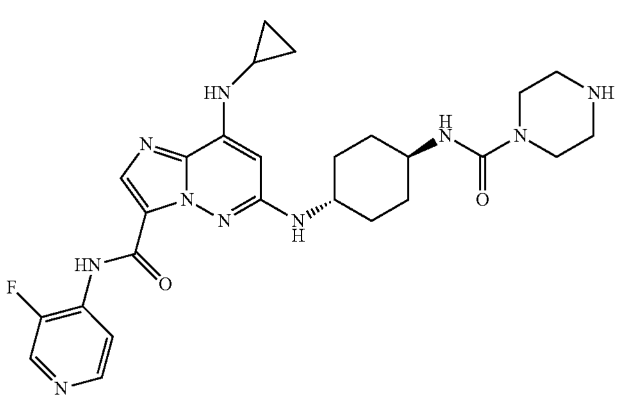 [SMILES: O=C(Nc1ccncc1F)c1cnc2c(NC3CC3)cc(N[C@H]3CC[C@H](NC(=O)N4CCNCC4)CC3)nn12] | 8-(cyclopropylamino)-N-(3-fluoro-4-pyridinyl)-6-((trans-4-((1-piperazinylcarbonyl)amino)cylcohexyl)amino)imidazo[1,2-b]pyridazine-3-carboxamide | 537.37 | 1.34[b] |

TABLE 4-continued

| Example | Structure | Name | [M + H] | HPLC Ret Time (min) |
|---|---|---|---|---|
| 251 | 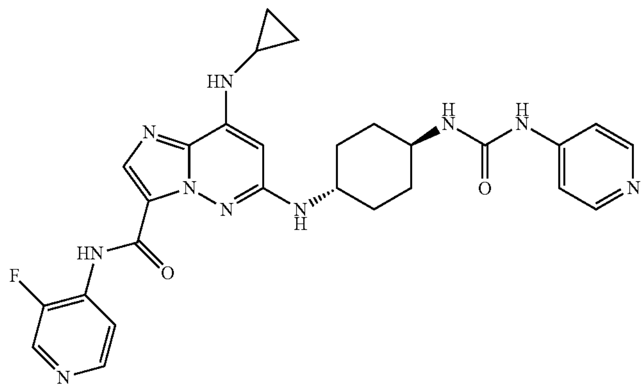 [SMILES: O=C(Nc1ccncc1)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-((4-pyridinylcarbamoyl)amino)cyclohexyl)amino)imidazo[1,2-b]pyridazine-3-carboxamide | 545.36 | 1.54[b] |
| 252 | 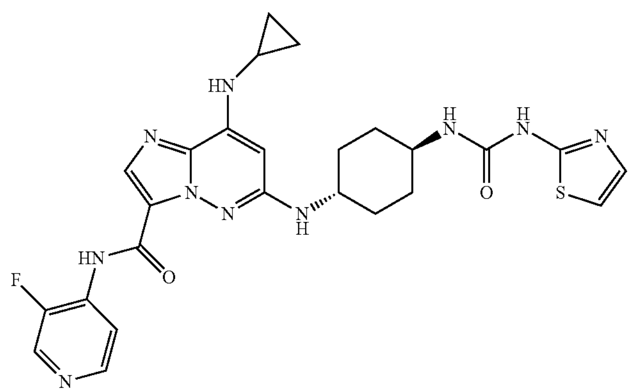 [SMILES: O=C(Nc1nccs1)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-((1,3-thiazol-2-ylcarbamoyl)amino)cylcohexyl)amino)imidazo[1,2-b]pyridazine-3-carboxamide | 551.29 | 1.74[b] |
| 253 | 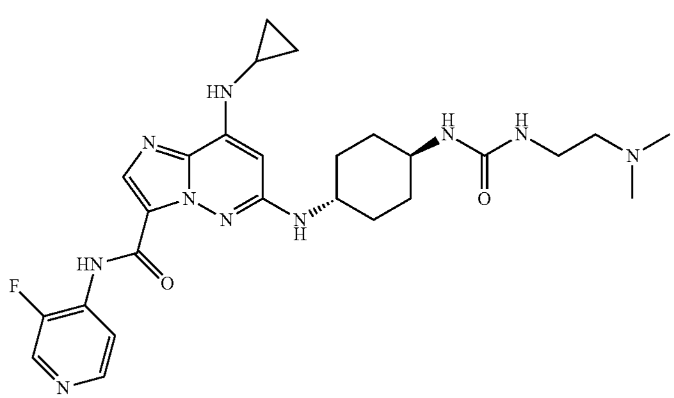 [SMILES: CN(C)CCNC(=O)N[C@H]1CC[C@H](Nc2cc(NC3CC3)c3ncc(C(=O)Nc4ccncc4F)n3n2)CC1] | 8-(cyclopropylamino)-6-((trans-4-(((2-(dimethylamino)ethyl)carbamoyl)amino)cyclohexylamino)-N-(3-fluoro-4-pyridinyl)imidazo[1,2-b]pyridazine-3-carboxamide | 539.4 | 1.4[b] |

TABLE 4-continued

| Example | Structure | Name | [M + H] | HPLC Ret Time (min) |
|---|---|---|---|---|
| 254 | 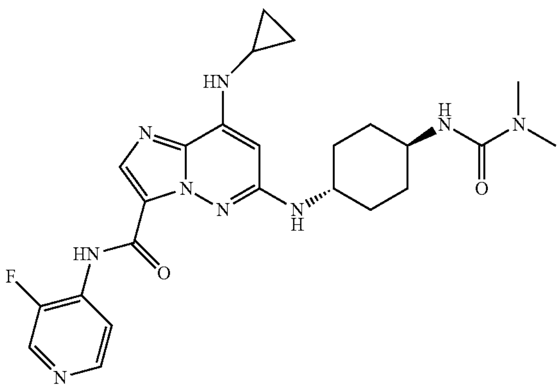 [SMILES: CN(C)C(=O)N[C@H]1CC[C@H](Nc2cc(NC3CC3)c3ncc(C(=O)Nc4ccncc4F)n3n2)CC1] | 8-(cyclopropylamino)-6-((trans-4-((dimethylcarbamoyl)amino)cyclohexyl)amino)-N-(3-fluoro-4-pyridinyl)imidazo[1,2-b]pyridazine-3-carboxamide | 496.30 | 1.583[b] |
| 255 | 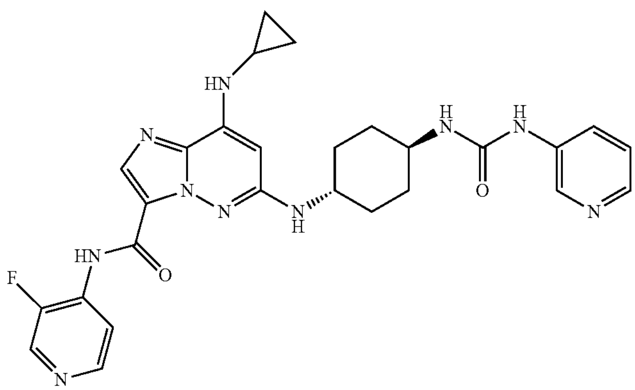 [SMILES: O=C(Nc1cccnc1)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-((3-pyridinylcarbamoyl)amino)cyclohexyl)amino)imidazo[1,2-b]pyridazine-3-carboxamide | 545.31 | 1.522[b] |

HPLC Conditions:

[a]Waters XBridge 4.6 × 50 mm 5 um C18 Column: 0%-100% solvent B. Solvent B: 95% CH$_3$CN, 5% H$_2$O, Modifier = 10 mM NH$_4$OAc). Solvent A: 5% CH$_3$CN, 95% H$_2$O, Modifier = 10 mM NH$_4$OAc). 4 min gradient, monitored at 220 nm.

[b]Phenomenex Luna 5 micron C18 4.6 × 30 mm: 0 to 100 B in 2 min with 1 min hold time. Flow rate = 5 mL/min, detection at 254 nm, Solvent A: 10% methanol/90% water/0.1% TFA; Solvent B: 10% water/90% methanol/0.1% TFA.

The following Examples in Table 5 may be prepared from 25B in a manner analogous the procedures described in Example 32.

TABLE 5

| Example | Structure | Name | [M + H] | HPLC Ret Time (min) |
|---|---|---|---|---|
| 256 | 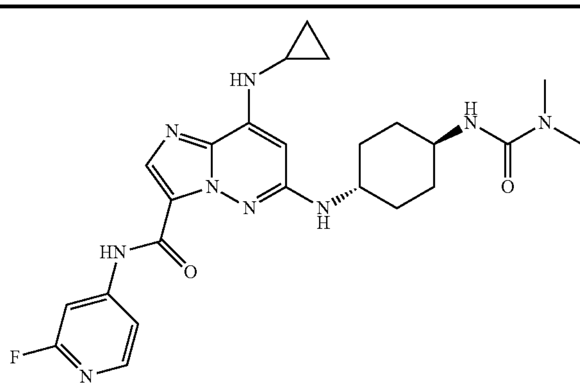 | 8-(cyclopropylamino)-6-((trans-4-((dimethylcarbamoyl)amino)cyclohexyl)amino)-N-(2-fluoro-4-pyridinyl)imidazo[1,2-b]pyridazine-3-carboxamide | 496.26 | 1.780 |

TABLE 5-continued

| Example | Structure | Name | [M + H] | HPLC Ret Time (min) |
|---|---|---|---|---|
| 257 | 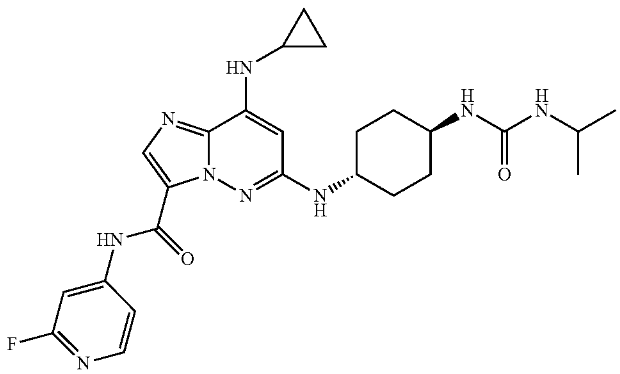 [SMILES: CC(C)NC(=O)N[C@H]1CC[C@H](Nc2cc(NC3CC3)c3ncc(C(=O)Nc4ccnc(F)c4)n3n2)CC1] | 8-(cyclopropylamino)-N-(2-fluoro-4-pyridinyl)-6-((trans-4-((isopropylcarbamoyl)amino)cyclohexyl)amino)imidazo[1,2-b]pyridazine-3-carboxamide | 1.895 | 510.18 |

HPLC Conditions:
Phenomenex Luna 5 micron C18 4.6 × 30 mm: 0 to 100 B in 2 min with 1 min hold time, Flow rate = 5 mL/min, detection at 254 nm,
Solvent A: 10% methanol/90% water/0.1% TFA;
Solvent B: 10% water/90% methanol/0.1% TFA.

The following Examples in Table 6 may be prepared from 23C in a manner analogous the procedures described in Example 32.

TABLE 6

| Example | Structure | Name | [M + H] | HPLC Ret Time (min) |
|---|---|---|---|---|
| 258 | 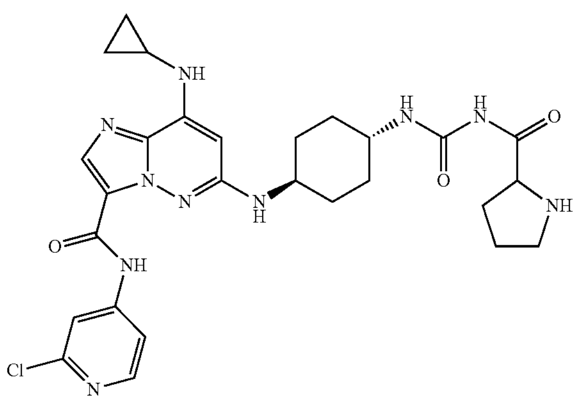 [SMILES: O=C(NC(=O)C1CCCN1)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-((prolylcarbamoyl)amino)cyclohexyl)amino)imidazo[1,2-b]pyridazine-3-carboxamide | 580.91 | 2.13 |
| 259 | 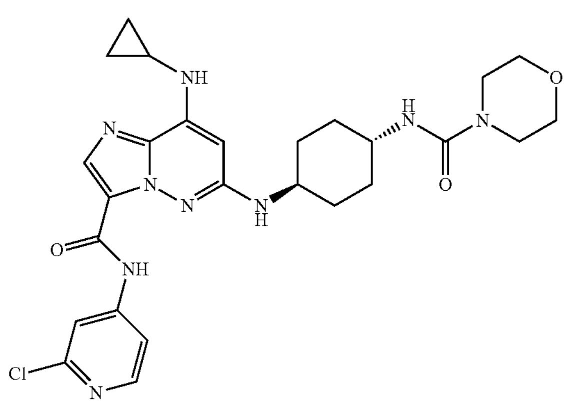 [SMILES: O=C(Nc1ccnc(Cl)c1)c1cnc2c(NC3CC3)cc(N[C@H]3CC[C@H](NC(=O)N4CCOCC4)CC3)nn12] | N-(2-chloro-4-pyridinyl)-8-(cyclopropylamino)-6-((trans-4-((4-morpholinylcarbonyl)amino)cylcohexyl)amino)imidazo[1,2-b]pyridazine-3-carboxamide | 553.87 | 2.26 |

TABLE 6-continued

| Example | Structure | Name | [M + H] | HPLC Ret Time (min) |
|---|---|---|---|---|
| 260 | 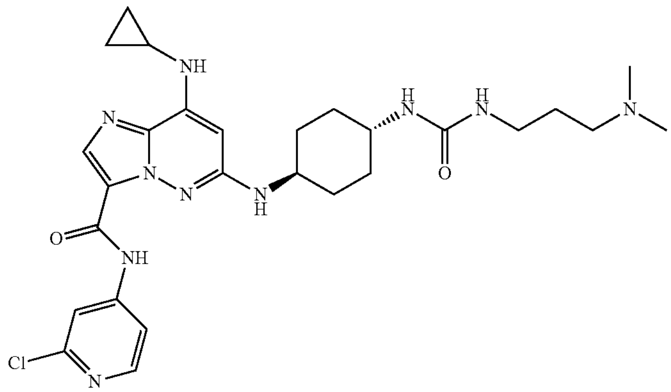 [SMILES: CN(C)CCCNC(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-(((3-(dimethylamino)propyl)carbamoyl)amino)cyclohexyl)amino)imidazo[1,2-b]pyridazine-3-carboxamide | 568.95 | 2.06 |
| 261 | 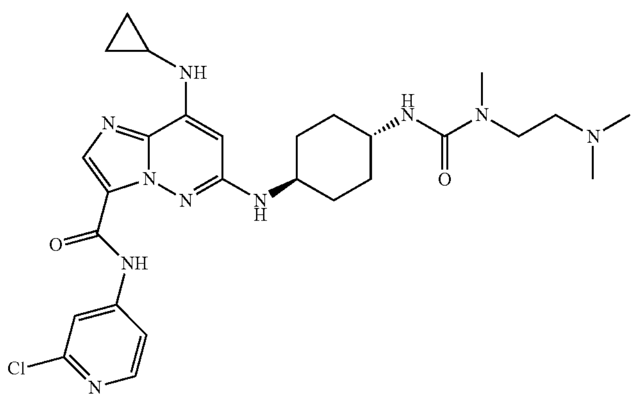 [SMILES: CN(C)CCN(C)C(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-(((2-(dimethylamino)ethyl)(methyl)carbamoyl)amino)cyclohexyl)amino)imidazo[1,2-b]pyridazine-3-carobxamide | 568.94 | 2.09 |
| 262 | 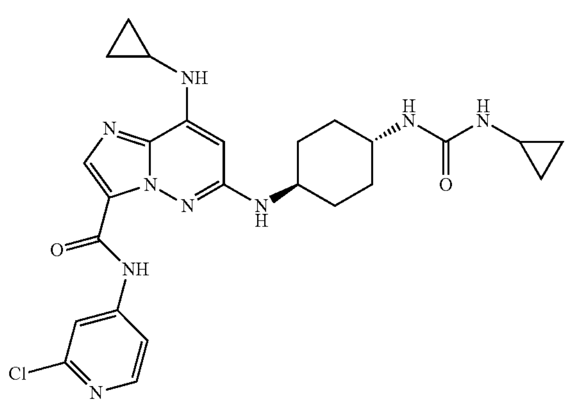 [SMILES: O=C(NC1CC1)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-((cyclopropylcarbamoyl)amino)cyclohexyl)amino)imidazo[1,2-b]pyridazine-3-carboxamide | 523.87 | 2.30 |

TABLE 6-continued

| Example | Structure | Name | [M + H] | HPLC Ret Time (min) |
|---|---|---|---|---|
| 263 | 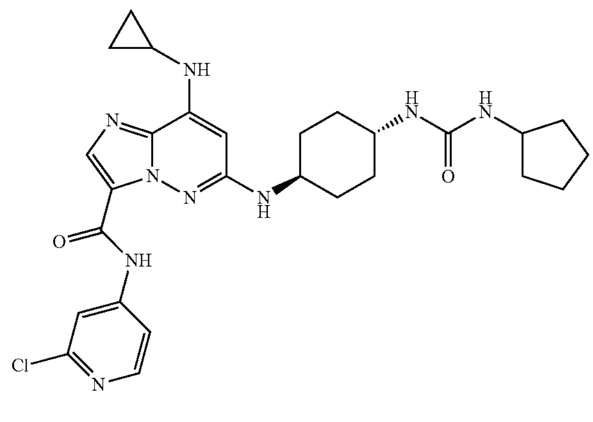 [SMILES: O=C(NC1CCCC1)N[C@H]1CC[C@H](Nc2cc(NC3CC3)c3ncc(C(=O)Nc4ccnc(Cl)c4)n3n2)CC1] | N-(2-chloro-4-pyridinyl)-6-((trans-4-((cyclopentylcarbamoyl)amino)cyclohexyl)amino)-8-(cyclopropylamino)imidazo[1,2-b]pyridazine-3-carboxamide | 551.90 | 2.50 |
| 264 | 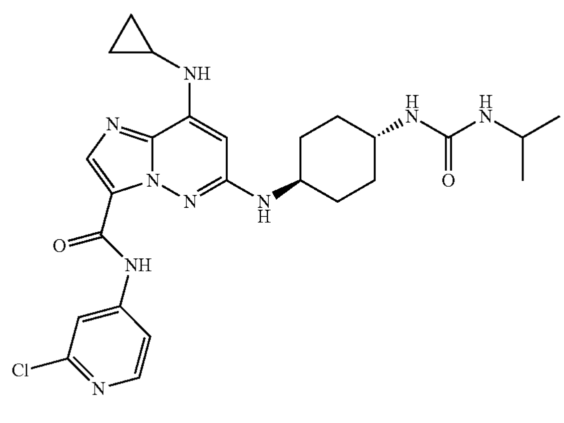 [SMILES: CC(C)NC(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-((isopropylcarba-moyl)amino)cyclohexyl)amino)imidazo[1,2-b]pyridazine-3-carboxamide | 525.89 | 2.39 |
| 265 | 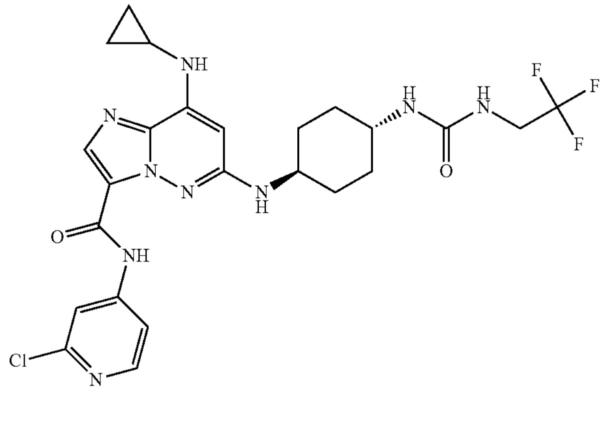 [SMILES: O=C(NCC(F)(F)F)N[C@H]1CC[C@H](Nc2cc(NC3CC3)c3ncc(C(=O)Nc4ccnc(Cl)c4)n3n2)CC1] | N-(2-chloro-4-pyridinyl)-8-(cylcopropylamino)-6-((trans-4-(((2,2,2-trifluoroethyl)carbamoyl)amino)cyclohexyl)amino)imidazo[1,2-b]pyridazine-3-carboxamide | 565.84 | 2.45 |

TABLE 6-continued

| Example | Structure | Name | [M + H] | HPLC Ret Time (min) |
|---|---|---|---|---|
| 266 | 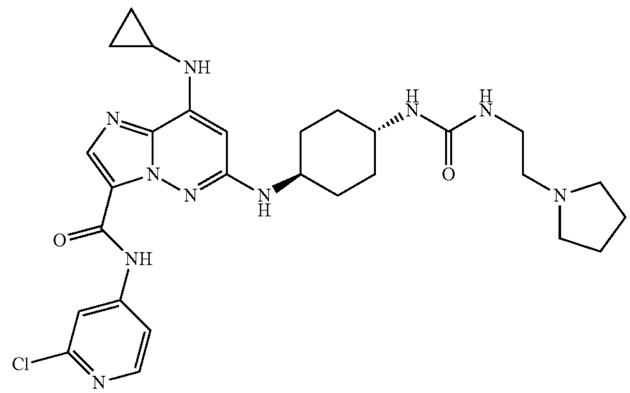 [SMILES: O=C(NCCN1CCCC1)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-(((2-(1-pyrrolidinyl)ethyl)carbamoyl)amino)cyclohexyl)amino)imidazo[1,2-b]pyridazine-3-carboxamide | 580.94 | 2.06 |
| 267 | 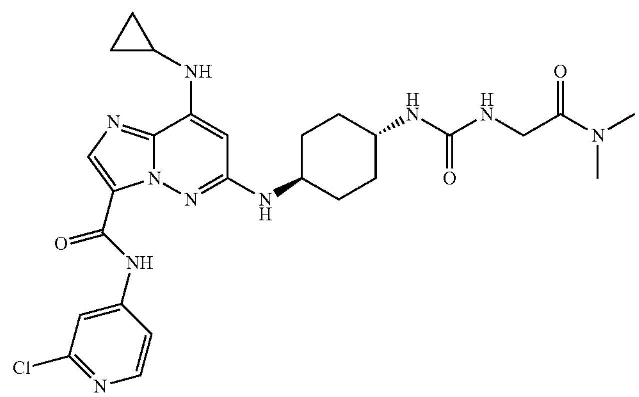 [SMILES: CN(C)C(=O)CNC(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-(((2-(dimethylamino)-2-oxoethyl)carbamoyl)amino)cyclohexyl)amino)imidazo[1,2-b]pyridazine-3-carboxamide | 568.90 | 2.12 |
| 268 | 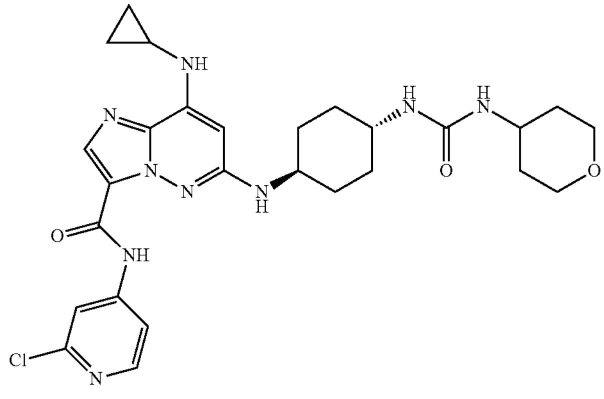 [SMILES: O=C(NC1CCOCC1)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-((tetrahydro-2H-pyran-4-ylcarbamoyl)amino)cyclohexyl)amino)imidazo[1,2-b]pyridazine-3-carboxamide | 567.90 | 2.25 |

TABLE 6-continued

| Example | Structure | Name | [M + H] | HPLC Ret Time (min) |
|---|---|---|---|---|
| 269 | 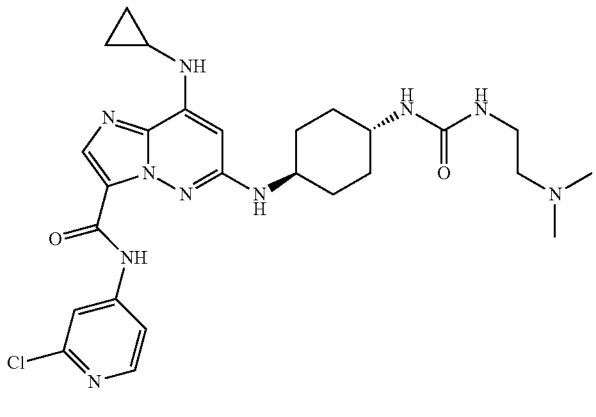 [SMILES: CN(C)CCNC(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-(((2-(dimethylamino)ethyl)carbamoyl)amino)cyclohexyl)amino)imidazo[1,2-b]pyridazine-3-carboxamide | 555.19 | 2.18 |
| 270 | 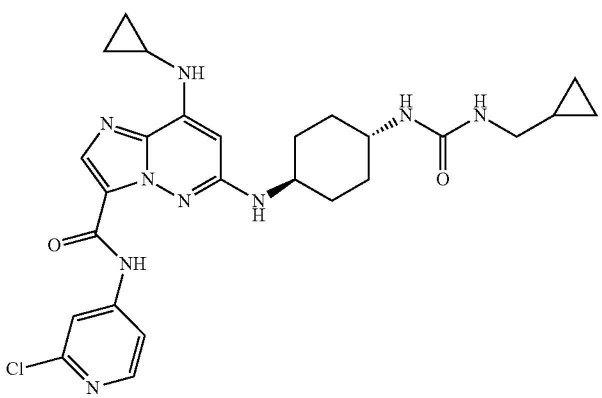 [SMILES: O=C(NCC1CC1)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-(((cyclopropylmethyl)carbamoyl)amino)cyclohexyl)amino)imidazo[1,2-b]pyridazine-3-carboxamide | 538.12 | 2.49 |
| 271 | 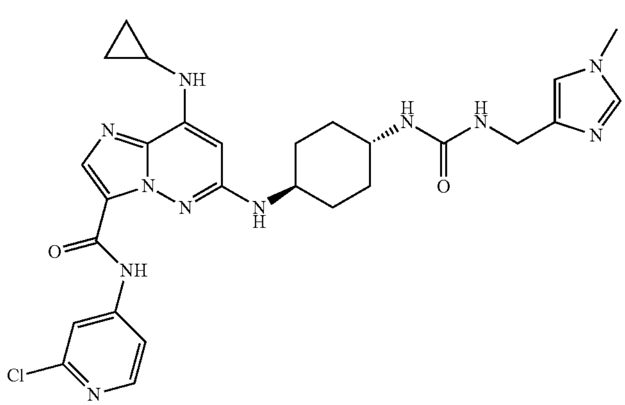 [SMILES: Cn1cnc(CNC(=O)N[C@H]2CC[C@H](Nc3cc(NC4CC4)c4ncc(C(=O)Nc5ccnc(Cl)c5)n4n3)CC2)c1] | N-(2-chloro-4-pyridinyl)-8-(cyclopropylamino)-6-((trans-4-(((((1-methyl-1H-imidazol-4-yl)methyl)carbamoyl)amino)cyclohexyl)amino)imidazo[1,2-b]pyridazine-3-carboxamide | 578.18 | 2.20 |

TABLE 6-continued

| Example | Structure | Name | [M + H] | HPLC Ret Time (min) |
|---|---|---|---|---|
| 272 | 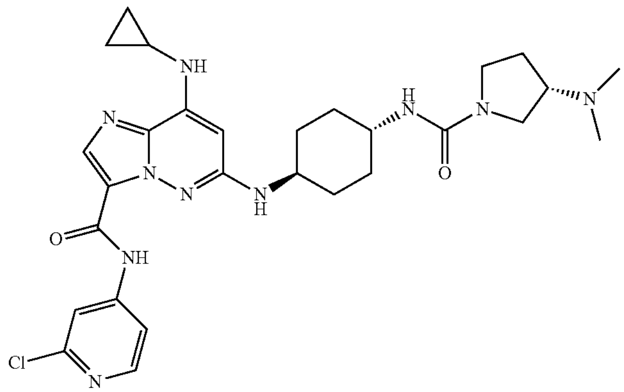 [SMILES: CN(C)[C@H]1CCN(C(=O)N[C@H]2CC[C@H](Nc3cc(NC4CC4)c4ncc(C(=O)Nc5ccnc(Cl)c5)n4n3)CC2)C1] | N-(2-chloro-4-pyridinyl)-8-(cyclopropylamino)-6-((trans-4-((((3S)-3-(dimethylamino)-1-pyrrolidinyl)carbonyl)amino)cyclohexyl)amino)imidazo[1,2-b]pyridazine-3-carboxamide | 581.21 | 2.18 |
| 273 | 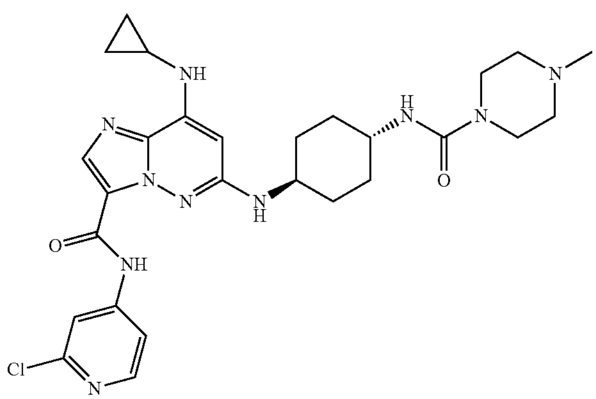 [SMILES: CN1CCN(C(=O)N[C@H]2CC[C@H](Nc3cc(NC4CC4)c4ncc(C(=O)Nc5ccnc(Cl)c5)n4n3)CC2)CC1] | N-(2-chloro-4-pyridinyl)-8-(cyclopropylamino)-6-((trans-4-(((4-methyl-1-piperazinyl)carbonyl)amino)cyclohexyl)amino)imidazo[1,2-b]pyridazine-3-carboxamide | 567.19 | 2.19 |
| 274 | 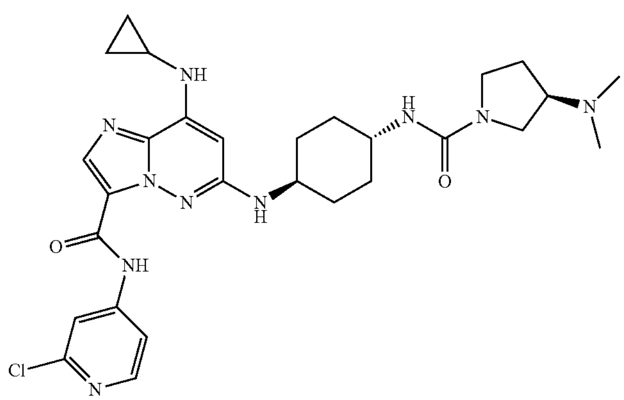 [SMILES: CN(C)[C@@H]1CCN(C(=O)N[C@H]2CC[C@H](Nc3cc(NC4CC4)c4ncc(C(=O)Nc5ccnc(Cl)c5)n4n3)CC2)C1] | N-(2-chloro-4-pyridinyl)-8-(cyclopropylamino)-6-((trans-4-((((3R)-3-(dimethylamino)-1-pyrrolidinyl)carbonyl)amino)cyclohexyl)amino)imidazo[1,2-b]pyridazine-3-carboxamide | 581.21 | 2.22 |

TABLE 6-continued

| Example | Structure | Name | [M + H] | HPLC Ret Time (min) |
|---|---|---|---|---|
| 275 | 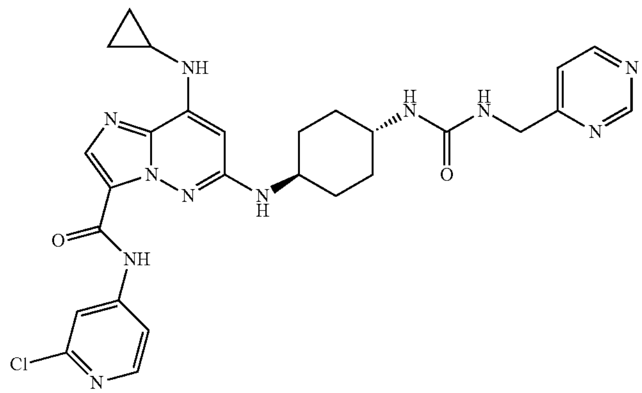 [SMILES: O=C(NCc1ccncn1)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-(((4-pyrimidinylmethyl)carbamoyl)amino)cyclohexyl)amino)imidazo[1,2-b]pyridazine-3-carboxamide | 576.15 | 2.24 |
| 276 | 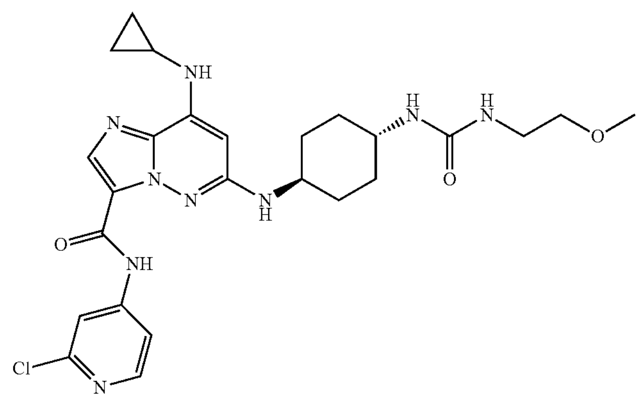 [SMILES: COCCNC(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-(((2-methoxyethyl)carbamoyl)amino)cyclohexyl)amino)imidazo[1,2-b]pyridazine-3-carboxamide | 542.14 | 2.28 |
| 277 | 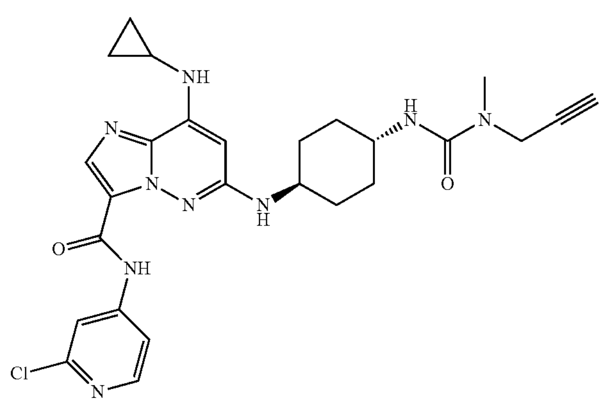 [SMILES: C#CCN(C)C(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-((methyl(2-propyn-1-yl)carbamoyl)amino)cyclohexyl)amino)imidazo[1,2-b]pyridazine-3-carboxamide | 536.14 | 2.38 |

TABLE 6-continued

| Example | Structure | Name | [M + H] | HPLC Ret Time (min) |
|---|---|---|---|---|
| 278 | 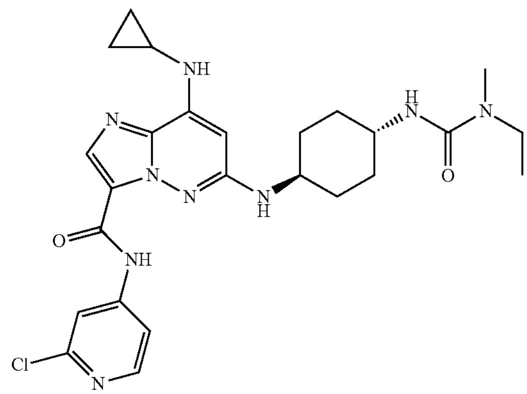 [SMILES: CCN(C)C(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-((ethyl(methyl)carbamoyl)amino)cyclohexyl)amino)imidazo[1,2-b]pyridazine-3-carboxamide | 526.13 | 2.46 |
| 279 | 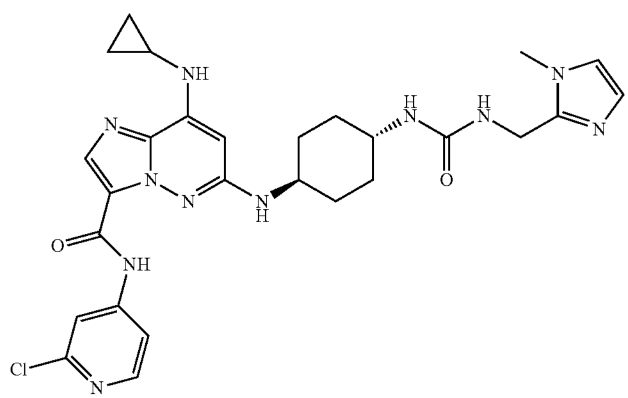 [SMILES: Cn1ccnc1CNC(=O)N[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-((((1-methyl-1H-imidazol-2-yl)methyl)carbamoyl)amino)cyclohexyl)amino)imidazo[1,2-b]pyridazine-3-carboxamide | 578.15 | 2.26 |
| 280 | 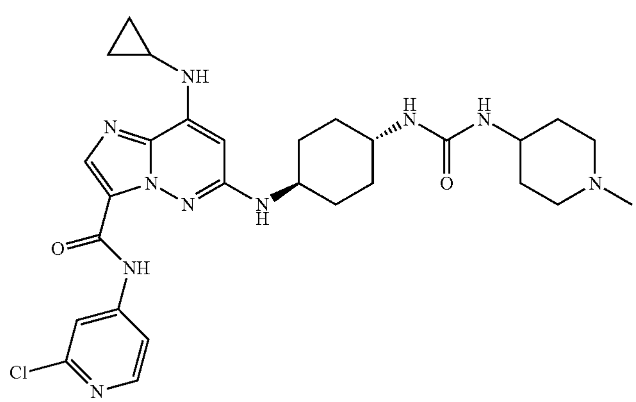 [SMILES: CN1CCC(NC(=O)N[C@H]2CC[C@H](Nc3cc(NC4CC4)c4ncc(C(=O)Nc5ccnc(Cl)c5)n4n3)CC2)CC1] | N-(2-chloro-4-pyridinyl)-8-(cyclopropylamino)-6-((trans-4-((((1-methyl-4-piperidinyl)carbamoyl)amino)cyclohexyl)amino)imidazo[1,2-b]pyridazine-3-carboxamide | 581.20 | 2.16 |

HPLC Conditions:

Waters XBridge 4.6 × 50 mm 5-um C18; A = 5:95 Acetonitrile:Water; B = 95:5 Acetonitrile:Water; Modifier = 10 mM NH4OAc; 0 to 100% in 4 min; flow 4 mL/min The following Examples in Table 7 may be prepared from 8B in a manner analogous the procedures described in Example 33.

TABLE 7

| Example | Structure | Name | [M + H] | HPLC Ret Time (min) |
|---|---|---|---|---|
| 281 | 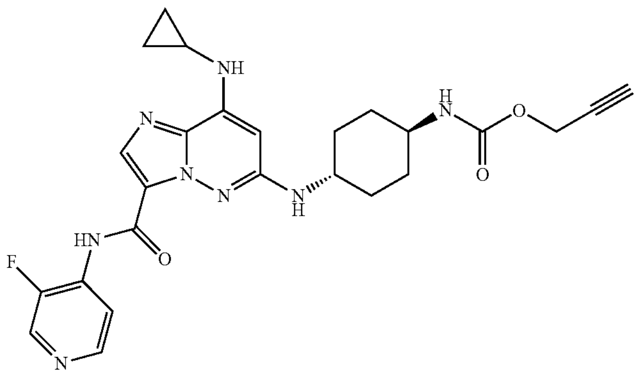 [SMILES: C#CCOC(=O)N[C@H]1CC[C@H](Nc2cc(NC3CC3)c3ncc(C(=O)Nc4ccncc4F)n3n2)CC1] | 2-propyn-1-yl (trans-4-((8-(cyclopropylamino)-3-((3-fluoro-4-pyridinyl)carbamoyl)imidazo[1,2-b]pyridazin-6-yl)amino)cyclohexyl)carbamate | 507.28 | 2.32[a] |
| 282 | 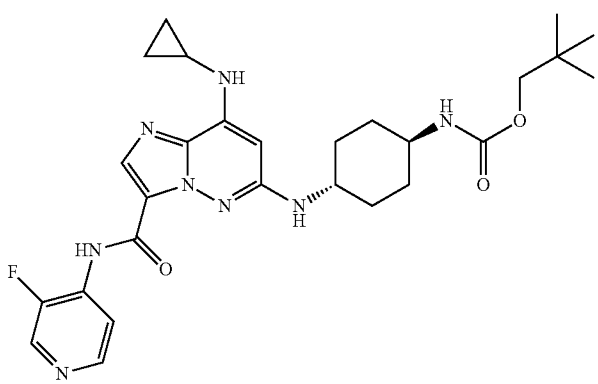 [SMILES: CC(C)(C)COC(=O)N[C@H]1CC[C@H](Nc2cc(NC3CC3)c3ncc(C(=O)Nc4ccncc4F)n3n2)CC1] | 2,2-dimethylpropyl (trans-4-((8-(cyclopropylamino)-3-((3-fluoro-4-pyridinyl)carbamoyl)imidazol[1,2-b]pyridazin-6-yl)amino)cyclohexyl)carbamate | 539.32 | 2.77[a] |
| 283 | 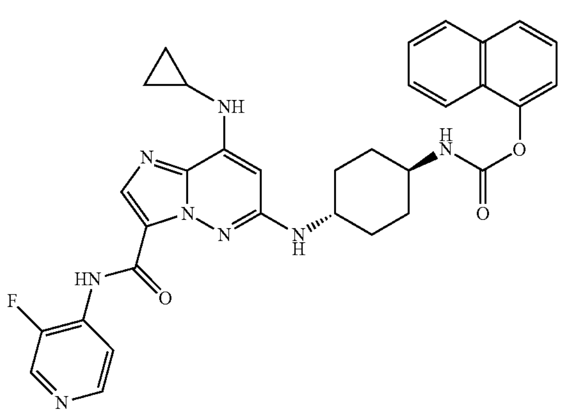 [SMILES: O=C(N[C@H]1CC[C@H](Nc2cc(NC3CC3)c3ncc(C(=O)Nc4ccncc4F)n3n2)CC1)Oc1cccc2ccccc12] | 1-naphthyl (trans-4-((8-(cyclopropylamino)-3-((3-fluoro-4-pyridinyl)carbamoyl)imidazo[1,2-b]pyridazin-6-yl)amino)cyclohexyl)carbamate | 595.32 | 2.87[a] |

TABLE 7-continued

| Example | Structure | Name | [M + H] | HPLC Ret Time (min) |
|---|---|---|---|---|
| 284 | 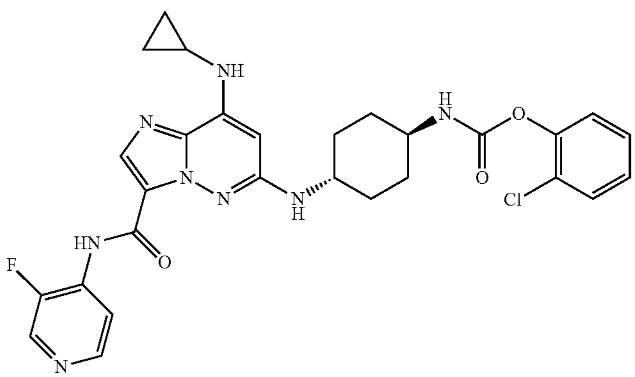 [SMILES: O=C(N[C@H]1CC[C@H](Nc2cc(NC3CC3)c3ncc(C(=O)Nc4ccncc4F)n3n2)CC1)Oc1ccccc1Cl] | 2-chlorophenyl (trans-4-((8-(cyclopropylamino)-3-((3-fluoro-4-pyridinyl)carbamoyl)imidazol[1,2-b]pyridazin-6-yl)amino)cyclohexyl)carbamate | 579.25 | 2.73[a] |
| 285 | 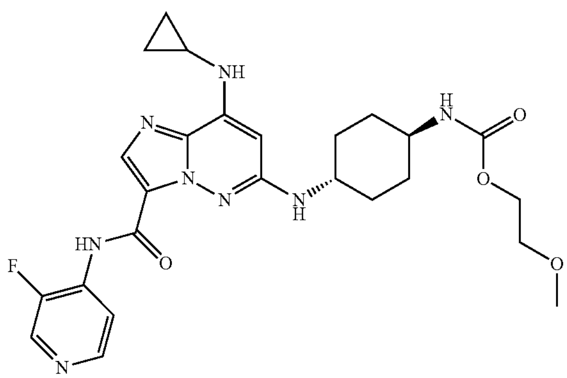 [SMILES: COCCOC(=O)N[C@H]1CC[C@H](Nc2cc(NC3CC3)c3ncc(C(=O)Nc4ccncc4F)n3n2)CC1] | 2-methoxyethyl (trans-4-((8-(cyclopropylamino)-3-((3-fluoro-4-pyridinyl)carbamoyl)imidazol[1,2-b]pyridazin-6-yl)amino)cyclohexyl)carbamate | 527.29 | 2.14[a] |
| 286 | 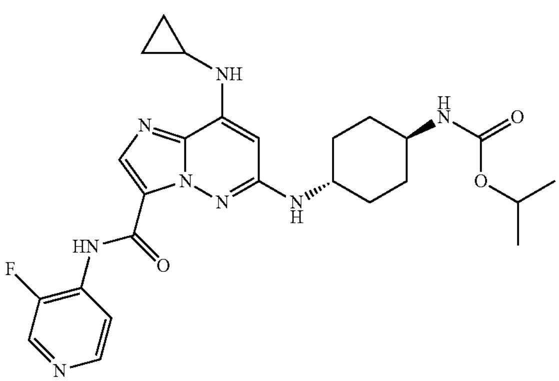 [SMILES: CC(C)OC(=O)N[C@H]1CC[C@H](Nc2cc(NC3CC3)c3ncc(C(=O)Nc4ccncc4F)n3n2)CC1] | isopropyl (trans-4-((8-cyclopropylamino)-3-((3-fluoro-4-pyridinyl)carbamoyl)imidazo[1,2-b]pyridazin-6-yl)amino)cyclohexyl)carbamate | 511.30 | 2.45[a] |
| 287 | 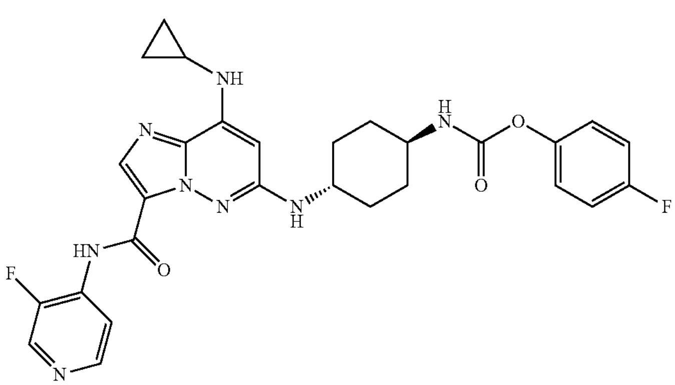 [SMILES: COc1ccc(OC(=O)N[C@H]2CC[C@H](Nc3cc(NC4CC4)c4ncc(C(=O)Nc5ccncc5F)n4n3)CC2)cc1] | 4-fluorophenyl (trans-4-((8-(cyclopropylamino)-3-((3-fluoro-4-pyridinyl)carbamoyl)imidazo[1,2-b]pyridazin-6-yl)amino)cyclohexyl)carbamate | 563.27 | 2.66[a] |

TABLE 7-continued

| Example | Structure | Name | [M + H] | HPLC Ret Time (min) |
|---|---|---|---|---|
| 288 | 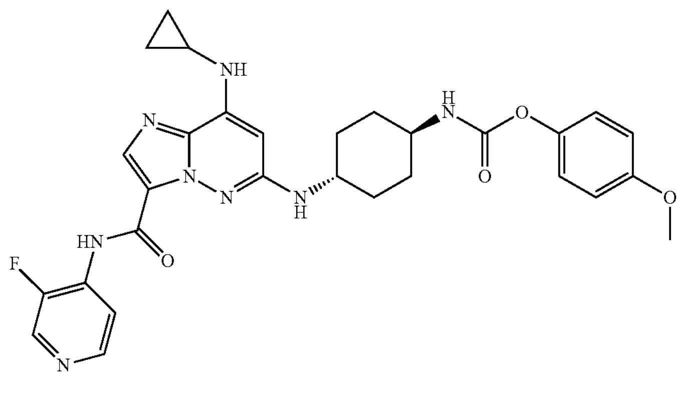 | 4-methoxyphenyl (trans-4-((8-(cyclopropylamino)-3-((3-fluoro-4-pyridinyl)carbamoyl)imidazo[1,2-b]pyridazin-6-yl)amino)cyclohexyl)carbamate | 574.98 | 2.65[a] |
| 289 | 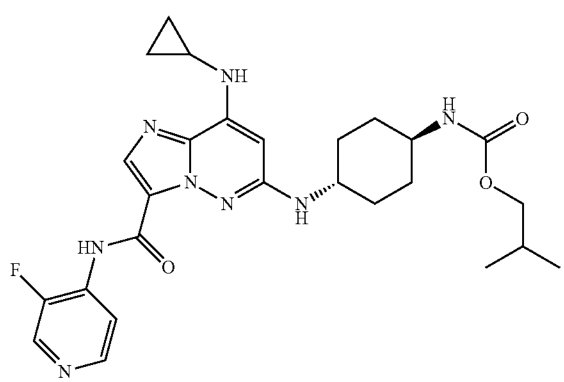 [SMILES: CC(C)COC(=O)N[C@H]1CC[C@H](Nc2cc(NC3CC3)c3ncc(C(=O)Nc4ccncc4F)n3n2)CC1] | isobutyl (trans-4-((8-(cyclopropylamino)-3-((3-fluoro-4-pyridinyl)carbamoyl)imidazo[1,2-b]pyridazin-6-yl)amino)cyclohexyl)carbamate | 524.98 | 2.71[a] |
| 290 | 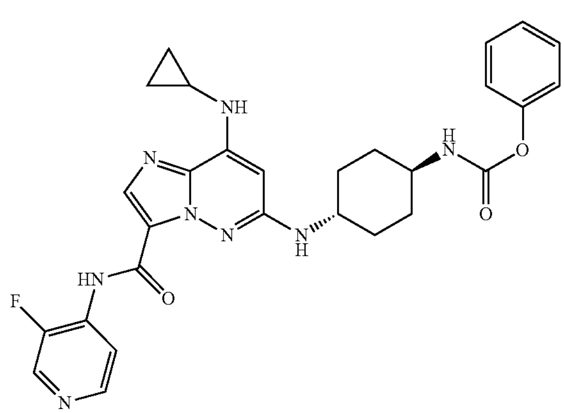 [SMILES: O=C(N[C@H]1CC[C@H](Nc2cc(NC3CC3)c3ncc(C(=O)Nc4ccncc4F)n3n2)CC1)Oc1ccccc1] | phenyl (trans-4-((8-(cyclopropylamino)-3-((3-fluoro-4-pyridinyl)carbamoyl)imidazol[1,2-b]pyridazin-6-yl)amino)cyclohexyl)carbamate | 545.30 | 2.59[a] |

TABLE 7-continued

| Example | Structure | Name | [M + H] | HPLC Ret Time (min) |
|---|---|---|---|---|
| 291 | 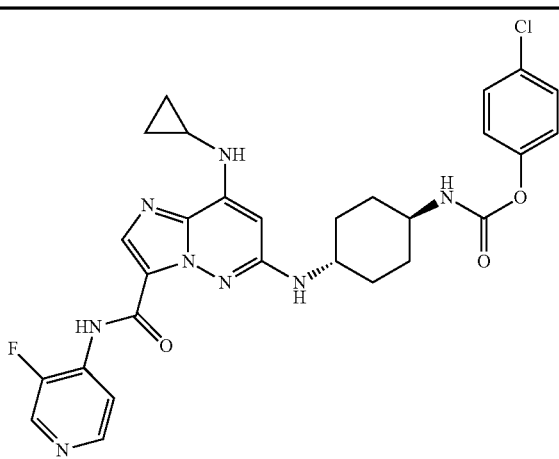 | 4-chlorophenyl (trans-4-((8-(cyclopropylamino)-3-((3-fluoro-4-pyridinyl)carbamoyl)imidazo[1,2-b]pyridazin-6-yl)amino)cyclohexyl)carbamate | 579.25 | 2.83[a] |
| 292 | 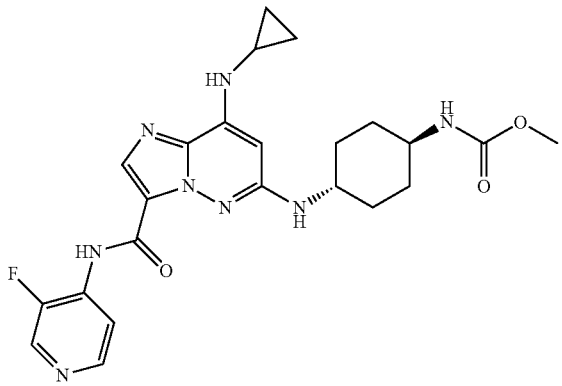 [SMILES: COC(=O)N[C@H]1CC[C@H](Nc2cc(NC3CC3)c3ncc(C(=O)Nc4ccncc4F)n3n2)CC1] | methyl (trans-4-((8-(cyclopropylamino)-3-((3-fluoro-4-pyridinyl)carbamoyl)imidazo[1,2-b]pyridazin-6-yl)amino)cyclohexyl)carbamate | 483.27 | 2.14[a] |
| 293 | 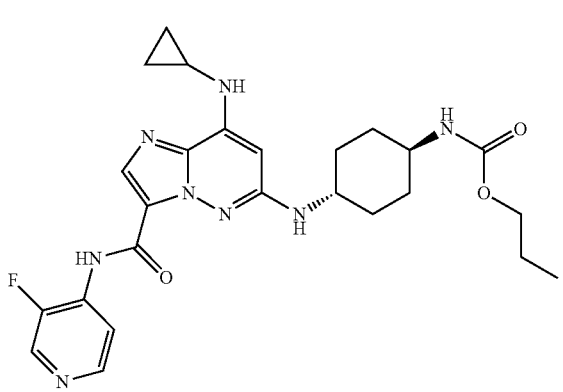 [SMILES: CCCOC(=O)N[C@H]1CC[C@H](Nc2cc(NC3CC3)c3ncc(C(=O)Nc4ccncc4F)n3n2)CC1] | propyl (trans-4-((8-(cyclopropylamino)-3-((3-fluoro-4-pyridinyl)carbamoyl)imidazo[1,2-b]pyridazin-6-yl)amino)cyclohexyl)carbamate | 511.32 | 2.47[a] |

TABLE 7-continued

| Example | Structure | Name | [M + H] | HPLC Ret Time (min) |
|---|---|---|---|---|
| 294 | 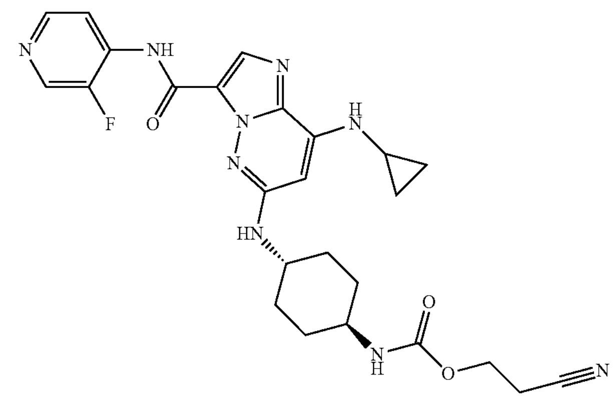 [SMILES: N#CCCOC(=O)N[C@H]1CC[C@H](Nc2cc(NC3CC3)c3ncc(C(=O)Nc4ccncc4F)n3n2)CC1] | 2-cyanoethyl (trans-4-((8-(cyclopropylamino)-3-((3-fluoro-4-pyridinyl)carbamoyl)imidazol[1,2-b]pyridazin-6-yl)amino)cyclohexyl)carbamate | 521.97 | 2.61[a] |
| 295 | 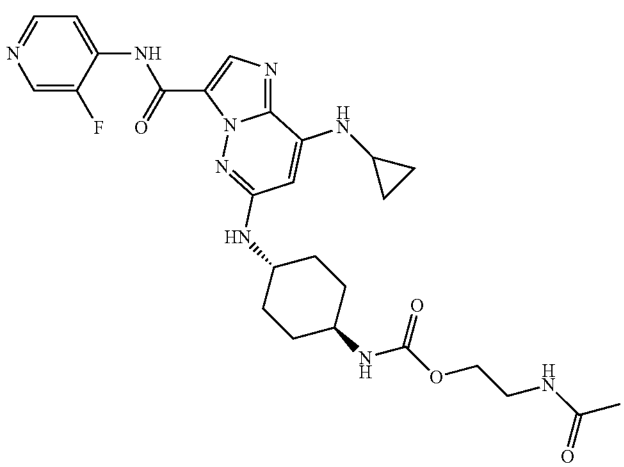 [SMILES: CC(=O)NCCOC(=O)N[C@H]1CC[C@H](Nc2cc(NC3CC3)c3ncc(C(=O)Nc4ccncc4F)n3n2)CC1] | 2-acetamidoethyl (trans-4-((8-(cyclopropylamino)-3-((3-fluoro-4-pyridinyl)carbamoyl)imidazol[1,2-b]pyridazin-6-yl)amino)cyclohexyl)carbamate | 554.00 | 2.42[a] |
| 296 | 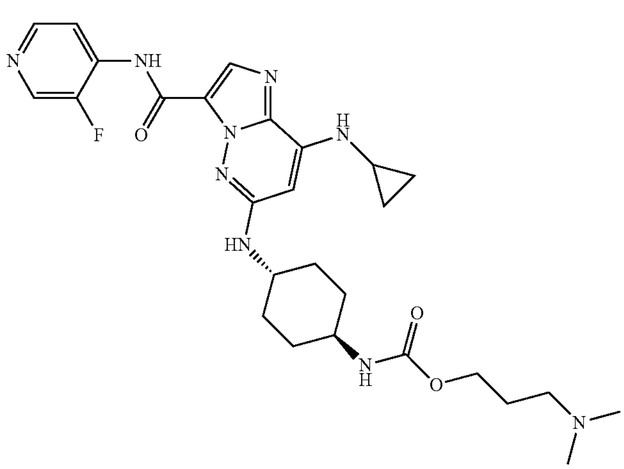 [SMILES: CN(C)CCCOC(=O)N[C@H]1CC[C@H](Nc2cc(NC3CC3)c3ncc(C(=O)Nc4ccncc4F)n3n2)CC1] | 3-(dimethylamino)propyl (trans-4-((8-(cyclopropylamino)-3-((3-fluoro-4-pyridinyl)carbamoyl)imidazol[1,2-b]pyridazin-6-yl)amino)cyclohexyl)carbamate | 554.03 | 2.3[a] |

TABLE 7-continued

| Example | Structure | Name | [M + H] | HPLC Ret Time (min) |
|---|---|---|---|---|
| 297 | 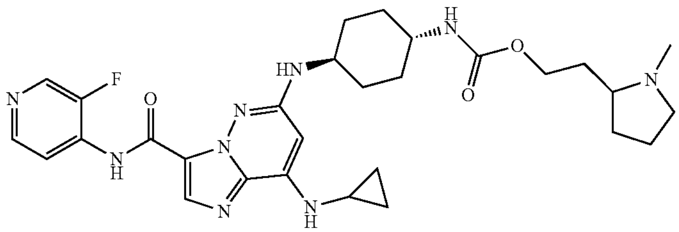 [SMILES: CN1CCCC1CCOC(=O)N[C@H]1CC[C@H](Nc2cc(NC3CC3)c3ncc(C(=O)Nc4ccncc4F)n3n2)CC1] | 2-(1-methyl-2-pyrrolidinyl)ethyl (trans-4-((8-(cyclopropylamino)-3-((3-fluoro-4-pyridinyl)carbamoyl)imidazo[1,2-b]pyridazin-6-yl)amino)cyclohexyl)carbamate | 580.03 | 2.39[a] |
| 298 | 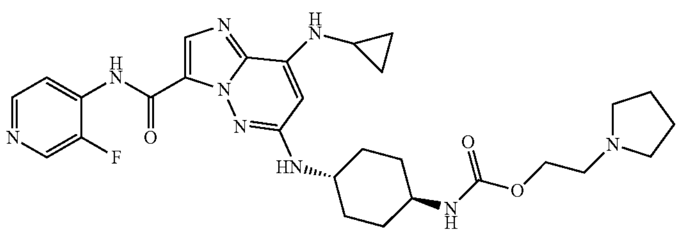 [SMILES: O=C(N[C@H]1CC[C@H](Nc2cc(NC3CC3)c3ncc(C(=O)Nc4ccncc4F)n3n2)CC1)OCCN1CCCC1] | 2-(1-pyrrolidinyl)ethyl (trans-4-((8-(cyclopropylamino)-3-((3-fluoro-4-pyridinyl)carbamoyl)imidazo[1,2-b]pyridazin-6-yl)amino)cyclohexyl)carbamate | 566.01 | 2.36[a] |
| 299 | 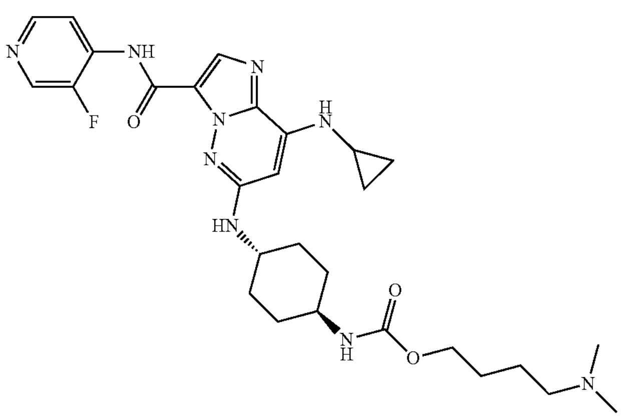 [SMILES: CN(C)CCCCOC(=O)N[C@H]1CC[C@H](Nc2cc(NC3CC3)c3ncc(C(=O)Nc4ccncc4F)n3n2)CC1] | 4-(diethylamino)butyl (trans-4-((8-(cyclopropylamino)-3-((3-fluoro-4-pyridinyl)carbamoyl)imidazol[1,2-b]pyridazin-6-yl)amino)cyclohexyl)carbamate | 568.03 | 2.36[a] |
| 300 | 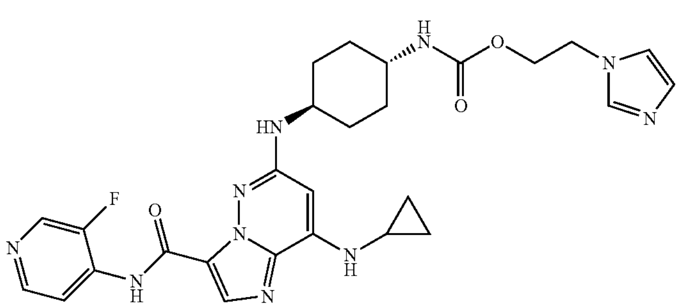 [SMILES: O=C(N[C@H]1CC[C@H](Nc2cc(NC3CC3)c3ncc(C(=O)Nc4ccncc4F)n3n2)CC1)OCCn1ccnc1] | 2-(1H-imidazol-1-yl)ethyl (trans-4-((8-(cyclopropylamino)-3-((3-fluoro-4-pyridinyl)carbamoyl)imidazo[1,2-b]pyridazin-6-yl)amino)cyclohexyl)carbamate | 562.98 | 2.43[a] |

| Example | Structure | Name | [M + H] | HPLC Ret Time (min) |
|---|---|---|---|---|
| 301 | 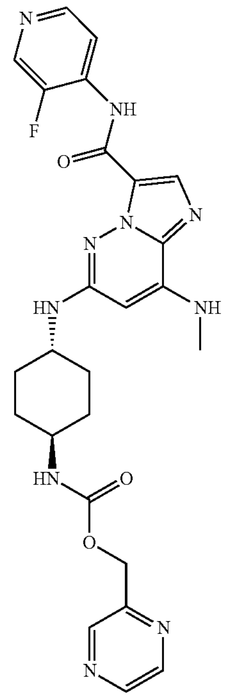 [SMILES: CNc1cc(N[C@H]2CC[C@H](NC(=O)OCc3cnccn3)CC2)nn2c(C(=O)Nc3ccncc3F)cnc12] | 2-pyrazinylmethyl (trans-4-((8-(cyclopropylamino)-3-((3-fluoro-4-pyridinyl)carbamoyl)imidazo[1,2-b]pyridazin-6-yl)amino)cyclohexyl)carbamate | 560.96 | 2.52[a] |
| 302 | 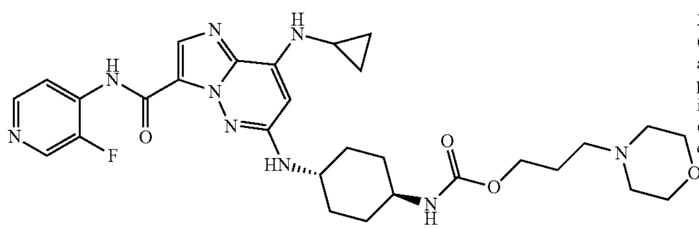 [SMILES: O=C(N[C@H]1CC[C@H](Nc2cc(NC3CC3)c3ncc(C(=O)Nc4ccncc4F)n3n2)CC1)OCCCN1CCOCC1] | 3-(4-morpholinyl)propyl (trans-4-((8-(cyclopropylamino)-3-((3-fluoro-4-pyridinyl)carbamoyl)imidazo[1,2-b]pyridazin-6-yl)amino)cyclohexyl)carbamate | 596.02 | 2.44[a] |
| 303 | 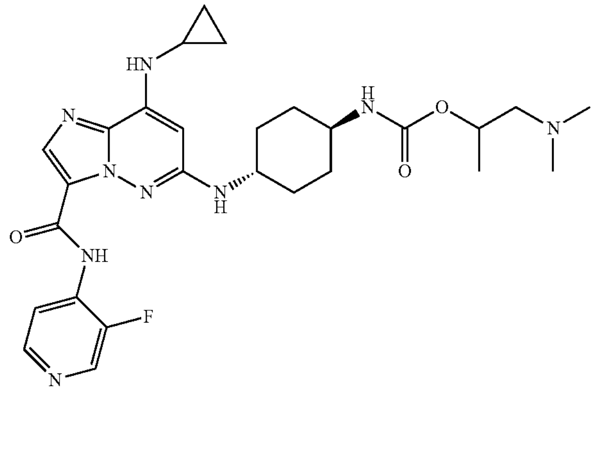 [SMILES: CC(CN(C)C)OC(=O)N[C@H]1CC[C@H](Nc2cc(NC3CC3)c3ncc(C(=O)Nc4ccncc4F)n3n2)CC1] | 2-(dimethylamino)-1-methylethyl (trans-4-((8-(cyclopropylamino)-3-((3-fluoro-4-pyridinyl)carbamoyl)imidazol[1,2-b]pyridazin-6-yl)amino)cyclohexyl)carbamate | 554.3 | 1.945[a] |

TABLE 7-continued

| Example | Structure | Name | [M + H] | HPLC Ret Time (min) |
|---|---|---|---|---|
| 304 | 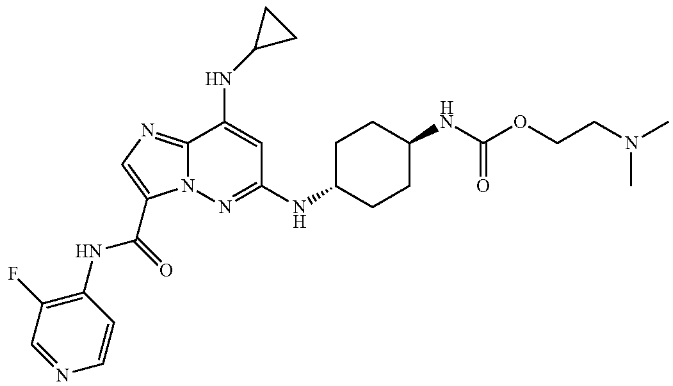 [SMILES: CN(C)CCOC(=O)N[C@H]1CC[C@H](Nc2cc(NC3CC3)c3ncc(C(=O)Nc4ccncc4F)n3n2)CC1] | 2-(dimethylamino)ethyl (trans-4-((8-(cyclopropyl-amino)-3-((3-fluoro-4-pyridinyl)carbamoyl) imidazo[1,2-b]pyridazin-6-yl)amino)cyclohexyl) carbamate | 540.37 | 1.41[c] |

HPLC Conditions:
[a]Waters XBridge 4.6 × 50 mm 5 um C18 Column: 0%-100% solvent B. Solvent B: 95% CH$_3$CN, 5% H$_2$O, Modifier = 10 mM NH$_4$OAc). Solvent A: 5% CH$_3$CN, 95% H$_2$O, Modifier = 10 mM NH$_4$OAc). 4 min gradient, monitored at 220 nm.
[b]Phenomenex Luna 5 micron C18 4.6 × 30 mm: 0 to 100 B in 2 min with 1 min hold time, Flow rate = 5 mL/min, detection at 254 nm, Solvent A: 10% methanol/90% water/0.1% TFA; Solvent B: 10% water/90% methanol/0.1% TFA.

The following Examples in Table 8 may be prepared from 23C in a manner analogous the procedures described in Example 33.

TABLE 8

| Example | Structure | Name | [M + H] | HPLC Ret Time (min) |
|---|---|---|---|---|
| 305 | 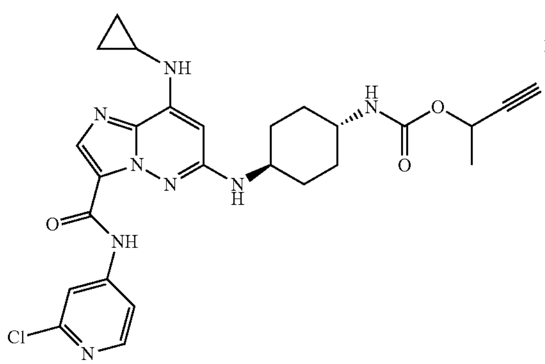 | 1-methyl-2-propyn-1-yl (trans-4-((3-((2-chloro-4-pyridinyl)carbamoyl)-8-(cyclopropylamino) imidazo[1,2-b]pyridazin-6-yl)amino)cyclohexyl) carbamate | 536.91 | 2.79 |
| 306 | 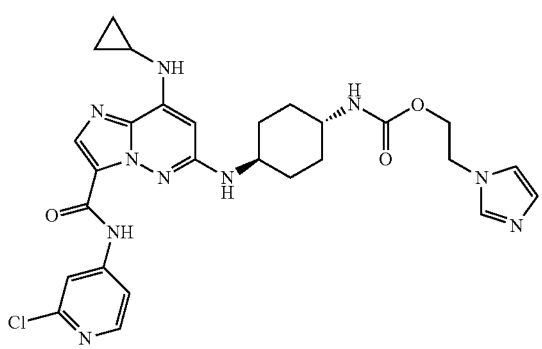 [SMILES: O=C(N[C@H]1CC[C@H](Nc2cc(NC3CC3)c3ncc(C(=O)Nc4ccnc(Cl)c4)n3n2)CC1)OCCn1ccnc1] | 2-(1H-imidazol-1-yl)ethyl (trans-4-((3-((2-chloro-4-pyridinyl)carbamoyl)-8-(cyclopropylamino) imidazo[1,2-b]pyridazin-6-yl)amino)cyclohexyl) carbamate | 578.88 | 2.26 |

TABLE 8-continued

| Example | Structure | Name | [M + H] | HPLC Ret Time (min) |
|---|---|---|---|---|
| 307 | 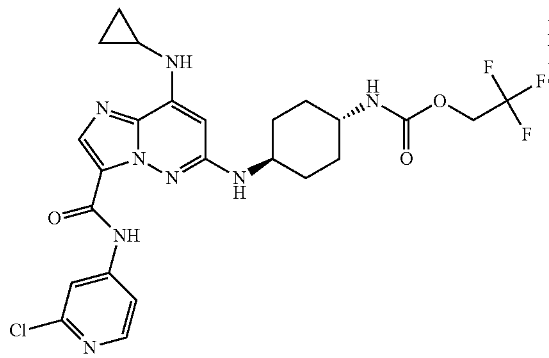 | 2,2,2-trifluoroethyl (trans-4-((3-((2-chloro-4-pyridinyl)carbamoyl)-8-(cyclopropylamino) imidazo[1,2-b]pyridazin-6-yl)amino)cyclohexyl) carbamate | 566.82 | 2.77 |

HPLC Conditions:
Waters XBridge 4.6 × 50 mm 5-um C18; A = 5:95 Acetonitrile:Water; B = 95:5 Acetonitrile:Water, Modifier = 10 mM NH4OAc; 0 to 100% in 4 min; flow 4 mL/min The following Examples in Table 9 may be prepared from 25B in a manner analogous the procedures described in Example 33.

TABLE 9

| Example | Structure | Name | [M + H] | HPLC Ret Time (min) |
|---|---|---|---|---|
| 308 | 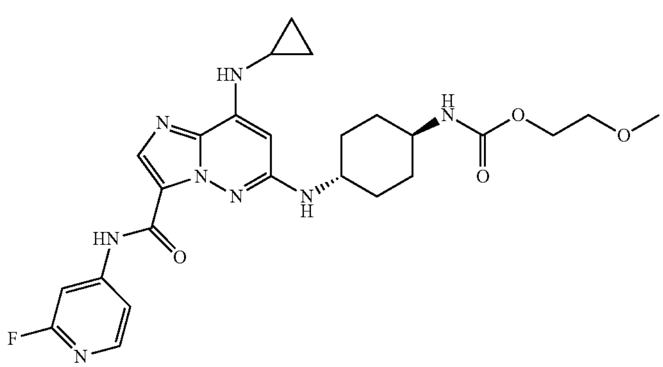 [SMILES: COCCOC(=O)N[C@H]1CC[C@H](Nc2cc(NC3CC3)c3ncc(C(=O)Nc4ccnc(F)c4)n3n2)CC1] | 2-methoxyethyl (trans-4-((8-(cyclo-propyl-amino)-3-((2-fluoro-4-pyridinyl)carbamoyl)imidazo [1,2-b]pyridazin-6-yl)amino) cyclohexyl)carbamate | 527.19 | 1.842 |
| 309 | 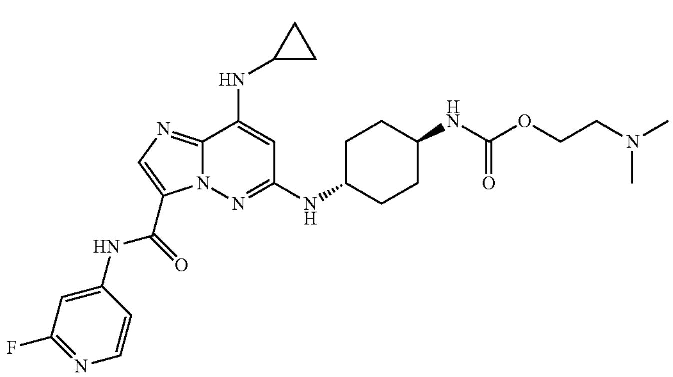 [SMILES: CN(C)CCOC(=O)N[C@H]1CC[C@H](Nc2cc(NC3CC3)c3ncc(C(=O)Nc4ccnc(F)c4)n3n2)CC1] | 2-(dimethylamino)ethyl (trans 4-((8-(cyclopropylamino)-3-((2-fluoro-4-pyridinyl)carbamoyl) imidazo[1,2-b]pyridazin-6-yl) amino)cyclohexyl)carbamate | 540.21 | 1.555 |

HPLC Conditions:
Phenomenex Luna 5 micron C18 4.6 × 30 mm: 0 to 100 B in 2 min with 1 min hold time, Flow rate = 5 mL/min, detection at 254 nm, Solvent A: 10% methanol/90% water/0.1% TFA; Solvent B: 10% water/90% methanol/0.1% TFA.

The following Examples in Table 10 may be prepared from 8B in a manner analogous the procedures described in Example 25.

TABLE 10

| Example | Structure | Name | [M + H] | HPLC Ret Time (min) |
|---|---|---|---|---|
| 310 | 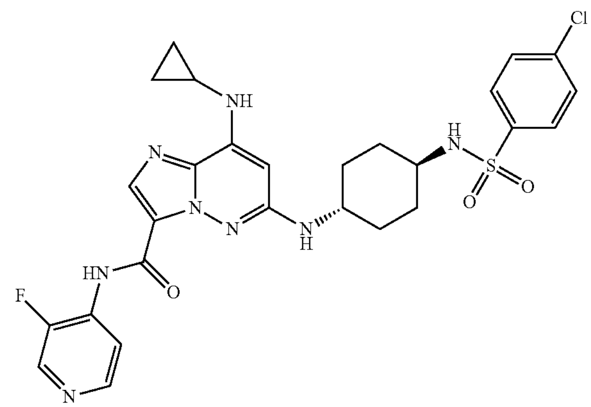 [SMILES: O=C(Nc1ccncc1F)c1cnc2c(NC3CC3)cc(N[C@H]3CC[C@H](NS(=O)(=O)c4ccc(Cl)cc4)CC3)nn12] | 6-((trans-4-(((4-chlorophenyl)sulfonyl)amino)cyclohexyl)amino)-8-(cyclopropylamino)-N-(3-fluoro-4-pyridinyl)imidazol[1,2-b]pyridazine-3-carboxamide | 598.89 | 2.74[a] |
| 311 | 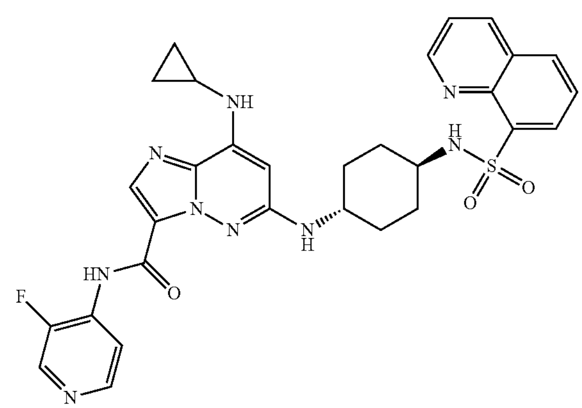 [SMILES: O=C(Nc1ccncc1F)c1cnc2c(NC3CC3)cc(N[C@H]3CC[C@H](NS(=O)(=O)c4cccc5cccnc45)CC3)nn12] | 8-(cyclopropylamino)-N-(3-fluoro-4-pyridinyl)-6-((trans-4-((8-quinolinylsulfonyl)amino)cyclohexyl)amino)imidazol[1,2-b]pyridazine-3-carboxamide | 615.95 | 2.55[a] |
| 312 | 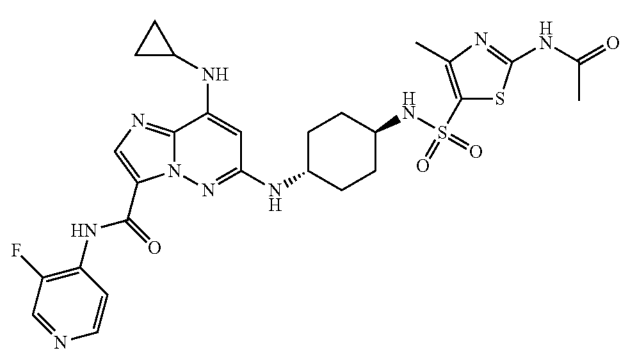 [SMILES: CC(=O)Nc1nc(C)c(S(=O)(=O)N[C@H]2CC[C@H](Nc3cc(NC4CC4)c4ncc(C(=O)Nc5ccncc5F)n4n3)CC2)s1] | 6-((trans-4-(((2-acetamido-4-methyl-1,3-thiazol-5-yl)sulfonyl)amino)cyclohexyl)amino)-8-(cyclopropylamino)-N-(3-fluoro-4-pyridinyl)imidazo[1,2-b]pyridazine-3-carboxamide | 643.28 | 2.23[a] |

TABLE 10-continued

| Example | Structure | Name | [M + H] | HPLC Ret Time (min) |
|---|---|---|---|---|
| 313 | 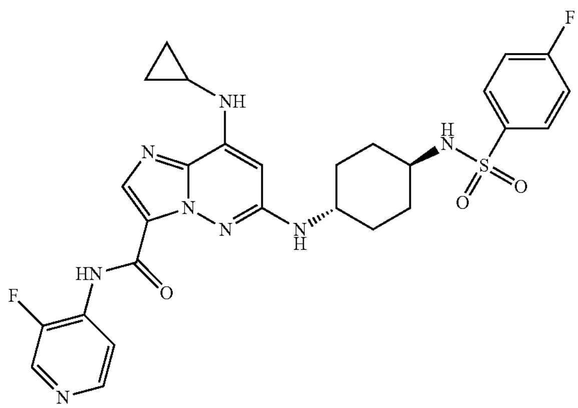 [SMILES: O=C(Nc1ccncc1F)c1cnc2c(NC3CC3)cc(N[C@H]3CC[C@H](NS(=O)(=O)c4ccc(F)cc4)CC3)nn12] | 8-(cyclopropylamino)-6-((trans-4-(((4-fluorophenyl)sulfonyl)amino)cyclohexyl)amino)-N-(3-fluoro-4-pyridinyl)imidazo[1,2-b]pyridazine-3-carboxamide | 583.26 | 2.52[a] |
| 314 | 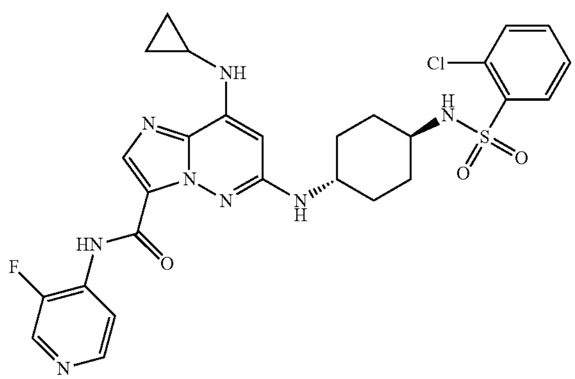 [SMILES: O=C(Nc1ccncc1F)c1cnc2c(NC3CC3)cc(N[C@H]3CC[C@H](NS(=O)(=O)c4ccccc4Cl)CC3)nn12] | 6-((trans-4-(((2-chlorophenyl)sulfonyl)amino)cyclohexyl)amino)-8-(cyclopropylamino)-N-(3-fluoro-4-pyridinyl)imidazol[1,2-b]pyridazine-3-carboxamide | 599.22 | 2.56[a] |
| 315 | 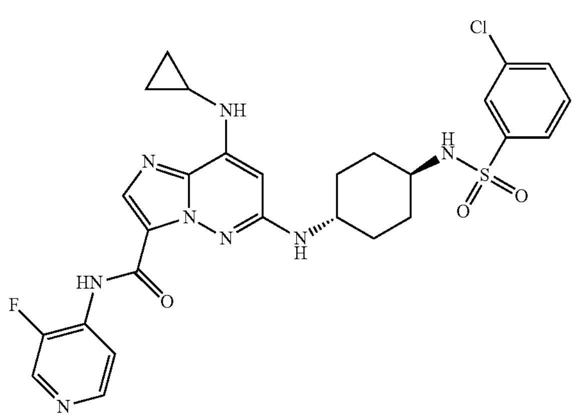 [SMILES: O=C(Nc1ccncc1F)c1cnc2c(NC3CC3)cc(N[C@H]3CC[C@H](NS(=O)(=O)c4cccc(Cl)c4)CC3)nn12] | 6-((trans-4-(((3-chlorophenyl)sulfonyl)amino)cyclohexyl)amino)-8-(cyclopropylamino)-N-(3-fluoro-4-pyridinyl)imidazo[1,2-b]pyridazine-3-carboxamide | 599.22 | 2.66[a] |

TABLE 10-continued

| Example | Structure | Name | [M + H] | HPLC Ret Time (min) |
|---|---|---|---|---|
| 316 | 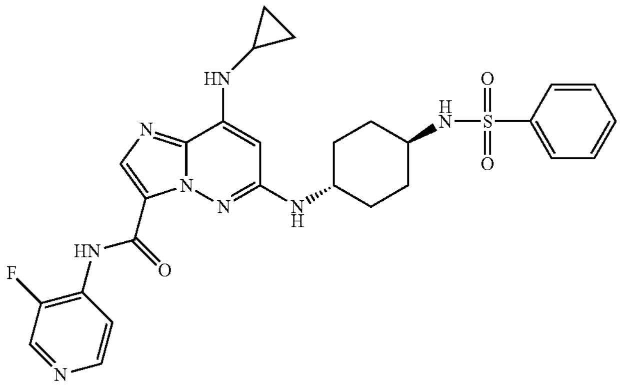 [SMILES: O=C(Nc1ccncc1F)c1cnc2c(NC3CC3)cc(N[C@H]3CC[C@H](NS(=O)(=O)c4ccccc4)CC3)nn12] | 8-(cyclopropylamino)-N-(3-fluoro-4-pyridinyl)-6-((trans-4-((phenylsulfonyl)amino)cyclohexyl)amino)imidazo[1,2-b]pyridazine-3-carboxamide | 565.29 | 1.71[a] |
| 317 | 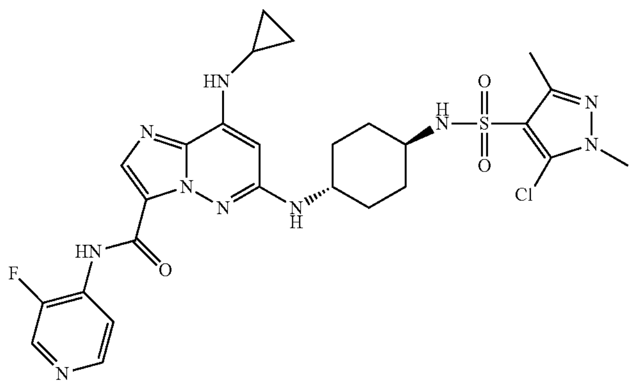 [SMILES: Cc1nn(C)c(Cl)c1S(=O)(=O)N[C@H]1CC[C@H](Nc2cc(NC3CC3)c3ncc(C(=O)Nc4ccncc4F)n3n2)CC1] | 6-((trans-4-(((5-chloro-1,3-dimethyl-1H-pyrazol-4-yl)sulfonyl)amino)cyclohexyl)amino)-8-(cyclopropylamino)-N-(3-fluoro-4-pyridinyl)imidazo[1,2-b]pyridazine-3-carboxamide | 617.29 | 1.65[a] |
| 318 | 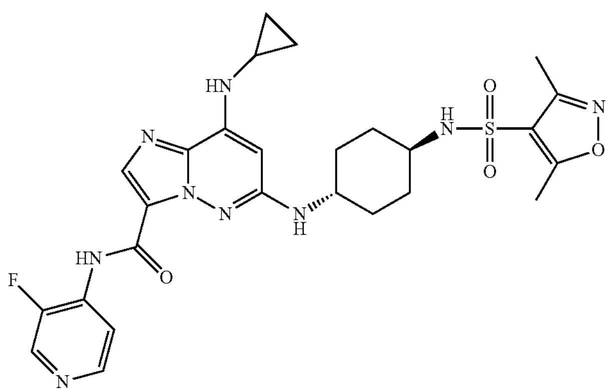 [SMILES: Cc1noc(C)c1S(=O)(=O)N[C@H]1CC[C@H](Nc2cc(NC3CC3)c3ncc(C(=O)Nc4ccncc4F)n3n2)CC1] | 8-(cyclopropylamino)-6-((trans-4-(((3,5-dimethyl-4-isoxazolyl)sulfonyl)amino)cyclohexyl)amino)-N-(3-fluoro-4-pyridinyl)imidazo[1,2-b]pyridazine-3-carboxamide | 584.21 | 1.72[a] |
| 319 | 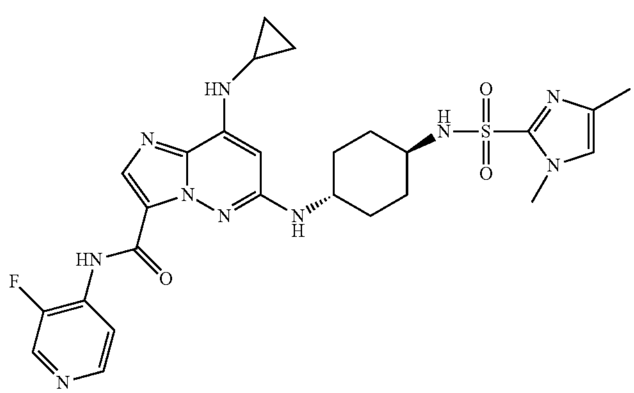 [SMILES: Cc1cn(C)c(S(=O)(=O)N[C@H]2CC[C@H](Nc3cc(NC4CC4)c4ncc(C(=O)Nc5ccncc5F)n4n3)CC2)n1] | 8-(cyclopropylamino)-6-((trans-4-(((1,4-dimethyl-1H-imidazol-2-yl)sulfonyl)amino)cyclohexyl)amino)-N-(3-fluoro-4-pyridinyl)imidazo[1,2-b]pyridazine-3-carboxamide | 583.32 | 1.47[a] |

TABLE 10-continued

| Example | Structure | Name | [M + H] | HPLC Ret Time (min) |
|---|---|---|---|---|
| 320 | 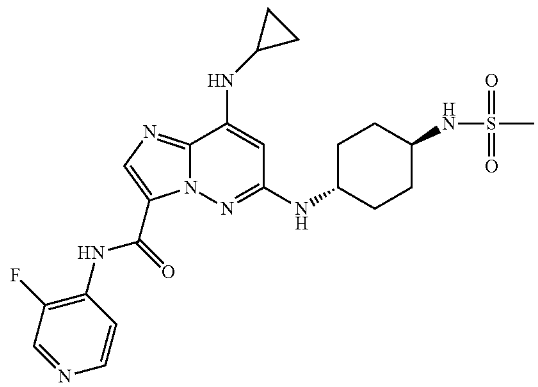 [SMILES: CS(=O)(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-((methylsulfonyl)amino)cyclohexyl)amino)imidazo[1,2-b]pyridazine-3-carboxamide | 503.26 | 1.505[b] |
| 321 | 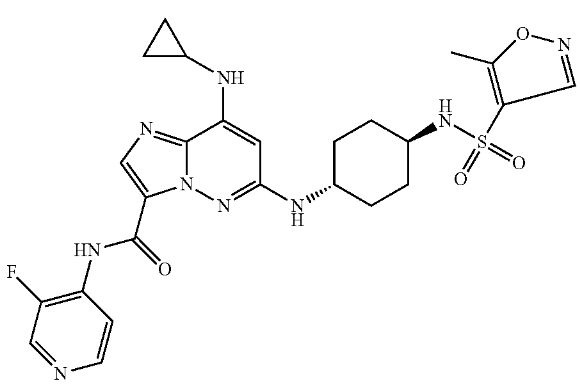 [SMILES: Cc1oncc1S(=O)(=O)N[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-(((5-methyl-4-isoxazolyl)sulfonyl)amino)cyclohexyl)amino)imidazo[1,2-b]pyridazine-3-carboxamide | 570.24 | 1.79[a] |

HPLC Conditions:

[a] Waters XBridge 4.6 × 50 mm 5 um C18 Column: 0%-100% solvent B. Solvent B: 95% $CH_3CN$, 5% $H_2O$, Modifier = 10 mM $NH_4OAc$). Solvent A: (5% $CH_3CN$, 95% $H_2O$, Modifier = 10 mM $NH_4OAc$). 4 min gradient, monitored at 220 nm

[b] Phenomenex Luna 5 micron C18 4.6 × 30 mm: 0 to 100 B in 2 min with 1 min hold time, Flow rate = 5 mL/min, detection at 254 nm, Solvent A: 10% methanol/90% water/0.1% TFA; Solvent B: 10% water/90% methanol/0.1% TFA.

The following Examples in Table 5 may be prepared in a manner analogous to the procedures described in Example 25.

TABLE 11

| Example | Structure | Name | [M + H] | HPLC Ret Time (min) |
|---|---|---|---|---|
| 322 | 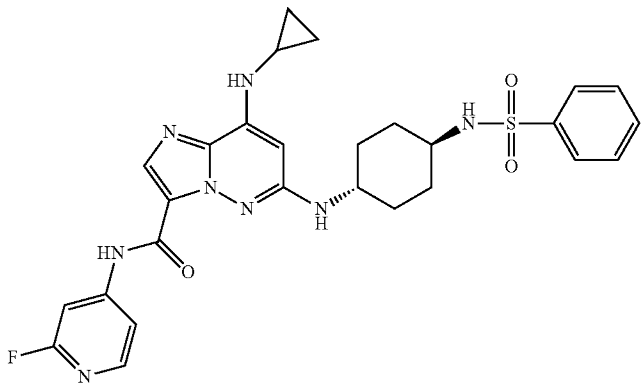 [SMILES: O=C(Nc1ccnc(F)c1)c1cnc2c(NC3CC3)cc(N[C@H]3CC[C@H](NS(=O)(=O)c4ccccc4)CC3)nn12] | 8-(cyclopropylamino)-N-(2-fluoro-4-pyridinyl)-6-((trans-4-((phenylsulfonyl)amino)cyclohexyl)amino)imidazo[1,2-b]pyridazine-3-carboxamide | 565.25 | 1.910 |

HPLC Conditions:
Phenomenex Luna 5 micron C18 4.6 × 30 mm: 0 to 100 B in 2 min with 1 min hold time, Flow rate = 5 mL/min, detection at 254 nm, Solvent A: 10% methanol/90% water/0.1% TFA; Solvent B: 10% water/90% methanol/0.1% TFA.

The following Examples in Table 12 may be prepared from 8B in a manner analogous to the procedures described in Examples 1-4.

TABLE 12

| Example | Structure | Name | [M + H] | HPLC Ret Time (min) |
|---|---|---|---|---|
| 323 | 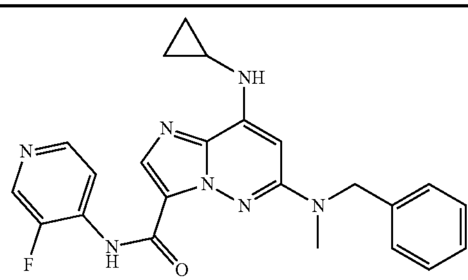 | 6-(benzyl(methyl)amino)-8-(cyclopropylamino)-N-(3-fluoro-4-pyridinyl)imidazo[1,2-b]pyridazine-3-carboxamide | 431.47 | 2.781[a] |
| 324 | 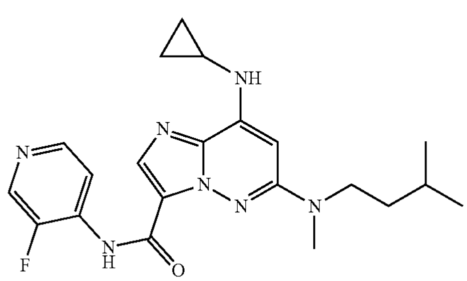 [SMILES: CC(C)CCN(C)c1cc(NC2CC2)c2ncc(C(=O)Nc3ccncc3F)n2n1] | 8-(cyclopropylamino)-N-(3-fluoro-4-pyridinyl)-6-(methyl(3-methylbutyl)amino)imidazo[1,2-b]pyridazine-3-carboxamide | 411.48 | 3.115[a] |

TABLE 12-continued

| Example | Structure | Name | [M + H] | HPLC Ret Time (min) |
|---|---|---|---|---|
| 325 | 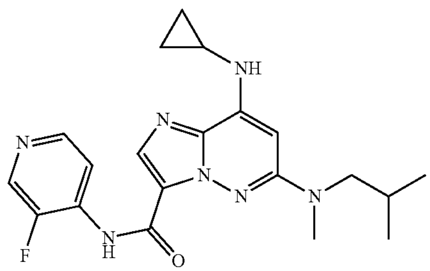 [SMILES: CC(C)CN(C)c1cc(NC2CC2)c2ncc(C(=O)Nc3ccncc3F)n2n1] | 8-(cyclopropylamino)-N-(3-fluoro-4-pyridinyl)-6-(isobutyl(methyl)amino)imidazo[1,2-b]pyridazine-3-carboxamide | 397.45 | 2.886[a] |
| 326 | 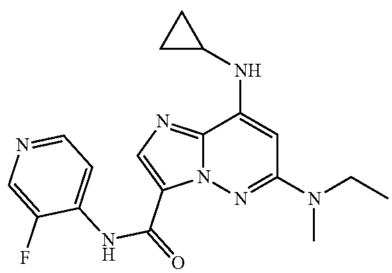 [SMILES: CCN(C)c1cc(NC2CC2)c2ncc(C(=O)Nc3ccncc3F)n2n1] | 8-(cyclopropylamino)-6-(ethyl(methyl)amino)-N-(3-fluoro-4-pyridinyl)imidazo[1,2-b]pyridazine-3-carboxamide | 369.4 | 2.485[a] |
| 327 | 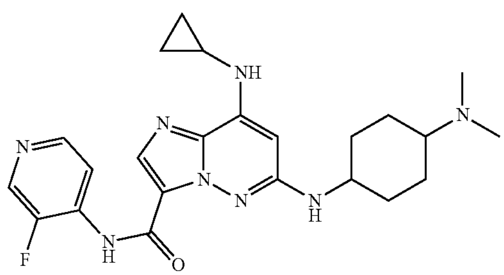 [SMILES: CN(C)C1CCC(Nc2cc(NC3CC3)c3ncc(C(=O)Nc4ccncc4F)n3n2)CC1] | 8-(cyclopropylamino)-6-((4-(dimethylamino)cyclohexyl)amino)-N-(3-fluoro-4-pyridinyl)imidazo[1,2-b]pyridazine-3-carboxamide | 452.53 | 1.58[a] |
| 328 | 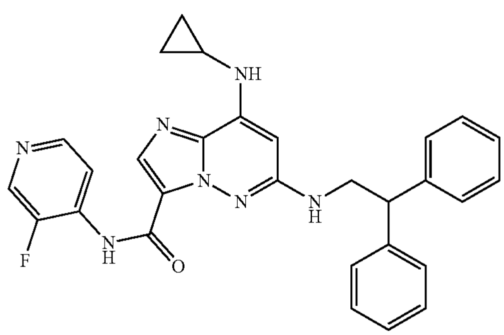 [SMILES: O=C(Nc1ccncc1F)c1cnc2c(NC3CC3)cc(NCC(c3ccccc3)c3ccccc3)nn12] | 8-(cyclopropylamino)-6-((2,2-diphenylethyl)amino)-N-(3-fluoro-4-pyridinyl)imidazo[1,2-b]pyridazine-3-carboxamide | 507.56 | 2.89[a] |
| 329 | 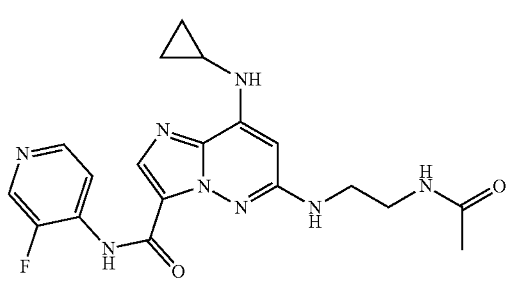 [SMILES: CC(=O)NCCNc1cc(NC2CC2)c2ncc(C(=O)Nc3ccncc3F)n2n1] | 6-((2-acetamidoethyl)amino)-8-(cyclopropylamino)-N-(3-fluoro-4-pyridinyl)imidazo[1,2-b]pyridazine-3-carboxamide | 412.42 | 1.57[a] |

TABLE 12-continued

| Example | Structure | Name | [M + H] | HPLC Ret Time (min) |
|---|---|---|---|---|
| 330 | 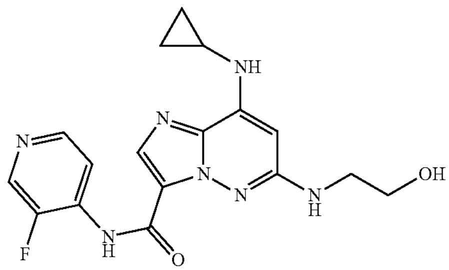 [SMILES: O=C(Nc1ccncc1F)c1cnc2c(NC3CC3)cc(NCCO)nn12] | 8-(cyclopropylamino)-N-(3-fluoro-4-pyridinyl)-6-((2-hydroxyethyl)amino)imidazo[1,2-b]pyridazine-3-carboxamide | 371.37 | 1.617[a] |
| 331 | 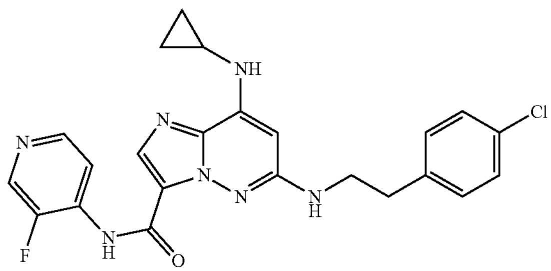 [SMILES: O=C(Nc1ccncc1F)c1cnc2c(NC3CC3)cc(NCCc3ccc(Cl)cc3)nn12] | 6-((2-(4-chlorophenyl)ethyl)amino)-8-(cyclopropylamino)-N-(3-fluoro-4-pyridinyl)imidazo[1,2-b]pyridazine-3-carboxamide | 465.91 | 2.816[a] |
| 332 | 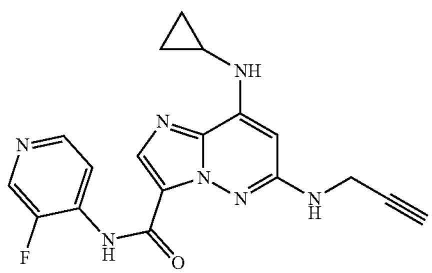 [SMILES: C#CCNc1cc(NC2CC2)c2ncc(C(=O)Nc3ccncc3F)n2n1] | 8-(cyclopropylamino)-N-(3-fluoro-4-pyridinyl)-6-(2-propya-1-ylamino)imidazo[1,2-b]pyridazine-3-carboxamide | 365.36 | 2.038[a] |
| 333 | 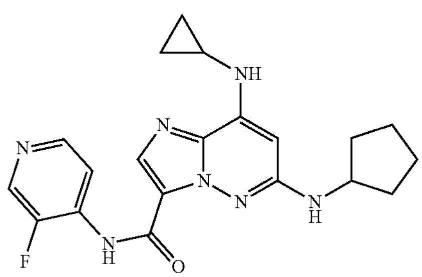 [SMILES: O=C(Nc1ccncc1F)c1cnc2c(NC3CC3)cc(NC3CCCC3)nn12] | 6-(cyclopentylamino)-8-(cyclopropylamino)-N-(3-fluoro-4-pyridinyl)imidazo[1,2-b]pyridazine-3-carboxamide | 395.43 | 2.593[a] |
| 334 | 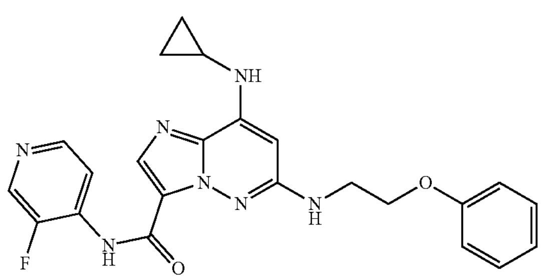 [SMILES: O=C(Nc1ccncc1F)c1cnc2c(NC3CC3)cc(NCCOc3ccccc3)nn12] | 8-(cyclopropylamino)-N-(3-fluoro-4-pyridinyl)-6-((2-phenoxyethyl)amino)imidazo[1,2-b]pyridazine-3-carboxamide | 447.46 | 2.587[a] |

TABLE 12-continued

| Example | Structure | Name | [M + H] | HPLC Ret Time (min) |
|---|---|---|---|---|
| 335 | 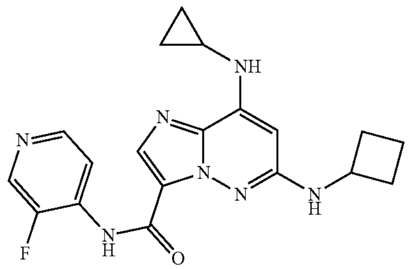 [SMILES: O=C(Nc1ccncc1F)c1cnc2c(NC3CC3)cc(NC3CCC3)nn12] | 6-(cyclobutylamino)-8-(cyclopropylamino)-N-(3-fluoro-4-pyridinyl)imidazo[1,2-b]pyridazine-3-carboxamide | 381.41 | 2.438[a] |
| 336 | 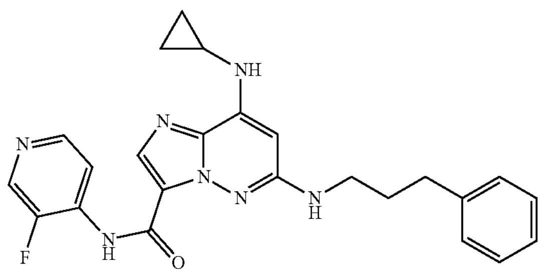 [SMILES: O=C(Nc1ccncc1F)c1cnc2c(NC3CC3)cc(NCCCc3ccccc3)nn12] | 8-(cyclopropylamino)-N-(3-fluoro-4-pyridinyl)-6-((3-phenylpropyl)amino)imidazo[1,2-b]pyridazine-3-carboxamide | 445.49 | 2.776[a] |
| 337 | 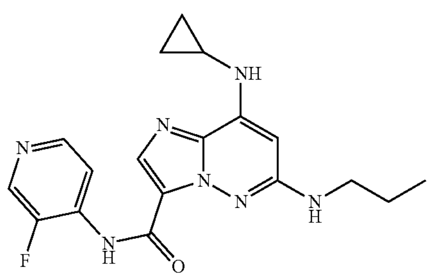 [SMILES: CCCNc1cc(NC2CC2)c2ncc(C(=O)Nc3ccncc3F)n2n1] | 8-(cyclopropylamino)-N-(3-fluoro-4-pyridinyl)-6-(propylamino)imidazo[1,2-b]pyridazine-3-carboxamide | 369.4 | 2.392[a] |
| 338 | 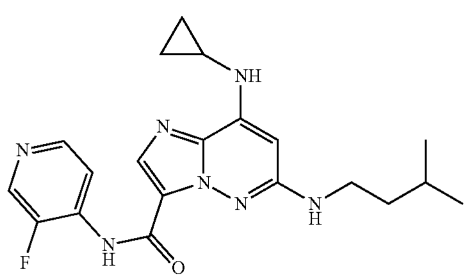 [SMILES: CC(C)CCNc1cc(NC2CC2)c2ncc(C(=O)Nc3ccncc3F)n2n1] | 8-(cyclopropylamino)-N-(3-fluoro-4-pyridinyl)-6-((3-methylbutyl)amino)imidazo[1,2-b]pyridazine-3-carboxamide | 397.45 | 2.753[a] |
| 339 | 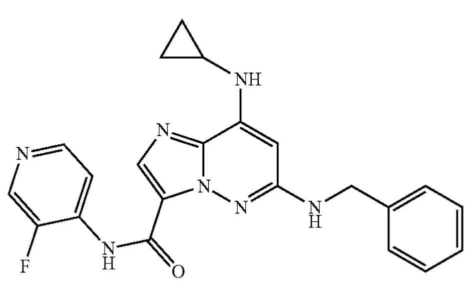 [SMILES: O=C(Nc1ccncc1F)c1cnc2c(NC3CC3)cc(NCc3ccccc3)nn12] | 6-(benzylamino)-8-(cyclopropylamino)-N-(3-fluoro-4-pyridinyl)imidazo[1,2-b]pyridazine-3-carboxamide | 417.44 | 2.503[a] |

TABLE 12-continued

| Example | Structure | Name | [M + H] | HPLC Ret Time (min) |
|---|---|---|---|---|
| 340 | 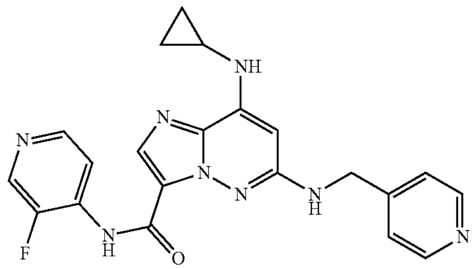 [SMILES: O=C(Nc1ccncc1F)c1cnc2c(NC3CC3)cc(NCc3ccncc3)nn12] | 8-(cyclopropylamino)-N-(3-fluoro-4-pyridinyl)-6-((4-pyridinylmethyl)amino)imidazo[1,2-b]pyridazine-3-carboxamide | 418.43 | 1.822[a] |
| 341 | 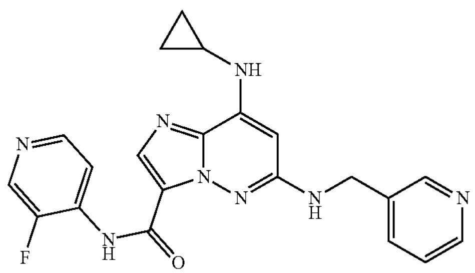 [SMILES: O=C(Nc1ccncc1F)c1cnc2c(NC3CC3)cc(NCc3cccnc3)nn12] | 8-(cyclopropylamino)-N-(3-fluoro-4-pyridinyl)-6-((3-pyridinylmethyl)amino)imidazo[1,2-b]pyridazine-3-carboxamide | 418.43 | 1.863[a] |
| 342 | 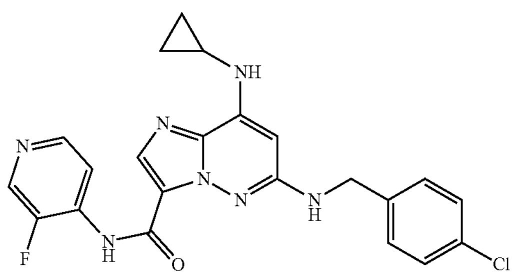 [SMILES: O=C(Nc1ccncc1F)c1cnc2c(NC3CC3)cc(NCc3ccc(Cl)cc3)nn12] | 6-((4-chlorobenzyl)amino)-8-(cyclopropylamino)-N-(3-fluoro-4-pyridinyl)imidazo[1,2-b]pyridazine-3-carboxamide | 451.88 | 2.696[a] |
| 343 | 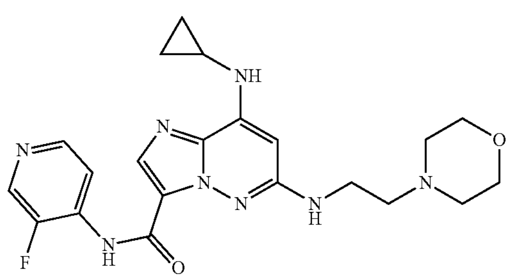 [SMILES: O=C(Nc1ccncc1F)c1cnc2c(NC3CC3)cc(NCCN3CCOCC3)nn12] | 8-(cyclopropylamino)-N-(3-fluoro-4-pyridinyl)-6-((2-(4-morpholinyl)ethyl)amino)imidazo[1,2-b]pyridazine-3-carboxamide | 440.47 | 1.852[a] |
| 344 | 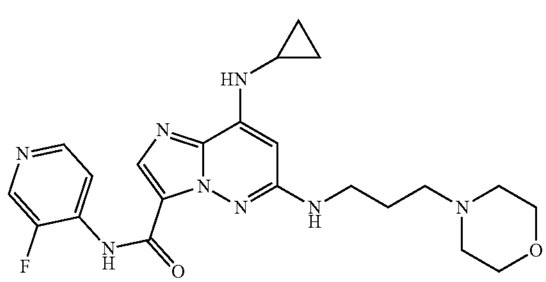 [SMILES: O=C(Nc1ccncc1F)c1cnc2c(NC3CC3)cc(NCCCN3CCOCC3)nn12] | 8-(cyclopropylamino)-N-(3-fluoro-4-pyridinyl)-6-((3-(4-morpholinyl)propyl)amino)imidazo[1,2-b]pyridazine-3-carboxamide | 455.3 | 1.757[b] |

TABLE 12-continued

| Example | Structure | Name | [M + H] | HPLC Ret Time (min) |
|---|---|---|---|---|
| 345 | 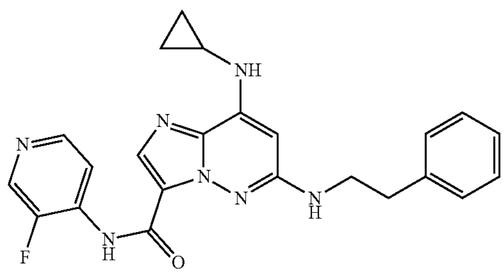 [SMILES: O=C(Nc1ccncc1F)c1cnc2c(NC3CC3)cc(NCCc3ccccc3)nn12] | 8-(cyclopropylamino)-N-(3-fluoro-4-pyridinyl)-6-((2-phenylethyl)amino)imidazo[1,2-b]pyridazine-3-carboxamide | 432.1 | 2.716[b] |
| 346 | 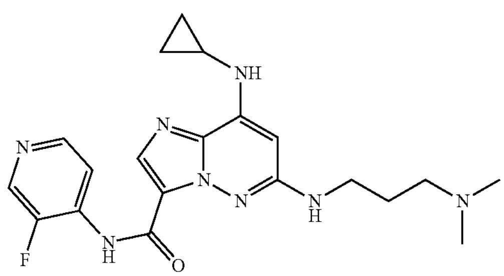 [SMILES: CN(C)CCCNc1cc(NC2CC2)c2ncc(C(=O)Nc3ccncc3F)n2n1] | 8-(cyclopropylamino)-6-((3-(dimethylamino)propyl)amino)-N-(3-fluoro-4-pyridinyl)imidazo[1,2-b]pyridazine-3-carboxamide | 413.1 | 1.810[b] |
| 347 | 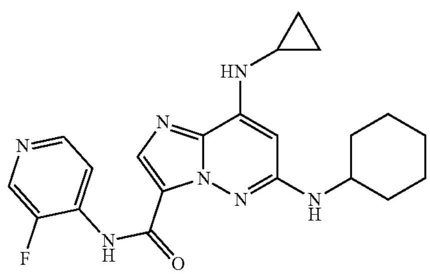 [SMILES: O=C(Nc1ccncc1F)c1cnc2c(NC3CC3)cc(NC3CCCCC3)nn12] | 6-(cyclohexylamino)-8-(cyclopropylamino)-N-(3-fluoro-4-pyridinyl)imidazo[1,2-b]pyridazine-3-carboxamide | 410 | 4.605[c] |
| 348 | 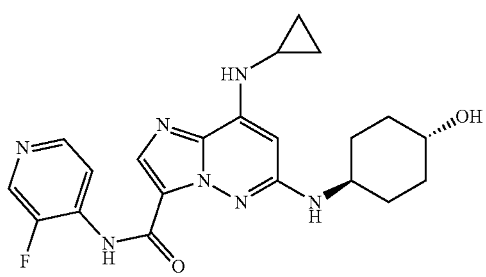 [SMILES: O=C(Nc1ccncc1F)c1cnc2c(NC3CC3)cc(N[C@H]3CC[C@H](O)CC3)nn12] | 8-(cyclopropylamino)-N-(3-fluoro-4-pyridinyl)-6-((trans-4-hydroxycyclohexyl)amino)imidazo[1,2-b]pyridazine-3-carboxamide | 426 | 3.693[c] |
| 349 | 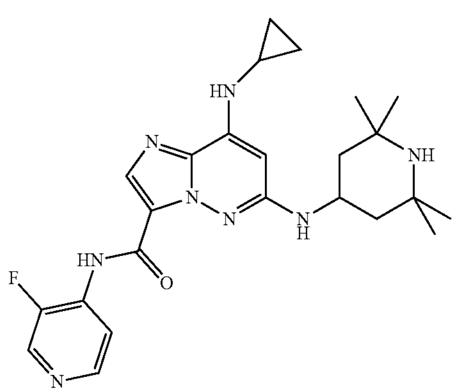 [SMILES: CC1(C)CC(Nc2cc(NC3CC3)c3ncc(C(=O)Nc4ccncc4F)n3n2)CC(C)(C)N1] | 8-(cyclopropylamino)-N-(3-fluoro-4-pyridinyl)-6-((2,2,6,6-tetramethyl-4-piperidinyl)amino)imidazo[1,2-b]pyridazine-3-carboxamide | 466 | 3.268[c] |

TABLE 12-continued

| Example | Name | [M + H] | HPLC Ret Time (min) |
|---|---|---|---|
| 350 | 8-(cyclopropylamino)-N-(3-fluoro-4-pyridinyl)-6-(4-morpholinyl)imidazo[1,2-b]pyridazine-3-carboxamide | 398 | 3.793[e] |
| 351 | 8-(cyclopropylamino)-N-(3-fluoro-4-pyridinyl)-6-(1-pyrrolidinyl)imidazo[1,2-b]pyridazine-3-carboxamide | 382 | 4.376[e] |
| 352 | 8-(cyclopropylamino)-N-(3-fluoro-4-pyridinyl)-6-((4-hydroxybutyl)amino)imidazo[1,2-b]pyridazine-3-carboxamide | 400 | 3.570[e] |
| 353 | 8-(cyclopropylamino)-6-((4-(dimethylamino)butyl)amino)-N-(3-fluoro-4-pyridinyl)imidazo[1,2-b]pyridazine-3-carboxamide | 427 | 2.816[e] |
| 354 | 6-((3-aminocyclohexyl)amino)-8-(cyclopropyl-amino)-N-(3-fluoro-4-pyridinyl)imidazo[1,2-b]pyridazine-3-carboxamide | 425 | 3.250[e] |

TABLE 12-continued

| Example | Structure | Name | [M + H] | HPLC Ret Time (min) |
|---|---|---|---|---|
| 355 | 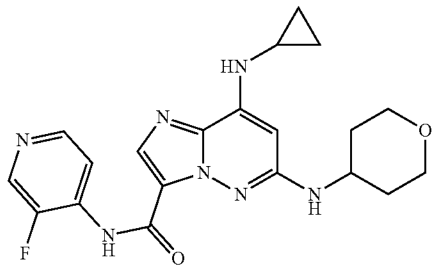 [SMILES: O=C(Nc1ccncc1F)c1cnc2c(NC3CC3)cc(NC3CCOCC3)nn12] | 8-(cyclopropylamino)-N-(3-fluoro-4-pyridinyl)-6-(tetrahydro-2H-pyran-4-ylamino)imidazo[1,2-b]pyridazine-3-carboxamide | 412.29 | 3.821[e] |
| 356 | 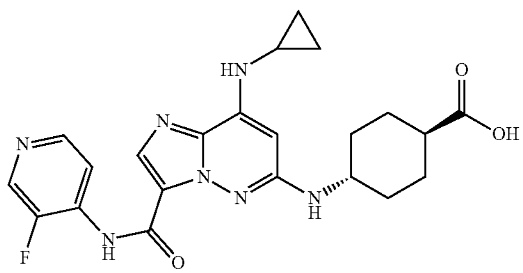 [SMILES: O=C(Nc1ccncc1F)c1cnc2c(NC3CC3)cc(N[C@H]3CC[C@H](C(=O)O)CC3)nn12] | trans-4-((8-(cyclopropylamino)-3-((3-fluoro-4-pyridinyl)carbamoyl)imidazo[1,2-b]pyridazin-6-yl)amino)cyclohexanecaroxylic acid | 454.3. | 3.018[e] |
| 357 | 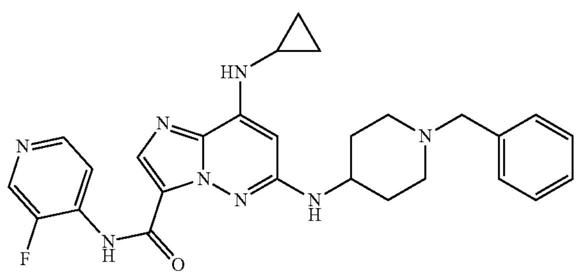 [SMILES: O=C(Nc1ccncc1F)c1cnc2c(NC3CC3)cc(NC3CCN(Cc4ccccc4)CC3)nn12] | 6-((1-benzyl-4-piperidinyl)amino)-8-(cyclopropylamino)-N-(3-fluoro-4-pyridinyl)imidazo[1,2-b]pyridazine-3-carboxamide | 501.36. | 3.288[e] |
| 358 | 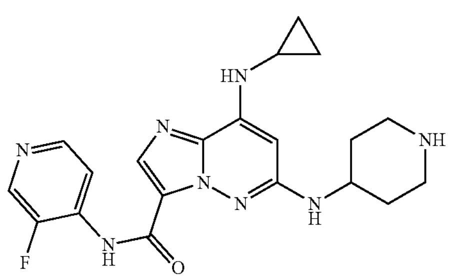 [SMILES: O=C(Nc1ccncc1F)c1cnc2c(NC3CC3)cc(NC3CCNCC3)nn12] | 8-(cyclopropylamino)-N-(3-fluoro-4-pyridinyl)-6-(4-piperidinylamino)imidazo[1,2-b]pyridazine-3-carboxamide | 411.32. | 2.786[e] |
| 359 | 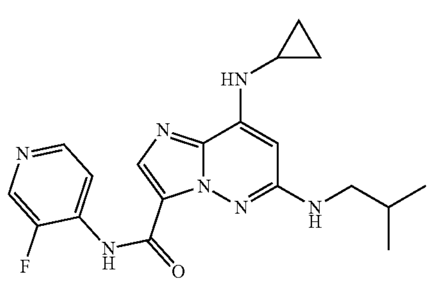 [SMILES: CC(C)CNc1cc(NC2CC2)c2ncc(C(=O)Nc3ccncc3F)n2n1] | 8-(cyclopropylamino)-N-(3-fluoro-4-pyridinyl)-6-(isobutylamino)imidazo[1,2-b]pyridazine-3-carboxamide | 384.31 | 4.350[e] |

TABLE 12-continued

| Example | Structure | Name | [M + H] | HPLC Ret Time (min) |
|---|---|---|---|---|
| 360 | 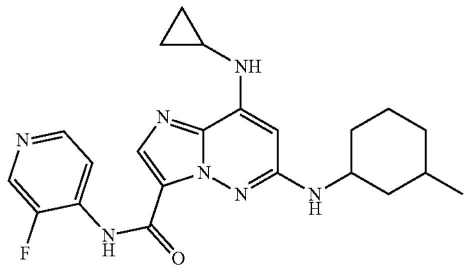 [SMILES: CC1CCCC(Nc2cc(NC3CC3)c3ncc(C(=O)Nc4ccncc4F)n3n2)C1] | 8-(cyclopropylamino)-N-(3-fluoro-4-pyridinyl)-6-((3-methylcyclohexyl)amino)imidazo[1,2-b]pyridazine-3-carboxamide | 424 | 4.755[e] |
| 361 | 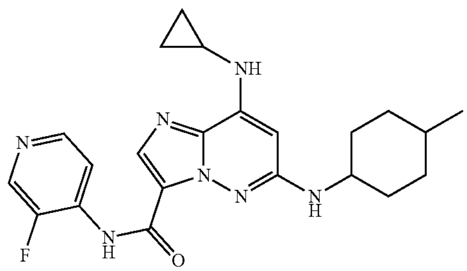 [SMILES: CC1CCC(Nc2cc(NC3CC3)c3ncc(C(=O)Nc4ccncc4F)n3n2)CC1] | 8-(cyclopropylamino)-N-(3-fluoro-4-pyridinyl)-6-((4-methylcyclohexyl)amino)imidazo[1,2-b]pyridazine-3-carboxamide | 424.4 | 4.805[e] |
| 362 | 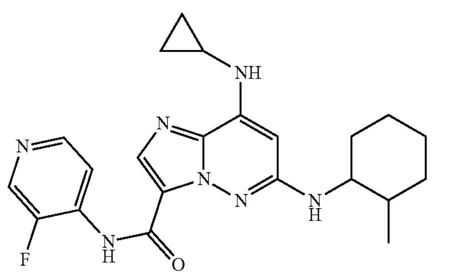 [SMILES: CC1CCCCC1Nc1cc(NC2CC2)c2ncc(C(=O)Nc3ccncc3F)n2n1] | 8-(cyclopropylamino)-N-(3-fluoro-4-pyridinyl)-6-((2-methylcyclohexyl)amino)imidazo[1,2-b]pyridazine-3-carboxamide | 424.3 | 4.613[e] |
| 363 | 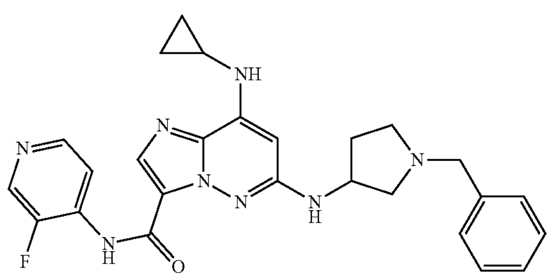 [SMILES: O=C(Nc1ccncc1F)c1cnc2c(NC3CC3)cc(NC3CCN(Cc4ccccc4)C3)nn12] | 6-((1-benzyl-3-pyrrolidinyl)amino)-8-(cyclopropylamino)-N-(3-fluoro-4-pyridinyl)imidazo[1,2-b]pyridazine-3-carboxamide | 487.1 | 3.101[e] |
| 364 | 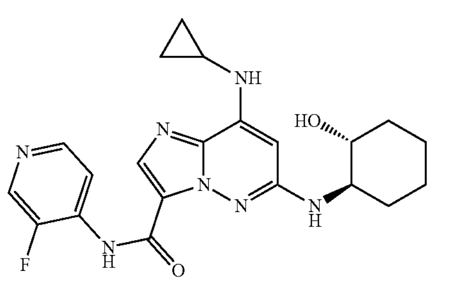 [SMILES: O=C(Nc1ccncc1F)c1cnc2c(NC3CC3)cc(N[C@@H]3CCCC[C@H]3O)nn12] | 8-(cyclopropylamino)-N-(3-fluoro-4-pyridinyl)-6-(((1R,2R)-2-hydroxycyclohexyl)amino)imidazo[1,2-b]pyridazine-3-carboxamide | 426.1 | 3.833[e] |

TABLE 12-continued

| Example | Structure | Name | [M + H] | HPLC Ret Time (min) |
|---|---|---|---|---|
| 365 | 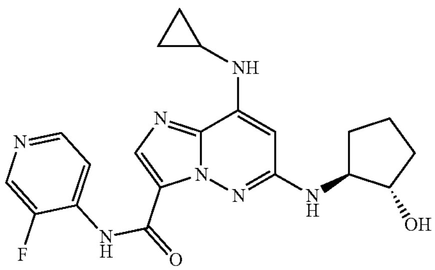 [SMILES: O=C(Nc1ccncc1F)c1cnc2c(NC3CC3)cc(N[C@H]3CCC[C@@H]3O)nn12] | 8-(cyclopropylamino)-N-(3-fluoro-4-pyridinyl)-6-(((1S,2S)-2-hydroxycyclopentyl)amino)imidazo[1,2-b]pyridazine-3-carboxamide | 412.1 | 3.995[e] |
| 366 | 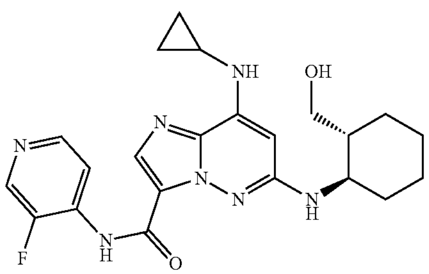 [SMILES: O=C(Nc1ccncc1F)c1cnc2c(NC3CC3)cc(N[C@@H]3CCCC[C@H]3CO)nn12] | 8-(cyclopropylamino)-N-(3-fluoro-4-pyridinyl)-6-(((1R,2R)-2-(hydroxymethyl)cyclohexyl)amino)imidazo[1,2-b]pyridazine-3-carboxamide | 440.1 | 4.013[e] |
| 367 | 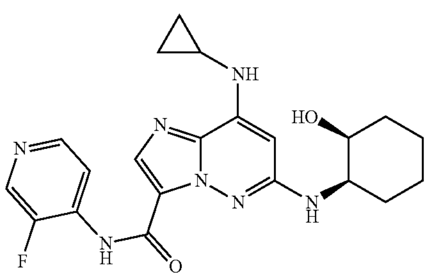 [SMILES: O=C(Nc1ccncc1F)c1cnc2c(NC3CC3)cc(N[C@@H]3CCCC[C@@H]3O)nn12] | 8-(cyclopropylamino)-N-(3-fluoro-4-pyridinyl)-6-(((1R,2S)-2-hydroxycyclohexyl)amino)imidazo[1,2-b]pyridazine-3-carboxamide | 426.1 | 3.981[e] |
| 368 | 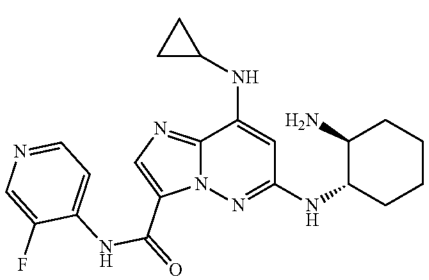 [SMILES: N[C@H]1CCCC[C@@H]1Nc1cc(NC2CC2)c2ncc(C(=O)Nc3ccncc3F)n2n1] | 6-(((1S,2S)-2-aminocyclohexyl)amino)-8-(cyclopropylamino)-N-(3-fluoro-4-pyridinyl)imidazo[1,2-b]pyridazine-3-carboxamide | 425.0 | 3.231[e] |
| 369 | 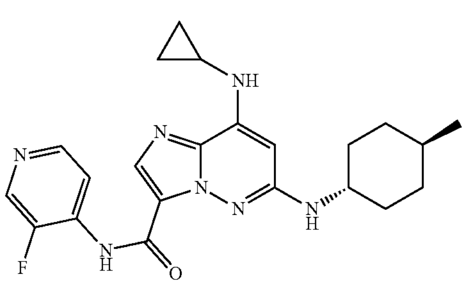 [SMILES: C[C@H]1CC[C@H](Nc2cc(NC3CC3)c3ncc(C(=O)Nc4ccncc4F)n3n2)CC1] | 8-(cyclopropylamino)-N-(3-fluoro-4-pyridinyl)-6-((trans-4-methylcyclohexyl)amino)imidazo[1,2-b]pyridazine-3-carboxamide | 424.1 | 4.713[e] |

TABLE 12-continued

| Example | Structure | Name | [M + H] | HPLC Ret Time (min) |
|---|---|---|---|---|
| 370 | 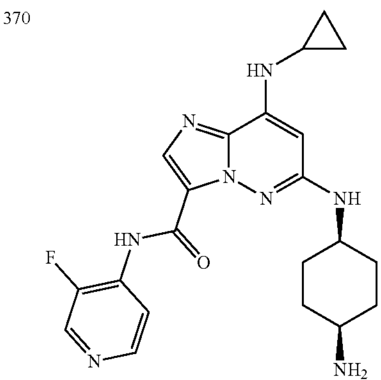 | 6-((cis-4-aminocyclohexyl)amino)-8-(cyclopropylamino)-N-(3-fluoro-4-pyridinyl)imidazo[1,2-b]pyridazine-3-carboxamide | 425.29 | 1.29[d] |

HPLC Conditions:

[a]Waters Sunflower 4.6 × 50 mm column: 0%-100% solvent B. Solvent B: 95% MeOH, 5% H$_2$O, 0.1% TFA). Solvent A: 5% MeOH, 95% H$_2$O, 0.1% TFA). 4 min gradient, UV detected at 220 nm.

[b]Waters XBridge 4.6 × 50 mm 5 um C18; 4 min gradient from 0% B to 100% B; flow rate 4 mL/min; A = 2:98 Acetonitrile:Water; B = 90:10 Acetonitrile:Water; Modifier = 10 mM NH$_4$OAc; Detection at 220 nm.

[c]YMC S-5 ODS-A 4.6 × 50 mm, 10-90% aqueous methanol containing 0.2% H$_3$PO$_4$, 4 min gradient, monitored at 220 nm

[d]Phenomenex Luna 5 micron C18 4.6 × 30 mm: 0 to 100 B in 2 min with 1 min hold time, Flow rate = 5 mL/min, detection at 254 nm, Solvent A: 10% methanol/90% water/0.1% TFA; Solvent B: 10% water/90% methanol/0.1% TFA The following Examples in Table 13 may be prepared according to the procedures detailed in Examples 1-4 and Example 24.

TABLE 13

| Example | Structure | Name | [M + H] | HPLC Ret Time (min) |
|---|---|---|---|---|
| 371 | 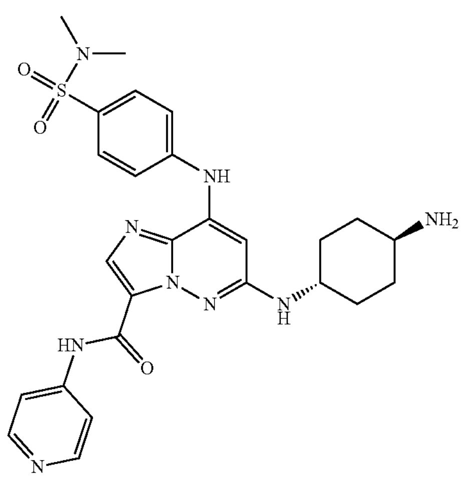 [SMILES: CN(C)S(=O)(=O)c1ccc(Nc2cc(N[C@H]3CC[C@H](N)CC3)nn3c(C(=O)Nc4ccncc4)cnc23)cc1] | 6-((trans-4-aminocyclohexyl)amino)-8-((4-(dimethylsulfamoyl)phenyl)amino)-N-4-pyridinylimidazo[1,2-b]pyridazine-3-carboxamide | 550.12 | 2.23[a] |

TABLE 13-continued

| Example | Structure | Name | [M + H] | HPLC Ret Time (min) |
|---|---|---|---|---|
| 372 | 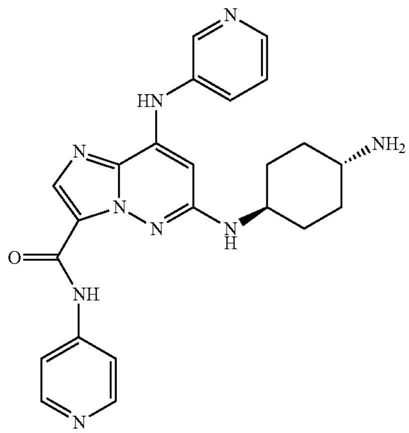 [SMILES: N[C@H]1CC[C@H](Nc2cc(Nc3cccnc3)c3ncc(C(=O)Nc4ccncc4)n3n2)CC1] | 8-cyclohexyl-11-methoxy-1a-((4-methyl-1,4-diazepan-1-yl)sulfonyl)-1,1a,2,12b-tetrahydrocyclopropa[d]indolo[2,1-a][2]benzazepine-5-carboxylic acid | 444.15 | 1.33[a] |
| 373 | 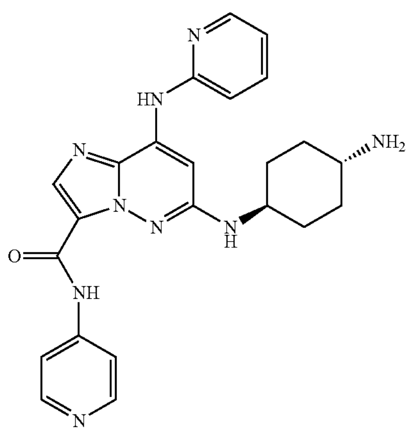 [SMILES: N[C@H]1CC[C@H](Nc2cc(Nc3ccccn3)c3ncc(C(=O)Nc4ccncc4)n3n2)CC1] | N-cyclopropyl-3-((2-((2R)-2-(2-pyridinyl)-1-pyrrolidinyl)pyrrolo[2,1-f][1,2,4]triazin-4-yl)amino)-1H-pyrazole-5-carboxamide | 444.16 | 2.02[a] |
| 374 | 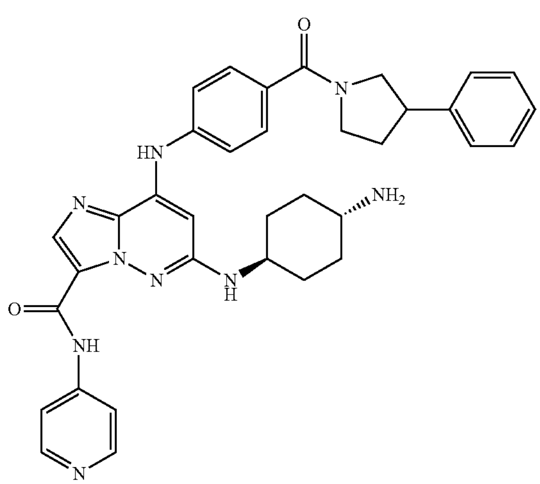 [SMILES: N[C@H]1CC[C@H](Nc2cc(Nc3ccc(C(=O)N4CCC(c5ccccc5)C4)cc3)c3ncc(C(=O)Nc4ccncc4)n3n2)CC1] | 6-((trans-4-aminocyclohexyl)amino)-8-((4-((3-phenyl-1-pyrrolidinyl)carbonyl)phenyl)amino)-N-4-pyridinylimidazo[1,2-b]pyridazine-3-carboxamide | 616.14 | 2.78[a] |

TABLE 13-continued

| Example | Structure | Name | [M + H] | HPLC Ret Time (min) |
|---|---|---|---|---|
| 375 | 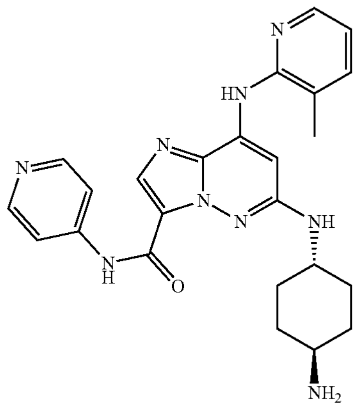 [SMILES: Cc1cccnc1Nc1cc(N[C@H]2CC[C@H](N)CC2)nn2c(C(=O)Nc3ccncc3)cnc12] | 6-((trans-4-aminocyclohexyl)amino)-8-((3-methyl-2-pyridinyl)amino)-N-4-pyridinyl-imidazo[1,2-b]pyridazine-3-carboxamide | 458.14 | 2.16[a] |
| 376 | 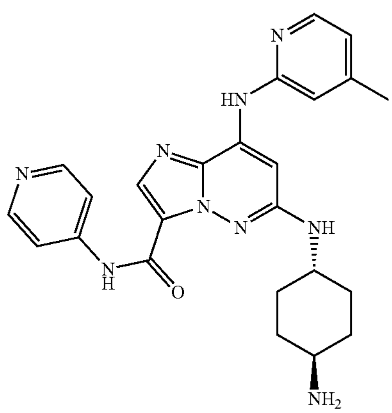 [SMILES: Cc1ccnc(Nc2cc(N[C@H]3CC[C@H](N)CC3)nn3c(C(=O)Nc4ccncc4)cnc23)c1] | 6-((trans-4-aminocyclohexyl)amino)-8-((4-methyl-2-pyridinyl)amino)-N-4-pyridinyl-imidazo[1,2-b]pyridazine-3-carboxamide | 458.14 | 1.99[a] |
| 377 | 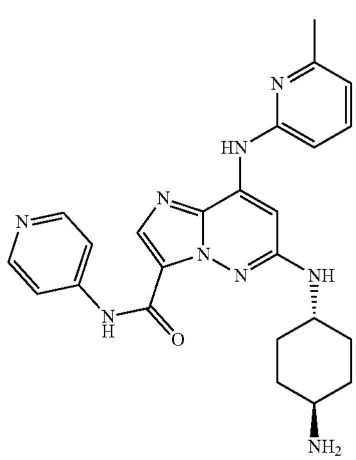 [SMILES: Cc1cccc(Nc2cc(N[C@H]3CC[C@H](N)CC3)nn3c(C(=O)Nc4ccncc4)cnc23)n1] | 6-((trans-4-aminocyclohexyl)amino)-8-((6-methyl-2-pyridinyl)amino)-N-4-pyridinyl-imidazo[1,2-b]pyridazine-3-carboxamide | 458.14 | 2.05[a] |

TABLE 13-continued

| Example | Structure | Name | [M + H] | HPLC Ret Time (min) |
|---|---|---|---|---|
| 378 | 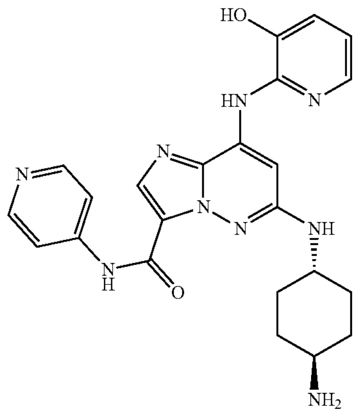 [SMILES: N[C@H]1CC[C@H](Nc2cc(Nc3ncccc3O)c3ncc(C(=O)Nc4ccncc4)n3n2)CC1] | 6-((trans-4-aminocyclohexyl)amino)-8-((3-hydroxy-2-pyridinyl)amino)-N-4-pyridinyl-imidazo[1,2-b]pyridazine-3-carboxamide | 460.12 | 2.08[a] |
| 379 | 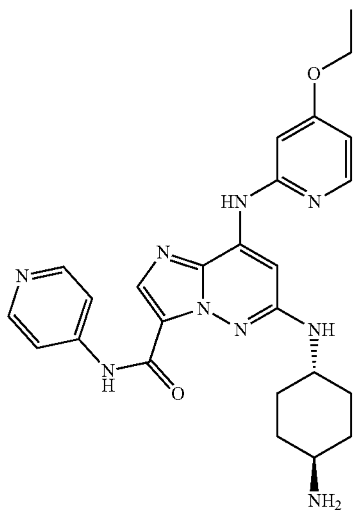 [SMILES: CCOc1ccnc(Nc2cc(N[C@H]3CC[C@H](N)CC3)nn3c(C(=O)Nc4ccncc4)cnc23)c1] | 6-((trans-4-aminocyclohexyl)amino)-8-((4-ethoxy-2-pyridinyl)amino)-N-4-pyridinyl-imidazo[1,2-b]pyridazine-3-carboxamide | 488.13 | 1.99[a] |
| 380 | 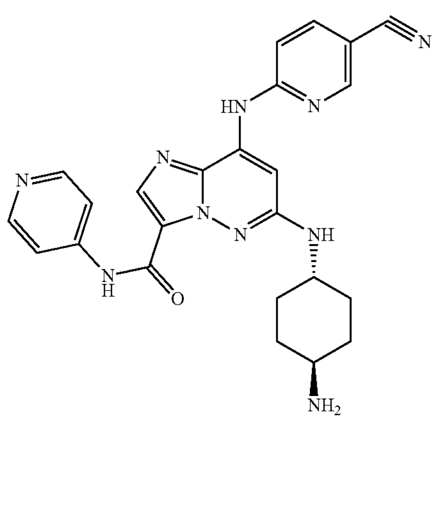 [SMILES: N#Cc1ccc(Nc2cc(N[C@H]3CC[C@H](N)CC3)nn3c(C(=O)Nc4ccncc4)cnc23)nc1] | 6-((trans-4-aminocyclohexyl)amino)-8-((5-cyano-2-pyridinyl)amino)-N-4-pyridinyl-imidazo[1,2-b]pyridazine-3-carboxamide | 469.18 | 2.22[a] |

TABLE 13-continued

| Example | Structure | Name | [M + H] | HPLC Ret Time (min) |
|---|---|---|---|---|
| 381 | 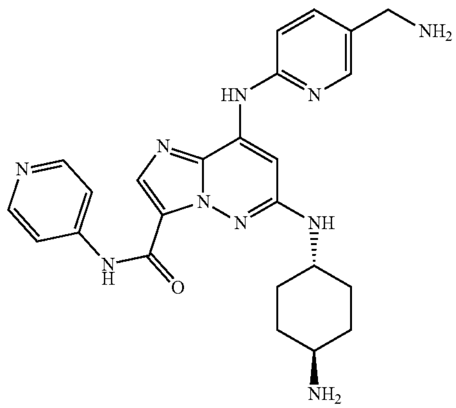 [SMILES: NCc1ccc(Nc2cc(N[C@H]3CC[C@H](N)CC3)nn3c(C(=O)Nc4ccncc4)cnc23)nc1] | 6-((trans-4-aminocyclohexyl)amino)-8-((5-(aminomethyl)-2-pyridinyl)amino)-N-4-pyridinylimidazo[1,2-b]pyridazine-3-carboxamide | 473.21 | 1.61[a] |
| 382 | 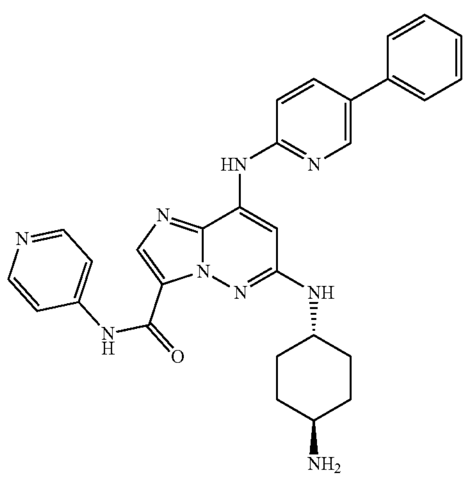 [SMILES: N[C@H]1CC[C@H](Nc2cc(Nc3ccc(-c4ccccc4)cn3)c3ncc(C(=O)Nc4ccncc4)n3n2)CC1] | 6-((trans-4-aminocyclohexyl)amino)-8-((5-phenyl-2-pyridinyl)amino)-N-4-pyridinyl-imidazo[1,2-b]pyridazine-3-carboxamide | 520.23 | 2.89[a] |
| 383 | 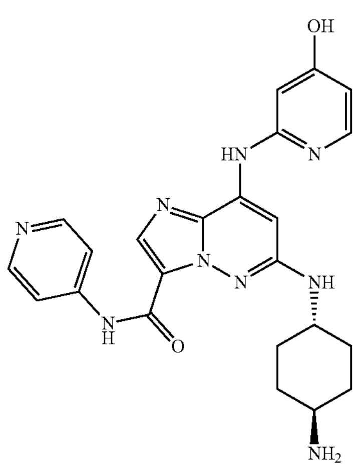 [SMILES: N[C@H]1CC[C@H](Nc2cc(Nc3cc(O)ccn3)c3ncc(C(=O)Nc4ccncc4)n3n2)CC1] | 6-((trans-4-aminocyclohexyl)amino)-8-((4-hydroxy-2-pyridinyl)amino)-N-4-pyridinyl-imidazo[1,2-b]pyridazine-3-carboxamide | 460.18 | 1.55[a] |

TABLE 13-continued

| Example | Structure | Name | [M + H] | HPLC Ret Time (min) |
|---|---|---|---|---|
| 384 | 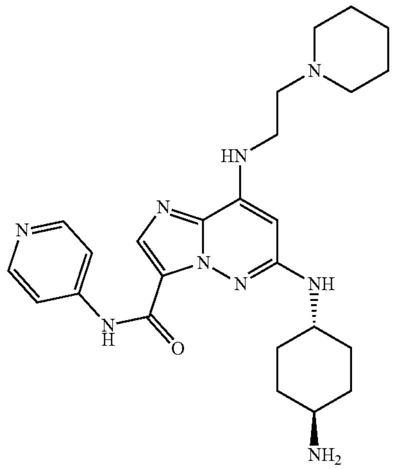 [SMILES: N[C@H]1CC[C@H](Nc2cc(NCCN3CCCCC3)c3ncc(C(=O)Nc4ccncc4)n3n2)CC1] | 6-((trans-4-aminocyclohexyl)amino)-8-((2-(1-piperidinyl)ethyl)amino)-N-4-pyridinyl-imidazo[1,2-b]pyridazine-3-carboxamide | 478.21 | 1.38[a] |
| 385 | 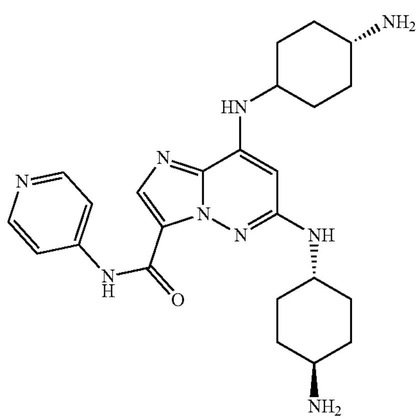 | 6-((trans-4-aminocyclohexyl)amino)-8-((4-aminocyclohexyl)amino)-N-4-pyridinyl-imidazo[1,2-b]pyridazine-3-carboxamide | 464.18 | 1.50[a] |
| 386 | 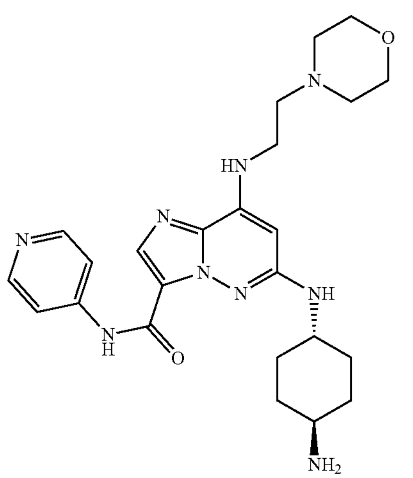 [SMILES: N[C@H]1CC[C@H](Nc2cc(NCCN3CCOCC3)c3ncc(C(=O)Nc4ccncc4)n3n2)CC1] | 6-((trans-4-aminocyclohexyl)amino)-8-((2-(4-morpholinyl)ethyl)amino)-N-4-pyridinyl-imidazo[1,2-b]pyridazine-3-carboxamide | 480.22 | 1.25[a] |

TABLE 13-continued

| Example | Structure | Name | [M + H] | HPLC Ret Time (min) |
|---|---|---|---|---|
| 387 | 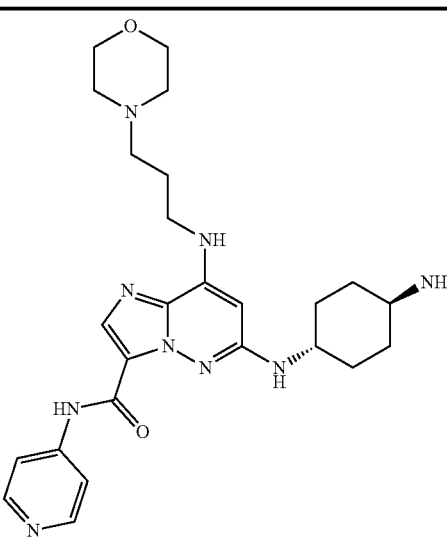 | 6-((trans-4-aminocyclohexyl)amino)-8-((3-(4-morpholinyl)propyl)amino)-N-4-pyridinyl-imidazo[1,2-b]pyridazine-3-carboxamide | 494.21 | 1.33[a] |
| 388 | 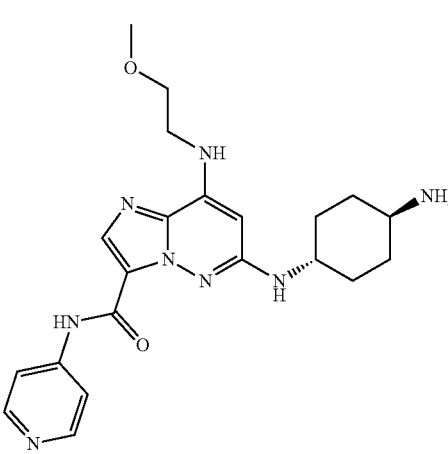 | 6-((trans-4-aminocyclohexyl)amino)-8-((2-methoxyethyl)amino)-N-4-pyridinylimidazo[1,2-b]pyridazine-3-carboxamide | 425.18 | 1.80[a] |
| 389 | 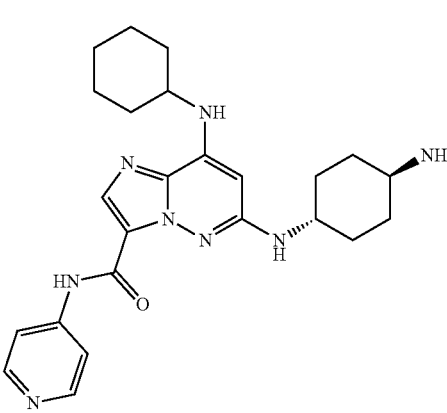 | 6-((trans-4-aminocyclohexyl)amino)-8-(cyclohexylamino)-N-4-pyridinylimidazo[1,2-b]pyridazine-3-carboxammide | 449.22 | 2.63[a] |

TABLE 13-continued

| Example | Name | [M + H] | HPLC Ret Time (min) |
|---|---|---|---|
| 390 | 6-((trans-4-aminocyclohexyl)amino)-8-(cyclopropylamino)-N-4-pyridinylimidazo[1,2-b]pyridazine-3-carboxamide | 407.16 | 1.98[a] |
| 391 | 6-((trans-4-aminocyclohexyl)amino)-8-((cyclopropylmethyl)amino)-N-4-pyridinylimidazo[1,2-b]pyridazine-3-carboxamide | 421.15 | 2.25[a] |
| 392 | 6-((trans-4-aminocyclohexyl)amino)-8-(benzylamino)-N-4-pyridinylimidazo[1,2-b]pyridazine-3-carboxamide | 457.15 | 2.38[a] |

TABLE 13-continued

| Example | Structure | Name | [M + H] | HPLC Ret Time (min) |
|---|---|---|---|---|
| 393 | 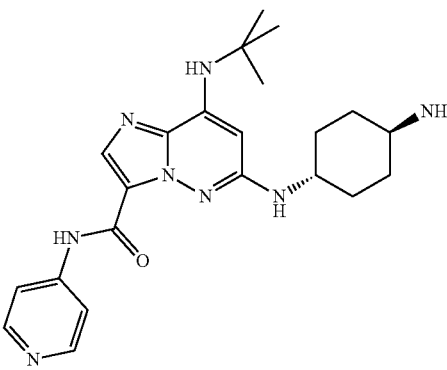 | 6-((trans-4-aminocyclohexyl)amino)-8-(tert-butylamino)-N-4-pyridinylimidazo[1,2-b]pyridazine-3-carboxamide | 423.13 | 2.24[a] |
| 394 | 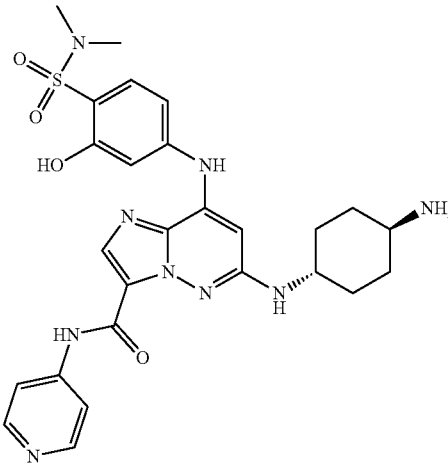 | 6-((trans-4-aminocyclohexyl)amino)-8-((4-(dimethylsulfamoyl)-3-hydroxyphenyl)amino)-N-4-pyridinylimidazo[1,2-b]pyridazine-3-carboxamide | 533.13 | 2.30[a] |
| 395 | 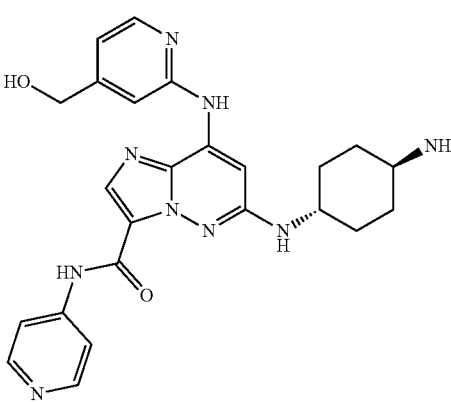 [SMILES: N[C@H]1CC[C@H](Nc2cc(Nc3cc(CO)ccn3)c3ncc(C(=O)Nc4ccncc4)n3n2)CC1] | 6-((trans-4-aminocyclohexyl)amino)-8-((4-(hydroxymethyl)-2-pyridinyl)amino)-N-4-pyridinylimidazo[1,2-b]pyridazine-3-carboxamide | 474.18 | 1.78[a] |

TABLE 13-continued

| Example | Structure | Name | [M + H] | HPLC Ret Time (min) |
|---|---|---|---|---|
| 396 | 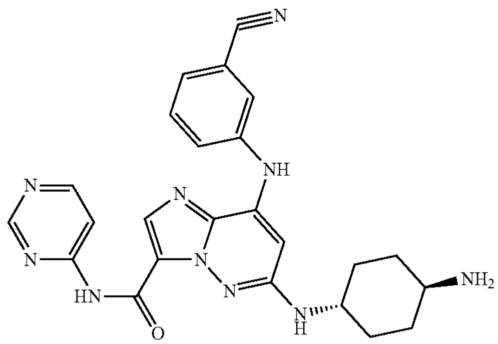 [SMILES: N#Cc1cccc(Nc2cc(N[C@H]3CC[C@H](N)CC3)nn3c(C(=O)Nc4ccncn4)cnc23)c1] | 6-((trans-4-aminocyclohexyl)amino)-8-((3-cyanophenyl)amino)-N-4-pyridinylimidazo[1,2-b]pyridazine-3-carboxamide | 469.30 | 2.86[a] |
| 397 | 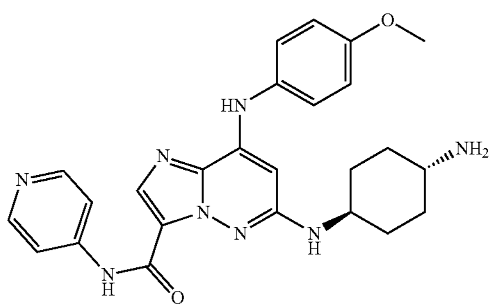 [SMILES: COc1ccc(Nc2cc(N[C@H]3CC[C@H](N)CC3)nn3c(C(=O)Nc4ccncc4)cnc23)cc1] | 6-((trans-4-aminocyclohexyl)amino)-8-((4-methoxyphenyl)amino)-N-4-pyridinyl-imidazo-[1,2-b]pyridazine-3-carboxamide | 473 | 2.723[b] |
| 398 | 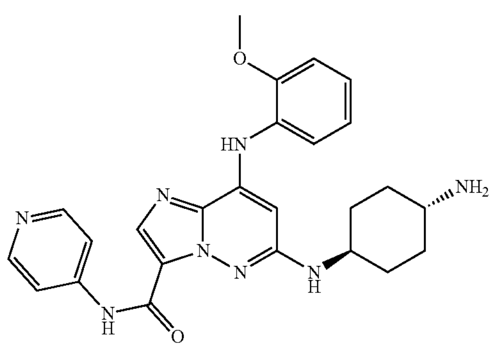 [SMILES: COc1ccccc1Nc1cc(N[C@H]2CC[C@H](N)CC2)nn2c(C(=O)Nc3ccncc3)cnc12] | 6-((trans-4-aminocyclohexyl)amino)-8-((2-methoxyphenyl)amino)-N-4-pyridinyl-imidazo[1,2-b]pyridazine-3-carboxamide | 473 | 2.795[b] |
| 399 | 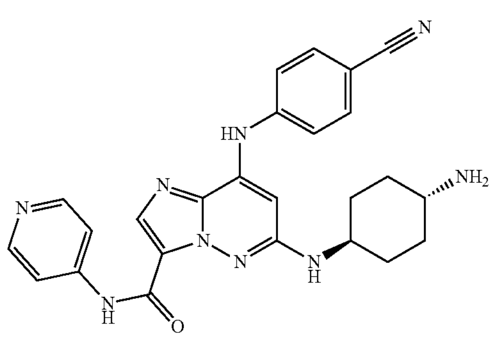 [SMILES: N#Cc1ccc(Nc2cc(N[C@H]3CC[C@H](N)CC3)nn3c(C(=O)Nc4ccncc4)cnc23)cc1] | 6-((trans-4-aminocyclohexyl)amino)-8-((4-cyanophenyl)amino)-N-4-pyridinyl-imidazo[1,2-b]pyridazine-3-carboxamide | 468 | 2.636[b] |

TABLE 13-continued

| Example | Structure | Name | [M + H] | HPLC Ret Time (min) |
|---|---|---|---|---|
| 400 | 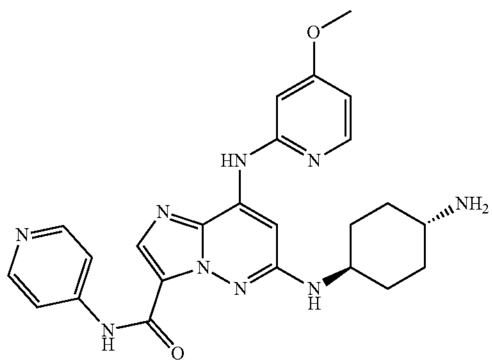 [SMILES: COc1ccnc(Nc2cc(N[C@H]3CC[C@H](N)CC3)nn3c(C(=O)Nc4ccncc4)cnc23)c1] | 6-((trans-4-aminocyclohexyl)amino)-8-((4-methoxy-2-pyridinyl)amino)-N-4-pyridinyl-imidazo[1,2-b]pyridazine-3-carboxamide | 474 | 2.142[b] |
| 401 | 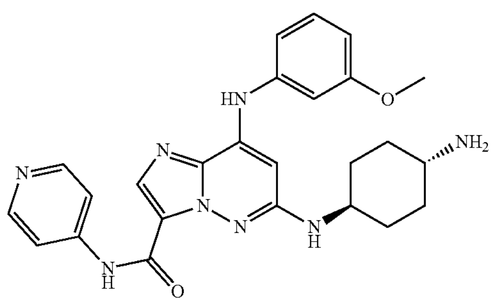 [SMILES: COc1cccc(Nc2cc(N[C@H]3CC[C@H](N)CC3)nn3c(C(=O)Nc4ccncc4)cnc23)c1] | 6-((trans-4-aminocyclohexyl)amino)-8-((3-methoxyphenyl)amino)-N-4-pyridinyl-imidazo[1,2-b]pyridazine-3-carboxamide | 473 | 2.821[b] |
| 402 | 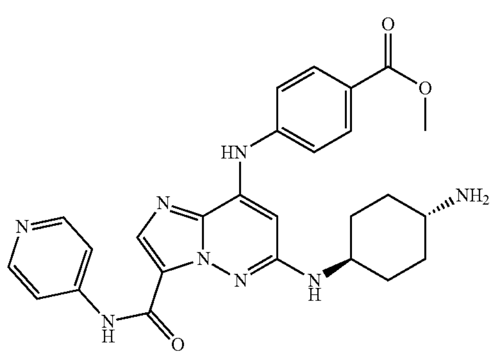 [SMILES: COC(=O)c1ccc(Nc2cc(N[C@H]3CC[C@H](N)CC3)nn3c(C(=O)Nc4ccncc4)cnc23)cc1] | methyl 4-((6-((trans-4-aminocyclohexyl)amino)-3-(4-pyridinylcarbamoyl)imidazo[1,2-b]pyridazin-8-yl)amino)benzoate | 501 | 2.926[b] |
| 403 | 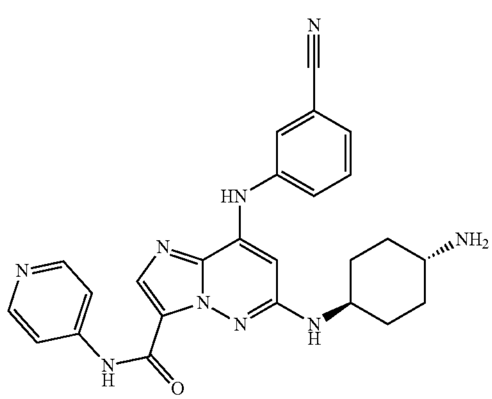 [SMILES: N#Cc1cccc(Nc2cc(N[C@H]3CC[C@H](N)CC3)nn3c(C(=O)Nc4ccncc4)cnc23)c1] | 6-((trans-4-aminocyclohexyl)amino)-8-((3-cyanophenyl)amino)-N-4-pyridinylimidazo[1,2-b]pyridazine-3-carboxamide | 468 | 2.635[b] |

TABLE 13-continued

| Example | Structure | Name | [M + H] | HPLC Ret Time (min) |
|---|---|---|---|---|
| 404 | 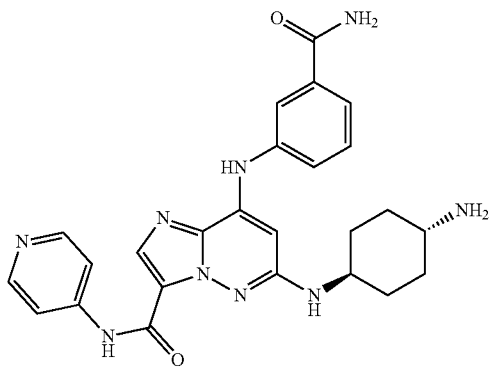 [SMILES: NC(=O)c1cccc(Nc2cc(N[C@H]3CC[C@H](N)CC3)nn3c(C(=O)Nc4ccncc4)cnc23)c1] | 6-((trans-4-aminocyclohexyl)amino)-8-((3-carbamoylphenyl)amino)-N-4-pyridinyl-imidazo[1,2-b]pyridazine-3-carboxamide | 486 | 2.443[b] |
| 405 | 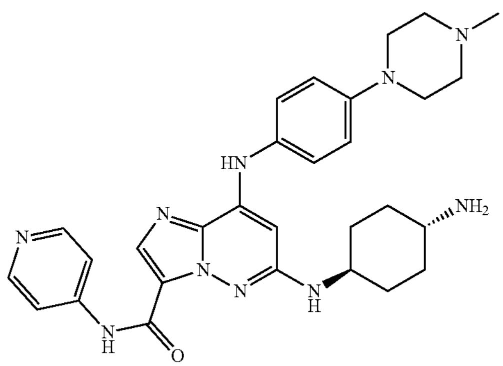 [SMILES: CN1CCN(c2ccc(Nc3cc(N[C@H]4CC[C@H](N)CC4)nn4c(C(=O)Nc5ccncc5)cnc34)cc2)CC1] | 6-((trans-4-aminocyclohexyl)amino)-8-((4-(4-methyl-1-piperazinyl)phenyl)amino)-N-4-pyridinylimidazo[1,2-b]pyridazine-3-carboxamide | 541 | 2.222[b] |
| 406 | 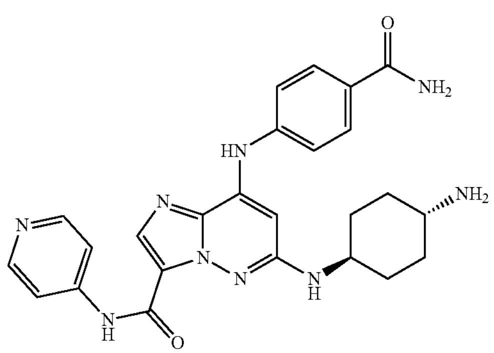 [SMILES: NC(=O)c1ccc(Nc2cc(N[C@H]3CC[C@H](N)CC3)nn3c(C(=O)Nc4ccncc4)cnc23)cc1] | 6-((trans-4-aminocyclohexyl)amino)-8-((4-carbamoylphenyl)amino)-N-4-pyridinyl-imidazo[1,2-b]pyridazine-3-carboxamide | 486 | 2.422[b] |
| 407 | 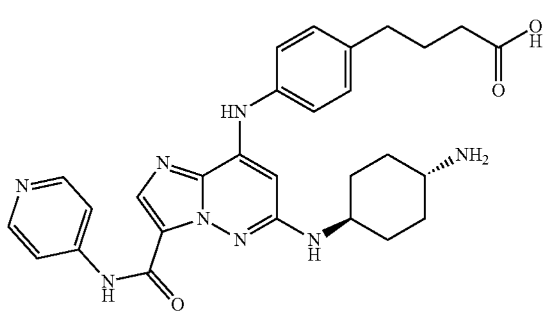 [SMILES: N[C@H]1CC[C@H](Nc2cc(Nc3ccc(CCCC(=O)O)cc3)c3ncc(C(=O)Nc4ccncc4)n3n2)CC1] | 4-(4-((6-((trans-4-aminocyclohexyl)amino)-3-(4-pyridinylcarbamoyl)imidazo[1,2-b]pyridazin-8-yl)amino)phenyl)butanoic acid | 529 | 3.006[b] |

TABLE 13-continued

| Example | Structure | Name | [M + H] | HPLC Ret Time (min) |
|---|---|---|---|---|
| 408 | 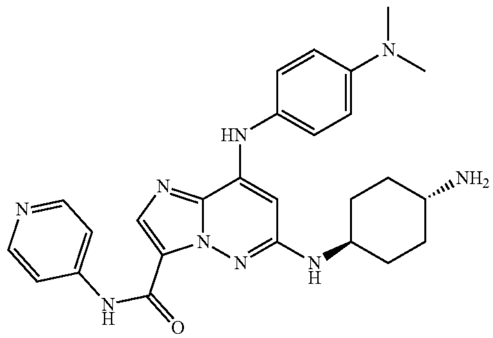 [SMILES: CN(C)c1ccc(Nc2cc(N[C@H]3CC[C@H](N)CC3)nn3c(C(=O)Nc4ccncc4)cnc23)cc1] | 6-((trans-4-aminocyclohexyl)amino)-8-((4-(dimethylamino)phenyl)amino)-N-4-pyridinylimidazo[1,2-b]pyridazine-3-carboxamide | 486 | 1.990[b] |
| 409 | 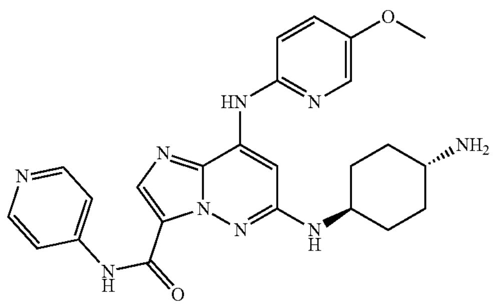 [SMILES: COc1ccc(Nc2cc(N[C@H]3CC[C@H](N)CC3)nn3c(C(=O)Nc4ccncc4)cnc23)nc1] | 6-((trans-4-aminocyclohexyl)amino)-8-((5-methoxy-2-pyridinyl)amino)-N-4-pyridinyl-imidazo[1,2-b]pyridazine-3-carboxamide | 474 | 2.750[b] |
| 410 | 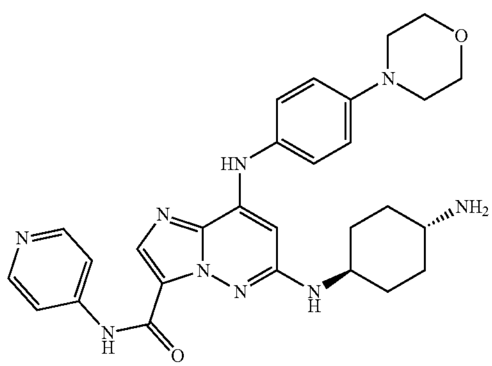 [SMILES: N[C@H]1CC[C@H](Nc2cc(Nc3ccc(N4CCOCC4)cc3)c3ncc(C(=O)Nc4ccncc4)n3n2)CC1] | 6-((trans-4-aminocyclohexyl)amino)-8-((4-(4-morpholinyl)phenyl)amino)-N-4-pyridinyl-imidazo[1,2-b]pyridazine-3-carboxamide | 528 | 2.626[b] |
| 411 | 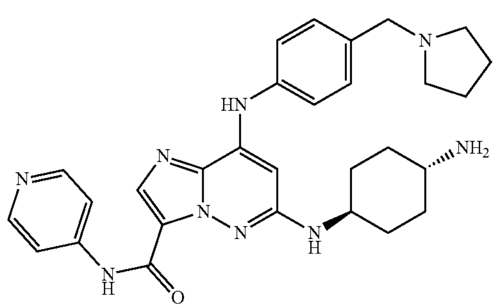 [SMILES: N[C@H]1CC[C@H](Nc2cc(Nc3ccc(CN4CCCC4)cc3)c3ncc(C(=O)Nc4ccncc4)n3n2)CC1] | 6-((trans-4-aminocyclohexyl)amino)-N-4-pyridinyl-8-((4-(1-pyrrolidinylmethyl)phenyl)amino)imidazo[1,2-b]pyridazine-3-carboxamide | 526 | 1.973[b] |

TABLE 13-continued

| Example | Structure | Name | [M + H] | HPLC Ret Time (min) |
|---|---|---|---|---|
| 412 | 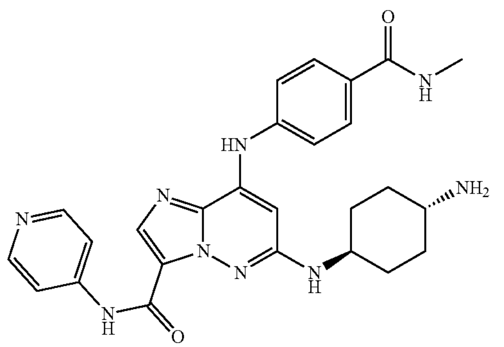 [SMILES: CNC(=O)c1ccc(Nc2cc(N[C@H]3CC[C@H](N)CC3)nn3c(C(=O)Nc4ccncc4)cnc23)cc1] | 6-((trans-4-aminocyclohexyl)amino)-8-((4-(methylcarbamoyl)phenyl)amino)-N-4-pyridinylimidazo[1,2-b]pyridazine-3-carboxamide | 500 | 2.502[b] |
| 413 | 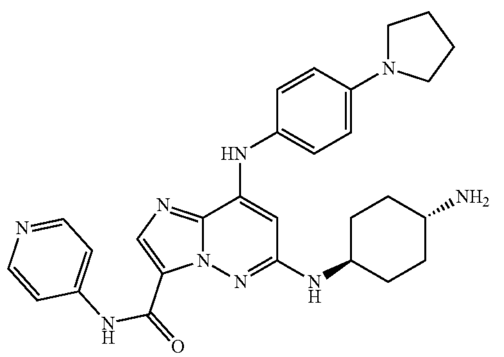 [SMILES: N[C@H]1CC[C@H](Nc2cc(Nc3ccc(N4CCCC4)cc3)c3ncc(C(=O)Nc4ccncc4)n3n2)CC1] | 6-((trans-4-aminocyclohexyl)amino)-N-4-pyridinyl-8-((4-(1-pyrrolidinyl)phenyl)amino)imidazo[1,2-b]pyridazine-3-carboxamide | 512 | 2.753[b] |
| 414 | 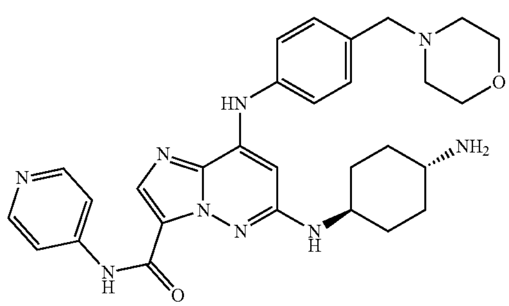 [SMILES: N[C@H]1CC[C@H](Nc2cc(Nc3ccc(CN4CCOCC4)cc3)c3ncc(C(=O)Nc4ccncc4)n3n2)CC1] | 6-((trans-4-aminocyclohexyl)amino)-8-((4-(4-morpholinylmethyl)phenyl)amino)-N-4-pyridinylimidazo[1,2-b]pyridazine-3-carboxamide | 542 | 1.930[b] |
| 415 | 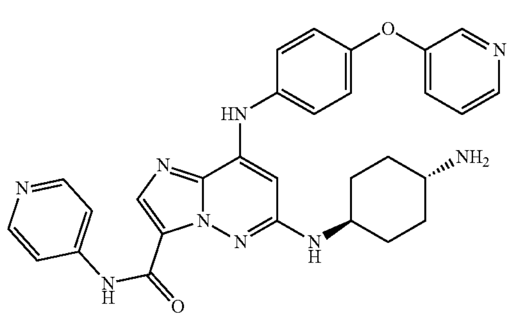 [SMILES: N[C@H]1CC[C@H](Nc2cc(Nc3ccc(Oc4cccnc4)cc3)c3ncc(C(=O)Nc4ccncc4)n3n2)CC1] | 6-((trans-4-aminocyclohexyl)amino)-N-4-pyridinyl-8-((4-(3-pyridinyloxy)phenyl)amino)imidazo[1,2-b]pyridazine-3-carboxamide | 536.31 | 2.553[b] |

TABLE 13-continued

| Example | Structure | Name | [M + H] | HPLC Ret Time (min) |
|---|---|---|---|---|
| 416 | 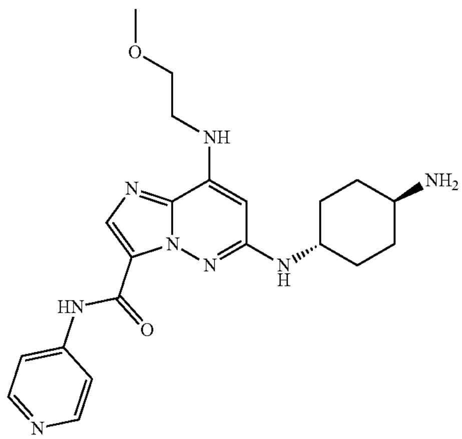 [SMILES: COCCNc1cc(N[C@H]2CC[C@H](N)CC2)nn2c(C(=O)Nc3ccncc3)cnc12] | 6-((trans-4-aminocyclohexyl)amino)-8-((2-methoxyethyl)amino)-N-4-pyridinylimidazo[1,2-b]pyridazine-3-carboxamide | 425.31 | 2.203[b] |
| 417 | 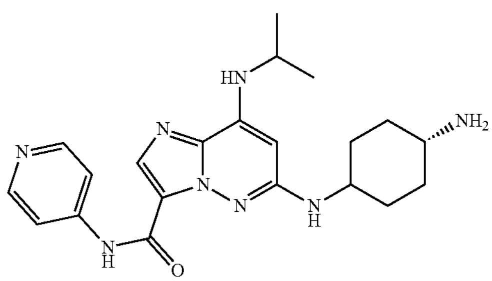 | 6-((4-aminocyclohexyl)amino)-8-(isopropylamino)-N-4-pyridinylimidazo[1,2-b]pyridazine-3-carboxamide | 409.52 | 2.365[b] |
| 418 | 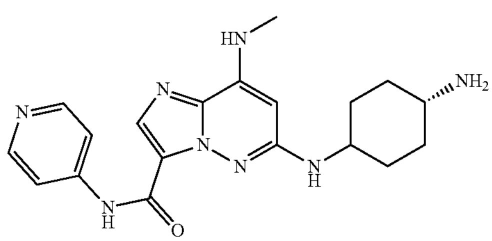 | 6-((4-aminocyclohexyl)amino)-8-(methylamino)-N-4-pyridinylimidazo[1,2-b]pyridazine-3-carboxamide | 381.5 | 1.958[b] |
| 419 | 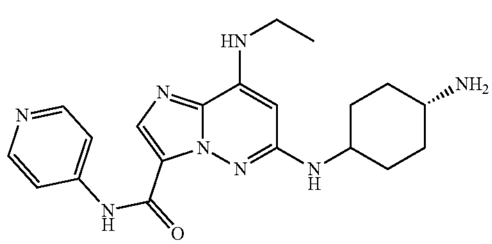 | 6-((4-aminocyclohexyl)amino)-8-(ethylamino)-N-4-pyridinylimidazo[1,2-b]pyridazine-3-carboxamide | 395.52 | 2.18[b] |
| 420 | 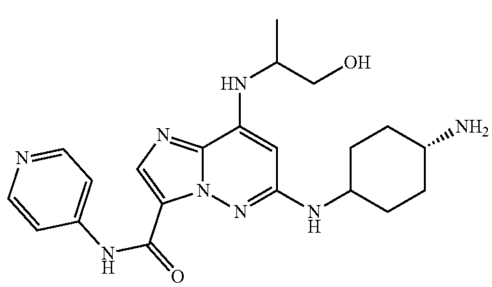 | 6-((4-aminocyclohexyl)amino)-8-((2-hydroxy-1-methylethyl)amino)-N-4-pyridinyl-imidazo[1,2-b]pyridazine-3-carboxamide | 425.37 | 2.033[b] |

TABLE 13-continued

| Example | Structure | Name | [M + H] | HPLC Ret Time (min) |
|---|---|---|---|---|
| 421 | 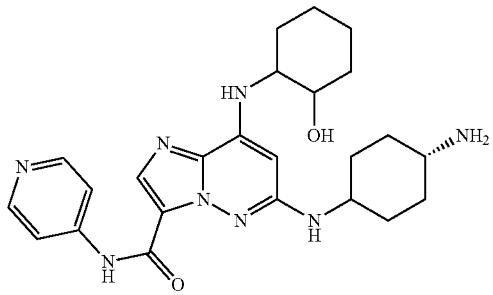 | 6-((4-aminocyclohexyl)amino)-8-((2-hydroxycyclohexyl)amino)-N-4-pyridinyl-imidazo[1,2-b]pyridazine-3-carboxamide | 465.4 | 2.452[b] |
| 422 | 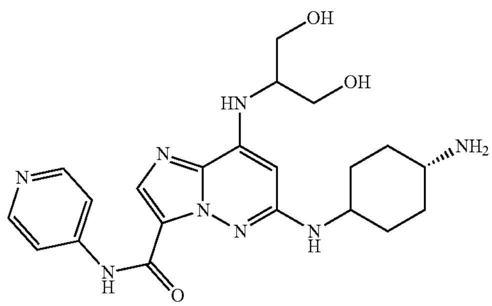 | 6-((4-aminocyclohexyl)amino)-8-((2-hydroxy-1-(hydroxymethyl)ethyl)amino)-N-4-pyridinylimidazo[1,2-b]pyridazine-3-carboxamide | 441 | 1.652[b] |
| 423 | 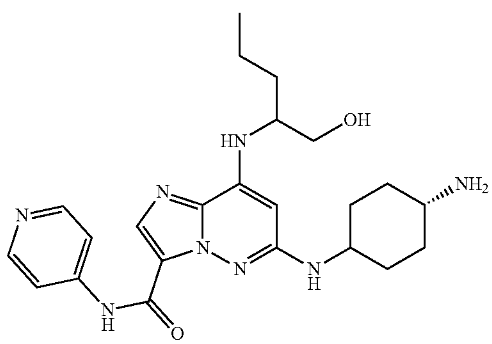 | 6-((4-aminocyclohexyl)amino)-8-((1-(hydroxymethyl)butyl)amino)-N-4-pyridinylimidazo[1,2-b]pyridazine-3-carboxamide | 453.4 | 2.437[b] |
| 424 | 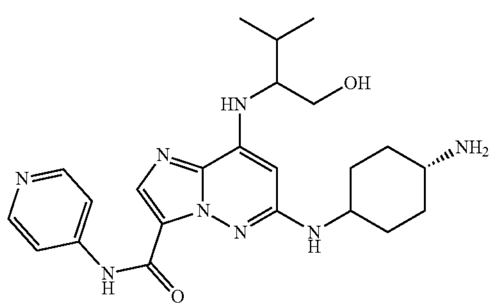 | 6-((4-aminocyclohexyl)amino)-8-((1-(hydroxy-methyl)-2-methylpropyl)amino)-N-4-pyridinyl-imidazo[1,2-b]pyridazine-3-carboxamide | 453.4 | 2.400[d] |
| 425 | 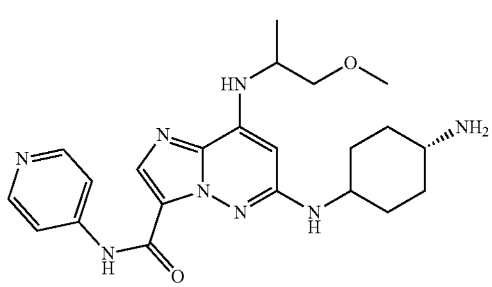 | 6-((4-aminocyclohexyl)amino)-8-((2-methoxy-1-methylethyl)amino)-N-4-pyridinylimidazo[1,2-b]pyridazine-3-carboxamide | 439.31 | 2.215[b] |

TABLE 13-continued

| Example | Structure | Name | [M + H] | HPLC Ret Time (min) |
|---|---|---|---|---|
| 426 | 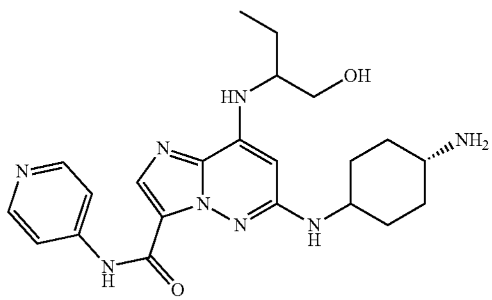 | 6-((4-aminocyclohexyl)amino)-8-((1-(hydroxymethyl)propyl)amino)-N-4-pyridinylimidazo[1,2-b]pyridazine-3-carboxamide | 439.3 | 2.285[b] |
| 427 | 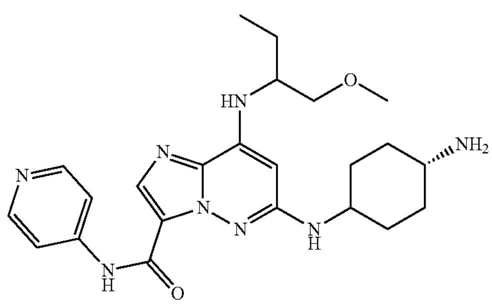 | 6-((4-aminocyclohexyl)amino)-8-((1-(methoxymethyl)propyl)amino)-N-4-pyridinylimidazo[1,2-b]pyridazine-3-carboxamide | 453.32 | 2.438[b] |
| 428 | 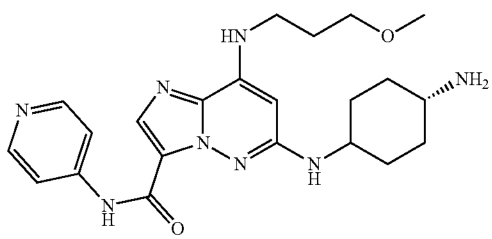 | 6-((4-aminocyclohexyl)amino)-8-((3-methoxypropyl)amino)-N-4-pyridinyl-imidazo[1,2-b]pyridazine-3-carboxamide | 439.31 | 2.332[b] |
| 429 | 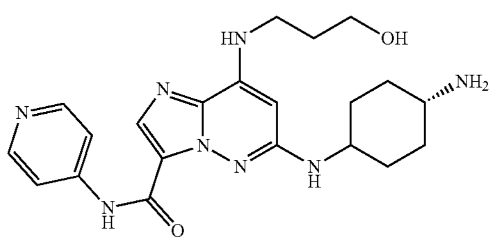 | 6-((4-aminocyclohexyl)amino)-8-((3-hydroxypropyl)amino)-N-4-pyridinyl-imidazo[1,2-b]pyridazine-3-carboxamide | 425.29 | 2.017[b] |
| 430 | 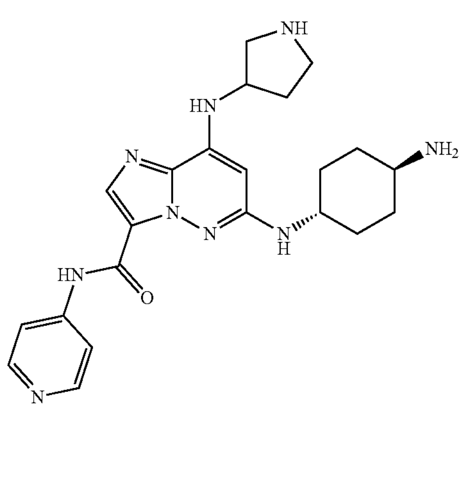 [SMILES: N[C@H]1CC[C@H](Nc2cc(NC3CCNC3)c3ncc(C(=O)Nc4ccncc4)n3n2)CC1] | 6-((trans-4-aminocyclohexyl)amino)-N-4-pyridinyl-8-(3-pyrrolidinylamino)imidazo[1,2-b]pyridazine-3-carboxamide | 436.3 | 1.620[b] |

TABLE 13-continued

| Example | Structure | Name | [M + H] | HPLC Ret Time (min) |
|---|---|---|---|---|
| 431 | 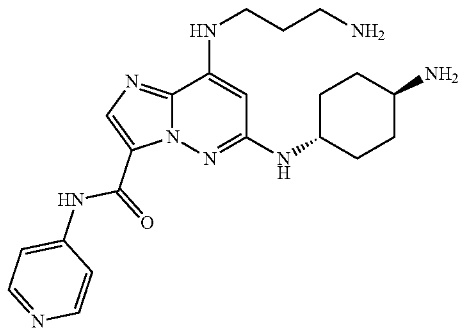 [SMILES: NCCCNc1cc(N[C@H]2CC[C@H](N)CC2)nn2c(C(=O)Nc3ccncc3)cnc12] | 6-((trans-4-aminocyclohexyl)amino)-8-((3-aminopropyl)amino)-N-pyridinyl-imidazo[1,2-b]pyridazine-3-carboxamide | 424.28 | 1.58[d] |
| 432 | 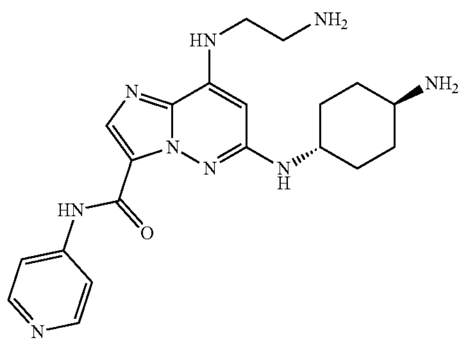 [SMILES: NCCNc1cc(N[C@H]2CC[C@H](N)CC2)nn2c(C(=O)Nc3ccncc3)cnc12] | 6-((trans-4-aminocyclohexyl)amino)-8-((2-aminoethyl)amino)-N-4-pyridinyl-imidazo[1,2-b]pyridazine-3-carboxamide | 410.29 | 1.523[b] |
| 433 | 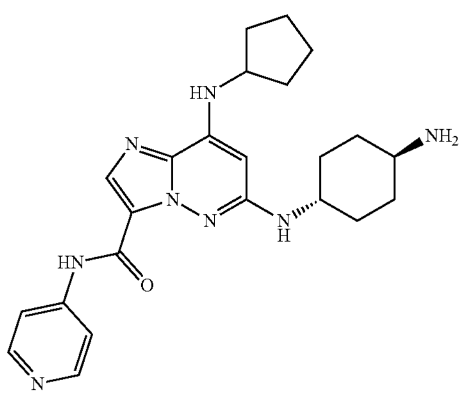 [SMILES: N[C@H]1CC[C@H](Nc2cc(NC3CCCC3)c3ncc(C(=O)Nc4ccncc4)n3n2)CC1] | 6-((trans-4-aminocyclohexyl)amino)-8-(cyclopentylamino)-N-4-pyridinyl-imidazo[1,2-b]pyridazine-3-carboxamide | 435.33 | 2.7[b] |
| 434 | 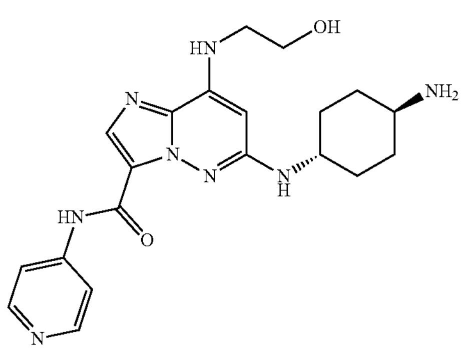 [SMILES: N[C@H]1CC[C@H](Nc2cc(NCCO)c3ncc(C(=O)Nc4ccncc4)n3n2)CC1] | 6-((trans-4-aminocyclohexyl)amino)-8-((2-hydroxyethyl)amino)-N-4-pyridinyl-imidazo[1,2-b]pyridazine-3-carboxamide | 411.3 | 1.91[b] |

TABLE 13-continued

| Example | Structure | Name | [M + H] | HPLC Ret Time (min) |
|---|---|---|---|---|
| 435 | 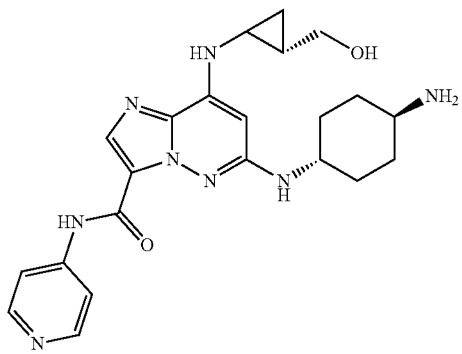 [SMILES: N[C@H]1CC[C@H](Nc2cc(NC3C[C@@H]3CO)c3ncc(C(=O)Nc4ccncc4)n3n2)CC1] | 6-((trans-4-aminocyclohexyl)amino)-8-(((2S)-2-(hydroxymethyl)cyclopropyl)amino)-N-4-pyridinylimidazo[1,2-b]pyridazine-3-carboxamide | 437.33 | 2.17[b] |

HPLC Conditions:
[a]Water Sunfire C18 column (4.6 × 50 mm): 0%-100% B. Solvent B: 90% MeOH, 10% H$_2$O, 0.1% TFA). Solvent A: 10% MeOH, 90% H$_2$O, 0.1% TFA). Gradient, start % B = 0, final % B = 100, gradient time 4 min, hold at 100% B 1 min, flow rate 4 mL/min.
[b]YMC S-5 ODS-A 4.6 × 50 mm, 10-90% aqueous methanol containing 0.2% H$_3$PO$_4$, 4 min gradient, monitored at 220 nm The following Examples in Table 14 may be prepared according to the procedures detailed in Examples 1-4 and Example 24.

TABLE 14

| Example | Structure | Name | [M + H] | HPLC Ret Time (min) |
|---|---|---|---|---|
| 436 | 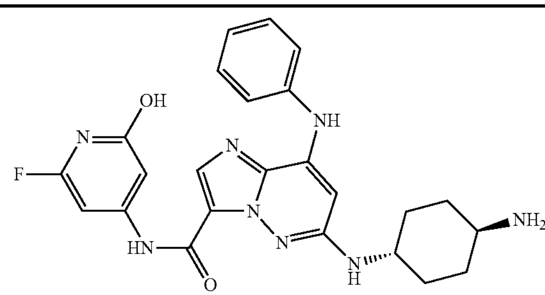 | 6-((trans-4-aminocyclohexyl)amino)-8-anilino-N-(6-fluoro-2-oxo-1,2-dihydro-4-pyridinyl)imidazo[1,2-b]pyridazine-3-carboxamide | 477.24 | 3.07[a] |
| 437 | 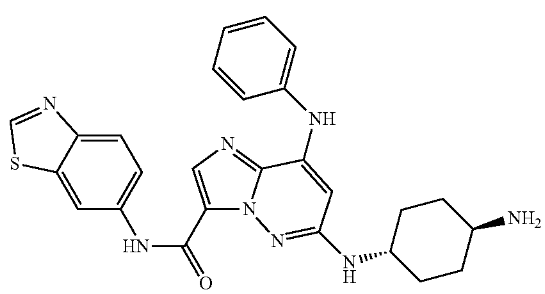 [SMILES: N[C@H]1CC[C@H](Nc2cc(Nc3ccccc3)c3ncc(C(=O)Nc4ccc5ncsc5c4)n3n2)CC1] | 6-((trans-4-aminocyclohexyl)amino)-8-anilino-N-1,3-benzothiazol-6-ylimidazo[1,2-b]pyridazine-3-carboxamide | 499.30 | 3.11[a] |
| 438 | 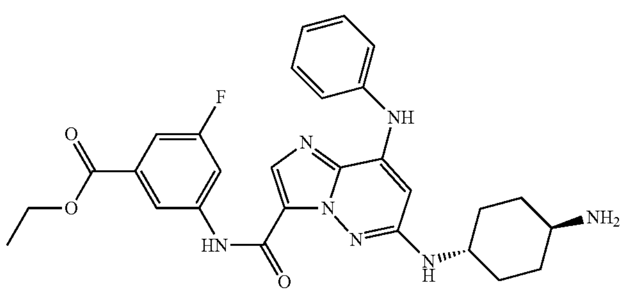 [SMILES: CCOC(=O)c1cc(F)cc(NC(=O)c2cnc3c(Nc4ccccc4)cc(N[C@H]4CC[C@H](N)CC4)nn23)c1] | ethyl 3-(((6-((trans-4-aminocyclohexyl)amino)-8-anilinoimidazo[1,2-b]pyridazin-3-yl)carbonyl)amino)-5-fluorobenzoate | 532.34 | 3.65[a] |

TABLE 14-continued

| Example | Structure | Name | [M + H] | HPLC Ret Time (min) |
|---|---|---|---|---|
| 439 | 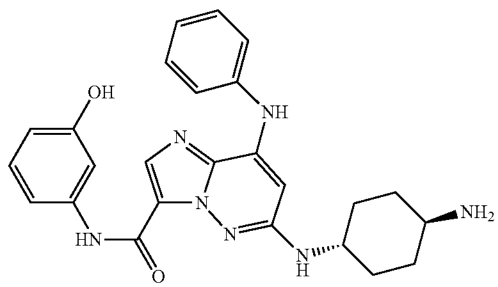 [SMILES: N[C@H]1CC[C@H](Nc2cc(Nc3ccccc3)c3ncc(C(=O)Nc4cccc(O)c4)n3n2)CC1] | 6-((trans-4-aminocyclohexyl)amino)-8-anilino-N-(3-hydroxyphenyl)imidazo[1,2-b]pyridazine-3-carboxamide | 458.30 | 2.82$^a$ |
| 450 | 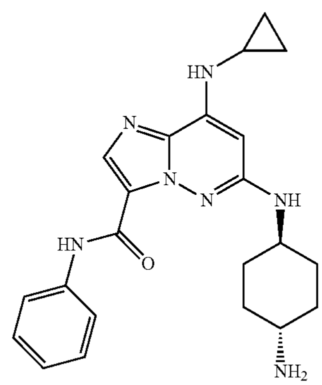 [SMILES: N[C@H]1CC[C@H](Nc2cc(NC3CC3)c3ncc(C(=O)Nc4ccccc4)n3n2)CC1] | 6-((trans-4-aminocyclohexyl)amino)-8-(cyclopropylamino)-N-phenylimidazo[1,2-b]pyridazine-3-carboxamide | 406.3 | 1.34$^b$ |
| 451 | 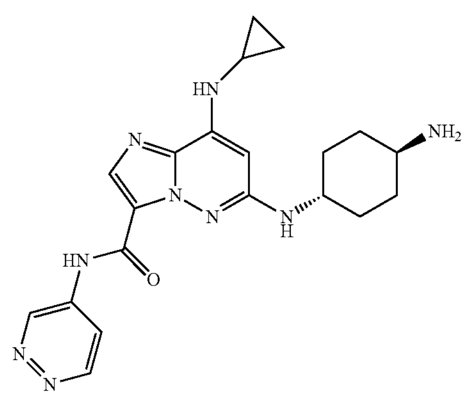 [SMILES: N[C@H]1CC[C@H](Nc2cc(NC3CC3)c3ncc(C(=O)Nc4ccnnc4)n3n2)CC1] | 6-((trans-4-aminocyclohexyl)amino)-8-(cyclopropylamino)-N-4-pyridazinylimidazo[1,2-b]pyridazine-3-carboxamide | 408.23 | 1.21$^b$ |

HPLC Conditions:
$^a$Waters Sunfire C18 column (4.6 × 50 mm): 0%-100% B. Solvent B: 90% MeOH, 10% H$_2$O, 0.1% TFA). Solvent A: 10% MeOH, 90% H$_2$O, 0.1% TFA). Gradient, start % B = 0, final % B = 100, gradient time 4 min, hold at 100% B 1 min, flow rate 4 mL/min.
$^b$Phenomenex Luna 5 micron C18 4.6 X 30 mm: 0 to 100% B in 2 min with 1 min hold time, Flow rate = 5 mL/min, detection at 254 nm, Solvent A: 10% methanol/90% water/0.1% TFA; Solvent B: 10% water/90% methanol/0.1% TFA The following Examples in Table 15 may be prepared in a manner analogous to the procedures described in Examples 14, 25 and 34.

TABLE 15

| Example | Structure | Name | [M + H] | HPLC Ret Time (min) |
|---|---|---|---|---|
| 452 | 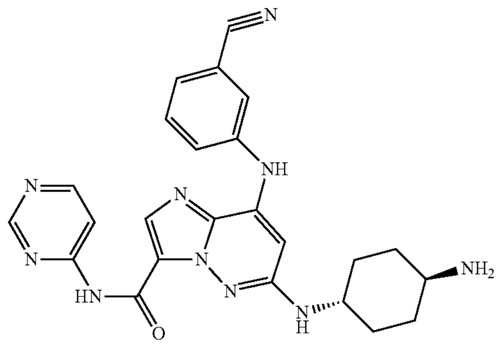 [SMILES: N#Cc1cccc(Nc2cc(N[C@H]3CC[C@H](N)CC3)nn3c(C(=O)Nc4ccncn4)cnc23)c1] | 6-((trans-4-aminocyclohexyl)amino)-8-((3-cyanophenyl)amino)-N-4-pyrimidinylimidazo[1,2-b]pyridazine-3-carboxamide | 469.30 | 2.86$^a$ |
| 453 | 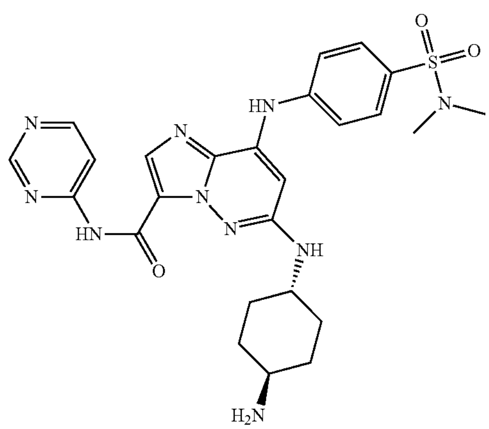 [SMILES: CN(C)S(=O)(=O)c1ccc(Nc2cc(N[C@H]3CC[C@H](N)CC3)nn3c(C(=O)Nc4ccncn4)cnc23)cc1] | 6-((trans-4-aminocyclohexyl)amino)-8-((4-(dimethylsulfamoyl)phenyl)amino)-N-4-pyrimidinylimidazo[1,2-b]pyridazine-3-carboxamide | 551.31 | 2.82$^a$ |
| 454 | 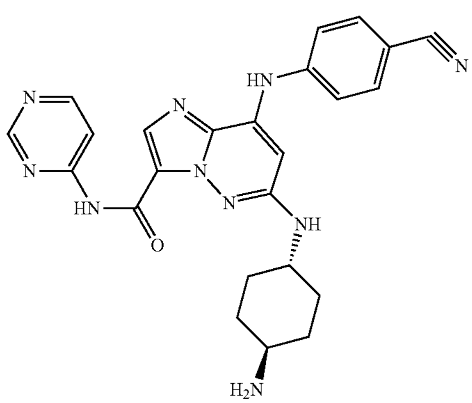 [SMILES: N#Cc1ccc(Nc2cc(N[C@H]3CC[C@H](N)CC3)nn3c(C(=O)Nc4ccncn4)cnc23)cc1] | 6-((trans-4-aminocyclohexyl)amino)-8-((4-cyanophenyl)amino)-N-4-pyrimidinylimidazo[1,2-b]pyridazine-3-carboxamide | 469.30 | 2.88$^a$ |

TABLE 15-continued

| Example | Structure | Name | [M + H] | HPLC Ret Time (min) |
|---|---|---|---|---|
| 455 | 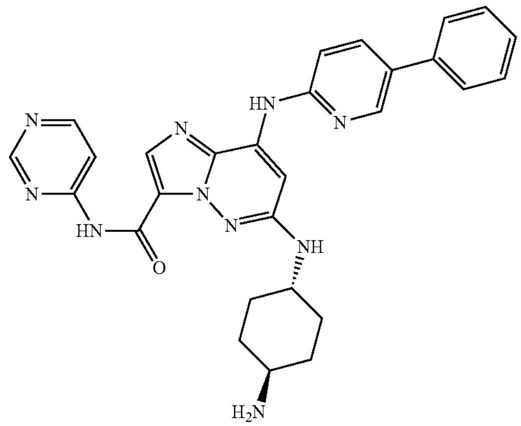 [SMILES: N[C@H]1CC[C@H](Nc2cc(Nc3ccc(-c4ccccc4)cn3)c3ncc(C(=O)Nc4ccncn4)n3n2)CC1] | 6-((trans-4-aminocyclohexyl)amino)-8-((5-phenyl-2-pyridinyl)amino)-N-4-pyrimidinylimidazo[1,2-b]pyridazine-3-carboxamide | 521.34 | 3.54$^a$ |
| 456 | 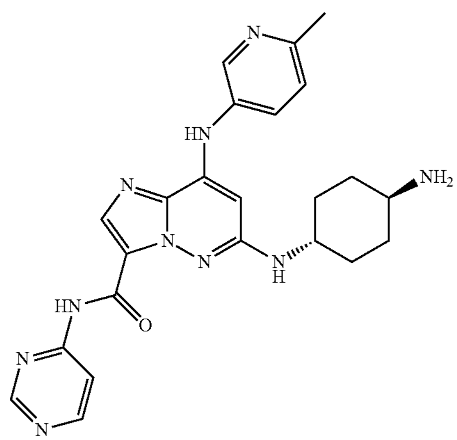 [SMILES: Cc1ccc(Nc2cc(N[C@H]3CC[C@H](N)CC3)nn3c(C(=O)Nc4ccncn4)cnc23)cn1] | 6-((trans-4-aminocyclohexyl)amino)-8-((5-methyl-2-pyridinyl)amino)-N-4-pyrimidinylimidazo[1,2-b]pyridazine-3-carboxamide | 459.20 | 1.578$^b$ |
| 457 | 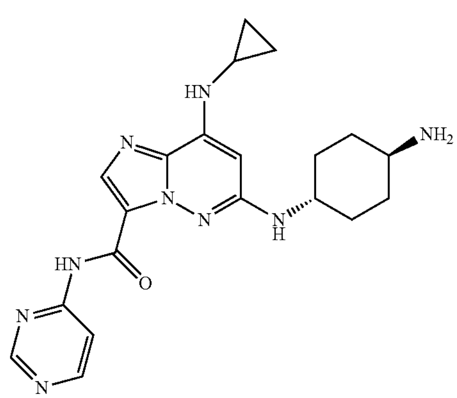 [SMILES: N[C@H]1CC[C@H](Nc2cc(NC3CC3)c3ncc(C(=O)Nc4ccncn4)n3n2)CC1] | 6-((trans-4-aminocyclohexyl)amino)-8-(cyclopropylamino)-N-4-pyrimidinylimidazo[1,2-b]pyridazine-3-carboxamide | 408.30 | 1.372$^b$ |

TABLE 15-continued

| Example | Structure | Name | [M + H] | HPLC Ret Time (min) |
|---|---|---|---|---|
| 458 | 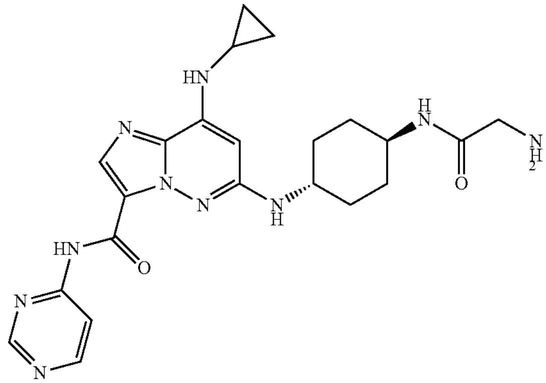 [SMILES: NCC(=O)N[C@H]1CC[C@H](Nc2cc(NC3CC3)c3ncc(C(=O)Nc4ccncn4)n3n2)CC1] | 8-(cyclopropylamino)-6-((trans-4-(glycylamino)cyclohexyl)amino)-N-4-pyrimidinylimidazo[1,2-b]pyridazine-3-carboxamide | 465.28 | 1.460[b] |
| 459 | 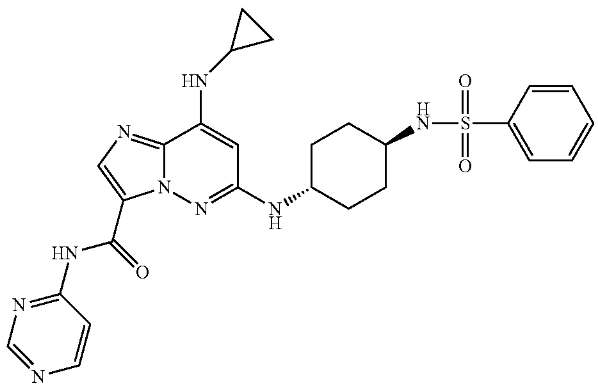 [SMILES: O=C(Nc1ccncn1)c1cnc2c(NC3CC3)cc(N[C@H]3CC[C@H](NS(=O)(=O)c4ccccc4)CC3)nn12] | 8-(cyclopropylamino)-6-((trans-4-((phenylsulfonyl)amino)cyclohexyl)amino)-N-4-pyrimidinylimidazo[1,2-b]pyridazine-3-carboxamide | 548.30 | 1.828[b] |
| 460 | 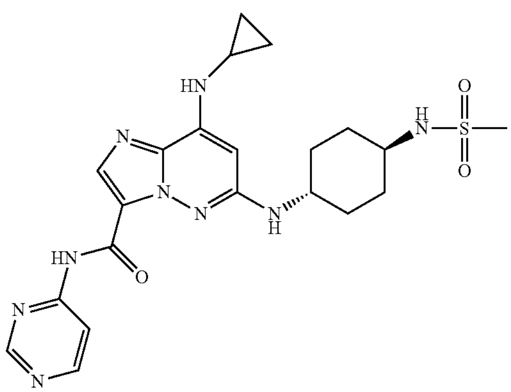 [SMILES: CS(=O)(=O)N[C@H]1CC[C@H](Nc2cc(NC3CC3)c3ncc(C(=O)Nc4ccncn4)n3n2)CC1] | 8-(cyclopropylamino)-6-((trans-4-((methylsulfonyl)amino)cyclohexyl)amino)-N-4-pyrimidinylimidazo[1,2-b]pyridazine-3-carboxamide | 486.28 | 1.637[b] |
| 461 | 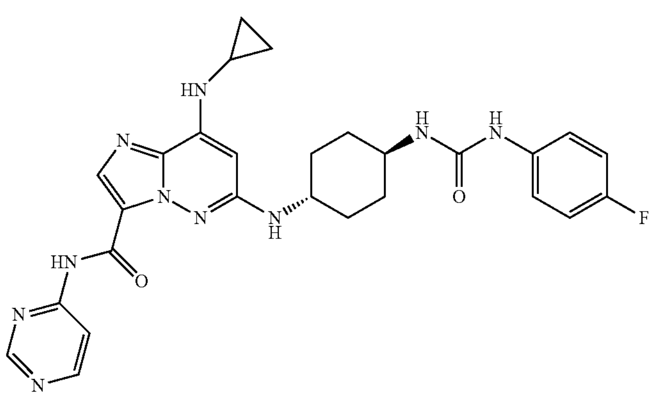 [SMILES: O=C(Nc1ccc(F)cc1)N[C@H]1CC[C@H](Nc2cc(NC3CC3)c3ncc(C(=O)Nc4ccncn4)n3n2)CC1] | 8-(cyclopropylamino)-6-((trans-4-(((4-fluorophenyl)carbamoyl)amino)cyclohexyl)amino)-N-4-pyrimidinylimidazo[1,2-b]pyridazine-3-carboxamide | 545.29 | 2.013[b] |

TABLE 15-continued

| Example | Structure | Name | [M + H] | HPLC Ret Time (min) |
|---|---|---|---|---|
| 462 | 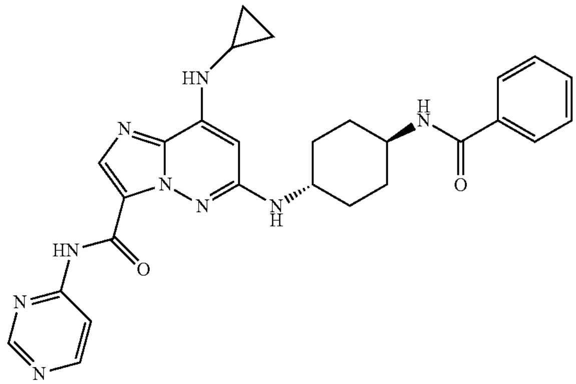 [SMILES: O=C(N[C@H]1CC[C@H](Nc2cc(NC3CC3)c3ncc(C(=O)Nc4ccncn4)n3n2)CC1)c1ccccc1] | 6-((trans-4-(benzoylamino) cyclohexyl)amino)-8- (cyclopropylamino)-N-4- pyrimidinylimidazo[1,2- b]pyridazine-3-carboxamide | 512.18 | 1.898[b] |
| 463 | 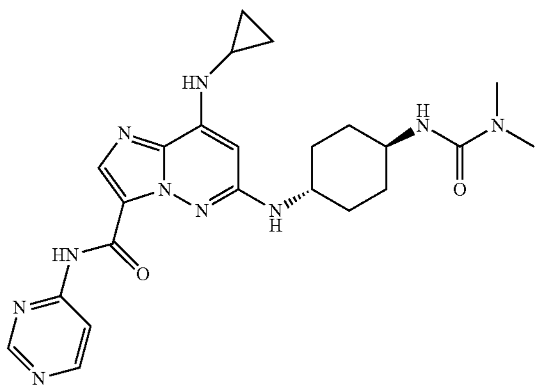 [SMILES: CN(C)C(=O)N[C@H]1CC[C@H](Nc2cc(NC3CC3)c3ncc(C(=O)Nc4ccncn4)n3n2)CC1] | 8-(cyclopropylamino)-6- ((trans-4- ((dimethylcarbamoyl)amino) cyclohexyl)amino)-N-4- pyrimidinylimidazo[1,2-b] pyridazine-3-carboxamide | 479.23 | 1.712[b] |
| 464 | 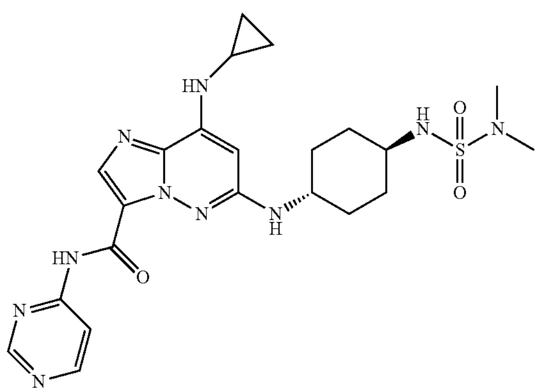 [SMILES: CN(C)S(=O)(=O)N[C@H]1CC[C@H](Nc2cc(NC3CC3)c3ncc(C(=O)Nc4ccncn4)n3n2)CC1] | 8-(cyclopropylamino)-6- ((trans-4- ((dimethylsulfamoyl)amino) cyclohexyl)amino)-N-4- pyrimidinylimidazo[1,2-b] pyridazine-3-carboxamide | 515.16 | 1.742[b] |
| 465 | 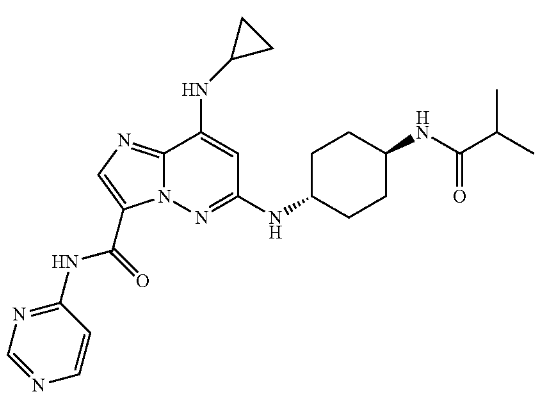 [SMILES: CC(C)C(=O)N[C@H]1CC[C@H](Nc2cc(NC3CC3)c3ncc(C(=O)Nc4ccncn4)n3n2)CC1] | 8-(cyclopropylamino)-6- ((trans-4- (isobutyrylamino)cyclohexyl) amino)-N-4- pyrimidinylimidazo[1,2-b] pyridazine-3-carboxamide | 478.20 | 1.833[b] |

TABLE 15-continued

| Example | Structure | Name | [M + H] | HPLC Ret Time (min) |
|---|---|---|---|---|
| 466 | 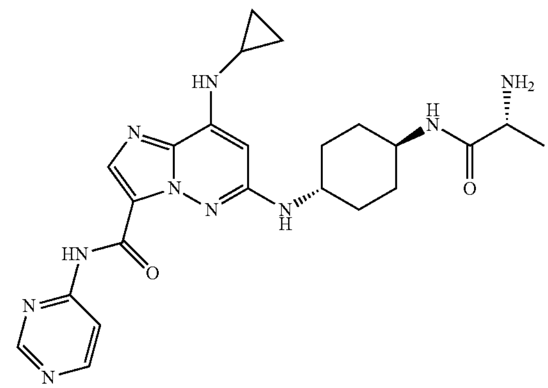 [SMILES: C[C@@H](N)C(=O)N[C@H]1CC[C@H](Nc2cc(NC3CC3)c3ncc(C(=O)Nc4ccncn4)n3n2)CC1] | 6-((trans-4-(D-alanylamino) cyclohexyl)amino)-8-(cyclopropylamino)-N-4-pyrimidinylimidazo[1,2-b]pyridazine-3-carboxamide | 479.23 | 1.490[b] |
| 467 | 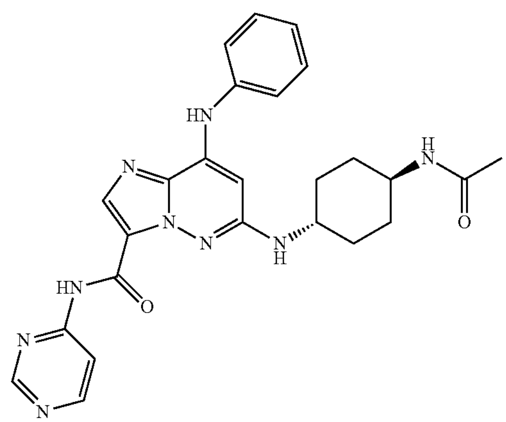 [SMILES: CC(=O)N[C@H]1CC[C@H](Nc2cc(Nc3ccccc3)c3ncc(C(=O)Nc4ccncn4)n3n2)CC1] | 6-((trans-4-acetamidocyclohexyl)amino)-8-anilino-N-4-pyrimidinylimidazo[1,2-b]pyridazine-3-carboxamide | 486.28 | 1.883[b] |

[a]Waters Sunfire C18 column (4.6 × 50 mm): 0%-100% B. Solvent B: 90% MeOH, 10% H$_2$O, 0.1% TFA. Solvent A: 10% MeOH, 90% H$_2$O, 0.1% TFA. Gradient, start % B = 0, final % B = 100, gradient time 4 min, hold at 100% B 1 min, flow rate 4 mL/min.
[b]Phenomenex Luna 5 micron C18 4.6 X 30 mm: 0 to 100 B in 2 min with 1 min hold time, Flow rate = 5 mL/min, detection at 254 nm, Solvent A: 10% methanol/90% water/0.1% TFA; Solvent B: 10% water/90% methanol/0.1% TFA The following Examples in Table 16 may be prepared from 8B in a manner analogous to the procedures described in Examples 1-4.

TABLE 16

| Example | Structure | Name | [M + H] | HPLC Ret. Time (min) |
|---|---|---|---|---|
| 468 | 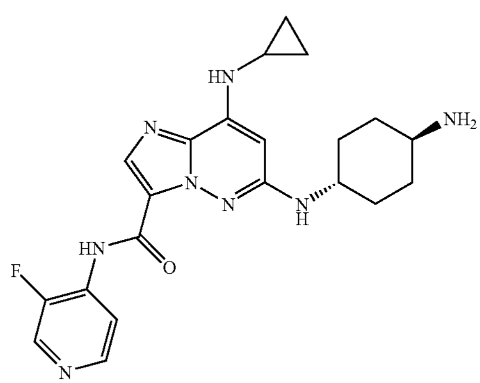 [SMILES: N[C@H]1CC[C@H](Nc2cc(NC3CC3)c3ncc(C(=O)Nc4ccncc4F)n3n2)CC1] | 6-((trans-4-aminocyclohexyl)amino)-8-(cyclopropylamino)-N-(3-fluoro-4-pyridinyl)imidazo[1,2-b]pyridazine-3-carboxamide | 425.3 | 3.081[a] |

TABLE 16-continued

| Example | Structure | Name | [M + H] | HPLC Ret. Time (min) |
|---|---|---|---|---|
| 469 | 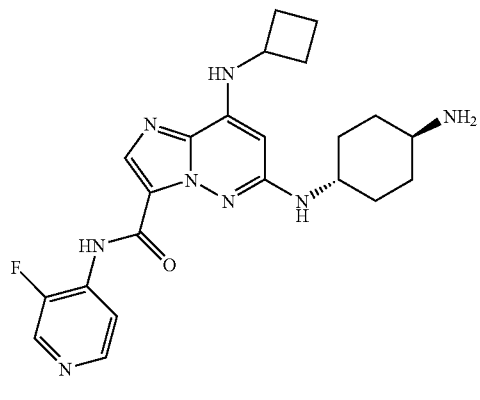 [SMILES: N[C@H]1CC[C@H](Nc2cc(NC3CCC3)c3ncc(C(=O)Nc4ccncc4F)n3n2)CC1] | 6-((trans-4-aminocyclohexyl)amino)-8-(cyclobutylamino)-N-(3-fluoro-4-pyridinyl)imidazo[1,2-b]pyridazine-3-carboxamide | 439.29 | 3.295[a] |
| 470 | 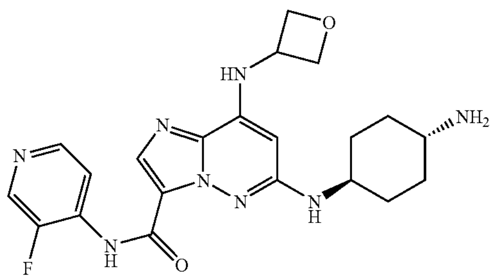 [SMILES: N[C@H]1CC[C@H](Nc2cc(NC3COC3)c3ncc(C(=O)Nc4ccncc4F)n3n2)CC1] | 6-((trans-4-aminocyclohexyl)amino)-N-(3-fluoro-4-pyridinyl)-8-(3-oxetanylamino)imidazo[1,2-b]pyridazine-3-carboxamide | 441.1. | 1.512[a] |
| 471 | 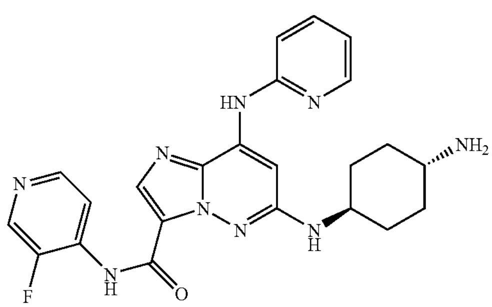 [SMILES: N[C@H]1CC[C@H](Nc2cc(Nc3ccccn3)c3ncc(C(=O)Nc4ccncc4F)n3n2)CC1] | 6-((trans-4-aminocyclohexyl)amino)-N-(3-fluoro-4-pyridinyl)-8-(2-pyridinylamino)imidazo[1,2-b]pyridazine-3-carboxamide | 462.0 | 3.318[b] |
| 472 | 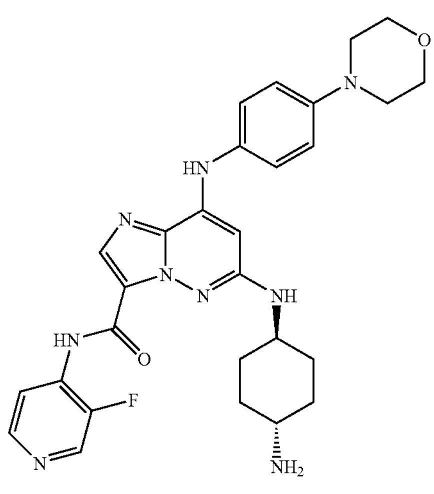 [SMILES: N[C@H]1CC[C@H](Nc2cc(Nc3ccc(N4CCOCC4)cc3)c3ncc(C(=O)Nc4ccncc4F)n3n2)CC1] | 6-((trans-4-aminocyclohexyl)amino)-N-(3-fluoro-4-pyridinyl)-8-((5-(4-morpholinyl)-2-pyridinyl)amino)imidazo[1,2-b]pyridazine-3-carboxamide | 547.0 | 3.355[a] |

TABLE 16-continued

| Example | Name | [M + H] | HPLC Ret. Time (min) |
|---|---|---|---|
| 473 | 6-((trans-4-aminocyclohexyl)amino)-N-(3-fluoro-4-pyridinyl)-8-((2,2,2-trifluoroethyl)amino)imidazo[1,2-b]pyridazine-3-carboxamide | 467.22 | 1.32[a] |
| 474 | 8-((1-acetyl-3-azetidinyl)amino)-6-((trans-4-aminocyclohexyl)amino)-N-(3-fluoro-4-pyridinyl)imidazo[1,2-b]pyridazine-3-carboxamide | 482 | 1.907[c] |
| 475 | 6-((trans-4-aminocyclohexyl)amino)-N-(3-fluoro-4-pyridinyl)-8-((trans-3-(hydroxymethyl)cyclobutyl)amino)imidazo[1,2-b]pyridazine-3-carboxamide | 469 | 2.152[c] |
| 476 | 6-((trans-4-aminocyclohexyl)amino)-N-(3-fluoro-4-pyridinyl)-8-((cis-3-(hydroxymethyl)cyclobutyl)amino)imidazo[1,2-b]pyridazine-3-carboxamide | 469 | 2.107[c] |

TABLE 16-continued

| Example | Structure | Name | [M + H] | HPLC Ret. Time (min) |
|---|---|---|---|---|
| 477 | 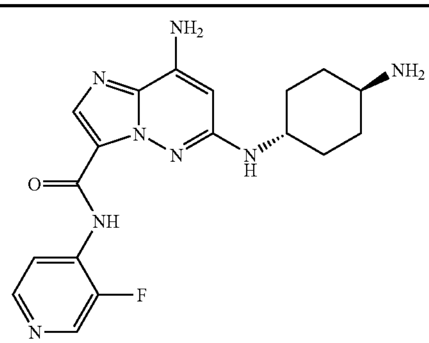 | 8-amino-6-((trans-4-aminocyclohexyl)amino)-N-(3-fluoro-4-pyridinyl)imidazo[1,2-b]pyridazine-3-carboxamide | 385 | 1.657[c] |
| 478 | 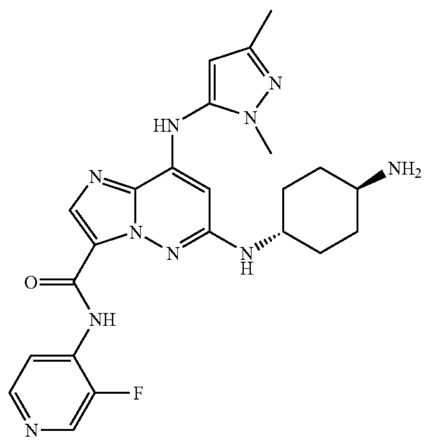 [SMILES: Cc1cc(Nc2cc(N[C@H]3CC[C@H](N)CC3)nn3c(C(=O)Nc4ccncc4F)cnc23)n(C)n1] | 6-((trans-4-aminocyclohexyl)amino)-8-((1,3-dimethyl-1H-pyrazol-5-yl)amino)-N-(3-fluoro-4-pyridinyl)imidazo[1,2-b]pyridazine-3-carboxamide | 479 | 2.285[c] |
| 479 | 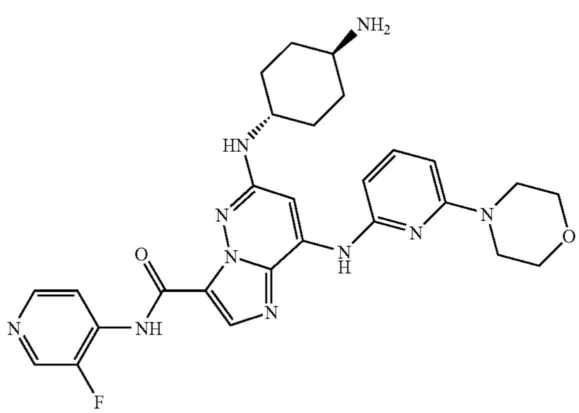 [SMILES: N[C@H]1CC[C@H](Nc2cc(Nc3cccc(N4CCOCC4)n3)c3ncc(C(=O)Nc4ccncc4F)n3n2)CC1] | 6-((trans-4-aminocyclohexyl)amino)-N-(3-fluoro-4-pyridinyl)-8-((6-(4-morpholinyl)-2-pyridinyl)amino)imidazo[1,2-b]pyridazine-3-carboxamide | 547 | 2.888[c] |
| 480 | 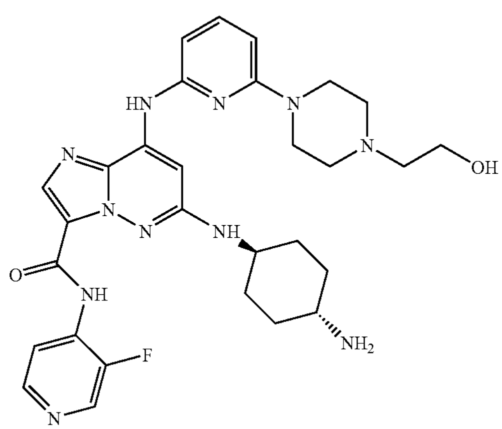 [SMILES: N[C@H]1CC[C@H](Nc2cc(Nc3cccc(N4CCN(CCO)CC4)n3)c3ncc(C(=O)Nc4ccncc4F)n3n2)CC1] | 6-((trans-4-aminocyclohexyl)amino)-N-(3-fluoro-4-pyridinyl)-8-((6-(4-(2-hydroxyethyl)-1-piperazinyl)-2-pyridinyl)amino)imidazo[1,2-b]pyridazine-3-carboxamide | 590 | 2.293[c] |

TABLE 16-continued

| Example | Structure | Name | [M + H] | HPLC Ret. Time (min) |
|---|---|---|---|---|
| 481 | 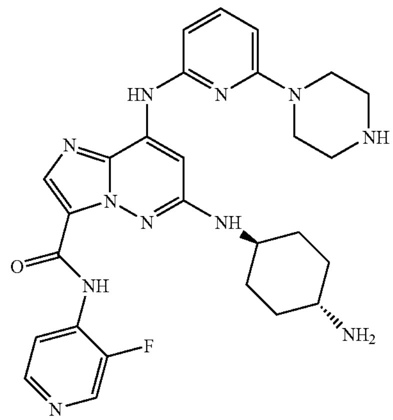 [SMILES: N[C@H]1CC[C@H](Nc2cc(Nc3cccc(N4CCNCC4)n3)c3ncc(C(=O)Nc4ccncc4F)n3n2)CC1] | 6-((trans-4-aminocyclohexyl)amino)-N-(3-fluoro-4-pyridinyl)-8-((6-(1-piperazinyl)-2-pyridinyl)amino)imidazo[1,2-b]pyridazine-3-carboxamide | 546 | 2.317[c] |
| 482 | 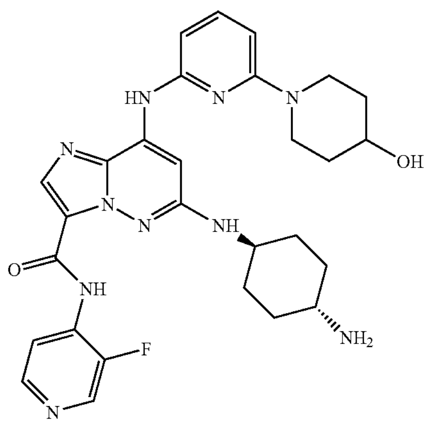 [SMILES: N[C@H]1CC[C@H](Nc2cc(Nc3cccc(N4CCC(O)CC4)n3)c3ncc(C(=O)Nc4ccncc4F)n3n2)CC1] | 6-((trans-4-aminocyclohexyl)amino)-N-(3-fluoro-4-pyridinyl)-8-((6-(4-hydroxy-1-piperidinyl)-2-pyridinyl)amino)imidazo[1,2-b]pyridazine-3-carboxamide | 561 | 2.666[c] |
| 483 | 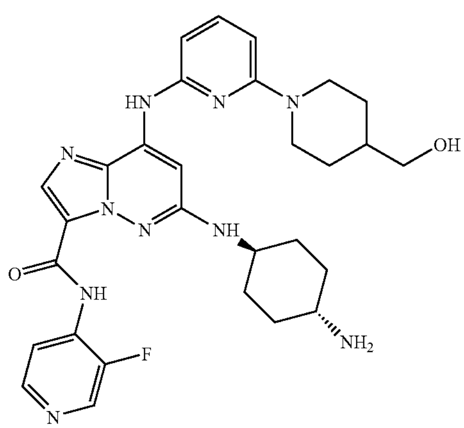 [SMILES: N[C@H]1CC[C@H](Nc2cc(Nc3cccc(N4CCC(CO)CC4)n3)c3ncc(C(=O)Nc4ccncc4F)n3n2)CC1] | 6-((trans-4-aminocyclohexyl)amino)-N-(3-fluoro-4-pyridinyl)-8-((6-(4-(hydroxymethyl)-1-piperidinyl)-2-pyridinyl)amino)imidazo[1,2-b]pyridazine-3-carboxamide | 575 | 2.756[c] |

TABLE 16-continued

| Example | Structure | Name | [M + H] | HPLC Ret. Time (min) |
|---------|-----------|------|---------|----------------------|
| 484 | 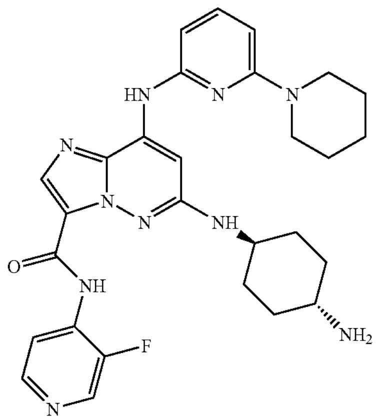 [SMILES: N[C@H]1CC[C@H](Nc2cc(Nc3cccc(N4CCCCC4)n3)c3ncc(C(=O)Nc4ccncc4F)n3n2)CC1] | 6-((trans-4-aminocyclohexyl)amino)-N-(3-fluoro-4-pyridinyl)-8-((6-(1-piperidinyl)-2-pyridinyl)amino)imidazo[1,2-b]pyridazine-3-carboxamide | 545 | 2.948[c] |
| 485 | 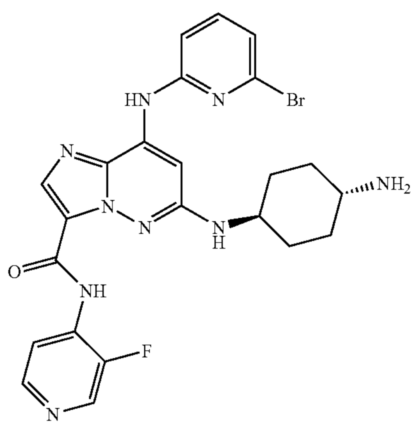 [SMILES: N[C@H]1CC[C@H](Nc2cc(Nc3cccc(Br)n3)c3ncc(C(=O)Nc4ccncc4F)n3n2)CC1] | 6-((trans-4-aminocyclohexyl)amino)-8-((6-bromo-2-pyridinyl)amino)-N-(3-fluoro-4-pyridinyl)imidazo[1,2-b]pyridazine-3-carboxamide | 540 | 2.921[c] |
| 486 | 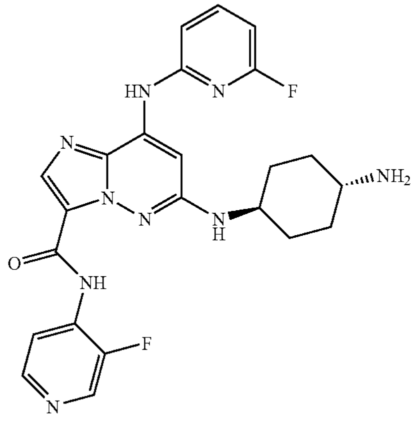 [SMILES: N[C@H]1CC[C@H](Nc2cc(Nc3cccc(F)n3)c3ncc(C(=O)Nc4ccncc4F)n3n2)CC1] | 6-((trans-4-aminocyclohexyl)amino)-N-(3-fluoro-4-pyridinyl)-8-((6-fluoro-2-pyridinyl)amino)imidazo[1,2-b]pyridazine-3-carboxamide | 480 | 2.736[c] |

TABLE 16-continued

| Example | Structure | Name | [M + H] | HPLC Ret. Time (min) |
|---|---|---|---|---|
| 487 | 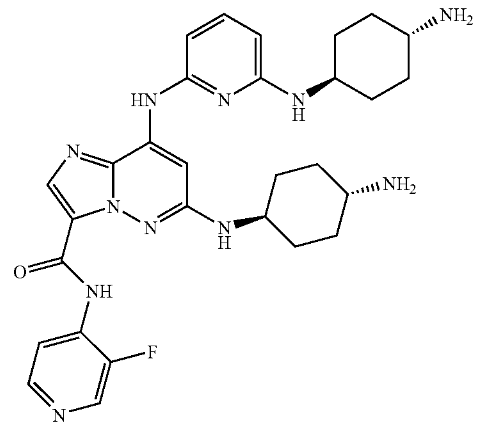 [SMILES: N[C@H]1CC[C@H](Nc2cccc(Nc3cc(N[C@H]4CC[C@H](N)CC4)nn4c(C(=O)Nc5ccncc5F)cnc34)n2)CC1] | 6-((trans-4-aminocyclohexyl)amino)-8-((6-((trans-4-aminocyclohexyl)amino)-2-pyridinyl)amino)-N-(3-fluoro-4-pyridinyl)imidazo[1,2-b]pyridazine-3-carboxamide | 574 | 2.205[c] |
| 488 | 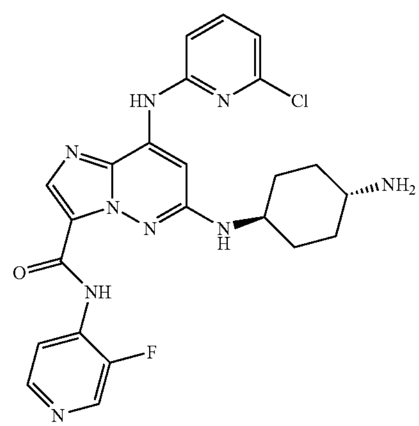 [SMILES: N[C@H]1CC[C@H](Nc2cc(Nc3cccc(Cl)n3)c3ncc(C(=O)Nc4ccncc4F)n3n2)CC1] | 6-((trans-4-aminocyclohexyl)amino)-8-((6-chloro-2-pyridinyl)amino)-N-(3-fluoro-4-pyridinyl)imidazo[1,2-b]pyridazine-3-carboxamide | 496 | 2.836[c] |
| 489 | 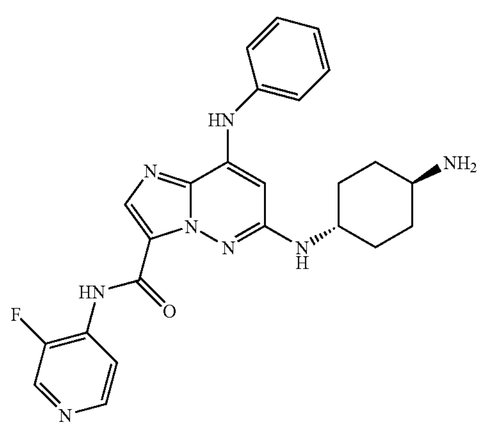 [SMILES: N[C@H]1CC[C@H](Nc2cc(Nc3ccccc3)c3ncc(C(=O)Nc4ccncc4F)n3n2)CC1] | 6-((trans-4-aminocyclohexyl)amino)-8-anilino-N-(3-fluoro-4-pyridinyl)imidazo[1,2-b]pyridazine-3-carboxamide | 461.26 | 1.522[d] |

TABLE 16-continued

| Example | Structure | Name | [M + H] | HPLC Ret. Time (min) |
|---|---|---|---|---|
| 490 | 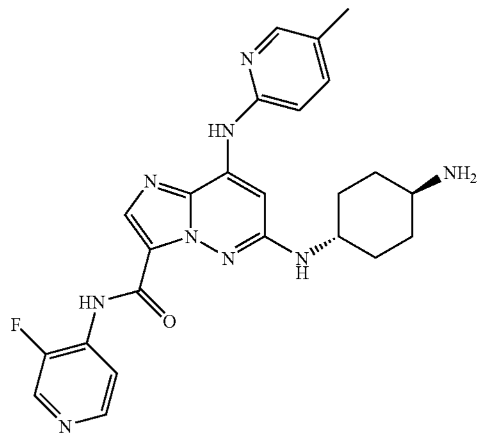 [SMILES: Cc1ccc(Nc2cc(N[C@H]3CC[C@H](N)CC3)nn3c(C(=O)Nc4ccncc4F)cnc23)nc1] | 6-((trans-4-aminocyclohexyl)amino)-N-(3-fluoro-4-pyridinyl)-8-((5-methyl-2-pyridinyl)amino)imidazo[1,2-b]pyridazine-3-carboxamide | 476.19 | 1.500[d] |
| 491 | 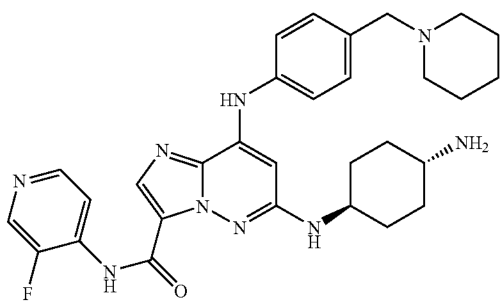 [SMILES: N[C@H]1CC[C@H](Nc2cc(Nc3ccc(CN4CCCCC4)cc3)c3ncc(C(=O)Nc4ccncc4F)n3n2)CC1] | 6-((trans-4-aminocyclohexyl)amino)-N-(3-fluoro-4-pyridinyl)-8-((4-(1-piperidinylmethyl)phenyl)amino)imidazo[1,2-b]pyridazine-3-carboxamide | 558 | 2.676[a] |
| 492 | 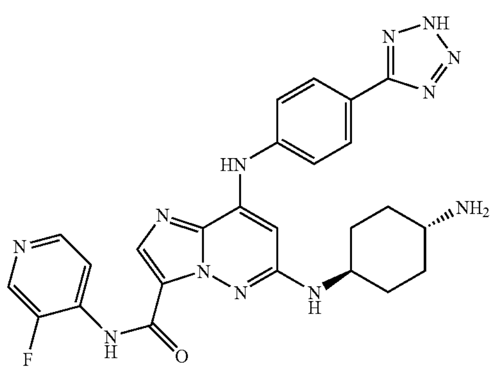 [SMILES: N[C@H]1CC[C@H](Nc2cc(Nc3ccc(-c4nn[nH]n4)cc3)c3ncc(C(=O)Nc4ccncc4F)n3n2)CC1] | 6-((trans-4-aminocyclohexyl)amino)-N-(3-fluoro-4-pyridinyl)-8-((4-(1H-tetrazol-5-yl)phenyl)amino)imidazo[1,2-b]pyridazine-3-carboxamide | 529 | 3.413[a] |
| 493 | 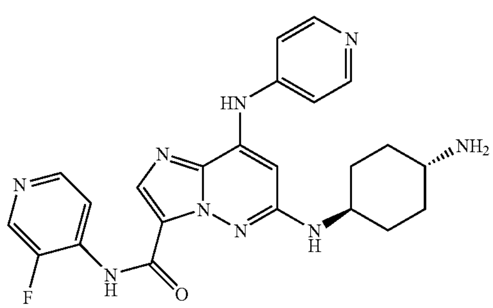 | 6-((trans-4-aminocyclohexyl)amino)-N-(3-fluoro-4-pyridinyl)-8-(4-pyridinylamino)imidazo[1,2-b]pyridazine-3-carboxamide | 462 | 2.002[a] |

TABLE 16-continued

| Example | Structure | Name | [M + H] | HPLC Ret. Time (min) |
|---|---|---|---|---|
| 494 | 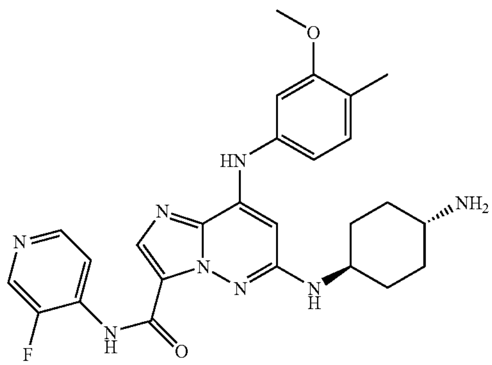 [SMILES: COc1cc(Nc2cc(N[C@H]3CC[C@H](N)CC3)nn3c(C(=O)Nc4ccncc4F)cnc23)ccc1C] | 6-((trans-4-aminocyclohexyl)amino)-N-(3-fluoro-4-pyridinyl)-8-((3-methoxy-4-methylphenyl)amino)imidazo[1,2-b]pyridazine-3-carboxamide | 505 | 3.845[a] |
| 495 | 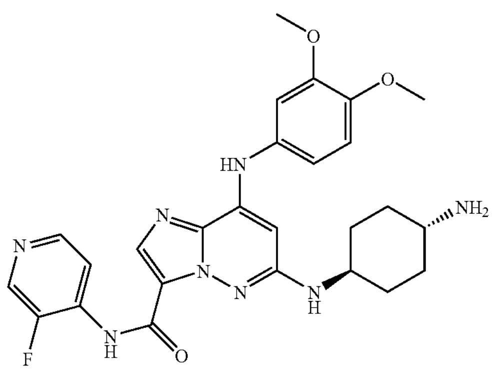 [SMILES: COc1ccc(Nc2cc(N[C@H]3CC[C@H](N)CC3)nn3c(C(=O)Nc4ccncc4F)cnc23)cc1OC] | 6-((trans-4-aminocyclohexyl)amino)-8-((3,4-dimethoxyphenyl)amino)-N-(3-fluoro-4-pyridinyl)imidazo[1,2-b]pyridazine-3-carboxamide | 521 | 3.398[a] |
| 496 | 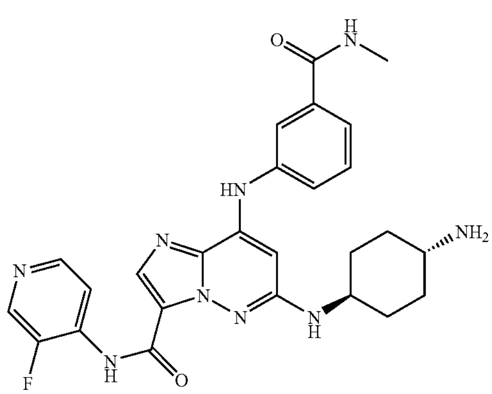 [SMILES: CNC(=O)c1cccc(Nc2cc(N[C@H]3CC[C@H](N)CC3)nn3c(C(=O)Nc4ccncc4F)cnc23)c1] | 6-((trans-4-aminocyclohexyl)amino)-N-(3-fluoro-4-pyridinyl)-8-((3-(methylcarbamoyl)phenyl)amino)imidazo[1,2-b]pyridazine-3-carboxamide | 518 | 3.198[a] |
| 497 | 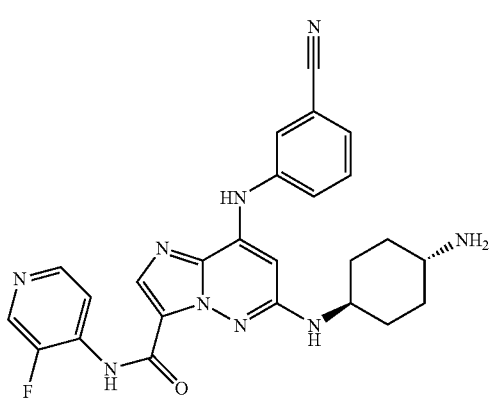 [SMILES: N#Cc1cccc(Nc2cc(N[C@H]3CC[C@H](N)CC3)nn3c(C(=O)Nc4ccncc4F)cnc23)c1] | 6-((trans-4-aminocyclohexyl)amino)-8-((3-cyanophenyl)amino)-N-(3-fluoro-4-pyridinyl)imidazo[1,2-b]pyridazine-3-carboxamide | 486 | 3.400[a] |

TABLE 16-continued

| Example | Structure | Name | [M + H] | HPLC Ret. Time (min) |
|---|---|---|---|---|
| 498 | 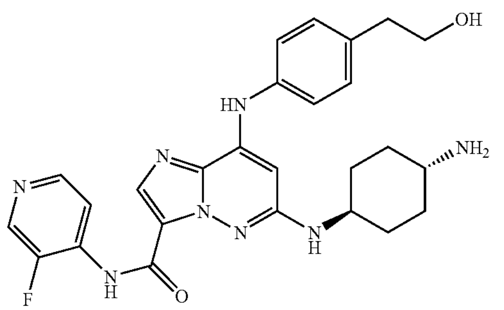 [SMILES: N[C@H]1CC[C@H](Nc2cc(Nc3ccc(CCO)cc3)c3ncc(C(=O)Nc4ccncc4F)n3n2)CC1] | 6-((trans-4-aminocyclohexyl)amino)-N-(3-fluoro-4-pyridinyl)-8-((4-(2-hydroxyethyl)phenyl)amino)imidazo[1,2-b]pyridazine-3-carboxamide | 505 | 3.330[a] |
| 499 | 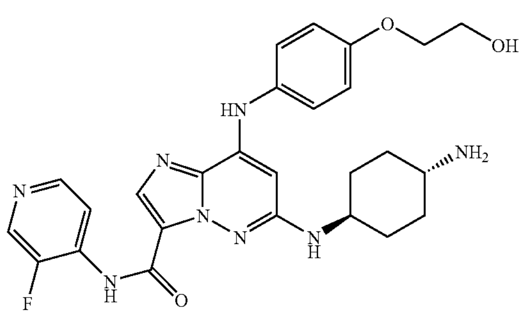 [SMILES: N[C@H]1CC[C@H](Nc2cc(Nc3ccc(OCCO)cc3)c3ncc(C(=O)Nc4ccncc4F)n3n2)CC1] | 6-((trans-4-aminocyclohexyl)amino)-N-(3-fluoro-4-pyridinyl)-8-((4-(2-hydroxyethoxy)phenyl)amino)imidazo[1,2-b]pyridazine-3-carboxamide | 521 | 3.266[a] |
| 500 | 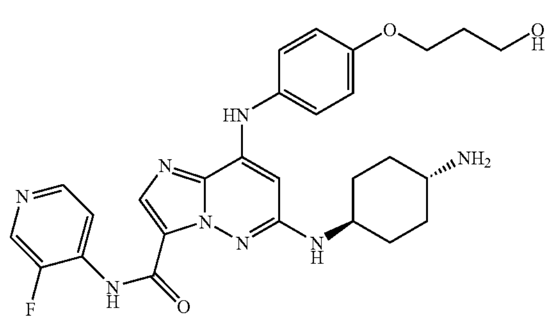 [SMILES: N[C@H]1CC[C@H](Nc2cc(Nc3ccc(OCCCO)cc3)c3ncc(C(=O)Nc4ccncc4F)n3n2)CC1] | 6-((trans-4-aminocyclohexyl)amino)-N-(3-fluoro-4-pyridinyl)-8-((4-(3-hydroxypropoxy)phenyl)amino)imidazo[1,2-b]pyridazine-3-carboxamide | 535 | 3.486[a] |
| 501 | 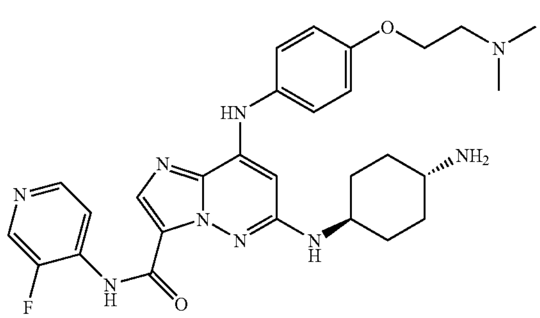 [SMILES: CN(C)CCOc1ccc(Nc2cc(N[C@H]3CC[C@H](N)CC3)nn3c(C(=O)Nc4ccncc4F)cnc23)cc1] | 6-((trans-4-aminocyclohexyl)amino)-8-((4-(2-(dimethylamino)ethoxy)phenyl)amino)-N-(3-fluoro-4-pyridinyl)imidazo[1,2-b]pyridazine-3-carboxamide | 548 | 2.680[a] |

TABLE 16-continued

| Example | Structure | Name | [M + H] | HPLC Ret. Time (min) |
|---|---|---|---|---|
| 502 | 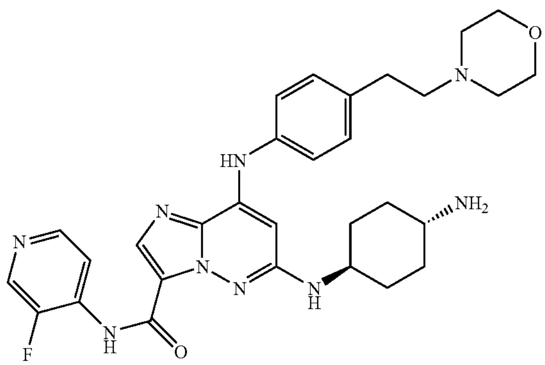 [SMILES: N[C@H]1CC[C@H](Nc2cc(Nc3ccc(CCN4CCOCC4)cc3)c3ncc(C(=O)Nc4ccncc4F)n3n2)CC1] | 6-((trans-4-aminocyclohexyl)amino)-N-(3-fluoro-4-pyridinyl)-8-((4-(2-(4-morpholinyl)ethyl)phenyl)amino)imidazo[1,2-b]pyridazine-3-carboxamide | 574 | 2.656[a] |
| 503 | 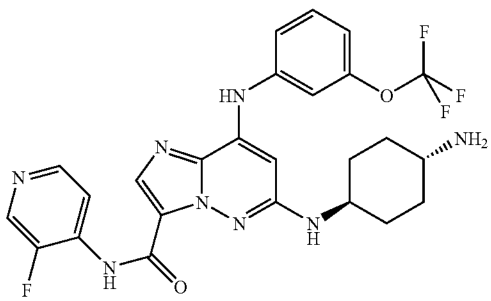 [SMILES: N[C@H]1CC[C@H](Nc2cc(Nc3cccc(OC(F)(F)F)c3)c3ncc(C(=O)Nc4ccncc4F)n3n2)CC1] | 6-((trans-4-aminocyclohexyl)amino)-N-(3-fluoro-4-pyridinyl)-8-((3-1,2-b]pyridazine-3-carboxamide | 545 | 3.958[a] |

HPLC Conditions:
[a] YMC S5 ODS 4.6 x 50 mm: 10-90% aqueous methanol containing 0.2% H$_3$PO$_4$, 4 min gradient, monitored at 220 nm
[b] Waters Sunfire 4.6 x 50 mm C18 5um: 4 min/1 min hold time 0-100% (A-B) A = 10% MeOH-90% water- 0.1% TFA, B = 90% MeOH-10% water-0.1% TFA
[c] Chromolith SpeedROD 4.6 x 50 mm: 10-90% aqueous methanol containing 0.1% TFA, 4 min gradient, monitored at 220 nm)
[d] Phenomenex Luna 5 micron C18 4.6 x 30 mm: 0 to 100 B in 2 min with 1 min hold time, Flow rate = 5 mL/min, detection at 254 nm, Solvent A: 10% methanol/90% water/0.1% TFA; Solvent B: 10% water/90% methanol/0.1 % TFA The following Examples in Table 17 may be prepared in a manner analogous to the procedures described in Examples 79.

TABLE 17

| Example | Structure | Name | [M + H] | HPLC Ret. Time (min) |
|---|---|---|---|---|
| 504 | 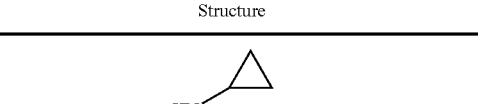 | 6-((trans-4-acetamidocyclohexyl)amino)-8-(cyclopropylamino)-N-(3-fluoro-4-pyridinyl)imidazo[1,2-b]pyridazine-3-carboxamide | 467.41 | 3.893[a] |

TABLE 17-continued

| Example | Structure | Name | [M + H] | HPLC Ret. Time (min) |
|---|---|---|---|---|
| 505 | 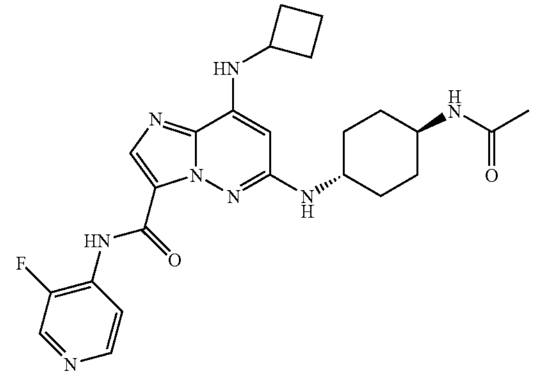 [SMILES: CC(=O)N[C@H]1CC[C@H](Nc2cc(NC3CCC3)c3ncc(C(=O)Nc4ccncc4F)n3n2)CC1] | 6-((trans-4-acetamidocyclohexyl)amino)-8-(cyclobutylamino)-N-(3-fluoro-4-pyridinyl)imidazo[1,2-b]pyridazine-3-carboxamide | 481.45 | 4.156[a] |
| 506 | 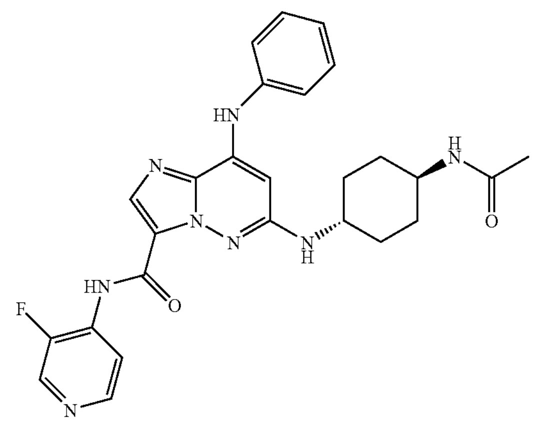 [SMILES: CC(=O)N[C@H]1CC[C@H](Nc2cc(Nc3ccccc3)c3ncc(C(=O)Nc4ccncc4F)n3n2)CC1] | 6-((trans-4-acetamidocyclohexyl)amino)-8-anilino-N-(3-fluoro-4-pyridinyl)imidazo[1,2-b]pyridazine-3-carboxamide | 503.23 | 1.78[b] |
| 507 | 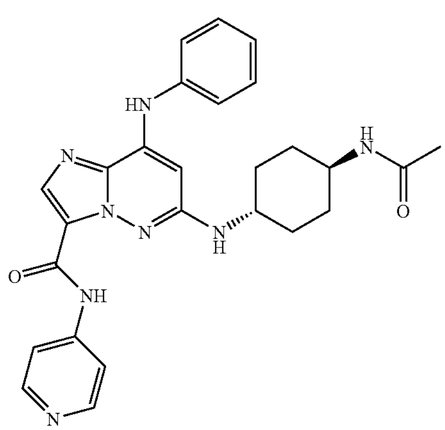 [SMILES: CC(=O)N[C@H]1CC[C@H](Nc2cc(Nc3ccccc3)c3ncc(C(=O)Nc4ccncc4)n3n2)CC1] | 6-((trans-4-acetamidocyclohexyl)amino)-8-anilino-N-4-pyridinylimidazo[1,2-b]pyridazine-3-carboxamide | 485.19 | 1.25[b] |

HPLC Conditions:
[a] YMC S5 ODS 4.6 x 50 mm, 10-90% aqueous methanol containing 0.2% H$_3$PO$_4$, 4 min gradient, monitored at 220 nm
[b] Phenomenex Luna 5 micron C18 4.6 x 30 mm: 0 to 100 B in 2 min with 1 min hold time, Flow rate = 5 mL/min, detection at 254 nm, Solvent A: 10% methanol/90% water/0.1% TFA; Solvent B: 10% water/90% methanol/0.1% TFA The following Examples in Table 18 were prepared according to the procedures detailed in Example 85.

TABLE 18

| Example | Structure | Name | [M + H] | HPLC Ret Time (min) |
|---|---|---|---|---|
| 508 | 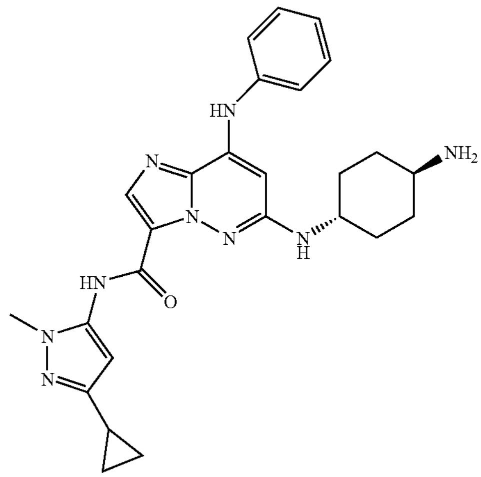 [SMILES: Cn1nc(C2CC2)cc1NC(=O)c1cnc2c(Nc3ccccc3)cc(N[C@H]3CC[C@H](N)CC3)nn12] | 6-((trans-4-aminocyclohexyl)amino)-8-anilino-N-(3-cyclopropyl-1methyl-1H-pyrazol-5-yl)imidazo[1,2-b]pyridazine-3-carboxamide | 486.24 | 1.577 |
| 509 | 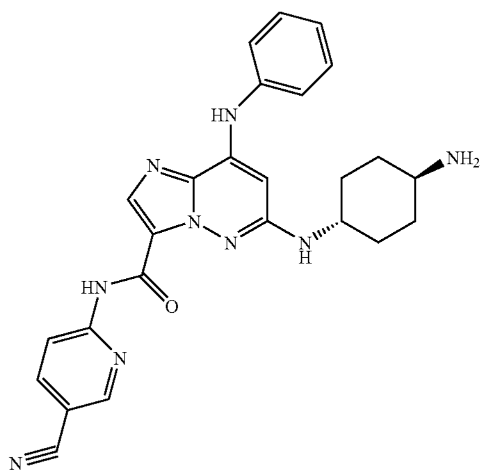 [SMILES: N#Cc1ccc(NC(=O)c2cnc3c(Nc4ccccc4)cc(N[C@H]4CC[C@H](N)CC4)nn23)nc1] | 6-((trans-4-aminocyclohexyl)amino)-8-anilino-N-(5-cyano-2-pyridinyl)imidazo[1,2-b]pyridazine-3-carboxamide | 468.22 | 1.733 |
| 510 | 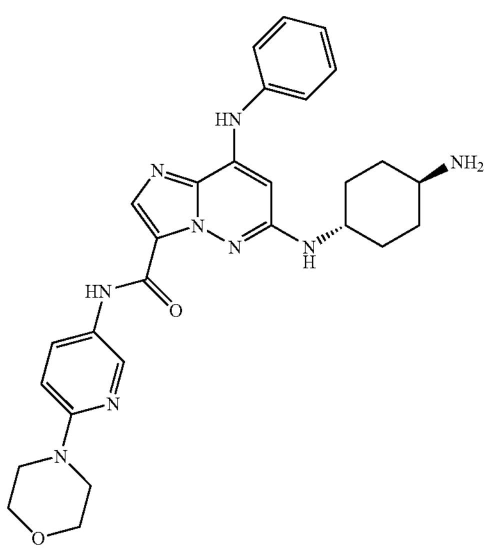 [SMILES: N[C@H]1CC[C@H](Nc2cc(Nc3ccccc3)c3ncc(C(=O)Nc4ccc(N5CCOCC5)nc4)n3n2)CC1] | 6-((trans-4-aminocyclohexyl)amino)-8-anilino-N-(6-(4-morpholinyl)-3-pyridinyl)imidazo[1,2-b]pyridazine-3-carboxamide | 528.35 | 1.415 |

TABLE 18-continued

| Example | Structure | Name | [M + H] | HPLC Ret Time (min) |
|---|---|---|---|---|
| 511 | 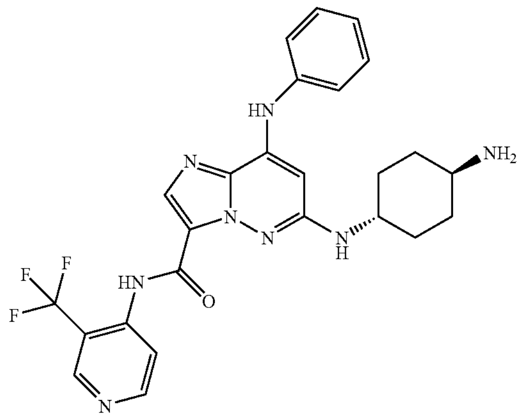 [SMILES: N[C@H]1CC[C@H](Nc2cc(Nc3ccccc3)c3ncc(C(=O)Nc4ccncc4C(F)(F)F)n3n2)CC1] | 6-((trans-4-aminocyclohexyl)amino)-8-anilino-N-(3-(trifluoromethyl)-4-pyridinyl)imidazo[1,2-b]pyridazine-3-carboxamide | 511.25 | 1.627 |
| 512 | 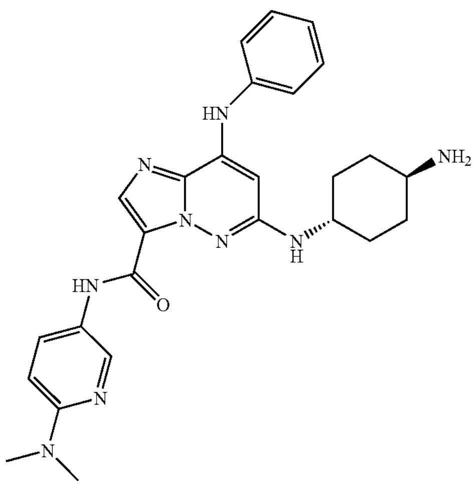 | 6-((trans-4-aminocyclohexyl)amino)-8-anilino-N-(6-(dimethylamino)-3-pyridinyl)imidazo[1,2-b]pyridazine-3-carboxamide | 486.29 | 1.298 |
| 513 | 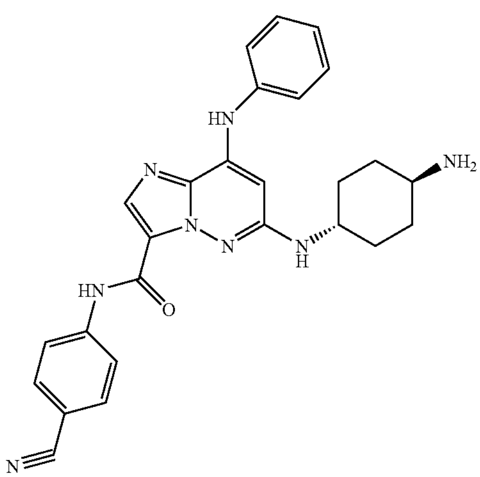 | 6-((trans-4-aminocyclohexyl)amino)-8-anilino-N-(4-cyanophenyl)imidazo[1,2-b]pyridazine-3-carboxamide | 467.27 | 1.658 |

TABLE 18-continued

| Example | Structure | Name | [M + H] | HPLC Ret Time (min) |
|---|---|---|---|---|
| 514 | 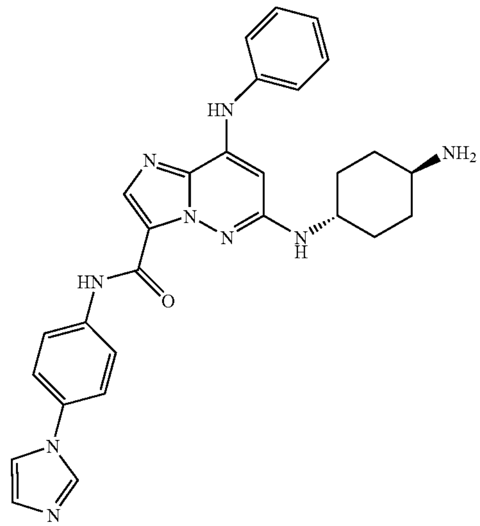 [SMILES: N[C@H]1CC[C@H](Nc2cc(Nc3ccccc3)c3ncc(C(=O)Nc4ccc(-n5ccnc5)cc4)n3n2)CC1] | 6-((trans-4-aminocyclohexyl)amino)-8-anilino-N-(4-(1H-imidazol-1-yl)phenyl)imidazo[1,2-b]pyridazine-3-carboxamide | 508.31 | 1.378 |
| 515 | 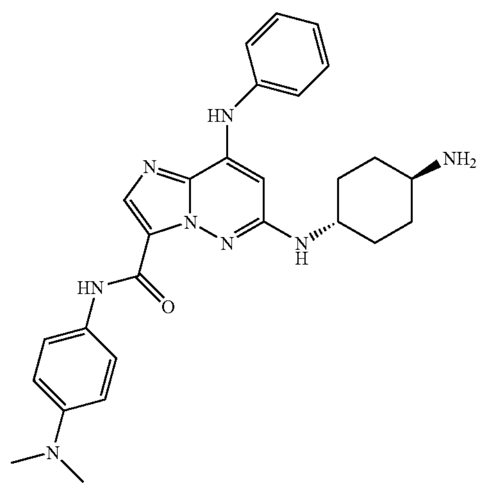 [SMILES: CN(C)c1ccc(NC(=O)c2cnc3c(Nc4ccccc4)cc(N[C@H]4CC[C@H](N)CC4)nn23)cc1] | 6-((trans-4-aminocyclohexyl)amino)-8-anilino-N-(4-(dimethylamino)phenyl)imidazo[1,2-b]pyridazine-3-carboxamide | 485.30 | 1.362 |
| 516 | 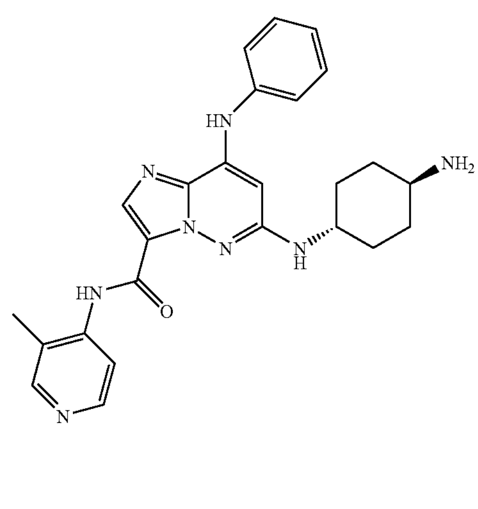 [SMILES: Cc1cnccc1NC(=O)c1cnc2c(Nc3ccccc3)cc(N[C@H]3CC[C@H](N)CC3)nn12] | 6-((trans-4-aminocyclohexyl)amino)-8-anilino-N-(3-methyl-4-pyridinyl)imidazo[1,2-b]pyridazine-3-carboxamide | 457.31 | 1.298 |

TABLE 18-continued

| Example | Structure | Name | [M + H] | HPLC Ret Time (min) |
|---|---|---|---|---|
| 517 | 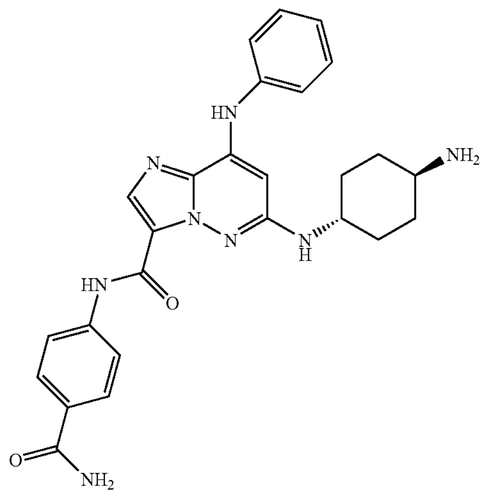 [SMILES: NC(=O)c1ccc(NC(=O)c2cnc3c(Nc4ccccc4)cc(N[C@H]4CC[C@H](N)CC4)nn23)cc1] | 6-((trans-4-aminocyclohexyl)amino)-8-anilino-N-(4-carbamoylphenyl)imidazo[1,2-b]pyridazine-3-carboxamide | 485.24 | 1.515 |
| 518 | 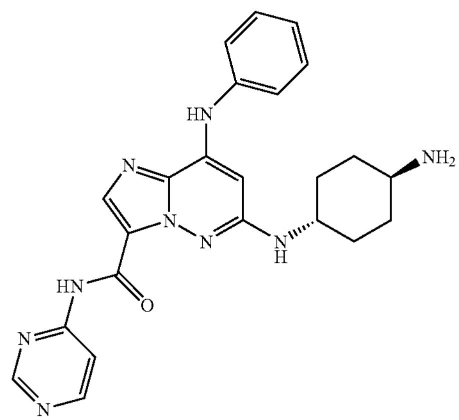 [SMILES: N[C@H]1CC[C@H](Nc2cc(Nc3ccccc3)c3ncc(C(=O)Nc4ccncn4)n3n2)CC1] | 6-((trans-4-aminocyclohexyl)amino)-8-anilino-N-4-pyrimidinylimidazo[1,2-b]pyridazine-3-carboxamide | 444.26 | 1.598 |
| 519 | 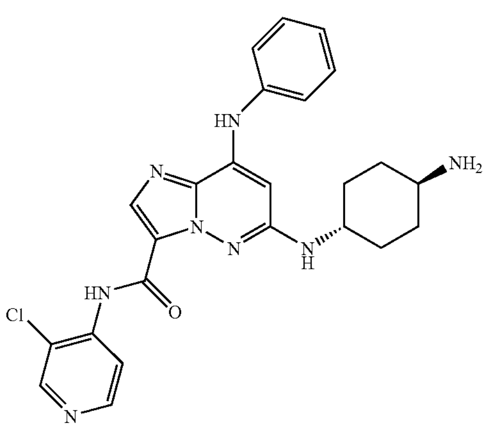 [SMILES: N[C@H]1CC[C@H](Nc2cc(Nc3ccccc3)c3ncc(C(=O)Nc4ccncc4Cl)n3n2)CC1] | 6-((trans-4-aminocyclohexyl)amino)-8-anilino-N-(3-chloro-4-pyridinyl)imidazo[1,2-b]pyridazine-3-carboxamide | 477.17 | 1.548 |

TABLE 18-continued

| Example | Structure | Name | [M + H] | HPLC Ret Time (min) |
|---|---|---|---|---|
| 520 | 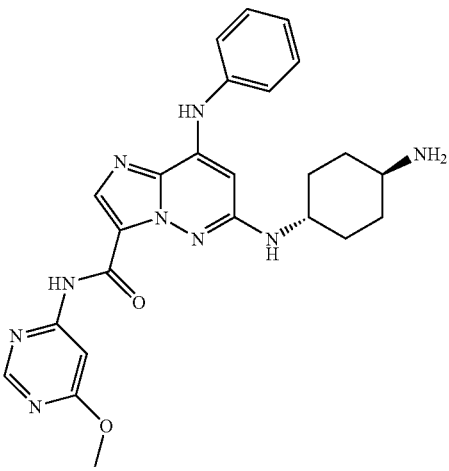 [SMILES: COc1cc(NC(=O)c2cnc3c(Nc4ccccc4)cc(N[C@H]4CC[C@H](N)CC4)nn23)ncn1] | 6-((trans-4-aminocyclohexyl)amino)-8-anilino-N-(6-methoxy-4-pyrimidinyl)imidazo[1,2-b]pyridazine-3-carboxamide | 474.26 | 1.765 |
| 521 | 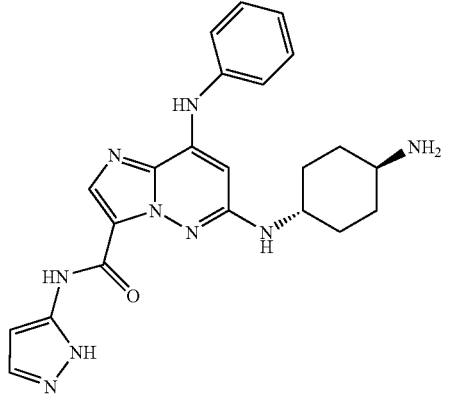 [SMILES: N[C@H]1CC[C@H](Nc2cc(Nc3ccccc3)c3ncc(C(=O)Nc4ccn[nH]4)n3n2)CC1] | 6-((trans-4-aminocyclohexyl)amino)-8-anilino-N-1H-pyrazol-5-ylimidazo[1,2-b]pyridazine-3-carboxamide | 432.26 | 1.422 |
| 522 | 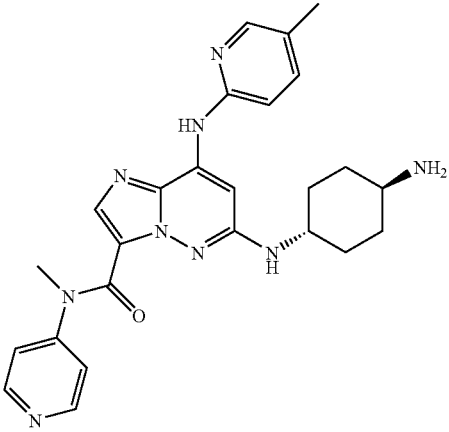 [SMILES: Cc1ccc(Nc2cc(N[C@H]3CC[C@H](N)CC3)nn3c(C(=O)N(C)c4ccncc4)cnc23)nc1] | 6-((trans-4-aminocyclohexyl)amino)-N-methyl-8-((5-methyl-2-pyridinyl)amino)-N-4-pyridinylimidazo[1,2-b]pyridazine-3-carboxamide | 472.19 | 0.985 |

HPLC Condition:

Phenomenex Luna 5 micron C18 4.6 x 30 mm: 0 to 100 B in 2 min with 1 min hold time, Flow rate = 5 mL/min, detection at 254 nm, Solvent A: 10% methanol/90% water/0.1% TFA; Solvent B: 10% water/90% methanol/0.1% TFA.

The following Examples in Table 19 may be prepared from 8B in a manner analogous to the procedures described in Examples 26-29.

TABLE 19

| Example | Structure | Name | [M + H] | HPLC Ret Time (min) |
|---|---|---|---|---|
| 523 | 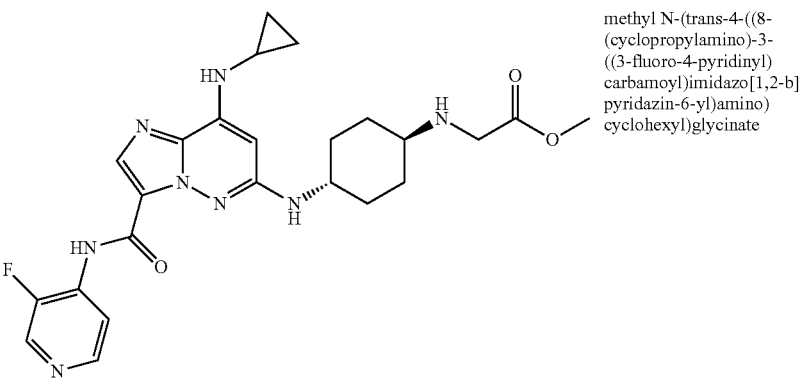 | methyl N-(trans-4-((8-(cyclopropylamino)-3-((3-fluoro-4-pyridinyl)carbamoyl)imidazo[1,2-b]pyridazin-6-yl)amino)cyclohexyl)glycinate | 497.30 | 1.317 |
| 524 | 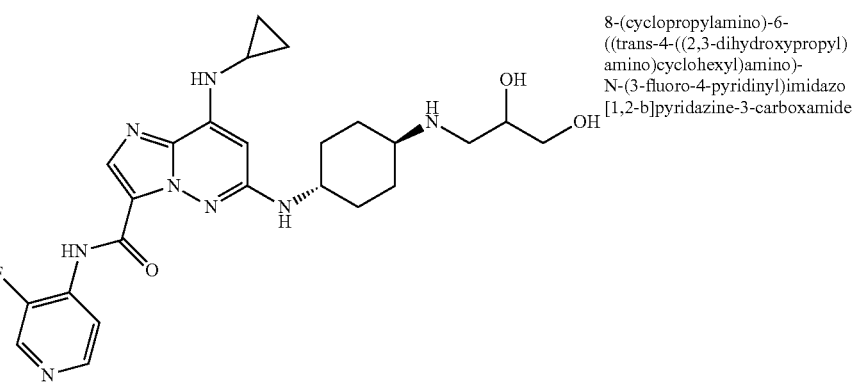 | 8-(cyclopropylamino)-6-((trans-4-((2,3-dihydroxypropyl)amino)cyclohexyl)amino)-N-(3-fluoro-4-pyridinyl)imidazo[1,2-b]pyridazine-3-carboxamide | 499.34 | 1.26 |
| 525 | 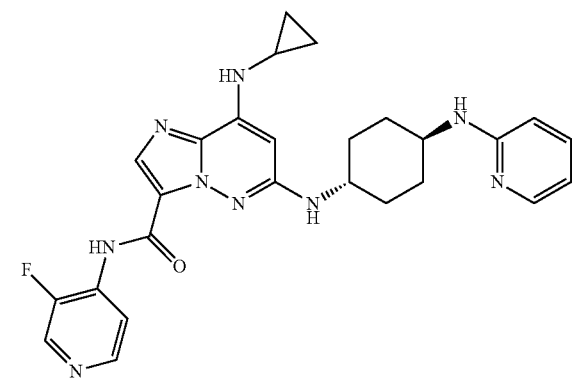 [SMILES: O=C(Nc1ccncc1F)c1cnc2c(NC3CC3)cc(N[C@H]3CC[C@H](Nc4ccccn4)CC3)nn12] | 8-(cyclopropylamino)-N-(3-fluoro-4-pyridinyl)-6-((trans-4-(2-pyridinylamino)cyclohexyl)amino)imidazo[1,2-b]pyridazine-3-carboxamide | 502.17 | 1.468 |

HPLC Conditions:

Phenomenex Luna 5 micron C18 4.6 × 30 mm; 0 to 100 B in 2 min with 1 min hold time, Flow rate = 5 mL/min, detection at 254 nm, Solvent A: 10% methanol/90% water/0.1% TFA; Solvent B: 10% water/90% methanol/0.1% TFA.

The following Examples in Table 20 may be prepared from 25B in a manner analogous to the procedures described in Examples 26-29.

TABLE 20

| Example | Structure | Name | [M + H] | HPLC Ret Time (min) |
|---|---|---|---|---|
| 526 | 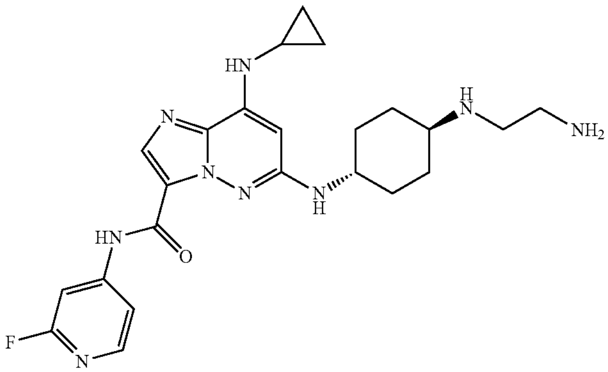 [SMILES: NCCN[C@H]1CC[C@H](Nc2cc(NC3CC3)c3ncc(C(=O)Nc4ccnc(F)c4)n3n2)CC1] | 6-((trans-4-((2-aminoethyl)amino)cyclohexyl)amino)-8-(cyclopropylamino)-N-(2-fluoro-4-pyridinyl)imidazo[1,2-b]pyridazine-3-carboxamide | 468.3 | 0.600[b] |
| 527 | 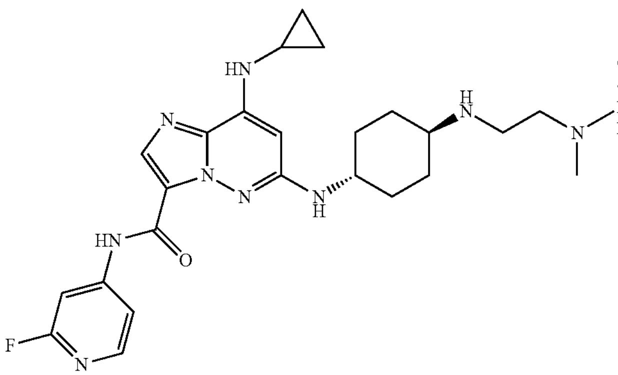 | 8-(cyclopropylamino)-6-((trans-4-((2-(dimethylamino)ethyl)amino)cyclohexyl)amino)-N-(2-fluoro-4-pyridinyl)imidazo[1,2-b]pyridazine-3-carboxamide | 496.2 | 1.737[a] |
| 528 | 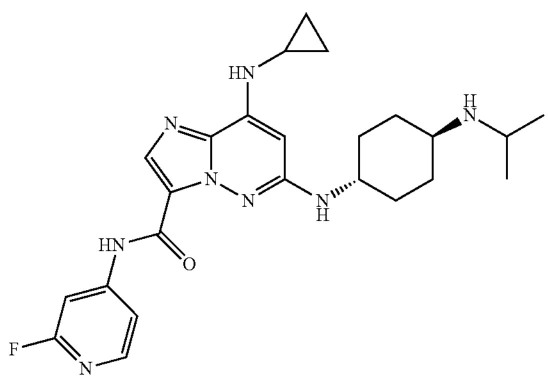 [SMILES: CC(C)N[C@H]1CC[C@H](Nc2cc(NC3CC3)c3ncc(C(=O)Nc4ccnc(F)c4)n3n2)CC1] | 8-(cyclopropylamino)-N-(2-fluoro-4-pyridinyl)-6-((trans-4-(isopropylamino)cyclohexyl)amino)imidazo[1,2-b]pyridazine-3-carboxamide | 476.3 | 0.690[b] |
| 529 | 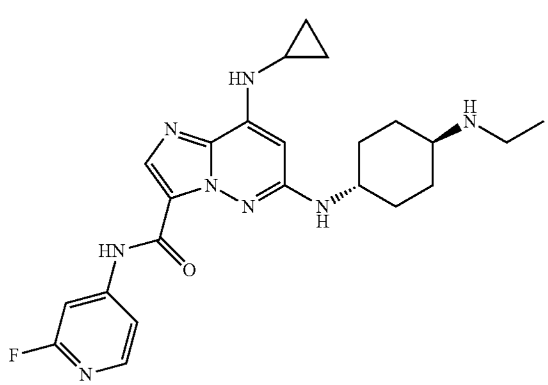 [SMILES: CCN[C@H]1CC[C@H](Nc2cc(NC3CC3)c3ncc(C(=O)Nc4ccnc(F)c4)n3n2)CC1] | 8-(cyclopropylamino)-6-((trans-4-(ethylamino)cyclohexyl)amino)-N-(2-fluoro-4-pyridinyl)imidazo[1,2-b]pyridazine-3-carboxamide | 453.2 | 0.670[b] |

TABLE 20-continued

| Example | Structure | Name | [M + H] | HPLC Ret Time (min) |
|---|---|---|---|---|
| 530 | 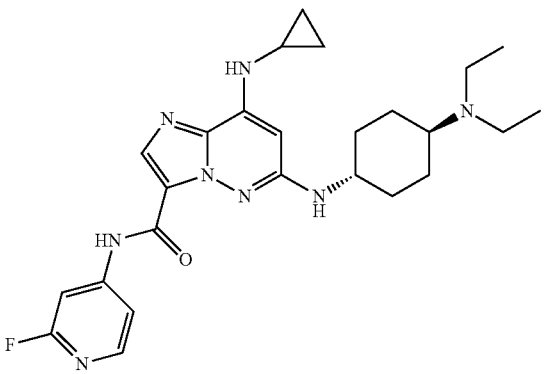 [SMILES: CCN(CC)[C@H]1CC[C@H](Nc2cc(NC3CC3)c3ncc(C(=O)Nc4ccnc(F)c4)n3n2)CC1] | 8-(cyclopropylamino)-6-((trans-4-(diethylamino)cyclohexyl)amino)-N-(2-fluoro-4-pyridinyl)imidazo[1,2-b]pyridazine-3-carboxamide | 481.3 | 0.690[b] |

HPLC Conditions:
[a] Phenomenex Luna 5 micron C18 4.6 × 30 mm, 0 to 100 B in 2 min with 1 min hold time, Flow rate = 5 mL/min, detection at 254 nm, Solvent A: 10% methanol/90% water/0.1% TFA; Solvent B: 10% water/90% methanol/0.1% TFA
[b] LC/MS (BEH C18 2.1 × 50 mm 1.7 u, Phenomenex Luna 5 micron C18 4.6 × 30 mm, 0 to 100 B in 2.2 min with 1 min hold time, Flow rate = 2 mL/min, detection at 254 nm, Solvent A: 100% water/0.05% TFA; Solvent B: 100% ACN/0.05% TFA).

The following Examples in Table 21 may be prepared from 23C in a manner analogous to the procedures described in Examples 26-29.

TABLE 21

| Example | Structure | Name | [M + H] | HPLC Ret Time (min) |
|---|---|---|---|---|
| 531 | 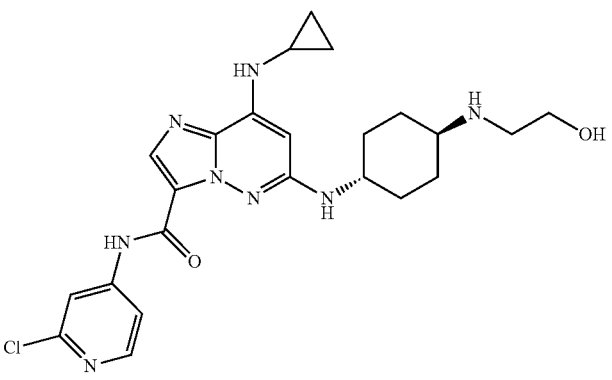 [SMILES: O=C(Nc1ccnc(Cl)c1)c1cnc2c(NC3CC3)cc(N[C@H]3CC[C@H](NCCO)CC3)nn12] | N-(2-chloro-4-pyridinyl)-8-(cyclopropylamino)-6-((trans-4-((2-hydroxyethyl)amino)cyclohexyl)amino)imidazo[1,2-b]pyridazine-3-carboxamide | 485.16 | 1.430[a] |
| 532 | 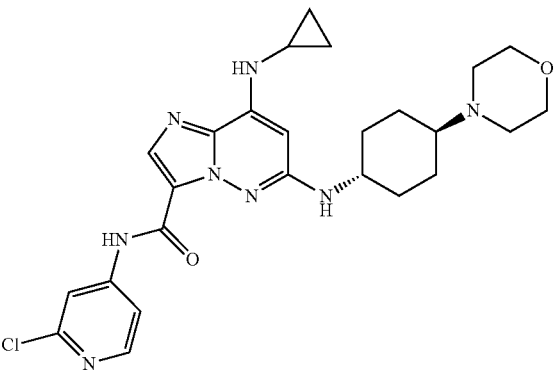 [SMILES: O=C(Nc1ccnc(Cl)c1)c1cnc2c(NC3CC3)cc(N[C@H]3CC[C@H](N4CCOCC4)CC3)nn12] | N-(2-chloro-4-pyridinyl)-8-(cyclopropylamino)-6-((trans-4-(4-morpholinyl)cyclohexyl)amino)imidazo[1,2-b]pyridazine-3-carboxamide | 511.2 | 1.437[a] |

TABLE 21-continued

| Example | Name | [M + H] | HPLC Ret Time (min) |
|---|---|---|---|
| 533 | N-(2-chloro-4-pyridinyl)-8-(cyclopropylamino)-6-((4-(dimethylamino)cyclohexyl)amino)imidazo[1,2-b]pyridazine-3-carboxamide | 496.2 | 0.680[b] |
| 534 | 6-((trans-4-(bis(2-hydroxyethyl)amino)cyclohexyl)amino)-N-(2-chloro-4-pyridinyl)-8-(cyclopropylamino)imidazo[1,2-b]pyridazine-3-carboxamide | 529.2 | 0.660[b] |
| 535 | N-(2-chloro-4-pyridinyl)-8-(cyclopropylamino)-6-((trans-4-(isopropylamino)cyclohexyl)amino)imidazo[1,2-b]pyridazine-3-carboxamide | 483.17 | 1.502[a] |
| 536 | N-(2-chloro-4-pyridinyl)-8-(cyclopropylamino)-6-((trans-4-((2-methoxyethyl)amino)cyclohexyl)amino)imidazo[1,2-b]pyridazine-3-carboxamide | 499.17 | 1.473[a] |

TABLE 21-continued

| Example | Structure | Name | [M + H] | HPLC Ret Time (min) |
|---|---|---|---|---|
| 537 | 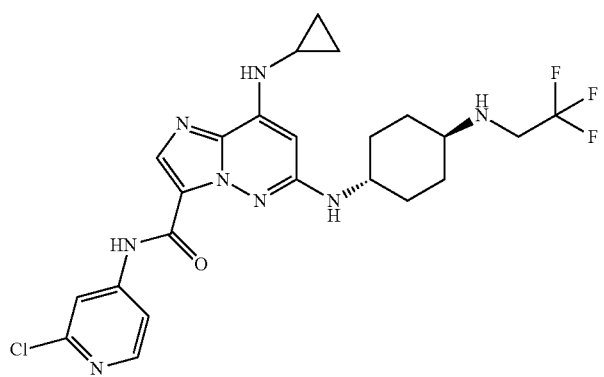 [SMILES: O=C(Nc1ccnc(Cl)c1)c1cnc2c(NC3CC3)cc(N[C@H]3CC[C@H](NCC(F)(F)F)CC3)nn12] | N-(2-chloro-4-pyridinyl)-8-(cyclopropylamino)-6-((trans-4-((2,2,2-trifluoroethyl)amino)cyclohexyl)amino)imidazo[1,2-b]pyridazine-3-carboxamide | 523.11 | 1.500[a] |
| 538 | 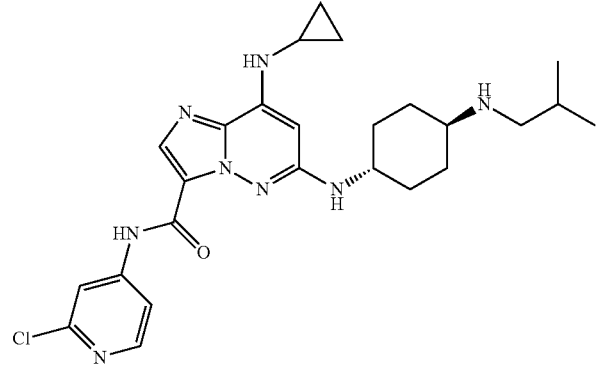 [SMILES: CC(C)CN[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-(isobutylamino)cyclohexyl)amino)imidazo[1,2-b]pyridazine-3-carboxamide | 497.18 | 1.583[a] |
| 539 | 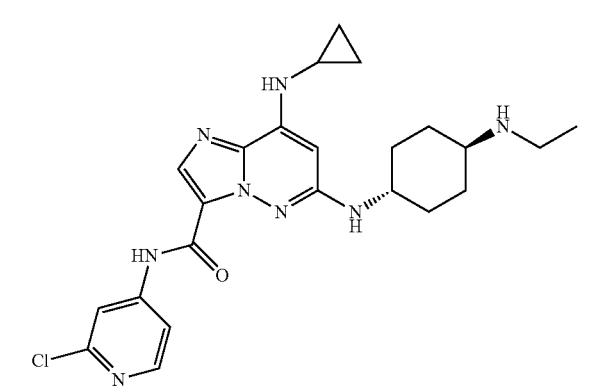 [SMILES: CCN[C@H]1CC[C@H](Nc2cc(NC3CC3)c3ncc(C(=O)Nc4ccnc(Cl)c4)n3n2)CC1] | N-(2-chloro-4-pyridinyl)-8-(cyclopropylamino)-6-((trans-4-(ethylamino)cyclohexyl)amino)imidazo[1,2-b]pyridazine-3-carboxamide | 469.2 | 0.710[b] |

TABLE 21-continued

| Example | Structure | Name | [M + H] | HPLC Ret Time (min) |
|---|---|---|---|---|
| 540 | 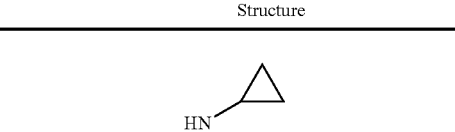 | 6-((trans-4-(2-butyn-1-ylamino)cyclohexyl)amino)-N-(2-chloro-4-pyridinyl)-8-(cyclopropylamino)imidazo[1,2-b]pyridazine-3-carboxamide | 493.2 | 0.730[b] |

HPLC Conditions:
[a]LC/MS (Phenomenex Luna 5 micron C18 4.6 × 30 mm, 0 to 100 B in 2 min with 1 min hold time, Flow rate = 5 mL/min, detection at 254 nm, Solvent A: 10% methanol/90% water/0.1% TFA; Solvent B: 10% water/90% methanol/0.1% TFA
[b]LC/MS (BEH C18 2.1 × 50 mm 1.7 u, Phenomenex Luna 5 micron C18 4.6 × 30 mm, 0 to 100 B in 2.2 min with 1 min hold time, Flow rate = 2 mL/min, detection at 254 nm, Solvent A: 100% water/0.05% TFA; Solvent B: 100% ACN/0.05% TFA).

The following Examples in Table 22 were prepared according to the procedures detailed in Example 86.

TABLE 22

| Example | Structure | Name | [M + H] | HPLC Ret Time (min) |
|---|---|---|---|---|
| 541 | 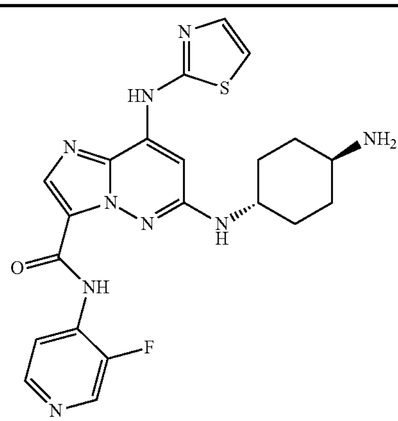 | 6-((trans-4-aminocyclohexyl)amino)-N-(3-fluoro-4-pyridinyl)-8-(1,3-thiazol-2-ylamino)imidazo[1,2-b]pyridazine-3-carboxamide | 468 | 2.432 |
| 542 | 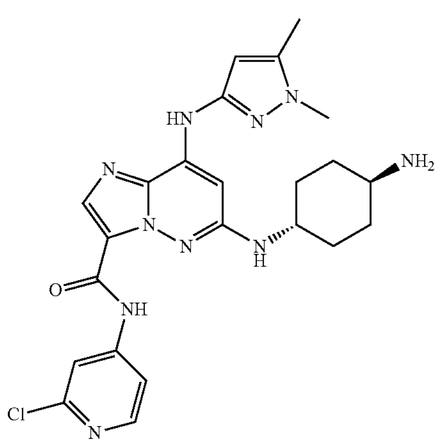 [SMILES: Cc1cc(Nc2cc(N[C@H]3CC[C@H](N)CC3)nn3c(C(=O)Nc4ccnc(Cl)c4)cnc23)nn1C] | 6-((trans-4-aminocyclohexyl)amino)-N-(2-chloro-4-pyridinyl)-8-((1,5-dimethyl-1H-pyrazol-3-yl)amino)imidazo[1,2-b]pyridazine-3-carboxamide | 495 | 2.868 |

TABLE 22-continued

| Example | Structure | Name | [M + H] | HPLC Ret Time (min) |
|---|---|---|---|---|
| 543 | 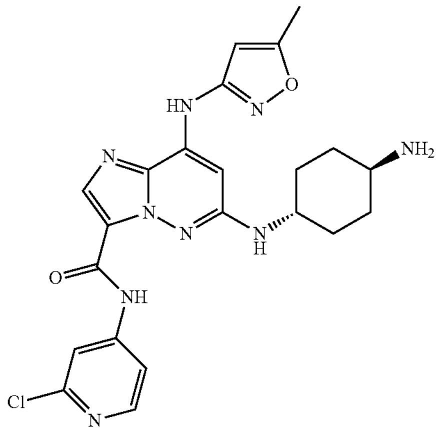 [SMILES: Cc1cc(Nc2cc(N[C@H]3CC[C@H](N)CC3)nn3c(C(=O)Nc4ccnc(Cl)c4)cnc23)no1] | 6-((trans-4-aminocyclohexyl)amino)-N-(2-chloro-4-pyridinyl)-8-((5-methyl-3-isoxazolyl)amino)imidazo[1,2-b]pyridazine-3-carboxamide | 482 | 2.921 |
| 544 | 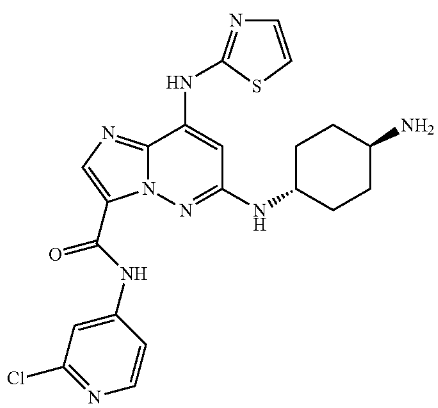 [SMILES: N[C@H]1CC[C@H](Nc2cc(Nc3nccs3)c3ncc(C(=O)Nc4ccnc(Cl)c4)n3n2)CC1] | 6-((trans-4-aminocyclohexyl)amino)-N-(2-chloro-4-pyridinyl)-8-(1,3-thiazol-2-ylamino)imidazo[1,2-b]pyridazine-3-carboxamide | 484 | 2.885 |
| 545 | 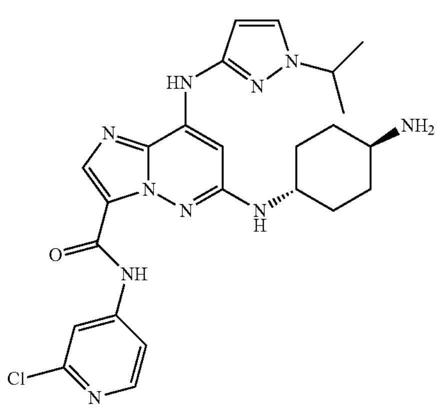 [SMILES: CC(C)n1ccc(Nc2cc(N[C@H]3CC[C@H](N)CC3)nn3c(C(=O)Nc4ccnc(Cl)c4)cnc23)n1] | 6-((trans-4-aminocyclohexyl)amino)-N-(2-chloro-4-pyridinyl)-8-((1-isopropyl-1H-pyrazol-3-yl)amino)imidazo[1,2-b]pyridazine-3-carboxamide | 509 | 3.006 |

TABLE 22-continued

| Example | Structure | Name | [M + H] | HPLC Ret Time (min) |
|---|---|---|---|---|
| 546 | 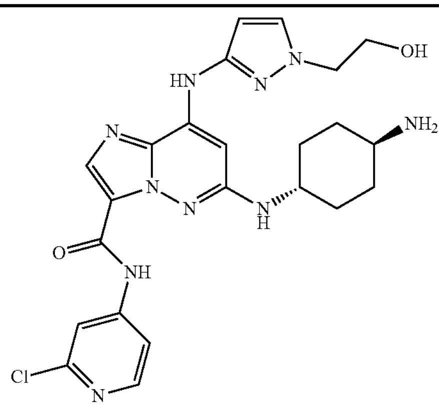 | 6-((trans-4-aminocyclohexyl)amino)-N-(2-chloro-4-pyridinyl)-8-((1-(2-hydroxyethyl)-1H-pyrazol-3-yl)amino)imidazo[1,2-b]pyridazine-3-carboxamide | 511 | 2.597 |

HPLC Conditions:
Chromolith SpeedROD 4.6 × 50 mm, 10-90% aqueous methanol containing 0.1% TFA, 4 min gradient, monitored at 220 nm The following Examples in Table 23 were prepared according to the procedures described in Example 48A and Example 44.

TABLE 23

| Example | Structure | Name | [M + H] | HPLC Ret Time (min) |
|---|---|---|---|---|
| 547 | 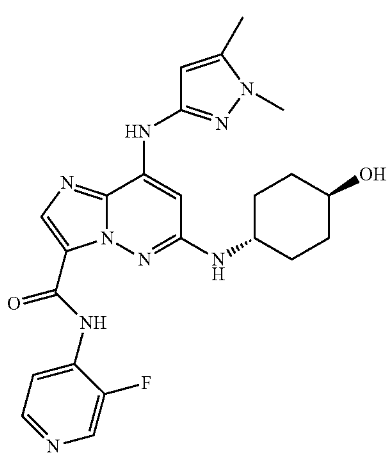 [SMILES: Cc1cc(Nc2cc(N[C@H]3CC[C@H](O)CC3)nn3c(C(=O)Nc4ccncc4F)cnc23)nn1C] | 8-((1,5-dimethyl-1H-pyrazol-3-yl)amino)-N-(3-fluoro-4-pyridinyl)-6-((trans-4-hydroxycyclohexyl)amino)imidazo[1,2-b]pyridazine-3-carboxamide | 480 | 2.70 |
| 548 | 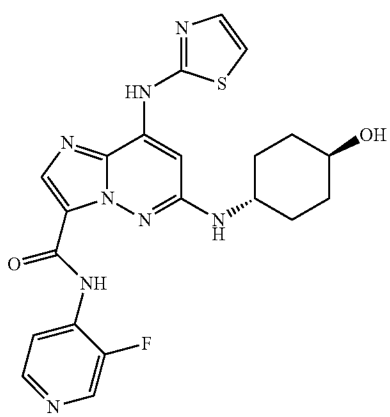 [SMILES: O=C(Nc1ccncc1F)c1cnc2c(Nc3nccs3)cc(N[C@H]3CC[C@H](O)CC3)nn12] | N-(3-fluoro-4-pyridinyl)-6-((trans-4-hydroxycyclohexyl)amino)-8-(1,3-thiazol-2-ylamino)imidazo[1,2-b]pyridazine-3-carboxamide | 469 | 2.731 |

TABLE 23-continued

| Example | Structure | Name | [M + H] | HPLC Ret Time (min) |
|---|---|---|---|---|
| 549 | 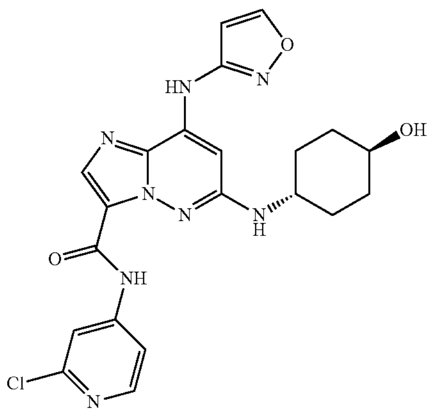 [SMILES: O=C(Nc1ccnc(Cl)c1)c1cnc2c(Nc3ccon3)cc(N[C@H]3CC[C@H](O)CC3)nn12] | N-(2-chloro-4-pyridinyl)-6-((trans-4-hydroxycyclohexyl)amino)-8-(3-isoxazolylamino)imidazo[1,2-b]pyridazine-3-carboxamide | 469 | 3.300 |
| 550 | 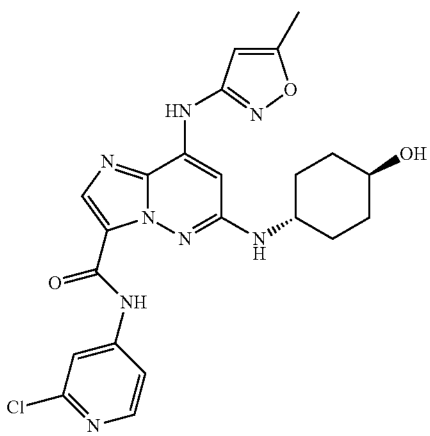 [SMILES: Cc1cc(Nc2cc(N[C@H]3CC[C@H](O)CC3)nn3c(C(=O)Nc4ccnc(Cl)c4)cnc23)no1] | N-(2-chloro-4-pyridinyl)-6-((trans-4-hydroxycyclohexyl)amino)-8-((5-methyl-3-isoxazolyl)amino)imidazo[1,2-b]pyridazine-3-carboxamide | 483 | 3.440 |
| 551 | 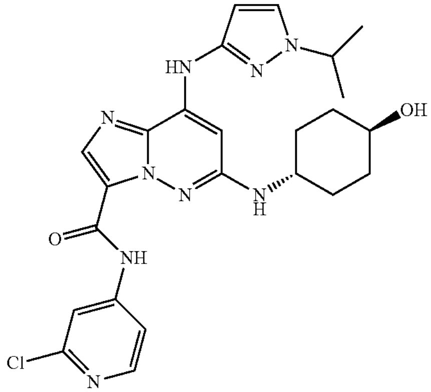 [SMILES: CC(C)n1ccc(Nc2cc(N[C@H]3CC[C@H](O)CC3)nn3c(C(=O)Nc4ccnc(Cl)c4)cnc23)n1] | N-(2-chloro-4-pyridinyl)-6-((trans-4-hydroxycyclohexyl)amino)-8-((1-isopropyl-1H-pyrazol-3-yl)amino)imidazo[1,2-b]pyridazine-3-carboxamide | 510 | 3.468 |

TABLE 23-continued

| Example | Structure | Name | [M + H] | HPLC Ret Time (min) |
|---------|-----------|------|---------|---------------------|
| 552 | 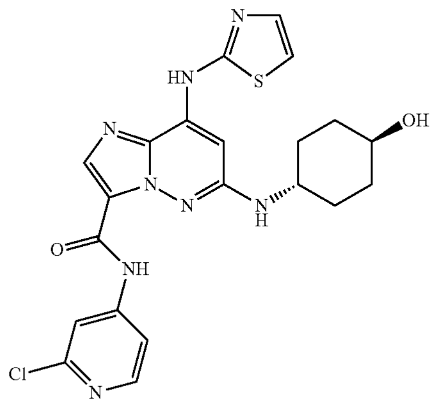 [SMILES: O=C(Nc1ccnc(Cl)c1)c1cnc2c(Nc3nccs3)cc(N[C@H]3CC[C@H](O)CC3)nn12] | N-(2-chloro-4-pyridinyl)-6-((trans-4-hydroxycyclohexyl)amino)-8-(1,3-thiazol-2-ylamino)imidazo[1,2-b]pyridazine-3-carboxamide | 485 | 3.398 |
| 553 | 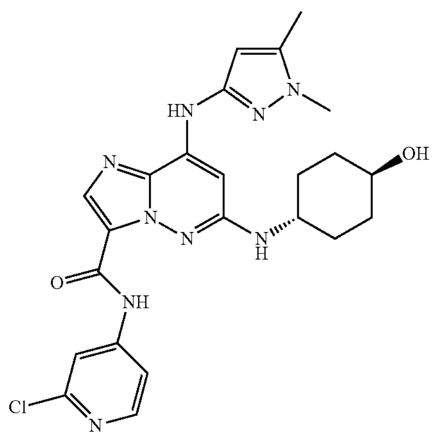 [SMILES: Cc1cc(Nc2cc(N[C@H]3CC[C@H](O)CC3)nn3c(C(=O)Nc4ccnc(Cl)c4)cnc23)nn1C] | N-(2-chloro-4-pyridinyl)-8-((1,5-dimethyl-1H-pyrazol-3-yl)amino)-6-((trans-4-hydroxycyclohexyl)amino)imidazo[1,2-b]pyridazine-3-carboxamide | 496 | 3.345 |
| 554 | 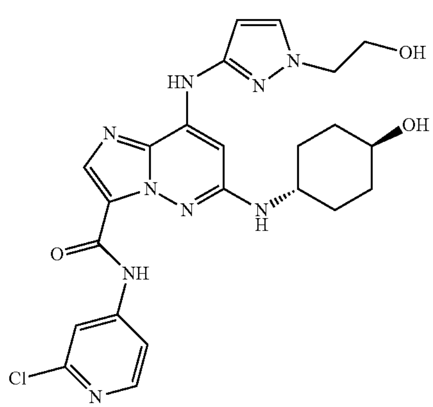 [SMILES: O=C(Nc1ccnc(Cl)c1)c1cnc2c(Nc3ccn(CCO)n3)cc(N[C@H]3CC[C@H](O)CC3)nn12] | N-(2-chloro-4-pyridinyl)-6-((trans-4-hydroxycyclohexyl)amino)-8-((1-(2-hydroxyethyl)-1H-pyrazol-3-yl)amino)imidazo[1,2-b]pyridazine-3-carboxamide | 512 | 3.016 |

HPLC Conditions:

Chromolith SpeedROD 4.6 × 50 mm, 10-90% aqueous methanol containing 0.1% TFA, 4 min gradient, monitored at 220 nm The following Examples in Table 24 were prepared according to the procedures detail in Example 41 and Example 40.

TABLE 24

| Example | Structure | Name | [M + H] | HPLC Ret Time (min) |
|---|---|---|---|---|
| 555 | 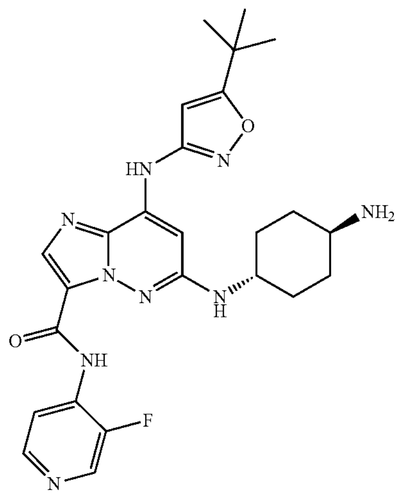 [SMILES: CC(C)(C)c1cc(Nc2cc(N[C@H]3CC[C@H](N)CC3)nn3c(C(=O)Nc4ccncc4F)cnc23)no1] | 6-((trans-4-aminocyclohexyl)amino)-8-((5-tert-butyl-3-isoxazolyl)amino)-N-(3-fluoro-4-pyridinyl)imidazo[1,2-b]pyridazine-3-carboxamide | 508 | 3.076 |
| 556 | 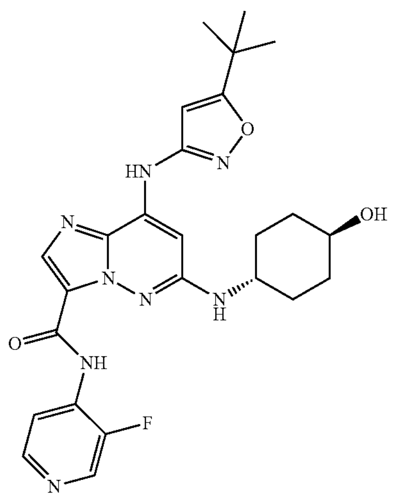 [SMILES: CC(C)(C)c1cc(Nc2cc(N[C@H]3CC[C@H](O)CC3)nn3c(C(=O)Nc4ccncc4F)cnc23)no1] | 8-((5-tert-butyl-3-isoxazolyl)amino)-N-(3-fluoro-4-pyridinyl)-6-((trans-4-hydroxycyclohexyl)amino)imidazo[1,2-b]pyridazine-3-carboxamide | 509 | 3.393 |
| 557 | 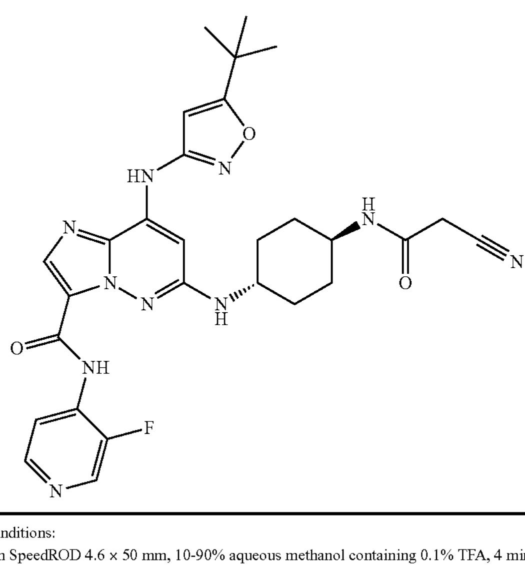 | 8-((5-tert-butyl-3-isoxazolyl)amino)-6-((trans-4-((cyanoacetyl)amino)cyclohexyl)amino)-N-(3-fluoro-4-pyridinyl)imidazo[1,2-b]pyridazine-3-carboxamide | 576 | 3.555 |

(HPLC Conditions:
Chromolith SpeedROD 4.6 × 50 mm, 10-90% aqueous methanol containing 0.1% TFA, 4 min gradient, monitored at 220 nm The following Examples in Table 25 were prepared according to the procedures detailed in Example 48A, Example 40 and Example 52.

TABLE 25

| Example | Structure | Name | [M + H] | HPLC Ret Time (min) |
|---------|-----------|------|---------|---------------------|
| 558 | 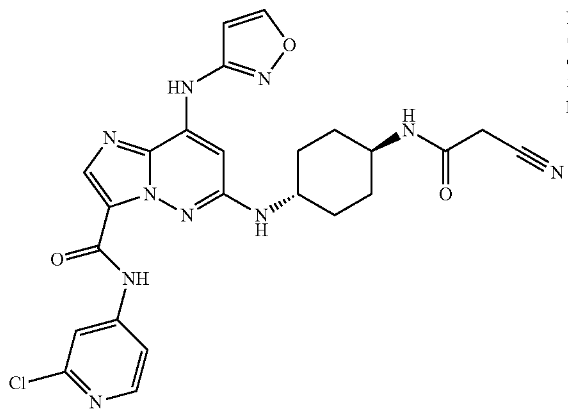 [SMILES: N#CCC(=O)N[C@H]1CC[C@H](Nc2cc(Nc3ccon3)c3ncc(C(=O)Nc4ccnc(Cl)c4)n3n2)CC1] | N-(2-chloro-4-pyridinyl)-6-((trans-4-((cyanoacetyl)amino)cyclohexyl)amino)-8-(3-isoxazolylamino)imidazo[1,2-b]pyridazine-3-carboxamide | 535 | 3.235 |
| 559 | 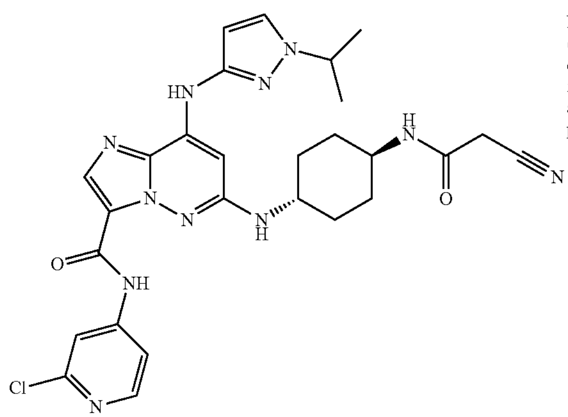 [SMILES: CC(C)n1ccc(Nc2cc(N[C@H]3CC[C@H](NC(=O)CC#N)CC3)nn3c(C(=O)Nc4ccnc(Cl)c4)cnc23)n1] | N-(2-chloro-4-pyridinyl)-6-((trans-4-((cyanoacetyl)amino)cyclohexyl)amino)-8-((1-isopropyl-1H-pyrazol-3-yl)amino)imidazo[1,2-b]pyridazine-3-carboxamide | 576 | 3.425 |
| 560 | 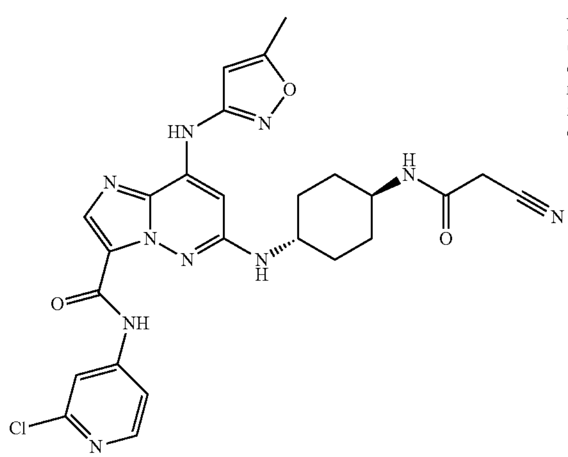 [SMILES: Cc1cc(Nc2cc(N[C@H]3CC[C@H](NC(=O)CC#N)CC3)nn3c(C(=O)Nc4ccnc(Cl)c4)cnc23)no1] | N-(2-chloro-4-pyridinyl)-6-((trans-4-((cyanoacetyl)amino)cyclohexyl)amino)-8-((5-methyl-3-isoxazolyl)amino)imidazo[1,2-b]pyridazine-3-carboxamide | 549 | 3.391 |

TABLE 25-continued

| Example | Structure | Name | [M + H] | HPLC Ret Time (min) |
|---|---|---|---|---|
| 561 | 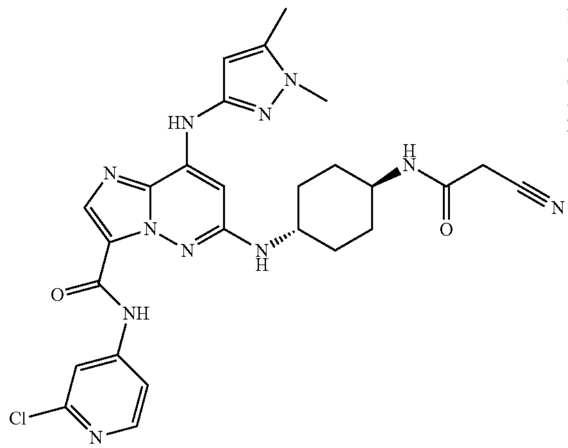 [SMILES: Cc1cc(Nc2cc(N[C@H]3CC[C@H](NC(=O)CC#N)CC3)nn3c(C(=O)Nc4ccnc(Cl)c4)cnc23)nn1C] | N-(2-chloro-4-pyridinyl)-6-((trans-4-((cyanoacetyl)amino)cyclohexyl)amino)-8-((1,5-dimethyl-1H-pyrazol-3-yl)amino)imidazo[1,2-b]pyridazine-3-carboxamide | 562 | 3.290 |
| 562 | 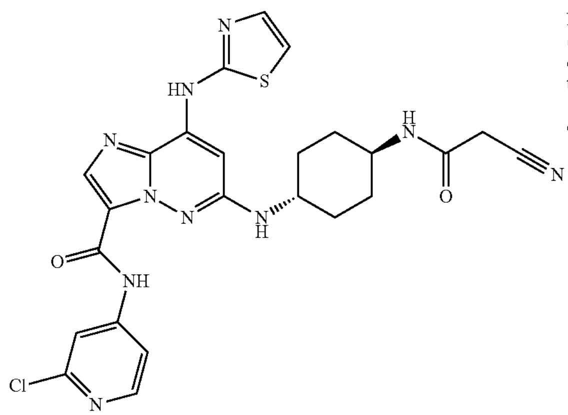 [SMILES: N#CCC(=O)N[C@H]1CC[C@H](Nc2cc(Nc3nccs3)c3ncc(C(=O)Nc4ccnc(Cl)c4)n3n2)CC1] | N-(2-chloro-4-pyridinyl)-6-((trans-4-((cyanoacetyl)amino)cyclohexyl)amino)-8-(1,3-thiazol-2-ylamino)imidazo[1,2-b]pyridazine-3-carboxamide | 551 | 3.341 |
| 563 | 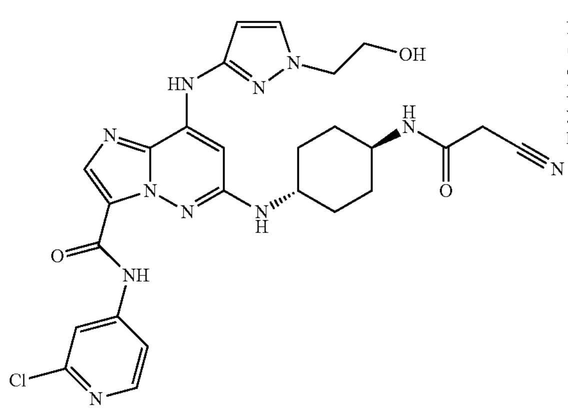 [SMILES: N#CCC(=O)N[C@H]1CC[C@H](Nc2cc(Nc3ccn(CCO)n3)c3ncc(C(=O)Nc4ccnc(Cl)c4)n3n2)CC1] | N-(2-chloro-4-pyridinyl)-6-((trans-4-((cyanoacetyl)amino)cyclohexyl)amino)-8-((1-(2-hydroxyethyl)-1H-pyrazol-3-yl)amino)imidazo[1,2-b]pyridazine-3-carboxamide | 578 | 3.031 |

HPLC Conditions:

Chromolith SpeedROD 4.6 × 50 mm, 10-90% aqueous methanol containing 0.1% TFA, 4 min gradient, monitored at 220 nm

Example 564

6-((trans-4-aminocyclohexyl)amino)-N-4-pyridinyl-8-(4-pyrimidinylamino)imidazo[1,2-b]pyridazine-3-carboxamide

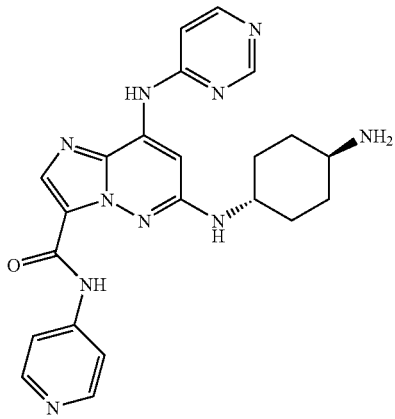 [SMILES: N[C@H]1CC[C@H](Nc2cc(Nc3ccncn3)c3ncc(C(=O)Nc4ccncc4)n3n2)CC1]

564A. Preparation of 6-chloro-N-(pyridin-4-yl)-8-(pyrimidin-4-ylamino)imidazo[1,2-b]pyridazine-3-carboxamide

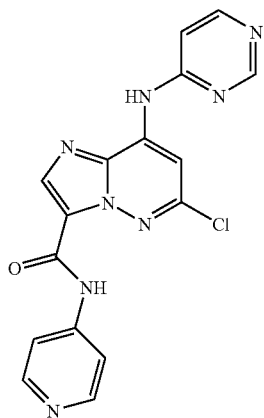 [SMILES: O=C(Nc1ccncc1)c1cnc2c(Nc3ccncn3)cc(Cl)nn12]

A solution of pyrimidin-4-amine (37.0 mg, 0.389 mmol) in degassed dioxane (4 mL) was treated with 6,8-dichloro-N-(pyridin-4-yl)imidazo[1,2-b]pyridazine-3-carboxamide (100 mg, 0.325 mmol), $Pd_2(dba)_3$ (14.86 mg, 0.016 mmol), 9,9-Dimethyl-4,5-bis(diphenylphosphino)xanthene (9.39 mg, 0.016 mmol), and $Cs_2CO_3$ (211 mg, 0.649 mmol). The reaction was purged with argon and heated to 100° C. for 4 hours. The reaction was then cooled to room temperature and concentrated. The crude reaction product was dissolved in a small amount of MeOH, filtered and purified by reversed phase HPLC (YMC ODS-A 5 um 30×250 mm, 10-90% aqueous methanol containing 0.1% TFA, 25 mL/min, 30 min gradient, monitored at 220 nm). The product (retention time=22.555 minutes) was isolated and lyophilized to dryness to afford 6-chloro-N-(pyridin-4-yl)-8-(pyrimidin-4-ylamino)imidazo[1,2-b]pyridazine-3-carboxamide (12 mg, 10.08%). HPLC Rt=2.463 min (YMC S5 ODS 4.6×50 mm, 10-90% aqueous methanol containing 0.2% $H_3PO_4$, 4 min gradient, monitored at 220 nm). [M+H+]=367.0.

564B. Preparation of 6-((trans-4-aminocyclohexyl)amino)-N-4-pyridinyl-8-(4-pyrimidinylamino)imidazo[1,2-b]pyridazine-3-carboxamide

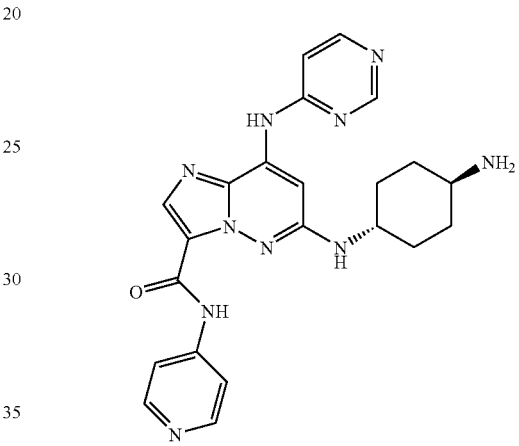

A solution of 6-chloro-N-(pyridin-4-yl)-8-(pyrimidin-4-ylamino)imidazo[1,2-b]pyridazine-3-carboxamide (12 mg, 0.033 mmol) in NMP (1 mL) was treated with (trans)-cyclohexane-1,4-diamine (37.4 mg, 0.327 mmol) and heated to 120° C. for 4 hours. The crude reaction product was dissolved in a small amount of MeOH and purified by reversed phase HPLC (YMC ODS-A 5 um 30×250 mm, 10-90% aqueous methanol containing 0.1% TFA, 25 mL/min, 30 min gradient, monitored at 220 nm). The product (retention time=19.202 minutes) was isolated and lyophilized to dryness to afford 6-((trans-4-aminocyclohexyl)amino)-N-4-pyridinyl-8-(4-pyrimidinylamino)imidazo[1,2-b]pyridazine-3-carboxamide (2.1 mg, 8.59%). $^1$H NMR (500 MHz, DMSO) δ ppm 8.87 (1H, s), 8.65-8.74 (3H, m), 8.51 (1H, d, J=10.45 Hz), 8.25 (2H, d, J=6.60 Hz), 8.21 (2H, s), 7.25 (1H, d, J=6.05 Hz), 3.82-3.93 (1H, m), 3.16-3.24 (1H, m), 2.39 (2H, d, J=14.57 Hz), 2.11-2.22 (3H, m), 1.45-1.68 (4H, m). HPLC Rt=1.888 min (YMC S5 ODS 4.6×50 mm, 10-90% aqueous methanol containing 0.2% $H_3PO_4$, 4 min gradient, monitored at 220 nm). [M+H+]=445.0.

The following Examples in Table 26 were prepared in a manner analogous to that for Example 564.

TABLE 26

| Example | Structure | Name | [M + H] | HPLC Ret. Time (min) |
|---|---|---|---|---|
| 565 | 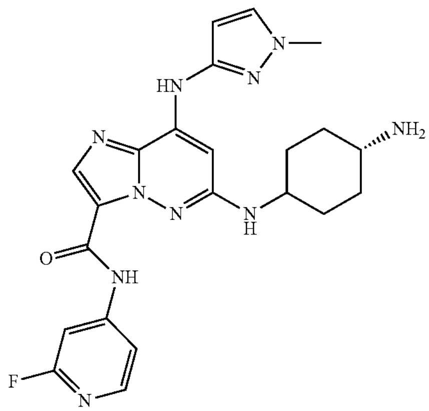 | 6-((trans-4-aminocyclohexyl)amino)-N-(2-fluoro-4-pyridinyl)-8-((1-methyl-1H-pyrazol-3-yl)amino) imidazo[1,2-b]pyridazine-3-carboxamide | 465.1 | 3.246 |
| 566 | 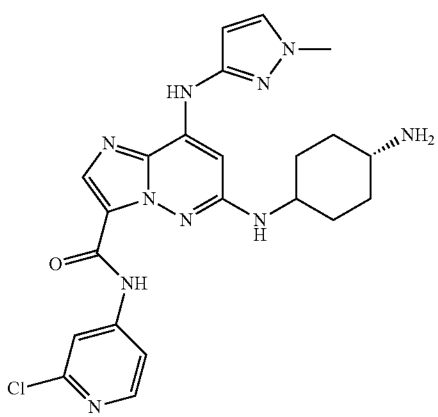 | 6-((trans-4-aminocyclohexyl)amino)-N-(2-chloro-4-pyridinyl)-8-((1-methyl-1H-pyrazol-3-yl)amino) imidazo[1,2-b]pyridazine-3-carboxamide | 481.0 | 3.358 |
| 567 | 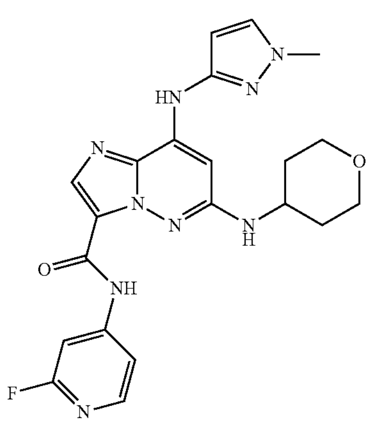 [SMILES: Cn1ccc(Nc2cc(NC3CCOCC3)nn3c(C(=O)Nc4ccnc(F)c4)cnc23)n1] | N-(2-fluoro-4-pyridinyl)-8-((1-methyl-1H-pyrazol-3-yl)amino)-6-(tetrahydro-2H-pyran-4-ylamino) imidazo[1,2-b]pyridazine-3-carboxamide | 452.0 | 3.978 |

TABLE 26-continued

| Example | Structure | Name | [M + H] | HPLC Ret. Time (min) |
|---|---|---|---|---|
| 568 | 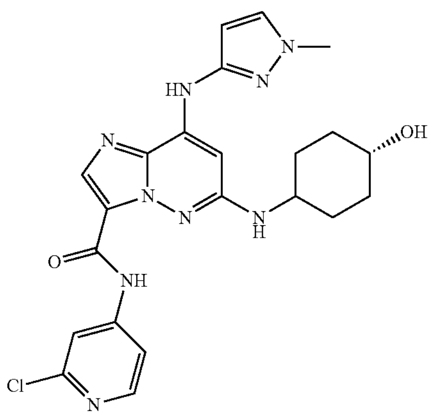 | N-(2-chloro-4-pyridinyl)-6-((trans-4-hydroxycyclohexyl)amino)-8-((1-methyl-1H-pyrazol-3-yl)amino)imidazo[1,2-b]pyridazine-3-carboxamide | 482.0 | 4.046 |

HPLC Conditions:
YMC S5 ODS 4.6 × 50 mm, 10-90% aqueous methanol containing 0.2% $H_3PO_4$, 4 min gradient, monitored at 220 nm

Example 569

8-(cyclopropylamino)-N-(3-fluoro-4-pyridinyl)-6-((1-methyl-4-piperidinyl)amino)imidazo[1,2-b]pyridazine-3-carboxamide

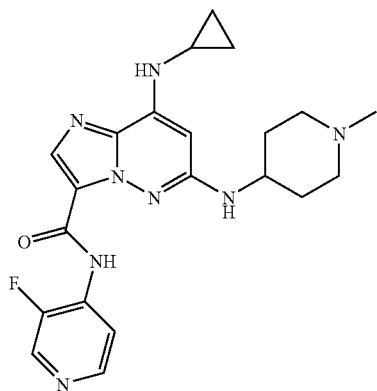 [SMILES: CN1CCC(Nc2cc(NC3CC3)c3ncc(C(=O)Nc4ccncc4F)n3n2)CC1]

A microwave tube was charged with 6-chloro-8-(cyclopropyl(4-methoxybenzyl)amino)-N-(3-fluoropyridin-4-yl)imidazo[1,2-b]pyridazine-3-carboxamide (35 mg, 0.075 mmol), 1-methylpiperidin-4-amine (86 mg, 0.750 mmol) and NMP (1 mL). The reaction mixture was irradiated in a microwave (300 W) for 20 minutes at 100° C. The crude reaction mixture was dissolved in a small amount of MeOH and purified by reversed phase HPLC (YMC ODS-A 5 um 30×250 mm, 10-90% aqueous methanol containing 0.1% TFA, 25 mL/min, 30 min gradient, monitored at 220 nm). The product (retention time=30.463 minutes) was isolated and lyophilized to dryness. The crude material was dissolved in $CH_2Cl_2$ (2 mL) and treated with TFA (0.5 mL) and stirred at room temperature for 2 hours, then concentrated to dryness. The crude reaction product was dissolved in a small amount of MeOH and purified by reversed phase HPLC (YMC ODS-A 5 um 30×250 mm, 10-90% aqueous methanol containing 0.1% TFA, 25 mL/min, 30 min gradient, monitored at 220 nm). The product (retention time=24.643 minutes) was isolated and lyophilized to dryness to afford 8-(cyclopropylamino)-N-(3-fluoropyridin-4-yl)-6-(1-methylpiperidin-4-ylamino)imidazo[1,2-b]pyridazine-3-carboxamide (8.5 mg, 14.42%). HPLC Rt=2.681 min (YMC S5 ODS 4.6×50 mm, 10-90% aqueous methanol containing 0.2% $H_3PO_4$, 4 min gradient, monitored at 220 nm). [M+H+]=425.0.

Example 570

8-(cyclopropylamino)-N-(3-fluoro-4-pyridinyl)-6-((2-oxo-3-azepanyl)amino)imidazo[1,2-b]pyridazine-3-carboxamide

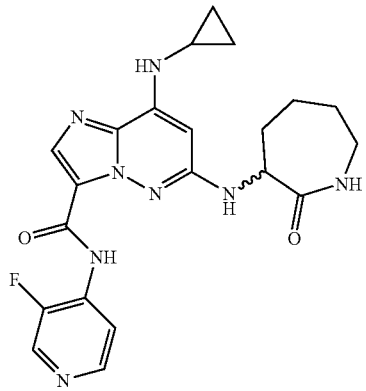 [SMILES: O=C(Nc1ccncc1F)c1cnc2c(NC3CC3)cc(NC3CCCCNC3=O)nn12]

A microwave tube was charged with 6-chloro-8-(cyclopropyl(4-methoxybenzyl)amino)-N-(3-fluoropyridin-4-yl)imidazo[1,2-b]pyridazine-3-carboxamide (35 mg, 0.075 mmol), DL-alpha-Amino-epsilon-caprolactam (96 mg, 0.750 mmol), and NMP (1 mL). The reaction mixture was irradiated (300 W) at 100° C. for 40 minutes. The crude reaction product was dissolved in a small amount of MeOH and purified by reversed phase HPLC (YMC ODS-A 5 um 30×250 mm, 10-90% aqueous methanol containing 0.1% TFA, 25 mL/min, 30 min gradient, monitored at 220 nm). The product (retention time=35.053 minutes) was isolated and lyophilized to dryness. The resulting material was dissolved in DCM (2 mL) and treated with TFA (0.5 mL, 6.49 mmol). Reaction was stirred at room temperature for three hours, and then concentrated to dryness. The crude reaction product was dissolved in a small amount of MeOH and purified by reversed phase HPLC(YMC ODS-A 5 um 30×250 mm, 10-90% aqueous methanol containing 0.1% TFA, 25 mL/min, 30 min gradient, monitored at 220 nm). The product (retention time=30.556 minutes) was isolated and lyophilized to dryness to afford 8-(cyclopropylamino)-N-(3-fluoropyridin-4-yl)-6-(2-oxoazepan-3-ylamino)imidazo[1,2-b]pyridazine-3-carboxamide (7 mg, 13.73%). $^1$H NMR (400 MHz, DMSO) δ ppm 11.24 (1H, s), 8.73 (1H, d, J=2.77 Hz), 8.45 (1H, d, J=5.54 Hz), 8.39 (1H, t), 8.01 (1H, s), 7.84 (1H, t, J=6.04 Hz), 7.66 (1H, s), 6.99 (1H, s), 6.31 (1H, s), 4.54 (1H, d, J=9.57 Hz), 2.98-3.24 (3H, m), 1.80-2.02 (2H, m), 1.67 (1H, d, J=14.10 Hz), 1.37-1.59 (2H, m), 1.20-1.32 (1H, m), 0.73-0.85 (2H, m), 0.54-0.70 (2H, m). HPLC Rt=3.633 min (YMC S5 ODS 4.6×50 mm, 10-90% aqueous methanol containing 0.2% $H_3PO_4$, 4 min gradient, monitored at 220 nm). [M+H+]=439.0.

Example 571

N-(2-chloro-4-pyridinyl)-8-(cyclopropylamino)-6-(tetrahydro-2H-thiopyran-4-ylamino)imidazo[1,2-b]pyridazine-3-carboxamide

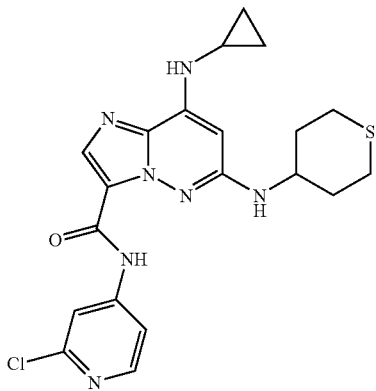 [SMILES: O=C(Nc1ccnc(Cl)c1)c1cnc2c(NC3CC3)cc(NC3CCSCC3)nn12]

571A. Preparation of N-(2-chloropyridin-4-yl)-8-(cyclopropyl(4-methoxybenzyl)amino)-6-(tetrahydro-2H-thiopyran-4-ylamino)imidazo[1,2-b]pyridazine-3-carboxamide

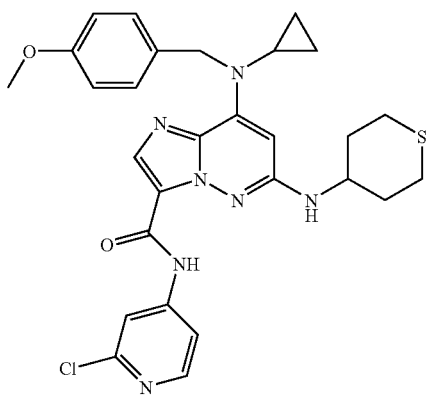 [SMILES: COc1ccc(CN(c2cc(NC3CCSCC3)nn3c(C(=O)Nc4ccnc(Cl)c4)cnc23)C2CC2)cc1]

A microwave tube was charged with 6-chloro-N-(2-chloropyridin-4-yl)-8-(cyclopropyl(4-methoxybenzyl)amino) imidazo[1,2-b]pyridazine-3-carboxamide (100 mg, 0.207 mmol), tetrahydro-2H-thiopyran-4-amine (121 mg, 1.034 mmol), and NMP (2 mL). The reaction mixture was irradiated at 120° C. (300 W) for 20 minutes. The crude reaction product was dissolved in a small amount of MeOH and purified by reversed phase HPLC (YMC ODS-A 5 um 30×250 mm, 10-90% aqueous methanol containing 0.1% TFA, 25 mL/min, 60 min gradient, monitored at 254 nm). The product (retention time=68.837 minutes) was isolated and lyophilized to dryness to afford N-(2-chloropyridin-4-yl)-8-(cyclopropyl(4-methoxybenzyl)amino)-6-(tetrahydro-2H-thiopyran-4-ylamino)imidazo[1,2-b]pyridazine-3-carboxamide (27 mg, 17.32%). HPLC Rt=4.816 min (YMC S5 ODS 4.6×50 mm, 10-90% aqueous methanol containing 0.2% $H_3PO_4$, 4 min gradient, monitored at 220 nm). [M+H+]=563.9.

571B. Preparation of N-(2-chloro-4-pyridinyl)-8-(cyclopropylamino)-6-(tetrahydro-2H-thiopyran-4-ylamino)imidazo[1,2-b]pyridazine-3-carboxamide

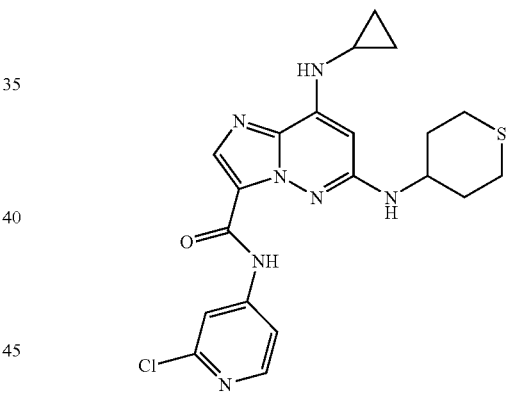

A solution of N-(2-chloropyridin-4-yl)-8-(cyclopropyl(4-methoxybenzyl)amino)-6-(tetrahydro-2H-thiopyran-4-ylamino)imidazo[1,2-b]pyridazine-3-carboxamide (27 mg, 0.048 mmol) in DCM (0.5 mL) was treated with TFA (1.0 mL, 12.98 mmol) and stirred at room temperature for 1 hour and then concentrated to dryness. The crude reaction product was dissolved in a small amount of MeOH and purified by reversed phase HPLC (YMC ODS-A 5 um 30×250 mm, 10-90% aqueous methanol containing 0.1% TFA, 25 mL/min, 30 min gradient, monitored at 254 nm). The product (retention time=36.913 minutes) was isolated and lyophilized to dryness to afford N-(2-chloropyridin-4-yl)-8-(cyclopropylamino)-6-(tetrahydro-2H-thiopyran-4-ylamino)imidazo[1,2-b]pyridazine-3-carboxamide (2.9 mg, 8.33%). HPLC Rt=4.481 min (YMC S5 ODS 4.6×50 mm, 10-90% aqueous methanol containing 0.2% H$_3$PO$_4$, 4 min gradient, monitored at 220 nm). [M+H+]=443.9.

Example 572

4-((3-((2-chloro-4-pyridinyl)carbamoyl)-8-(cyclopropylamino)imidazo[1,2-b]pyridazin-6-yl)amino)tetrahydro-2H-thiopyranium-1-olate

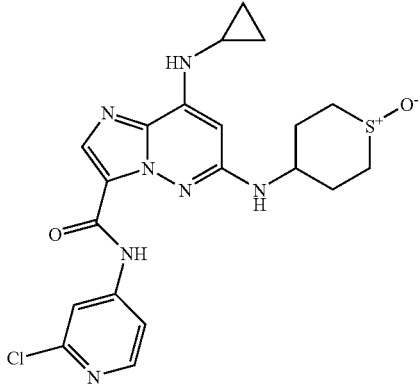 [SMILES: O=C(Nc1ccnc(Cl)c1)c1cnc2c(NC3CC3)cc(NC3CC[S+]([O-])CC3)nn12]

A solution of N-(2-chloropyridin-4-yl)-8-(cyclopropyl(4-methoxybenzyl)amino)-6-(tetrahydro-2H-thiopyran-4-ylamino)imidazo[1,2-b]pyridazine-3-carboxamide (27 mg, 0.048 mmol) in DCM (0.5 mL) was treated with TFA (1.0 mL, 12.98 mmol) and stirred at room temperature for 1 hour and then concentrated to dryness. The crude reaction product was dissolved in a small amount of MeOH and purified by reversed phase HPLC (YMC ODS-A 5 um 30×250 mm, 10-90% aqueous methanol containing 0.1% TFA, 25 mL/min, 30 min gradient, monitored at 254 nm). The product (retention time=32.303 minutes) was isolated and lyophilized to dryness to afford 443-((2-chloro-4-pyridinyl)carbamoyl)-8-(cyclopropylamino)imidazo[1,2-b]pyridazin-6-yl)amino)tetrahydro-2H-thiopyranium-1-olate (1.6 mg, 4.76%). HPLC Rt=3.816 min (YMC S5 ODS 4.6×50 mm, 10-90% aqueous methanol containing 0.2% H$_3$PO$_4$, 4 min gradient, monitored at 220 nm). [M+H+]=459.9.

Example 573

N-(2-chloro-4-pyridinyl)-8-(cyclopropylamino)-6-(tetrahydro-2H-pyran-4-ylamino)imidazo[1,2-b]pyridazine-3-carboxamide

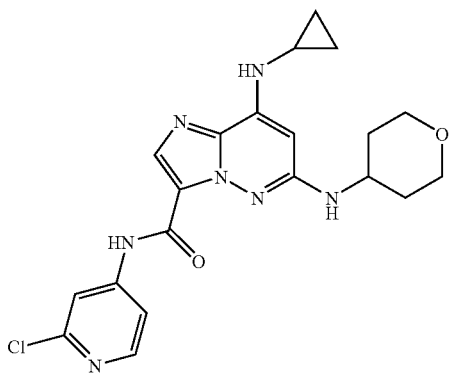 [SMILES: O=C(Nc1ccnc(Cl)c1)c1cnc2c(NC3CC3)cc(NC3CCOCC3)nn12]

573A. Preparation of N-(2-chloropyridin-4-yl)-8-(cyclopropyl(4-methoxybenzyl)amino)-6-(tetrahydro-2H-pyran-4-ylamino)imidazo[1,2-b]pyridazine-3-carboxamide

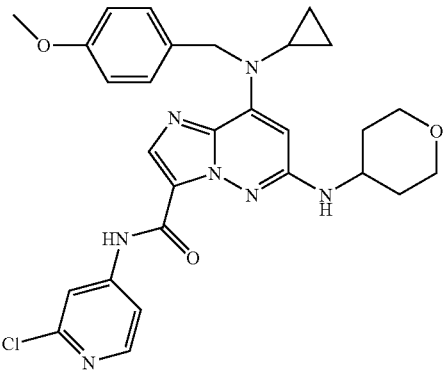 [SMILES: COc1ccc(CN(c2cc(NC3CCOCC3)nn3c(C(=O)Nc4ccnc(Cl)c4)cnc23)C2CC2)cc1]

A solution of tetrahydro-2H-pyran-4-amine (105 mg, 1.034 mmol) and 6-chloro-N-(2-chloropyridin-4-yl)-8-(cyclopropyl(4-methoxybenzyl)amino)imidazo[1,2-b]pyridazine-3-carboxamide (50 mg, 0.103 mmol) in NMP (1 mL) was heated to 140° C. The reaction was stirred for 16 hours until starting material was consumed and then cooled to room temperature. The crude reaction product was dissolved in a small amount of MeOH and purified by reversed phase HPLC (YMC ODS-A 5 um 30×250 mm, 10-90% aqueous methanol containing 0.1% TFA, 25 mL/min, 40 min gradient, monitored at 220 nm). The product (retention time=47.580 minutes) was isolated and lyophilized to dryness. to afford N-(2-chloropyridin-4-yl)-8-(cyclopropyl(4-methoxybenzyl)amino)-6-(tetrahydro-2H-pyran-4-ylamino)imidazo[1,2-b]pyridazine-3-carboxamide (7 mg, 11.57%). HPLC Rt=4.595 min (YMC S5 ODS 4.6×50 mm, 10-90% aqueous methanol containing 0.2% H$_3$PO$_4$, 4 min gradient, monitored at 220 nm). [M+H+]=548.0.

573B. Preparation of N-(2-chloro-4-pyridinyl)-8-(cyclopropylamino)-6-(tetrahydro-2H-pyran-4-ylamino)imidazo[1,2-b]pyridazine-3-carboxamide

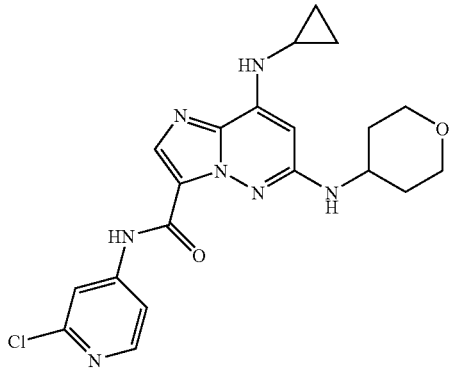 [SMILES: O=C(Nc1ccnc(Cl)c1)c1cnc2c(NC3CC3)cc(NC3CCOCC3)nn12]

A solution of N-(2-chloropyridin-4-yl)-8-(cyclopropyl(4-methoxybenzyl)amino)-6-(tetrahydro-2H-pyran-4-ylamino)imidazo[1,2-b]pyridazine-3-carboxamide (7 mg, 0.013 mmol) in DCM (1 mL) was treated with TFA (0.5 mL, 6.49 mmol) and stirred at room temperature overnight. The reaction mixture was concentrated to dryness. The crude reaction product was dissolved in a small amount of MeOH and purified by reversed phase HPLC (YMC ODS-A 5 um 30×250 mm, 10-90% aqueous methanol containing 0.1% TFA, 25 mL/min, 30 min gradient, monitored at 220 nm). The product (retention time=35.169 minutes) was isolated and lyophilized to dryness to afford N-(2-chloropyridin-4-yl)-8-(cyclopropylamino)-6-(tetrahydro-2H-pyran-4-ylamino)imidazo[1,2-b]pyridazine-3-carboxamide (2.5 mg, 35.9%). $^1$H NMR 400 MHz, DMSO-D6) δ ppm 11.40 (1H, s), 8.38 (1H, d, J=5.54 Hz), 7.97 (1H, s), 7.75 (1H, s), 7.70 (1H, d, J=5.79 Hz), 7.65 (1H, s), 7.10 (1H, d, J=6.55 Hz), 6.00 (1H, s), 3.85-4.06 (3H, m), 1.93-2.08 (2H, m), 1.43-1.61 (2H, m), 0.71-0.81 (2H, m, J=5.54 Hz), 0.57-0.68 (2H, m). HPLC Rt=4.160 min (YMC S5 ODS 4.6×50 mm, 10-90% aqueous methanol containing 0.2% H$_3$PO$_4$, 4 min gradient, monitored at 220 nm). [M+H+]= 428.0.

What is claimed is:

1. A compound according to formula I:

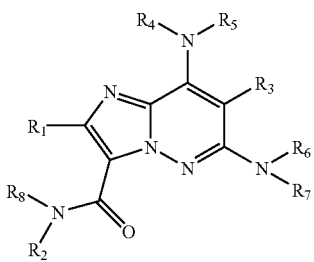

or a pharmaceutically acceptable salt thereof, wherein $R_1$ and $R_3$ are each independently selected from hydrogen, halogen, cyano, and $C_{1-4}$alkyl;

$R_2$ is selected from cycloalkyl, substituted cycloalkyl, heterocyclo, substituted heterocyclo, aryl, substituted aryl, heteroaryl, and substituted heteroaryl;

$R_4$ is selected from hydrogen, alkyl, substituted alkyl, —C(=O)alkyl, —S(O)$_2$alkyl, cycloalkyl, substituted cycloalkyl, heterocyclo, substituted heterocyclo, aryl, substituted aryl, heteroaryl, and substituted heteroaryl;

$R_5$ is selected from hydrogen and $C_{1-4}$alkyl;

$R_6$ is selected from alkyl, substituted alkyl, cycloalkyl, substituted cycloalkyl, heterocyclo, substituted heterocyclo, aryl, substituted aryl, heteroaryl, and substituted heteroaryl; and $R_7$ is selected from hydrogen and $C_{1-4}$alkyl; or $R_6$ and $R_7$ together with the nitrogen atom to which they are attached form an optionally substituted 5-, 6- or 7-membered monocyclic heteroaryl or heterocyclo ring, or an optionally substituted 7- to 11-membered bicyclic heteroaryl or heterocyclo ring;

$R_8$ is selected from hydrogen and $C_{1-4}$alkyl; and provided that if $R_2$ is

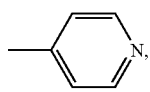

$R_4$ is

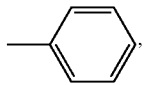

$R_6$ is

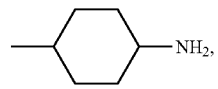

then $R_3$ is not hydrogen;

wherein:

said heterocyclo is a fully saturated or unsaturated, aromatic or nonaromatic cyclic group, which is a 4 to 7 membered monocyclic, 7 to 11 membered bicyclic, or 10 to 15 membered tricyclic ring system, which has at least one heteroatom selected from nitrogen, oxygen, and sulfur in at least one carbon atom-containing ring; said heterocyclo may be attached at any heteroatom or carbon atom;

said heteroaryl is a 4 to 7 membered monocyclic, 7 to 11 membered bicyclic, or 10 to 15 membered tricyclic aromatic ring system, which has at least one heteroatom selected from nitrogen, oxygen, and sulfur and at least one carbon atom-containing ring; and said heterocyclo and heteroaryl are substituted with one to four substituents selected from alkyl, substituted alkyl, alkenyl, substituted alkenyl, alkynyl, substituted alkynyl, arylalkyl, arylalkyloxy, halo, haloalkyl, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, substituted sulfonamido, ureido, nitro, cyano, carboxy, carboxyalkyl, carbamyl, substituted carbamyl, alkoxycarbonyl, aryl, substituted aryl, guanidino, and heterocyclyl, and substituted heterocyclyl.

2. The compound according to claim 1, wherein
$R_2$ is selected from aryl, substituted aryl, $C_{3-7}$cycloalkyl, substituted $C_{3-7}$cycloalkyl, 5- or 6-membered heterocyclo and heteroaryl, and substituted 5- or 6-membered heterocyclo and heteroaryl.

3. The compound according to claim 2, wherein
$R_2$ is selected from phenyl, cyclohexyl, pyridyl, pyrimidinyl, pyrazinyl, benzothiazolyl, pyridazinyl pyrrolidinyl, pyrrolyl, pyrazolyl, imidazolyl, thiazolyl, thienyl, piperidinyl, piperazinyl, morpholinyl, thiamorpholinyl, triazinyl, and triazolyl, wherein each $R_2$ is optionally substituted with halogen, cyano, $C_{1-4}$alkyl, substituted $C_{1-4}$alkyl, alkenyl, substituted alkenyl, alkynyl, substituted alkynyl, $C_{1-4}$alkoxy, haloalkyl, $C_{3-7}$cycloalkyl, heterocyclo, heteroaryl, —OR$_{2a}$, —NR$_{2a}$R$_{2b}$, —NR$_{2a}$C(=O)R$_{2b}$, C(=O)NR$_{2a}$R$_{2b}$—C(=O)OR$_{2a}$, wherein $R_{2a}$ and $R_{2b}$ are each independently selected from hydrogen and $C_{1-4}$alkyl.

4. The compound according to claim 1, wherein $R_4$ is selected from alkyl, aryl, cycloalkyl, heterocyclo, and heteroaryl, wherein each $R_4$ is optionally substituted by one to three groups, $T_1$, $T_2$, and/or $T_3$;

$T_1$, $T_2$, and $T_3$ are each independently selected from halogen, alkyl, substituted alkyl, alkenyl, substituted alkenyl, alkynyl, substituted alkynyl, nitro, cyano, —(CHR)$_r$SO$_3$H, —(CHR)$_r$SR$_9$, —(CHR)$_r$S(O)$_p$R$_{11}$, —(CHR)$_r$S(O)$_p$NR$_9$R$_{10}$, —(CHR)$_r$NR$_9$S(O)$_p$R$_{11}$, —(CHR)$_r$OR$_9$, —(CHR)$_r$CN, —(CHR)$_r$NR$_9$R$_{10}$, —(CHR)$_r$NR$_9$C(=O)R$_{10}$, —(CHR)$_r$NR$_9$C(=O)NR$_9$R$_{10}$, —(CHR)$_r$C(=O)OR$_9$, —(CHR)$_r$C(=O)R$_9$, —(CHR)$_r$OC(=O)R$_9$, —(CHR)$_r$C(=O)NR$_9$R$_{10}$, —(CHR)$_r$-cycloalkyl, —(CHR)$_r$-heterocyclo, —(CHR)$_r$-aryl, and —(CHR)$_r$-heteroaryl, wherein said cycloalkyl, heterocyclo, aryl, or heteroaryl is optionally substituted as valence allows from one to three groups, $R_{12}$, $R_{13}$ and/or $R_{14}$; each p is independently 1 or 2; each r is independently zero, 1, 2, or 3; or $T_1$ and $T_2$, located on adjacent ring atoms are taken together with the ring atoms to which they are attached to form a fused cycloalkyl, aryl, heteroaryl, or heterocyclo, wherein said cycloalkyl, aryl, heteroaryl, or heterocyclo is optionally substituted as valence allows from one to three groups, $R_{12}$, $R_{13}$ and/or $R_{14}$;

each R is independently selected from alkyl, substituted alkyl, alkenyl, substituted alkenyl, alkynyl, substituted alkynyl, cycloalkyl, aryl, heteroaryl, and heterocyclo;

$R_9$ and $R_{10}$ are each independently selected from hydrogen, alkyl, substituted alkyl, alkenyl, substituted alkenyl, cycloalkyl, substituted cycloalkyl, aryl, substituted aryl, heteroaryl, substituted heteroaryl, heterocyclo, and substituted heterocyclo; or $R_9$ and $R_{10}$ together with the nitrogen atom to which they are attached form a heteroaryl or heterocyclo, wherein said heteroaryl or heterocyclo is optionally substituted as valence allows from one to three groups, $R_{12}$, $R_{13}$ and/or $R_{14}$;

each $R_{11}$ is independently selected from alkyl, substituted alkyl, alkenyl, substituted alkenyl, alkynyl, substituted alkynyl, cycloalkyl, aryl, heteroaryl, and heterocyclo;

$R_{12}$, $R_{13}$, and $R_{14}$ are each independently selected from $C_{1-4}$alkyl, substituted $C_{1-4}$alkyl, $C_{2-4}$alkenyl, substituted $C_{2-4}$alkenyl, halogen, hydroxy, cyano, nitro, $CF_3$, —O($C_{1-4}$alkyl), —OCF$_3$, —C(=O)H, —C(=O)($C_{1-4}$alkyl), —CO$_2$H, —CO$_2$($C_{1-4}$alkyl), —NHCO$_2$($C_{1-4}$alkyl), —S($C_{1-4}$alkyl), —NH$_2$, —NH($C_{1-4}$alkyl), —N($C_{1-4}$alkyl)$_2$, —N($C_{1-4}$alkyl)$_3^+$, —SO$_2$($C_{1-4}$alkyl), —C(=O)($C_{1-4}$alkylene)NH$_2$, —C(=O)($C_{1-4}$alkylene)NH(alkyl), —C(=O)($C_{1-4}$alkylene)N($C_{1-4}$alkyl)$_2$, and optionally substituted phenyl.

5. The compound according to claim 4, wherein $R_4$ is selected from $C_{1-6}$alkyl, $C_{3-6}$cycloalkyl, phenyl, a 4-, 5-, or 6-membered monocyclic heteroaryl or heterocyclo, each group optionally substituted by one to three groups, $T_1$, $T_2$, and/or $T_3$; and $T_1$, $T_2$, and $T_3$ are each independently selected from F, Cl, Br, $C_{1-4}$alkyl, haloalkyl, —(CH$_2$)$_r$OR$_9$, —(CH$_2$)$_r$C(=O)R$_9$, —(CH$_2$)$_r$C(=O)OR$_9$, —(CH$_2$)$_r$C(=O)NR$_9$R$_{10}$, —(CH$_2$)$_r$NR$_9$R$_{10}$, —(CH$_2$)$_r$NR$_9$C(=O)R$_{10}$, —(CH$_2$)$_r$CN, —(CH$_2$)$_r$NR$_9$C(=O)NR$_9$R$_{10}$, —(CH$_2$)$_r$S(O)$_2$R$_{11}$, —(CH$_2$)$_r$S(O)$_2$NR$_9$R$_{10}$, —(CH$_2$)$_r$OH, —(CH$_2$)$_r$CN, —(CH$_2$)$_r$-$C_{3-6}$cyclohexyl, —(CH$_2$)$_r$phenyl, —(CH$_2$)$_r$morpholinyl, —(CH$_2$)$_r$pyridyl, —(CH$_2$)$_r$pyrazolyl, —(CH$_2$)$_r$tetrazolyl, —(CH$_2$)$_r$cyclopropyl, —(CH$_2$)$_r$pyrrolidinyl, —(CH$_2$)$_r$piperidinyl, —(CH$_2$)$_r$furyl, —(CH$_2$)$_r$imidazolyl, —(CH$_2$)$_r$pyrimidinyl, —(CH$_2$)$_r$piperazinyl, and —(CH$_2$)$_r$pyradizinyl, —(CH$_2$)$_r$imidazolyl, —(CH$_2$)$_r$pyrazolyl, —(CH$_2$)$_r$triazolyl, —(CH$_2$)$_r$thiazolyl, each ring group optionally substituted as valence allows from one to three groups, $R_{12}$, $R_{13}$ and/or $R_{14}$; each r is independently zero, 1, or 2;

$R_9$ and $R_{10}$ are each independently selected from hydrogen, $C_{1-4}$alkyl, haloC$_{1-4}$alkyl, —(CH$_2$)$_v$OH, —(CH$_2$)$_v$N(alkyl)$_2$, $C_{3-6}$cycloalkyl, phenyl, pyrrolidinyl, morpholinyl, and pyridyl, wherein said $C_{3-6}$cycloalkyl, pyrrolidinyl, morpholinyl, and pyridyl are optionally substituted with NH$_2$, hydroxy, $C_{1-4}$alkyl and aryl; each v is independently 1, 2, or 3;

$R_{12}$, $R_{13}$, and $R_{14}$ are each independently selected from hydroxy, $C_{1-4}$alkyl and phenyl optionally substituted with hydroxy, nitro, and halogen.

6. The compound according to claim 1, wherein $R_6$ is selected from $C_{1-4}$alkyl, aryl, $C_{3-7}$cycloalkyl, 5- or 6-membered monocyclic heterocyclo and heteroaryl, wherein $R_6$ is optionally substituted by one to three groups, $T_4$, $T_5$, and/or $T_6$;

$T_4$, $T_5$ and $T_6$ are independently selected from halogen, alkyl, substituted alkyl, alkenyl, substituted alkenyl, alkynyl, substituted alkynyl, nitro, cyano, —(CHR)$_r$SR$_{15}$, —(CHR)$_r$S(O)$_q$R$_{17}$, —(CHR)$_r$S(O)$_q$NR$_{15}$R$_{16}$, —(CHR)$_r$NR$_{15}$S(O)$_q$R$_{17}$, —(CHR)$_r$NR$_{15}$S(O)$_q$NR$_{15}$R$_{16}$, —(CHR)$_r$OR$_{15}$, —(CHR)$_r$NR$_{15}$R$_{16}$, —(CHR)$_r$NR$_{15}$C(=O)R$_{16}$, —(CHR)$_r$NR$_{15}$C(=O)OR$_{16}$, —(CHR)$_r$NR$_{15}$C(=O)NR$_{15}$R$_{16}$, —(CHR)$_r$C(=O)R$_{15}$, —(CHR)$_r$C(=O)OR$_{15}$, —(CHR)$_r$OC(=O)R$_{15}$, —(CHR)$_r$SO$_3$H, —(CHR)$_r$C(=O)NR$_{15}$R$_{16}$, —(CHR)$_r$-cycloalkyl, —(CHR)$_r$-heterocyclo, —(CHR)$_r$-aryl, and —(CHR)$_r$-heteroaryl, wherein said cycloalkyl, heterocyclo, aryl, or heteroaryl is optionally substituted with OH and NH$_2$; each q is independently 1 or 2; each r is independently zero, 1, 2, or 3;

$R_{15}$ and $R_{16}$ are each independently selected from hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclo, and substituted heterocyclo;

each $R_{17}$ is independently selected from alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclo, and substituted heterocyclo.

7. The compound according to claim 6, wherein $R_6$ is $C_{3-7}$cycloalkyl optionally substituted by one to three groups, $T_4$, $T_5$, and/or $T_6$;

$T_4$, $T_5$ and $T_6$ are each independently selected from —(CH$_2$)$_r$OR$_{15}$, —(CH$_2$)$_r$NR$_{15}$R$_{16}$, —(CH$_2$)$_r$NR$_{15}$S(O)$_q$R$_{17}$, —(CH$_2$)$_r$NR$_{15}$S(O)$_q$NR$_{15}$R$_{16}$, —(CH$_2$)$_r$NR$_{15}$C(=O)R$_{16}$, —(CH$_2$)$_r$NR$_{15}$C(=O)OR$_{16}$, —(CH$_2$)$_r$NR$_{15}$C(=O)NR$_{15}$R$_{16}$, —(CH$_2$)$_r$C(=O)OR$_{15}$, each q is independently 1 or 2; and each r is independently zero, 1 or 2;

$R_{15}$ and $R_{16}$ are each independently selected from hydrogen, —(CR$_{20}$R$_{21}$)$_w$R$_{22}$, —(CR$_{20}$R$_{21}$)$_w$NR$_{18}$R$_{19}$, —(CR$_{20}$R$_{21}$)$_w$C(=O)R$_{18}$, —(CR$_{20}$R$_{21}$)$_w$C(=O)OR$_{18}$, —(CR$_{20}$R$_{21}$)$_w$OR$_{18}$, alkenyl, substituted alkenyl, alkynyl, substituted alkynyl cycloalkyl, substituted cycloalkyl, aryl, substituted aryl, heteroaryl, substituted heteroaryl, heterocyclo, substituted heterocyclo; each w is independently 1, 2, or 3;

$R_{17}$ is independently selected from —(CR$_{20}$R$_{21}$)$_w$R$_{22}$, —(CR$_{20}$R$_{21}$)$_w$NR$_{18}$R$_{19}$, —(CR$_{20}$R$_{21}$)$_w$C(=O)R$_{18}$, —(CR$_{20}$R$_{21}$)$_w$C(=O)OR$_{18}$, —(CR$_{20}$R$_{21}$)$_w$OR$_{18}$, alkenyl, substituted alkenyl, alkynyl, substituted alkynyl cycloalkyl, substituted cycloalkyl, aryl, substituted aryl, heteroaryl, substituted heteroaryl, heterocyclo, substituted heterocyclo; each w is independently 1, 2, or 3;

$R_{18}$ and $R_{19}$ are each independently selected from hydrogen, $C_{1-4}$alkyl, $C_{2-4}$alkenyl, and $C_{2-4}$alkynyl, each optionally substituted with $C_{1-6}$ alkyl —$(CH_2)_r$—$C_{3-6}$ cycloalkyl, F, Cl, Br, CN, $NO_2$, $NH_2$, $CO_2H$, —OC$(CH_3)_3$, —$(CH_2)_rOC_{1-5}$ alkyl, OH, SH; or $R_{18}$ and $R_{19}$ together with the nitrogen atom to which they are attached form an optionally substituted 5-, 6- or 7-membered monocyclic heterocyclo or heteroaryl;

$R_{20}$ and $R_{21}$ are each independently selected from hydrogen, F, Cl, Br, CN, $NO_2$, $NH_2$, $CO_2H$, —OC$(CH_3)_3$, —$(CH_2)_rOC_{1-5}$ alkyl, OH, SH, $C_{1-4}$alkyl, $C_{2-4}$alkenyl, $C_{2-4}$alkynyl, $C_{3-6}$cycloalkyl, aryl, heterocyclo, and heteroaryl; and $R_{22}$ is selected from hydrogen, $C_{1-4}$alkyl, $C_{2-4}$alkenyl, $C_{2-4}$alkynyl, halogen, hydroxy, cyano, nitro, $CF_3$, —O($C_{1-4}$alkyl), —NHCO$_2$($C_{1-4}$alkyl), —S($C_{1-4}$alkyl), —SO$_2$($C_{1-4}$alkyl), —C(=O)($C_{1-4}$alkylene)NH$_2$, —C(=O)($C_{1-4}$alkylene)NH(alkyl), NHC(=NH)NH$_2$, —C(=O)($C_{1-4}$alkylene)N($C_{1-4}$alkyl)$_2$, heterocyclo, substituted heterocyclo, heteroaryl, substituted heteroaryl, phenyl, and substituted phenyl.

8. The compound according to claim 6, wherein $R_6$ is $C_{1-4}$ alkyl optionally substituted by one to three groups, $T_4$, $T_5$, and/or $T_6$;

$T_4$, $T_5$ and $T_6$ are each independently selected from $OR_{15}$, $NR_{15}R_{16}$, $NR_{15}C(=O)R_{16}$, $NR_{15}C(=O)OR_{16}$, $NR_{15}C(=O)NR_{15}R_{16}$, —C(=O)OR$_{15}$, cycloalkyl, heterocyclo, aryl, and heteroaryl;

$R_{15}$ and $R_{16}$ are each independently selected from hydrogen, alkyl, cycloalkyl, substituted cycloalkyl, aryl, substituted aryl, heteroaryl, substituted heteroaryl, heterocyclo, and substituted heterocyclo;

$R_7$ is selected from hydrogen and $C_{1-3}$alkyl; or $R_6$ and $R_7$ together with the nitrogen atom to which they are attached form an optionally substituted 5-, 6- or 7-membered monocyclic heteroaryl or heterocyclo ring, or an optionally substituted 7- to 11-membered bicyclic heteroaryl or heterocyclo ring.

9. A compound having the formula I(a):

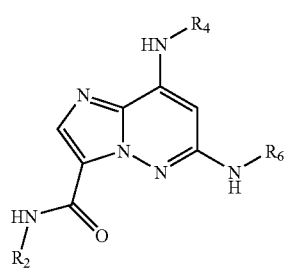

Ia or a pharmaceutically-acceptable salt thereof, wherein:

$R_2$ is selected from aryl, substituted aryl, C3-7cycloalkyl, substituted C3-7cycloalkyl, 5- or 6-membered heterocyclo and heteroaryl, and substituted 5- or 6-membered heterocyclo and heteroaryl optionally substituted with halogen, cyano, hydroxy, C1-4alkyl, substituted C1-4alkyl, alkenyl, substituted alkenyl, alkynyl, substituted alkynyl, $C_{1-4}$alkoxy, haloalkyl, $C_{3-7}$cycloalkyl, heterocyclo, heteroaryl, —$OR_{2a}$, —$NR_{2a}R_{2b}$, —$NR_{2a}C$(=O)$R_{2b}$, C(=O)$NR_{2a}R_{2b}$—C(=O)$OR_{2a}$, wherein $R_{2a}$ and $R_{2b}$ are each independently selected from hydrogen and $C_{1-4}$alkyl;

$R_4$ is selected from hydrogen, $C_{1-4}$alkyl, aryl, $C_{3-7}$cycloalkyl, heterocyclo, and heteroaryl, each group optionally substituted by one to three groups, $T_1$, $T_2$, and/or $T_3$;

$T_1$, $T_2$, and $T_3$ are each independently selected from halogen, alkyl, substituted alkyl, alkenyl, substituted alkenyl, alkynyl, substituted alkynyl, nitro, cyano, —$(CH_2)_r$ SO$_9$H, —$(CH_2)_rSR_9$, —$(CH_2)_rS(O)_pR_{11}$, —$(CH_2)_rS(O)_pNR_9R_{10}$, —$(CH_2)_rNR_9S(O)_pR_{11}$, —$(CH_2)_rOR_9$, —$(CH_2)_rCN$, —$(CH_2)_rNR_9R_{10}$, —$(CH_2)_rNR_9C(=O)R_{10}$, —$(CH_2)_rNR_9C(=O)NR_9R_{10}$, —$(CH_2)_rC(=O)OR_9$, —$(CH_2)_rC(=O)R_9$, —$(CH_2)_rOC(=O)R_9$, —$(CH_2)_rC(=O)NR_9R_{10}$, —$(CH_2)_r$-cycloalkyl, —$(CH_2)_r$-heterocyclo, —$(CH_2)_r$-aryl, and —$(CH_2)_r$-heteroaryl, wherein said cycloalkyl, heterocyclo, aryl, or heteroaryl is optionally substituted as valence allows from one to three groups, $R_{12}$, $R_{13}$ and/or $R_{14}$; or $T_1$ and $T_2$, located on adjacent ring atoms are taken together with the ring atoms to which they are attached to form a fused cycloalkyl, aryl, heteroaryl, or heterocyclo, wherein said cycloalkyl, aryl, heteroaryl, or heterocyclo is optionally substituted as valence allows from one to three groups, $R_{12}$, $R_{13}$ and/or $R_{14}$; each p is independently 1 or 2; each r is independently zero, 1, 2, or 3;

$R_9$ and $R_{10}$ are each independently selected from hydrogen, alkyl, substituted alkyl, alkenyl, substituted alkenyl, cycloalkyl, substituted cycloalkyl, aryl, substituted aryl, heteroaryl, substituted heteroaryl, heterocyclo, and substituted heterocyclo; or $R_9$ and $R_{10}$ together with the nitrogen atom to which they are attached form a heteroaryl or heterocyclo, wherein said heteroaryl or heterocyclo is optionally substituted as valence allows from one to three groups, $R_{12}$, $R_{13}$ and/or $R_{14}$;

each $R_{11}$ is independently selected from alkyl, substituted alkyl, alkenyl, substituted alkenyl, alkynyl, substituted alkynyl, cycloalkyl, aryl, heteroaryl, and heterocyclo;

$R_{12}$, $R_{13}$, and $R_{14}$ are each independently selected from $C_{1-4}$alkyl, substituted $C_{1-4}$alkyl, $C_{2-4}$alkenyl, substituted $C_{2-4}$alkenyl, halogen, hydroxy, cyano, nitro, $CF_3$, —O($C_{1-4}$alkyl), —OCF$_3$, —C(=O)H, —C(=O)($C_{1-4}$ alkyl), —CO$_2$H, —CO$_2$($C_{1-4}$alkyl), —NHCO$_2$($C_{1-4}$ alkyl), —S($C_{1-4}$alkyl), —NH$_2$, —NH($C_{1-4}$alkyl), —N($C_{1-4}$alkyl)$_2$, —N($C_{1-4}$alkyl)$_3^+$, —SO$_2$($C_{1-4}$alkyl), —C(=O)($C_{1-4}$alkylene)NH$_2$, —C(=O)($C_{1-4}$alkylene) NH(alkyl), —C(=O)($C_{1-4}$alkylene)N($C_{1-4}$alkyl)$_2$, and optionally substituted phenyl;

$R_6$ is selected from $C_{1-4}$alkyl, aryl, $C_{3-7}$cycloalkyl, 5- or 6-membered monocyclic heterocyclo and heteroaryl, wherein $R_6$ is optionally substituted by one to three groups, $T_4$, $T_5$, and/or $T_6$;

$T_4$, $T_5$ and $T_6$ are independently selected from halogen, alkyl, substituted alkyl, alkenyl, substituted alkenyl, alkynyl, substituted alkynyl, nitro, cyano, —$(CH_2)_r$ SR$_{15}$, —$(CH_2)_rS(O)_qR_{17}$, —$(CH_2)_rS(O)_qNR_{15}R_{16}$, —$(CH_2)_rNR_{15}S(O)_qR_{17}$, —$(CH_2)_rNR_{15}S(O)_q$ NR$_{15}R_{16}$, —$(CH_2)_rOR_{15}$, —$(CH_2)_rNR_{15}R_{16}$, —$(CH_2)_r$ NR$_{15}C(=O)R_{16}$, —$(CH_2)_rNR_{15}C(=O)OR_{16}$, —$(CH_2)_rNR_{15}C(=O)NR_{15}R_{16}$, —$(CH_2)_rNR_{15}C(=O)$ NR$_{15}C(=O)OR_{16}$, —$(CH_2)_rC(=O)R_{15}$, —$(CH_2)_rC(=O)OR_{15}$, —$(CH_2)_rOC(=O)R_{15}$, —$(CH_2)_rSO_3H$, —$(CH_2)_rC(=O)NR_{15}R_{16}$, —$(CH_2)_r$-cycloalkyl, —$(CH_2)_r$-heterocyclo, —$(CH_2)_r$-aryl, and —$(CH_2)_r$- heteroaryl, wherein said cycloalkyl, heterocyclo, aryl, or heteroaryl is optionally substituted with OH or $NH_2$; each q is independently 1 or 2; each r is independently zero, 1, 2, or 3;

$R_{15}$ and $R_{16}$ are each independently selected from hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclo, and substituted heterocyclo; or $R_{15}$ and $R_{16}$ together with the nitrogen atom to which they are attached form a optionally substituted 5-, 6- or 7-membered monocyclic heterocyclo or heteroaryl;

each $R_{17}$ is independently selected from alkyl, substituted alkyl, alkenyl, substituted alkenyl, alkynyl, substituted alkynyl, cycloalkyl, aryl, heteroaryl, and heterocyclo;

wherein said heterocyclo is a fully saturated or unsaturated, aromatic or nonaromatic cyclic group, which is a 4 to 7 membered monocyclic, 7 to 11 membered bicyclic, or 10 to 15 membered tricyclic ring system, which has at least one heteroatom selected from nitrogen, oxygen, and sulfur in at least one carbon atom-containing ring; said heterocyclo may be attached at any heteroatom or carbon atom;

said heteroaryl is a 4 to 7 membered monocyclic, 7 to 11 membered bicyclic, or 10 to 15 membered tricyclic aromatic ring system, which has at least one heteroatom selected from nitrogen, oxygen, and sulfur and at least one carbon atom-containing ring; and said heterocyclo and heteroaryl are substituted with one to four substituents selected from alkyl, substituted alkyl, alkenyl, substituted alkenyl, alkynyl, substituted alkynyl, arylalkyl, arylalkyloxy, halo, haloalkyl, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, substituted sulfonamido, ureido, nitro, cyano, carboxy, carboxyalkyl, carbamyl, substituted carbamyl, alkoxycarbonyl, aryl, substituted aryl, guanidino, and heterocyclyl, and substituted heterocyclyl.

10. The compound according to claim 9, wherein $R_2$ is selected from phenyl, pyrazolyl, pyridyl, pyridazinyl, pyrimidinyl and benzothiazolyl, wherein each $R_2$ is optionally substituted with F, Cl, Br, cyano, $C_{1-4}$alkyl, $C_{1-4}$alkoxy, haloalkyl, $C_{3-7}$cycloalkyl, heterocyclo, heteroaryl, $-OR_{2a}$, $-NR_{2a}R_{2b}$, $-NHC(=O)R_{2a}$, $-C(=O)NR_{2a}R_{2b}$ wherein $R_{2a}$ and $R_{2b}$ are each independently selected from hydrogen and $C_{1-4}$alkyl;

$R_4$ is selected from $C_{1-4}$alkyl, phenyl, $C_{3-6}$cycloalkyl, and 4-, 5-, or 6-membered monocyclic heteroaryl or heterocyclo, each optionally substituted by one to two groups, $T_1$, and/or $T_2$;

$T_1$ and $T_2$ are each independently selected from F, Cl, Br, $C_{1-4}$alkyl, haloalkyl, $-(CH_2)_rOR_9$, $-(CH_2)_rC(=O)R_9$, $-(CH_2)_rC(=O)OR_9$, $-(CH_2)_rC(=O)NR_9R_{10}$, $-(CH_2)_rNR_9R_{10}$, $-(CH_2)_rNR_9C(=O)R_{10}$, $-(CH_2)_rNR_9C(=O)NR_9R_{10}$, $-(CH_2)_rS(O)_2R_{11}$, $-(CH_2)_rS(C)_2NR_9R_{10}$, $-(CH_2)_rCN$, $-(CH_2)_r$cyclohexyl, $-(CH_2)_r$phenyl, $-(CH_2)_r$morpholinyl, $-(CH_2)_r$pyridyl, $-(CH_2)_r$pyrazolyl, $-(CH_2)_r$cyclopropyl, $-(CH_2)_r$pyrrolidinyl, $-(CH_2)_r$piperidinyl, $-(CH_2)_r$furyl, $-(CH_2)_r$imidazolyl, $-(CH_2)_r$pyrimidinyl, $-(CH_2)_r$piperazinyl, and $-(CH_2)_r$pyradizinyl, $-(CH_2)_r$imidazolyl, $-(CH_2)_r$pyrazolyl, $-(CH_2)_r$triazolyl, $-(CH_2)_r$tetrazolyl, $-(CH_2)_r$thiazolyl, each group optionally substituted as valence allows from one to three groups, $R_{12}$, $R_{13}$ and/or $R_{14}$; each r is independently zero, 1, 2, or 3;

$R_9$ and $R_{10}$ are each independently selected from hydrogen, $C_{1-4}$alkyl, halo$C_{1-4}$alkyl, $-(CH_2)_rOH$, $-(CH_2)_rN(alkyl)_2$, $C_{3-6}$cycloalkyl, phenyl, pyrrolidinyl, morpholinyl, and pyridyl, each ring group optionally substituted with $NH_2$, $C_{1-4}$alkyl and aryl;

each $R_{11}$ is selected from alkyl, substituted alkyl, alkenyl, substituted alkenyl, alkynyl, substituted alkynyl, cycloalkyl, aryl, heteroaryl, and heterocyclo;

$R_{12}$, $R_{13}$, and $R_{14}$, are each independently selected from hydroxy, $C_{1-4}$alkyl optionally substituted with hydroxy and halogen and phenyl;

$R_6$ is selected from $C_{1-4}$alkyl, $C_{3-7}$cycloalkyl, a 5- to 6-membered monocyclic heteroaryl or heterocyclo, each group optionally substituted by one to two groups, $T_4$ and $T_5$;

$T_4$ and $T_5$ are each independently selected from $C_{1-4}$alkyl, $-(CH_2)_rNR_{15}R_{16}$, $-(CH_2)_rNR_{15}S(O)_qR_{17}$, $-(CH_2)_rNR_{15}S(O)_qNR_{15}R_{16}$, $-(CH_2)_rOR_{15}$, $-(CH_2)_rNR_{15}C(=O)R_{16}$, $-(CH_2)_rNR_{15}C(=O)NR_{15}C(=O)R_{16}$, $-(CH_2)_rNR_{15}C(=O)OR_{16}$, $-(CH_2)_rNR_{15}C(=O)NR_{15}R_{16}$, $-(CH_2)_rC(=O)OR_{15}$, $-(CH_2)_r$-cycloalkyl, $-(CH_2)_r$-aryl, $-(CH_2)_r$-heteroaryl, and $-(CH_2)_r$-heterocyclo; each q is independently 1 or 2, each r is independently zero, 1, or 2;

$R_{15}$ and $R_{16}$ are each independently selected from hydrogen, cyano, $-(CR_{20}R_{21})_wR_{22}$, $-(CR_{20}R_{21})_wNR_{18}R_{19}$, $-(CR_{20}R_{21})_wNR_{18}C(=O)R_{19}$, $-(CR_{20}R_{21})_wC(=O)R_{18}$, $-(CR_{20}R_{21})_wC(=O)NR_{18}R_{19}$, $-(CR_{20}R_{21})_wC(=O)OR_{18}$, $-(CR_{20}R_{21})_wOR_{18}$, $-(CR_{20}R_{21})_wS(O)_2R_{22}$, alkenyl, substituted alkenyl, alkynyl, substituted alkynyl, cycloalkyl, substituted cycloalkyl, aryl, substituted aryl, heteroaryl, substituted heteroaryl, heterocyclo, substituted heterocyclo, wherein the substituent is selected from $C_{1-4}$alkyl, F, Cl, Br, $NH_2$, $NO_2$, CN, and OH; or $R_{15}$ and $R_{16}$ together with the nitrogen atom to which they are attached form a 5-, 6- or 7-membered monocyclic heterocyclo or heteroaryl optionally substituted with OH, $C_{1-4}$alkyl unsubstituted and substituted with $-O(C_{1-4}$alkyl); each w is independently 1, 2, or 3;

$R_{17}$ is independently selected from cyano, $-(CR_{20}R_{21})_wR_{22}$, $(CR_{20}R_{21})_wNR_{18}R_{19}$, $-(CR_{20}R_{21})_wNR_{18}C(=O)R_{19}$, $-(CR_{20}R_{21})_wC(=O)R_{18}R_{19}$, $-(CR_{20}R_{21})_wC(=O)OR_{18}$, $-(CR_{20}R_{21})_wOR_{18}$, each w is independently 1, 2, or 3; alkenyl, substituted alkenyl, alkynyl, substituted alkynyl, cycloalkyl, substituted cycloalkyl, aryl, substituted aryl, heteroaryl, substituted heteroaryl, heterocyclo, substituted heterocyclo, wherein the substituent is selected from $C_{1-4}$alkyl, F, Cl, Br, $NH_2$, $NO_2$, CN, and OH;

$R_{18}$ and $R_{19}$ are each independently selected from hydrogen, $C_{1-4}$alkyl, $C_{2-4}$alkenyl, and $C_{2-4}$alkynyl, each optionally substituted with $C_{1-6}$ alkyl $-(CH_2)_r-C_{3-6}$ cycloalkyl, F, Cl, Br, CN, $NO_2$, $NH_2$, $CO_2H$, $-OC(CH_3)_3$, $-(CH_2)_rOC_{1-6}$ alkyl, OH, SH; or $R_{18}$ and $R_{19}$ together with the nitrogen atom to which they are attached form an optionally substituted 5-, 6- or 7-membered monocyclic heterocyclo or heteroaryl;

$R_{20}$ and $R_{21}$ are each independently selected from hydrogen, F, Cl, Br, CN, $NO_2$, $NH_2$, $CO_2H$, —$OC(CH_3)_3$, —$(CH_2)_rOC_{1-5}$ alkyl, OH, SH, $C_{1-4}$alkyl, $C_{2-4}$alkenyl, $C_{2-4}$alkynyl, $C_{3-6}$cycloalkyl, aryl, heterocyclo, and heteroaryl;

$R_{22}$ is selected from hydrogen, $C_{1-4}$alkyl, $C_{2-4}$alkenyl, $C_{2-4}$alkynyl, halogen, hydroxy, cyano, nitro, $CF_3$, —$O(C_{1-4}$alkyl), —$NHCO_2(C_{1-4}$alkyl), —$S(C_{1-4}$alkyl), —$SO_2(C_{1-4}$alkyl), —$C(=O)(C_{1-4}$alkylene)$NH_2$, —$C(=O)(C_{1-4}$alkylene)NH(alkyl), NHC(=NH)$NH_2$, —$C(=O)(C_{1-4}$alkylene)$N(C_{1-4}$alkyl$)_2$, heterocyclo, heteroaryl, and phenyl, wherein said heterocyclo, heteroaryl, and phenyl are optionally substituted with $C_{1-4}$alkyl, halogen, and =O.

11. A pharmaceutical composition comprising one or more compounds of claim 1, and a pharmaceutically acceptable carrier.

12. The compound according to claim 1, selected from 6-((trans-4-aminocyclohexyl)amino)-8-((4-(cyclopropylcarbamoyl)phenyl)amino)-N-4-pyridinylimidazo[1,2-b]pyridazine-3-carboxamide 6-((trans-4-aminocyclohexyl)amino)-8-(3-azetidinylamino)-N-4-pyridinylimidazo[1,2-b]pyridazine-3-carboxamide 6-((trans-4-aminocyclohexyl)amino)-8-(cyclobutylamino)-N-4-pyridinylimidazo[1,2-b]pyridazine-3-carboxamide 6-((trans-4-aminocyclohexyl)amino)-8-(ethylamino)-N-(3-fluoro-4-pyridinyl)imidazo[1,2-b]pyridazine-3-carboxamide 6-((trans-4-((dimethylcarbamoyl)amino)cyclohexyl)amino)-N-(3-fluoro-4-pyridinyl)-8-(2-pyridinylamino)imidazo[1,2-b]pyridazine-3-carboxamide 6-((trans-4-(D-alanylamino)cyclohexyl)amino)-N-(3-fluoro-4-pyridinyl)-8-(2-pyridinylamino)imidazo[1,2-b]pyridazine-3-carboxamide Methyl trans-4-((8-(cyclopropylamino)-3-((3-fluoro-4-pyridinyl)carbamoyl)imidazo[1,2-b]pyridazin-6-yl)amino)cyclohexanecarboxylate Methyl (trans-4-((8-(cyclopropylamino)-3-((3-fluoro-4-pyridinyl)carbamoyl)imidazo[1,2-b]pyridazin-6-yl)amino)cyclohexyl)carbamate 8-(cyclopropylamino)-N-(3-fluoro-4-pyridinyl)-6-((trans-4-((isopropylcarbamoyl)amino)cyclohexyl)amino)imidazo[1,2-b]pyridazine-3-carboxamide 6-((trans-4-(L-alanylamino)cyclohexyl)amino)-8-(cyclopropylamino)-N-(3-fluoro-4-pyridinyl)imidazo[1,2-b]pyridazine-3-carboxamide 8-(cyclopropylamino)-6-((trans-4-((dimethylsulfamoyl)amino)cyclohexyl)amino)-N-(3-fluoro-4-pyridinyl)imidazo[1,2-b]pyridazine-3-carboxamide Methyl N-(trans-4-((8-(cyclopropylamino)-3-((2-fluoro-4-pyridinylcarbamoyl)imidazo[1,2-b]pyridazin-6-yl)amino)cyclohexyl)glycinate 8-(cyclopropylamino)-N-(2-fluoro-4-pyridinyl)-6-((trans-4-hydroxycyclohexyl)amino)imidazo[1,2-b]pyridazine-3-carboxamide 8-(cyclopropylamino)-6-((trans-4-(3-pyridin-3-ylureido)cyclohexylamino)-N-(pyrimidin-4-yl)imidazo[1,2-b]pyridazine-3-carboxamide 6-((trans-4-(D-alanylamino)cyclohexyl)amino)-8-(cyclopropylamino)-N-(6-oxo-1,6-dihydro-4-pyrimidinyl)imidazo[1,2-b]pyridazine-3-carboxamide 6-((trans-4-aminocyclohexyl)amino)-N-(3-fluoro-4-pyridinyl)-8-((5-fluoro-2-pyridinyl)amino)imidazo[1,2-b]pyridazine-3-carboxamide 6-((trans-4-aminocyclohexyl)amino)-N-(3-fluoro-4-pyridinyl)-8-((6-(4-methyl-1-piperazinyl)-2-pyridinyl)amino)imidazo[1,2-b]pyridazine-3-carboxamide 6-((trans-4-aminocyclohexyl)amino)-N-(3-fluoro-4-pyridinyl)-8-((1-methyl-1H-pyrazol-3-yl)amino)imidazo[1,2-b]pyridazine-3-carboxamide 8-acetamido-6-((trans-4-aminocyclohexyl)amino)-N-(3-fluoro-4-pyridinyl)imidazo[1,2-b]pyridazine-3-carboxamide 6-((trans-4-aminocyclohexyl)amino)-N-(3-fluoro-4-pyridinyl)-8-((methylsulfonyl)amino)imidazo[1,2-b]pyridazine-3-carboxamide 6-((trans)-4-aminocyclohexylamino)-8-(5-cyanopyridin-2-ylamino)-N-(3-fluoropyridin-4-yl)imidazo[1,2-b]pyridazine-3-carboxamide 6-(6-((trans)-4-aminocyclohexylamino)-3-(3-fluoropyridin-4-ylcarbamoyl)imidazo[1,2-b]pyridazin-8-ylamino)nicotinic acid 6-((trans)-4-aminocyclohexylamino)-N-(2-chloropyridin-4-yl)-8-(cyclopropylamino)imidazo[1,2-b]pyridazine-3-carboxamide 6-((trans)-4-aminocyclohexylamino)-8-((5-methyl-2-pyridinyhamino)-N-4-pyridinylimidazo[1,2-b]pyridazine-3-carboxamide 8-(cyclopropylamino)-N-(2-fluoropyridin-4-yl)-6-((trans)-4-(phenylsulfonamido)cyclohexylamino)imidazo[1,2-b]pyridazine-3-carboxamide Methyl 2-((trans)-4-(8-(cyclopropylamino)-3-(6-hydroxypyrimidin-4-ylcarbamoyl)imidazo[1,2-b]pyridazin-6-ylamino)cyclohexylamino)acetate 8-(cyclopropylamino)-N-(2-fluoropyridin-4-yl)-6-((trans)-4-morpholinocyclohexylamino)imidazo[1,2-b]pyridazine-3-carboxamide 8-(cyclopropylamino)-N-(2-fluoropyridin-4-yl)-6-((trans)-4-(2-hydroxyethylamino)cyclohexylamino)imidazo[1,2-b]pyridazine-3-carboxamide 6-((trans)-4-(bis(2-hydroxyethyl)amino)cyclohexylamino)-8-(cyclopropylamino)-N-(2-fluoropyridin-4-yl)imidazo[1,2-b]pyridazine-3-carboxamide 8-(cyclopropylamino)-6-((trans)-4-(ethylamino)cyclohexylamino)-N-(2-fluoropyridin-4-yl)imidazo[1,2-b]pyridazine-3-carboxamide 8-(cyclopropylamino)-6-((trans)-4-(diethylamino)cyclohexylamino)-N-(2-fluoropyridin-4-yl)imidazo[1,2-b]pyridazine-3-carboxamide N-(2-chloropyridin-4-yl)-8-(cyclopropylamino)-6-((trans)-4-(2-hydroxy-2-methylpropylamino)cyclohexylamino)imidazo[1,2-b]pyridazine-3-carboxamide 6-((trans)-4-aminocyclohexylamino)-8-(cyclopropylamino)-N-(6-hydroxypyrimidin-4-yl)imidazo[1,2-b]pyridazine-3-carboxamide Preparation of 8-(cyclopropylamino)-N-(3-fluoropyridin-4-yl)-6-((trans)-4-(piperazine-1-carboxamido)cyclohexylamino)imidazo[1,2-b]pyridazine-3-carboxamide Preparation of 2-(dimethylamino)ethyl (trans)-4-(8-(cyclopropylamino)-3-(3-fluoropyridin-4-ylcarbamoyl)imidazo[1,2-b]pyridazin-6-ylamino)cyclohexylcarbamate N-(2-chloropyridin-4-yl)-6-((trans)-4-(2-cyanoacetamido)cyclohexylamino)-8-(cyclopropylamino)imidazo[1,2-b]pyridazine-3-carboxamide 6-((trans-4-aminocyclohexylamino)-7-methyl-8-(5-methylpyridin-2-ylamino)-N-(pyridin-4-yl)imidazo[1,2-b]pyridazine-3-carboxamide 6-((trans-4-aminocyclohexyl)amino)-8-anilino-7-methyl-N-4-pyridinylimidazo[1,2-b]pyridazine-3-carboxamide (S)-6-(1-benzylpiperidin-3-ylamino)-8-(pyridin-2-ylamino)-N-(pyridin-4-yl)imidazo[1,2-b]pyridazine-3-carboxamide (S)-6-(piperidin-3-ylamino)-8-(pyridin-2-ylamino)-N-(pyridin-4-yl)imidazo[1,2-b]pyridazine-3-carboxamide (S)-6-(piperidin-3-ylamino)-8-(pyridin-2-ylamino)-N-(pyridin-4-yl)imidazo[1,2-b]pyridazine-3-carboxamide 8-((6-amino-4-chloro-2-pyridinyl)amino)-6-((trans-4-aminocyclohexyl)amino)-N-(3-fluoro-4-pyridinyl)imidazo[1,2-b]pyridazine-3-carboxamide 8-((6-acetamido-4-chloro-2-pyridinyl)amino)-6-((trans-4-aminocyclohexyl)amino)-N-(3-fluoro-4-pyridinyl)imidazo[1,2-b]pyridazine-3-carboxamide 6-((trans-4-aminocyclohexyl)amino)-N-(3-fluoro-4-pyridinyl)-8-(4-pyrimidinylamino)imidazo[1,2-b]pyridazine-3-carboxamide 6-((trans-4-aminocyclohexyl)amino)-N-(3-fluoro-4-pyridinyl)-8-(3-isoxazolylamino)imidazo[1,2-b]pyridazine-3-carboxamide N-(3-fluoro-4-pyridinyl)-6-((trans-4-hydroxycyclohexyl)amino)-8-(3-isoxazolylamino)imidazo[1,2-b]pyridazine-3-carboxamide N-(3-fluoro-4-pyridinyl)-6-((trans-4-hydroxycyclohexyl)amino)-8-((6-((trans-4-hydroxycyclohexyl)amino)-2-pyridinyl)amino)imidazo[1,2-b]pyridazine-3-carboxamide 6-((trans-4-aminocyclohexyl)amino)-N-(3-fluoro-4-pyridinyl)-8-((6-((trans-4-hydroxycyclohexyl)amino)-2-pyridinyl)amino)imidazo[1,2-b]pyridazine-3-carboxamide 6-((trans-4-aminocyclohexyl)amino)-N-(3-fluoro-4-pyridinyl)-8-((6-((2-hydroxyethyl)amino)-2-pyridinyl)amino)imidazo[1,2-b]pyridazine-3-carboxamide 6-((trans-4-aminocyclohexyl)amino)-N-(3-fluoro-4-pyridinyl)-8-(3-isopropyl-1H-pyrazol-3-yl)amino)imidazo[1,2-b]pyridazine-3-carboxamide N-(3-fluoro-4-pyridinyl)-6-((trans-4-hydroxycyclohexyl)amino)-8-(3-isopropyl-1H-pyrazol-3-yl)amino)imidazo[1,2-b]pyridazine-3-carboxamide 6-((trans-4-aminocyclohexyl)amino)-N-(3-fluoro-4-pyridinyl)-8-(3-(2-hydroxyethyl)-1H-pyrazol-3-yl)amino)imidazo[1,2-b]pyridazine-3-carboxamide 6-((trans-4-aminocyclohexyl)amino)-N-(3-fluoro-4-pyridinyl)-8-((5-methyl-3-isoxazolyl)amino)imidazo[1,2-b]pyridazine-3-carboxamide 6-((trans-4-((cyanoacetyl)amino)cyclohexyl)amino)-N-(3-fluoro-4-pyridinyl)-8-(3-isopropyl-1H-pyrazol-3-yl)amino)imidazo[1,2-b]pyridazine-3-carboxamide 6-((trans)-4-aminocyclohexylamino)-8-(5-cyanopyridin-2-ylamino)-N-(3-fluoropyridin-4-yl)imidazo[1,2-b]pyridazine-3-carboxamide 6-(6-(((trans)-4-aminocyclohexylamino)-3-(3-fluoropyridin-4-ylcarbamoyl)imidazo[1,2-b]pyridazin-8-ylamino)nicotinic acid 6-((trans)-4-aminocyclohexylamino)-N-(4-fluorophenyl)-8-(phenylamino)imidazo[1,2-b]pyridazine-3-carboxamide 6-((trans)-2-aminocyclohexylamino)-N-(2-fluorophenyl)-8-(phenylamino)imidazo[1,2-b]pyridazine-3-carboxamide 6-((trans)-4-aminocyclohexylamino)-8-(phenylamino)-N-(pyridin-3-yl)imidazo[1,2-b]pyridazine-3-carboxamide 6-((trans)-4-aminocyclohexylamino)-N-phenyl-8-(phenylamino)imidazo[1,2-b]pyridazine-3-carboxamide 6-((trans-4-acetamidocyclohexyl)amino)-8-(cyclobutylamino)-N-4-pyridinylimidazo[1,2-b]pyridazine-3-carboxamide 8-(cyclobutylamino)-N-(3-fluoro-4-pyridinyl)-6-((trans-4-hydroxycyclohexyl)amino)imidazo[1,2-b]pyridazine-3-carboxamide 8-(cyclobutylamino)-6-(cyclohexylamino)-N-(3-fluoro-4-pyridinyl)imidazo[1,2-b]pyridazine-3-carboxamide 6-((trans-4-aminocyclohexyl)amino)-N-(2-fluoro-4-pyridinyl)-8-(2-pyridinylamino)imidazo[1,2-b]pyridazine-3-carboxamide 6-((trans-4-(L-alanylamino)cyclohexyl)amino)-N-(2-fluoro-4-pyridinyl)-8-(2-pyridinylamino)imidazo[1,2-b]pyridazine-3-carboxamide 6-((trans-4-(D-alanylamino)cyclohexyl)amino)-N-(2-fluoro-4-pyridinyl)-8-(2-pyridinylamino)imidazo[1,2-b]pyridazine-3-carboxamide 6-((trans-4-aminocyclohexyl)amino)-N-(3-fluoro-4-pyridinyl)-8-(2-pyridinylamino)imidazo[1,2-b]pyridazine-3-carboxamide N-(3-fluoro-4-pyridinyl)-6-((trans-4-(glycylamino)cyclohexyl)amino)-8-(2-pyridinylamino)imidazo[1,2-b]pyridazine-3-carboxamide Methyl N-(trans-4-((3-((3-fluoro-4-pyridinyl)carbamoyl)-8-(2-pyridinylamino)imidazo[1,2-b]pyridazin-6-yl)amino)cyclohexyl)glycinate N-(2-chloro-4-pyridinyl)-8-(cyclopropylamino)-6-((trans-4-hydroxycyclohexyl)amino)imidazo[1,2-b]pyridazine-3-carboxamide Methyl N-(trans-4-((3-((2-fluoro-4-pyridinylcarbamoyl)-8-(2-pyridinylamino)imidazo[1,2-b]pyridazin-6-yl)amino)cyclohexyl 2-methoxyethyl (trans-4-((8-(cyclopropylamino)-3-((6-oxo-1,6-dihydro-4-pyrimidinyl)carbamoyl)imidazo[1,2-b]pyridazin-6-yl)amino)cyclohexyl)carbamate 6-((trans-4-aminocyclohexyhamino)-N-(2-chloro-4-pyridinyl)-8-(2-pyridinylamino)imidazo[1,2-b]pyridazine-3-carboxamide N-(2-chloro-4-pyridinyl)-6-((trans-4-hydroxycyclohexyl)amino)-8-(2-pyridinylamino)imidazo[1,2-b]pyridazine-3-carboxamide N-(2-fluoro-4-pyridinyl)-6-((trans-4-hydroxycyclohexyl)amino)-8-(2-pyridinylamino)imidazo[1,2-b]pyridazine-3-carboxamide N-(2-fluoro-4-pyridinyl)-6-((trans-4-hydroxycyclohexyl)amino)-8-((5-methyl-2-pyridinyl)amino)imidazo[1,2-b]pyridazine-3-carboxamide N-(2-chloro-4-pyridinyl)-6-((trans-4-hydroxycyclohexyl)amino)-8-((5-methyl-2-pyridinyl)amino)imidazo[1,2-b]pyridazine-3-carboxamide 6-((trans-4-aminocyclohexyl)amino)-N-(2-chloro-4-pyridinyl)-8-((5-methyl-2-pyridinyl)amino)imidazo[1,2-b]pyridazine-3-carboxamide 6-((trans-4-aminocyclohexyl)amino)-N-(2-fluoro-4-pyridinyl)-8-((5-methyl-2-pyridinyl)amino)imidazo[1,2-b]pyridazine-3-carboxamide 6-((trans-4-aminocyclohexyl)amino)-N-(2-cyano-4-pyridinyl)-8-(cyclopropylamino)imidazo[1,2-b]pyridazine-3-carboxamide 6-((trans-4-acetamidocyclohexyl)amino)-8-(cyclopropylamino)-N-4-pyridinylimidazo[1,2-b]pyridazine-3-carboxamide 6-((4-acetamidocyclohexyl)amino)-8-((6-methyl-2-pyridinyl)amino)-N-4-pyridinylimidazo[1,2-b]pyridazine-3-carboxamide 6-((trans-4-acetamidocyclohexyl)amino)-8-((4-methyl-2-pyridinyl)amino)-N-4-pyridinylimidazo[1,2-b]pyridazine-3-carboxamide 8-(ethylamino)-6-((trans-4-(((4-fluorophenyl)carbamoyl)amino)cyclohexyl)amino)-N-(3-fluoro-4-pyridinyl)imidazo[1,2-b]pyridazine-3-carboxamide N-(3-acetamidophenyl)-6-((trans)-4-aminocyclohexylamino)-8-(cyclopropylamino)imidazo[1,2-b]pyridazine-3-carboxamide 6-((trans)-4-(2-aminoacetamido)cyclohexylamino)-8-(ethylamino)-N-(3-fluoropyridin-4-yl)imidazo[1,2-b]pyridazine-3-carboxamide 6-((trans-4-aminocyclohexyl)amino)-8-anilino-N-(2-methyl-4-pyridinyl)imidazo[1,2-b]pyridazine-3-carboxamide 6-((trans-4-aminocyclohexyl)amino)-8-((1,5-dimethyl-1H-pyrazol-3-yl)amino)-N-(3-fluoro-4-pyridinyl)imidazo[1,2-b]pyridazine-3-carboxamide N~1~-(trans-4-((8-(cyclopropylamino)-3-((3-fluoro-4-pyridinyl)carbamoyl)imidazo[1,2-b]pyridazin-6-yl)amino)cyclohexyl)-L-aspartamide 6-((trans-4-(((2S)-2-amino-2-phenylacetyl)amino)cyclohexyl)amino)-8-(cyclopropylamino)-N-(3-fluoro-4-pyridinyl)imidazo[1,2-b]pyridazine-3-carboxamide 6-((trans-4-(benzoylamino)cyclohexyl)amino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-((trans-4-((methoxyacetyl)amino)cyclohexyl)amino)imidazo[1,2-b]pyridazine-3-carboxamide 8-(cyclopropylamino)-6-((trans-4-((cyclopropylcarbonyl)amino)cyclohexyl) amino)-N-(3-fluoro-4-pyridinyl)imidazo[1,2-b]pyridazine-3-carboxamide 6-((trans-4-((cyanoacetyl)amino)cyclohexyl)amino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-((trans-4-((2-pyrazinylcarbonyl)amino)cyclohexyl)amino)imidazo[1,2-b]pyridazine-3-carboxamide 8-(cyclopropylamino)-N-(3-fluoro-4-pyridinyl)-6-((trans-4-((2-pyridinylcarbonyl)amino)cyclohexyl)amino)imidazo[1,2-b]pyridazine-3-carboxamide 8-(cyclopropylamino)-N-(3-fluoro-4-pyridinyl)-6-((trans-4-((3-pyridinylcarbonyl)amino)cyclohexyl)amino)imidazo[1,2-b]pyridazine-3-carboxamide 8-(cyclopropylamino)-N-(3-fluoro-4-pyridinyl)-6-((trans-4-((2-pyridinylacetyl)amino)cyclohexyl)amino)imidazo[1,2-b]pyridazine-3-carboxamide 6-((trans-4-((4-aminobutanoyl)amino)cyclohexyl)amino)-8-(cyclopropylamino)-N-(3-fluoro-4-pyridinyl)imidazo[1,2-b]pyridazine-3-carboxamide 6-((trans-4-(beta-alanylamino)cyclohexyl)amino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-((trans-4-(L-prolylamino)cyclohexyl)amino)imidazo[1,2-b]pyridazine-3-carboxamide 8-(cyclopropylamino)-N-(3-fluoro-4-pyridinyl)-6-((trans-4-((N-methylglycyl)amino)cyclohexyl)amino)imidazo[1,2-b]pyridazine-3-carboxamide 8-(cyclopropylamino)-N-(3-fluoro-4-pyridinyl)-6-((trans-4-(D-leucylamino)cyclohexyl)amino)imidazo[1,2-b]pyridazine-3-carboxamide 8-(cyclopropylamino)-N-(3-fluoro-4-pyridinyl)-6-((trans-4-((1,2,3-thiadiazol-4-ylcarbonyl)amino)cyclohexyl)amino)imidazo[1,2-b]pyridazine-3-carboxamide 6-((trans-4-(((2R)-2-amino-2-phenylacetyl)amino)cyclohexyl)amino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-((trans-4-(D-prolylamino)cyclohexyl)amino)imidazo[1,2-b]pyridazine-3-carboxamide N~1~-(trans-4-((8-(cyclopropylamino)-3-((3-fluoro-4-pyridinyl)carbamoyl)imidazo[1,2-b]pyridazin-6-yl)amino)cyclohexyl)-D-aspartamide 8-(cyclopropylamino)-N-(3-fluoro-4-pyridinyl)-6-((trans-4-(L-leucylamino)cyclohexyl)amino)imidazo[1,2]pyridazine-3-carboxamide 8-(cyclopropylamino)-N-(3-fluoro-4-pyridinyl)-6-((trans-4-((3-(3-pyridinyl)-D-alanyhamino)cyclohexyl)amino)imidazo[1,2-b]pyridazine-3-carboxamide N-(trans-4-((8-(cyclopropylamino)-3-((3-fluoro-4-pyridinyl)carbamoyl)imidazo[1,2-b]pyridazin-6-yl)amino)cyclohexyl)-L-alpha-asparagine 8-(cyclopropylamino)-N-(3-fluoro-4-pyridinyl)-6-((trans-4-(L-serylamino)cyclohexyl)amino)imidazo[1,2-b]pyridazine-3-carboxamide 8-(cyclopropylamino)-N-(3-fluoro-4-pyridinyl)-6-((trans-4-((3-(1,3-thiazol-4-yl)-D-alanyhamino)cyclohexyl)amino)imidazo[1,2-b]pyridazine-3-carboxamide 8-(cyclopropylamino)-N-(3-fluoro-4-pyridinyl)-6-((trans-4-((3-(3-pyridinyl)-L-alanyhamino)cyclohexyl)amino)imidazo[1,2-b]pyridazine-3-carboxamide 8-(cyclopropylamino)-N-(3-fluoro-4-pyridinyl)-6-((trans-4-(L-threonylamino)cyclohexyl)amino)imidazo[1,2-b]pyridazine-3-carboxamide 8-(cyclopropylamino)-N-(3-fluoro-4-pyridinyl)-6-((trans-4-(D-ornithylamino)cyclohexyl)amino)imidazo[1,2-b]pyridazine-3-carboxamide 8-(cyclopropylamino)-N-(3-fluoro-4-pyridinyl)-6-((trans-4-(L-ornithylamino)cyclohexyl)amino)imidazo[1,2-b]pyridazine-3-carboxamide 8-(cyclopropylamino)-N-(3-fluoro-4-pyridinyl)-6-((trans-4-((3-(2-pyridinyl)-L-alanyl)amino)cyclohexyl)amino)imidazo[1,2-b]pyridazine-3-carboxamide 6-((trans-4-(L-arginylamino)cyclohexyl)amino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-((trans-4-(D-threonylamino)cyclohexyl)amino)imidazo[1,2-b]pyridazine-3-carboxamide 8-(cyclopropylamino)-N-(3-fluoro-4-pyridinyl)-6-((trans-4-(((2R)-2-piperidinylcarbonyl)amino)cyclohexyl)amino)imidazo[1,2-b]pyridazine-3-carboxamide 8-(cyclopropylamino)-N-(3-fluoro-4-pyridinyl)-6-((trans-4-((3-piperidinylcarbonyl)amino)cyclohexyl)amino)imidazo[1,2-b]pyridazine-3-carboxamide 6-((trans-4-(((((1R,2S)-2-aminocyclopentyl) carbonyl)amino)cyclohexyl)amino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-((trans-4-(D-prolylamino)cyclohexyl)amino)imidazo[1,2-b]pyridazine-3-carboxamide 8-(cyclopropylamino)-N-(3-fluoro-4-pyridinyl)-6-((trans-4-((3-(1,3-thiazol-4-yl)-L-alanyl)amino)cyclohexyl)amino)imidazo[1,2-b]pyridazine-3-carboxamide 8-(cyclopropylamino)-N-(3-fluoro-4-pyridinyl)-6-((trans-4-((3-(2-pyridinyl)-D-alanyl)amino)cyclohexyl)amino)imidazo[1,2-b]pyridazine-3-carboxamide 8-(cyclopropylamino)-N-(3-fluoro-4-pyridinyl)-6-((trans-4-(glycylamino)cyclohexyl)amino)imidazo[1,2-b]pyridazine-3-carboxamide 6-((trans-4-(D-alanylamino)cyclohexyl)amino)-8-(cyclopropylamino)-N-(3-fluoro-4-pyridinyl)imidazo[1,2-b]pyridazine-3-carboxamide
8-(cyclopropylamino)-N-(3-fluoro-4-pyridinyl)-6-((trans-4-(isobutyrylamino)cyclohexyl)amino)imidazo[1,2-b]pyridazine-3-carboxamide
8-(cyclopropylamino)-6-((trans-4-((N,N-dimethylglycyl)amino)cyclohexyl)amino)-N-(3-fluoro-4-pyridinyl)imidazo[1,2-b]pyridazine-3-carboxamide
8-(cyclopropylamino)-N-(3-fluoro-4-pyridinyl)-6-((trans-4-(glycoloylamino)cyclohexyl)amino)imidazo[1,2-b]pyridazine-3-carboxamide
6-((trans-4-((4-chlorobenzoyl)amino)cyclohexyl)amino)-8-(cyclopropylamino)-N-(3-fluoro-4-pyridinyl)imidazo[1,2-b]pyridazine-3-carboxamide
6-((trans-4-((3-chlorobenzoyl)amino)cyclohexyl)amino)-8-(cyclopropylamino)-N-(3-fluoro-4-pyridinyl)imidazo[1,2-b]pyridazine-3-carboxamide
6-((trans-4-((2-chlorobenzoyl)amino)cyclohexyl)amino)-8-(cyclopropylamino)-N-(3-fluoro-4-pyridinyl)imidazo[1,2-b]pyridazine-3-carboxamide
6-((trans-4-(D-alanylamino)cyclohexyl)amino)-8-(cyclopropylamino)-N-(2-fluoro-4-pyridinyl)imidazo[1,2-b]pyridazine-3-carboxamide
8-(cyclopropylamino)-N-(2-fluoro-4-pyridinyl)-6-((trans-4-(D-serylamino)cyclohexyl)amino)imidazo[1,2-b]pyridazine-3-carboxamide
6-((trans-4-(L-alanylamino)cyclohexyl)amino)-8-(cyclopropylamino)-N-(2-fluoro-4-pyridinyl)imidazo[1,2-b]pyridazine-3-carboxamide
8-(cyclopropylamino)-N-(2-fluoro-4-pyridinyl)-6-((trans-4-(glycoloylamino)cyclohexyl)amino)imidazo[1,2-b]pyridazine-3-carboxamide
8-(cyclopropylamino)-6-((trans-4-((cyclopropylcarbonyl)amino)cyclohexyl)amino)-N-(2-fluoro-4-pyridinyl)imidazo[1,2-b]pyridazine-3-carboxamide
8-(cyclopropylamino)-N-(2-fluoro-4-pyridinyl)-6-((trans-4-(isobutyrylamino)cyclohexyl)amino)imidazo[1,2-b]pyridazine-3-carboxamide
6-((trans-4-((cyanoacetyl)amino)cyclohexyl)amino)-8-(cyclopropylamino)-N-(2-fluoro-4-pyridinyl)imidazo[1,2-b]pyridazine-3-carboxamide
8-(cyclopropylamino)-N-(2-fluoro-4-pyridinyl)-6-((trans-4-(glycylamino)cyclohexyl)amino)imidazo[1,2-b]pyridazine-3-carboxamide
8-(cyclopropylamino)-N-(2-fluoro-4-pyridinyl)-6-((trans-4-((1,2,3-thiadiazol-4-ylcarbonyl)amino)cyclohexyl)amino)imidazo[1,2-b]pyridazine-3-carboxamide
8-(cyclopropylamino)-6-((trans-4-((N,N-dimethylglycyl)amino)cyclohexyl)amino)-N-(2-fluoro-4-pyridinyl)imidazo[1,2-b]pyridazine-3-carboxamide
8-(cyclopropylamino)-N-(2-fluoro-4-pyridinyl)-6-((trans-4-((N-methylglycyl)amino)cyclohexyl)amino)imidazo[1,2-b]pyridazine-3-carboxamide
6-((trans-4-((4-aminobutanoyl)amino)cyclohexyl)amino)-8-(cyclopropylamino)-N-(2-fluoro-4-pyridinyl)imidazo[1,2-b]pyridazine-3-carboxamide
8-(cyclopropylamino)-N-(2-fluoro-4-pyridinyl)-6-((trans-4-((3-piperidinylcarbonyl)amino)cyclohexyl)amino)imidazo[1,2-b]pyridazine-3-carboxamide
8-(cyclopropylamino)-N-(2-fluoro-4-pyridinyl)-6-((trans-4-(L-valylamino)cyclohexyl)amino)imidazo[1,2-b]pyridazine-3-carboxamide
6-((trans-4-(((2R)-3-amino-2-methylpropanoyl)amino)cyclohexyl)amino)-N-(2-chloro-4-pyridinyl)-8-(cyclopropylamino)imidazo[1,2-b]pyridazine-3-carboxamide
6-((trans-4-(((2S)-3-amino-2-methylpropanoyl)amino)cyclohexyl)amino)-N-(2-chloro-4-pyridinyl)-8-(cyclopropylamino)imidazo[1,2-b]pyridazine-3-carboxamide
6-((trans-4-(((3S)-3-aminobutanoyl)amino)cyclohexyl)amino)-N-(2-chloro-4-pyridinyl)-8-(cyclopropylamino)imidazo[1,2-b]pyridazine-3-carboxamide
6-((trans-4-(((((1S,3R)-3-aminocyclopentyl)carbonyl)amino)cyclohexyl)amino)-N-(2-chloro-4-pyridinyl)-8-(cyclopropylamino)imidazo[1,2-b]pyridazine-3-carboxamide
N-(2-chloro-4-pyridinyl)-8-(cyclopropylamino)-6-((trans-4-((3-(1,3-thiazol-4-yl)-L-alanyl)amino)cyclohexyl)amino)imidazo[1,2-b]pyridazine-3-carboxamide
6-((trans-4-((3-amino-3-cyclopropylpropanoyl)amino)cyclohexyl) amino)-N-(2-chloro-4-pyridinyl)-8-(cyclopropylamino)imidazo[1,2-b]pyridazine-3-carboxamide
N-(2-chloro-4-pyridinyl)-8-(cyclopropylamino)-6-((trans-4-(((3R)-3-pyrrolidinylacetyl)amino)cyclohexyl)amino)imidazo[1,2-b]pyridazine-3-carboxamide
N-(2-chloro-4-pyridinyl)-8-(cyclopropylamino)-6-((trans-4-((N-methyl-beta-alanyl)amino)cyclohexyl)amino) imidazo[1,2-b]pyridazine-3-carboxamide
N-(2-chloro-4-pyridinyl)-8-(cyclopropylamino)-6-((trans-4-((N-methyl-D-alanyl)amino)cyclohexyl)amino) imidazo[1,2-b]pyridazine-3-carboxamide
6-((trans-4-(((2S)-2-amino-4-(methylsulfonyl) butanoyl)amino)cyclohexyl)amino)-N-(2-chloro-4-pyridinyl)-8-(cyclopropylamino)imidazo[1,2-b]pyridazine-3-carboxamide
6-((trans-4-((3-azetidinylcarbonyl)amino)cyclohexyl)amino)-N-(2-chloro-4-pyridinyl)-8-(cyclopropylamino)imidazo[1,2-b]pyridazine-3-carboxamide
N-(2-chloro-4-pyridinyl)-8-(cyclopropylamino)-6-((trans-4-(((3S)-3-pyrrolidinylacetyl)amino)cyclohexyl)amino)imidazo[1,2-b]pyridazine-3-carboxamide
N-(2-chloro-4-pyridinyl)-8-(cyclopropylamino)-6-((trans-4-((4-piperidinylcarbonyl)amino)cyclohexyl)amino)imidazo[1,2-b]pyridazine-3-carboxamide
N-(2-chloro-4-pyridinyl)-8-(cyclopropylamino)-6-((trans-4-((N,2-dimethylalanyl)amino)cyclohexyl)amino) imidazo[1,2-b]pyridazine-3-carboxamide
N-(2-chloro-4-pyridinyl)-8-(cyclopropylamino)-6-((trans-4-(((2S)-2-pyrrolidinylacetyl)amino)cyclohexyl)amino)imidazo[1,2-b]pyridazine-3-carboxamide
N-(2-chloro-4-pyridinyl)-8-(cyclopropylamino)-6-((trans-4-((cyclopropylcarbonyl)amino)cyclohexyl)amino)imidazo[1,2-b]pyridazine-3-carboxamide
N-(2-chloro-4-pyridinyl)-6-((trans-4-((cyclobutylcarbonyl)amino)cyclohexyl)amino)-8-(cyclopropylamino)imidazo[1,2-b]pyridazine-3-carboxamide
N-(2-chloro-4-pyridinyl)-8-(cyclopropylamino)-6-((trans-4-(glycylamino)cyclohexyl)amino)imidazo[1,2-b]pyridazine-3-carboxamide
N-(2-chloro-4-pyridinyl)-8-(cyclopropylamino)-6-((trans-4-((3-methylbutanoyl)amino)cyclohexyl)amino)imidazo[1,2-b]pyridazine-3-carboxamide
N-(2-chloro-4-pyridinyl)-8-(cyclopropylamino)-6-((trans-4-(propionylamino)cyclohexyl)amino)imidazo[1,2-b]pyridazine-3-carboxamide
N-(2-chloro-4-pyridinyl)-8-(cyclopropylamino)-6-((trans-4-((N,N-dimethylglycyl)amino)cyclohexyl)amino) imidazo[1,2-b]pyridazine-3-carboxamide
N-(2-chloro-4-pyridinyl)-8-(cyclopropylamino)-6-((trans-4-((methoxyacetyl)amino)cyclohexyl)amino) imidazo[1,2-b]pyridazine-3-carboxamide N-(2-chloro-4-pyridinyl)-8-(cyclopropylamino)-6-((trans-4-(propioloylamino)cyclohexyl)amino)imidazo[1,2-b]pyridazine-3-carboxamide N-(2-chloro-4-pyridinyl)-8-(cyclopropylamino)-6-((trans-4-(4-pentynoylamino)cyclohexyl)amino)imidazo [1,2-b]pyridazine-3-carboxamide N-(2-chloro-4-pyridinyl)-8-(cyclopropylamino)-6-((trans-4-((1H-pyrazol-4-ylcarbonyl)amino)cyclohexyl)amino) imidazo[1,2-b]pyridazine-3-carboxamide 6-((trans-4-acetamidocyclohexyl)amino)-N-(2-chloro-4-pyridinyl)-8-(cyclopropylamino)imidazo[1,2-b]pyridazine-3-carboxamide 6-((trans-4-(((2R)-2-amino-2-phenylacetyl)amino)cyclohexyl)amino)-N-(2-chloro-4-pyridinyl)-8-(cyclopropylamino)imidazo[1,2-b]pyridazine-3-carboxamide 6-((trans-4-(D-alanylamino)cyclohexyl)amino)-N-(2-chloro-4-pyridinyl)-8-(cyclopropylamino)imidazo[1,2-b]pyridazine-3-carboxamide 6-((trans-4-((4-aminobutanoyl)amino)cyclohexyl)amino)-N-(2-chloro-4-pyridinyl)-8-(cyclopropylamino)imidazo[1,2-b]pyridazine-3-carboxamide N-(2-chloro-4-pyridinyl)-8-(cyclopropylamino)-6-((trans-4-(L-prolylamino)cyclohexyl)amino)imidazo[1,2-b]pyridazine-3-carboxamide N-(2-chloro-4-pyridinyl)-8-(cyclopropylamino)-6-((trans-4-(D-prolylamino)cyclohexyl)amino)imidazo[1,2-b]pyridazine-3-carboxamide N-1 --(trans-4-((3-((2-chloro-4-pyridinyl)carbamoyl)-8-(cyclopropylamino)imidazo[1,2-b]pyridazin-6-yl)amino)cyclohexyl)-D-aspartamide N-1 --(trans-4-((3-((2-chloro-4-pyridinyl)carbamoyl)-8-(cyclopropylamino)imidazo[1,2-b]pyridazin-6-yl)amino)cyclohexyl)-L-aspartamide N-(2-chloro-4-pyridinyl)-8-(cyclopropylamino)-6-((trans-4-((3-(1,3-thiazol-4-yl)-D-alanyl)amino)cyclohexyl)amino)imidazo[1,2-b]pyridazine-3-carboxamide N-(2-chloro-4-pyridinyl)-8-(cyclopropylamino)-6-((trans-4-((3-piperidinylcarbonyl)amino)cyclohexyl)amino)imidazo[1,2-b]pyridazine-3-carboxamide N-(2-chloro-4-pyridinyl)-8-(cyclopropylamino)-6-((trans-4-(D-leucylamino)cyclohexyl)amino)imidazo[1,2-b]pyridazine-3-carboxamide N-(2-chloro-4-pyridinyl)-8-(cyclopropylamino)-6-((trans-4-(((2R)-2-hydroxypropanoyl)amino)cyclohexyl)amino) imidazo[1,2-b]pyridazine-3-carboxamide N-(2-chloro-4-pyridinyl)-8-(cyclopropylamino)-6-((trans-4-(L-threonylamino)cyclohexyl)amino)imidazo[1,2-b]pyridazine-3-carboxamide N-(2-chloro-4-pyridinyl)-8-(cyclopropylamino)-6-((trans-4-((N-methyl-L-seryhamino)cyclohexyl)amino)imidazo[1,2-b]pyridazine-3-carboxamide N-(2-chloro-4-pyridinyl)-8-(cyclopropylamino)-6-((trans-4-(((4R)-4-hydroxy-L-prolypamino)cyclohexyl)amino)imidazo[1,2-b]pyridazine-3-carboxamide N-(2-chloro-4-pyridinyl)-8-(cyclopropylamino)-6-((trans-4-((N-methyl-L-alanyl)amino)cyclohexyl)amino)imidazo[1,2-b]pyridazine-3-carboxamide 6-((trans-4-(beta-alanylamino)cyclohexyl)amino)-N-(2-chloro-4-pyridinyl)-8-(cyclopropylamino)imidazo[1,2-b]pyridazine-3-carboxamide N-(2-chloro-4-pyridinyl)-8-(cyclopropylamino)-6-((trans-4-((N,N-dimethyl-beta-alanyl)amino)cyclohexyl)amino)imidazo[1,2-b]pyridazine-3-carboxamide N-(2-chloro-4-pyridinyl)-8-(cyclopropylamino)-6-((trans-4-(D-ornithylamino)cyclohexyl)amino)imidazo[1,2-b]pyridazine-3-carboxamide N-(2-chloro-4-pyridinyl)-8-(cyclopropylamino)-6-((trans-4-((N-methylglycyl)amino)cyclohexyl)amino)imidazo[1,2-b]pyridazine-3-carboxamide N-(2-chloro-4-pyridinyl)-6-((trans-4-(((1-cyanocyclopropyl)carbonyl)amino) cyclohexyl)amino)-8-(cyclopropylamino)imidazo[1,2-b]pyridazine-3-carboxamide N-(2-chloro-4-pyridinyl)-8-(cyclopropylamino)-6-((trans-4-(((2S)-2-piperidinylcarbonyl)amino)cyclohexyl)amino)imidazo[1,2-b]pyridazine-3-carboxamide N-(2-chloro-4-pyridinyl)-8-(cyclopropylamino)-6-((trans-4-(L-leucylamino)cyclohexyl)amino)imidazo[1,2-b]pyridazine-3-carboxamide N-(2-chloro-4-pyridinyl)-8-(cyclopropylamino)-6-((trans-4-(L-ornithylamino)cyclohexyl)amino)imidazo[1,2-b]pyridazine-3-carboxamide N-(2-chloro-4-pyridinyl)-8-(cyclopropylamino)-6-((trans-4-(((3R)-3-hydroxybutanoyl)amino)cyclohexyl)amino) imidazo[1,2-b]pyridazine-3-carboxamide N-(2-chloro-4-pyridinyl)-8-(cyclopropylamino)-6-((trans-4-(D-serylamino)cyclohexyl)amino)imidazo[1,2-b]pyridazine-3-carboxamide N-(2-chloro-4-pyridinyl)-8-(cyclopropylamino)-6-((trans-4-(L-serylamino)cyclohexyl)amino)imidazo[1,2-b]pyridazine-3-carboxamide N-(2-chloro-4-pyridinyl)-8-(cyclopropylamino)-6-((trans-4-((3-morpholinylcarbonyl)amino)cyclohexyl)amino)imidazo[1,2-b]pyridazine-3-carboxamide 6-((trans-4-(((1-aminocyclopropyl) carbonyl)amino)cyclohexyl)amino)-N-(2-chloro-4-pyridinyl)-8-(cyclopropylamino)imidazo[1,2-b]pyridazine-3-carboxamide N-(2-chloro-4-pyridinyl)-8-(cyclopropylamino)-6-((trans-4-((N-methyl-L-leucyl)amino)cyclohexyl)amino)imidazo[1,2-b]pyridazine-3-carboxamide 6-((trans-4-(((2S)-2-amino-2-phenylacetyl)amino)cyclohexyl)amino)-N-(2-chloro-4-pyridinyl)-8-(cyclopropylamino)imidazo[1,2-b]pyridazine-3-carboxamide N-(2-chloro-4-pyridinyl)-8-(cyclopropylamino)-6-((trans-4-((3-(3-pyridinyl)-D-alanyl)amino)cyclohexyl)amino)imidazo[1,2-b]pyridazine-3-carboxamide N-(2-chloro-4-pyridinyl)-8-(cyclopropylamino)-6-((trans-4-((3-(4-pyridinyl)-D-alanyl)amino)cyclohexyl)amino)imidazo[1,2-b]pyridazine-3-carboxamide N-(2-chloro-4-pyridinyl)-6-((trans-4-((cyanoacetyl)amino)cyclohexyl)amino)-8-(cyclopropylamino)imidazo[1,2-b]pyridazine-3-carboxamide 8-(cyclopropylamino)-6-((trans-4-(((3,5-dichlorophenyl)carbamoyl)amino)cyclohexyl) amino)-N-(3-fluoro-4-pyridinyl)imidazo[1,2-b]pyridazine-3-carboxamide 8-(cyclopropylamino)-N-(3-fluoro-4-pyridinyl)-6-((trans-4-((((1R,2S)-2-phenylcyclopropyl)carbamoyl)amino) cyclohexyl)amino)imidazo[1,2-b]pyridazine-3-carboxamide 8-(cyclopropylamino)-N-(3-fluoro-4-pyridinyl)-6-((trans-4-((phenylcarbamoyl)amino)cyclohexyl)amino)imidazo[1,2-b]pyridazine-3-carboxamide 8-(cyclopropylamino)-6-((trans-4-(((2-fluorophenyl)carbamoyl)amino)cyclohexyl) amino)-N-(3-fluoro-4-pyridinyl)imidazo[1,2-b]pyridazine-3-carboxamide 6-((trans-4-(((2-chlorophenyl)carbamoyl)amino) cyclohexyl)amino)-8-(cyclopropylamino)-N-(3-fluoro-4-pyridinyl)imidazo[1,2-b]pyridazine-3-carboxamide 8-(cyclopropylamino)-6-((trans-4-(((3-fluorophenyl)carbamoyl)amino)cyclohexyl) amino)-N-(3-fluoro-4-pyridinyl)imidazo[1,2-b]pyridazine-3-carboxamide 6-((trans-4-(((3-chlorophenyl)carbamoyl)amino) cyclohexyl)amino)-8-(cyclopropylamino)-N-(3-fluoro-4-pyridinyl)imidazo[1,2-b]pyridazine-3-carboxamide 6-((trans-4-(((4-chlorophenyl)carbamoyl)amino) cyclohexyl)amino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-((trans-4-((methylcarbamoyl)amino)cyclohexyl)amino)imidazo[1,2-b]pyridazine-3-carboxamide ethyl N-((trans-4-((8-(cyclopropylamino)-3-((3-fluoro-4-pyridinyl)carbamoyl)imidazo[1,2-b]pyridazin-6-yl)amino)cyclohexyl)carbamoyl glycinate 8-(cyclopropylamino)-6-((trans-4-((ethylcarbamoyl) amino)cyclohexyl)amino)-N-(3-fluoro-4-pyridinyl) imidazo[1,2-b]pyridazine-3-carboxamide 6-((trans-4-((cyclohexylcarbamoyl)amino)cyclohexyl) amino)-8-(cyclopropylamino)-N-(3-fluoro-4-pyridinyl)imidazo[1,2-b]pyridazine-3-carboxamide methyl O-tert-butyl-N-((trans-4-((8-(cyclopropylamino)-3-((3-fluoro-4-pyridinyl)carbamoyl)imidazo[1,2-b]pyridazin-6-yl)amino)cyclohexyl)carbamoyl)-L-serinate 8-(cyclopropylamino)-6-((trans-4-(((4-fluorophenyl)carbamoyl)amino)cyclohexyl) amino)-N-(3-fluoro-4-pyridinyl)imidazo[1,2-b]pyridazine-3-carboxamide 8-(cyclopropylamino)-N-(3-fluoro-4-pyridinyl)-6-((trans-4-(((3-nitrophenyl)carbamoyl)amino)cyclohexyl) amino)imidazo[1,2-b]pyridazine-3-carboxamide 8-(cyclopropylamino)-6-((trans-4-((cyclopropylcarbamoyl)amino)cyclohexyl) amino)-N-(3-fluoro-4-pyridinyl)imidazo[1,2-b]pyridazine-3-carboxamide 6-((trans-4-((cyclobutylcarbamoyl)amino)cyclohexyl) amino)-8-(cyclopropylamino)-N-(3-fluoro-4-pyridinyl)imidazo[1,2-b]pyridazine-3-carboxamide 6-((trans-4-((cyclopentylcarbamoyl)amino)cyclohexyl) amino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-((trans-4-(((2-(1-methyl-2-pyrrolidinyl)ethyl)carbamoyl) amino)cyclohexyl)amino)imidazo[1,2-b]pyridazine-3-carboxamide 8-(cyclopropylamino)-N-(3-fluoro-4-pyridinyl)-6-((trans-4-(((2-(1-pyrrolidinyl)ethyl)carbamoyl)amino)cyclohexyl)amino)imidazo[1,2-b]pyridazine-3-carboxamide 8-(cyclopropylamino)-N-(3-fluoro-4-pyridinyl)-6-((trans-4-(((3-(2-oxo-1-pyrrolidinyl)propyl)carbamoyl)amino) cyclohexyl)amino)imidazo[1,2-b]pyridazine-3-carboxamide 8-(cyclopropylamino)-N-(3-fluoro-4-pyridinyl)-6-((trans-4-((1,3-thiazolid in-3-ylcarbonyl)amino)cyclohexyl) amino)imidazo[1,2-b]pyridazine-3-carboxamide 8-(cyclopropylamino)-N-(3-fluoro-4-pyridinyl)-6-((trans-4-((1-pyrrolidinylcarbonyl)amino)cyclohexyl)amino) imidazo[1,2-b]pyridazine-3-carboxamide 8-(cyclopropylamino)-N-(3-fluoro-4-pyridinyl)-6-((trans-4-((4-morpholinylcarbonyl)amino)cyclohexyl)amino) imidazo[1,2-b]pyridazine-3-carboxamide 8-(cyclopropylamino)-N-(3-fluoro-4-pyridinyl)-6-((trans-4-((1-piperidinylcarbonyl)amino) cyclohexyl)amino) imidazo[1,2-b]pyridazine-3-carboxamide 8-(cyclopropylamino)-N-(3-fluoro-4-pyridinyl)-6-((trans-4-(((4-hydroxy-1-piperidinyl)carbonyl) amino)cyclohexyl)amino)imidazo[1,2-b]pyridazine-3-carboxamide 8-(cyclopropylamino)-N-(3-fluoro-4-pyridinyl)-6-((trans-4-(((2-(4-morpholinyl)ethyl)carbamoyl)amino)cyclohexyl)amino)imidazo[1,2-b]pyridazine-3-carboxamide 8-(cyclopropylamino)-N-(3-fluoro-4-pyridinyl)-6-((trans-4-(((3-(4-morpholinyl)propyl)carbamoyl)amino)cyclohexyl)amino)imidazo[1,2-b]pyridazine-3-carboxamide 6-((trans-4-((1-azepanylcarbonyl)amino)cyclohexyl) amino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-((trans-4-((isopropylcarbamoyl)amino)cyclohexyl)amino)imidazo[1,2-b]pyridazine-3-carboxamide 8-(cyclopropylamino)-6-((trans-4-(((1-ethylpropyl)carbamoyl)amino)cyclohexyl)amino)-N-(3-fluoro-4-pyridinyl)imidazo[1,2-b]pyridazine-3-carboxamide 8-(cyclopropylamino)-6-((trans-4-(((3-(dimethylamino) propyl)carbamoyl)amino) cyclohexyl)amino)-N-(3-fluoro-4-pyridinyl)imidazo[1,2-b]pyridazine-3-carboxamide 8-(cyclopropylamino)-6-((trans-4-((ethyl(methyl) carbamoyl)amino)cyclohexyl)amino)-N-(3-fluoro-4-pyridinyl)imidazo[1,2-b]pyridazine-3-carboxamide 8-(cyclopropylamino)-6-((trans-4-((diethylcarbamoyl) amino)cyclohexyl)amino)-N-(3-fluoro-4-pyridinyl) imidazo[1,2-b]pyridazine-3-carboxamide 8-(cyclopropylamino)-N-(3-fluoro-4-pyridinyl)-6-((trans-4-(((3-(1H-imidazol-1-yl)propyl)carbamoyl)amino)cyclohexyl)amino)imidazo[1,2-b]pyridazine-3-carboxamide 8-(cyclopropylamino)-N-(3-fluoro-4-pyridinyl)-6-((trans-4-((((2S)-2-(methoxymethyl)-1-pyrrolidinyl)carbonyl) amino)cyclohexyl)amino) imidazo[1,2-b]pyridazine-3-carboxamide 8-(cyclopropylamino)-6-((trans-4-(((2-(dimethylamino) ethyl)(methyl)carbamoyl)amino)cyclohexyl)amino)-N-(3-fluoro-4-pyridinyl)imidazo[1,2-b]pyridazine-3-carboxamide 8-(cyclopropylamino)-N-(3-fluoro-4-pyridinyl)-6-((trans-4-((isobutyl(methyl)carbamoyl)amino)cyclohexyl) amino)imidazo[1,2-b]pyridazine-3-carboxamide 8-(cyclopropylamino)-N-(3-fluoro-4-pyridinyl)-6-((trans-4-((isopropyl(methyl)carbamoyl)amino)cyclohexyl) amino)imidazo[1,2-b]pyridazine-3-carboxamide 8-(cyclopropylamino)-N-(3-fluoro-4-pyridinyl)-6-((trans-4-(((4-methyl-1,4-diazepan-1-yl)carbonyl)amino)cyclohexyl)amino)imidazo[1,2-b]pyridazine-3-carboxamide 8-(cyclopropylamino)-6-((trans-4-(((4-ethyl-1-piperazinyl)carbonyl)amino)cyclohexyl)amino)-N-(3-fluoro-4-pyridinyl)imidazo[1,2-b]pyridazine-3-carboxamide 8-(cyclopropylamino)-6-((trans-4-(M2R,6S)-2,6-dimethyl-1-piperidinyl)carbonyl)amino)cyclohexyl) amino)-N-(3-fluoro-4-pyridinyl)imidazo[1,2-b]pyridazine-3-carboxamide 8-(cyclopropylamino)-6-((trans-4-(((4-fluorophenyl)carbamoyl)amino)cyclohexyl) amino)-N-(3-fluoro-4-pyridinyl)imidazo[1,2-b]pyridazine-3-carboxamide 6-((trans-4-((benzylcarbamoyl)amino)cyclohexyl) amino)-8-(cyclopropylamino)-N-(3-fluoro-4-pyridinyl)imidazo[1,2-b]pyridazine-3-carboxamide 8-(cyclopropylamino)-6-((trans-4-(((3-(dimethylamino) propyl)(methyl)carbamoyl)amino)cyclohexyl)amino)-N-(3-fluoro-4-pyridinyl)imidazo[1,2pyridazine-3-carboxamide 8-(cyclopropylamino)-N-(3-fluoro-4-pyridinyl)-6-((trans-4-((1-piperazinylcarbonyl)amino)cyclohexyl)amino)imidazo[1,2-b]pyridazine-3-carboxamide 8-(cyclopropylamino)-N-(3-fluoro-4-pyridinyl)-6-((trans-4-((4-pyridinylcarbamoyl)amino)cyclohexyl)amino)imidazo[1,2-b]pyridazine-3-carboxamide 8-(cyclopropylamino)-N-(3-fluoro-4-pyridinyl)-6-((trans-4-((1,3-thiazol-2-ylcarbamoyl)amino)cyclohexyl)amino)imidazo[1,2-b]pyridazine-3-carboxamide 8-(cyclopropylamino)-6-((trans-4-(((2-(dimethylamino)ethyl)carbamoyl)amino) cyclohexyl)amino)-N-(3-fluoro-4-pyridinyl)imidazo[1,2-b]pyridazine-3-carboxamide 8-(cyclopropylamino)-6-((trans-4-((dimethylcarbamoyl)amino)cyclohexyl)amino)-N-(3-fluoro-4-pyridinyl)imidazo[1,2-b]pyridazine-3-carboxamide 8-(cyclopropylamino)-N-(3-fluoro-4-pyridinyl)-6-((trans-4-((3-pyridinylcarbamoyl)amino)cyclohexyl)amino)imidazo[1,2-b]pyridazine-3-carboxamide 8-(cyclopropylamino)-6-((trans-4-((dimethylcarbamoyl)amino)cyclohexyl)amino)-N-(2-fluoro-4-pyridinyl)imidazo[1,2-b]pyridazine-3-carboxamide 8-(cyclopropylamino)-N-(2-fluoro-4-pyridinyl)-6-((trans-4-((isopropylcarbamoyl)amino)cyclohexyl)amino)imidazo[1,2-b]pyridazine-3-carboxamide N-(2-chloro-4-pyridinyl)-8-(cyclopropylamino)-6-((trans-4-((prolylcarbamoyl)amino)cyclohexyl)amino)imidazo[1,2-b]pyridazine-3-carboxamide N-(2-chloro-4-pyridinyl)-8-(cyclopropylamino)-6-((trans-4-((4-morpholinylcarbonyl)amino)cyclohexyl)amino)imidazo[1,2-b]pyridazine-3-carboxamide N-(2-chloro-4-pyridinyl)-8-(cyclopropylamino)-6-((trans-4-(((3-(dimethylamino)propyl)carbamoyl)hamino)cyclohexyl)amino)imidazo[1,2-b]pyridazine-3-carboxamide N-(2-chloro-4-pyridinyl)-8-(cyclopropylamino)-6-((trans-4-(((2-(dimethylamino)ethyl)(methyl)carbamoyl)amino)cyclohexyl)amino)imidazo[1,2-b]pyridazine-3-carboxamide N-(2-chloro-4-pyridinyl)-8-(cyclopropylamino)-6-((trans-4-((cyclopropylcarbamoyl)amino)cyclohexyl)amino)imidazo[1,2-b]pyridazine-3-carboxamide N-(2-chloro-4-pyridinyl)-6-((trans-4-((cyclopentylcarbamoyl)amino)cyclohexyl) amino)-8-(cyclopropylamino)imidazo[1,2-b]pyridazine-3-carboxamide N-(2-chloro-4-pyridinyl)-8-(cyclopropylamino)-6-((trans-4-((isopropylcarbamoyl)amino)cyclohexyl)amino)imidazo[1,2-b]pyridazine-3-carboxamide N-(2-chloro-4-pyridinyl)-8-(cyclopropylamino)-6-((trans-4-(((2,2,2-trifluoroethyl)carbamoyl)amino)cyclohexyl)amino)imidazo[1,2-b]pyridazine-3-carboxamide N-(2-chloro-4-pyridinyl)-8-(cyclopropylamino)-6-((trans-4-(((2-(1-pyrrolidinyl)ethyl)carbamoyl)amino)cyclohexyl)amino)imidazo[1,2-b]pyridazine-3-carboxamide N-(2-chloro-4-pyridinyl)-8-(cyclopropylamino)-6-((trans-4-(((2-(dimethylamino)-2-oxoethyl)carbamoyl)amino)cyclohexyl)amino) imidazo[1,2-b]pyridazine-3-carboxamide N-(2-chloro-4-pyridinyl)-8-(cyclopropylamino)-6-((trans-4-((tetrahydro-2H-pyran-4-ylcarbamoyl)amino)cyclohexyl)amino)imidazo[1,2-b ]pyridazine-3-carboxamide N-(2-chloro-4-pyridinyl)-8-(cyclopropylamino)-6-((trans-4-(((2-(dimethylamino)ethyl)carbamoyl)amino)cyclohexyl)amino)imidazo[1,2-b]pyridazine-3-carboxamide N-(2-chloro-4-pyridinyl)-8-(cyclopropylamino)-6-((trans-4-(((cyclopropylmethyl)carbamoyl)amino)cyclohexyl)amino)imidazo[1,2-b]pyridazine-3-carboxamide N-(2-chloro-4-pyridinyl)-8-(cyclopropylamino)-6-((trans-4-((((1-methyl-1H-imidazol-4-yl)methyl)carbamoyl)amino)cyclohexyl)amino) imidazo[1,2-b]pyridazine-3-carboxamide N-(2-chloro-4-pyridinyl)-8-(cyclopropylamino)-6-((trans-4-((((3S)-3-(dimethylamino)-1-pyrrolidinyl)carbonyl)amino)cyclohexyl)amino) imidazo[1,2-b]pyridazine-3-carboxamide N-(2-chloro-4-pyridinyl)-8-(cyclopropylamino)-6-((trans-4-(((4-methyl-1-piperazinyl)carbonyl)amino)cyclohexyl)amino)imidazo[1,2-b]pyridazine-3-carboxamide N-(2-chloro-4-pyridinyl)-8-(cyclopropylamino)-6-((trans-4-((((3R)-3-(dimethylamino)-1-pyrrolidinyl)carbonyl)amino)cyclohexyl)amino) imidazo[1,2-b]pyridazine-3-carboxamide N-(2-chloro-4-pyridinyl)-8-(cyclopropylamino)-6-((trans-4-(((4-pyrimidinylmethyl)carbamoyl)amino)cyclohexyl)amino)imidazo[1,2-b ]pyridazine-3-carboxamide N-(2-chloro-4-pyridinyl)-8-(cyclopropylamino)-6-((trans-4-(((2-methoxyethyl)carbamoyl)amino)cyclohexyl)amino)imidazo[1,2-b]pyridazine-3-carboxamide N-(2-chloro-4-pyridinyl)-8-(cyclopropylamino)-6-((trans-4-((methyl(2-propyn-1-yl)carbamoyl)amino)cyclohexyl)amino)imidazo[1,2-b]pyridazine-3-carboxamide N-(2-chloro-4-pyridinyl)-8-(cyclopropylamino)-6-((trans-4-((ethyl(methyl)carbamoyl)amino)cyclohexyl)amino)imidazo[1,2-b]pyridazine-3-carboxamide N-(2-chloro-4-pyridinyl)-8-(cyclopropylamino)-6-((trans-4-((((1-methyl-1H-imidazol-2-yl)methyl)carbamoyl)amino)cyclohexyl)amino) imidazo[1,2-b]pyridazine-3-carboxamide N-(2-chloro-4-pyridinyl)-8-(cyclopropylamino)-6-((trans-4-(((1-methyl-4-piperidinyl)carbamoyl)amino)cyclohexyl)amino)imidazo[1,2-b]pyridazine-3-carboxamide 2-propyn-1-yl (trans-4-((8-(cyclopropylamino)-3-((3-fluoro-4-pyridinyl)carbamoyl)imidazo[1,2-b]pyridazin-6-yl)amino)cyclohexyl)carbamate 2,2-dimethylpropyl (trans-4-((8-(cyclopropylamino)-3-((3-fluoro-4-pyridinyl)carbamoyl)imidazo[1,2-b]pyridazin-6-yl)amino)cyclohexyl)carbamate 1-naphthyl (trans-4-((8-(cyclopropylamino)-3-((3-fluoro-4-pyridinyl)carbamoyl)imidazo[1,2-b]pyridazin-6-yl)amino)cyclohexyl)carbamate 2-chlorophenyl (trans-4-((8-(cyclopropylamino)-3-((3-fluoro-4-pyridinyl)carbamoyl)imidazo[1,2-b]pyridazin-6-yl)amino)cyclohexyl)carbamate 2-methoxyethyl (trans-4-((8-(cyclopropylamino)-3-((3-fluoro-4-pyridinyl)carbamoyl)imidazo[1,2-b]pyridazin-6-yl)amino)cyclohexyl)carbamate isopropyl (trans-4-((8-(cyclopropylamino)-3-((3-fluoro-4-pyridinyl)carbamoyl)imidazo[1,2-b]pyridazin-6-yl)amino)cyclohexyl)carbamate 4-fluorophenyl (trans-4-((8-(cyclopropylamino)-3-((3-fluoro-4-pyridinyl)carbamoyl)imidazo[1,2-b]pyridazin-6-yl)amino)cyclohexyl)carbamate 4-methoxyphenyl (trans-4-((8-(cyclopropylamino)-3-((3-fluoro-4-pyridinyl)carbamoyl)imidazo[1,2-b]pyridazin-6-yl)amino)cyclohexyl)carbamate isobutyl (trans-4-((8-(cyclopropylamino)-3-((3-fluoro-4-pyridinyl)carbamoyl)imidazo[1,2-b]pyridazin-6-yl)amino)cyclohexyl)carbamate phenyl (trans-4-((8-(cyclopropylamino)-3-((3-fluoro-4-pyridinyhcarbamoyl)imidazo[1,2-b]pyridazin-6-yl)amino)cyclohexyl)carbamate 4-chlorophenyl (trans-4-((8-(cyclopropylamino)-3-((3-fluoro-4-pyridinyl)carbamoyl)imidazo[1,2-b]pyridazin-6-yl)amino)cyclohexyl)carbamate methyl (trans-4-((8-(cyclopropylamino)-3-((3-fluoro-4-pyridinyl)carbamoyl)imidazo[1,2-b]pyridazin-6-yl)amino)cyclohexyl)carbamate propyl (trans-4-((8-(cyclopropylamino)-3-((3-fluoro-4-pyridinyl)carbamoyl)imidazo[1,2-b]pyridazin-6-yl)amino)cyclohexyl)carbamate 2-cyanoethyl (trans-4-((8-(cyclopropylamino)-3-((3-fluoro-4-pyridinyl)carbamoyl)imidazo[1,2-b]pyridazin-6-yl)amino)cyclohexyl)carbamate 2-acetamidoethyl (trans-4-((8-(cyclopropylamino)-3-((3-fluoro-4-pyridinyl)carbamoyl)imidazo[1,2-b]pyridazin-6-yl)amino)cyclohexyl)carbamate 3-(dimethylamino)propyl (trans-4-((8-(cyclopropylamino)-3-((3-fluoro-4-pyridinyl)carbamoyl)imidazo[1,2-b]pyridazin-6-yl)amino)cyclohexyl)carbamate 2-(1-methyl-2-pyrrolidinyl)ethyl (trans-4-((8-(cyclopropylamino)-3-((3-fluoro-4-pyridinyl)carbamoyl)imidazo[1,2-b]pyridazin-6-yl)amino)cyclohexyl)carbamate 2-(1-pyrrolidinyl)ethyl (trans-4-((8-(cyclopropylamino)-3-((3-fluoro-4-pyridinyl)carbamoyl)imidazo[1,2-b]pyridazin-6-yl)amino)cyclohexyl)carbamate 4-(dimethylamino)butyl (trans-4-((8-(cyclopropylamino)-3-((3-fluoro-4-pyridinyl)carbamoyl)imidazo[1,2-b]pyridazin-6-yl)amino)cyclohexyl)carbamate 2-(1H-imidazol-1-yl)ethyl (trans-4-((8-(cyclopropylamino)-3-((3-fluoro-4-pyridinyl)carbamoyl)imidazo[1,2-b]pyridazin-6-yl)amino)cyclohexyl)carbamate 2-pyrazinylmethyl (trans-4-((8-(cyclopropylamino)-3-((3-fluoro-4-pyridinyl)carbamoyl)imidazo[1,2-b]pyridazin-6-yl)amino)cyclohexyl)carbamate 3-(4-morpholinyl)propyl (trans-4-((8-(cyclopropylamino)-3-((3-fluoro-4-pyridinyl)carbamoyl)imidazo[1,2-b]pyridazin-6-yl)amino)cyclohexyl)carbamate 2-(dimethylamino)-1-methylethyl (trans-4-((8-(cyclopropylamino)-3-((3-fluoro-4-pyridinyl)carbamoyl)imidazo[1,2-b]pyridazin-6-yl)amino)cyclohexyl)carbamate 2-(dimethylamino)ethyl (trans-4-((8-(cyclopropylamino)-3-((3-fluoro-4-pyridinyl)carbamoyl)imidazo[1,2-b]pyridazin-6-yl)amino)cyclohexyl)carbamate 1-methyl-2-propyn-1-yl (trans-4-((3-((2-chloro-4-pyridinyl)carbamoyl)-8-(cyclopropylamino)imidazo[1,2-b]pyridazin-6-yl)amino)cyclohexyl)carbamate 2-(1H-imidazol-1-yl)ethyl (trans-4-((3-((2-chloro-4-pyridinyl)carbamoyl)-8-(cyclopropylamino)imidazo[1,2-b]pyridazin-6-yl)amino)cyclohexyl)carbamate 2,2,2-trifluoroethyl (trans-4-((3-((2-chloro-4-pyridinyl)carbamoyl)-8-(cyclopropylamino)imidazo[1,2-b]pyridazin-6-yl)amino)cyclohexyl)carbamate 2-methoxyethyl (trans-4-((8-(cyclopropylamino)-3-((2-fluoro-4-pyridinyl)carbamoyl)imidazo[1,2-b]pyridazin-6-yl)amino)cyclohexyl)carbamate 2-(dimethylamino)ethyl (trans-4-((8-(cyclopropylamino)-3-((2-fluoro-4-pyridinyl)carbamoyl)imidazo[1,2-b]pyridazin-6-yl)amino)cyclohexyl)carbamate 6-((trans-4-(((4-chlorophenyl)sulfonyl)amino)cyclohexyl)amino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-((trans-4-((8-quinolinylsulfonyl)amino)cyclohexyl)amino)imidazo[1,2-b]pyridazine-3-carboxamide 6-((trans-4-(((2-acetamido-4-methyl-1,3-thiazol-5-yl)sulfonyl)amino)cyclohexyl)amino)-8-(cyclopropylamino)-N-(3-fluoro-4-pyridinyl)imidazo[1,2-b ]pyridazine-3-carboxamide 8-(cyclopropylamino)-6-((trans-4-(((4-fluorophenyl)sulfonyl)amino)cyclohexyl)amino)-N-(3-fluoro-4-pyridinyl)imidazo[1,2-b]pyridazine-3-carboxamide 6-((trans-4-(((2-chlorophenyl)sulfonyl)amino)cyclohexyl)amino)-8-(cyclopropylamino)-N-(3-fluoro-4-pyridinyl)imidazo[1,2-b]pyridazine-3-carboxamide 6-((trans-4-(((3-chlorophenyl)sulfonyl)amino)cyclohexyl)amino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-((trans-4-((phenylsulfonyl)amino)cyclohexyl)amino)imidazo[1,2-b]pyridazine-3-carboxamide 6-((trans-4-(((5-chloro-1,3-dimethyl-1H-pyrazol-4-yl)sulfonyl)amino)cyclohexyl)amino)-8-(cyclopropylamino)-N-(3-fluoro-4-pyridinyl)imidazo[1,2-b ]pyridazine-3-carboxamide 8-(cyclopropylamino)-6-((trans-4-(((3,5-dimethyl-4-isoxazolyl)sulfonyl)amino)cyclohexyl)amino)-N-(3-fluoro-4-pyridinyl)imidazo[1,2-b]pyridazine-3-carboxamide 8-(cyclopropylamino)-6-((trans-4-(((1,4-dimethyl-1H-imidazol-2-yl)sulfonyl)amino)cyclohexyl)amino)-N-(3-fluoro-4-pyridinyl)imidazo[1,2-b]pyridazine-3-carboxamide 8-(cyclopropylamino)-N-(3-fluoro-4-pyridinyl)-6-((trans-4-((methylsulfonyl)amino)cyclohexyl)amino)imidazo[1,2-b]pyridazine-3-carboxamide 8-(cyclopropylamino)-N-(3-fluoro-4-pyridinyl)-6-((trans-4-(((5-methyl-4-isoxazolyl)sulfonyl)amino)cyclohexyl)amino)imidazo[1,2-b]pyridazine-3-carboxamide 8-(cyclopropylamino)-N-(2-fluoro-4-pyridinyl)-6-((trans-4-((phenylsulfonyl)amino)cyclohexyl)amino)imidazo[1,2-b]pyridazine-3-carboxamide 6-(benzyl(methyl)amino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-(methyl(3-methylbutyl)amino)imidazo[1,2-b]pyridazine-3-carboxamide 8-(cyclopropylamino)-N-(3-fluoro-4-pyridinyl)-6-(isobutyl(methyl)amino)imidazo[1,2-b]pyridazine-3-carboxamide 8-(cyclopropylamino)-6-(ethyl(methyl)amino)-N-(3-fluoro-4-pyridinyl)imidazo[1,2-b]pyridazine-3-carboxamide 8-(cyclopropylamino)-6-((4-(dimethylamino)cyclohexyl)amino)-N-(3-fluoro-4-pyridinyl)imidazo[1,2-b]pyridazine-3-carboxamide 8-(cyclopropylamino)-6-((2,2-diphenylethyl)amino)-N-(3-fluoro-4-pyridinyl)imidazo[1,2-b]pyridazine-3-carboxamide 6-((2-acetamidoethyl)amino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-((2-hydroxyethyl)amino)imidazo[1,2-b]pyridazine-3-carboxamide 6-((2-(4-chlorophenyl)ethyl)amino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-(2-propyn-1-ylamino)imidazo[1,2-b]pyridazine-3-carboxamide 6-(cyclopentylamino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-((2-phenoxyethyl)amino)imidazo[1,2-b]pyridazine-3-carboxamide 6-(cyclobutylamino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-((3-phenylpropyl)amino)imidazo[1,2-b]pyridazine-3-carboxamide 8-(cyclopropylamino)-N-(3-fluoro-4-pyridinyl)-6-(propylamino)imidazo[1,2-b]pyridazine-3-carboxamide 8-(cyclopropylamino)-N-(3-fluoro-4-pyridinyl)-6-((3-methylbutyl)amino)imidazo[1,2-b]pyridazine-3-carboxamide 6-(benzylamino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-((4-pyridinylmethyl)amino)imidazo[1,2-b]pyridazine-3-carboxamide 8-(cyclopropylamino)-N-(3-fluoro-4-pyridinyl)-6-((3-pyridinylmethyl)amino)imidazo[1,2-b]pyridazine-3-carboxamide 6-((4-chlorobenzyl)amino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-((2-(4-morpholinyl)ethyl)amino)imidazo[1,2-b]pyridazine-3-carboxamide 8-(cyclopropylamino)-N-(3-fluoro-4-pyridinyl)-6-((3-(4-morpholinyl)propyl)amino)imidazo[1,2-b]pyridazine-3-carboxamide 8-(cyclopropylamino)-N-(3-fluoro-4-pyridinyl)-6-((2-phenylethyl)amino)imidazo[1,2-b]pyridazine-3-carboxamide 8-(cyclopropylamino)-6-((3-(dimethylamino)propyl)amino)-N-(3-fluoro-4-pyridinyl)imidazo[1,2-b]pyridazine-3-carboxamide 6-(cyclohexylamino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-((trans-4-hydroxycyclohexyl)amino)imidazo[1,2-b]pyridazine-3-carboxamide 8-(cyclopropylamino)-N-(3-fluoro-4-pyridinyl)-6-((2,2,6,6-tetramethyl-4-piperidinyl)amino)imidazo[1,2-b]pyridazine-3-carboxamide 8-(cyclopropylamino)-N-(3-fluoro-4-pyridinyl)-6-(4-morpholinyl)imidazo[1,2-b]pyridazine-3-carboxamide 8-(cyclopropylamino)-N-(3-fluoro-4-pyridinyl)-6-(1-pyrrolidinyl)imidazo[1,2-b]pyridazine-3-carboxamide 8-(cyclopropylamino)-N-(3-fluoro-4-pyridinyl)-6-((4-hydroxybutyl)amino)imidazo[1,2-b]pyridazine-3-carboxamide 8-(cyclopropylamino)-6-((4-(dimethylamino)butyl)amino)-N-(3-fluoro-4-pyridinyl)imidazo[1,2-b]pyridazine-3-carboxamide 6-((3-aminocyclohexyl)amino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-(tetrahydro-2H-pyran-4-ylamino)imidazo[1,2-b]pyridazine-3-carboxamide trans-4-((8-(cyclopropylamino)-3-((3-fluoro-4-pyridinyl)carbamoyl)imidazo[1,2-b]pyridazin-6-yl)amino)cyclohexanecarboxylic acid 6-((1-benzyl-4-piperidinyl)amino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-(4-piperidinylamino)imidazo[1,2-b]pyridazine-3-carboxamide 8-(cyclopropylamino)-N-(3-fluoro-4-pyridinyl)-6-(isobutylamino)imidazo[1,2-b]pyridazine-3-carboxamide 8-(cyclopropylamino)-N-(3-fluoro-4-pyridinyl)-6-((3-methylcyclohexyl)amino)imidazo[1,2-b]pyridazine-3-carboxamide 8-(cyclopropylamino)-N-(3-fluoro-4-pyridinyl)-6-((4-methylcyclohexyl)amino)imidazo[1,2-b]pyridazine-3-carboxamide 8-(cyclopropylamino)-N-(3-fluoro-4-pyridinyl)-6-((2-methylcyclohexyl)amino)imidazo[1,2-b]pyridazine-3-carboxamide 6-((1-benzyl-3-pyrrolidinyl)amino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-(((1R,2R)-2-hydroxycyclohexyl)amino)imidazo[1,2-b]pyridazine-3-carboxamide 8-(cyclopropylamino)-N-(3-fluoro-4-pyridinyl)-6-(((1S,2S)-2-hydroxycyclopentyl)amino)imidazo[1,2-b]pyridazine-3-carboxamide 8-(cyclopropylamino)-N-(3-fluoro-4-pyridinyl)-6-(((1R,2R)-2-(hydroxymethyl)cyclohexyl)amino)imidazo[1,2-b]pyridazine-3-carboxamide 8-(cyclopropylamino)-N-(3-fluoro-4-pyridinyl)-6-(((1R,2S)-2-hydroxycyclohexyl)amino)imidazo[1,2-b]pyridazine-3-carboxamide 6-(((1S,2S)-2-aminocyclohexyl)amino)-8-(cyclopropylamino)-N-(3-fluoro-4-pyridinyl)imidazo[1,2-b]pyridazine-3-carboxamide 8-(cyclopropylamino)-N-(3-fluoro-4-pyridinyl)-6-((trans-4-methylcyclohexyl)amino)imidazo[1,2-b]pyridazine-3-carboxamide 6-((cis-4-aminocyclohexyl)amino)-8-(cyclopropylamino)-N-(3-fluoro-4-pyridinyl)imidazo[1,2-b]pyridazine-3-carboxamide 6-((trans-4-aminocyclohexyl)amino)-8-((4-(dimethylsulfamoyl)phenyl)amino)-N-4-pyridinylimidazo[1,2-b]pyridazine-3-carboxamide 8-cyclohexyl-11-methoxy-1a-((4-methyl-1,4-diazepan-1-yl)sulfonyl)-1,1a,2,12b-tetrahydrocyclopropa[d]indolo[2,1-a][2]benzazepine-5-carboxylic acid N-cyclopropyl-3-((2-((2R)-2-(2-pyridinyl)-1-pyrrolidinyl)pyrrolo[2,1-f][1,2,4]triazin-4-yl)amino)-1H-pyrazole-5-carboxamide 6-((trans-4-aminocyclohexyl)amino)-8-((4-((3-phenyl-1-pyrrolidinyl)carbonyl)phenyl)amino)-N-4-pyridinylimidazo[1,2-b]pyridazine-3-carboxamide 6-((trans-4-aminocyclohexyl)amino)-8-((3-methyl-2-pyridinyl)amino)-N-4-pyridinylimidazo[1,2-b]pyridazine-3-carboxamide

- 6-((trans-4-aminocyclohexyl)amino)-8-((4-methyl-2-pyridinyl)amino)-N-4-pyridinylimidazo[1,2-b]pyridazine-3-carboxamide
- 6-((trans-4-aminocyclohexyl)amino)-8-((6-methyl-2-pyridinyl)amino)-N-4-pyridinylimidazo[1,2-b]pyridazine-3-carboxamide
- 6-((trans-4-aminocyclohexyl)amino)-8-((3-hydroxy-2-pyridinyl)amino)-N-4-pyridinylimidazo[1,2-b]pyridazine-3-carboxamide
- 6-((trans-4-aminocyclohexyl)amino)-8-((4-ethoxy-2-pyridinyl)amino)-N-4-pyridinylimidazo[1,2-b]pyridazine-3-carboxamide
- 6-((trans-4-aminocyclohexyl)amino)-8-((5-cyano-2-pyridinyl)amino)-N-4-pyridinylimidazo[1,2-b]pyridazine-3-carboxamide
- 6-((trans-4-aminocyclohexyl)amino)-8-((5-(aminomethyl)-2-pyridinyl)amino)-N-4-pyridinylimidazo[1,2-b]pyridazine-3-carboxamide
- 6-((trans-4-aminocyclohexyl)amino)-8-((5-phenyl-2-pyridinyl)amino)-N-4-pyridinylimidazo[1,2-b]pyridazine-3-carboxamide
- 6-((trans-4-aminocyclohexyl)amino)-8-((4-hydroxy-2-pyridinyl)amino)-N-4-pyridinylimidazo[1,2-b]pyridazine-3-carboxamide
- 6-((trans-4-aminocyclohexyl)amino)-8-((2-(1-piperidinyl)ethyl)amino)-N-4-pyridinylimidazo[1,2-b]pyridazine-3-carboxamide
- 6-((trans-4-aminocyclohexyl)amino)-8-((4-aminocyclohexyl)amino)-N-4-pyridinylimidazo[1,2-b]pyridazine-3-carboxamide
- 6-((trans-4-aminocyclohexyl)amino)-8-((2-(4-morpholinyl)ethyl)amino)-N-4-pyridinylimidazo[1,2-b]pyridazine-3-carboxamide
- 6-((trans-4-aminocyclohexyl)amino)-8-((3-(4-morpholinyl)propyl)amino)-N-4-pyridinylimidazo[1,2-b]pyridazine-3-carboxamide
- 6-((trans-4-aminocyclohexyl)amino)-8-((2-methoxyethyl)amino)-N-4-pyridinylimidazo[1,2-b]pyridazine-3-carboxamide
- 6-((trans-4-aminocyclohexyl)amino)-8-(cyclohexylamino)-N-4-pyridinylimidazo[1,2-b]pyridazine-3-carboxamide
- 6-((trans-4-aminocyclohexyl)amino)-8-(cyclopropylamino)-N-4-pyridinylimidazo[1,2-b]pyridazine-3-carboxamide
- 6-((trans-4-aminocyclohexyl)amino)-8-(cyclopropylmethyl)amino)-N-4-pyridinylimidazo[1,2-b]pyridazine-3-carboxamide
- 6-((trans-4-aminocyclohexyl)amino)-8-(benzylamino)-N-4-pyridinylimidazo[1,2-b]pyridazine-3-carboxamide
- 6-((trans-4-aminocyclohexyl)amino)-8-(tert-butylamino)-N-4-pyridinylimidazo[1,2-b]pyridazine-3-carboxamide
- 6-((trans-4-aminocyclohexyl)amino)-8-((4-(dimethylsulfamoyl)-3-hydroxyphenyl)amino)-N-4-pyridinylimidazo[1,2-b]pyridazine-3-carboxamide
- 6-((trans-4-aminocyclohexyl)amino)-8-((4-(hydroxymethyl)-2-pyridinyl)amino)-N-4-pyridinylimidazo[1,2-b]pyridazine-3-carboxamide
- 6-((trans-4-aminocyclohexyl)amino)-8-((3-cyanophenyl)amino)-N-4-pyrimidinylimidazo[1,2-b]pyridazine-3-carboxamide
- 6-((trans-4-aminocyclohexyl)amino)-8-((4-methoxyphenyl)amino)-N-4-pyridinylimidazo[1,2-b]pyridazine-3-carboxamide
- 6-((trans-4-aminocyclohexyl)amino)-8-((2-methoxyphenyl)amino)-N-4-pyridinylimidazo[1,2-b]pyridazine-3-carboxamide
- 6-((trans-4-aminocyclohexyl)amino)-8-((4-cyanophenyl)amino)-N-4-pyridinylimidazo[1,2-b]pyridazine-3-carboxamide
- 6-((trans-4-aminocyclohexyl)amino)-8-((4-methoxy-2-pyridinyl)amino)-N-4-pyridinylimidazo[1,2-b]pyridazine-3-carboxamide
- 6-((trans-4-aminocyclohexyl)amino)-8-((3-methoxyphenyl)amino)-N-4-pyridinylimidazo[1,2-b]pyridazine-3-carboxamide
- methyl 4-((6-((trans-4-aminocyclohexyl)amino)-3-(4-pyridinylcarbamoyl)imidazo[1,2-b]pyridazin-8-yl)amino)benzoate
- 6-((trans-4-aminocyclohexyl)amino)-8-((3-cyanophenyl)amino)-N-4-pyridinylimidazo[1,2-b]pyridazine-3-carboxamide
- 6-((trans-4-aminocyclohexyl)amino)-8-((3-carbamoylphenyl)amino)-N-4-pyridinylimidazo[1,2-b]pyridazine-3-carboxamide
- 6-((trans-4-aminocyclohexyl)amino)-8-((4-(4-methyl-1-piperazinyl)phenyl)amino)-N-4-pyridinylimidazo[1,2-b]pyridazine-3-carboxamide
- 6-((trans-4-aminocyclohexyl)amino)-8-((4-carbamoylphenyl)amino)-N-4-pyridinylimidazo[1,2-b]pyridazine-3-carboxamide
- 4-(4-((6-((trans-4-aminocyclohexyl)amino)-3-(4-pyridinylcarbamoyl)imidazo[1,2-b]pyridazin-8-yl)amino)phenyl)butanoic acid
- 6-((trans-4-aminocyclohexyl)amino)-8-((4-(dimethylamino)phenyl)amino)-N-4-pyridinylimidazo[1,2-b]pyridazine-3-carboxamide
- 6-((trans-4-aminocyclohexyl)amino)-8-((5-methoxy-2-pyridinyl)amino)-N-4-pyridinylimidazo[1,2-b]pyridazine-3-carboxamide
- 6-((trans-4-aminocyclohexyl)amino)-8-((4-(4-morpholinyl)phenyl)amino)-N-4-pyridinylimidazo[1,2-b]pyridazine-3-carboxamide
- 6-((trans-4-aminocyclohexyl)amino)-N-4-pyridinyl-8-((4-(1-pyrrolidinylmethyl)phenyl)amino)imidazo[1,2-b]pyridazine-3-carboxamide
- 6-((trans-4-aminocyclohexyl)amino)-8-((4-(methylcarbamoyl)phenyl)amino)-N-4-pyridinylimidazo[1,2-b]pyridazine-3-carboxamide
- 6-((trans-4-aminocyclohexyl)amino)-N-4-pyridinyl-8-((4-(1-pyrrolidinyl)phenyl)amino)imidazo[1,2-b]pyridazine-3-carboxamide
- 6-((trans-4-aminocyclohexyl)amino)-8-((4-(4-morpholinylmethyl)phenyl)amino)-N-4-pyridinylimidazo[1,2-b]pyridazine-3-carboxamide
- 6-((trans-4-aminocyclohexyl)amino)-N-4-pyridinyl-8-((4-(3-pyridinyloxy)phenyl)amino)imidazo[1,2-b]pyridazine-3-carboxamide
- 6-((trans-4-aminocyclohexyl)amino)-8-((2-methoxyethyl)amino)-N-4-pyridinylimidazo[1,2-b]pyridazine-3-carboxamide
- 6-((4-aminocyclohexyl)amino)-8-(isopropylamino)-N-4-pyridinylimidazo[1,2-b]pyridazine-3-carboxamide
- 6-((4-aminocyclohexyl)amino)-8-(methylamino)-N-4-pyridinylimidazo[1,2-b]pyridazine-3-carboxamide
- 6-((4-aminocyclohexyl)amino)-8-(ethylamino)-N-4-pyridinylimidazo[1,2-b]pyridazine-3-carboxamide
- 6-((4-aminocyclohexyl)amino)-8-((2-hydroxy-1-methylethyl)amino)-N-4-pyridinylimidazo[1,2-b]pyridazine-3-carboxamide 6-((4-aminocyclohexyl)amino)-8-((2-hydroxycyclohexyl)amino)-N-4-pyridinylimidazo[1,2-b]pyridazine-3-carboxamide
6-((4-aminocyclohexyl)amino)-8-((2-hydroxy-1-(hydroxymethyl)ethyl)amino)-N-4-pyridinylimidazo[1,2-b]pyridazine-3-carboxamide
6-((4-aminocyclohexyl)amino)-8-((1-(hydroxymethyl)butyl)amino)-N-4-pyridinylimidazo[1,2-b]pyridazine-3-carboxamide
6-((4-aminocyclohexyl)amino)-8-((1-(hydroxymethyl)-2-methylpropyl)amino)-N-4-pyridinylimidazo[1,2-b]pyridazine-3-carboxamide
6-((4-aminocyclohexyl)amino)-8-((2-methoxy-1-methylethyl)amino)-N-4-pyridinylimidazo[1,2-b]pyridazine-3-carboxamide
6-((4-aminocyclohexyl)amino)-8-((1-(hydroxymethyl)propyl)amino)-N-4-pyridinylimidazo[1,2-b]pyridazine-3-carboxamide
6-((4-aminocyclohexyl)amino)-8-((1-(methoxymethyl)propyl)amino)-N-4-pyridinylimidazo[1,2-b]pyridazine-3-carboxamide
6-((4-aminocyclohexyl)amino)-8-((3-methoxypropyl)amino)-N-4-pyridinylimidazo[1,2-b]pyridazine-3-carboxamide
6-((4-aminocyclohexyl)amino)-8-((3-hydroxypropyl)amino)-N-4-pyridinylimidazo[1,2-b]pyridazine-3-carboxamide
6-((trans-4-aminocyclohexyl)amino)-N-4-pyridinyl-8-(3-pyrrolidinylamino)imidazo[1,2-b]pyridazine-3-carboxamide
6-((trans-4-aminocyclohexyl)amino)-8-((3-aminopropyl)amino)-N-4-pyridinylimidazo[1,2-b]pyridazine-3-carboxamide
6-((trans-4-aminocyclohexyl)hamino)-8-((2-aminoethyl)amino)-N-4-pyridinylimidazo[1,2-b]pyridazine-3-carboxamide
6-((trans-4-aminocyclohexyl)amino)-8-(cyclopentylamino)-N-4-pyridinylimidazo[1,2-b]pyridazine-3-carboxamide
6-((trans-4-aminocyclohexyl)amino)-8-((2-hydroxyethyl)amino)-N-4-pyridinylimidazo[1,2-b]pyridazine-3-carboxamide
6-((trans-4-aminocyclohexyl)amino)-8-M2S)-2-(hydroxymethyl)cyclopropyl)amino)-N-4-pyridinylimidazo[1,2-b]pyridazine-3-carboxamide
6-((trans-4-aminocyclohexyl)amino)-8-anilino-N-(6-fluoro-2-oxo-1,2-dihydro-4-pyridinyl)imidazo[1,2-b]pyridazine-3-carboxamide
6-((trans-4-aminocyclohexyl)amino)-8-anilino-N-1,3-benzothiazol-6-ylimidazo[1,2-b]pyridazine-3-carboxamide
ethyl 3-(((6-((trans-4-aminocyclohexyl)amino)-8-anilinoimidazo[1,2-b]pyridazin-3-yl)carbonyl)amino)-5-fluorobenzoate
6-((trans-4-aminocyclohexyl)amino)-8-anilino-N-(3-hydroxyphenyl)imidazo[1,2-b]pyridazine-3-carboxamide
6-((trans-4-aminocyclohexyl)amino)-8-(cyclopropylamino)-N-phenylimidazo[1,2-b]pyridazine-3-carboxamide
6-((trans-4-aminocyclohexyl)amino)-8-(cyclopropylamino)-N-pyridazinylimidazo[1,2-b]pyridazine-3-carboxamide
6-((trans-4-aminocyclohexyl)amino)-8-((3-cyanophenyl)amino)-N-4-pyrimidinylimidazo[1,2-b]pyridazine-3-carboxamide
6-((trans-4-aminocyclohexyl)amino)-8-((4-(dimethylsulfamoyl)phenyl)amino)-N-4-pyrimidinylimidazo[1,2-b]pyridazine-3-carboxamide
6-((trans-4-aminocyclohexyl)amino)-8-((4-cyanophenyl)amino)-N-4-pyrimidinylimidazo[1,2-b]pyridazine-3-carboxamide
6-((trans-4-aminocyclohexyl)amino)-8-((5-phenyl-2-pyridinyl)amino)-N-4-pyrimidinylimidazo[1,2-b]pyridazine-3-carboxamide
6-((trans-4-aminocyclohexyl)amino)-8-((5-methyl-2-pyridinyl)amino)-N-4-pyrimidinylimidazo[1,2-b]pyridazine-3-carboxamide
6-((trans-4-aminocyclohexyl)amino)-8-(cyclopropylamino)-N-4-pyrimidinylimidazo[1,2-b]pyridazine-3-carboxamide
8-(cyclopropylamino)-6-((trans-4-(glycylamino)cyclohexyl)amino)-N-4-pyrimidinylimidazo[1,2-b]pyridazine-3-carboxamide
8-(cyclopropylamino)-6-((trans-4-((phenylsulfonyl)amino)cyclohexyl)amino)-N-4-pyrimidinylimidazo[1,2-b]pyridazine-3-carboxamide
8-(cyclopropylamino)-6-((trans-4-((methylsulfonyl)amino)cyclohexyl)amino)-N-4-pyrimidinylimidazo[1,2-b]pyridazine-3-carboxamide
8-(cyclopropylamino)-6-((trans-4-(((4-fluorophenyhcarbamoyl)amino)cyclohexyl)amino)-N-4-pyrimidinylimidazo[1,2-b]pyridazine-3-carboxamide
6-((trans-4-(benzoylamino)cyclohexyl)amino)-8-(cyclopropylamino)-N-4-pyrimidinylimidazo[1,2-b]pyridazine-3-carboxamide
8-(cyclopropylamino)-6-((trans-4-((dimethylcarbamoyl)amino)cyclohexyl)amino)-N-4-pyrimidinylimidazo[1,2-b]pyridazine-3-carboxamide
8-(cyclopropylamino)-6-((trans-4-((dimethylsulfamoyl)amino)cyclohexyl)amino)-N-4-pyrimidinylimidazo[1,2-b]pyridazine-3-carboxamide
8-(cyclopropylamino)-6-((trans-4-(isobutyrylamino)cyclohexyl)amino)-N-4-pyrimidinylimidazo[1,2-b]pyridazine-3-carboxamide
6-((trans-4-(D-alanylamino)cyclohexyl)amino)-8-(cyclopropylamino)-N-4-pyrimidinylimidazo[1,2-b]pyridazine-3-carboxamide
6-((trans-4-acetamidocyclohexyl)amino)-8-anilino-N-4-pyrimidinylimidazo[1,2-b]pyridazine-3-carboxamide
6-((trans-4-aminocyclohexyl)amino)-8-(cyclopropylamino)-N-(3-fluoro-4-pyridinyl)imidazo[1,2-b]pyridazine-3-carboxamide
6-((trans-4-aminocyclohexyl)amino)-8-(cyclobutylamino)-N-(3-fluoro-4-pyridinyl)imidazo[1,2-b]pyridazine-3-carboxamide
6-((trans-4-aminocyclohexyl)amino)-N-(3-fluoro-4-pyridinyl)-8-(3-oxetanylamino)imidazo[1,2-b]pyridazine-3-carboxamide
6-((trans-4-aminocyclohexyl)amino)-N-(3-fluoro-4-pyridinyl)-8-(2-pyridinylamino)imidazo[1,2-b]pyridazine-3-carboxamide
6-((trans-4-aminocyclohexyl)amino)-N-(3-fluoro-4-pyridinyl)-8-((5-(4-morpholinyl)-2-pyridinyl)amino)imidazo[1,2-b]pyridazine-3-carboxamide
6-((trans-4-aminocyclohexyl)amino)-N-(3-fluoro-4-pyridinyl)-8-((2,2,2-trifluoroethyl)amino)imidazo[1,2-b]pyridazine-3-carboxamide
8-((1-acetyl-3-azetidinyl)amino)-6-((trans-4-aminocyclohexyl)amino)-N-(3-fluoro-4-pyridinyl)imidazo[1,2-b]pyridazine-3-carboxamide 6-((trans-4-aminocyclohexyl)amino)-N-(3-fluoro-4-pyridinyl)-8-((trans-3-(hydroxymethyl)cyclobutyl)amino)imidazo[1,2-b]pyridazine-3-carboxamide
6-((trans-4-aminocyclohexyl)amino)-N-(3-fluoro-4-pyridinyl)-8-((cis-3-(hydroxymethyl)cyclobutyl)amino)imidazo[1,2-b]pyridazine-3-carboxamide
8-amino-6-((trans-4-aminocyclohexyl)amino)-N-(3-fluoro-4-pyridinyl)imidazo[1,2-b]pyridazine-3-carboxamide
6-((trans-4-aminocyclohexyl)amino)-8-((1,3-dimethyl-1H-pyrazol-5-yl)amino)-N-(3-fluoro-4-pyridinyl)imidazo[1,2-b]pyridazine-3-carboxamide
6-((trans-4-aminocyclohexyl)amino)-N-(3-fluoro-4-pyridinyl)-8-((6-(4-morpholinyl)-2-pyridinyl)amino)imidazo[1,2-b]pyridazine-3-carboxamide
6-((trans-4-aminocyclohexyl)amino)-N-(3-fluoro-4-pyridinyl)-8-((6-(4-(2-hydroxyethyl)-1-piperazinyl)-2-pyridinyl)amino)imidazo[1,2-b]pyridazine-3-carboxamide
6-((trans-4-aminocyclohexyl)amino)-N-(3-fluoro-4-pyridinyl)-8-((6-(1-piperazinyl)-2-pyridinyl)amino)imidazo[1,2-b]pyridazine-3-carboxamide
6-((trans-4-aminocyclohexyl)amino)-N-(3-fluoro-4-pyridinyl)-8-((6-(4-hydroxy-1-piperidinyl)-2-pyridinyl)amino)imidazo[1,2-b]pyridazine-3-carboxamide
6-((trans-4-aminocyclohexyl)amino)-N-(3-fluoro-4-pyridinyl)-8-((6-(4-(hydroxymethyl)-1-piperidinyl)-2-pyridinyl)amino)imidazo[1,2-b]pyridazine-3-carboxamide
6-((trans-4-aminocyclohexyl)amino)-N-(3-fluoro-4-pyridinyl)-8-((6-(1-piperidinyl)-2-pyridinyl)amino)imidazo[1,2-b]pyridazine-3-carboxamide
6-((trans-4-aminocyclohexyl)amino)-8-((6-bromo-2-pyridinyl)amino)-N-(3-fluoro-4-pyridinyl)imidazo[1,2-b]pyridazine-3-carboxamide
6-((trans-4-aminocyclohexyl)amino)-N-(3-fluoro-4-pyridinyl)-8-((6-fluoro-2-pyridinyl)amino)imidazo[1,2-b]pyridazine-3-carboxamide
6-((trans-4-aminocyclohexyl)amino)-8-((6-((trans-4-aminocyclohexyl)amino)-2-pyridinyl)amino)-N-(3-fluoro-4-pyridinyl)imidazo[1,2-b]pyridazine-3-carboxamide
6-((trans-4-aminocyclohexyl)amino)-8-((6-chloro-2-pyridinyl)amino)-N-(3-fluoro-4-pyridinyl)imidazo[1,2-b]pyridazine-3-carboxamide
6-((trans-4-aminocyclohexyl)amino)-8-anilino-N-(3-fluoro-4-pyridinyl)imidazo[1,2-b]pyridazine-3-carboxamide
6-((trans-4-aminocyclohexyl)amino)-N-(3-fluoro-4-pyridinyl)-8-((5-methyl-2-pyridinyl)amino)imidazo[1,2-b]pyridazine-3-carboxamide
6-((trans-4-aminocyclohexyl)amino)-N-(3-fluoro-4-pyridinyl)-8-((4-(1-piperidinylmethyl)phenyl)amino)imidazo[1,2-b]pyridazine-3-carboxamide
6-((trans-4-aminocyclohexyl)amino)-N-(3-fluoro-4-pyridinyl)-8-((4-(1H-tetrazol-5-phenyl)amino)imidazo[1,2-b]pyridazine-3-carboxamide
6-((trans-4-aminocyclohexyl)amino)-N-(3-fluoro-4-pyridinyl)-8-(4-pyridinylamino)imidazo[1,2-b]pyridazine-3-carboxamide
6-((trans-4-aminocyclohexyl)amino)-N-(3-fluoro-4-pyridinyl)-8-((3-methoxy-4-methylphenyl)amino)imidazo[1,2-b]pyridazine-3-carboxamide
6-((trans-4-aminocyclohexyl)amino)-8-((3,4-dimethoxyphenyl)amino)-N-(3-fluoro-4-pyridinyl)imidazo[1,2-b]pyridazine-3-carboxamide
6-((trans-4-aminocyclohexyl)amino)-N-(3-fluoro-4-pyridinyl)-8-((3-(methylcarbamoyl)phenyl)amino)imidazo[1,2-b]pyridazine-3-carboxamide
6-((trans-4-aminocyclohexyl)amino)-8-((3-cyanophenyl)amino)-N-(3-fluoro-4-pyridinyl)imidazo[1,2-b]pyridazine-3-carboxamide
6-((trans-4-aminocyclohexyl)amino)-N-(3-fluoro-4-pyridinyl)-8-((4-(2-hydroxyethyl)phenyl)amino)imidazo[1,2-b]pyridazine-3-carboxamide
6-((trans-4-aminocyclohexyl)amino)-N-(3-fluoro-4-pyridinyl)-8-((4-(2-hydroxyethoxy)phenyl)amino)imidazo[1,2-b]pyridazine-3-carboxamide
6-((trans-4-aminocyclohexyl)amino)-N-(3-fluoro-4-pyridinyl)-8-((4-(3-hydroxypropoxy)phenyl)amino)imidazo[1,2-b]pyridazine-3-carboxamide
6-((trans-4-aminocyclohexyl)amino)-8-((4-(2-(dimethylamino)ethoxy)phenyl)amino)-N-(3-fluoro-4-pyridinyl)imidazo[1,2-b]pyridazine-3-carboxamide
6-((trans-4-aminocyclohexyl)amino)-N-(3-fluoro-4-pyridinyl)-8-((4-(2-(4-morpholinyl)ethyl)phenyl)amino)imidazo[1,2-b]pyridazine-3-carboxamide
6-((trans-4-aminocyclohexyl)amino)-N-(3-fluoro-4-pyridinyl)-8-((3-(trifluoromethoxy)phenyl)amino)imidazo[1,2-b]pyridazine-3-carboxamide
6-((trans-4-acetamidocyclohexyl)amino)-8-(cyclopropylamino)-N-(3-fluoro-4-pyridinyl)imidazo[1,2-b]pyridazine-3-carboxamide
6-((trans-4-acetamidocyclohexyl)amino)-8-(cyclobutylamino)-N-(3-fluoro-4-pyridinyl)imidazo[1,2-b]pyridazine-3-carboxamide
6-((trans-4-acetamidocyclohexyl)amino)-8-anilino-N-(3-fluoro-4-pyridinyl)imidazo[1,2-b]pyridazine-3-carboxamide
6-((trans-4-acetamidocyclohexyl)amino)-8-anilino-N-4-pyridinylimidazo[1,2-b]pyridazine-3-carboxamide
6-((trans-4-aminocyclohexyl)amino)-8-anilino-N-(3-cyclopropyl-1-methyl-1H-pyrazol-5-yl)imidazo[1,2-b]pyridazine-3-carboxamide
6-((trans-4-aminocyclohexyl)amino)-8-anilino-N-(5-cyano-2-pyridinyl)imidazo[1,2-b]pyridazine-3-carboxamide
6-((trans-4-aminocyclohexyl)amino)-8-anilino-N-(6-(4-morpholinyl)-3-pyridinyl)imidazo[1,2-b]pyridazine-3-carboxamide
6-((trans-4-aminocyclohexyl)amino)-8-anilino-N-(3-(trifluoromethyl)-4-pyridinyl)imidazo[1,2-b]pyridazine-3-carboxamide
6-((trans-4-aminocyclohexyl)amino)-8-anilino-N-(6-(dimethylamino)-3-pyridinyl)imidazo[1,2-b]pyridazine-3-carboxamide
6-((trans-4-aminocyclohexyl)amino)-8-anilino-N-(4-cyanophenyl)imidazo[1,2-b]pyridazine-3-carboxamide
6-((trans-4-aminocyclohexyl)amino)-8-anilino-N-(4-(1H-imidazol-1-yl)phenyl)imidazo[1,2-Npyridazine-3-carboxamide
6-((trans-4-aminocyclohexyl)amino)-8-anilino-N-(4-(dimethylamino)phenyl)imidazo[1,2-b]pyridazine-3-carboxamide
6-((trans-4-aminocyclohexyl)amino)-8-anilino-N-(3-methyl-4-pyridinyl)imidazo[1,2-b]pyridazine-3-carboxamide
6-((trans-4-aminocyclohexyl)amino)-8-anilino-N-(4-carbamoylphenyl)imidazo[1,2-b]pyridazine-3-carboxamide
6-((trans-4-aminocyclohexyl)amino)-8-anilino-N-4-pyrimidinylimidazo[1,2-b]pyridazine-3-carboxamide 6-((trans-4-aminocyclohexyl)amino)-8-anilino-N-(3-chloro-4-pyridinyl)imidazo[1,2-b]pyridazine-3-carboxamide 6-((trans-4-aminocyclohexyl)amino)-8-anilino-N-(6-methoxy-4-pyrimidinyl)imidazo[1,2-b]pyridazine-3-carboxamide 6-((trans-4-aminocyclohexyl)amino)-8-anilino-N-1H-pyrazol-5-ylimidazo[1,2-b]pyridazine-3-carboxamide 6-((trans-4-aminocyclohexyl)amino)-N-methyl-8-((5-methyl-2-pyridinyl)amino)-N-4-pyridinylimidazo[1,2-b]pyridazine-3-carboxamide methyl N-(trans-4-((8-(cyclopropylamino)-3-((3-fluoro-4-pyridinyl)carbamoyl)imidazo[1,2-b]pyridazin-6-yl)amino)cyclohexyl)glycinate 8-(cyclopropylamino)-6-((trans-4-((2,3-dihydroxypropyl)amino)cyclohexyl)amino)-N-(3-fluoro-4-pyridinyl)imidazo[1,2-b]pyridazine-3-carboxamide 8-(cyclopropylamino)-N-(3-fluoro-4-pyridinyl)-6-((trans-4-(2-pyridinylamino)cyclohexyl)amino)imidazo[1,2-b]pyridazine-3-carboxamide 6-((trans-4-((2-aminoethyl)amino)cyclohexyl)amino)-8-(cyclopropylamino)-N-(2-fluoro-4-pyridinyl)imidazo[1,2-b]pyridazine-3-carboxamide 8-(cyclopropylamino)-6-((trans-4-((2-(dimethylamino)ethyl)amino)cyclohexyl)amino)-N-(2-fluoro-4-pyridinyl)imidazo[1,2-b]pyridazine-3-carboxamide 8-(cyclopropylamino)-N-(2-fluoro-4-pyridinyl)-6-((trans-4-(isopropylamino)cyclohexyl)amino)imidazo[1,2-b]pyridazine-3-carboxamide 8-(cyclopropylamino)-6-((trans-4-(ethylamino)cyclohexyl)amino)-N-(2-fluoro-4-pyridinyl)imidazo[1,2-b]pyridazine-3-carboxamide 8-(cyclopropylamino)-6-((trans-4-(diethylamino)cyclohexyl)amino)-N-(2-fluoro-4-pyridinyl)imidazo[1,2-b]pyridazine-3-carboxamide N-(2-chloro-4-pyridinyl)-8-(cyclopropylamino)-6-((trans-4-((2-hydroxyethyhamino)cyclohexyl)amino)imidazo[1,2-b]pyridazine-3-carboxamide N-(2-chloro-4-pyridinyl)-8-(cyclopropylamino)-6-((trans-4-(4-morpholinyl)cyclohexyl)amino)imidazo[1,2-b]pyridazine-3-carboxamide N-(2-chloro-4-pyridinyl)-8-(cyclopropylamino)-6-((4-(dimethylamino)cyclohexyl)amino)imidazo[1,2-b]pyridazine-3-carboxamide 6-((trans-4-(bis(2-hydroxyethyl)amino)cyclohexyl)amino)-N-(2-chloro-4-pyridinyl)-8-(cyclopropylamino)imidazo[1,2-b]pyridazine-3-carboxamide N-(2-chloro-4-pyridinyl)-8-(cyclopropylamino)-6-((trans-4-(isopropylamino)cyclohexyl)amino)imidazo[1,2-b]pyridazine-3-carboxamide N-(2-chloro-4-pyridinyl)-8-(cyclopropylamino)-6-((trans-4-((2-methoxyethyl)amino)cyclohexyl)amino)imidazo[1,2-b]pyridazine-3-carboxamide N-(2-chloro-4-pyridinyl)-8-(cyclopropylamino)-6-((trans-4-((2,2,2-trifluoroethyl)amino)cyclohexyl)amino)imidazo[1,2-b]pyridazine-3-carboxamide N-(2-chloro-4-pyridinyl)-8-(cyclopropylamino)-6-((trans-4-(isobutylamino)cyclohexyl)amino)imidazo[1,2-b]pyridazine-3-carboxamide N-(2-chloro-4-pyridinyl)-8-(cyclopropylamino)-6-((trans-4-(ethylamino)cyclohexyl)amino)imidazo[1,2-b]pyridazine-3-carboxamide 6-((trans-4-(2-butyn-1-ylamino)cyclohexyl)amino)-N-(2-chloro-4-pyridinyl)-8-(cyclopropylamino)imidazo[1,2-b]pyridazine-3-carboxamide 6-((trans-4-aminocyclohexyl)amino)-N-(3-fluoro-4-pyridinyl)-8-(1,3-thiazol-2-ylamino)imidazo[1,2-b]pyridazine-3-carboxamide 6-((trans-4-aminocyclohexyl)amino)-N-(2-chloro-4-pyridinyl)-8-((1,5-dimethyl-1H-pyrazol-3-yl)amino)imidazo[1,2-b]pyridazine-3-carboxamide 6-((trans-4-aminocyclohexyl)amino)-N-(2-chloro-4-pyridinyl)-8-((5-methyl-3-isoxazolyl)amino)imidazo[1,2-b]pyridazine-3-carboxamide 6-((trans-4-aminocyclohexyl)amino)-N-(2-chloro-4-pyridinyl)-8-(1,3-thiazol-2-ylamino)imidazo[1,2-b]pyridazine-3-carboxamide 6-((trans-4-aminocyclohexyl)amino)-N-(2-chloro-4-pyridinyl)-8-((1-isopropyl-1H-pyrazol-3-yl)amino)imidazo[1,2-b]pyridazine-3-carboxamide 6-((trans-4-aminocyclohexyl)amino)-N-(2-chloro-4-pyridinyl)-8-((1-(2-hydroxyethyl)-1H-pyrazol-3-yl)amino)imidazo[1,2-b]pyridazine-3-carboxamide 8-((1,5-dimethyl-1H-pyrazol-3-yl)amino)-N-(3-fluoro-4-pyridinyl)-6-((trans-4-hydroxycyclohexyl)amino)imidazo[1,2-b]pyridazine-3-carboxamide N-(3-fluoro-4-pyridinyl)-6-((trans-4-hydroxycyclohexyl)amino)-8-(1,3-thiazol-2-ylamino)imidazo[1,2-b]pyridazine-3-carboxamide N-(2-chloro-4-pyridinyl)-6-((trans-4-hydroxycyclohexyl)amino)-8-(3-isoxazolylamino)imidazo[1,2-b]pyridazine-3-carboxamide N-(2-chloro-4-pyridinyl)-6-((trans-4-hydroxycyclohexyl)amino)-8-((5-methyl-3-isoxazolyl)amino)imidazo[1,2-b]pyridazine-3-carboxamide N-(2-chloro-4-pyridinyl)-6-((trans-4-hydroxycyclohexyl)amino)-8-((1-isopropyl-1H-pyrazol-3-yl)amino)imidazo[1,2-b]pyridazine-3-carboxamide N-(2-chloro-4-pyridinyl)-6-((trans-4-hydroxycyclohexyl)amino)-8-(1,3-thiazol-2-ylamino)imidazo[1,2-b]pyridazine-3-carboxamide N-(2-chloro-4-pyridinyl)-8-((1,5-dimethyl-1H-pyrazol-3-yl)amino)-6-((trans-4-hydroxycyclohexyl)amino)imidazo[1,2-b]pyridazine-3-carboxamide N-(2-chloro-4-pyridinyl)-6-((trans-4-hydroxycyclohexyl)amino)-8-((1-(2-hydroxyethyl)-1H-pyrazol-3-yl)amino)imidazo[1,2-b]pyridazine-3-carboxamide 6-((trans-4-aminocyclohexyl)amino)-8-((5-tert-butyl-3-isoxazolyl)amino)-N-(3-fluoro-4-pyridinyl)imidazo[1,2-b]pyridazine-3-carboxamide 8-((5-tert-butyl-3-isoxazolyl)amino)-N-(3-fluoro-4-pyridinyl)-6-((trans-4-hydroxycyclohexyl)amino)imidazo[1,2-b]pyridazine-3-carboxamide 8-((5-tert-butyl-3-isoxazolyl)amino)-6-((trans-4-((cyanoacetyl)amino)cyclohexyl)amino)-N-(3-fluoro-4-pyridinyl)imidazo[1,2-b]pyridazine-3-carboxamide N-(2-chloro-4-pyridinyl)-6-((trans-4-((cyanoacetyl)amino)cyclohexyl)amino)-8-(3-isoxazolylamino)imidazo[1,2-b]pyridazine-3-carboxamide N-(2-chloro-4-pyridinyl)-6-((trans-4-((cyanoacetyl)amino)cyclohexyl)amino)-8-((1-isopropyl-1H-pyrazol-3-yl)amino)imidazo[1,2-b]pyridazine-3-carboxamide N-(2-chloro-4-pyridinyl)-6-((trans-4-((cyanoacetyl)amino)cyclohexyl)amino)-8-((5-methyl-3-isoxazolyl)amino)imidazo[1,2-b]pyridazine-3-carboxamide N-(2-chloro-4-pyridinyl)-6-((trans-4-((cyanoacetyl)amino)cyclohexyl)amino)-8-((1,5-dimethyl-1H-pyrazol-3-yl)amino)imidazo[1,2-b]pyridazine-3-carboxamide N-(2-chloro-4-pyridinyl)-6-((trans-4-((cyanoacetyl)amino)cyclohexyl)amino)-8-(1,3-thiazol-2-ylamino)imidazo[1,2-b]pyridazine-3-carboxamide N-(2-chloro-4-pyridinyl)-6-((trans-4-((cyanoacetyl) amino)cyclohexyl)amino)-8-((1-(2-hydroxyethyl)-1H-pyrazol-3-yl)amino)imidazo[1,2-b]pyridazine-3-carboxamide 6-((trans-4-aminocyclohexyl)amino)-N-4-pyridinyl-8-(4-pyrimidinylamino)imidazo[1,2-b]pyridazine-3-carboxamide 6-((trans-4-aminocyclohexyl)amino)-N-(2-fluoro-4-pyridinyl)-8-((1-methyl-1H-pyrazol-3-yl)amino)imidazo[1,2-b]pyridazine-3-carboxamide 6-((trans-4-aminocyclohexyl)amino)-N-(2-chloro-4-pyridinyl)-8-(1-methyl-1H-pyrazol-3-yl)amino)imidazo[1,2-b]pyridazine-3-carboxamide N-(2-fluoro-4-pyridinyl)-8-((1-methyl-1H-pyrazol-3-yl)amino)-6-(tetrahydro-2H-pyran-4-ylamino)imidazo[1,2-b]pyridazine-3-carboxamide N-(2-chloro-4-pyridinyl)-6-((trans-4-hydroxycyclohexyl)amino)-8-(0-methyl-1H-pyrazol-3-yl)amino)imidazo[1,2-b]pyridazine-3-carboxamide 8-(cyclopropylamino)-N-(3-fluoro-4-pyridinyl)-6-(1-methyl-4-piperidinyl)amino)imidazo[1,2-b]pyridazine-3-carboxamide 8-(cyclopropylamino)-N-(3-fluoro-4-pyridinyl)-6-((2-oxo-3-azepanyl)amino)imidazo[1,2-b]pyridazine-3-carboxamide N-(2-chloro-4-pyridinyl)-8-(cyclopropylamino)-6-(tetrahydro-2H-thiopyran-4-ylamino)imidazo[1,2-b]pyridazine-3-carboxamide 4-((3-((2-chloro-4-pyridinyl)carbamoyl)-8-(cyclopropylamino)imidazo[1,2-b]pyridazin-6-yl)amino)tetrahydro-2H-thiopyranium-1-olate N-(2-chloro-4-pyridinyl)-8-(cyclopropylamino)-6-(tetrahydro-2H-pyran-4-ylamino)imidazo[1,2-b]pyridazine-3-carboxamide or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 8,389,527 B2 | Page 1 of 4 |
| APPLICATION NO. | : 12/866365 | |
| DATED | : March 5, 2013 | |
| INVENTOR(S) | : Brian E. Fink et al. | |

It is certified that error appears in the above-identified patent and that said Letters Patent is hereby corrected as shown below:

On the Title Page:

Item (56), References Cited, under OTHER PUBLICATIONS:

Column 2, McMahon, G. reference, line 1, change "Angiogenisis." to -- Angiogenesis. --.

Column 2, Graninger et al. reference, line 2, change "Rhematol." to -- Rheumatol. --.

In the Claims:

Claim 9:

Column 418, line 11, change "-$(CH_2)_r$ $SO_9H$," to -- -$(CH_2)_rSO_3H$, --.

Claim 10:

Column 419, lines 64 and 65, change "-$(CH_2)_rS$ $(C)_2NR_9R_{10}$," to -- -$(CH_2)_rS(O)_2NR_9R_{10}$, --.

Column 420, line 64, change "-$(CH_2)_rOC_{1-6}$" to -- -$(CH_2)_rOC_{1-5}$ --.

Claim 12:

Column 422, lines 22 and 23, change "pyridinyhamino" to -- pyridinyl)amino --.

Column 423, line 37, change "8-(3-isopropyl" to -- 8-((1-isopropyl --.

Column 423, line 40, change "8-(3-isopropyl" to -- 8-((1-isopropyl --.

Column 423, line 43, change "8-(3-(2-hydroxyethyl)" to -- 8-((1-(2-hydroxyethyl) --.

Column 423, line 49, change "8-(3-isopropyl" to -- 8-((1-isopropyl --.

Column 424, line 32, change "pyridinyhcarbamoyl" to -- pyridinyl)carbamoyl --.

Column 424, line 38, change "aminocyclohexyhamino" to -- aminocyclohexyl)amino --.

Column 425, line 20, change "N~1~-" to -- N-1- --.

Column 425, line 21, change "[1 ,2-b]" to -- [1,2-b] --.

Column 425, line 40, change "[1 ,2-b]" to -- [1,2-b] --.

Column 425, line 43, change "[1 ,2-b]" to -- [1,2-b] --.

Signed and Sealed this
Seventh Day of April, 2015

Michelle K. Lee
*Director of the United States Patent and Trademark Office*

CERTIFICATE OF CORRECTION (continued)
U.S. Pat. No. 8,389,527 B2

In the Claims:

Claim 12 (continued):

Column 425, line 46, change "[1 ,2-b]" to -- [1,2-b] --.

Column 425, line 49, change "[1 ,2-b]" to -- [1,2-b] --.

Column 425, line 61, change "[1 ,2-b]" to -- [1,2-b] --.

Column 425, line 63, change "[1 ,2-b]" to -- [1,2-b] --.

Column 425, line 67, change "[1 ,2-b]" to -- [1,2-b] --.

Column 426, line 3, change "[1 ,2-b]" to -- [1,2-b] --.

Column 426, line 5, change "[1 ,2-b]" to -- [1,2-b] --.

Column 426, line 7, change "N~1~-" to -- N-1- --.

Column 426, line 8, change "[1 ,2-b]" to -- [1,2-b] --.

Column 426, line 11, change "[1 ,2]" to -- [1,2-b] --.

Column 426, line 14, change "alanyhamino" to -- alanyl)amino --.

Column 426, line 15, change "[1 ,2-b]" to -- [1,2-b] --.

Column 426, line 17, change "[1 ,2-b]" to -- [1,2-b] --.

Column 426, line 20, change "[1 ,2-b]" to -- [1,2-b] --.

Column 426, line 23, change "4-((3-(1 ,3-thiazol-4-yl)-D-alanyhamino)cyclohexyl" to -- 4-((3-(1,3-thiazol-4-yl)-D-alanyl)amino)cyclohexyl --.

Column 426, line 24, change "[1 ,2-b]" to -- [1,2-b] --.

Column 426, line 26, change "alanyhamino" to -- alanyl)amino --.

Column 426, line 29, change "[1 ,2-b]" to -- [1,2-b] --.

Column 426, line 32, change "[1 ,2-b]" to -- [1,2-b] --.

Column 426, line 35, change "[1 ,2-b]" to -- [1,2-b] --.

Column 426, line 39, change "[1 ,2-b]" to -- [1,2-b] --.

Column 426, lines 41 and 42, change "[1 ,2-b]" to -- [1,2-b] --.

Column 426, lines 44 and 45, change "[1 ,2-b]" to -- [1,2-b] --.

Column 426, line 46, change "pyridinyI)" to -- pyridinyl) --.

Column 427, line 66, change "[1,2-b ]" to -- [1,2-b] --.

Column 428, line 3, change "[1,2-b ]" to -- [1,2-b] --.

Column 428, line 7, change "[1,2-b ]" to -- [1,2-b] --.

Column 429, line 2, change "propioloylamino" to -- propionylamino --.

Column 429, lines 19 and 20, change "[1 ,2-b]" to -- [1,2-b] --.

Column 429, line 23, change "[1 ,2-b]" to -- [1,2-b] --.

Column 429, line 30, change "N-1 --(trans" to -- N-1-(trans --.

Column 429, line 31, change "[1 ,2-b]" to -- [1,2-b] --.

CERTIFICATE OF CORRECTION (continued)

U.S. Pat. No. 8,389,527 B2

In the Claims:

Claim 12 (continued):

Column 429, line 34, change "N-1 --(trans" to -- N-1-(trans --.

Column 429, line 35, change "[1 ,2-b]" to -- [1,2-b] --.

Column 429, line 39, change "[1 ,2-b]" to -- [1,2-b] --.

Column 429, line 43, change "[1 ,2-b]" to -- [1,2-b] --.

Column 429, lines 45 and 46, change "[1 ,2-b]" to -- [1,2-b] --.

Column 429, line 49, change "[1 ,2-b]" to -- [1,2-b] --.

Column 429, line 54, change "[1 ,2-b]" to -- [1,2-b] --.

Column 429, line 56, change "seryhamino" to -- seryl)amino --.

Column 429, line 57, change "[1 ,2-b]" to -- [1,2-b] --.

Column 429, line 59, change "prolypamino" to -- prolyl)amino --.

Column 429, line 60, change "[1 ,2-b]" to -- [1,2-b] --.

Column 429, line 64, change "[1 ,2-b]" to -- [1,2-b] --.

Column 429, lines 66 and 67, change "[1 ,2-b]" to -- [1,2-b] --.

Column 430, line 3, change "[1 ,2-b]" to -- [1,2-b] --.

Column 431, line 57, change "thiazolid in" to -- thiazolid --.

Column 431, line 58, change "[1 ,2-b]" to -- [1,2-b] --.

Column 432, line 2, change "carbonyl) amino)" to -- carbonyl)amino) --.

Column 432, line 54, change "(M2R,6S)" to -- ((((2R,6S) --.

Column 432, line 66, change "[1,2pyridazine" to -- [1,2-b]pyridazine --.

Column 433, lines 35 and 36, change "carbamoyhamino)" to -- carbamoyl)amino) --.

Column 433, line 66, change "[1,2-b ]" to -- [1,2-b] --.

Column 434, line 25, change "(cyclopropylam ino)" to -- (cyclopropylamino) --.

Column 434, line 27, change "[1,2-b ]" to -- [1,2-b] --.

Column 435, line 8, change "pyridinyhcarbamoyl)" to -- pyridinyl)carbamoyl) --.

Column 436, line 12, change "[1,2-b ]" to -- [1,2-b] --.

Column 436, line 28, change "[1,2-b ]" to -- [1,2-b] --.

Column 441, line 36, change "aminocyclohexyl)hamino" to -- aminocyclohexyl)amino --.

Column 441, line 45, change "amino)-8-M2S)-2" to -- amino)-8-(((2S)-2 --.

Column 442, lines 26 and 27, change "fluorophenyhcarbamoyl" to
-- fluorophenyl)carbamoyl --.

Column 443, line 57, change "5-phenyl)amino" to -- 5-yl)phenyl)amino --.

Column 444, line 55, change "[1,2-Npyridazine" to -- [1,2-b]pyridazine --.

Column 445, line 39, change "(2-hydroxyethyhamino)" to -- (2-hydroxyethyl)amino) --.

CERTIFICATE OF CORRECTION (continued)
U.S. Pat. No. 8,389,527 B2

In the Claims:

Claim 12 (continued):

Column 446, line 23, change "[1 ,2-b]" to -- [1,2-b] --.

Column 446, line 26, change "[1 ,2-b]" to -- [1,2-b] --.

Column 446, line 37, change "((1 ,5-dimethyl" to -- ((1,5-dimethyl --.

Column 446, line 54, change "[1 ,2-b]" to -- [1,2-b] --.

Column 447, line 3, change "[1 ,2-b]" to -- [1,2-b] --.

Column 447, line 12, change "8-(1-methyl" to -- 8-((1-methyl --.

Column 447, line 14, change "8-((1 -methyl" to -- 8-((1-methyl --.

Column 447, line 17, change "8-(0-methyl" to -- 8-((1-methyl --.

Column 448, lines 1 and 2, change "6-(1-methyl" to -- 6-((1-methyl --.